United States Patent
Herz et al.

(10) Patent No.: US 10,428,049 B2
(45) Date of Patent: *Oct. 1, 2019

(54) TRPA1 MODULATORS

(71) Applicant: Algomedix, Inc., Mill Creek, WA (US)

(72) Inventors: Jeffrey M. Herz, Mill Creek, WA (US); Edward A. Kesicki, Mill Creek, WA (US)

(73) Assignee: ALGOMEDIX, INC., Mill Creek, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/909,652

(22) Filed: Mar. 1, 2018

(65) Prior Publication Data

US 2019/0016701 A1   Jan. 17, 2019

Related U.S. Application Data

(63) Continuation of application No. 15/203,774, filed on Jul. 6, 2016, now Pat. No. 9,951,046, which is a continuation-in-part of application No. PCT/US2014/072291, filed on Dec. 23, 2014.

(60) Provisional application No. 61/924,119, filed on Jan. 6, 2014.

(51) Int. Cl.

| | |
|---|---|
| *C07D 401/14* | (2006.01) |
| *C07D 405/14* | (2006.01) |
| *C07D 413/14* | (2006.01) |
| *C07D 471/04* | (2006.01) |
| *C07D 471/10* | (2006.01) |
| *C07D 491/107* | (2006.01) |
| *C07D 495/10* | (2006.01) |
| *C07D 498/04* | (2006.01) |
| *C07D 513/10* | (2006.01) |
| *A61K 45/06* | (2006.01) |
| *A61K 31/167* | (2006.01) |
| *A61K 31/4045* | (2006.01) |
| *A61K 31/415* | (2006.01) |
| *A61K 31/4439* | (2006.01) |
| *A61K 31/4545* | (2006.01) |
| *A61K 31/46* | (2006.01) |
| *A61K 31/485* | (2006.01) |
| *A61K 31/496* | (2006.01) |
| *A61K 31/497* | (2006.01) |
| *A61K 31/498* | (2006.01) |
| *A61K 31/4985* | (2006.01) |
| *A61K 31/513* | (2006.01) |
| *A61K 31/536* | (2006.01) |
| *A61K 31/537* | (2006.01) |
| *A61K 31/538* | (2006.01) |
| *A61K 31/635* | (2006.01) |
| *A61K 31/444* | (2006.01) |
| *C07D 401/04* | (2006.01) |
| *C07D 417/14* | (2006.01) |
| *C07D 491/113* | (2006.01) |

(52) U.S. Cl.
CPC .......... *C07D 401/14* (2013.01); *A61K 31/167* (2013.01); *A61K 31/4045* (2013.01); *A61K 31/415* (2013.01); *A61K 31/444* (2013.01); *A61K 31/4439* (2013.01); *A61K 31/4545* (2013.01); *A61K 31/46* (2013.01); *A61K 31/485* (2013.01); *A61K 31/496* (2013.01); *A61K 31/497* (2013.01); *A61K 31/498* (2013.01); *A61K 31/4985* (2013.01); *A61K 31/513* (2013.01); *A61K 31/536* (2013.01); *A61K 31/537* (2013.01); *A61K 31/538* (2013.01); *A61K 31/635* (2013.01); *A61K 45/06* (2013.01); *C07D 401/04* (2013.01); *C07D 405/14* (2013.01); *C07D 413/14* (2013.01); *C07D 417/14* (2013.01); *C07D 471/04* (2013.01); *C07D 471/10* (2013.01); *C07D 491/107* (2013.01); *C07D 491/113* (2013.01); *C07D 495/10* (2013.01); *C07D 498/04* (2013.01); *C07D 513/10* (2013.01)

(58) Field of Classification Search
CPC . C07D 401/14; A61K 31/167; A61K 31/4045
USPC ....................................................... 514/180
See application file for complete search history.

(56) References Cited

U.S. PATENT DOCUMENTS

| | | | |
|---|---|---|---|
| 6,503,930 | B1 | 1/2003 | Hanson et al. |
| 7,671,061 | B2 | 3/2010 | Moran et al. |
| 7,977,358 | B2 | 7/2011 | Aebi et al. |
| 8,178,542 | B2 | 5/2012 | Moran et al. |
| 8,389,529 | B2 | 3/2013 | Moran et al. |
| 8,541,423 | B2 | 9/2013 | Moran et al. |
| 8,703,805 | B2 | 4/2014 | Busch et al. |
| 8,829,196 | B2 | 9/2014 | Bilodeau et al. |

(Continued)

FOREIGN PATENT DOCUMENTS

| | | |
|---|---|---|
| AU | 2004200420 A1 | 9/2004 |
| CA | 2857441 A1 | 6/2013 |

(Continued)

OTHER PUBLICATIONS

Bennett et al. A peripheral mononeuropathy in rat that produces disorders of pain sensation like those seen in man. Pain 33(1):87-107 (1988).

(Continued)

*Primary Examiner* — Melenie L Gordon
*Assistant Examiner* — Taina D Matos Negron
(74) *Attorney, Agent, or Firm* — Wilson Sonsini Goodrich & Rosati

(57) ABSTRACT

This disclosure relates to polycyclic heteroaromatic compounds useful as TRPA1 modulators, as well as compositions and methods of treating pain that include the compounds.

21 Claims, 2 Drawing Sheets
Specification includes a Sequence Listing.

(56) References Cited

U.S. PATENT DOCUMENTS

| | | |
|---|---|---|
| 8,877,784 B2 | 11/2014 | Perner et al. |
| 9,133,128 B2 | 9/2015 | Fulp et al. |
| 9,533,952 B2 | 1/2017 | Arvela et al. |
| 9,951,046 B2 | 4/2018 | Herz et al. |
| 2006/0205765 A1 | 9/2006 | Bilodeau et al. |

FOREIGN PATENT DOCUMENTS

| | | |
|---|---|---|
| EP | 0178035 A1 | 4/1986 |
| EP | 1698626 A1 | 9/2006 |
| JP | S60246371 A | 12/1985 |
| JP | 2002514640 A | 5/2002 |
| JP | 2006524254 A | 10/2006 |
| JP | 2008509188 A | 3/2008 |
| WO | WO-9958523 A1 | 11/1999 |
| WO | WO-2005040166 A1 | 5/2005 |
| WO | WO-2005063737 A1 | 7/2005 |
| WO | WO-2006015860 A2 | 2/2006 |
| WO | WO-2009089083 A1 | 7/2009 |
| WO | WO-2009147079 A1 | 12/2009 |
| WO | WO-2010125469 A1 | 11/2010 |
| WO | WO-2011043954 A1 | 4/2011 |
| WO | WO-2012174362 A1 | 12/2012 |
| WO | WO-2013079586 A1 | 6/2013 |
| WO | WO-2015103060 A1 | 7/2015 |
| WO | WO-2018009717 A1 | 1/2018 |

OTHER PUBLICATIONS

Chaplan et al. Quantitative assessment of tactile allodynia in the rat paw. J Neurosci Methods 53 (1):55-63 (1994).

Chen et al. Selective blockade of TRPA1 channel attenuates pathological pain without altering noxious cold sensation or body temperature regulation. PAIN 152:1165-1172 (2011).

Courteix et al. Study of the sensitivity of the diabetes-induced pain model in rats to a range of analgesics. Pain 57(2):153-160 (1994).

Cubist Pharmaceuticals and Hydra Biosciences Announce Plans to Begin Phase 1 Clinical Trial for Novel TRPA1 Modulator to Treat Acute Pain, Business Wire, Jan. 10, 2012, 4 pages.

Eid et al. HC-030031, a TRPAI selective antagonist, attenuates inflammatory-and neuropathy-induced mechanical hypersensitivity. Molecular Pain 4:48 (10 pages) (Oct. 27, 2008).

EP14876732.0 Extended European Search Report dated May 11, 2017.

Finn et al. Discovery of a potent and selective series of pyrazole bacterial methionyl-tRNA synthetase inhibitors. J Bioorg Med Chem Lett 13:2231-2234 (2003).

Flatters et al. Ethosuximide reverses paclitaxel- and vincristine-induced painful peripheral neuropathy. Pain 109:150-161 (2004).

IUPAC 1974 Recommendations for Section E, Fundamental Stereochemistry, Pure Appl. Chem. 45:11-30 (1976).

Kim. Channelopathies. Korea Journal of Pediatrics 57(1):1-18 (2014).

Kim et al. An experimental model for peripheral neuropathy produced by segmental spinal nerve ligation in the rat. Pain 50(3):355-363 (1992).

Kremeyer et al. A Gain-of-Function Mutation in TRPA1 Causes Familial Episodic Pain Syndrome. Neuron 66:671-680 (Jun. 10, 2010).

Nativi et al. A TRPA1 antagonist reverts oxaliplatin-induced neuropathic pain. Scientific Reports 3, Article No. 2005 pp. 1-10 (2013).

PCT/US2014/072291 International Preliminary Report on Patentability dated Jul. 21, 2016.

PCT/US2014/072291 International Search Report and Written Opinion dated Mar. 24, 2015.

PCT/US2017/40976 International Search Report and Written Opinion dated Sep. 21, 2017.

PubChem Substance summary for CID 17757795, https://pubchem.ncbi.nlm.nih.gov/compound/1775779, Dec. 3, 2007, pp. 1-8.

PubChem Substance summary for CID 23558944, https://pubchem.ncbi.nlm.nih.gov/compound/23558944#section=Top, Dec. 6, 2007, pp. 1-6.

PubChem Substance summary for CID 51351161, https://pubchem.ncbi.nlm.nih.gov/compound/51351161, May 18, 2011 pp. 1-5.

Skerratt et al. Ion channel therapeutics for pain. Channels 9(6):344-351 (Nov./Dec. 2015).

Strassmaier et al. Transient Receptor Potential A1 Modulators. Current Topics in Medicinal Chemistry 11:2227-2236 (2011).

U.S. Appl. No. 15/203,774 Office Action dated May 26, 2017.

Walz et al. Synthesis of 4-anilinopiperidine methyl esters, intermediates in the production of carfentanil, sufentanil, and remifentanil. Tetrahedron Letters 55:501-502 (2007).

Wei et al. Attenuation of Mechanical Hypersensitivity by an Antagonist of the TRPA1 Ion channel in Diabetic Animals. Anesthesiology 111(1):147-154 (2009).

Whiteside et al. Predictive validity of animal pain models? A comparison of the pharmacokinetic- pharmacodynamic relationship for pain drugs in rats and humans. Nueuropharmacology 54:767-775 (2008).

TRPA1 MODULATORS

CROSS-REFERENCES TO RELATED APPLICATIONS

The present application, U.S. patent application Ser. No. 15/909,652, was filed on Mar. 1, 2018 as a continuation of U.S. patent application Ser. No. 15/203,774, which was filed on Jul. 6, 2016 as a continuation-in-part that claims the priority of International Patent Application No. PCT/US2014/7229 (filed Dec. 23, 2014), which claims the priority of U.S. Provisional Patent Application No. 61/924,119 (filed Jan. 6, 2014). U.S. patent application Ser. Nos. 15/909,652 and 15/203,774 and International Patent Application No. PCT/US2014/7229 are incorporated herein by reference in their entirety.

STATEMENT AS TO RIGHTS TO INVENTIONS MADE UNDER FEDERALLY SPONSORED RESEARCH AND DEVELOPMENT

This invention was made with government support under grant 1R43DA031516, awarded by National Institute on Drug Abuse. The U.S. government has certain rights in the invention.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named "AMDX-01-0116USC1_2018-03-01_US15909652_SEQLIST," created Mar. 1, 2018, and containing 66,956 bytes. The material contained in this text file is incorporated by reference in its entirety for all purposes.

FIELD OF THE INVENTION

This disclosure relates to TRPA1-modulating compounds useful for treating pain as well as compositions and methods that include the compounds. In some embodiments, the compounds of the present invention have applications in preventing, reducing or inhibiting acute or chronic pain in a variety of operative and interventional procedures, including surgical, diagnostic and therapeutic procedures.

BACKGROUND OF THE INVENTION

More than 100 million Americans suffer from chronic pain. Furthermore, problems with use of illicit drugs include pain-reliever misuse, abuse, and addiction. Because of this, it is increasingly difficult for patients with legitimate medical needs for opioid-containing drugs, like Vicodin, to obtain prescriptions. The U.S. Substance Abuse and Mental Health Services Administration estimated 20.1 million Americans were illicit-drug users and an estimated 4.7 million of those persons used pain relievers non-medically in 2008. Thus, an effective treatment for chronic pain that has less addictive potential and abuse liability is a major unmet need in medicine today.

Transient receptor potential cation channel, subfamily A, member 1, ("TRPA1"; wild-type, SEQ ID NO:1; variants, SEQ ID NOS:2-7) is a non-selective cation channel present in mammalian cells. TRPA1-receptor/channels play a highly specific function in sensory nerves that transmit the sensations of pain and hyperalgesia in response to inflammation as well as nerve injury, particularly in chronic conditions. Recent progress in understanding the function and identification of endogenous ligands for TRPA1 channels suggests that TRPA1 is relevant to detecting nociceptive signals.

BRIEF SUMMARY OF THE INVENTION

In one aspect, the invention provides a compound of Formula I:

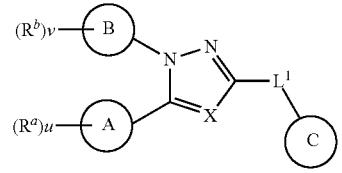

or a pharmaceutically acceptable salt thereof;
wherein:
A is a cyclic group of Formula Ia:

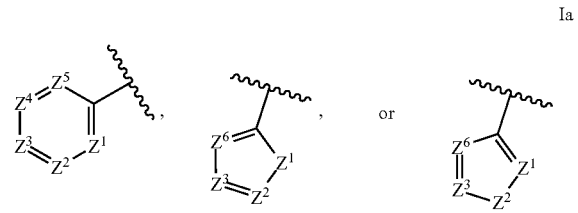

Ia wherein $Z^1$, $Z^2$, $Z^3$, $Z^4$, $Z^5$, and $Z^6$ are each a member selected from the group consisting of N, CH, $CR^a$, and $NR^c$; or, alternatively for $Z^1$ or $Z^6$, the member $Z^1$ or $Z^6$ and X, together with atoms in the rings to which they are attached, form an additional fused, five- to eight-membered cycloalkyl or heterocyclyl ring with from 0 to 4 $R^z$ substituents;
with the proviso that at least one member selected from the group consisting of $Z^2$, $Z^3$, $Z^4$, and $Z^6$ is N;
each $R^z$ is a member independently selected from the group consisting of halo, $C_1$-$C_3$ alkyl, $C_1$-$C_3$ haloalkyl, and $C_1$-$C_3$ alkoxy; or, alternatively, two $R^z$ substituents, together with the carbon atom to which they are attached, join to form an oxo, spirocycloalkyl, or spiroheterocyclyl group;
B is a cyclic group of Formula Ib:

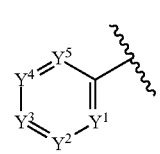

Ib wherein $Y^1$, $Y^2$, $Y^3$, $Y^4$, and $Y^5$ are each a member independently selected from the group consisting of N, CH, and $CR^b$; or, alternatively, the members —$Y^2$=$Y^3$— or —$Y^4$=$Y^5$— are combined into a single member selected from the group consisting of $NR^c$, O, and S;

each $R^a$ and $R^b$ is a member independently selected from the group consisting of cyano, carboxyl, $C_1$-$C_4$ alkyl, $C_1$-$C_4$ hydroxyalkyl, $C_3$-$C_8$ cycloalkyl, $C_1$-$C_4$ alkoxy, $C_1$-$C_4$ haloalkyl, $C_1$-$C_4$ haloalkoxy, halo, $C_0$-$C_6$ amino, $C_1$-$C_6$ amido, $C_1$-$C_4$ alkyloxycarbonyl, $C_1$-$C_6$ alkylsulfonyl, and hydroxyl; or, alternatively, two adjacent $R^a$ or $R^b$, together with the atoms in groups A or B to which they are attached, form an additional fused aryl, heteroaryl, cycloalkyl, or heterocyclyl ring with from 0 to 4 $R^z$ substituents;

each $R^c$ is a member independently selected from the group consisting of hydrogen, $C_1$-$C_4$ alkyl, $C_1$-$C_4$ haloalkyl, $C_3$-$C_6$ cycloalkyl, $(C_3$-$C_6$ cycloalkyl)$C_1$-$C_3$alkyl, and $C_1$-$C_7$ acyl;

each u is an integer independently selected from 0 to 4;

v is an integer from 0 to 5;

X is N or $CR^d$; or, alternatively, X is $CR^d$, wherein X and the member $Z^1$, together with atoms in the rings in which they are included, form the additional fused, five- to eight-membered cycloalkyl or heterocyclyl ring with from 0 to 4 $R^z$ substituents;

each $R^d$ is a member independently selected from the group consisting of halo, cyano, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, and $C_3$-$C_6$ cycloalkoxy;

each $L^1$, $L^2$, and $L^3$, if present, is a member independently selected from the group consisting of C=O, C=S, and C=$NR^c$;

C is a cyclic group of Formula Ic:

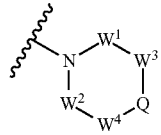

Ic wherein Q is a member selected from the group consisting of $C(R^e)(D)$, N(E), F, and G; or, alternatively, the members —$W^3$-Q- or —$W^4$-Q- join to form a member H; and wherein $W^1$, $W^2$, $W^3$, and $W^4$ are each an independently selected $C(R^f)_2$; or, alternatively, the members —$W^3$-Q- or —$W^4$-Q- join to form a member H;

$R^e$ is a member selected from the group consisting of hydrogen, $C_1$-$C_3$ alkyl, and $C_1$-$C_3$ fluoroalkyl; or, alternatively, $R^e$ and an $R^f$ substituent of $W^1$, $W^2$, $W^3$, or $W^4$ join to form a —$(C(R^z)_2)_t$— bridge, wherein t is an integer selected from 2 or 3;

each $R^f$ is a member independently selected from the group consisting of hydrogen, $C_1$-$C_3$ alkyl, $C_1$-$C_3$ fluoroalkyl, and halo; or, alternatively, two adjacent $R^f$, together with the atoms in group C to which they are attached, form an additional aryl, heteroaryl, cycloalkyl, or heterocyclyl fused ring with from 0 to 4 $R^z$ substituents; or, alternatively, two geminal $R^f$, together with the atom in group C to which they are attached, form a spirocycloalkyl or spiroheterocyclyl ring with from 0 to 4 $R^z$ substituents; or, alternatively, two axial $R^f$ substituents of a pair of $W^m$ selected from the group consisting of ($W^1$ and $W^2$), ($W^2$ and $W^3$), and ($W^3$ and $W^4$) join to form a —$(C(R^z)_2)_t$— bridge; or, alternatively, $R^e$ and an $R^f$ substituent of $W^1$, $W^2$, $W^3$, or $W^4$ join to form a —$(C(R^z)_2)_t$— bridge;

each t is an integer selected from 2 or 3;

D is a bicyclic group of Formula Id:

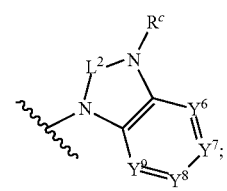

Id

E is a bicyclic group of Formula Ie:

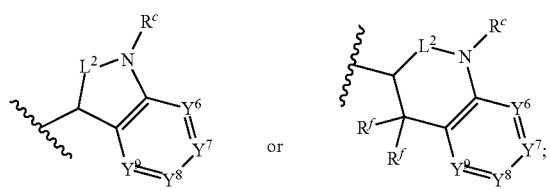

Ie

F is a spirocyclic group of Formula If:

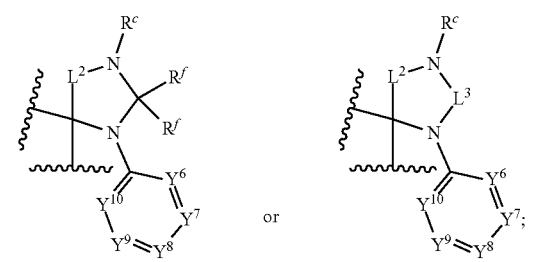

If

G is a bicyclic spirocyclic group of Formula Ig:

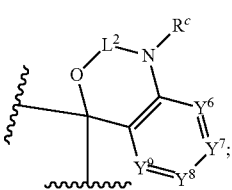

Ig

H is a fused group of Formula Ih:

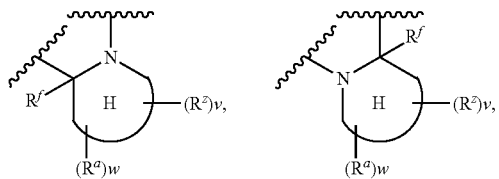

Ih

-continued

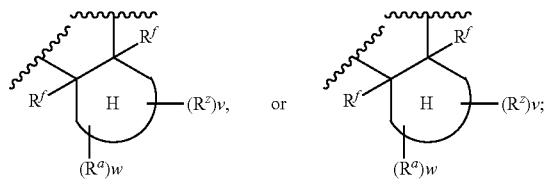

wherein the H ring is a fused, five- to eight-membered cycloalkyl or heterocyclyl ring;
wherein v is an integer from 0 to 4; and
wherein w is an integer from 0 to 2; and $Y^6$, $Y^7$, $Y^8$, $Y^9$, and $Y^{10}$, if present, are each a member independently selected from the group consisting of N, CH, and $CR^b$; or, alternatively for $Y^8$ and $Y^9$, the members —$Y^6$=$Y^7$— or —$Y^8$=$Y^9$— are combined into a single member selected from the group consisting of $NR^c$, O, and S.

In one preferred aspect, the invention provides a compound of Formula I:

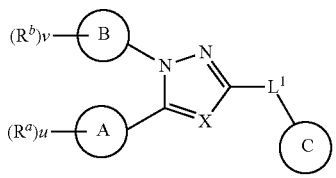

or a pharmaceutically acceptable salt thereof;

wherein:

A is a cyclic group of Formula Ia:

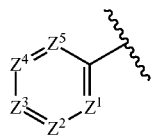

wherein $Z^1$, $Z^2$, $Z^3$, $Z^4$, and $Z^5$ are each a member selected from the group consisting of N, CH, and $CR^a$; or, alternatively for $Z^1$, the member $Z^1$ and X, together with atoms in the rings to which they are attached, form an additional fused, five- to eight-membered cycloalkyl or heterocyclyl ring with from 0 to 4 $R^z$ substituents;

with the proviso that at least one member selected from the group consisting of $Z^2$, $Z^3$, and $Z^4$ is N;

each $R^z$ is a member independently selected from the group consisting of halo, $C_1$-$C_3$ alkyl, $C_1$-$C_3$ haloalkyl, and $C_1$-$C_3$ alkoxy; or, alternatively, two $R^z$ substituents, together with the carbon atom to which they are attached, join to form an oxo, spirocycloalkyl, or spiroheterocyclyl group;

B is a cyclic group of Formula Ib:

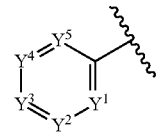

wherein $Y^1$, $Y^2$, $Y^3$, $Y^4$, and $Y^5$ are each a member independently selected from the group consisting of N, CH, and $CR^b$; or, alternatively, the members —$Y^2$=$Y^3$— or —$Y^4$=$Y^5$— are combined into a single member selected from the group consisting of $NR^c$, O, and S;

each $R^a$ and $R^b$ is a member independently selected from the group consisting of cyano, carboxyl, $C_1$-$C_4$ alkyl, $C_1$-$C_4$ hydroxyalkyl, $C_3$-$C_8$ cycloalkyl, $C_1$-$C_4$ alkoxy, $C_1$-$C_4$ haloalkyl, $C_1$-$C_4$ haloalkoxy, halo, $C_0$-$C_6$ amino, $C_1$-$C_6$ amido, $C_1$-$C_4$ alkyloxycarbonyl, $C_1$-$C_6$ alkylsulfonyl, and hydroxyl; or, alternatively, two adjacent $R^a$ or $R^b$, together with the atoms in groups A or B to which they are attached, form an additional fused aryl, heteroaryl, cycloalkyl, or heterocyclyl ring with from 0 to 4 $R^z$ substituents;

each $R^c$ is a member independently selected from the group consisting of hydrogen, $C_1$-$C_4$ alkyl, $C_1$-$C_4$ haloalkyl, $C_3$-$C_6$ cycloalkyl, ($C_3$-$C_6$ cycloalkyl)$C_1$-$C_3$alkyl, and $C_1$-$C_7$ acyl;

each u is an integer independently selected from 0 to 4;
v is an integer from 0 to 5;

X is N or $CR^d$; or, alternatively, X is $CR^d$, wherein X and the member $Z^1$, together with atoms in the rings in which they are included, form the additional fused, five- to eight-membered cycloalkyl or heterocyclyl ring with from 0 to 4 $R^z$ substituents;

each $R^d$ is a member independently selected from the group consisting of hydrogen, halo, cyano, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, and $C_3$-$C_6$ cycloalkoxy;

each $L^1$, $L^2$, and $L^3$, if present, is a member independently selected from the group consisting of C=O, C=S, and C=$NR^c$;

C is a cyclic group of Formula Ic:

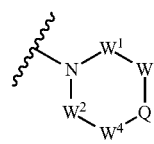

wherein Q is a member selected from the group consisting of C($R^e$)(D), N(E), F, and G; or, alternatively, the members —$W^3$-Q- or —$W^4$-Q- join to form a member H; and wherein $W^1$, $W^2$, $W^3$, and $W^4$ are each an independently selected C($R^f$)$_2$; or, alternatively, the members —$W^3$-Q- or —$W^4$-Q- join to form a member H;

$R^e$ is a member selected from the group consisting of hydrogen, $C_1$-$C_3$ alkyl, and $C_1$-$C_3$ fluoroalkyl; or, alternatively, $R^e$ and an $R^f$ substituent of $W^1$, $W^2$, $W^3$, or $W^4$ join to form a —(C($R^z$)$_2$)$_t$— bridge, wherein t is an integer selected from 2 or 3;

each $R^f$ is a member independently selected from the group consisting of hydrogen, $C_1$-$C_3$ alkyl, $C_1$-$C_3$ fluoroalkyl, and halo; or, alternatively, two adjacent $R^f$, together with the atoms in group C to which they are attached, form an additional aryl, heteroaryl, cycloalkyl, or heterocyclyl fused ring with from 0 to 4 $R^z$ substituents; or, alternatively, two geminal $R^f$, together with the atom in group C to which they are attached, form a spirocycloalkyl or spiroheterocyclyl ring with from 0 to 4 $R^z$ substituents; or, alternatively, two axial $R^f$ substituents of a pair of $W^m$ selected from the group consisting of ($W^1$ and $W^2$), ($W^2$ and $W^3$), and ($W^3$ and $W^4$) join to form a —$(C(R^z)^2)_t$— bridge; or, alternatively, $R^e$ and an $R^f$ substituent of $W^1$, $W^2$, $W^3$, or $W^4$ join to form a —$(C(R^z)_2)_t$— bridge;

each t is an integer selected from 2 or 3;

D is a bicyclic group of Formula Id:

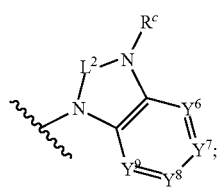

E is a bicyclic group of Formula Ie:

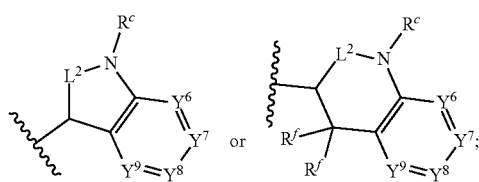

F is a spirocyclic group of Formula If:

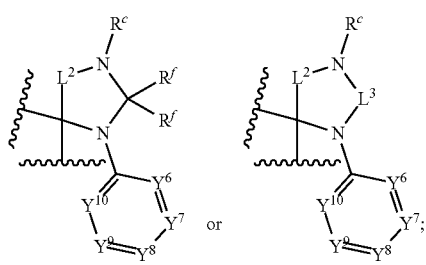

G is a bicyclic spirocyclic group of Formula Ig:

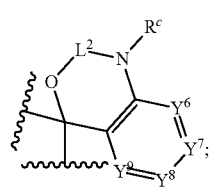

H is a fused group of Formula Ih:

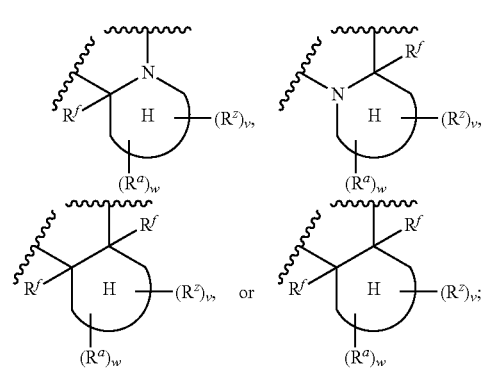

wherein the H ring is a fused, five- to eight-membered cycloalkyl or heterocyclyl ring;

wherein v is an integer from 0 to 4; and wherein w is an integer from 0 to 2; and $Y^6$, $Y^7$, $Y^8$, $Y^9$, and $Y^{10}$, if present, are each a member independently selected from the group consisting of N, CH, and $CR^b$; or, alternatively for $Y^8$ and $Y^9$, the members —$Y^6$=$Y^7$— or —$Y^8$=$Y^9$— are combined into a single member selected from the group consisting of $NR^c$, O, and S.

In one aspect, the invention provides a compound of Formula II:

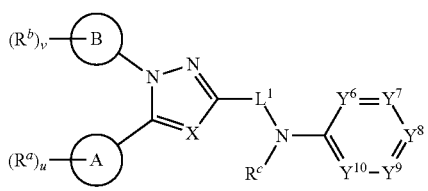

or a pharmaceutically acceptable salt thereof;

wherein:

A is a cyclic group of Formula IIa:

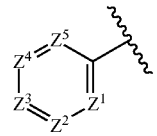

wherein $Z^1$, $Z^2$, $Z^3$, $Z^4$, and $Z^5$ are each a member selected from the group consisting of N, CH, and $CR^a$; or, alternatively for $Z^1$, the member $Z^1$ and X, together with atoms in the rings to which they are attached, form an additional fused, five- to eight-membered cycloalkyl or heterocyclyl ring with from 0 to 5 $R^z$ substituents;

with the proviso that at least one member selected from the group consisting of $Z^2$, $Z^3$, and $Z^4$ is N;

each $R^z$ is a member independently selected from the group consisting of halo, $C_1$-$C_3$ alkyl, $C_1$-$C_3$ haloalkyl, and $C_1$-$C_3$ alkoxy; or, alternatively, two $R^z$ substituents, together with the carbon atom to which they are attached, join to form an oxo, spirocycloalkyl, or spiroheterocyclyl group;

B is a cyclic group of Formula IIb:

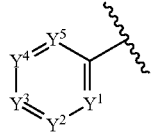

IIb wherein $Y^1$, $Y^2$, $Y^3$, $Y^4$, and $Y^5$ are each a member independently selected from the group consisting of N, CH, and $CR^b$; or, alternatively, the members —$Y^2$═$Y^3$— or —$Y^4$═$Y^5$— are combined into a single member selected from the group consisting of $NR^c$, O, and S;

each $R^a$ and $R^b$ is a member independently selected from the group consisting of cyano, carboxyl, $C_1$-$C_4$ alkyl, $C_1$-$C_4$ hydroxyalkyl, $C_3$-$C_8$ cycloalkyl, $C_1$-$C_4$ alkoxy, $C_1$-$C_4$ haloalkyl, $C_1$-$C_4$ haloalkoxy, halo, $C_0$-$C_6$ amino, $C_1$-$C_6$ amido, $C_1$-$C_4$ alkyloxycarbonyl, $C_1$-$C_6$ alkylsulfonyl, and hydroxyl; or, alternatively, two adjacent $R^a$ or $R^b$, together with the atoms in groups A or B to which they are attached, form an additional fused aryl, heteroaryl, cycloalkyl, or heterocyclyl ring with from 0 to 5 $R^z$ substituents;

each $R^c$ is a member independently selected from the group consisting of hydrogen, $C_1$-$C_4$ alkyl, $C_1$-$C_4$ haloalkyl, $C_3$-$C_6$ cycloalkyl, ($C_3$-$C_6$ cycloalkyl)$C_1$-$C_3$alkyl, and $C_1$-$C_7$ acyl;

each u is an integer independently selected from 0 to 4;

v is an integer from 0 to 5;

X is N or $CR^d$; or, alternatively, X is $CR^d$, wherein X and the member $Z^1$, together with atoms in the rings in which they are included, form the additional fused, five- to eight-membered cycloalkyl or heterocyclyl ring with from 0 to 5 $R^z$ substituents;

each $R^d$ is a member independently selected from the group consisting of halo, cyano, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, and $C_3$-$C_6$ cycloalkoxy;

$L^1$ is a member selected from the group consisting of C═O, C═S, and C═$NR^c$;

$Y^6$, $Y^7$, $Y^8$, $Y^9$, and $Y^{10}$, if present, are each a member independently selected from the group consisting of N, CH, and $CR^b$; or, alternatively for $Y^8$ and $Y^9$, the members —$Y^6$═$Y^7$— or —$Y^8$═$Y^9$— are combined into a single member selected from the group consisting of $NR^c$, O, and S.

In another aspect, the invention provides a pharmaceutical composition comprising a therapeutically effective amount of a compound of Formula I or II and at least one pharmaceutically acceptable carrier, excipient, or diluent.

In another aspect, the invention provides a method of treating or preventing pain comprising administering to a patient in need thereof a therapeutically effective amount, or a prophylactically effective amount, of a compound of Formula I or II.

Certain other aspects and embodiments of the present invention are set forth herein and will be apparent to those of skill in the art.

DETAILED DESCRIPTION OF THE INVENTION

I. Definitions

Figure 1:
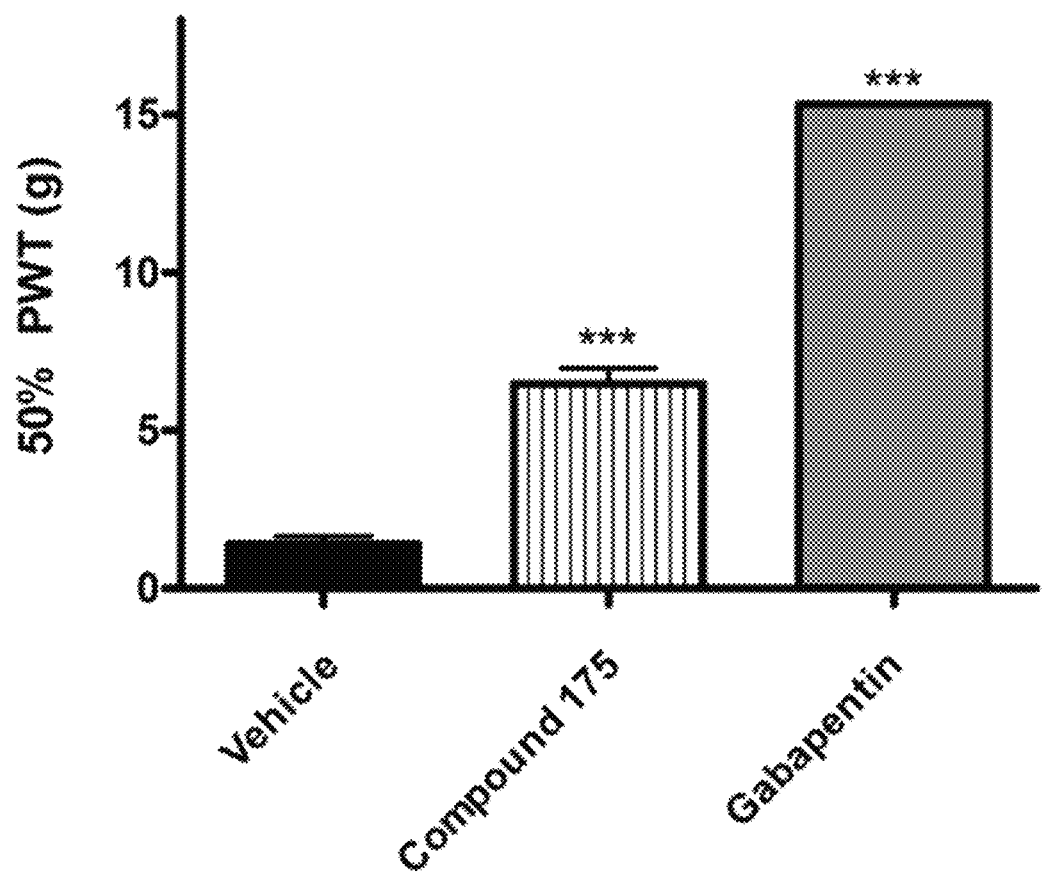
FIG. 1 shows the paw withdrawal threshold (PWT in g) observed in rats treated with a compound of the invention after spinal nerve ligation.

Unless otherwise stated, the following terms used in this application, including the specification and claims, have the definitions given below. Definition of standard chemistry terms may be found in reference works, including Carey and Sundberg (2007) *Advanced Organic Chemistry* 5th Ed. Vols. A and B, Springer Science+Business Media LLC, New York.

It must be noted that, as used in the specification and the appended claims, the singular forms "a," "an" and "the" include plural referents unless the context clearly dictates otherwise. For example, an embodiment including "a TRPA1-modulating compound and an excipient" should be understood to present certain aspects with at least a second TRPA1-modulating compound, at least a second excipient, or both.

The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in *March's Advanced Organic Chemistry: Reactions, Mechanisms, and Structure,* 6th Edition, M. B. Smith and J. March, John Wiley & Sons, Inc., Hoboken, N.J., 2007. Although methods and materials similar or equivalent to those described herein can be used in the practice or testing of the present invention, suitable methods and materials are described below. The materials, methods, and examples are illustrative only and not intended to be limiting.

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

The term "acyl" as used herein includes an alkanoyl, aroyl, heterocycloyl, or heteroaroyl group as defined herein. Examples of acyl groups include, but are not limited to, acetyl, benzoyl, and nicotinoyl.

The term "agonist" embraces agents that, e.g., increase, hasten, or activate the expression of a described target protein or bind to, stimulate, increase, open, activate, enhance, increase activation, sensitize or up-regulate the activity of one or more proteins (or encoding polynucleotide (s)). As used herein, "agonist" generally includes partial agonists, full agonists, and superagonists (i.e., greater than full agonism). Assays for determining whether a compound "agonizes" or "does not agonize" a protein include, e.g., contacting the protein(s) with the compound and then determining the functional effects on the protein activity or contacting cells expressing protein(s) with the compound and then determining the functional effects on the described target protein activity. One of skill in the art will be able to determine whether an assay is suitable for determining whether a compound agonizes or does not agonize a protein. Samples or assays comprising a TRPA1 target are treated with a test compound and are compared to control samples without the test compound (and to positive control samples activated by exposure to a known TRPA1 agonist) to measure the extent of effect on TRPA1 activity. Control samples (untreated with agonists) are used to establish a baseline activity value. Agonism of the TRPA1 protein or channel is achieved when the activity value increases relative to the untreated control (e.g., increases by 20%, 30%, 40%, 50%, 75%, or 100%, or even more).

The term "antagonist" embraces agents that, e.g., slow or reduce the expression of a described target protein or block, destimulate, decrease, close, deactivate, interfere with, reduce activation, desensitize or down-regulate the activity of one or more proteins (or encoding polynucleotide(s)). As used herein, "antagonist" generally includes partial antagonists and full antagonists. Assays for determining whether a compound "antagonizes" or "does not antagonize" a protein include, e.g., contacting the protein(s) with the test compound and then determining the functional effects on the protein activity or contacting cells expressing protein(s) with the test compound and then determining the functional effects on the described target protein activity. One of skill in the art will be able to determine whether an assay is suitable for determining whether a compound antagonizes or does not antagonize a protein. Samples or assays comprising a TRPA1 target are treated with a putative antagonist and are compared to control samples without the compound (and to control samples activated by a known agonist) to measure the extent of effect on TRPA1 activity. Agonist-activated control samples (untreated with antagonists) are assigned a relative activity value of 100%. Antagonism of the TRPA1 protein or channel activity is achieved when the activity value relative to the agonist-activated control is less than 100% (e.g., 80%, 50%, 40%, 30%, 20%, or 10%, or even lower).

Cells used to determine the agonist or antagonist activity of a compound of the present invention can be cells or cell lines transiently or permanently transfected or transformed with the appropriate nucleic acid encoding TRPA1 or can be cells or cell lines that express TRPA1 from endogenous genes. Typically, the TRPA1 receptor-channel is expressed on the surface of a recombinant host cell such as human embryonic kidney (HEK), CHO, SH-SY5Y or COS-7 cells. Alternatively, cells endogenously expressing TRPA1, such as dorsal root ganglion neurons can be isolated from an animal, cultured and used to determine antagonist activity. Examples of cell lines that endogenously express TRPA1 that are suitable for use also include, but are not limited to the human WI-38 cell line, the differentiated human neuroblastoma IMR-32 cell line and the differentiated rat PC12 cell line. The assays described herein can also be performed with cells that express variant TRPA1 proteins. Methods for performing assays to determine if a compound is an agonist or antagonist of the TRPA1 channel are well known in the art. One non-limiting example involves a spectrofluorometric assay in which cells loaded with a fluorescent dye which is sensitive to intracellular calcium concentrations are subsequently contacted with the compounds of interest to determine their ability to alter intracellular calcium levels. Another method involves testing compounds using an electrophysiological assay, such as patch clamping.

The term "alkanoyl" as used herein embraces an alkyl-C (O)— group wherein the alkyl group is as defined herein. Examples of alkanoyl groups include, but are not limited to, acetyl and propanoyl.

The term "alkyl," either alone or within other terms such as "haloalkyl" and "alkylamino," embraces linear or branched radicals having one to about twelve carbon atoms. "Lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylene" embraces bridging divalent linear and branched alkyl radicals. Examples include methylene, ethylene, propylene, isopropylene and the like.

The term "alkenyl" embraces linear or branched radicals having at least one carbon-carbon double bond of two to about twelve carbon atoms. "Lower alkenyl" embraces radicals having two to about six carbon atoms. Examples of alkenyl radicals include ethenyl, propenyl, allyl, propenyl, butenyl and 4-methylbutenyl. The terms "alkenyl" and "lower alkenyl," embrace radicals having "cis" and "trans" orientations, or alternatively, "E" and "Z" orientations.

The term "alkoxy" as used herein contemplates an oxygen with a lower alkyl group as a substituent and includes methoxy, ethoxy, butoxy, and the like.

The term "alkynyl" denotes linear or branched radicals having at least one carbon-carbon triple bond and having two to about twelve carbon atoms. "Lower alkynyl" radicals have two to about six carbon atoms. Examples of such radicals include propargyl, butynyl, and the like.

The term "aroyl" as used herein embraces an aryl-CO— group wherein aryl is as defined herein. Examples include, but are not limited to, benzoyl, naphth-1-oyl and naphth-2-oyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl.

The term "comprising" is meant to be open ended, including the indicated component, but not excluding other elements.

"Conservatively modified variants" embrace both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

The term "cyclic group" means a cycloalkyl, heterocyclyl, aryl, or heteroaryl.

The term "cycloalkyl" includes saturated carbocyclic groups of 3 to 10 carbons. Lower cycloalkyl groups include $C_3$-$C_6$ rings. Examples include cyclopentyl, cyclopropyl, and cyclohexyl.

As used herein, "cycloalkylalkyl" embraces an alkyl group wherein the alkyl group includes one or more cycloalkyl substituents (typically one). Examples include, but are not limited to, cyclohexylmethyl, cyclopentylmethyl, and cyclopropylmethyl.

The term "geminal" embraces two or more substituents that are directly attached to the same atom. An example is 3,3-dimethyl substitution on a cyclohexyl or spirocyclohexyl ring.

The term "halo" means halogens such as fluorine, chlorine, bromine or iodine atoms (i.e., fluoro, chloro, bromo, or iodo).

The term "haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means an alkyl radical having all hydrogen atoms replaced with fluoro atoms. Examples include trifluoromethyl and pentafluoroethyl.

The term "haloalkoxy" means alkoxy radicals wherein any one or more of the alkyl carbon atoms is substituted with one or more halo as defined above. Examples include monohaloalkoxy, dihaloalkoxy and polyhaloalkoxy radicals including perhaloalkoxy. Examples further include difluoromethoxy, trifluoromethoxy and trifluoroethoxy.

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroaroyl" embraces a heteroaryl-C(O)— group wherein heteroaryl is as defined herein. Heteroaroyl groups include, but are not limited to, thiophenyl, nicotinoyl, pyrrol-2-ylcarbonyl, and pyridinoyl.

The term "heterocyclyl" (or "heterocyclo") embraces saturated, and partially saturated, heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions.

Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

Heterocyclo groups also includes radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms

[e.g. benzofuryl, benzothienyl, 2,3-dihydro-benzo[1,4]dioxinyl and dihydrobenzofuryl].

The term "heterocycloyl" embraces a heterocyclyl-C(O)— group wherein heterocyclyl is as defined herein. Examples include, but are not limited to, N-methyl prolinoyl and tetrahydrofuranoyl.

The term "hydroxy" or "hydroxyl" embraces —OH.

The term "hydroxyalkyl" embraces radicals wherein any one or more of the alkyl carbon atoms is substituted with one or more hydroxy groups. Examples include hydroxymethyl, 2-hydroxyethyl, and (R)- or (S)-1-hydroxyethyl.

When any two substituent groups or any two instances of the same substituent group are "independently selected" from a list of alternatives, the groups may be the same or different. For example, if $R^a$ and $R^b$ are independently selected from alkyl, fluoro, amino, and hydroxyalkyl, then a molecule with two $R^a$ groups and two $R^b$ groups could have all groups be an alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different). In some embodiments, multiple instances of variables that may be selected from a list of alternatives are independently selected.

The term "interventional procedure" embraces any medical procedure used for diagnosis or treatment that involves incision, puncture, entry into a body cavity, or the use of ionizing, electromagnetic or acoustic energy.

As used herein, "or" should in general be construed non-exclusively. For example, an embodiment of "a composition comprising A or B" would typically present an aspect with a composition comprising both A and B, and an embodiment of "a method to treat or to prevent" could treat, prevent, or do a combination of both. "Or" should, however, be construed to exclude those aspects presented that cannot be combined without contradiction (e.g., a composition pH that is between 9 and 10 or between 7 and 8).

The term "oxo" as used herein contemplates an oxygen atom attached with a double bond.

The term "periprocedurally" embraces administration of the compound during (intraprocedurally), before (preprocedurally), or after an medical procedure (postprocedurally). In one embodiment, a compound of the present invention is administered (i) preprocedurally or postprocedurally; and (ii) intraprocedurally. The compounds of the present invention are administered to a surgical, diagnostic, or therapeutic procedure site by techniques well known to those of ordinary skill in the art. The compound may be administered periprocedurally, which may include perioperatively (i.e., before, during or after a surgical procedure).

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable (i.e., non-toxic at the therapeutic dosage) and that possesses the desired pharmacological activity of the parent compound. Such salts include, for example, acid addition salts and base addition salts. Examples of pharmaceutically acceptable salts include inorganic acid addition salts, such as chloride, bromide, sulfate, phosphate, and nitrate; organic acid addition salts, such as acetate, galactarate, propionate, succinate, lactate, glycolate, malate, tartrate, citrate, maleate, fumarate, methanesulfonate, p-toluenesulfonate, and ascorbate; salts with acidic amino acid, such as aspartate and glutamate; alkali metal salts, such as sodium salt and potassium salt; alkaline earth metal salts, such as magnesium salt and calcium salt; ammonium salt; organic base salts, such as trimethylamine salt, triethylamine salt, pyridine salt, picoline salt, dicyclohexylamine salt, and N,N'-dibenzylethylenediamine salt; and salts with a basic amino acid, such as lysine salt and arginine salt. The salts may be in some cases hydrates or ethanol solvates.

As used herein, a reference to a composition of formula A, B, C, or a salt thereof embraces A, a salt of A, B, a salt of B, C, or a salt of C.

The term "spirocycloalkyl" embraces a cycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a cyclopropyl ring incorporating the carbon to which $R^1$ and $R^2$ were bonded, this would be a spirocycloalkyl group (i.e., spirocyclopropyl).

The term "spiroheterocyclyl" embraces a heterocycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a pyrrolidine ring incorporating the carbon to which $R^1$ and $R^2$ were bonded, this would be a spiroheterocyclyl group.

The term "TRPA1 modulator" is a composition that measurably increases or decreases the activity of TRPA1.

Compounds of the present disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 *Recommendations for Section E, Fundamental Stereochemistry, Pure Appl. Chem.*, (1976), 45: 13-30, hereby incorporated by reference. The present disclosure contemplates various stereoisomers and mixtures thereof, and these isomers (e.g., a substantially pure (R) or (S) enantiomer of a chiral compound of the present invention) are specifically included within the scope of the present disclosure. Stereoisomers include enantiomers, diastereomers, and mixtures of enantiomers or diastereomers. Individual stereoisomers of compounds of the present disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

In some embodiments, the compounds of the invention can be obtained as N-oxides. Conversion of a tertiary amine group (i.e., a compound having the formula $R_3N$) in a compound of the invention to the corresponding N-oxide (i.e., a compound having the formula $R_3N^{\oplus}—O^{\ominus}$) can be conducted chemically according to methods that are known in the art. Conversion of a compound to the N-oxide can also occur after administration to a subject or patient. In certain cases, such conversion is catalyzed enzymatically (e.g., by a cytochrome P450 enzyme). In some instances, the N-oxide can be a metabolite of a tertiary amine present in a compound of the invention. The N-oxide can be an intermediate between the tertiary amine and its N-dealkylated analogs. Depending on the particular compound, an N-oxide can be more active or less active than its parent amine.

Where compounds of the present disclosure include F, I, C or H, the disclosure is not limited to the most common isotopes of these elements. Compounds containing for example $^{18}F$, $^{19}F$, $^{11}C$, $^{13}C$, $^{14}C$, $^{123}I$, $^{125}I$, $^{3}H$ and $^{2}H$ are specifically contemplated as being included in the disclosure. A compound of the invention can be radiolabeled according to a number of known techniques. A compound can be radiolabeled, for example, by appending one or more radioisotopes of a halogen (e.g., $^{125}I$) to an aromatic ring, or by alkylating a nitrogen of a compound of the invention with a group comprising a radioisotope. Radiolabeled compounds can be used to measure binding of the compounds to TRPA1; to detect the compounds in cells, tissues, or organs of a subject to whom the compounds are administered; to enable analysis of compound metabolism; or for radiotherapeutic techniques. Radiolabeled compounds of the invention can also be used as competitive binders in studies for characterizing natural TRPA1 ligands. Isotopes of still other elements can be used in conjunction with the compounds and methods of the invention.

In the Summary of the Invention above, Detailed Description, and the claims below, reference is made to particular features and aspects of the invention, including method steps. The disclosure of the invention in this specification includes all possible combinations of such particular features within the embodiments of the invention disclosed, at least to the extent that such combinations are non-contradictory. For example, if the Detailed Description presents aspects A, B, and C of an embodiment, it is understood that this also discloses particular embodiments including both aspects A and B, both aspects B and C, and both aspects A and C, as well as an embodiment with aspects A, B, and C.

II. Compounds of the Invention

In one aspect, the invention sets forth a compound of Formula I:

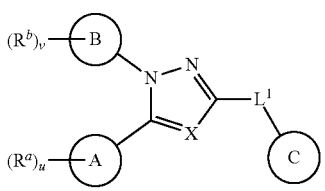

or a pharmaceutically acceptable salt thereof, wherein:
A is a cyclic group of Formula Ia:

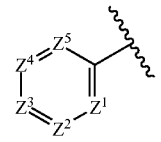

Ia wherein $Z^1$, $Z^2$, $Z^3$, $Z^4$, and $Z^5$ are each a member selected from the group consisting of N, CH, and $CR^a$; or, alternatively for $Z^1$, the member $Z^1$ and X, together with atoms in the rings to which they are attached, form an additional fused, five- to eight-membered cycloalkyl or heterocyclyl ring with from 0 to 4 $R^z$ substituents;
with the proviso that at least one member selected from the group consisting of $Z^2$, $Z^3$, and $Z^4$ is N;
each $R^z$ is a member independently selected from the group consisting of halo, $C_1$-$C_3$ alkyl, $C_1$-$C_3$ haloalkyl, and $C_1$-$C_3$ alkoxy; or, alternatively, two $R^z$ substituents, together with the carbon atom to which they are attached, join to form an oxo, spirocycloalkyl, or spiroheterocyclyl group;
B is a cyclic group of Formula Ib:

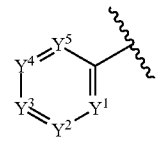

Ib wherein $Y^1$, $Y^2$, $Y^3$, $Y^4$, and $Y^5$ are each a member independently selected from the group consisting of N, CH, and $CR^b$; or, alternatively, the members $—Y^2=Y^3—$ or $—Y^4=Y^5—$ are combined into a single member selected from the group consisting of $NR^c$, O, and S;
each $R^a$ and $R^b$ is a member independently selected from the group consisting of cyano, carboxyl, $C_1$-$C_4$ alkyl, $C_3$-$C_8$ cycloalkyl, $C_1$-$C_4$ alkoxy, $C_1$-$C_4$ haloalkyl, $C_1$-$C_4$ haloalkoxy, halo, $C_0$-$C_6$ amino, $C_1$-$C_6$ amido, $C_1$-$C_4$ alkyloxycarbonyl, $C_1$-$C_6$ alkylsulfonyl, and hydroxyl; or, alternatively, two adjacent $R^a$ or $R^b$, together with the atoms in groups A or B to which they are attached, form an additional fused aryl, heteroaryl, cycloalkyl, or heterocyclyl ring with from 0 to 4 $R^z$ substituents;
each $R^c$ is a member independently selected from the group consisting of hydrogen, $C_1$-$C_4$ alkyl, $C_1$-$C_4$ haloalkyl, $C_3$-$C_6$ cycloalkyl, ($C_3$-$C_6$ cycloalkyl)$C_1$-$C_3$alkyl, and $C_1$-$C_7$ acyl;
each u is an integer independently selected from 0 to 4;
v is an integer from 0 to 5;
X is N or $CR^d$; or, alternatively, X is $CR^d$, wherein X and the member $Z^1$, together with atoms in the rings in which they are included, form the additional fused, five- to eight-membered cycloalkyl or heterocyclyl ring with from 0 to 4 $R^z$ substituents;
each $R^d$ is a member independently selected from the group consisting of halo, cyano, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, and $C_3$-$C_6$ cycloalkoxy;

each $L^1$, $L^2$, and $L^3$, if present, is a member independently selected from the group consisting of C=O, C=S, and C=$NR^c$;

C is a cyclic group of Formula Ic:

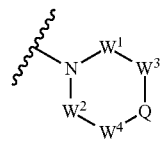

Ic wherein Q is a member selected from the group consisting of $C(R^e)(D)$, N(E), F, and G; or, alternatively, the members —$W^3$-Q- or —$W^4$-Q- join to form a member H; and wherein $W^1$, $W^2$, $W^3$, and $W^4$ are each an independently selected $C(R^f)_2$; or, alternatively, the members —$W^3$-Q- or —$W^4$-Q- join to form a member H;

$R^e$ is a member selected from the group consisting of hydrogen, $C_1$-$C_3$ alkyl, and $C_1$-$C_3$ fluoroalkyl; or, alternatively, $R^e$ and an $R^f$ substituent of $W^1$, $W^2$, $W^3$, or $W^4$ join to form a —$(C(R^z)_2)_t$— bridge, wherein t is an integer selected from 2 or 3;

each $R^f$ is a member independently selected from the group consisting of hydrogen, $C_1$-$C_3$ alkyl, $C_1$-$C_3$ fluoroalkyl, and halo; or, alternatively, two adjacent $R^f$, together with the atoms in group C to which they are attached, form an additional aryl, heteroaryl, cycloalkyl, or heterocyclyl fused ring with from 0 to 4 $R^z$ substituents; or, alternatively, two geminal $R^f$, together with the atom in group C to which they are attached, form a spirocycloalkyl or spiroheterocyclyl ring with from 0 to 4 $R^z$ substituents; or, alternatively, two axial $R^f$ substituents of a pair of $W^n$ selected from the group consisting of ($W^1$ and $W^2$), ($W^2$ and $W^3$), and ($W^3$ and $W^4$) join to form a —$(C(R^z)_2)_t$— bridge; or, alternatively, $R^e$ and an $R^f$ substituent of $W^1$, $W^2$, $W^3$, or $W^4$ join to form a —$(C(R^z)_2)_t$— bridge;

each t is an integer selected from 2 or 3;

D is a bicyclic group of Formula Id:

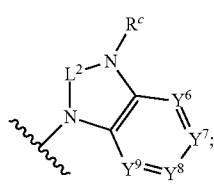

Id

E is a bicyclic group of Formula Ie:

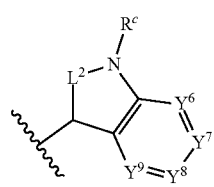

Ie

F is a spirocyclic group of Formula If:

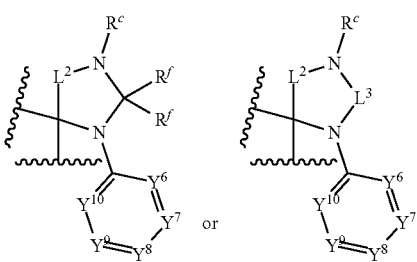

If

G is a bicyclic spirocyclic group of Formula Ig:

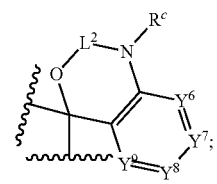

Ig

H is a fused group of Formula Ih:

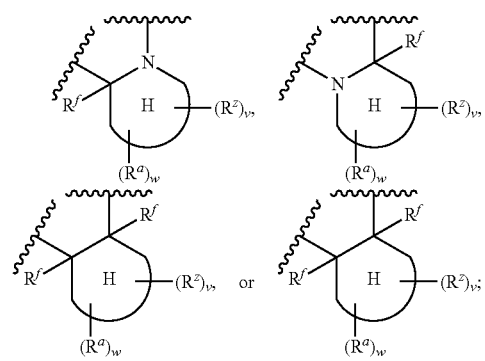

Ih wherein the H ring is a fused, five- to eight-membered cycloalkyl or heterocyclyl ring;

wherein v is an integer from 0 to 4; and wherein w is an integer from 0 to 2; and $Y^6$, $Y^7$, $Y^8$, $Y^9$, and $Y^{10}$, if present, are each a member independently selected from the group consisting of N, CH, and $CR^b$; or, alternatively for $Y^8$ and $Y^9$, the members —$Y^6$=$Y^7$— or —$Y^8$=$Y^9$— are combined into a single member selected from the group consisting of $NR^c$, O, and S.

In some embodiments, Q is $C(R^e)(D)$. In some embodiments, Q is N(E). In some embodiments, Q is F. In some embodiments, Q is G. In some embodiments, the members —$W^3$-Q- or —$W^4$-Q- join to form a member H.

In some embodiments, $W^1$, $W^2$, $W^3$, and $W^4$ comprise from 1 to 4 independently selected $R^f$ groups other than hydrogen. In some embodiments, $W^1$, $W^2$, $W^3$, and $W^4$ comprise from 1 to 4 independently selected $R^f$ alkyl groups.

In some embodiments, $W^1$ and $W^2$ are combined into a single moiety W2 (e.g., to form a pyrrolidine-based five-membered C ring rather than a piperidine- or piperazine-based six-membered C ring).

In some embodiments, C is a member selected from the group consisting of:

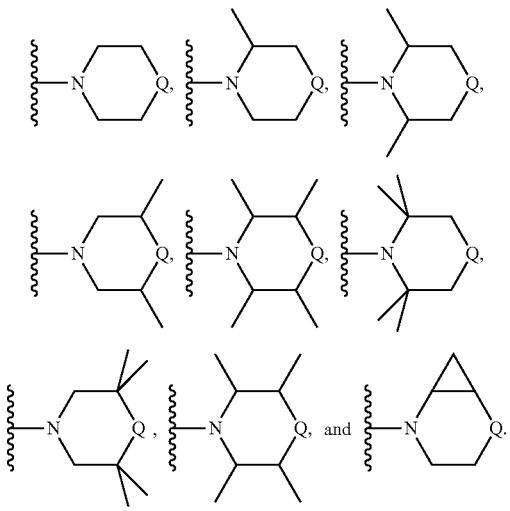

In some embodiments, C is a member selected from the group consisting of:

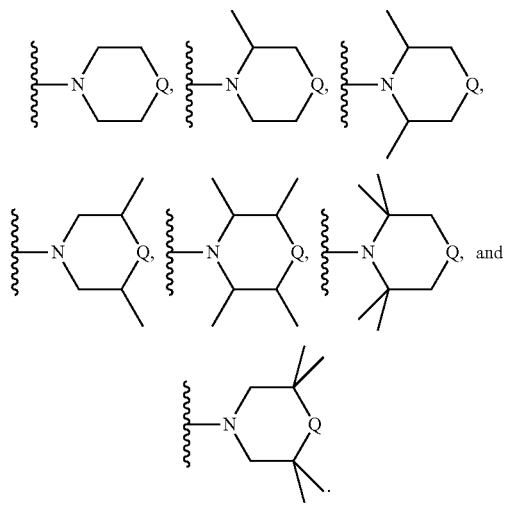

In some embodiments, the pair of W″ is selected from the group consisting of (W¹ and W²) and (W³ and W⁴). In some embodiments, C is a member selected from the group consisting of:

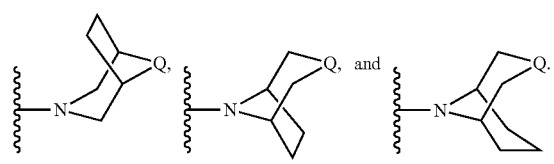

In some embodiments, D is a member selected from the group consisting of:

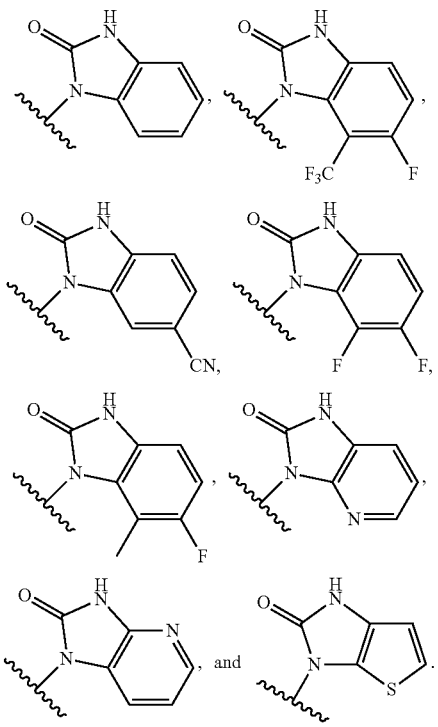

In some embodiments, D is a member selected from the group consisting of:

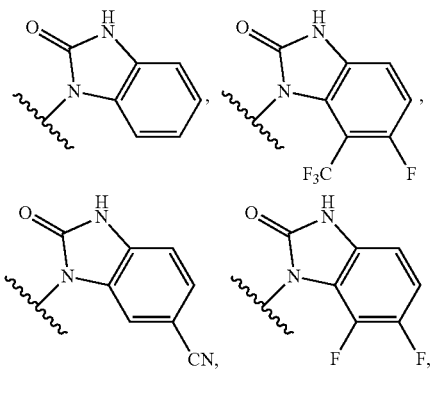

In some embodiments, D is a member selected from the group consisting of:

In some embodiments, D is a member selected from the group consisting of:

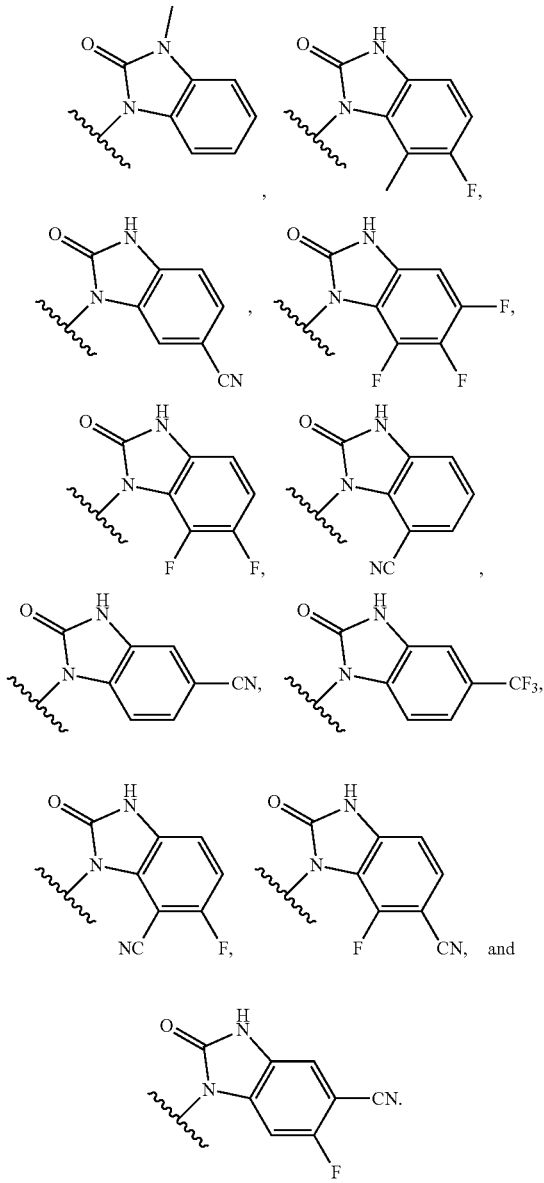

In some embodiments, $L^1$ is C=O. In some embodiments, $L^2$ is C=O. In some embodiments, $L^3$ is C=O.

In some embodiments, the compound is selected from the group consisting of the compounds listed in Table 7. In some embodiments, the compound is selected from the group consisting of the compounds listed in Table 7 as having "A"-level activity. In some embodiments, the compound is selected from compound 49, 55, 77, 99, 175, and 177.

In some embodiments, the compound is selected from the group consisting of 1-(4-fluoro-3,5-dimethylphenyl)-8-{1-[4-fluoro-3-(trifluoromethyl)phenyl]-5-(pyridin-3-yl)-1H-pyrazole-3-carbonyl}-1,3,8-triazaspiro[4.5]decan-4-one; 6,7-difluoro-1-(1-{1-[4-fluoro-3-(trifluoromethyl)phenyl]-5-(pyridin-3-yl)-1H-pyrazole-3-carbonyl}piperidin-4-yl)-2,3-dihydro-1H-1,3-benzodiazol-2-one; 1'-{1-[4-fluoro-3-(trifluoromethyl)phenyl]-5-(pyridin-3-yl)-1H-pyrazole-3-carbonyl}-6-(trifluoromethyl)-1,2-dihydrospiro[3,1-benzoxazine-4,4'-piperidine]-2-one; 1'-{1-[4-fluoro-3-(trifluoromethyl)phenyl]-5-(pyridin-3-yl)-1H-pyrazole-3-carbonyl}-6-(trifluoromethyl)-1,2-dihydrospiro[3,1-benzoxazine-4,4'-piperidine]-2-one; 1'-{1-[4-fluoro-3-(trifluoromethyl)phenyl]-5-(pyridin-3-yl)-1H-pyrazole-3-carbonyl}-6-(trifluoromethyl)-1,2-dihydrospiro[3,1-benzoxazine-4,4'-piperidine]-2-one; 1'-{1-[4-fluoro-3-(trifluoromethyl)phenyl]-5-(pyridin-3-yl)-1H-pyrazole-3-carbonyl}-6-(trifluoromethyl)-1,2-dihydrospiro[3,1-benzoxazine-4,4'-piperidine]-2-one; 2-fluoro-4-{3-[1-(4- fluoro-3,5-dimethylphenyl)-4-oxo-1,3,8-triazaspiro[4.5]decane-8-carbonyl]-5-(pyridin-3-yl)-1H-pyrazol-1-yl}benzonitrile; 8-{1-[4-fluoro-3-(trifluoromethyl)phenyl]-5-(pyridin-3-yl)-1H-pyrazole-3-carbonyl}-1-(4-fluorophenyl)-1,3,8-triazaspiro[4.5]decan-4-one; 3-(1-{1-[4-fluoro-3-(trifluoromethyl)phenyl]-5-(pyridin-3-yl)-1H-pyrazole-3-carbonyl}piperidin-4-yl)-2-oxo-2,3-dihydro-1H-1,3-benzodiazole-5-carbonitrile; 6,7-difluoro-1-(1-{1-[4-iodo-3-(trifluoromethyl)phenyl]-5-(pyridin-3-yl)-1H-pyrazole-3-carbonyl}piperidin-4-yl)-2,3-dihydro-1H-1,3-benzodiazol-2-one; 6,7-difluoro-1-(1-{1-[4-iodo-3-(trifluoromethyl)phenyl]-5-(pyridin-3-yl)-1H-pyrazole-3-carbonyl}piperidin-4-yl)-2,3-dihydro-1H-1,3-benzodiazol-2-one; 8-{1-[4-fluoro-3-(trifluoromethyl)phenyl]-5-(pyridin-3-yl)-1H-pyrazole-3-carbonyl}-3'-(4-fluorophenyl)-8-azaspiro[bicyclo[3.2.1]octane-3,4'-imidazolidine]-5'-one; 6,7-difluoro-1-(1-{1-[4-fluoro-3-(trifluoromethyl)phenyl]-1H,4H,5H-pyrido[2,3-g]indazole-3-carbonyl}piperidin-4-yl)-2,3-dihydro-1H-1,3-benzodiazol-2-one; 5,6,7-trifluoro-1-(1-{1-[4-fluoro-3-(trifluoromethyl)phenyl]-5-(pyridin-3-yl)-1H-pyrazole-3-carbonyl}piperidin-4-yl)-2,3-dihydro-1H-1,3-benzodiazole-2-thione; 6,7-difluoro-1-(1-{1-[4-fluoro-3-methyl-5-(trifluoromethyl)phenyl]-5-(pyridin-3-yl)-1H-pyrazole-3-carbonyl}piperidin-4-yl)-2,3-dihydro-1H-1,3-benzodiazol-2-one; 6-fluoro-2-oxo-1-{1-[5-(pyridin-3-yl)-1-(3,4,5-trifluorophenyl)-1H-pyrazole-3-carbonyl]piperidin-4-yl}-2,3-dihydro-1H-1,3-benzodiazole-5-carbonitrile; 1-{1-[5-(6-chloropyridin-3-yl)-1-[3-fluoro-4-(trifluoromethyl)phenyl]-1H-pyrazole-3-carbonyl]piperidin-4-yl}-6,7-difluoro-2,3-dihydro-1H-1,3-benzodiazol-2-one; 6,7-difluoro-1'-{1-[4-fluoro-3-(trifluoromethyl)phenyl]-5-(pyridin-3-yl)-1H-pyrazole-3-carbonyl}-1,2-dihydrospiro[3,1-benzoxazine-4,4'-piperidine]-2-one; 6,7-difluoro-1-{1-[1-(4-iodophenyl)-5-(pyridin-3-yl)-1H-pyrazole-3-carbonyl]piperidin-4-yl}-2,3-dihydro-1H-1,3-benzodiazol-2-one; 1-(4-fluorophenyl)-8-[1-(4-iodophenyl)-5-(pyridin-3-yl)-1H-pyrazole-3-carbonyl]-1,3,8-triazaspiro[4.5]decan-4-one; 6,7-difluoro-1-(1-{1-[4-fluoro-3-(trifluoromethyl)phenyl]-1H,4H,5H-pyrido[3,2-g]indazole-3-carbonyl}piperidin-4-yl)-2,3-dihydro-1H-1,3-benzodiazol-2-one; 1-{1-[5-(2-chloropyridin-3-yl)-1-[3-fluoro-4-(trifluoromethyl)phenyl]-1H-pyrazole-3-carbonyl]piperidin-4-yl}-6,7-difluoro-2,3-dihydro-1H-1,3-benzodiazol-2-one; 6,7-difluoro-1-{8-[5-(pyridin-3-yl)-1-(3,4,5-trifluorophenyl)-1H-pyrazole-3-carbonyl]-8-azabicyclo[3.2.1]octan-3-yl}-2,3-dihydro-1H-1,3-benzodiazol-2-one; 1-(4-fluorophenyl)-8-{1-[4-iodo-3-(trifluoromethyl)phenyl]-5-(pyridin-3-yl)-1H-pyrazole-3-carbonyl}-1,3,8-triazaspiro[4.5]decan-4-one; 5,6,7-trifluoro-1-(1-{1-[4-fluoro-3-(trifluoromethyl)phenyl]-5-(pyridin-3-yl)-1H-pyrazole-3-carbonyl}piperidin-4-yl)-2,3-dihydro-1H-1,3-benzodiazol-2-one; 8-[5-(6-chloropyridin-3-yl)-1-[3-fluoro-4-(trifluoromethyl)phenyl]-1H-pyrazole-3-carbonyl]-1-(4-fluorophenyl)-1,3,8-triazaspiro[4.5]decan-4-one; 6,7-difluoro-1-(1-{1-[4-fluoro-3-(trifluoromethyl)phenyl]-5-(pyridin-3-yl)-1H-pyrazole-3-carbonyl}piperidin-4-yl)-2,3-dihydro-1H-1,3-benzodiazole-2-thione; 1-(1-{1-[3,4-bis(trifluoromethyl)phenyl]-5-(pyridin-3-yl)-1H-pyrazole-3-carbonyl}piperidin-4-yl)-6,7-difluoro-2,3-dihydro-1H-1,3-benzodiazol-2-one; 1-{1-[4-bromo-5-(pyridin-3-yl)-1-(3,4,5-trifluorophenyl)-1H-pyrazole-3-carbonyl]piperidin-4-yl}-6,7-difluoro-2,3-dihydro-1H-1,3-benzodiazol-2-one; (8aS)-7-{1-[3-fluoro-4-(trifluoromethyl)phenyl]-5-(pyridin-3-yl)-1H-pyrazole-3-carbonyl}-hexahydro-1H-[1,3]oxazolo[3,4-a]piperazin-3-one; 2-fluoro-5-{3-[1-(4-fluoro-3,5-dimethylphenyl)-4-oxo-1,3,8-triazaspiro[4.5]decane-8-carbonyl]-5-(pyridin-3-yl)-1H-pyrazol-1-yl}benzonitrile; 5,6-difluoro-1'-{1-[4-fluoro-3-(trifluoromethyl)phenyl]-5-(pyridin-3-yl)-1H-pyrazole-3-carbonyl}-1,2-dihydrospiro[3,1-benzoxazine-4,4'-piperidine]-2-one; 8-{1-[4-fluoro-3-(trifluoromethyl)phenyl]-5-(pyrazin-2-yl)-1H-pyrazole-3-carbonyl}-1-(4-fluorophenyl)-1,3,8-triazaspiro[4.5]decan-4-one; 6,7-difluoro-1-(1-{1-[4-fluoro-3-(trifluoromethyl)phenyl]-5-(pyrazin-2-yl)-1H-pyrazole-3-carbonyl}piperidin-4-yl)-2,3-dihydro-1H-1,3-benzodiazol-2-one; 8-{1-[4-fluoro-3-(trifluoromethyl)phenyl]-1H,4H,5H-pyrido[2,3-g]indazole-3-carbonyl}-1-(4-fluorophenyl)-1,3,8-triazaspiro[4.5]decan-4-one; 1-(3,5-dichloro-4-fluorophenyl)-8-{1-[4-fluoro-3-(trifluoromethyl)phenyl]-5-(pyridin-3-yl)-1H-pyrazole-3-carbonyl}-1,3,8-triazaspiro[4.5]decan-4-one; 8-{1-[3-fluoro-4-(trifluoromethyl)phenyl]-5-(pyridin-3-yl)-1H-pyrazole-3-carbonyl}-3'-(4-fluorophenyl)-8-azaspiro[bicyclo[3.2.1]octane-3,4'-imidazolidine]-5'-one; 6-fluoro-1-(1-{1-[3-fluoro-4-(trifluoromethyl)phenyl]-5-(pyridin-3-yl)-1H-pyrazole-3-carbonyl}piperidin-4-yl)-7-(trifluoromethyl)-2,3-dihydro-1H-1,3-benzodiazol-2-one; 8-{1-[4-chloro-3-(trifluoromethyl)phenyl]-5-(pyridin-3-yl)-1H-pyrazole-3-carbonyl}-1-(4-fluorophenyl)-1,3,8-triazaspiro[4.5]decan-4-one; 5-{3-[4-(6,7-difluoro-2-oxo-2,3-dihydro-1H-1,3-benzodiazol-1-yl)piperidine-1-carbonyl]-5-(pyridin-3-yl)-1H-pyrazol-1-yl}-2-fluorobenzonitrile; 4-{3-[1-(3,4-difluorophenyl)-4-oxo-1,3,8-triazaspiro[4.5]decane-8-carbonyl]-5-(pyridin-3-yl)-1H-pyrazol-1-yl}-2-fluorobenzonitrile; 1-(4-fluoro-3,5-dimethylphenyl)-8-{1-[3-fluoro-4-(trifluoromethyl)phenyl]-5-(pyridin-3-yl)-1H-pyrazole-3-carbonyl}-1,3,8-triazaspiro[4.5]decan-4-one; 4-{3-[4-(6,7-difluoro-2-oxo-2,3-dihydro-1H-1,3-benzodiazol-1-yl)piperidine-1-carbonyl]-5-(pyridin-3-yl)-1H-pyrazol-1-yl}-2-(trifluoromethyl)benzonitrile; 5-fluoro-3-(1-{1-[3-fluoro-4-(trifluoromethyl)phenyl]-5-(pyridin-3-yl)-1H-pyrazole-3-carbonyl}piperidin-4-yl)-2-oxo-2,3-dihydro-1H-1,3-benzodiazole-4-carbonitrile; 6,7-difluoro-1-(1-{1-[2-methyl-4-(trifluoromethoxy)phenyl]-5-(pyridin-3-yl)-1H-pyrazole-3-carbonyl}piperidin-4-yl)-2,3-dihydro-1H-1,3-benzodiazol-2-one; 1-(1-{1-[2,5-difluoro-4-(trifluoromethyl)phenyl]-5-(pyridin-3-yl)-1H-pyrazole-3-carbonyl}piperidin-4-yl)-6,7-difluoro-2,3-dihydro-1H-1,3-benzodiazol-2-one; 1-(1-{1-[3-fluoro-4-(trifluoromethyl)phenyl]-5-(pyridin-3-yl)-1H-pyrazole-3-carbonyl}piperidin-4-yl)-2-oxo-2,3-dihydro-1H-1,3-benzodiazole-5-carbonitrile; 1-(1-{1-[4-chloro-3-(trifluoromethyl)phenyl]-5-(pyridin-3-yl)-1H-pyrazole-3-carbonyl}piperidin-4-yl)-6,7-difluoro-2,3-dihydro-1H-1,3-benzodiazol-2-one; 6-fluoro-1-(1-{1-[3-fluoro-4-(trifluoromethyl)phenyl]-5-(pyridin-3-yl)-1H-pyrazole-3-carbonyl}piperidin-4-yl)-2-oxo-2,3-dihydro-1H-1,3-benzodiazole-5-carbonitrile; 1-(4-fluoro-3,5-dimethylphenyl)-8-[5-(pyridin-3-yl)-1-(3,4,5-trifluorophenyl)-1H-pyrazole-3-carbonyl]-1,3,8-triazaspiro[4.5]decan-4-one; 6-fluoro-1'-{1-[3-fluoro-4-(trifluoromethyl)phenyl]-5-(pyridin-3-yl)-1H-pyrazole-3-carbonyl}-1,2-dihydrospiro[3,1-benzoxazine-4,4'-piperidine]-2-one; 4-{3-[4-(6,7-difluoro-2-oxo-2,3-dihydro-1H-1,3-benzodiazol-1-yl)piperidine-1-carbonyl]-5-(pyridin-3-yl)-1H-pyrazol-1-yl}-2-fluorobenzonitrile; 6,7-difluoro-1-(1-{1-[3-fluoro-4-(trifluoromethyl)phenyl]-5-(4-methylpyridin-3-yl)-1H-pyrazole-3-carbonyl}piperidin-4-yl)-2,3-dihydro-1H-1,3-benzodiazol-2-one; 5-fluoro-2-oxo-3-{1-[5-(pyridin-3-yl)-1-(3,4,5-trifluorophenyl)-1H-pyrazole-3-carbonyl]piperidin-4-yl}-2,3-dihydro-1H-1,3-benzodiazole-4-carbonitrile; 1-(1-{1-[2,3-difluoro-4-(trifluoromethyl)phenyl]-5-(pyridin-3-yl)-1H-pyrazole-3-carbonyl}piperidin-4-yl)-6,7-difluoro-2,3-dihydro-1H-1,3- benzodiazol-2-one; 2-fluoro-4-(3-{[3'-(4-fluorophenyl)-5'-oxo-8-azaspiro[bicyclo[3.2.1]octane-3,4'-imidazolidine]-8-yl]carbonyl}-5-(pyridin-3-yl)-1H-pyrazol-1-yl)benzonitrile; 8-{1-[4-fluoro-3-(trifluoromethyl)phenyl]-1H,4H,5H-pyrido[3,2-g]indazole-3-carbonyl}-1-(4-fluorophenyl)-1,3,8-triazaspiro[4.5]decan-4-one; 6-fluoro-1'-{1-[4-fluoro-3-(trifluoromethyl)phenyl]-5-(pyridin-3-yl)-1H-pyrazole-3-carbonyl}-1,2-dihydrospiro[3,1-benzoxazine-4,4'-piperidine]-2-one; 6,7-difluoro-1-(1-{1-[3-fluoro-4-(trifluoromethyl)phenyl]-5-(5-fluoropyridin-3-yl)-1H-pyrazole-3-carbonyl}piperidin-4-yl)-2,3-dihydro-1H-1,3-benzodiazol-2-one; 6,7-difluoro-1-(8-{1-[4-fluoro-3-(trifluoromethyl)phenyl]-5-(pyridin-3-yl)-1H-pyrazole-3-carbonyl}-8-azabicyclo[3.2.1]octan-3-yl)-2,3-dihydro-1H-1,3-benzodiazol-2-one; 6,7-difluoro-1-(1-{1-[3-fluoro-4-(trifluoromethyl)phenyl]-5-(pyridazin-4-yl)-1H-pyrazole-3-carbonyl}piperidin-4-yl)-2,3-dihydro-1H-1,3-benzodiazol-2-one; 6-chloro-1'-{1-[4-fluoro-3-(trifluoromethyl)phenyl]-5-(pyridin-3-yl)-1H-pyrazole-3-carbonyl}-1,2-dihydrospiro[3,1-benzoxazine-4,4'-piperidine]-2-one; 6,7-difluoro-1-{1-[5-(pyridazin-4-yl)-1-(3,4,5-trifluorophenyl)-1H-pyrazole-3-carbonyl]piperidin-4-yl}-2,3-dihydro-1H-1,3-benzodiazol-2-one; 6,7-difluoro-1-(1-{1-[4-fluoro-3-(trifluoromethyl)phenyl]-5-(pyridin-3-yl)-1H-pyrazole-3-carbonyl}-2-methylpiperidin-4-yl)-2,3-dihydro-1H-1,3-benzodiazol-2-one; 7-fluoro-1'-{1-[4-fluoro-3-(trifluoromethyl)phenyl]-5-(pyridin-3-yl)-1H-pyrazole-3-carbonyl}-1,2-dihydrospiro[3,1-benzoxazine-4,4'-piperidine]-2-one; 1-(1-{1-[2,4-difluoro-3-(trifluoromethyl)phenyl]-5-(pyridin-3-yl)-1H-pyrazole-3-carbonyl}piperidin-4-yl)-6,7-difluoro-2,3-dihydro-1H-1,3-benzodiazol-2-one; 8-{1-[2,4-difluoro-3-(trifluoromethyl)phenyl]-5-(pyridin-3-yl)-1H-pyrazole-3-carbonyl}-1-(4-fluorophenyl)-1,3,8-triazaspiro[4.5]decan-4-one; 1-{1-[5-(1-benzyl-1H-imidazol-4-yl)-1-[4-fluoro-3-(trifluoromethyl)phenyl]-1H-pyrazole-3-carbonyl]piperidin-4-yl}-6,7-difluoro-2,3-dihydro-1H-1,3-benzodiazol-2-one; and 8-[5-(1-benzyl-1H-imidazol-4-yl)-1-[4-fluoro-3-(trifluoromethyl)phenyl]-1H-pyrazole-3-carbonyl]-1-(4-fluorophenyl)-1,3,8-triazaspiro[4.5]decan-4-one.

In some embodiments, $Z^1$, $Z^2$, $Z^3$, $Z^4$, and $Z^5$ are each a member selected from the group consisting of N, CH, and $CR^a$.

In some embodiments, $Z^1$ and X, together with atoms in the rings to which they are attached, form an additional fused, five- to eight-membered cycloalkyl or heterocyclyl ring with from 0 to 4 $R^z$ substituents.

In some embodiments, $Z^2$ is N. In some preferred embodiments, $Z^3$ or $Z^4$ is N. In some embodiments, $Z^3$ is N. In some embodiments, $Z^4$ is N.

In some embodiments, A is a member selected from the group consisting of:

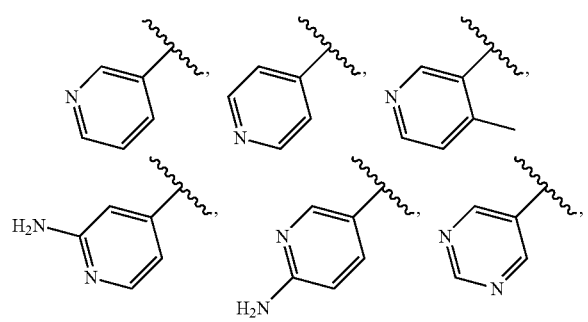

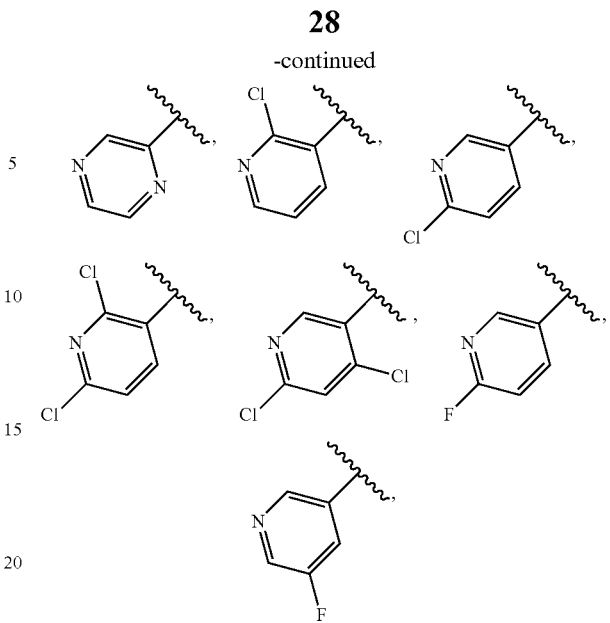

and salts thereof.

In some embodiments, A is a member selected from the group consisting of:

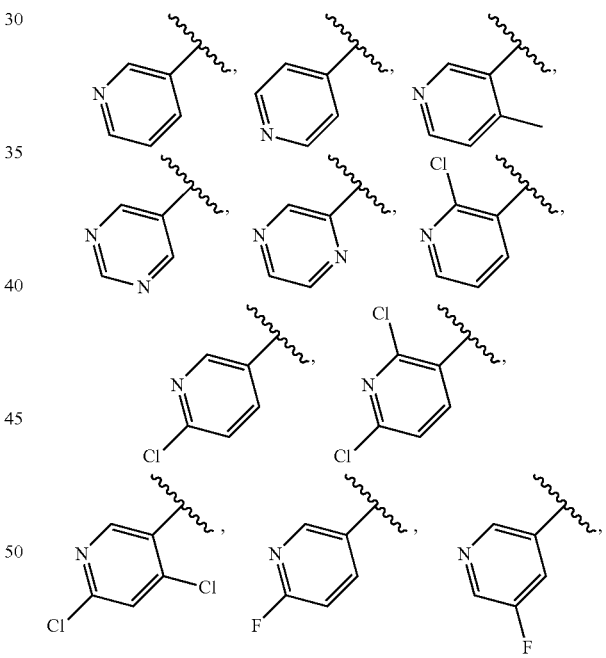

and salts thereof.

In some embodiments, A is a member selected from the group consisting of:

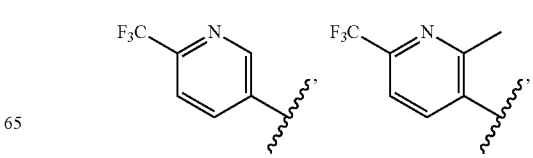

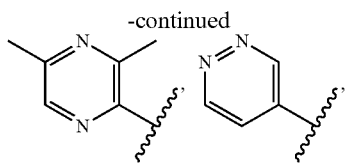

and salts thereof.

In some embodiments, A is a member selected from the group consisting of:

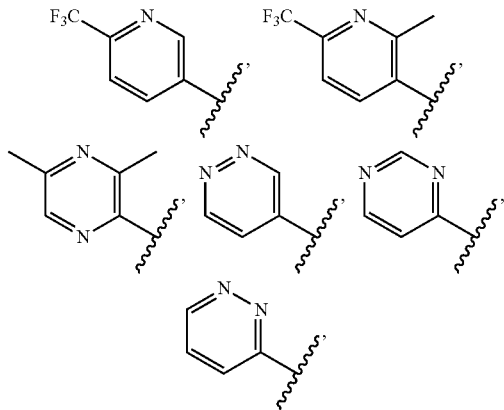

and salts thereof.

In some embodiments, $Y^1$, $Y^2$, $Y^3$, $Y^4$, and $Y^5$ are each a member independently selected from the group consisting of N, CH, and $CR^b$.

In some embodiments, $Y^1$ is N. In some embodiments, $Y^1$ is CH.

In some embodiments, $Y^1$ is $CR^b$. In some embodiments, the $Y^1$ $R^b$ is a member selected from the group consisting of chloro, cyano, fluoro, methyl, trifluoromethyl, and trifluoromethoxy.

In some embodiments, $Y^2$ is N. In some embodiments, $Y^2$ is CH.

In some embodiments, $Y^2$ is $CR^b$. In some embodiments, the $Y^2$ $R^b$ is a member selected from the group consisting of chloro, cyano, fluoro, methyl, trifluoromethyl, and trifluoromethoxy.

In some embodiments, $Y^3$ is N. In some embodiments, $Y^3$ is CH.

In some embodiments, $Y^3$ is $CR^b$. In some embodiments, the $Y^3$ $R^b$ is a member selected from the group consisting of chloro, cyano, fluoro, methyl, trifluoromethyl, and trifluoromethoxy.

In some embodiments, $Y^4$ is N. In some embodiments, $Y^4$ is CH.

In some embodiments, $Y^4$ is $CR^b$. In some embodiments, the $Y^4$ $R^b$ is a member selected from the group consisting of chloro, cyano, fluoro, methyl, trifluoromethyl, and trifluoromethoxy.

In some embodiments, $Y^5$ is N. In some embodiments, $Y^5$ is CH.

In some embodiments, $Y^5$ is $CR^b$. In some embodiments, the $Y^5$ $R^b$ is a member selected from the group consisting of chloro, cyano, fluoro, methyl, trifluoromethyl, and trifluoromethoxy.

In some embodiments, B is a member selected from the group consisting of:

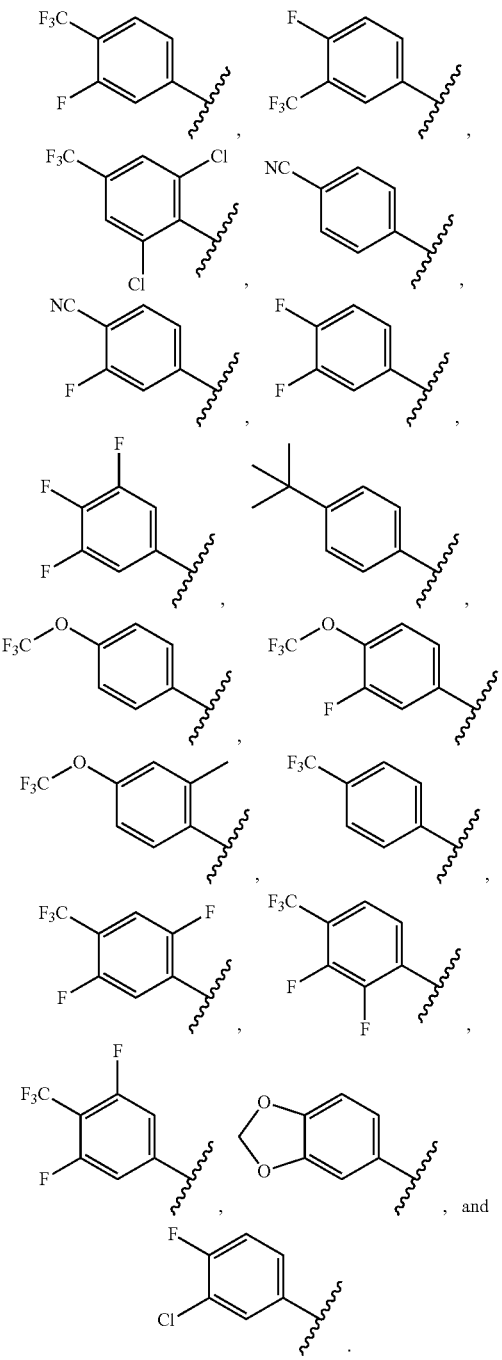

and

In some embodiments, B is a member selected from the group consisting of:

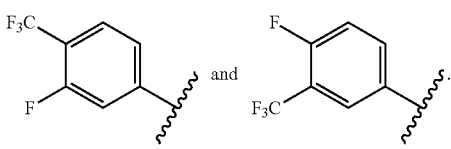 [SMILES: *c1ccc(C(F)(F)F)c(F)c1 ; *c1ccc(F)c(C(F)(F)F)c1]

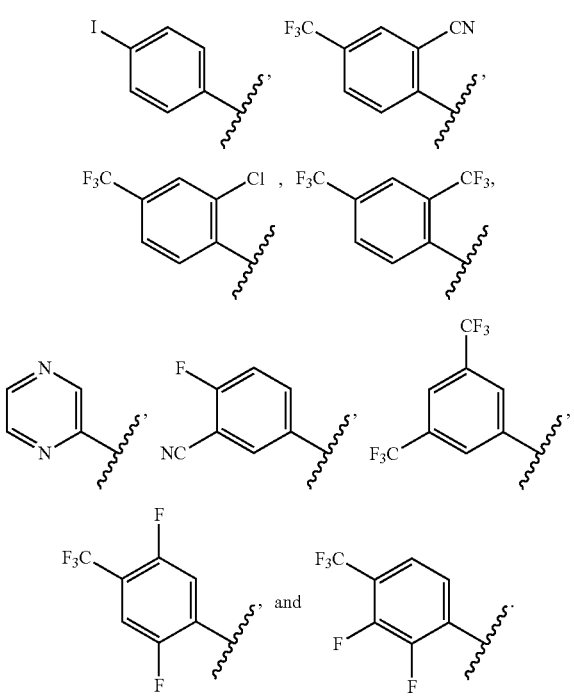

In some embodiments, B is a member selected from the group consisting of:

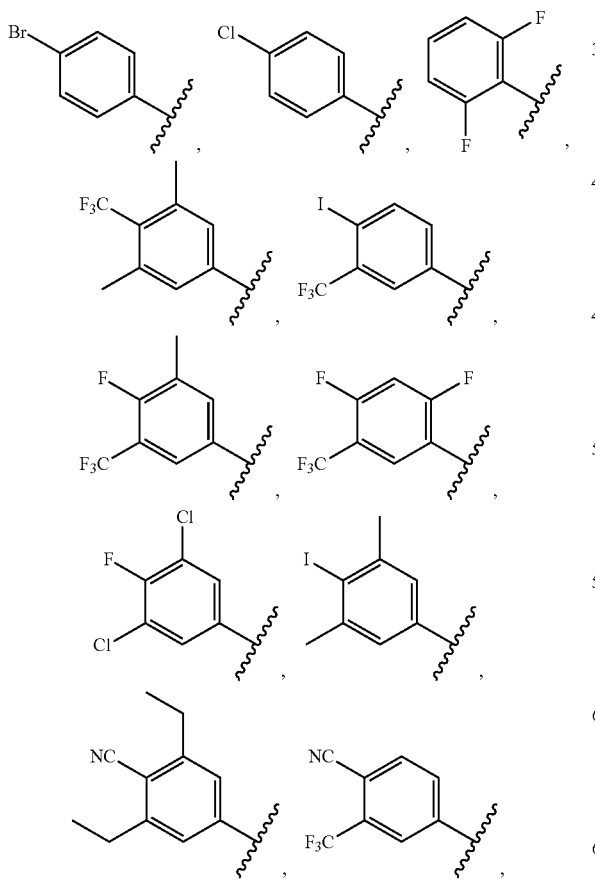

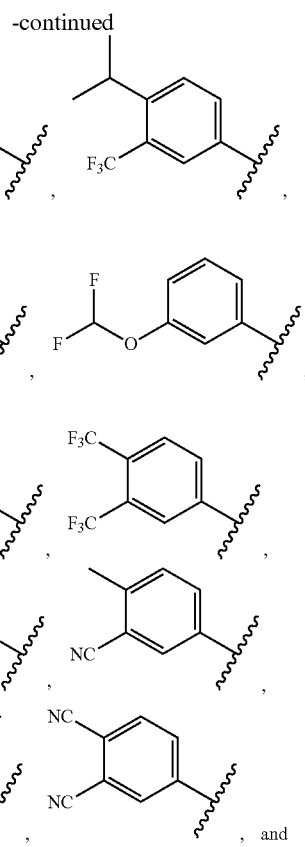

In some embodiments, each $R^a$ and $R^b$ is a member independently selected from the group consisting of cyano, $C_1$-$C_4$ alkyl, $C_1$-$C_4$ alkoxy, $C_1$-$C_4$ haloalkyl, $C_1$-$C_4$ haloalkoxy, halo, $C_0$-$C_6$ amino, $C_1$-$C_6$ amido, and hydroxyl. In some embodiments, each $R^a$ and $R^b$ is a member independently selected from the group consisting of cyano, $C_1$-$C_4$ alkyl, $C_1$-$C_4$ alkoxy, $C_1$-$C_4$ haloalkyl, $C_1$-$C_4$ haloalkoxy, and halo.

In some embodiments, u is an integer independently selected from 0 to 3 (e.g., 0, 1, 2, or 3). In some embodiments, u is an integer independently selected from 0 to 4 (e.g., 0, 1, 2, 3, or 4). In some embodiments, u is an integer independently selected from 0 to 5 (e.g., 0, 1, 2, 3, 4, or 5).

In some embodiments, v is an integer independently selected from 0 to 3 (e.g., 0, 1, 2, or 3). In some embodiments, v is an integer independently selected from 0 to 4 (e.g., 0, 1, 2, 3, or 4). In some embodiments, v is an integer independently selected from 0 to 5 (e.g., 0, 1, 2, 3, 4, or 5).

In some embodiments, X is N.

In some embodiments, each $R^c$ is independently selected from the group consisting of hydrogen, cyano, $C_1$-$C_3$ alkyl, trifluoromethyl, cycloalkyl, trifluoromethoxy, and $C_1$-$C_3$ alkoxy. In some embodiments, each $R^c$ is independently selected from the group consisting of hydrogen, cyano, $C_1$-$C_3$ alkyl, trifluoromethyl, cyclopropyl, trifluoromethoxy, and $C_1$-$C_3$ alkoxy. In some embodiments, each $R^c$ is independently selected from the group consisting of hydrogen, methyl, bromo, chloro, trifluoromethyl, ethyl, isopropyl, isobutyl, cyclopropyl, cyclobutyl, and cyclopropylmethyl.

In some embodiments, $Y^6$ is N. In some embodiments, $Y^6$ is CH.

In some embodiments, $Y^6$ is $CR^b$. In some embodiments, the $Y^6$ $R^b$ is a member selected from the group consisting of chloro, cyano, fluoro, methyl, trifluoromethyl, and trifluoromethoxy. In some embodiments, the $Y^6$ $R^b$ is a member selected from the group consisting of chloro, cyano, fluoro, methyl, trifluoromethyl, trifluoromethoxy, —C(O)N(H)Me, —NMe$_2$, and —SO$_2$Me.

In some embodiments, $Y^7$ is N. In some embodiments, $Y^7$ is CH.

In some embodiments, $Y^7$ is $CR^b$. In some embodiments, the $Y^7$ $R^b$ is a member selected from the group consisting of chloro, cyano, fluoro, methyl, trifluoromethyl, and trifluoromethoxy. In some embodiments, the $Y^7$ $R^b$ is a member selected from the group consisting of chloro, cyano, fluoro, methyl, trifluoromethyl, trifluoromethoxy, —C(O)N(H)Me, —NMe$_2$, and —SO$_2$Me.

In some embodiments, $Y^8$ is N. In some embodiments, $Y^8$ is CH.

In some embodiments, $Y^8$ is $CR^b$. In some embodiments, the $Y^8$ $R^b$ is a member selected from the group consisting of chloro, cyano, fluoro, methyl, trifluoromethyl, and trifluoromethoxy. In some embodiments, the $Y^8$ $R^b$ is a member selected from the group consisting of chloro, cyano, fluoro, methyl, trifluoromethyl, trifluoromethoxy, —C(O)N(H)Me, —NMe$_2$, and —SO$_2$Me.

In some embodiments, $Y^9$ is N. In some embodiments, $Y^9$ is CH.

In some embodiments, $Y^9$ is $CR^b$. In some embodiments, the $Y^9$ $R^b$ is a member selected from the group consisting of chloro, cyano, fluoro, methyl, trifluoromethyl, and trifluoromethoxy. In some embodiments, the $Y^9$ $R^b$ is a member selected from the group consisting of chloro, cyano, fluoro, methyl, trifluoromethyl, trifluoromethoxy, —C(O)N(H)Me, —NMe$_2$, and —SO$_2$Me.

In some embodiments, $Y^{10}$ is N. In some embodiments, $Y^{10}$ is CH.

In some embodiments, $Y^{10}$ is $CR^b$. In some embodiments, the $Y^{10}$ $R^b$ is a member selected from the group consisting of chloro, cyano, fluoro, methyl, trifluoromethyl, and trifluoromethoxy. In some embodiments, the $Y^{10}$ $R^b$ is a member selected from the group consisting of chloro, cyano, fluoro, methyl, trifluoromethyl, trifluoromethoxy, —C(O)N(H)Me, —NMe$_2$, and —SO$_2$Me.

In aspects or embodiments directed to Markush groups, in some further embodiments, the present invention is directed only to a single member of the Markush group.

In some embodiments,

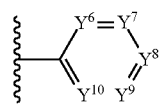

is a member selected from the group consisting of:

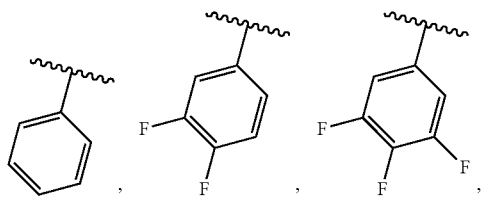

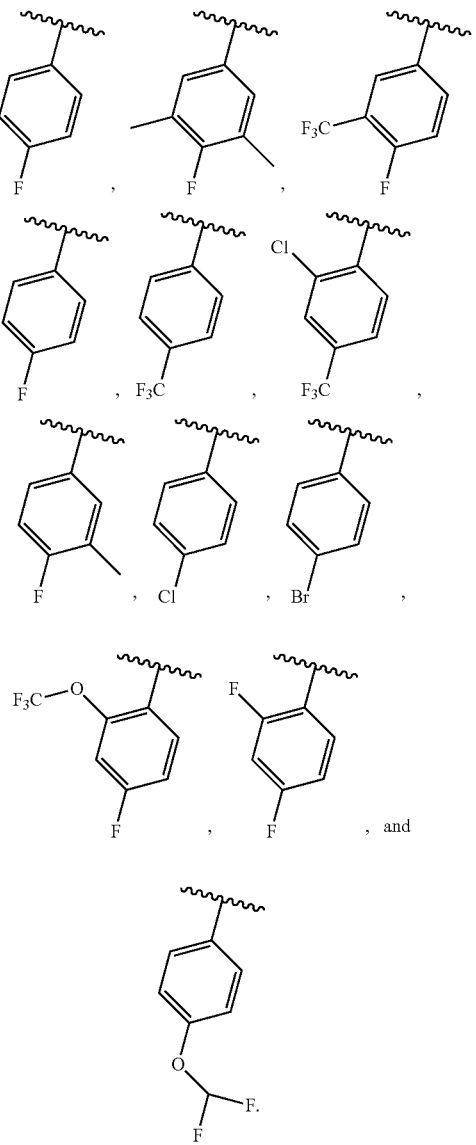

In some embodiments,

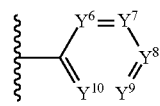

is a member selected from the group consisting of:

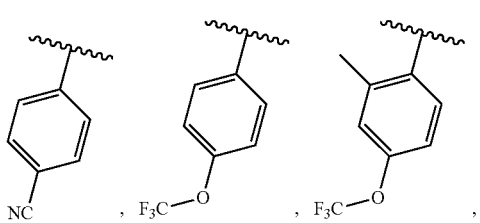

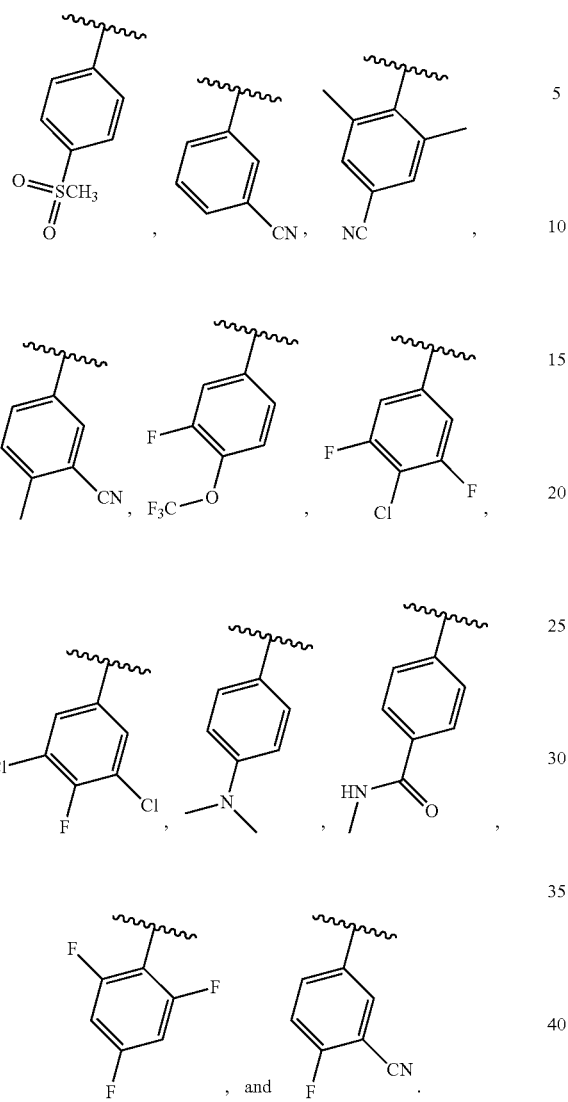
In aspects or embodiments directed to Markush groups, in some further embodiments, the present invention is directed only to a single member of the Markush group.
In some embodiments, the compound is selected from the group consisting of:
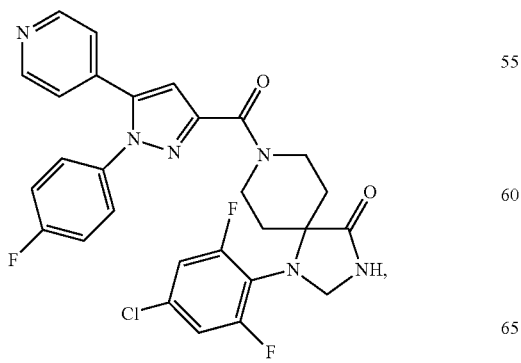
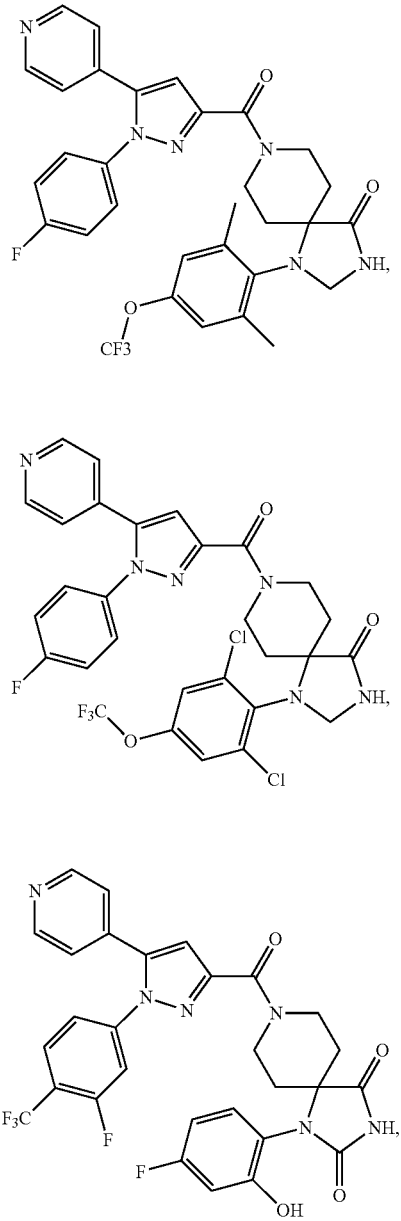
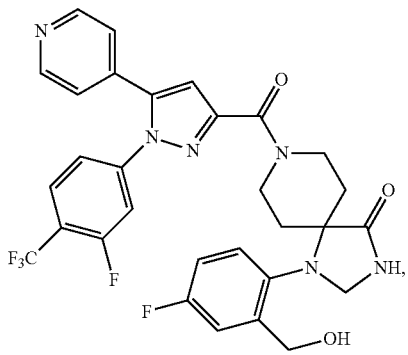

-continued
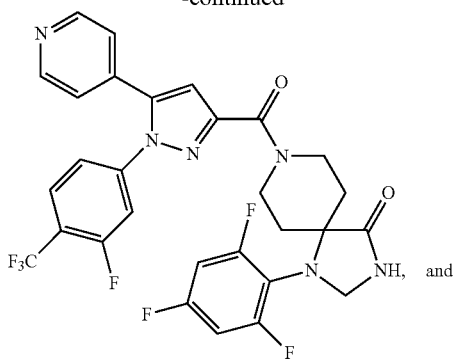
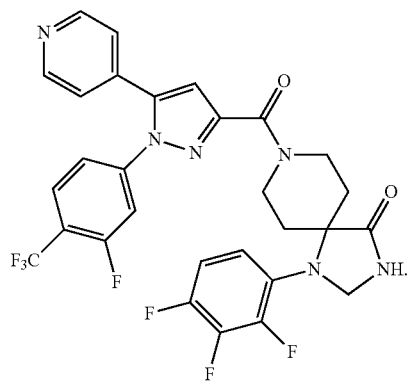
In some embodiments, the compound is selected from the group consisting of:
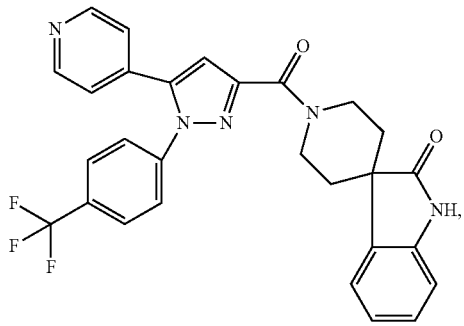
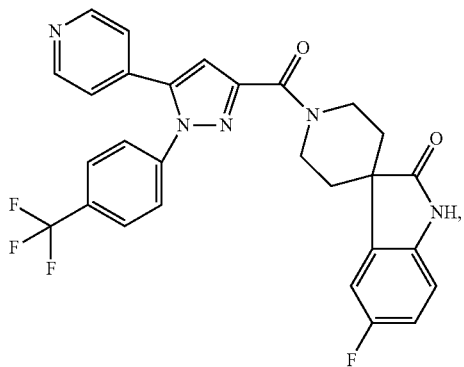
-continued
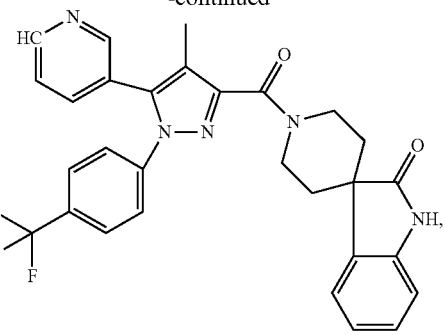
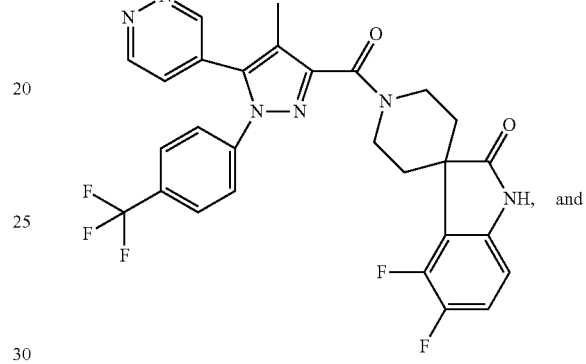
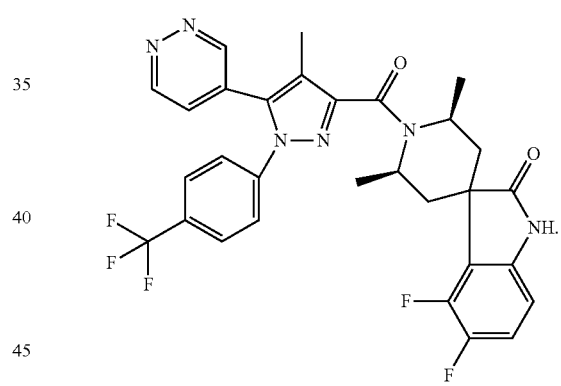
In some embodiments, the compound is selected from the group consisting of:
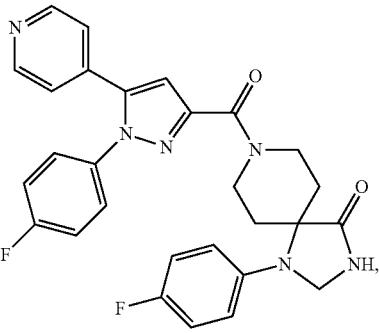

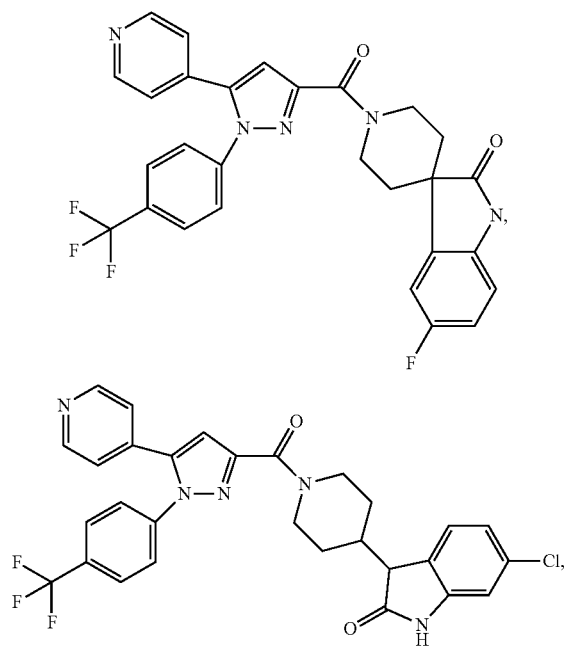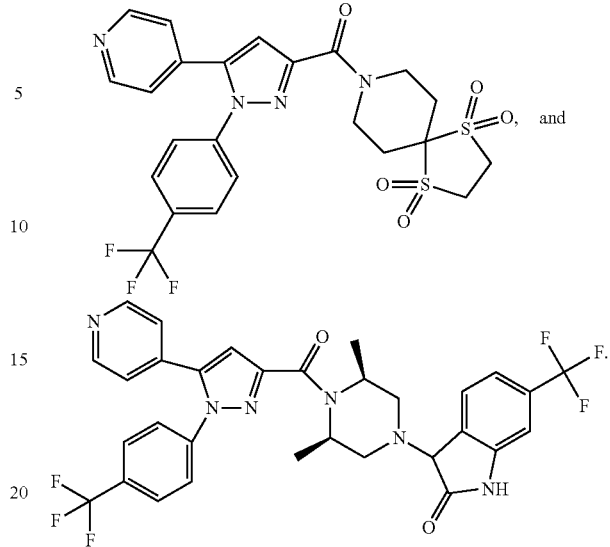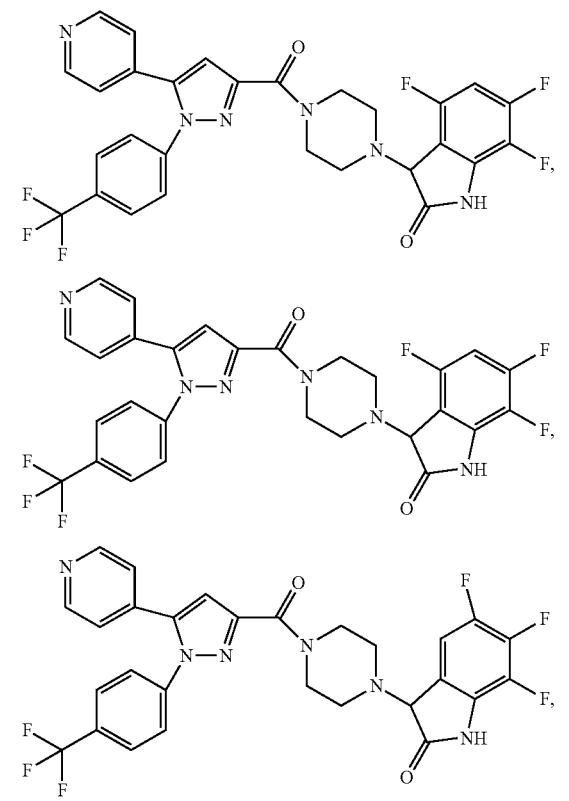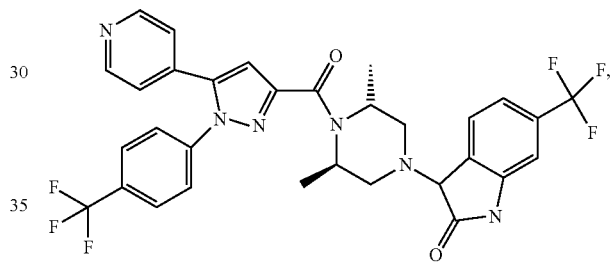
In some embodiments, the compound is selected from the group consisting of:
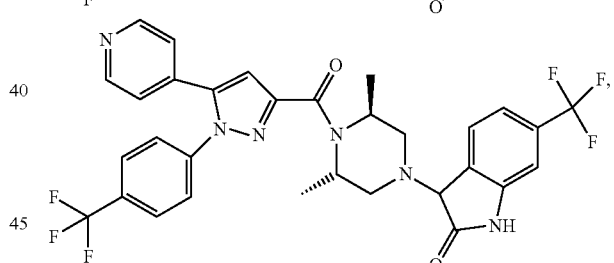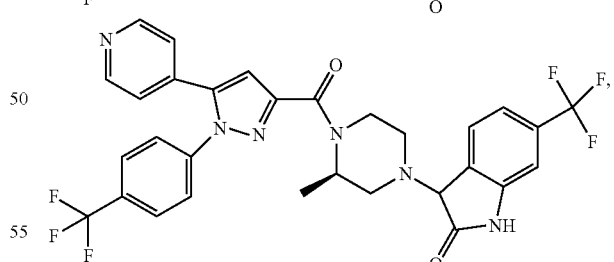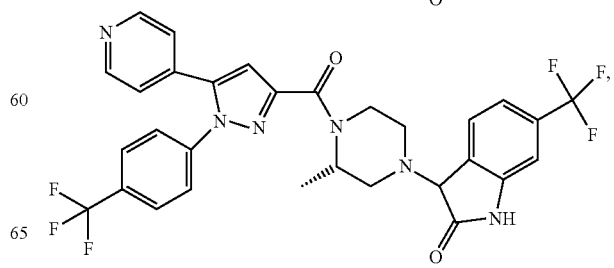

41
-continued
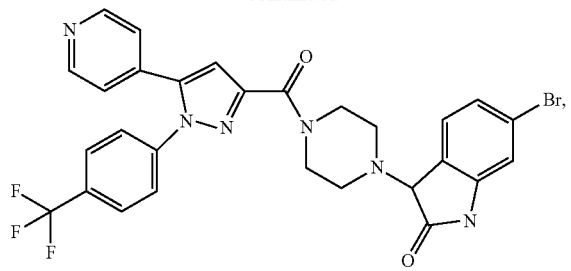
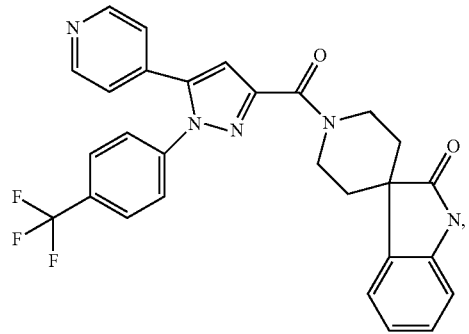
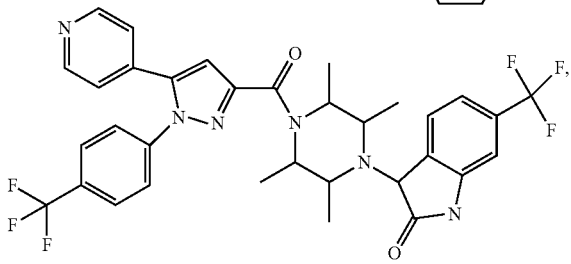
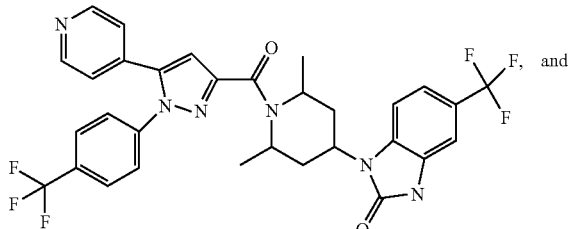
In some embodiments, the compound is selected from the group consisting of:
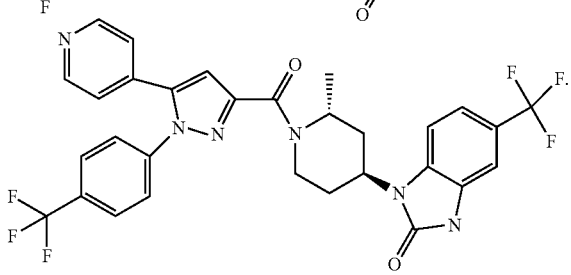
42
-continued
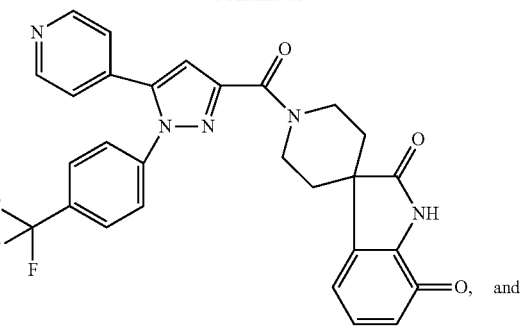
In some embodiments, the compound is selected from the group consisting of:
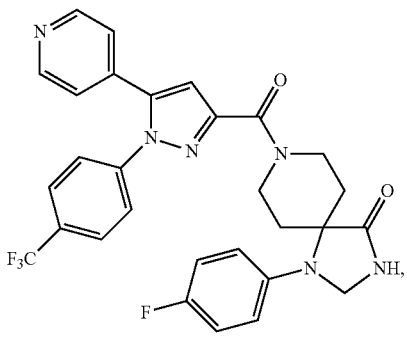
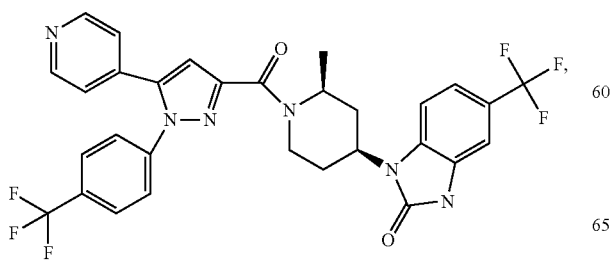
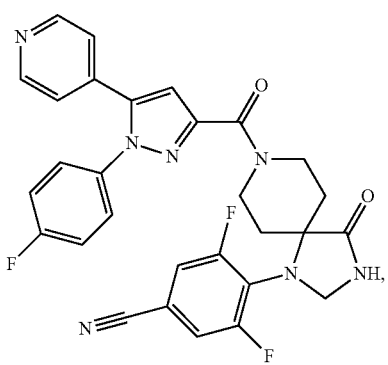

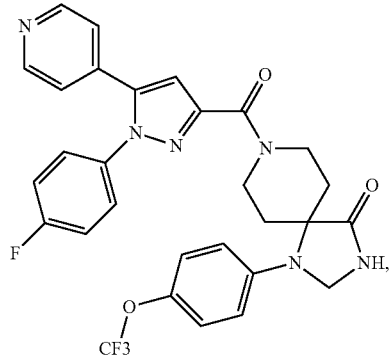
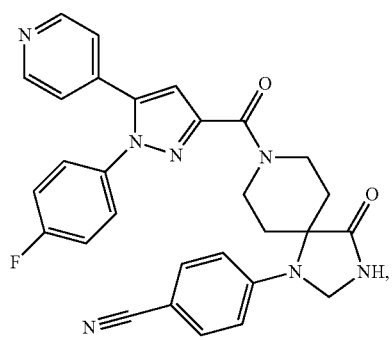
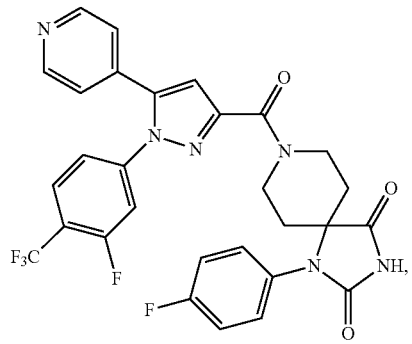
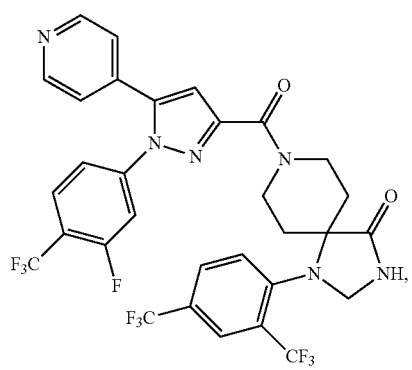
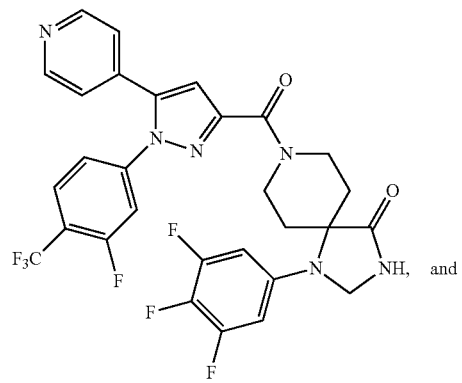
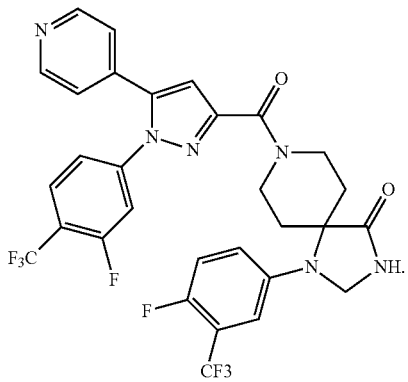
In some embodiments, the compound is selected from the group consisting of:
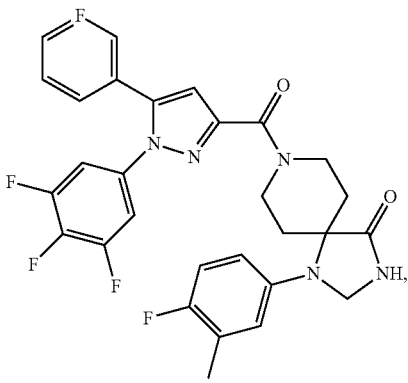 [SMILES: Cc1cc(N2CNC(=O)C23CCN(C(=O)c2cc(-c4cccnc4)n(-c4cc(F)c(F)c(F)c4)n2)CC3)cc(C)c1F]
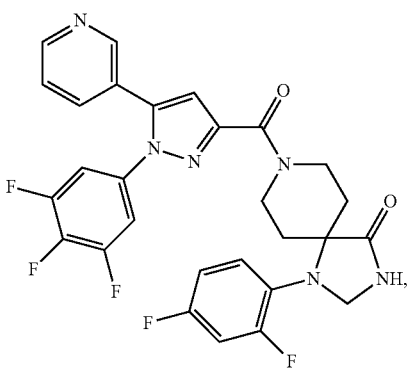

-continued
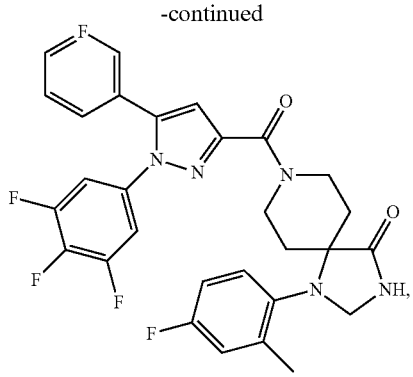
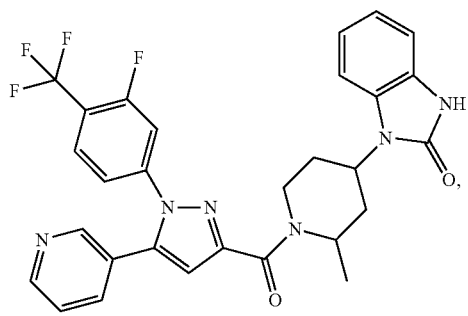
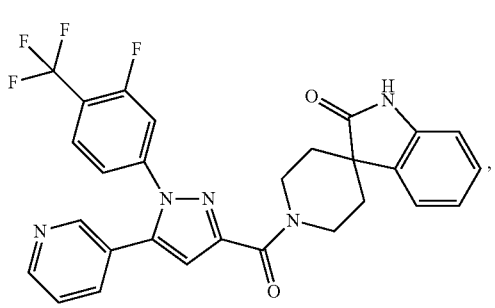
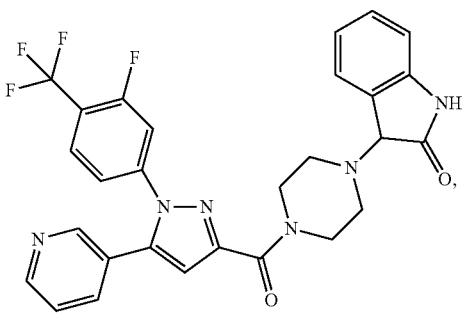
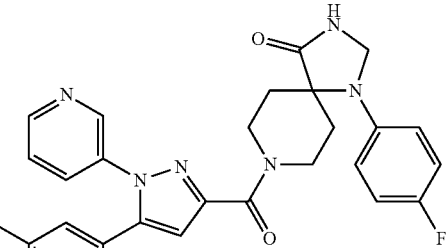
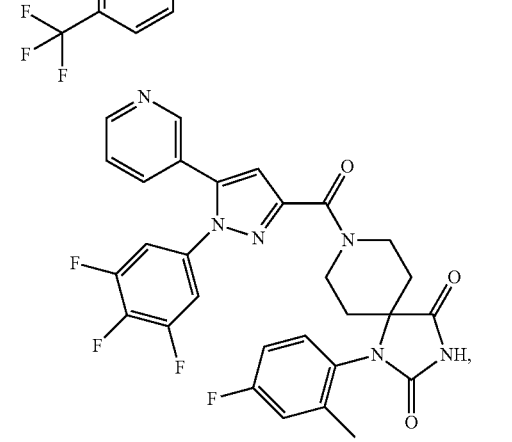
In some embodiments, the compound is selected from the group consisting of:

47
-continued
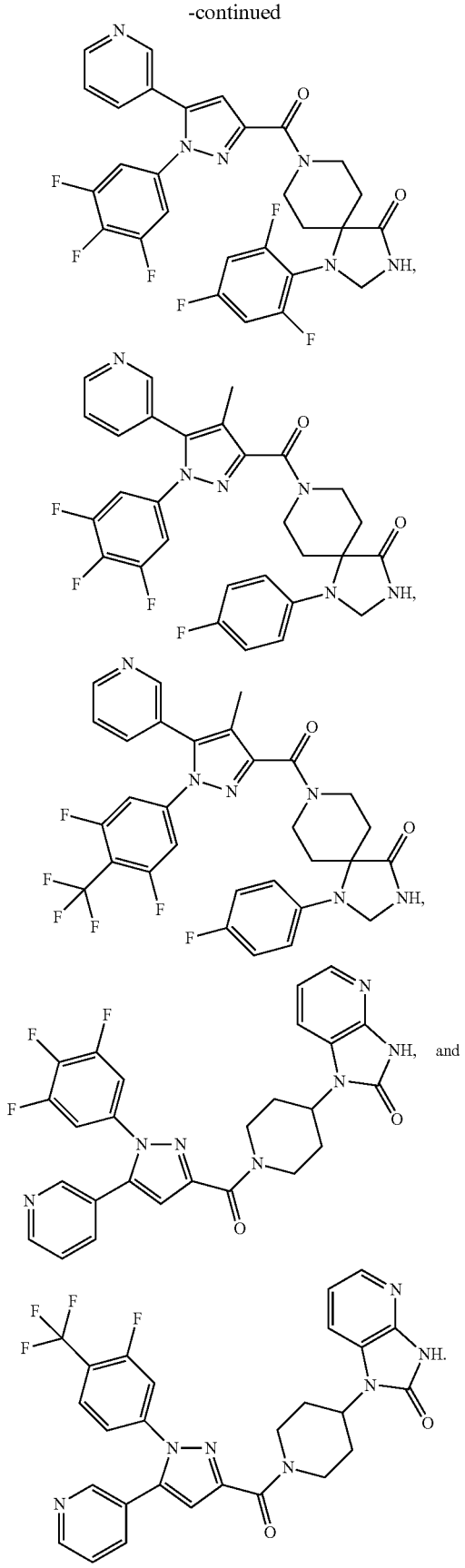
48
In some embodiments, the compound is selected from the group consisting of:
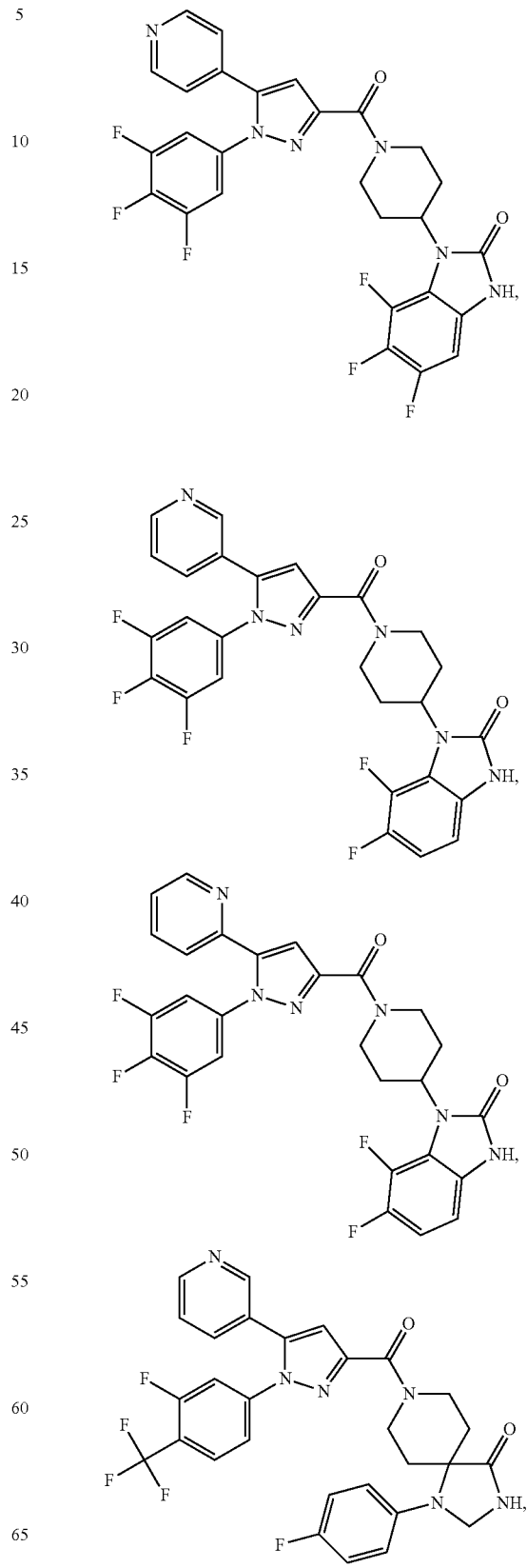

-continued
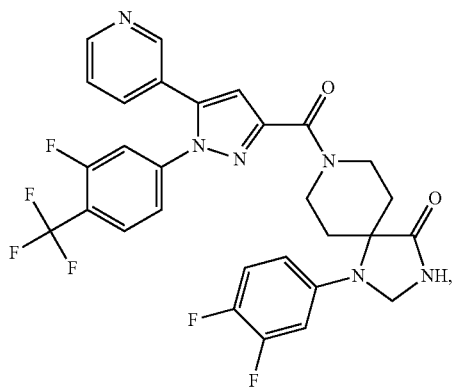
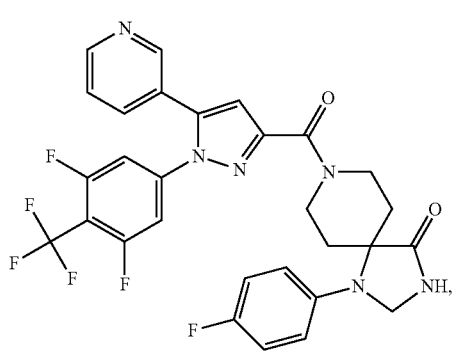
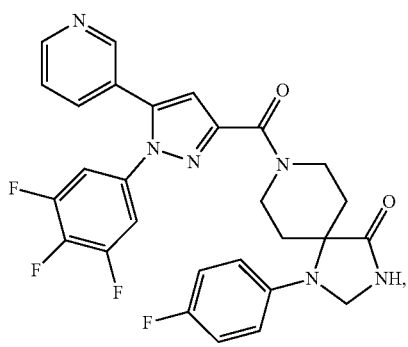
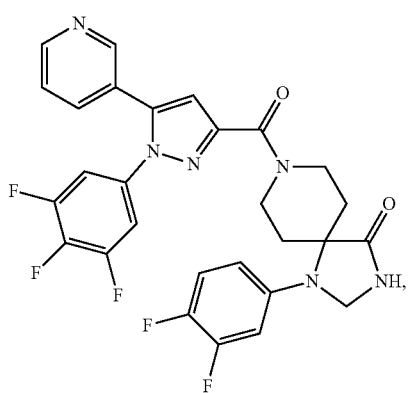
-continued
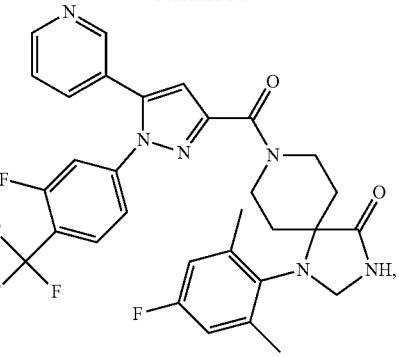
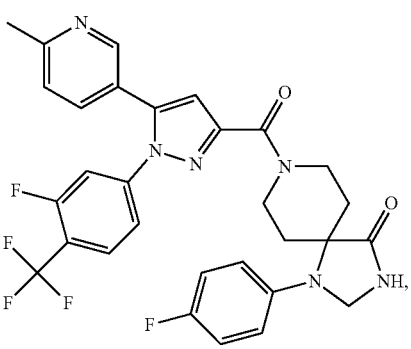
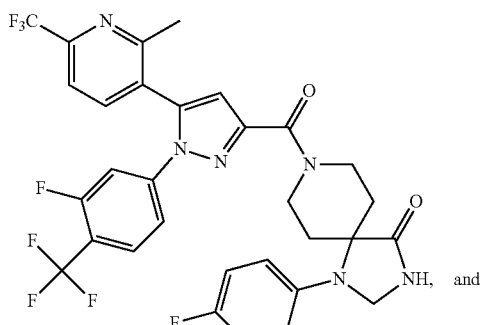   and
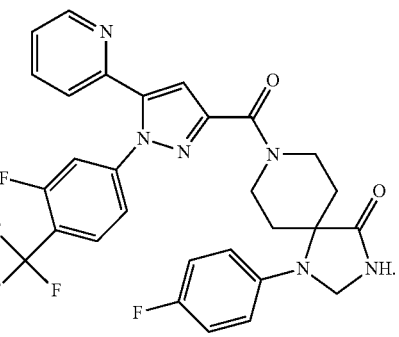
In some embodiments, the compound incorporates the features of one or more of the structural features of embodiments set forth for Formula II or Formula III. In some embodiments, the compound combines the features of two (or more) embodiments.
In one aspect, the invention provides a compound of Formula II:

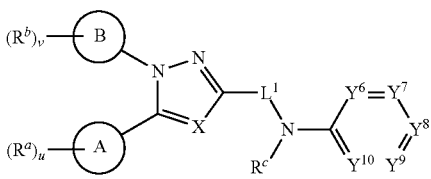

or a pharmaceutically acceptable salt thereof;
wherein:
A is a cyclic group of Formula IIa:

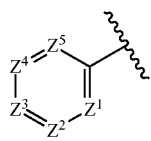

IIa wherein $Z^1$, $Z^2$, $Z^3$, $Z^4$, and $Z^5$ are each a member selected from the group consisting of N, CH, and $CR^a$; or, alternatively for $Z^1$, the member $Z^1$ and X, together with atoms in the rings to which they are attached, form an additional fused, five- to eight-membered cycloalkyl or heterocyclyl ring with from 0 to 5 $R^z$ substituents;
with the proviso that at least one member selected from the group consisting of $Z^2$, $Z^3$, and $Z^4$ is N;
each $R^z$ is a member independently selected from the group consisting of halo, $C_1$-$C_3$ alkyl, $C_1$-$C_3$ haloalkyl, and $C_1$-$C_3$ alkoxy; or, alternatively, two $R^z$ substituents, together with the carbon atom to which they are attached, join to form an oxo, spirocycloalkyl, or spiroheterocyclyl group;
B is a cyclic group of Formula IIb:

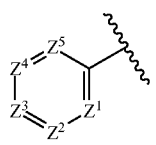

IIb wherein $Y^1$, $Y^2$, $Y^3$, $Y^4$, and $Y^5$ are each a member independently selected from the group consisting of N, CH, and $CR^b$; or, alternatively, the members —$Y^2$=$Y^3$— or —$Y^4$=$Y^5$— are combined into a single member selected from the group consisting of NH, $NR^c$, O, and S;
each $R^a$ and $R^b$ is a member independently selected from the group consisting of cyano, carboxyl, $C_1$-$C_4$ alkyl, $C_1$-$C_4$ hydroxyalkyl, $C_3$-$C_8$ cycloalkyl, $C_1$-$C_4$ alkoxy, $C_1$-$C_4$ haloalkyl, $C_1$-$C_4$ haloalkoxy, halo, $C_0$-$C_6$ amino, $C_1$-$C_6$ amido, $C_1$-$C_4$ alkyloxycarbonyl, $C_1$-$C_6$ alkylsulfonyl, and hydroxyl; or, alternatively, two adjacent $R^a$ or $R^b$, together with the atoms in groups A or B to which they are attached, form an additional fused aryl, heteroaryl, cycloalkyl, or heterocyclyl ring with from 0 to 5 $R^z$ substituents;
each $R^c$ is a member independently selected from the group consisting of hydrogen, $C_1$-$C_4$ alkyl, $C_1$-$C_4$ haloalkyl, $C_3$-$C_6$ cycloalkyl, ($C_3$-$C_6$ cycloalkyl)$C_1$-$C_3$alkyl, and $C_1$-$C_7$ acyl;

each u is an integer independently selected from 0 to 4;
v is an integer from 0 to 5;
X is N or $CR^d$; or, alternatively, X is $CR^d$, wherein X and the member $Z^1$, together with atoms in the rings in which they are included, form the additional fused, five- to eight-membered cycloalkyl or heterocyclyl ring with from 0 to 5 $R^z$ substituents;
each $R^d$ is a member independently selected from the group consisting of halo, cyano, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, and $C_3$-$C_6$ cycloalkoxy;
$L^1$ is a member selected from the group consisting of C=O, C=S, and C=$NR^c$;
$Y^6$, $Y^7$, $Y^8$, $Y^9$, and $Y^{10}$, if present, are each a member independently selected from the group consisting of N, CH, and $CR^b$; or, alternatively for $Y^8$ and $Y^9$, the members —$Y^6$=$Y^7$— or —$Y^8$=$Y^9$— are combined into a single member selected from the group consisting of $NR^c$, O, and S.

In some embodiments, the compound incorporates the features of one or more of the structural features of embodiments set forth for Formula I or Formula III. In some embodiments, the compound combines the features of two (or more) embodiments.

In one aspect, the invention provides compounds according to Formula III or a pharmaceutically acceptable salt thereof:

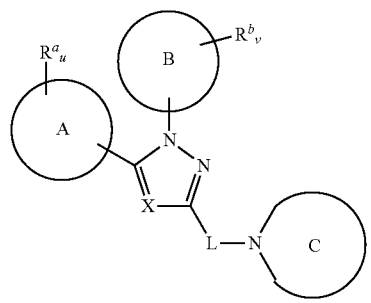

IIIa or

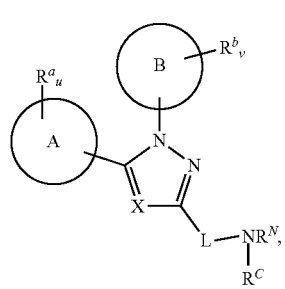

IIIb wherein:
Ring A and Ring B are each independently:
a 5- or 6-membered cyclic group with the proviso that Ring A and Ring B are not both unsubstituted phenyl; or
a 9-10-membered fused aromatic bicyclic ring with optionally 1, 2, 3, or 4 heteroatoms selected from N, O or S as part of the 9-10 members;

$R^a$ and $R^b$ are each independently selected from the group consisting of —CN, $C_1$-$C_4$ alkyl, $C_1$-$C_4$ alkoxy, $C_1$-$C_4$ haloalkyl, $C_1$-$C_4$ haloalkoxy, halogen, and hydroxy;

optionally, two $R^a$, together with the atoms in Ring A to which they are attached, join to form a ring;

optionally, two $R^b$, together with the atoms in Ring B to which they are attached, join to form a ring;

u and v are each independently 0, 1, 2, or 3;

X is $CR^x$ or N, wherein $R^x$ is selected from H, —CN, $C_1$-$C_3$ alkyl, —$CF_3$ cyclopropyl, and $C_1$-$C_3$ alkoxy;

L is —$[C(O)]_{0,1}$—$(CH_2)_{0,1,2}$—

Ring C is option A, option B, or option C wherein:
option A is

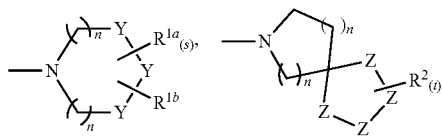

or a fused 8-14 member bi- or tri-cyclic cyclic group optionally having 1-4 heteroatoms selected from N and O and optionally substituted with 1-4 $R^3$ wherein:

Y is a bond, —$CH_2$—, —$S(O)_2$—, —$S(O)$—, —$C(O)$—, —NH—, or —O—; with the proviso that if two Y are bonds, the third Y is —$CH_2$—;

each Z is independently —$CH_2$—, —NH—, —S—, or —O— with the proviso that at least 2 of Z are —$CH_2$—;

each n is independently 0, 1 or 2 provided that if one n is 0, the other n is not 0;

s is 0, 1, 2, 3, or 4;

t is 1, 2, 3, or 4;

each $R^{1a}$ is independently $C_1$-$C_4$ alkyl, $C_1$-$C_4$ alkoxy, $C_1$-$C_4$ haloalkoxy, $C_1$-$C_4$ haloalkyl, —CN, or halogen;

$R^{1b}$ is:

an 8- to 9-membered bicyclic cyclic group having 0, 1, or 2 heteroatoms selected from S, N, and O, substituted by one or more oxo or (═S) and optionally substituted by one or more substituents selected from the group consisting of halogen, $C_1$-$C_4$ alkyl, $C_1$-$C_4$ haloalkoxy, and $C_1$-$C_4$ haloalkyl, or —$R^4$-$R^5$ wherein each of $R^4$ and $R^5$ are a 5- to 6-membered cyclic group having 0, 1, or 2 heteroatoms selected from N and O and each optionally substituted with oxo, halogen, $C_1$-$C_4$ alkyl, $C_1$-$C_4$ haloalkoxy, and $C_1$-$C_4$ haloalkyl;

each $R^2$ is independently selected from the group consisting of —CN, $C_1$-$C_4$ alkyl, $C_1$-$C_4$ alkoxy, $C_1$-$C_4$ haloalkoxy, —($C_1$-$C_4$ alkyl)-OH, $C_1$-$C_4$ haloalkyl, halogen, oxo, hydroxy, and 5- to 9-membered mono- or bicyclic cyclic group having 0, 1, or 2 heteroatoms selected from N and O, and wherein:

if one $R^2$ is oxo, t is 2 or 3 and one $R^2$ is other than oxo, if $R^2$ is a cyclic group, it is optionally substituted by one or more substituents selected from the group consisting of —CN, halogen, $C_1$-$C_4$ alkyl, and $C_1$-$C_4$ haloalkyl, and optionally, two $R^2$, together with the atoms to which they are attached, join to form a 5- or 6-membered cyclic group optionally substituted with 1-4 substituents selected from the group consisting of —CN, halogen, $C_1$-$C_4$ alkyl, $C_1$-$C_4$ haloalkoxy, and $C_1$-$C_4$ haloalkyl;

one $R^3$ is oxo and any remaining $R^3$ is independently selected from the group consisting of 5- to 9-membered mono- or bicyclic cyclic group having 0, 1, or 2 heteroatoms selected from N and O, —CN, $C_1$-$C_4$ alkyl, $C_1$-$C_4$ alkoxy, $C_1$-$C_4$ haloalkoxy, $C_1$-$C_4$ haloalkyl, halogen, oxo, and hydroxyl, and if $R^3$ is a cyclic group, it is optionally substituted by one or more substituents selected from the group consisting of halogen, $C_1$-$C_4$ alkyl and $C_1$-$C_4$ haloalkyl;

option B is if Ring A is a 6-membered cyclic group, Ring C is selected from the group consisting of a fused 8-14 member bi- or tri-cyclic cyclic group optionally having 1-4 heteroatoms selected from N and O and optionally substituted by 1-3 $R^3$,

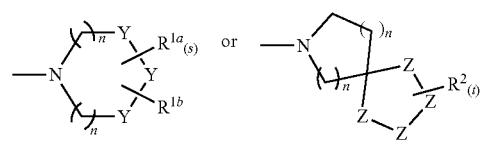

wherein:

Y is a bond, —$CH_2$—, —$S(O)_2$—, —$S(O)$—, —$C(O)$—, —NH—, or —O— with the proviso that if two Y are bonds, the third Y is —$CH_2$—;

each n is independently 0, 1 or 2 provided that if one n is 0, the other n is not 0;

each Z is independently —$CH_2$—, —NH—, —S— or —O—, with the proviso that at least 2 of Z are —$CH_2$—;

each $R^{1a}$ is independently $C_1$-$C_4$ alkyl, $C_1$-$C_4$ alkoxy, $C_1$-$C_4$ haloalkoxy, $C_1$-$C_4$ haloalkyl, —CN, or halogen;

$R^{1b}$ is:

a 5- to 9-membered mono- or bicyclic cyclic group having 0, 1, or 2 heteroatoms selected from S, N and O optionally substituted by one or more substituents selected from the group consisting of (═S), oxo, halogen, $C_1$-$C_4$ alkyl, $C_1$-$C_4$ haloalkoxy and $C_1$-$C_4$ haloalkyl and wherein if Ring C is

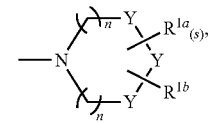

each n is 1 and s is 0, then $R^{1b}$ is not phenyl, pyridine, or pyrimidine, or —$R^4$-$R^5$ wherein each of $R^4$ and $R^5$ are a 5- to 6-membered cyclic group having 0, 1 or 2 heteroatoms selected from N and O and each optionally substituted with oxo, halogen, $C_1$-$C_4$ alkyl, $C_1$-$C_4$ haloalkoxy and $C_1$-$C_4$ haloalkyl;

each $R^2$ and $R^3$ is independently selected from the group consisting of 5- to 9-membered mono- or bicyclic cyclic group having 0, 1 or 2 heteroatoms selected from N and O, —CN, $C_1$-$C_4$ alkyl, —($C_1$-$C_4$ alkyl)-OH, $C_1$-$C_4$ alkoxy, $C_1$-$C_4$ haloalkoxy, $C_1$-$C_4$ haloalkyl, halogen, oxo, and hydroxy and if $R^2$ is a cyclic group, it is optionally substituted by one or more substituents selected from the group consisting of —CN, halogen, $C_1$-$C_4$ alkyl, and $C_1$-$C_4$ haloalkyl;

optionally, two $R^2$, together with the atoms to which they are attached, join to form a 5- or 6-membered cyclic group optionally substituted with 1-4 substituents selected from the group consisting of —CN, halogen, $C_1$-$C_4$ alkyl, $C_1$-$C_4$ haloalkoxy, and $C_1$-$C_4$ haloalkyl;
s is 0, 1, 2, 3 or 4; and
t is 0, 1, 2, 3 or 4;
with the proviso that, in option B, if X is N, Ring C is not

or
option C is if Ring A is a 6-membered cyclic group other than pyridine, Ring C is selected from the group consisting of a fused 8-14 member bi- or tri-cyclic cyclic group optionally having 1-4 heteroatoms selected from N and O and optionally substituted by 1-3 $R^3$,

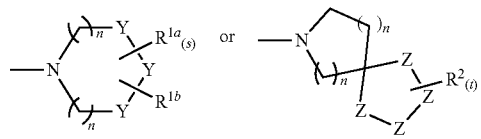

wherein:
Y is a bond, —$CH_2$—, —$S(O)_2$—, —S(O)—, —C(O)—, —NH—, or —O— with the proviso that if two Y are bonds, the third Y is —$CH_2$—;
each n is independently 0, 1 or 2 provided that if one n is 0, the other n is not 0;
each Z is independently —$CH_2$—, —NH—, —S—, or —O— with the proviso that at least 2 of Z are —$CH_2$—;
each $R^{1a}$ is independently $C_1$-$C_4$ alkyl, $C_1$-$C_4$ alkoxy, $C_1$-$C_4$ haloalkoxy, $C_1$-$C_4$ haloalkyl, —CN, or halogen;
$R^{1b}$ is:
  a 5- to 9-membered mono- or bicyclic cyclic group having 0, 1 or 2 heteroatoms selected from S, N and O optionally substituted by one or more substituents selected from the group consisting of (=S), oxo, halogen, $C_1$-$C_4$ alkyl, $C_1$-$C_4$ haloalkoxy, and $C_1$-$C_4$ haloalkyl, or
  —$R^4$-$R^5$ wherein each of $R^4$ and $R^5$ are a 5- to 6-membered cyclic group having 0, 1, or 2 heteroatoms selected from N and O and each optionally substituted with oxo, halogen, $C_1$-$C_4$ alkyl, $C_1$-$C_4$ haloalkoxy and $C_1$-$C_4$ haloalkyl;
each $R^2$ and $R^3$ is independently selected from the group consisting of 5- to 9-membered mono- or bicyclic cyclic group having 0, 1 or 2 heteroatoms selected from N and O, —CN, —$C_1$-$C_4$ alkyl, —($C_1$-$C_4$ alkyl)-OH, $C_1$-$C_4$ alkoxy, $C_1$-$C_4$ haloalkoxy, $C_1$-$C_4$ haloalkyl, halogen, oxo and hydroxy and if $R^2$ is a cyclic group, it is optionally substituted by one or more substituents selected from the group consisting of —CN, halogen, $C_1$-$C_4$ alkyl and $C_1$-$C_4$ haloalkyl;
optionally, two $R^2$, together with the atoms to which they are attached, join to form a 5- or 6-membered cyclic group optionally substituted with 1-4 substituents selected from the group consisting of —CN, halogen, $C_1$-$C_4$ alkyl, $C_1$-$C_4$ haloalkoxy, and $C_1$-$C_4$ haloalkyl;
s is 0, 1, 2, 3, or 4; and
t is 0, 1, 2, 3, or 4;

with the proviso that, in option C, if X is N, Ring C is not

$R^N$ is H or $C_1$-$C_4$ alkyl; and
$R^c$ is:
  a 5-6 membered heteroaryl optionally substituted by 1-4 $R^4$;
  a fused 8-10 member cyclic group having 0, 1, or 2 heteroatoms selected from N and O and optionally substituted by 1-3 $R^4$ if $R^N$ is other than H; or
  if Ring A is a 6-membered cyclic group, $R^c$ is a fused 8-10 member cyclic group having 0, 1, or 2 heteroatoms selected from N and O and optionally substituted by 1-3 $R^4$ wherein:
  each $R^4$ is independently selected from the group consisting of 5- to 9-membered mono- or bicyclic cyclic group having 0, 1 or 2 heteroatoms selected from N and O, —CN, —$C_1$-$C_4$ alkyl, —($C_1$-$C_4$ alkyl)-OH, $C_1$-$C_4$ alkoxy, $C_1$-$C_4$ haloalkoxy, $C_1$-$C_4$ haloalkyl, halogen, oxo, and hydroxy; and
  if $R^4$ is a cyclic group, it is optionally substituted by one or more substituents selected from the group consisting of —CN, halogen, $C_1$-$C_4$ alkyl, and $C_1$-$C_4$ haloalkyl.
In some embodiments two $R^2$, together with the atoms to which they are attached, join to form a 5- or 6-membered aryl or heteroaryl group optionally substituted with 1-4 substituents selected from the group consisting of —CN, halogen, $C_1$-$C_4$ alkyl, $C_1$-$C_4$ haloalkoxy, and $C_1$-$C_4$ haloalkyl.
In some embodiments two $R^2$, together with the atoms to which they are attached, join to form a 5- or 6-membered aryl or heteroaryl group optionally substituted with 1-4 substituents selected from the group consisting of halogen, $C_1$-$C_4$ alkyl, $C_1$-$C_4$ haloalkoxy, and $C_1$-$C_4$ haloalkyl.
In some embodiments at least one of Ring A or Ring B is an aryl or heteroaryl group.
In some embodiments at least one of Ring A or Ring B is a 6-membered aryl or 6-membered heteroaryl group.
In some embodiments both of Ring A and Ring B are either a 6-membered aryl or a 6-membered heteroaryl group.
In some embodiments both of Ring A and Ring B are not phenyl.
In some embodiments at least one of Ring A and Ring B is a 5-membered cyclic group having two heteroatoms.
In some embodiments Ring A is a 6-membered cyclic group or a 5-membered cyclic group wherein the 5-membered cyclic group includes 0, 2, or 3 heteroatoms.
In some embodiments Ring B is a 6-membered cyclic group or a 5-membered cyclic group wherein the 5-membered cyclic group includes 0, 2 or 3 heteroatoms.
In some embodiments each $R^a$ is independently —CN, halogen, a $C_1$-$C_4$ haloalkoxy, a $C_1$-$C_4$ haloalkyl, or $C_1$-$C_4$ alkyl; independently halogen, a $C_1$-$C_4$ haloalkoxy, a $C_1$-$C_4$ haloalkyl or $C_1$-$C_4$ alkyl; independently —CN, F, Cl, —$OCF_3$, —$OCHF_2$, —$CF_3$ or —$CH_3$; or independently F, Cl, —$OCF_3$, —$OCHF_2$, —$CF_3$, or —$CH_3$.
In some embodiments u is 1, 2, or 3, and each $R^a$ is independently F or —$CF_3$.
In some embodiments each $R^b$ is independently —CN, halogen, a $C_1$-$C_4$ haloalkoxy, a $C_1$-$C_4$ haloalkyl, or $C_1$-$C_4$ alkyl; independently halogen, a $C_1$-$C_4$ haloalkoxy, a $C_1$-$C_4$ haloalkyl or $C_1$-$C_4$ alkyl; independently —CN, F, Cl, —OCF$_3$, —OCHF$_2$, —CF$_3$ or —CH$_3$; or independently F, Cl, —OCF$_3$, —OCHF$_2$, —CF$_3$, or —CH$_3$.

In some embodiments each R$^b$ is independently —CN, halogen, a C$_1$-C$_4$ haloalkoxy, a C$_1$-C$_4$ haloalkyl, or C$_1$-C$_4$ alkyl.

In some embodiments each R$^b$ is independently —CN, F, Cl, —OCF$_3$, —OCHF$_2$, —CF$_3$, or —CH$_3$.

In some embodiments v is 1, 2 or 3 and each R$^b$ is independently F or —CF$_3$.

In a first aspect Ring C is

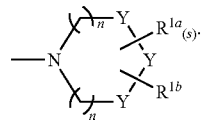

In a second aspect Ring C is

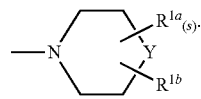

In some embodiments of the first or second aspects Y is —CH$_2$—.

In some embodiments of the first or second aspects R$^{1b}$ is a 5- to 9-membered mono- or bicyclic cyclic group having 0, 1, 2, or 3 heteroatoms selected from S, N and O and substituted by one or more substituents selected from the group consisting of oxo, halogen, C$_1$-C$_4$ alkyl, C$_1$-C$_4$ haloalkoxy, and C$_1$-C$_4$ haloalkyl.

In some embodiments of the first or second aspects R$^{1b}$ is

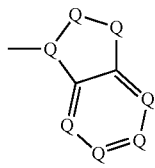

which is optionally substituted by one or more substituents selected from the group consisting of (=S), oxo, halogen, C$_1$-C$_4$ alkyl, C$_1$-C$_4$ haloalkoxy and C$_1$-C$_4$ haloalkyl and wherein each Q is independently selected from —N—, —NH—, —CH— and —CH$_2$— provided that nor more than three Q are —N— or —NH—. In some embodiments of the first or second aspects R$^{1b}$ is

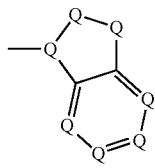

which is optionally substituted by one or more substituents selected from the group consisting of oxo, halogen, C$_1$-C$_4$ alkyl, C$_1$-C$_4$ haloalkoxy and C$_1$-C$_4$ haloalkyl and wherein each Q is independently selected from —N—, —NH—, —CH—, and —CH$_2$— provided that nor more than three Q are —N— or —NH—.

In some embodiments of the first or second aspects R$^{1b}$ is

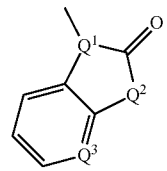

which is optionally substituted by one or more substituents selected from the group consisting of (=S), oxo, halogen, C$_1$-C$_4$ alkyl, C$_1$-C$_4$ haloalkoxy, and C$_1$-C$_4$ haloalkyl; and wherein Q$^1$ is —C— or —N—; Q$^2$ is —CH$_2$—, —NH—, —O—, or —S—; and Q$^3$ is —CH— or —N—. In some embodiments of the first or second aspects R$^{1b}$ is

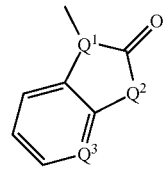

which is optionally substituted by one or more substituents selected from the group consisting of halogen, C$_1$-C$_4$ alkyl, C$_1$-C$_4$ haloalkoxy and C$_1$-C$_4$ haloalkyl and wherein Q$^1$ is —C— or —N—; Q$^2$ is —CH$_2$—, —NH—, —O—, or —S—; and Q$^3$ is —CH— or —N—.

In some embodiments of the first or second aspects R$^{1b}$ is

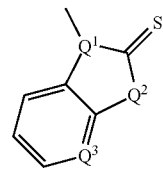

which is optionally substituted by one or more substituents selected from the group consisting of (=S), oxo, halogen, C$_1$-C$_4$ alkyl, C$_1$-C$_4$ haloalkoxy, and C$_1$-C$_4$ haloalkyl; and wherein Q$^1$ is —C— or —N—; Q$^2$ is —CH$_2$—, —NH—, —O—, or —S—; and Q$^3$ is —CH— or —N—. In some embodiments of the first or second aspects R$^{1b}$ is

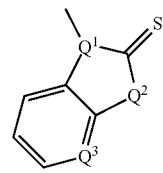

which is optionally substituted by one or more substituents selected from the group consisting of halogen, C$_1$-C$_4$ alkyl, C$_1$-C$_4$ haloalkoxy and C$_1$-C$_4$ haloalkyl and wherein Q$^1$ is —C— or —N—; Q$^2$ is —CH$_2$—, —NH—, —O—, or —S—; and Q$^3$ is —CH— or —N—.

In some embodiments of the first or second aspects R$^{1b}$ is substituted with F, Cl, Br, I, —CF$_3$, —OCF$_3$, —OH, or C$_1$-C$_4$ alkyl.

In some embodiments of the first or second aspects $R^{1b}$ is a 9-membered bicyclic cyclic group substituted by oxo and optionally substituted by one or more substituents selected from the group consisting of halogen, $C_1$-$C_4$ alkyl, $C_1$-$C_4$ haloalkoxy, and $C_1$-$C_4$ haloalkyl.

In some embodiments of the first or second aspects $R^{1b}$ is

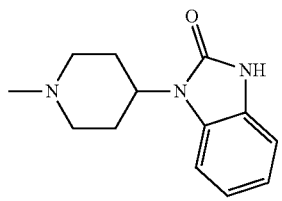 [SMILES: CN1CCC(n2c(=O)[nH]c3ccccc32)CC1]

and wherein

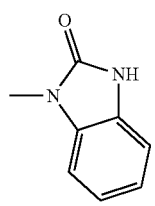

is optionally substituted by one or more substituents selected from the group consisting of (=S), oxo, halogen, $C_1$-$C_4$ alkyl, $C_1$-$C_4$ haloalkoxy, and $C_1$-$C_4$ haloalkyl. In some embodiments of the first or second aspects $R^{1b}$ is

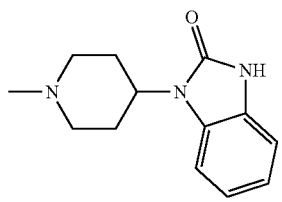 [SMILES: CN1CCC(n2c(=O)[nH]c3ccccc32)CC1]

and wherein

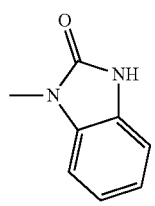

is optionally substituted by one or more substituents selected from the group consisting of oxo, halogen, $C_1$-$C_4$ alkyl, $C_1$-$C_4$ haloalkoxy, and $C_1$-$C_4$ haloalkyl. In some embodiments of the first or second aspects $R^{1b}$ is

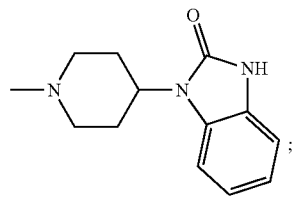 [SMILES: CN1CCC(n2c(=O)[nH]c3ccccc32)CC1]

and wherein

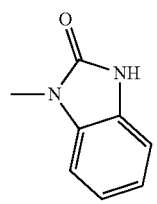

is optionally substituted by one or more substituents selected from the group consisting of halogen, $C_1$-$C_4$ alkyl, $C_1$-$C_4$ haloalkoxy, and $C_1$-$C_4$ haloalkyl.

In a third aspect, Ring C is

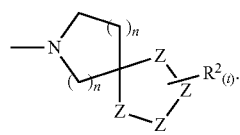

In some embodiments of the third aspect Ring C is

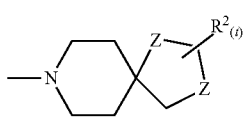

wherein each Z is independently $CH_2$, NH, or O; t is 1 or 2 and at least one $R^2$ is oxo.

In some embodiments of the third aspect t is 2 and the two $R^2$ are oxo and phenyl, which is optionally substituted with a fluorine, 1-3 halogens or 2-3 halogens of which one is fluorine.

In some embodiments of the third aspect one Z is O and one Z is —$CH_2$—; t is 2 and both $R^2$ are halogens.

In some embodiments of the third aspect X is —$CR^x$— and Ring C is

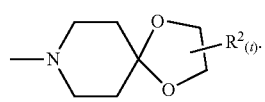

In a fourth aspect, Ring C is a fused tricyclic cyclic group optionally substituted with 1-4 $R^3$.

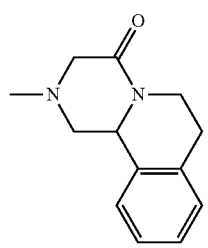 [SMILES: CN1CC(=O)N2CCc3ccccc3C2C1]

In some embodiments of the fourth aspect Ring C is optionally substituted with 1-4 $R^3$.

Also provided is a pharmaceutical composition comprising a therapeutically effective amount of a compound as claimed in any of the aspects or embodiments herein; and a pharmaceutically acceptable carrier, excipient, diluent or a mixture thereof.

In some embodiments, the pharmaceutical composition comprises a second therapeutic agent selected from the group consisting of: i) opioid receptor agonists, ii) opioid receptor antagonists, iii) calcium channel antagonists, iv) 5-HT receptor agonists, v) 5-HT receptor antagonists vi) sodium channel antagonists, vii) NMDA receptor agonists, viii) NMDA receptor antagonists, ix) COX-2 selective inhibitors, x) neurokinin receptor antagonists, including NK1 antagonists, xi) non-steroidal anti-inflammatory drugs, xii) selective serotonin reuptake inhibitors, xiii) selective serotonin and norepinephrine reuptake inhibitors, xiv) tricyclic antidepressant drugs, xv) norepinephrine modulators, xvi) 5-lipoxygenase inhibitors, xvii) cannabinoid receptor agonists, xviii) inhibitors of fatty acid amide hydrolase, ixx) beta-adrenergic receptor agonists, x) prostanoid receptor antagonists, xxi) leukotriene receptor antagonists, xxii) histamine receptor antagonists, xxiii) steroids, xxiv) CGRP antagonists, xxv) peroxisome proliferator-activated receptor (PPAR) agonists, and xxvi) acetaminophen.

Also provided is a method of treating or preventing pain comprising administering to a patient in need thereof a therapeutically effective amount, or a prophylactically effective amount, of a disclosed compound. In some embodiments the pain treated comprises acute pain, nociceptive pain, inflammatory pain, neuropathic pain, and periprocedural pain (e.g., post-surgical). In some embodiments the neuropathic pain is diabetic peripheral neuropathic pain or chemotherapeutic-induced peripheral neuropathic pain.

In some embodiments the method of treating further comprises administering a second therapeutic agent selected from the group consisting of: i) opioid receptor agonists, ii) opioid receptor antagonists, iii) calcium channel antagonists, iv) 5-HT receptor agonists, v) 5-HT receptor antagonists vi) sodium channel antagonists, vii) NMDA receptor agonists, viii) NMDA receptor antagonists, ix) COX-2 selective inhibitors, x) neurokinin receptor antagonists, including NK1 antagonists, xi) non-steroidal anti-inflammatory drugs, xii) selective serotonin reuptake inhibitors, xiii) selective serotonin and norepinephrine reuptake inhibitors, xiv) tricyclic antidepressant drugs, xv) antiepileptic drugs, xvi) 5-lipoxygenase inhibitors, xvii) cannabinoid receptor agonists, xviii) inhibitors of fatty acid amide hydrolase (FAAH), ixx) beta-adrenergic receptor agonists, xx) prostanoid receptor antagonists, xxi) leukotriene receptor antagonists, xxii) histamine receptor antagonists, xxiii) steroids, xxiv) CGRP antagonists, xxv) peroxisome proliferator-activated receptor (PPAR) agonists, and xxvi) acetaminophen.

In some embodiments the 5-HT receptor agonist is a $5\text{-HT}_{1B}$ receptor agonist or a $5\text{HT}_{1D}$ receptor agonist. In some embodiments the 5-HT receptor agonist is a triptan. In some embodiments the triptan is sumatriptan, rizatriptan, naratriptan, zolmitriptan, eletriptan, almotriptan, or frovatriptan.

In some embodiments the opioid receptor agonist is morphine, codeine, oxymorphone, pentazocine, fentanyl, sufentanil, tramadol, meperidine, methadone, or etorphine. In some embodiments the opioid receptor agonist is morphine, codeine, hydrocodone, oxycodone, hydromorphone, oxymorphone, pentazocine, fentanyl, sufentanil, alfentanil, tramadol, O-desmethyltramadol, tapentadol, cebranopadol, ciramdol, meperidine, methadone, nalbuphine, buprenorphine, or etorphine.

In some embodiments the nonsteroidal anti-inflammatory drug (NSAID) is aspirin, ibuprofen, naproxen, ketoprofen, dexketoprofen, loxoprofen, flurbiprofen, oxaprozin, fenoprofen, indomethacin, ketorolac, sulindac, etodolac, diclofenac, aceclofenac, mefanamic acid, meclofenamic acid, flufenamic acid, tolfenamic acid, piroxicam, meloxicam, tenoxicam, salicylic acid, nabumetone, or phenylbutazone. In some embodiments the NSAID is aspirin, ibuprofen, naproxen, ketoprofen, loxoprofen, meloxicam, or diclofenac.

In some embodiments the COX-2 inhibitor is celecoxib, etoricoxib, lumiracoxib, parecoxib, rofecoxib, or valdecoxib.

Also provided is a method of treating or preventing pain before, during or after surgical procedure, comprising the step of administering to a patient in need thereof a therapeutically effective amount, or a prophylactically effective amount, of a disclosed compound.

III. Pharmaceutical Compositions

Pharmaceutical compositions comprising the disclosed compounds are also provided. In a first embodiment, the pharmaceutical composition further comprises one or more pharmaceutically acceptable excipients or vehicles, and optionally other therapeutic and/or prophylactic ingredients. Such excipients are known to those of skill in the art. A thorough discussion of pharmaceutically acceptable excipients and salts is available in *Remington's Pharmaceutical Sciences*, 18th Edition (Easton, Pa.: Mack Publishing Company, 1990). The compositions can be administered orally, mucosally, parenterally, topically, transdermally, intranasally, intravenously or by inhalation.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

Pharmaceutical compositions comprise a disclosed compound including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule non-aqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

Parenteral administration includes intraarticular, intravesical, intravenous, intramuscular, intradermal, intraperitoneal, intraocular, intravitreal, intrathecal and subcutaneous administration. The compositions for parenteral administration include aqueous and non-aqueous, isotonic sterile injection solutions, which can contain antioxidants, buffers, bacteriostats, and solutes that render the formulation isotonic with the physiological fluids of the intended recipient, and aqueous and non-aqueous sterile suspensions that can include suspending agents, solubilizers, thickening agents, stabilizers, and preservatives.

Another mode of administration of a compound of the present invention is for use in regional analgesia. Epidural analgesia and spinal analgesia are commonly employed techniques of providing pain relief during labor, surgical procedures and diagnostic procedures. Epidural analgesia can be administered by injection into the epidural space or an indwelling catheter can be directed into the epidural space and the patient receives a continuous infusion or multiple injections of the compound of the present invention. Administration may also encompass a combination of epidural and spinal analgesia. In addition, administration may include wound infiltration or injection to create a plexus block.

Compositions for topical, inhalation and transdermal routes of administration include powders, sprays, ointments, pastes, creams, gels, lotions, solutions, patches and inhalants. The ointments, pastes, creams and gels may contain, in addition to an a disclosed composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. A dry powder formulation or aerosol formulation of the disclosed compound is useful for pulmonary delivery.

Powders, aerosols and sprays can contain, in addition to a disclosed compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. Transdermal patches have the added advantage of providing controlled delivery of a disclosed compound to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as within the scope of the disclosure. Formulations for opthalmic administration include are generally formulated as sterile aqueous solutions and to be compatible with the eye. The ophthalmic formulations intended for direct application to the eye are formulated so as to have a pH and tonicity that are compatible with the eye. Example pH ranges are 4 to 9, more preferably 5.5 to 8.5, and most preferably 7 to 8. The osmolality of one or more of the disclosed compounds in the solution is 200 to 350 milliosmoles per kilogram (mOsm/kg), or 250 to 330 mOsm/kg. The use of nonionic osmolality-adjusting agents is preferred. Examples include propylene glycol, glycerol, xylitol or combinations thereof. Boric acid may also be utilized as an osmolality-adjusting agent in the opthalmic formulations. Boric acid, if utilized, will be present in the compositions as a mixture of ionic and nonionic species. The opthalmic formulations may contain various types of pharmaceutical excipients, such as surfactants, viscosity-modifying agents such as carboxymethylcellulose, glycerin, polyvinylpyrrolidone, polyethylene glycol and so on, provided that such excipients are non-ionic. One or more conventional antimicrobial preservatives, such as benzalkonium chloride, polyquarternium-1 or EDTA can be present in the opthalmic formulations. The overall composition may include sufficient antimicrobial activity to satisfy USP/FDA/ISO preservative efficacy requirements. Opthalmic formulations can be made for single or multi-dose packaging.

The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation.

IV. Methods of Treatment

Pain

Provided are methods of treating pain by the disclosed compounds. Exemplary types of pain treated by the provided compounds include (1) acute, chronic, visceral, inflammatory and/or neuropathic pain syndromes; (2) pain resulting from, or associated with, traumatic nerve injury, nerve compression or entrapment, acute herpetic and postherpetic neuralgia, trigeminal neuralgia, fibromyalgia, diabetic neuropathy, cancer and/or chemotherapy-induced peripheral neuropathy; (3) lower back pain; (4) phantom limb pain; (5) pain resulting from inflammatory disease, including osteoarthritis, rheumatoid arthritis, juvenile rheumatoid arthritis, gout, neuropathic arthropathy, psoriatic arthritis, ankylosing spondylitis, other spondyloarthropathies, crystalline arthropathies or systemic lupus erythematosus (SLE); (6) headache pain, migraine pain and cluster headache pain; (7) HIV- and HIV treatment-induced neuropathy, chronic pelvic pain, neuroma pain, complex regional pain syndrome; (8) stroke or neural trauma or (9) cold pain sensitivity.

In some embodiments the neuropathic pain is diabetic peripheral neuropathic pain or chemotherapeutic-induced peripheral neuropathic pain (CIPN). CIPN is a painful adverse effect caused by commonly used chemotherapeutic agents, which include the taxanes (e.g. Abraxane; Paclitaxel), platinum-based compounds (e.g. Eloxatin: oxaliplatin), and numerous other anti-cancer drugs. Therapeutic consequences of CIPN include chemotherapeutic dose reduction, changes in dosing schedules and termination of treatment leading to decreased survival. Sensory symptoms including pain, numbness and tingling are the most common, but the initial acute peripheral neuropathy observed in CIPN transitions to chronic neuropathic pain in many patients after discontinuation of chemotherapy. Oxaliplatin-induced peripheral neuropathy appears in almost all patients rapidly after infusion and is either triggered or exacerbated by cold, indicating a role for a TRP channel in this process. Recent studies have identified TRPA1 channels as a promising target for novel analgesic drugs for treating or preventing induction of CIPN.

The compounds of the present invention have applications in preventing, reducing or inhibiting acute and/or chronic pain in a variety of operative and interventional procedures, including surgical, diagnostic and therapeutic procedures. An interventional procedure is defined as any procedure used for diagnosis or treatment that involves incision; puncture; entry into a body cavity; or the use of ionizing, electromagnetic or acoustic energy.

Also provided is a method of treating a subject suffering from or diagnosed with a disease, disorder, or medical condition mediated by TRPA1 activity, comprising administering to the subject in need of such treatment an effective amount of at least one chemical entity as disclosed herein.

Respiratory Disorders or Asthma

In some embodiments, the compounds described herein are useful for the treatment or prevention of respiratory disorders, such as asthma. Such conditions can affect the lung, pleural cavity, bronchial tubes, trachea, upper respiratory tract as well as the nerves and muscles involved in breathing. The airways are densely innervated by sensory nerves, the majority of which are afferent C-fibers. TRPA1 is expressed on bronchopulmonary C-fiber nerve endings. Evidence suggests that TRPA1 is a mediator of allergic airway mediated inflammation and can also be activated by a variety of irritants, and is thus a molecular target for suppression of inflammation and airway hyper-reactivity in asthma as shown by experimental animal asthma studies.

Respiratory diseases, including asthma, that may be treated with the compounds described herein include obstructive diseases such as chronic obstructive pulmonary disease (COPD), emphysema, chronic bronchitis, cystic fibrosis, bronchiectasis, bronchiolitis, allergic bronchopulmonary aspergillosis, and tuberculosis; restrictive lung disease including asbestosis, radiation fibrosis, hypersensitivity pneumonitis, infant respiratory distress syndrome, idiopathic pulmonary fibrosis, idiopathic pulmonary fibrosis, idiopathic interstitial pneumonia sarcoidosis, eosinophilic pneumonia, lymphangioleiomyomatosis, pulmonary Langerhan's cell histiocytosis, and pulmonary alveolar proteinosis; respiratory tract infections including upper respiratory tract infections (e.g., common cold, sinusitis, tonsillitis, pharyngitis and laryngitis) and lower respiratory tract infections (e.g., pneumonia); pleural cavity diseases (e.g., emphysema and mesothelioma); and pulmonary vascular diseases (e.g, pulmonary embolism, pulmonary arterial hypertension, pulmonary edema). Other conditions that may be treated include disorders that affect breathing mechanics (e.g., obstructive sleep apnea, central sleep apnea, amyotrophic lateral sclerosis, and myasthenia gravis). The present compounds can also be useful for treating, reducing, or preventing one or more symptoms associated with respiratory conditions including, for example, shortness of breath or dyspnea, cough, chest pain including pleuritic chest pain, noisy breathing, wheezing, and cyanosis. Other conditions include cough, as well as allergy-induced cough and angiotensin converting enzyme inhibitor-induced cough.

Dermatological Diseases and Pruritus

In some embodiments, the compounds described herein are useful for the treatment or prevention of dermatological diseases and conditions, including pruritus, and atopic dermatitis. Influx of calcium across plasma membrane of skin cells is a critical signaling element involved in cellular differentiation in the skin epidermis. Regulating or modulating the calcium entry pathway, can be a critical control point for skin cell growth, and can treat or prevent skin diseases or disorders that are characterized by epidermal hyperplasia, a condition in which skin cells both proliferate too rapidly and differentiate poorly.

TRPA1 is known to be expressed in human keratinocytes as well as nerve fibers in the skin and thus compounds of the present invention can be used for controlling calcium entry through TRPA1. Such diseases include psoriasis, atopic dermatitis, and basal and squamous cell carcinomas. Psoriasis, estimated to affect up to 7 million Americans, afflicts sufferers with mild to extreme discomfort, enhanced susceptibility to secondary infections, and psychological impact due to disfigurement of the affected areas (Lebwohl and Ali, 2001 J. Am. Acad. Dermatol. 45:487-498).

Many dermatological disorders are accompanied by itch (pruritus). Chronic debilitating pruritus is a cardinal feature of atopic dermatitis (AD). An IL-13 transgenic mouse model can be utilized to demonstrate the efficacy of compounds of the present invention in inhibiting itch evoked scratching in AD (Oh, et al., 2013, J. Immunol. 191: 5371-5382). Pruritus and pain share many overlapping mediators and receptors, and mechanistic similarities. Decreasing neuronal excitability, particularly C-fiber excitability may alleviate pruritus associated with dialysis, dermatitis, pregnancy, poison ivy, allergy, dry skin, chemotherapy and eczema. Toll-like receptors may also mediate activation of TRPA1 to cause itch. Hence, TRPA1 antagonists of the present invention, compositions and methods provided herein may also be used in connection with treatment of psoriasis, atopic dermatitis and other dermatological diseases.

Inflammatory Diseases and Disorders

In some embodiments, compositions and methods provided herein may also be used in connection with treatment of inflammatory diseases. These diseases include but are not limited to rheumatoid arthritis, osteoarthritis, inflammatory bowel disease, Crohn's disease, ulcerative colitis, glomerulonephritis, neuroinflammatory diseases such as multiple sclerosis, periodontitis, and disorders of the immune system.

Peripheral neuropathy, for example diabetic neuropathy, is a particular condition that involves both a neuronal and an inflammatory component. Without being bound by a mechanistic theory, the TRPA1 antagonists of the invention may be useful in treating peripheral neuropathies including, but not limited to, diabetic neuropathy. In addition to their use in the treatment of peripheral neuropathies (e.g., reducing inflammation), the subject inhibitors may also be useful in reducing the pain associated with peripheral neuropathy.

Neurogenic inflammation often occurs when neuronal hyperexcitability leads to the release of peptides that trigger inflammation. These peptides include substance P and CGRP. Blocking TRPA1 activation on nociceptive nerve endings will reduce neuronal activity and thus block neurogenic inflammation, reducing the levels of substance P or CGRP released.

Pancreatitis is an inflammation of the pancreas. Acute pancreatitis usually begins with pain in the upper abdomen that may last for a few days. The pain may be severe and may become constant. The pain may be isolated to the abdomen or it may reach to the back and other areas. Severe cases of acute pancreatitis may cause dehydration and low blood pressure, and may even lead to organ failure, internal bleeding, or death. During acute pancreatitis attacks, the blood levels of amylase and lipase are often increased by at least 3-fold. In some embodiments, the compounds disclosed herein can be used to relieve the pain associated with acute pancreatitis.

Incontinence and Overactive Bladder

Incontinence is a significant social and medical problem affecting both men and women. Incontinence has many causes including, but not limited to, age, pregnancy, radiation exposure, surgery, injury, cancer, enlargement of the prostatic, prostatic hyperplasia, and diseases of the bladder or musculature that supports the urethra. In some embodiments, compounds of the invention can be used to treat incontinence due to any of the foregoing, as well as incontinence of unknown causes. In some embodiments, the compounds disclosed herein are used to reduce bladder hyperactivity by decreasing the activity of the neurons that innervate the bladder. In some embodiments, incontinence is accompanied by pain. For example, incontinence incident to bladder cystitis or incontinence incident to an injury may be accompanied by pain. When incontinence is accompanied by pain, the compound may be administered to treat both incontinence and to reduce pain. The compounds may be administered either directly to the bladder (intravesically) or systemically, or by other means. Established animal models of incontinence and bladder hyperactivity can be utilized to test and demonstrate efficacy of compounds which can modulate abnormal bladder contractility or increases in the frequency or magnitude of bladder contractions. Since TRPA1 mRNA is expressed in neurons that innervate bladder, inhibiting TRPA1 activity with a TRPA1 antagonist may be an effective treatment for bladder hyperreactivty, overactive bladder, and incontinence.

Cold-Temperature Hypersensitity

TRPA1 is known to be activated by cold temperatures in both man and rodent species. In some embodiments, compounds of the invention can also be used to modulate abnormal thermal sensitivity that occurs in certain disease states or conditions. Given that TRPA1 channels are thermal responsive channels involved in the detection and sensation of cold stimuli, TRPA1 antagonists can be used to modulate the abnormal sensations of cool, cold and decreased temperatures that often accompany pain, including neuropathic pain. In some embodiments, compounds of the present invention may be useful to modulate the cold-hypersensitivity that accompanies treatment with anti-cancer drugs.

Allergies

In some embodiments, the compounds disclosed herein can also be used to treat seasonal allergies, e.g., allergic rhinitis.

General Methods

In some embodiments, the compound is administered periprocedurally, which may include perioperatively. In some embodiments, the compound of the present invention is administered preprocedurally or postprocedurally as well as intraprocedurally. In some embodiments, the compounds of the present invention are administered to a surgical, diagnostic or therapeutic procedure site by techniques well known to those of ordinary skill in the art. In some embodiments, post-surgical pain is treated by the methods of the invention.

The methods of treating pain generally comprise administering a compound of the invention to a subject in need thereof. In some embodiments, the method of treating pain comprises modulating the activity of TRPA1 (SEQ ID NO: 1) or a variant thereof (e.g., a variant selected from SEQ ID NOS:2-7) in the subject. Modulating the activity of TRPA1 can include activating TRPA1 or inhibiting TRPA1. In some embodiments, the method of treating pain comprises administering a compound of the invention to a subject and modulating the activity of TRPA1 (SEQ ID NO: 1) in the subject. In some embodiments, the method of treating pain comprises administering a compound of the invention to a subject and inhibiting the activity of TRPA1 (SEQ ID NO: 1) in the subject.

In some embodiments, compounds of the invention inhibit the activity of a TRPA1 protein that has a single amino acid substitution relative to SEQ ID NO: 1 that arise from a naturally occurring variant TRPA1 gene. Such variant TRPA1 genes may result from single nucleotide polymorphism (SNP) sequences which comprise a TRPA1 SNP variant in such a subject. Examples of human SNP variants include, but are not limited to TRPA1: R3C, R58T, Y69C, E179K, K186N A366D, E477K, D573A, R797T, S804N, N855S, and H1018R. In some embodiments, the method of treating pain comprises administering a compound of the invention to a subject and inhibiting the activity of a TRPA1 protein that has a single amino acid substitution relative to TRPA1 seq ID No:1 that arise from a naturally occurring variant TRPA1 gene.

In some embodiments, the treatment of pain comprises administering a disclosed compound and a second compound selected from one or more of the following classes: i) opioid receptor agonists, ii) opioid receptor antagonists, iii) calcium channel antagonists, iv) serotonin (5-HT) receptor agonists, v) 5-HT receptor antagonist vi) sodium channel antagonist, vii) NMDA receptor agonists, viii) NMDA receptor antagonists, ix) COX-2 selective inhibitors, x) neurokinin receptor antagonists, including NK1 antagonists, xi) non-steroidal anti-inflammatory drugs (NSAIDs), xii) selective serotonin reuptake inhibitors, xiii) selective serotonin and norepinephrine reuptake inhibitors, xiv) tricyclic antidepressant drugs, xv) norepinephrine modulators, xvi) 5-lipoxygenase inhibitors, xvii) cannabinoid receptor agonists, xviii) inhibitor of fatty acid amide hydrolases, ixx) beta-adrenergic receptor agonists, x) prostanoid receptor antagonists, xxi) leukotriene receptor antagonists, xxii) histamine receptor antagonists, xxiii) steroids, xxiv) CGRP antagonists, xxv) peroxisome proliferator-activated receptor (PPAR) agonists, xxvi) chemotherapeutic drugs, and xxvii) acetaminophen.

Examples of 5-HT receptor agonists include 5-HT$_{1B}$ receptor agonists and 5-HT$_{1D}$ receptor agonists. Examples of 5-HT$_{1B}$ and 5-HT$_{1D}$ receptor agonists include triptans such as sumatriptan, rizatriptan, naratriptan, zolmitriptan, eletriptan, almotriptan, and frovatriptan. Example opioid receptor agonists include morphine, codeine, hydrocodone, oxymorphone, pentazocine, nalbuphine, fentanyl, sufentanil, tramadol, meperidine, methadone, and etorphine. Examples of NSAIDs include aspirin, ibuprofen, naproxen, ketoprofen, flurbiprofen, loxoprofen, indomethacin, etodolac, diflunisal, ketorolac, nabumetone, oxaprozin, piroxicam, meloxicam, and diclofenac. Examples of COX-2 inhibitors include celecoxib, etoricoxib, lumiracoxib, parecoxib, rofecoxib, and valdecoxib. Examples of PPAR agonists include PPAR-γ subtypes such as thiazolidinediones, examples of which include rosiglitazone, pioglitazone and troglitazone. Useful PPAR agonists also include PPAR-α subtype agonists. Examples of sodium channel antagonists include lidocaine, bupivacaine, etidocaine, ropivicaine, mepivicaine, procaine, 2-chloroprocaine, pramoxine, prilocaine, proparacaine and tetracaine. Examples of chemotherapeutic drugs include paclitaxel, docetaxel, abraxane, taxotere, oxaliplatin, cisplatin, carboplatin, vorinostat, romidepsin, and other histone deacetylase (HDAC) inhibitor drugs.

In some embodiments, the method of treating pain further comprises administering an analgesic, antidepressant, anxiolytic, antiemetic, anti-epileptic or anticonvulsant.

The compounds can be administered at any suitable dose in the methods of the invention. In general, compounds of the invention are administered at doses ranging from about 0.01 milligrams to about 100 milligrams per kilogram of a subject's body weight (i.e., about 0.01-100 mg/kg). The dose of a compound can be, for example, about 0.01-100 mg/kg, or about 0.5-50 mg/kg, or about 1-25 mg/kg, or about 2-10 mg/kg. The dose of the compound can be about 0.01, 0.05, 0.1, 0.25, 0.50, 0.75, 1, 2, 3, 4, 5, 10, 15, 20, 25, 30, 35, 40, 45, 50, 55, 60, 65, 70, 75, 85, 90, 95, or 100 mg/kg. The dosages can be varied depending upon the particular compound used, the requirements of the patient, the type and severity of the pain being treated, and the particular formulation being administered. In general, the dose administered to a patient is sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the pain.

In some embodiments, the invention sets forth a compound or formulation as set forth in one of the embodiments herein for use in a medicament. In some embodiments, the invention sets forth the use of a compound or formulation as set forth in one of the embodiments herein for the manufacture of a medicament for the treatment of pain (e.g., for one of the disorders set forth in the method embodiments herein).

Compounds of the invention can be administered using any of the pharmaceutical compositions described herein. One of skill in the art will appreciate that type of composition and route of administration will depend, in part, on factors such as the type and severity of pain being treated. In some embodiments, acute pain is treated by parenteral injection of a solution or suspension of a compound of the invention. In certain other embodiments, chronic pain is treated by oral administration of a compound of the invention in a form such as a tablet, pill, or capsule.

Administration of compounds of the invention can be conducted for a period of time which will vary depending upon the type of pain being treated, its severity, and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or at other intervals. Following treatment, a patient can be monitored for changes in his or her condition and for pain alleviation. The dosage of the compounds can either be increased in the event the patient does not respond significantly to a particular dosage level, or the dose can be decreased if an alleviation or absence of pain is observed, or if unacceptable side effects are seen with a particular dosage.

A therapeutically effective amount of a compound of the invention can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if pain subsides or generally improves in the patient, the dosage may be maintained or kept at lower than maximum amount. If the pain recurs, the first dosage regimen can be resumed until an improvement is seen, and the second dosing regimen can be implemented again. This cycle can be repeated multiple times as necessary.

Animal Pain Models for In Vivo Testing

Animal models are useful for understanding the mechanism of pain and development of effective therapy for its optimal management. Numerous pain models have been developed to simulate clinical pain conditions with diverse etiology. Development of these models has contributed immensely in understanding acute and chronic pain and underlying peripheral mechanisms. This includes the role of TRPA1 in acute and chronic pain models. Based on these animal pain models, research has resulted in the development of new therapeutic agents for pain management, and the preclinical data obtained using these animal models have been successively translated to effective pain management in clinical studies. Each animal model has been created with specific methodology. Data from each different model is interpreted in the context of the specific pain model.

Data Analysis for Pain Models

Compounds are evaluated in well characterized in vivo models to assess acute, inflammatory, neuropathic pain and periprocedural (e.g., post-surgical) pain. Animals are randomly assigned to each treatment group. Results are presented as mean+S.E.M. Percent Reversal is calculated as (post-dose−pre-dose)/(pre-injury−pre-dose)×100 for each rat or mouse. 100% corresponds to complete reversal of hyperalgesia or allodynia, equivalent to non-injured values, and 0% corresponds to values not different from baseline post-injury. As appropriate, results are analyzed using either 1-way ANOVA or 2-way ANOVA (for dose and time post-dose) test followed by Bonferroni post-tests for multiple comparisons (Prism, Graph Pad, San Diego, Calif.). $ED_{50}$ values are calculated as doses corresponding to a 50% effect (100% effect corresponding to recovery or reversal to baseline values in the absence of injury). In general, experimental and control groups contain at least six animals per group.

V. Examples

Example 1. Synthesis of Compounds of the Invention

For the lettered schemes (e.g., Scheme A), analytical TLC was performed on Merck silica gel 60 $F_{254}$ aluminium-backed plates. Compounds were visualised by UV light and/or stained with either I₂ or potassium permanganate solution followed by heating. Flash column chromatography was performed on silica gel. ¹H-NMR spectra were recorded on a Bruker Avance-400 MHz spectrometer with a BBO (Broad Band Observe) and BBFO (Broad Band Fluorine Observe) probe. Chemical shifts (δ) are expressed in parts per million (ppm) downfield by reference to tetramethylsilane as the internal standard. Splitting patterns are designated as s (singlet), d (doublet), t (triplet), q (quartet), m (multiplet) and br s (broad singlet). Coupling constants (J) are given in hertz (Hz). LCMS analyses were performed either on an Acquity BEH C-18 column (2.10×100 mm, 1.70 μm) or Acquity HSS-T3 (2.1×100 mm, 1.8 μm) using the Electrospray Ionisation (ESI) technique.

The following solvents, reagents or scientific terminology may be referred to by their abbreviations:
TLC Thin Layer Chromatography
CDCl₃ Deuterated chloroform
DCM Dichloromethane
THF Tetrahydrofuran
MeOH Methanol
EtOH Ethanol
IPA Isopropanol
EtOAc Ethyl acetate
Et₂O Diethyl ether
DMF N,N-Dimethylformamide
TEA/Et₃N Triethylamine
DIPEA Diisopropylethylamine (Hunig's base)
LiHMDS Lithium bis(trimethylsilyl)amide
HATU N,N,N,N-Tetramethyl-O-(7-azabenzotriazol-1-1) uroniumhexafluorophosphate
AcOH Acetic acid
TFA Trifluoroacetic acid
NBS N-Bromosuccinimide
mL milliliters
mmol millimoles
h hour or hours
min minute or minutes
g grams
mg milligrams
L microliters
M molar concentration
M micromolar concentration
m micrometer or micron
N Normal concentration
eq equivalents
rt or RT Room temperature, ambient, about 27° C.
MS Mass spectrometry
Hz Hertz In the below schemes like-numbered compounds are not necessarily the same. Numbering restarts with each scheme.

The disclosed compounds can be made by the following general scheme A.

Scheme A

*J. Finn et al./Bioorg. Med. Chem. Lett.* 13 (2003) 2231-2234

This scheme may be modified to provide the various rings A and B as well as ring C or —N(R$^N$)(R$^C$) of the disclosed compounds by replacing the various starting materials with those that provide the desired rings or —N(R$^N$)(R$^C$). Using the below Scheme A-1 in place of A, compositions with a substitution on the 4-position of the pyrazole (such as —CH₃) as shown here, can be made.

Scheme A-1

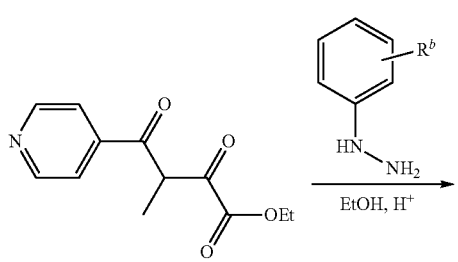
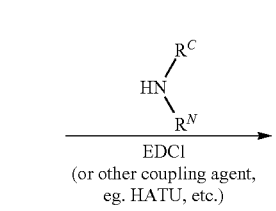
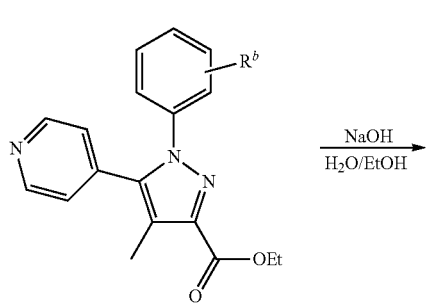
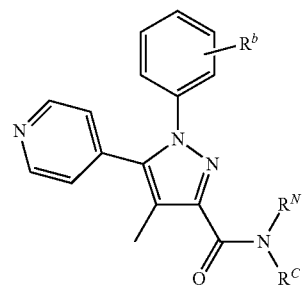
In one embodiment, compounds can be prepared according to Scheme B.
Scheme B
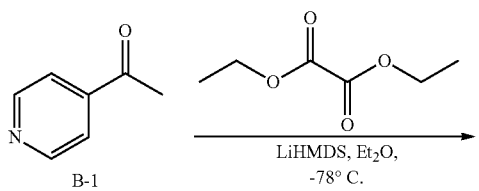
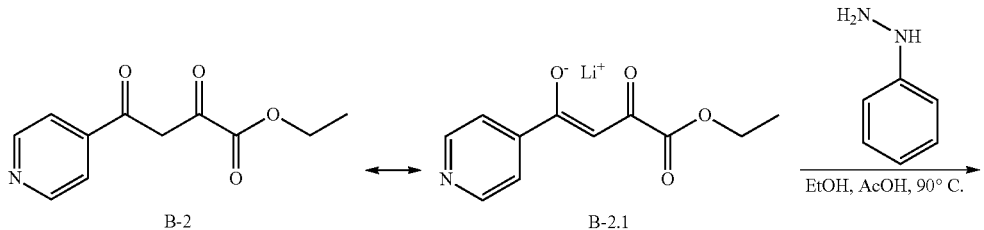
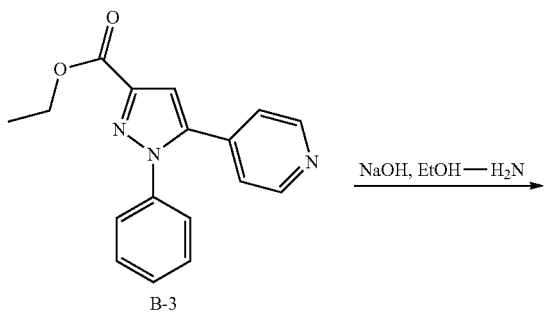

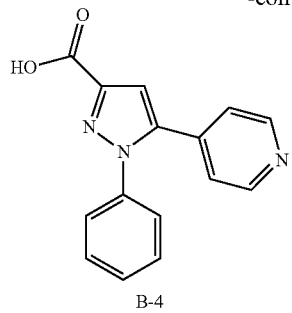

B-4

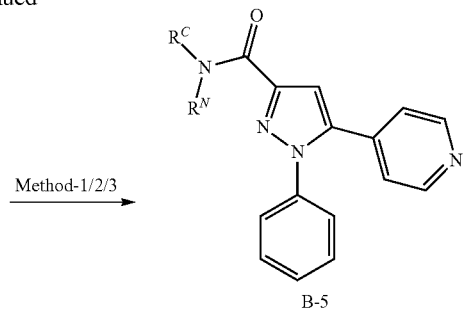

B-5

Method-1/2/3

Preparation of ethyl 2,4-dioxo-4-(pyridin-4-yl)butanoate (B-2)

A solution of 4-acetyl pyridine (10.0 g, 82.55 mmol) in diethyl ether (160 mL) was cooled to −78° C. followed by addition of LiHMDS (15.16 g, 90.80 mmol). The resulting reaction mixture was stirred at −78° C. for 45 min followed by dropwise addition of diethyl oxalate in about 30 min. The reaction mixture was then left to stir at room temperature for 16 h. After completion of the reaction (TLC and MS monitoring), the solution was then cooled 0° C. and the resulting precipitate was filtered to get the desired product as an off-white solid (18.0 g, 98%), which was carried forward to the next step without purification. $^1$H-NMR (400 MHz, DMSO-$d_6$): δ 8.66 (d, J=4.80 Hz, 2H), 7.70 (d, J=5.20 Hz, 2H), 6.43 (s, 1H), 4.15 (q, J=7.20 Hz, 2H) and 1.25 (t, J=7.20 Hz, 3H).

Preparation of ethyl 1-phenyl-5-(pyridin-4-yl)-1H-pyrazole-3-carboxylate (B-3)

To a solution of ethyl 2,4-dioxo-4-(pyridin-4-yl)butanoate B-2 (18 g, 81.45 mmol) in EtOH (500 mL) was added phenyl hydrazine hydrochloride (9.68 g, 89.59 mmol) and acetic acid (140.0 mL). The resulting reaction mixture was stirred at 90° C. for 3-4 h. After completion the reaction (TLC monitoring) the solvent was evaporated and the residue was directly purified over silica gel (100-200 Mesh, 10% EtOAc-hexane) to get the desired product (8.0 g, 33%). $^1$H-NMR (400 MHz, DMSO-$d_6$): δ 8.55 (d, J=6.0 Hz, 2H), 7.51 (m, 3H), 7.38 (m, 3H), 7.24 (m, 2H), 4.35 (q, J=7.20 Hz, 2H) and 1.32 (t, J=7.20 Hz, 3H).

Preparation of 1-phenyl-5-(pyridin-4-yl)-1H-pyrazole-3-carboxylic acid (B-4)

To an ice-cold solution of ethyl 1-phenyl-5-(pyridin-4-yl)-1H-pyrazole-3-carboxylate B-3 (5.50 g, 18.77 mmol) in EtOH (110 mL) was added dropwise an aqueous solution of sodium hydroxide (2.25 g dissolved in 5.50 mL $H_2O$). The resulting solution was stirred at room temperature for 4 h. After completion of the reaction (TLC monitoring), the solvent was evaporated, added $H_2O$ to the residue followed by extraction with EtOAc (2×100 mL). The organic layer was discarded and the pH of the aqueous layer was adjusted to ~4-5 by adding 1N HCl followed by extraction with EtOAc (3×200 mL). The combined organics were dried over anhydrous $Na_2SO_4$, filtered and concentrated under reduced pressure to get the desired product (3.0 g, 61%) as a white solid. $^1$H-NMR (400 MHz, DMSO-$d_6$): δ 13.11 (br s, 1H), 8.55 (d, J=5.60 Hz, 2H), 7.50 (m, 3H), 7.38 (m, 3H), 7.31 (s, 1H) and 7.23 (d, J=6.0 Hz, 2H).

Preparing Final Compounds Having Pyridinyl Ring A and Phenyl Ring B

Method 1:

To an ice-cold solution of 1-phenyl-5-(pyridin-4-yl)-1H-pyrazole-3-carboxylic acid 4 (0.10 g, 0.38 mmol, 1.0 eq), in DMF (2.0 mL) was added DIPEA (0.145 g, 1.13 mmol, 3.0 eq) and HATU (0.214 g, 0.56 mmol, 1.50 eq). The resulting mixture was stirred under nitrogen atmosphere at 0° C. for 15 min followed by addition of the respective amine (2.0 eq). The reaction mixture was then stirred at room temperature for 4-6 h. After the completion of the reaction (TLC monitoring), the solution was diluted with ice cold water (30 mL) followed by extraction with EtOAc (3×50 mL). The combined organics were washed with brine, dried over anhydrous $Na_2SO_4$, filtered and concentrated under reduced pressure. The crude residue was purified over silica gel (100-200 Mesh, 1-5% MeOH-DCM) to give the desired products generally in good to excellent yields (18-96%). Individual yields and solvent systems are shown in Table 1. Compounds 14, 31, 38 and 39 were directly obtained after the work-up by tritrating the residue with the solvents disclosed in Table 1. Compound 40 was purified via prep-TLC using the solvent system 5% MeOH-DCM.

Method 2:

To an ice-cold solution of 1-phenyl-5-(pyridin-4-yl)-1H-pyrazole-3-carboxylic acid 4 (0.10 g, 0.38 mmol, 1.0 eq) in DMA (5 mL) was added methanesulfonyl chloride (0.129 g, 1.13 mmol, 3.0 eq) and 2,6-lutidine (0.12 g, 1.13 mmol, 3.0 eq) dropwise. The resulting mixture was stirred under nitrogen atmosphere at 0° C. for 15 min followed by addition of the respective amine (1.30 eq) and then left to stir at 50° C. for 6 h. After completion of the reaction (TLC monitoring), the solution was then cooled to room temperature, diluted with ice-cold water (25-50 mL) followed by extraction with EtOAc (3×50 mL). The combined organics were washed with brine, dried over anhydrous $Na_2SO_4$, filtered and concentrated under reduced pressure. The crude residue was purified over silica gel (100-200 Mesh, 1-2% MeOH-DCM) to give the desired products in moderate yields (21-54%). Individual yields and the solvent system in which the compounds were eluted are in Table 1.

Method 3:

A mixture of 1-phenyl-5-(pyridin-4-yl)-1H-pyrazole-3-carboxylic acid 4 (0.10 g, 0.38 mmol, 1.0 eq) and $SOCl_2$ (0.15 g, 1.13 mmol, 3.0 eq) was heated to 90° C. for 2 h. After the completion of the reaction (TLC monitoring by adding MeOH to convert it to Me ester), the reaction mixture was concentrated under reduced pressure. Meanwhile in another RB flask, to an ice-cold solution of corresponding amine (1.50 eq with respect to the acid) in THF (5 mL) was added NaH (1.50 eq with respect to the acid or 1.0 eq with respect to the amine). The reaction mixture was stirred at room temperature for 1 h followed by addition of a solution of acid chloride thus generated in THF. The resulting reaction mixture was stirred at room temperature for 5-6 h. After the completion of the reaction (TLC monitoring), the reaction mass was quenched with ice-cold water and extracted with EtOAc (3×50 mL). The combined organics were washed with brine, dried over anhydrous $Na_2SO_4$, filtered and concentrated under reduced pressure. The crude residue was purified over silica gel (100-200 Mesh, 2-5% MeOH-DCM) to give the desired products in moderate yields (10-15%). Individual yields and the solvent system in which the compounds were eluted is provided in Table 1.

Analytical Instrument Details: The $^1$H-NMR spectra were obtained on Bruker 400 MHz spectrometer, while the LCMS analyses were performed on an Acquity C-18 column (2.10 mm×100 mm, 1.70 m) using the electrospray ionization (ESI) technique (make: Waters). Chemical shifts (δ) are expressed in parts per million (ppm) downfield by reference to tetramethylsilane as the internal standard. Splitting patterns are designated as s (singlet), d (doublet), t (triplet), q (quartet), m (multiplet) and br s (broad singlet). Coupling constants (J) are given in Hz.

Table 1 shows tabulated data of the final compounds including the method by which the final compounds were synthesized. The amines used in preparing the below compounds (via Methods 1, 2 or 3) are commercially available or can be synthesized by one of ordinary skill.

TABLE 1

Exemplary Compounds

| Cpd. ID | Structure | Method | Yield | Purification technique | LCMS | NMR data (DMSO-$d_6$, 400 MHz) |
|---|---|---|---|---|---|---|
| 4 | 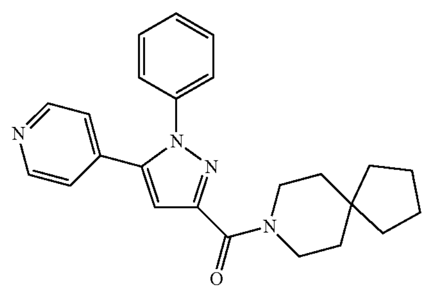 [SMILES: O=C(c1cc(-c2ccncc2)n(-c2ccccc2)n1)N1CCC2(CCCC2)CC1] | 1 | 36% | Column chromatography (2% MeOH-DCM) | 387.21 (M + H)$^+$, 97.49% | 8.50 (d, J = 4.80 Hz, 2H), 7.48 (m, 3H), 7.36 (m, 2H), 7.30 (d, J = 4.80 Hz, 2H), 7.07 (s, 1H), 3.93 (m, 2H), 3.76 (m, 2H), 1.67 (m, 4H) and 1.55-1.60 (m, 8H) |
| 6 | 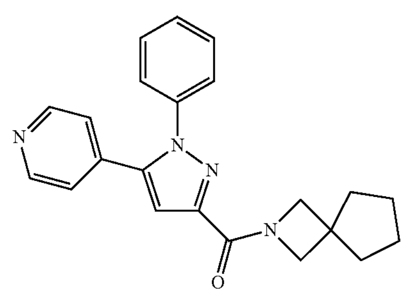 [SMILES: O=C(c1cc(-c2ccncc2)n(-c2ccccc2)n1)N1CC2(CCCC2)C1] | 1 | 26% | Column chromatography (1-2% MeOH-DCM) | 359.20 (M + H)$^+$, 96.08% | 8.55 (d, J = 5.20 Hz, 2H), 7.48 (m, 3H), 7.36 (m, 2H), 7.22 (m, 3H), 4.36 (s, 2H), 3.89 (s, 2H), 1.78 (br s, 4H) and 1.57 (br s, 4H) |
| 8 | 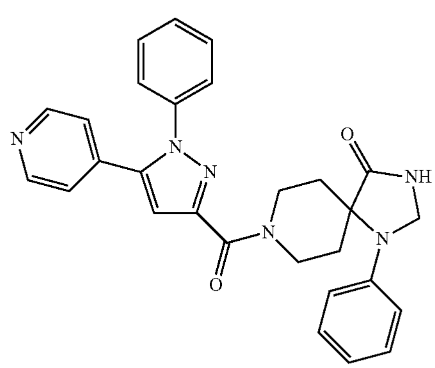 [SMILES: O=C(c1cc(-c2ccncc2)n(-c2ccccc2)n1)N1CCC2(CC1)C(=O)NCN2c1ccccc1] | 1 | 39% | Column chromatography (2-5% MeOH-DCM) | 479.23 (M + H)$^+$, 97.60% | 8.84 (br s, 1H), 8.56 (d, J = 5.60 Hz, 2H), 7.46 (m, 3H), 7.37 (m, 2H), 7.19-7.25 (m, 5H), 6.75 (m, 3H), 4.56-4.61 (m, 3H), 4.50 (m, 1H), 3.87 (m, 1H), 3.52 (m, 1H), 2.55 (m, 2H) and 1.75 (m, 2H) |

TABLE 1-continued

Exemplary Compounds

| Cpd. ID | Structure | Method | Yield | Purification technique | LCMS | NMR data (DMSO-d$_6$, 400 MHz) |
|---|---|---|---|---|---|---|
| 12 | 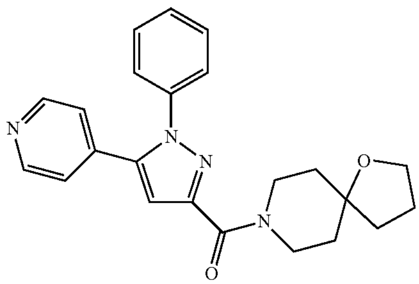 [SMILES: O=C(c1cc(-c2ccncc2)n(-c2ccccc2)n1)N1CCC2(CCCO2)CC1] | 1 | 43% | Column chromatography (1-2% MeOH-DCM) | 389.22 (M + H)$^+$, 93.94% | 8.55 (d, J = 5.20 Hz, 2H), 7.54 (m, 3H), 7.48 (m, 2H), 7.23 (m, 2H), 7.13 (s, 1H), 4.07 (m, 1H), 3.96 (m, 1H), 3.66-3.76 (m, 3H), 3.40 (m, 1H), 1.87 (m, 2H), 1.69 (m, 2H) and 1.59 (m, 4H) |
| 13 | 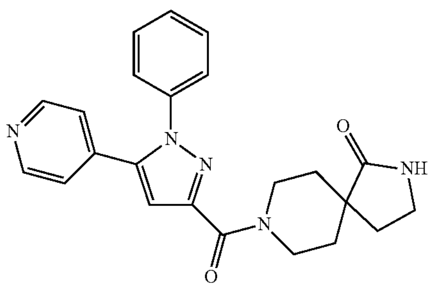 [SMILES: O=C(c1cc(-c2ccncc2)n(-c2ccccc2)n1)N1CCC2(CCNC2=O)CC1] | 1 | 35% | Column chromatography (2-5% MeOH-DCM) | 402.23 (M + H)$^+$, 96.39% | 8.55 (d, J = 5.20 Hz, 2H), 7.63 (br s, 1H), 7.49 (m, 3H), 7.37 (m, 2H), 7.24 (d, J = 5.20 Hz, 2H), 7.15 (s, 1H), 4.32-4.46 (m, 2H), 3.40 (m, 1H), 3.19 (m, 2H), 3.08 (m, 1H), 2.03 (m, 2H), 1.60-1.70 (m, 2H) and 1.40-1.48 (m, 2H) |
| 16 | 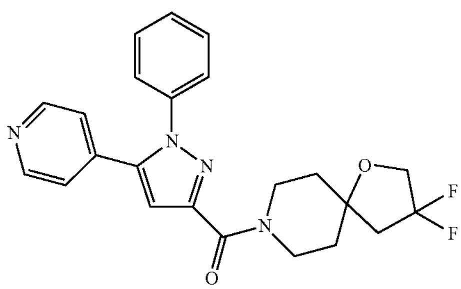 [SMILES: O=C(c1cc(-c2ccncc2)n(-c2ccccc2)n1)N1CCC2(CC1)CC(F)(F)CO2] | 1 | 20% | Column chromatography (2% MeOH-DCM) | 425.19 (M + H)$^+$, 97.81% | 8.55 (m, 2H), 7.49 (m, 3H), 7.37 (m, 2H), 7.23 (m, 2H), 7.14 (s, 1H), 3.93-4.14 (m, 4H), 3.71 (m, 1H), 3.43 (m, 1H), 2.38 (m, 2H) and 1.76 (m, 4H) |
| 18 | 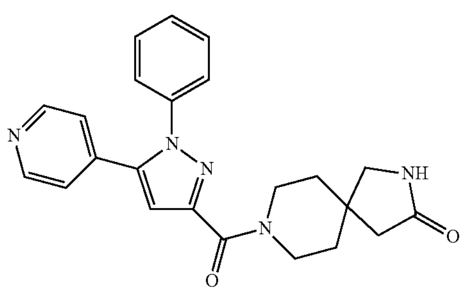 [SMILES: O=C1CC2(CCN(C(=O)c3cc(-c4ccncc4)n(-c4ccccc4)n3)CC2)CN1] | 1 | 96% | Column chromatography (2-5% MeOH-DCM) | 402.20 (M + H)$^+$, 97.0% | 8.55 (d, J = 4.80 Hz, 2H), 7.57 (br s, 1H), 7.48 (m, 3H), 7.37 (m, 2H), 7.23 (d, J = 5.20 Hz, 2H), 7.13 (s, 1H), 3.95-3.98 (m, 1H), 3.75 (m, 2H), 3.52 (m, 1H), 3.12 (br s, 2H), 2.13 (br s, 2H) and 1.59 (br s, 4H) |
| 25 | 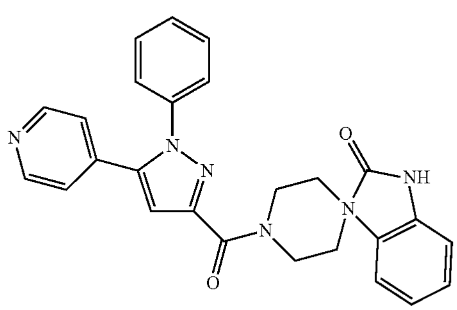 | 1 | 61% | Column chromatography (2-5% MeOH-DCM) | 465.22 (M + H)$^+$, 95.79% | 10.86 (br s, 1H), 8.56 (d, J = 5.60 Hz, 2H), 7.48 (m, 3H), 7.37 (m, 2H), 7.18-7.25 (m, 4H), 6.96 (m, 3H), 4.70-4.84 (m, 2H), 4.53 (m, 1H), 3.32 (m, 1H), 2.91 (m, 1H), 2.31 (m, 2H) and 1.79 (m, 2H) |

TABLE 1-continued

Exemplary Compounds

| Cpd. ID | Structure | Method | Yield | Purification technique | LCMS | NMR data (DMSO-d$_6$, 400 MHz) |
|---|---|---|---|---|---|---|
| 28 | 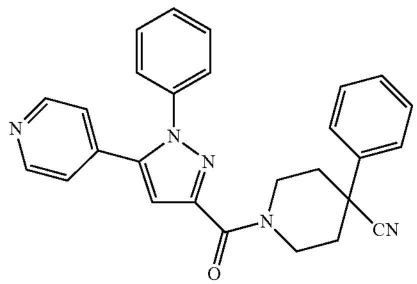 [SMILES: N#CC1(c2ccccc2)CCN(C(=O)c2cc(-c3ccncc3)n(-c3ccccc3)n2)CC1] | 1 | 55% | Column chromatography (2% MeOH-DCM) | 434.23 (M + H)$^+$, 98.27% | 8.61 (d, J = 5.60 Hz, 2H), 7.58 (d, J = 7.60 Hz, 2H), 7.31-7.50 (m, 8H), 7.32 (d, J = 6.0 Hz, 2H), 7.26 (s, 1H), 4.89 (m, 1H), 4.77 (m, 1H), 3.49 (m, 1H), 3.10 (m, 1H), 2.25 (m, 2H) and 2.10 (m, 2H) |
| 29 | 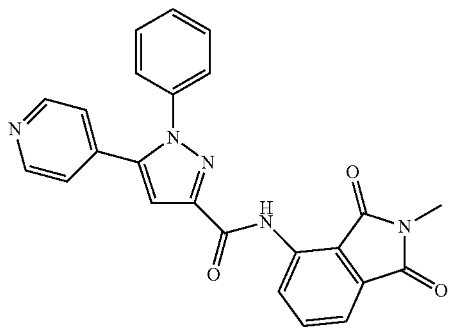 [SMILES: CN1C(=O)c2cccc(NC(=O)c3cc(-c4ccncc4)n(-c4ccccc4)n3)c2C1=O] | 1 | 33% | Column chromatography (2-5% MeOH-DCM) | 424.18 (M + H)$^+$, 94.76% | 10.91 (br s, 1H), 8.80 (d, J = 4.40 Hz, 1H), 8.58 (d, J = 4.80 Hz, 2H), 7.84 (t, J = 8.0 Hz, 1H), 7.58 (m, 4H), 7.47 (m, 3H), 7.29 (d, J = 5.20 Hz, 2H) and 3.02 (s, 3H) |
| 30 | 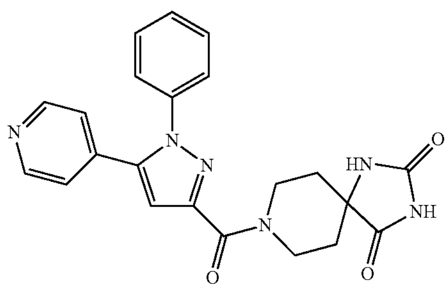 [SMILES: O=C1NC(=O)C2(CCN(C(=O)c3cc(-c4ccncc4)n(-c4ccccc4)n3)CC2)N1] | 1 | 22% | Column chromatography (2-5% MeOH-DCM) | 417.18 (M + H)$^+$, 98.45% | 8.54-8.67 (m, 4H), 7.48 (m, 3H), 7.38 (m, 2H), 7.19-7.23 (m, 3H), 4.47 (d, J = 8.40 Hz, 1H), 4.33 (d, J = 8.80 Hz, 1H), 3.60 (m, 1H), 3.28 (m, 1H), 1.84 (m, 2H) and 1.69 (m, 2H) |
| 31 | 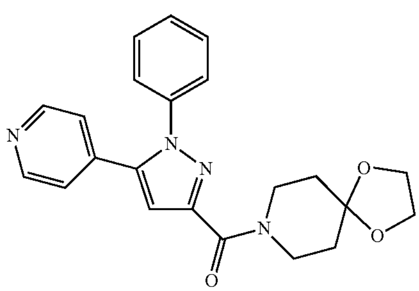 [SMILES: O=C(c1cc(-c2ccncc2)n(-c2ccccc2)n1)N1CCC2(CC1)OCCO2] | 1 | 77% | Triturating with n-pentane | 391.19 (M + H)$^+$, 98.18% | 8.55 (d, J = 5.20 Hz, 2H), 7.48 (m, 3H), 7.37 (m, 2H), 7.23 (d, J = 5.20 Hz, 2H), 7.16 (s, 1H), 3.92 (m, 6H), 3.71 (m, 2H) and 1.69 (m, 4H) |
| 32 | 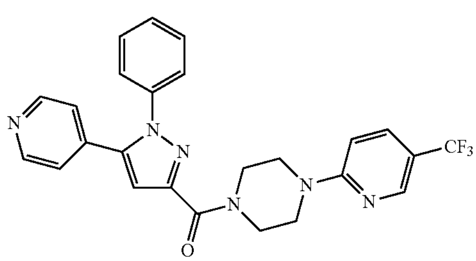 [SMILES: O=C(c1cc(-c2ccncc2)n(-c2ccccc2)n1)N1CCN(c2ccc(C(F)(F)F)cn2)CC1] | 1 | 24% | Column chromatography (2% MeOH-DCM) | 479.22 (M + H)$^+$, 99.12% | 8.56 (d, J = 5.60 Hz, 2H), 8.43 (s, 1H), 7.84 (d, J = 8.40 Hz, 1H), 7.49 (m, 3H), 7.40 (m, 2H), 7.22-7.25 (m, 3H), 6.99 (d, J = 8.80 Hz, 1H), 4.11 (br s, 2H) and 3.72 (br s, 6H) |

TABLE 1-continued

Exemplary Compounds

| Cpd. ID | Structure | Method | Yield | Purification technique | LCMS | NMR data (DMSO-d$_6$, 400 MHz) |
|---|---|---|---|---|---|---|
| 33 | 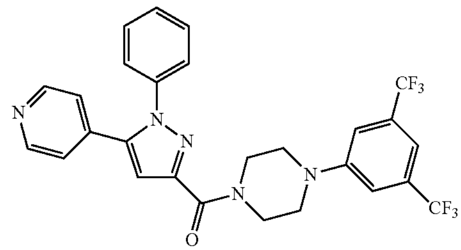 [SMILES: O=C(c1cc(-c2ccncc2)n(-c2ccccc2)n1)N1CCN(c2cc(C(F)(F)F)cc(C(F)(F)F)c2)CC1] | 1 | 57% | Column chromatography (2% MeOH-DCM) | 546.24 (M + H)$^+$, 98.67% | 8.56 (d, J = 3.60 Hz, 2H), 7.50 (m, 5H), 7.40 (m, 2H), 7.33 (s, 1H), 7.22-7.25 (m, 3H), 4.17 (br s, 2H), 3.82 (br s, 2H) and 3.46-3.49 (m, 4H) |
| 34 | 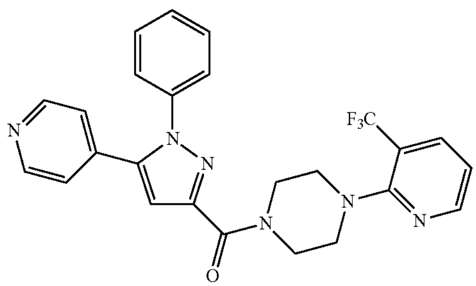 [SMILES: O=C(c1cc(-c2ccncc2)n(-c2ccccc2)n1)N1CCN(c2ncccc2C(F)(F)F)CC1] | 1 | 50% | Column chromatography (2% MeOH-DCM) | 479.22 (M + H)$^+$, 92.47% | 8.56 (m, 3H), 8.11 (d, J = 7.60 Hz, 1H), 7.50 (m, 3H), 7.40 (m, 2H), 7.24 (m, 3H), 7.19 (s, 1H), 4.08 (br s, 2H), 3.81 (br s, 2H) and 3.25 (br s, 4H) |
| 35 | 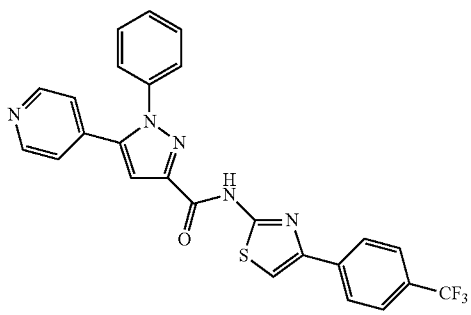 [SMILES: O=C(Nc1nc(-c2ccc(C(F)(F)F)cc2)cs1)c1cc(-c2ccncc2)n(-c2ccccc2)n1] | 3 | 15% | Column chromatography (2-5% MeOH-DCM) | 492.09 (M + H)$^+$, 95.88% | 12.70 (br s, 1H), 8.60 (d, J = 5.20 Hz, 2H), 8.18 (d, J = 8.0 Hz, 2H), 7.97 (s, 1H), 7.83 (d, J = 8.0 Hz, 2H), 7.59 (s, 1H), 7.46-7.52 (m, 5H) and 7.28 (d, J = 5.20 Hz, 2H) |
| 36 | 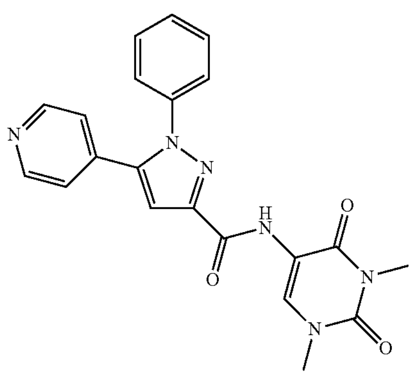 [SMILES: Cn1cc(NC(=O)c2cc(-c3ccncc3)n(-c3ccccc3)n2)c(=O)n(C)c1=O] | 1 | 88% | Column chromatography (2-5% MeOH-DCM) | 403.16 (M + H)$^+$, 98.74% | 9.13 (s, 1H), 8.56 (d, J = 4.80 Hz, 2H), 8.47 (s, 1H), 7.53 (m, 3H), 7.44 (m, 2H), 7.38 (s, 1H), 7.27 (d, J = 4.80 Hz, 2H), 3.39 (s, 3H) and 3.24 (s, 3H) |
| 37 | 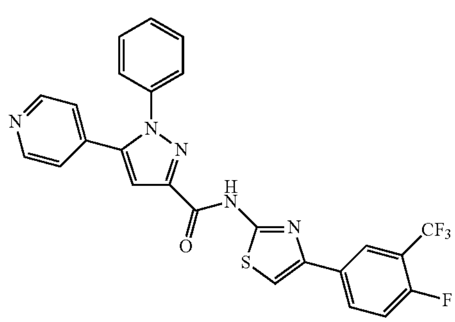 [SMILES: O=C(Nc1nc(-c2ccc(F)c(C(F)(F)F)c2)cs1)c1cc(-c2ccncc2)n(-c2ccccc2)n1] | 3 | 10% | Column chromatography (2-5% MeOH-DCM) | 510.12 (M + H)$^+$, 94.04% | 12.67 (br s, 1H), 8.60 (d, J = 5.20 Hz, 2H), 8.34 (m, 2H), 7.96 (s, 1H), 7.46-7.65 (m, 7H) and 7.27 (d, J = 5.20 Hz, 2H) |

TABLE 1-continued

Exemplary Compounds

| Cpd. ID | Structure | Method | Yield | Purification technique | LCMS | NMR data (DMSO-$d_6$, 400 MHz) |
|---|---|---|---|---|---|---|
| 38 | 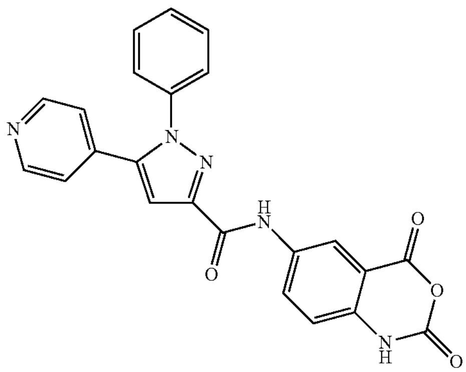 [SMILES: O=C(Nc1ccc2[nH]c(=O)oc(=O)c2c1)c1cc(-c2ccncc2)n(-c2ccccc2)n1] | 1 | 19% | Triturating with diethyl ether-MeOH (1:1) | 426.12 (M + H)$^+$, 96.14% | 11.71 (br s, 1H), 10.58 (br s, 1H), 8.57 (d, J = 5.60 Hz, 2H), 8.50 (s, 1H), 8.14 (d, J = 6.40 Hz, 1H), 7.52 (m, 3H), 7.48 (m, 2H), 7.41 (s, 1H), 7.28 (d, J = 5.20 Hz, 2H) and 7.16 (d, J = 4.80 Hz, 1H) |
| 39 | 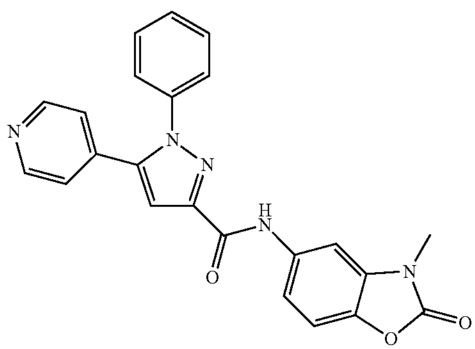 [SMILES: Cn1c(=O)oc2ccc(NC(=O)c3cc(-c4ccncc4)n(-c4ccccc4)n3)cc21] | 1 | 70% | Triturating with n-pentane and diethyl ether (1:1) | 412.14 (M + H)$^+$, 96.25% | 10.37 (br s, 1H), 8.57 (d, J = 5.60 Hz, 2H), 7.82 (s, 1H), 7.53 (m, 4H), 7.47 (m, 2H), 7.39 (s, 1H), 7.26-7.31 (m, 3H) and 3.33 (s, 3H) |
| 40 | 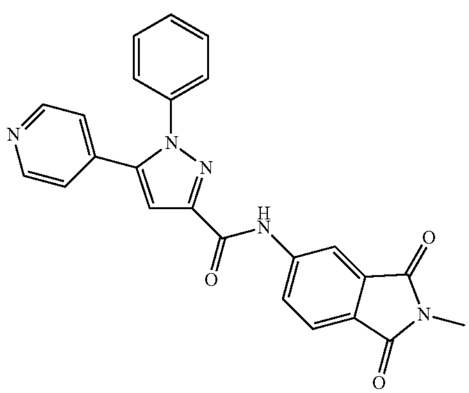 [SMILES: CN1C(=O)c2ccc(NC(=O)c3cc(-c4ccncc4)n(-c4ccccc4)n3)cc2C1=O] | 1 | 44% | Prep-TLC (5% MeOH-DCM) | 424.11 (M + H)$^+$, 99.70% | 10.90 (br s, 1H), 8.57 (d, J = 6.0 Hz, 2H), 8.42 (d, J = 1.20 Hz, 1H), 8.22 (dd, J = 1.60 and 8.0 Hz respectively, 1H), 7.86 (d, J = 8.0 Hz, 1H), 7.54 (m, 3H), 7.46-7.50 (m, 3H), 7.27 (m, 2H) and 3.02 (s, 3H) |

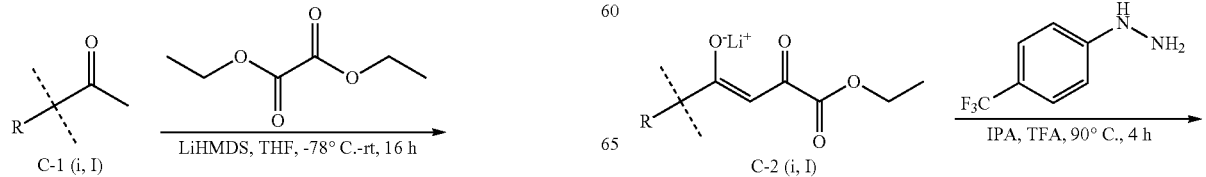

Scheme C

-continued

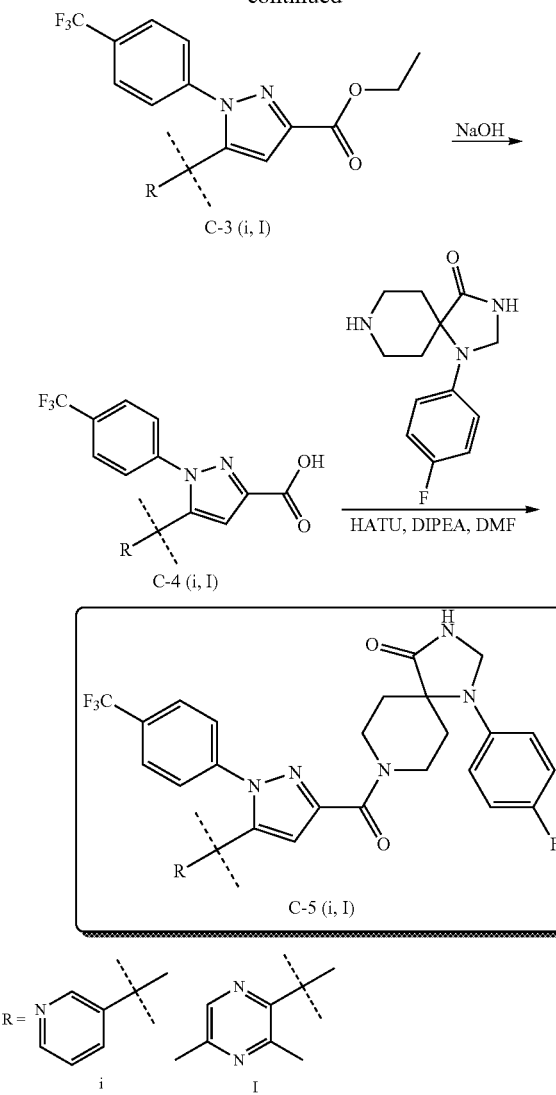

General Procedure for the Preparation of Compounds C-2 (i, l):

A solution of compound C-1 (i, l) (1 eq) in diethyl ether was cooled to −78° C. followed by addition of LiHMDS (1.10 eq). The resulting reaction mixture was stirred at −78° C. for 45 min followed by dropwise addition of diethyl oxalate (1.20 eq) in about 30 min. The reaction mixture was then left to stir at room temperature for 16 h. After completion of the reaction (TLC and MS monitoring), the solution was then cooled 0° C. and the resulting precipitate was filtered to get the desired product as off-white solids C-2 (i, l), which were carried forward to the next step without purification.

4-Ethoxy-3,4-dioxo-1-(pyridin-3-yl)but-1-en-1-olate Lithium Salt (C-2i)

$^1$H-NMR (400 MHz, DMSO-d$_6$): δ 8.97 (s, 1H), 7.70 (s, 1H), 8.14 (m, 1H), 7.43 (m, 1H), 6.41 (s, 1H), 4.13 (q, J=6.8 Hz, 2H) and 1.23 (t, J=7.2 Hz, 3H). MS: 220.12 (M−H)$^+$. Yield: 88%.

1-(3,5-Dimethylpyrazin-2-yl)-4-ethoxy-3,4-dioxobut-1-en-1-olate Lithium Salt (C-2l)

$^1$H-NMR (400 MHz, DMSO-d$_6$): δ 8.40 (s, 1H), 6.35 (s, 1H), 4.12 (q, J=7.2 Hz, 2H), 2.55 (s, 3H), 2.32 (s, 3H) and 1.21 (t, J=6.8 Hz, 3H). MS: 249.09 (M−H)$^+$. Yield: 96%.

General Procedure for the Preparation of Compounds C-3 (i, l):

To an ice-cold solution of compound C-2 (i, l), (1.0 eq) in IPA was added (4-(trifluoromethyl)phenyl) hydrazine (1.10 eq) and TFA (2.0 eq). The resulting reaction mixture was warmed up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 Mesh, 10-15% EtOAc-hexane) to get the desired products C-3 (i, l).

Ethyl 5-(pyridin-3-yl)-1-(4-(trifluoromethyl)phenyl)-1H-pyrazole-3-carboxylate (C-3i)

LCMS: 362.14 (M+H)$^+$, 90.26%. Yield: 71%.

Ethyl 5-(3,5-dimethylpyrazin-2-yl)-1-(4-(trifluoromethyl)phenyl)-1H-pyrazole-3-carboxylate (C-3l)

$^1$H-NMR (400 MHz, CDCl$_3$): δ 8.46 (s, 1H), 7.76 (d, J=8.4 Hz, 2H), 7.44 (d, J=8.0 Hz, 2H), 7.33 (s, 1H), 3.99 (q, J=7.20 Hz, 2H), 2.43 (s, 3H), 2.26 (s, 3H) and 1.15 (t, J=7.2 Hz, 3H). Yield: 26%.

General Procedure for the Preparation of Compounds C-4 (i, l):

To an ice-cold solution of compound C-3 (i, l) (1.0 eq) in EtOH, an aqueous solution of sodium hydroxide (3.0 eq) was added dropwise. The resulting solution was stirred at room temperature for 4 h. After completion of the reaction (TLC monitoring), the solvent was evaporated, H$_2$O added to the residue followed by extraction with EtOAc (2×100 mL). The organic layer was discarded and the pH of the aqueous layer was adjusted to ~6 by adding 1N HCl. The resulting precipitate was filtered and dried under vacuum to get the desired products C-4 (i, l) as white solids.

5-(Pyridin-3-yl)-1-(4-(trifluoromethyl)phenyl)-1H-pyrazole-3-carboxylic Acid (C-4i)

$^1$H-NMR (400 MHz, DMSO-d$_6$): δ 8.56 (dd, J=1.6 & 4.8 Hz respectively, 1H), 8.52 (d, J=1.6 Hz, 1H), 7.82 (d, J=8.4 Hz, 2H), 7.66 (d, J=8.0 Hz, 1H), 7.55 (d, J=8.4 Hz, 2H), 7.40 (m, 1H) and 7.11 (s, 1H). LCMS: 334.11 (M+H)$^+$, 97.80%. Yield: 83%.

5-(3,5-Dimethylpyrazin-2-yl)-1-(4-(trifluoromethyl)phenyl)-1H-pyrazole-3-carboxylic Acid (C-4l)

$^1$H-NMR (400 MHz, DMSO-d$_6$): δ 8.46 (s, 1H), 7.76 (d, J=8.4 Hz, 2H), 7.44 (d, J=8.0 Hz, 2H), 7.33 (s, 1H), 2.43 (s, 3H) and 2.26 (s, 3H). LCMS: 363.16 (M+H)$^+$, 97.35%. Yield: 67.50%.

General Procedure for the Preparation of Final Compounds C-5 (i, l):

To an ice-cold solution of carboxylic acids C-4 (i, l) (1.0 eq), in DMF (2.0 mL) was added DIPEA (3.0 eq) and HATU (1.50 eq). The resulting mixture was stirred under nitrogen atmosphere at 0° C. for 15 min followed by addition of the 1-(4-fluorophenyl)-1,3,8-triazaspiro[4.5]decan-4-one (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-TLC using the solvent system 3-5% MeOH-DCM. The final step was performed on a 50-100 mg scale.

In some embodiments, 1-(4-fluorophenyl)-1,3,8-triazaspiro[4.5]decan-4-one is made according to Synthetic Scheme D.

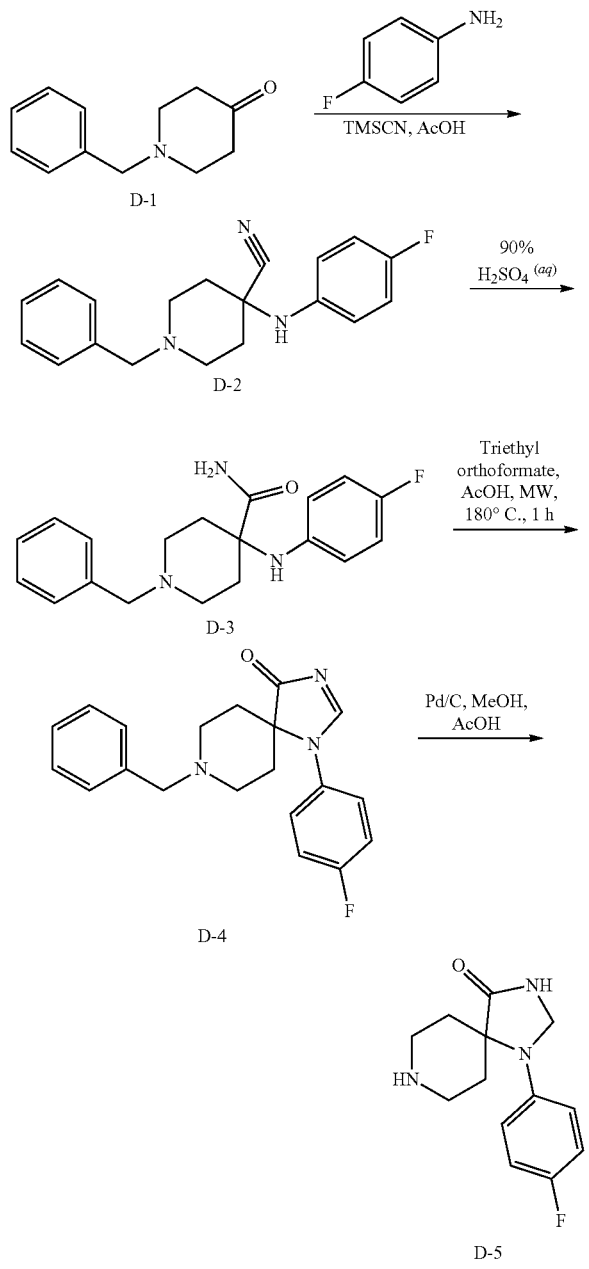

Preparation of 1-benzyl-4-(4-fluorophenylamino) piperidine-4-carbonitrile (D-2)

To an ice-cold solution of 1-benzylpiperidin-4-one (D-1) (25 g, 132.10 mmol) in acetic acid (80 mL) was added 4-fluoroaniline (14.0 mL, 145.31 mmol) and trimethylsilyl cyanide (26.42 mL, 198.15 mmol). The resulting reaction mass was stirred at RT for 18 h. After completion of the reaction (TLC monitoring), the reaction mass was cooled to 0° C. and the pH adjusted to ~10 using 5.0 N sodium hydroxide solution. The aqueous part was extracted with DCM (3×250 mL). The combined organics were dried over anhydrous Na$_2$SO$_4$, filtered and concentrated. The crude was triturated with diethyl ether to get the desired product D-2 (30 g, 75%) as a pale yellow solid. $^1$H-NMR (400 MHz, CDCl$_3$): δ 7.32-7.34 (m, 5H), 6.91-6.94 (m, 4H), 3.55 (s, 2H), 3.47 (br s, 1H), 2.81-2.84 (m, 2H), 2.39-2.45 (m, 2H), 2.21-2.24 (m, 2H) and 1.87-1.94 (m, 2H). LC-MS: 310.13 (M+H)$^+$, 96.16%.

Preparation of 1-benzyl-4-(4-fluorophenylamino) piperidine-4-carboxamide (D-3)

To an ice-cold solution of 1-benzyl-4-(4-fluorophenylamino)piperidine-4-carbonitrile (D-2) (30 g, 97.06 mmol) was added 90% aqueous sulphuric acid (150 mL) and the resulting reaction mixture was stirred at room temperature for 16 h. After completion of the reaction (TLC monitoring), the reaction mass was cooled to 0° C. and the pH adjusted to ~10 using 5.0 N sodium hydroxide solution. The aqueous part was extracted with DCM (3×250 mL). The combined organics were dried over anhydrous sodium sulphate, filtered and concentrated. The crude was triturated with diethyl ether to get the desired product D-3 (27 g, 87%) as an off-white solid. $^1$H-NMR (400 MHz, CDCl$_3$): δ 7.23-7.30 (m, 5H), 6.87-6.91 (m, 3H), 6.55-6.59 (m, 2H), 5.47 (br s, 1H), 3.93 (s, 1H), 3.48 (s, 2H), 2.72-2.75 (m, 2H), 2.28-2.35 (m, 2H), 2.04-2.10 (m, 2H) and 1.86-1.89 (m, 2H). LCMS: 328.12 (M+H)$^+$, 99.60%.

Preparation of 8-benzyl-1-(4-fluorophenyl)-1,3,8-triazaspiro[4.5]dec-2-en-4-one (D-4)

A solution of 1-benzyl-4-(4-fluorophenylamino)piperidine-4-carboxamide (2.50 g, 7.63 mmol) in triethylorthoformate (3.20 mL) and AcOH (1.20 mL) was irradiated by microwave in a sealed tube to 180° C. for 30 min. The reaction mixture was diluted with water and extracted with EtOAc (3×100 mL). The combined organics were washed with brine, dried over anhydrous Na$_2$SO$_4$, filtered and concentrated. The residue was purified over silica gel (100-200 M, 4% MeOH-DCM) to get the desired product D-4 (1.20 g, 60%) as a pale yellow solid. LCMS: 338.22 (M+H)$^+$, 82.22%.

Preparation of 1-(4-fluorophenyl)-1,3,8-triazaspiro [4.5]decan-4-one (D-5)

To a solution of 8-benzyl-1-(4-fluorophenyl)-1,3,8-triazaspiro[4.5]dec-2-en-4-one (1.30 g, 3.85 mmol) in MeOH (16 mL) and AcOH (0.40 mL) were added 10% Pd—C (0.34 g) and the resulting solution was stirred under hydrogen atmosphere (1 atm) at ambient temperature for 16 h. The reaction mixture was filtered through a diatomaceous earth (Celite™) bed and the filtrate was concentrated under reduced pressure to get the desired product D-5 (0.95 g, 99%) as an off-white solid, which was used as such for the next step without further purification. LCMS: 250.13 (M+H)$^+$, 81.19%.

Scheme D can be modified to provide substitutions at positions other than the 4-position on the phenyl ring as well as provide substitutions other than fluorine.

Table 2 shows individual compounds yields for compounds made according to schemes C and D:

TABLE 2

| | Exemplary Compounds | | | |
|---|---|---|---|---|
| Cpd. ID | Structure | Yield (%) | LCMS | NMR data (DMSO-$d_6$, 400 MHz), unless otherwise specified |
| 49 | | 8 | 565.46 (M + H)+, 95.45% | δ 8.80 (br s, 1H), 8.59 (dd, J = 1.60 and 4.80 Hz, respectively, 1H), 8.55 (d, J = 2.0 Hz, 1H), 7.83 (d, J = 8.80 Hz, 2H), 7.67-7.70 (m, 1H), 7.56 (d, J = 8.40 Hz, 2H), 7.42-7.45 (m, 1H), 7.16 (s, 1H), 7.07-7.14 (m, 2H), 6.84-6.88 (m, 2H), 4.59 (d, J = 3.20 Hz, 2H), 4.42-4.52 (m, 2H), 3.88 (m, 1H), 3.53 (m, 1H), 2.20-2.32 (m, 2H) and 1.74-1.83 (m, 2H) |
| 52 | | 12 | 594.45 (M + H)+, 99.83% | δ 8.81 (br s, 1H), 8.47 (s, 1H), 7.75 (d, J = 8.40 Hz, 2H), 7.44 (d, J = 8.40 Hz, 2H), 7.22 (s, 1H), 7.10 (t, J = 8.80 Hz, 2H), 6.85-6.88 (m, 2H), 4.59 (d, J = 3.20 Hz, 2H), 4.43-4.51 (m, 2H), 3.90 (t, J = 12.40 Hz, 1H), 3.55 (t, J = 10.40 Hz, 1H), 2.43 (s, 3H), 2.27-2.32 (m, 5H) and 1.75-1.84 (m, 2H) |

In some embodiments, disclosed compounds are made according to Scheme E.

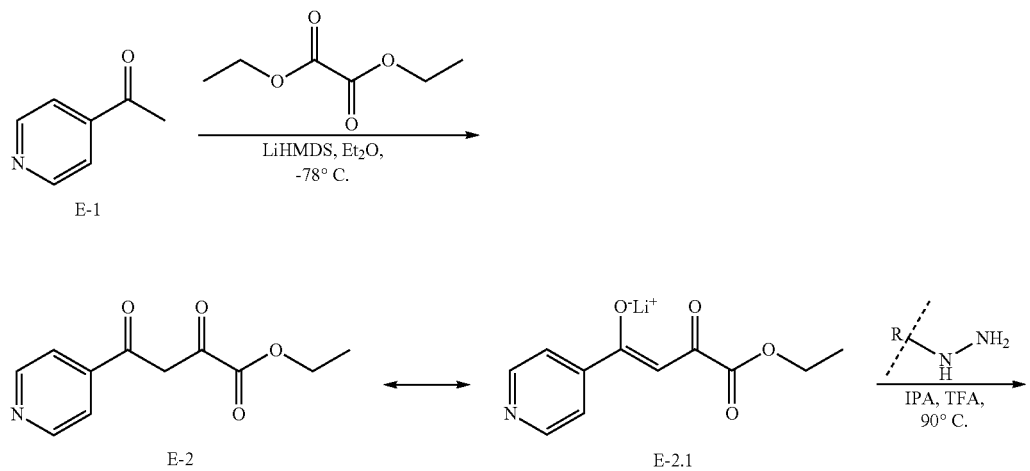

Scheme E

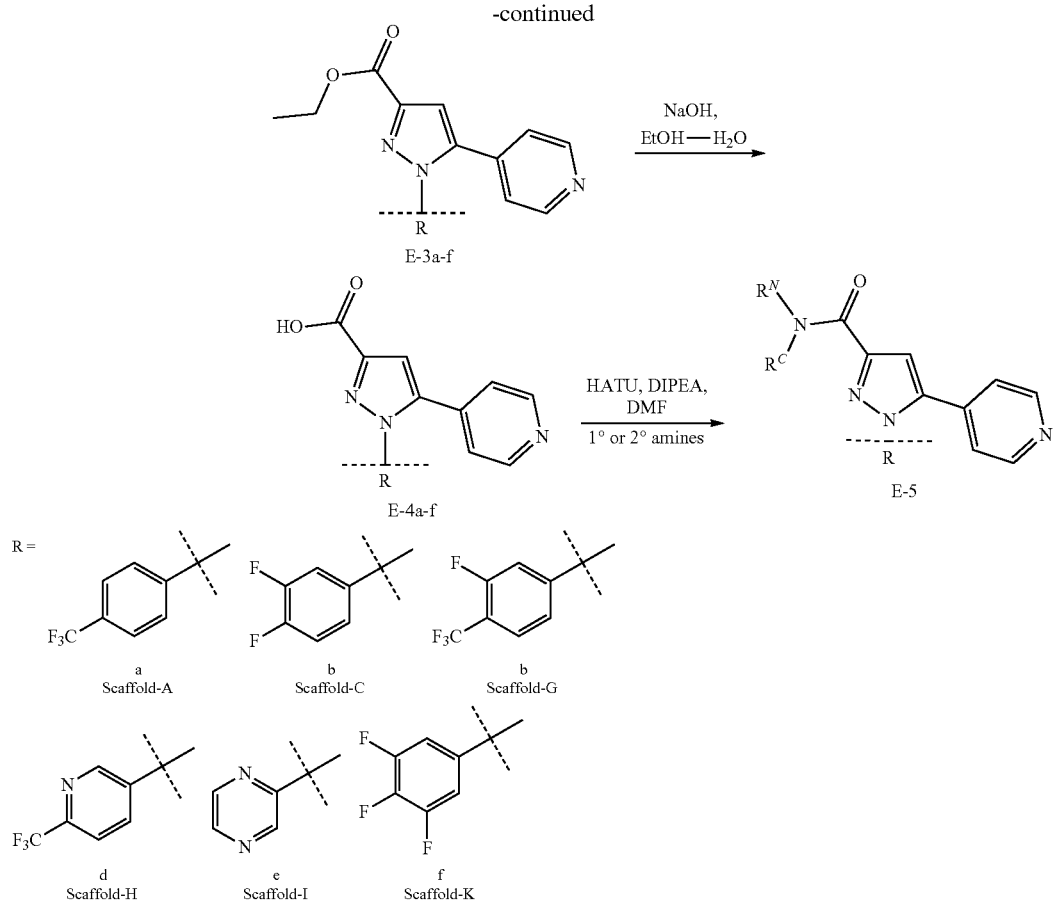

Preparation of ethyl 2,4-dioxo-4-(pyridin-4-yl)butanoate (E-2)

A solution of 4-acetyl pyridine (10.0 g, 82.55 mmol) in di-ethyl ether (160 mL) was cooled to −78° C. followed by addition of LiHMDS (15.16 g, 90.80 mmol). The resulting reaction mixture was stirred at −78° C. for 45 min followed by dropwise addition of diethyl oxalate (13.5 mL, 98.92 mmol) in about 30 min. The reaction mixture was then left to stir at room temperature for 16 h. After completion of the reaction (TLC and MS monitoring), the solution was then cooled 0° C. and the resulting precipitate was filtered to get the desired product as an off-white solid (18.0 g, 98%), which was carried forward to the next step without purification.

$^1$H-NMR (400 MHz, DMSO-$d_6$): δ 8.66 (d, J=4.80 Hz, 2H), 7.70 (d, J=5.20 Hz, 2H), 6.43 (s, 1H), 4.15 (q, J=7.20 Hz, 2H) and 1.25 (t, J=7.20 Hz, 3H).

General Procedure for the Preparation of Compounds E-3a-f:

To an ice-cold solution of ethyl 2,4-dioxo-4-(pyridin-4-yl)butanoate E-2 (1.0 eq) in IPA was added a respective hydrazine (1.10 eq) and TFA (2.0 eq). The resulting reaction mixture was warmed up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 Mesh, 10-15% EtOAc-hexane) to get the desired product.

Ethyl 5-(pyridin-4-yl)-1-(4-(trifluoromethyl)phenyl)-1H-pyrazole-3-carboxylate (E-3a)

$^1$H-NMR (400 MHz, CDCl$_3$): δ 8.61 (d, J=6.0 Hz, 2H), 7.66 (d, J=8.4 Hz, 2H), 7.47 (d, J=8.4 Hz, 2H), 7.17 (s, 1H), 7.11 (m, 2H), 4.44 (q, J=7.20 Hz, 2H) and 1.41 (t, J=7.20 Hz, 3H). LCMS: 362.21 (M+H)$^+$, 99.95%. Yield: 50%.

Ethyl 1-(3,4-difluorophenyl)-5-(pyridin-4-yl)-1H-pyrazole-3-carboxylate (E-3b)

$^1$H-NMR (400 MHz, CDCl$_3$): δ 8.61 (d, J=6.0 Hz, 2H), 7.31 (m, 1H), 7.30 (s, 1H), 7.19 (m, 1H), 7.04 (m, 2H), 7.01 (m, 1H), 4.43 (q, J=7.20 Hz, 2H) and 1.39 (t, J=7.20 Hz, 3H). LCMS: 330.14 (M+H)$^+$, 93.07%. Yield: 55%.

Ethyl 1-(3-fluoro-4-(trifluoromethyl)phenyl)-5-(pyridin-4-yl)-1H-pyrazole-3-carboxylate (E-3c)

$^1$H-NMR (400 MHz, CDCl$_3$): δ 8.68 (dd, J=1.6 & 4.40 Hz, 2H), 7.60 (m, 1H), 7.36 (m, 1H), 7.14 (m, 4H), 4.44 (q, J=7.20 Hz, 2H) and 1.39 (t, J=6.80 Hz, 3H). MS: 380.0 (M+H)$^+$. Yield: 45%.

Ethyl 5-(pyridin-4-yl)-1-(6-(trifluoromethyl)pyridin-3-yl)-1H-pyrazole-3-carboxylate (E-3d)

$^1$H-NMR (400 MHz, CDCl$_3$): δ 8.67 (m, 3H), 7.92 (dd, J=2.0 & 8.40 Hz, 1H), 7.76 (s, 1H), 7.18 (m, 3H), 4.45 (q,

J=7.20 Hz, 2H) and 1.42 (t, J=6.80 Hz, 3H). LCMS: 362.89 (M+H)+, 98.45%. Yield: 50%.

Ethyl 1-(pyrazin-2-yl)-5-(pyridin-4-yl)-1H-pyrazole-3-carboxylate (E-3e)

$^1$H-NMR (400 MHz, CDCl$_3$): δ 9.21 (d, J=1.20 Hz, 1H), 8.62 (m, 2H), 8.60 (m, 1H), 8.23 (dd, J=1.2 & 2.40 Hz, 1H), 7.17 (d, J=6.0 Hz, 2H), 7.14 (s, 1H), 4.45 (q, J=7.20 Hz, 2H) and 1.42 (t, J=6.80 Hz, 3H). LCMS: 296.18 (M+H)+, 96.22%. Yield: 30%.

Ethyl 5-(pyridin-4-yl)-1-(3,4,5-trifluorophenyl)-1H-pyrazole-3-carboxylate (E-3f)

$^1$H-NMR (400 MHz, CDCl$_3$): δ 8.72 (d, J=5.60 Hz, 2H), 7.31 (m, 2H), 7.21 (s, 1H), 7.05 (m, 2H), 4.47 (q, J=6.80 Hz, 2H) and 1.43 (t, J=6.80 Hz, 3H). MS: 348.12 (M+H)+. Yield: 76%.

General Procedure for the Preparation of Compounds E-4a-f:

To an ice-cold solution of compound (E-3a-f) (1.0 eq) in EtOH was added dropwise an aqueous solution of sodium hydroxide (3.0 eq). The resulting solution was stirred at room temperature for 4 h. After completion of the reaction (TLC monitoring), the solvent was evaporated, H$_2$O added to the residue followed by extraction with EtOAc (2×100 mL). The organic layer was discarded and the pH of the aqueous layer was adjusted to ~6 by adding 1N HCl. The resulting precipitate was filtered and dried under vacuum to get the desired product (60-80%) as a white solid.

5-(Pyridin-4-yl)-1-(4-(trifluoromethyl)phenyl)-1H-pyrazole-3-carboxylic Acid (E-4a)

Scaffold A. $^1$H-NMR (400 MHz, DMSO-d$_6$): δ 12.84 (br s, 1H), 8.58 (d, J=5.60 Hz, 2H), 7.87 (d, J=8.4 Hz, 2H), 7.59 (d, J=8.4 Hz, 2H), 7.28 (m, 3H). LCMS: 334.13 (M+H)+, 97.98%. Yield: 95%.

1-(3,4-Difluorophenyl)-5-(pyridin-4-yl)-1H-pyrazole-3-carboxylic Acid (E-4b)

Scaffold C. $^1$H-NMR (400 MHz, DMSO-d$_6$): δ 13.17 (br s, 1H), 8.57 (d, J=5.60 Hz, 2H), 7.69 (m, 1H), 7.54 (m, 1H), 7.22 (m, 4H). MS: 302.18 (M+H)+. Yield: 78%.

1-(3-Fluoro-4-(trifluoromethyl)phenyl)-5-(pyridin-4-yl)-1H-pyrazole-3-carboxylic Acid (E-4c)

Scaffold G. $^1$H-NMR (400 MHz, DMSO-d$_6$): δ 8.60 (d, J=5.6 Hz, 2H), 7.88 (m, 1H), 7.67 (s, 1H), 7.32 (m, 4H). LCMS: 352.17 (M+H)+, 98.60%. Yield: 92%.

5-(Pyridin-4-yl)-1-(6-(trifluoromethyl)pyridin-3-yl)-1H-pyrazole-3-carboxylic Acid (E-4d)

Scaffold H. $^1$H-NMR (400 MHz, DMSO-d$_6$): δ 13.07 (br s, 1H), 8.81 (s, 1H), 8.60 (d, J=6.0 Hz, 2H), 8.05 (m, 2H), 7.34 (m, 3H). LCMS: 335.13 (M+H)+, 97.97%. Yield: 75%.

1-(Pyrazin-2-yl)-5-(pyridin-4-yl)-1H-pyrazole-3-carboxylic Acid (E-4e)

Scaffold I. $^1$H-NMR (400 MHz, DMSO-d$_6$): δ 13.40 (br s, 1H), 9.15 (s, 1H), 8.75 (d, J=6.4 Hz, 1H), 8.56 (m, 2H), 8.43 (s, 1H), 7.33 (s, 3H). LCMS: 268.17 (M+H)+, 99.0%. Yield: 74%.

5-(pyridin-4-yl)-1-(3,4,5-trifluorophenyl)-1H-pyrazole-3-carboxylic Acid (E-4f)

Scaffold K. $^1$H-NMR (400 MHz, DMSO-d$_6$): δ 8.58 (d, J=5.60 Hz, 2H), 7.58 (m, 2H), 7.29 (d, J=6.0 Hz, 2H) and 7.16 (s, 1H). LCMS: 320.09 (M+H)+, 94.66%. Yield: 91%.

General Procedure for the Preparation of Final Compounds (E-5):

To an ice-cold solution of carboxylic acids E-4 (a-f) (1.0 eq), in DMF (2.0 mL) was added DIPEA (3.0 eq) and HATU (1.50 eq). The resulting mixture was stirred under nitrogen atmosphere at 0° C. for 15 min followed by addition of the respective amine (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-TLC using the solvent systems 3-5% MeOH-DCM. The final step was performed on 50-100 mg scale.

Where needed, 1-(4-fluorophenyl)-1,3,8-triazaspiro[4.5]decan-4-one is made according to Synthetic Scheme D. Scheme D can be modified to provide substitutions at positions other than the 4-position on the phenyl ring as well as provide substitutions other than fluorine. Other amines used in the preparation of the final compounds illustrated in Table 5 according to Scheme E are commercially available or can be synthesized by one of ordinary skill.

TABLE 5

| | Exemplary Compounds | | | |
|---|---|---|---|---|
| Cpd ID | Structure | Yield (%) | LCMS | NMR data (DMSO-d$_6$, 400 MHz), unless otherwise specified |
| 54 | 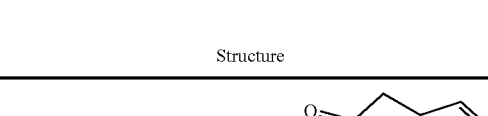 | 48% | 532.18 (M + H)+, 91.71% | δ 8.60-8.61 (m, 2H), 7.87 (d, J = 8.40 Hz, 2H), 7.61 (d, J = 8.40 Hz, 2H), 7.31 (m, 2H), 7.22-7.26 (m, 3H), 7.15-1.17 (m, 1H), 6.97-7.0 (m, 1H), 4.68-4.76 (m, 2H), 4.42 (m, 1H), 3.53 (s, 2H), 2.94 (m, 1H), 2.68 (m, 1H), 2.28-2.39 (m, 2H) and 1.59-1.79 (m, 2H) |

TABLE 5-continued

| | | Exemplary Compounds | | |
|---|---|---|---|---|
| Cpd ID | Structure | Yield (%) | LCMS | NMR data (DMSO-$d_6$, 400 MHz), unless otherwise specified |
| 55 | | 35% | 565.19 (M + H)$^+$, 94.13% | δ 8.80 (br s, 1H), 8.59-8.61 (m, 2H), 7.85 (d, J = 8.0 Hz, 2H), 7.58 (d, J = 8.0 Hz, 2H), 7.30 (m, 2H), 7.21 (s, 1H), 7.09 (t, J = 8.40 Hz, 1H), 6.86 (m, 2H), 4.59 (s, 2H), 4.46 (m, 2H), 3.88 (m, 1H), 3.54 (m, 1H), 2.19-2.30 (m, 2H) and 1.74-1.78 (m, 2H) |
| 56 | | 31% | 581.39 (M + H)$^+$, 95.05% | δ 8.88 (br s, 1H), 8.61 (d, J = 5.20 Hz, 2H), 7.85 (d, J = 8.0 Hz, 2H), 7.59 (d, J = 8.0 Hz, 2H), 7.32 (d, J = 5.60 Hz, 2H), 7.24-7.26 (m, 3H), 6.77 (d, J = 8.80 Hz, 2H), 4.61 (s, 2H), 4.50 (m, 2H), 3.85-3.90 (m, 1H), 3.51-3.57 (m, 1H), 2.36-2.40 (m, 2H) and 1.71-1.81 (m, 2H) |
| 57 | | 53% | 505.13 (M + H)$^+$, 95.89% | δ 8.61 (d, J = 5.60 Hz, 2H), 7.87 (d, J = 8.40 Hz, 2H) 7.61 (d, J = 8.40 Hz, 2H), 7.29-7.31 (m, 6H), 7.21 (s, 1H), 5.04 (s, 2H), 4.59-4.61 (m, 2H), 3.47-3.54 (m, 1H), 3.11-3.16 (m, 1H), 1.90-2.0 (m, 2H) and 1.68-1.77 (m, 2H) |
| 58 | | 56% | 519.18 (M + H)$^+$, 97.08% | δ 8.61 (m, 2H), 7.76-7.88 (m, 5H), 7.60-7.63 (m, 3H), 7.31 (m, 2H), 7.24 (s, 1H), 4.76-4.79 (m, 1H), 4.67-4.70 (m, 1H), 3.51-3.57 (m, 1H), 3.14-3.21 (m, 1H), 2.26-2.37 (m, 2H) and 1.71-1.80 (m, 2H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 177 | 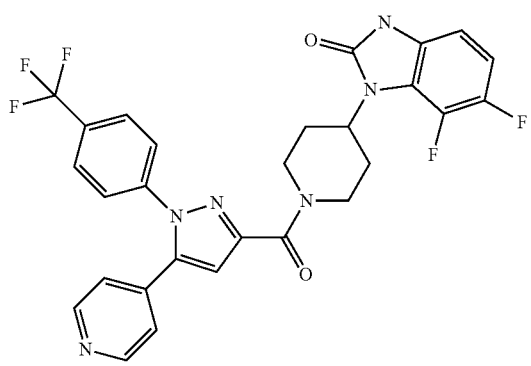 [SMILES: O=C(c1cc(-c2ccncc2)n(-c2ccc(C(F)(F)F)cc2)n1)N1CCC(n2c(=O)[nH]c3ccc(F)c(F)c32)CC1] | 37% | 569.42 (M + H)$^+$, 98.48% | δ 11.25 (br s, 1H), 8.61 (d, J = 6.0 Hz, 2H), 7.87 (d, J = 8.40 Hz, 2H), 7.61 (d, J = 8.40 Hz, 2H), 7.32 (d, J = 6.0 Hz, 2H), 7.22 (s, 1H), 7.0-7.06 (m, 1H), 6.77-6.80 (m, 1H), 4.79-4.82 (m, 1H), 4.62-4.70 (m, 2H), 3.32 (m, 1H), 2.93-2.99 (m, 1H), 2.11-2.21 (m, 2H) and 1.84-1.92 (m, 2H) |
| 178 | 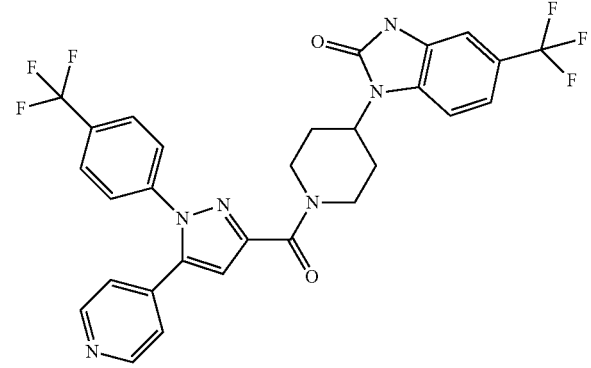 [SMILES: O=C(c1cc(-c2ccncc2)n(-c2ccc(C(F)(F)F)cc2)n1)N1CCC(n2c(=O)[nH]c3cc(C(F)(F)F)ccc32)CC1] | 25% | 601.43 (M + H)$^+$, 99.83% | δ 11.27 (br s, 1H), 8.61 (d, J = 6.0 Hz, 2H), 7.87 (d, J = 8.40 Hz, 2H), 7.61 (d, J = 8.40 Hz, 2H), 7.45-7.48 (m, 1H), 7.35-7.37 (m, 1H), 7.32 (d, J = 6.0 Hz, 2H), 7.23 (d, J = 5.60 Hz, 2H), 4.71-4.80 (m, 2H), 4.54-4.60 (m, 1H), 3.32 (m, 1H), 2.93-2.99 (m, 1H), 2.29-2.37 (m, 2H) and 1.79-1.90 (m, 2H) |
| 60 | 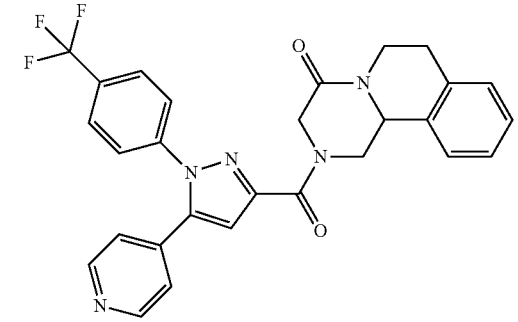 [SMILES: O=C(c1cc(-c2ccncc2)n(-c2ccc(C(F)(F)F)cc2)n1)N1CC(=O)N2CCc3ccccc3C2C1] | 52% | 518.35 (M + H)$^+$, 96.48% | (DMSO-d6 @ 373° K.) δ 8.61 (d, J = 6.0 Hz, 2H), 7.86 (d, J = 8.40 Hz, 2H), 7.66 (d, J = 8.40 Hz, 2H), 7.31 (d, J = 5.60 Hz, 2H), 7.22 (m, 5H), 5.22 (m, 1H), 5.05 (m, 1H), 4.85 (m, 1H), 4.60 (m, 1H), 4.25 (m, 1H), 3.46 (m, 1H) and 2.82 (m, 2H) |
| 61 | 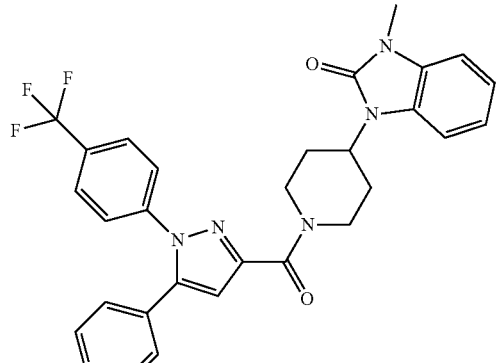 | 41% | 547.18 (M + H)$^+$, 93.76% | δ 8.61 (m, 2H), 7.87 (d, J = 8.80 Hz, 2H), 7.61 (d, J = 8.40 Hz, 2H), 7.31 (m, 3H), 7.23 (s, 1H), 7.15 (m, 1H), 7.02-7.06 (m, 2H), 4.70-4.78 (m, 2H), 4.54 (m, 1H), 3.37 (m, 1H), 3.30 (m, 2H), 2.97 (m, 2H), 2.30-2.39 (m, 2H) and 1.77-1.86 (m, 2H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 62 | 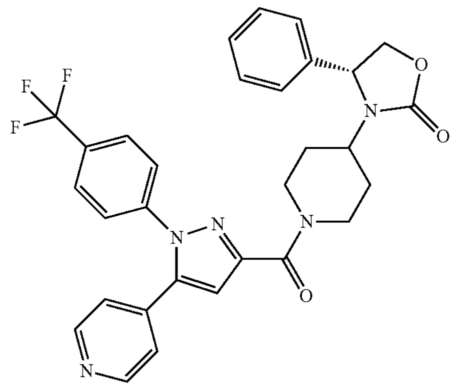 [SMILES: O=C(c1cc(-c2ccncc2)n(-c2ccc(C(F)(F)F)cc2)n1)N1CCC(N2C(=O)OC[C@H]2c2ccccc2)CC1] | 47% | 562.18 (M + H)$^+$, 97.04% | δ 8.59 (m, 2H), 7.86 (m, 2H), 7.59 (d, J = 8.0 Hz, 1H), 7.53 (d, J = 8.0 Hz, 1H), 7.40 (m, 5H), 7.26-7.29 (m, 2H), 7.06-7.13 (m, 1H), 5.01 (m, 1H), 4.52-4.66 (m, 2H), 4.45 (m, 1H), 3.98 (m, 1H), 3.60 (m, 1H), 3.05 (m, 1H), 2.66 (m, 1H), 1.90 (m, 1H), 1.56-1.76 (m, 2H) and 1.26 (m, 1H) |
| 63 | 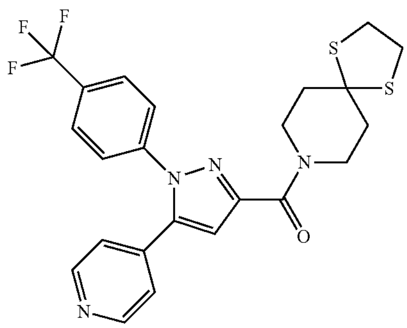 [SMILES: O=C(c1cc(-c2ccncc2)n(-c2ccc(C(F)(F)F)cc2)n1)N1CCC2(CC1)SCCS2] | 50% | 491.18 (M + H)$^+$, 98.64% | δ 8.60 (d, J = 5.60 Hz, 2H), 7.87 (d, J = 8.40 Hz, 2H), 7.60 (d, J = 8.40 Hz, 2H), 7.30 (m, 2H), 7.18 (s, 1H), 3.95 (m, 2H), 3.74 (m, 2H), 3.34 (m, 4H) and 2.09 (m, 4H) |
| 65 | 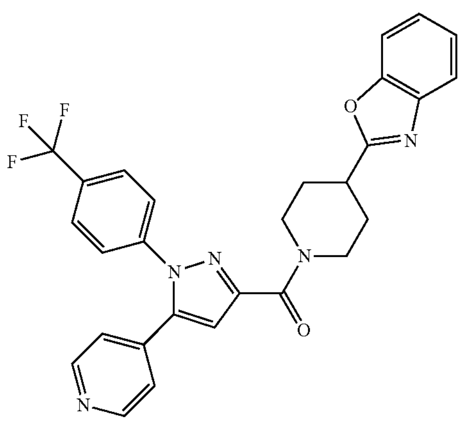 [SMILES: O=C(c1cc(-c2ccncc2)n(-c2ccc(C(F)(F)F)cc2)n1)N1CCC(c2nc3ccccc3o2)CC1] | 81% | 518.35 (M + H)$^+$, 98.95% | δ 8.61 (d, J = 6.0 Hz, 2H), 7.88 (d, J = 8.40 Hz, 2H), 7.67-7.71 (m, 2H), 7.61 (d, J = 8.40 Hz, 2H), 7.30-7.38 (m, 4H), 7.20 (s, 1H), 4.48-4.56 (m, 2H), 3.40-3.52 (m, 2H), 3.15 (m, 1H), 2.21 (m, 2H) and 1.80-1.88 (m, 2H) |
| 66 | 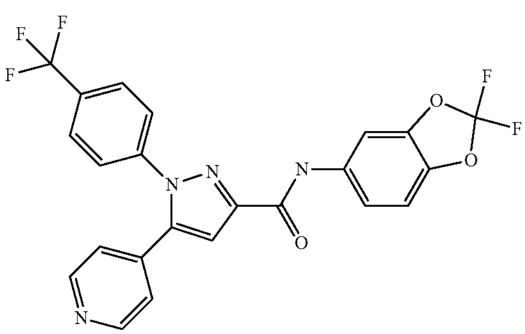 [SMILES: O=C(Nc1ccc2c(c1)OC(F)(F)O2)c1cc(-c2ccncc2)n(-c2ccc(C(F)(F)F)cc2)n1] | 41% | 489.13 (M + H)$^+$, 99.36% | δ 10.54 (br s, 1H), 8.61 (m, 2H), 7.90-7.93 (m, 3H), 7.70 (m, 2H), 7.63 (m, 1H), 7.42 (m, 2H) and 7.33 (m, 2H) |

TABLE 5-continued

| Cpd ID | Structure | Yield (%) | LCMS | NMR data (DMSO-d$_6$, 400 MHz), unless otherwise specified |
|---|---|---|---|---|
| 67 | 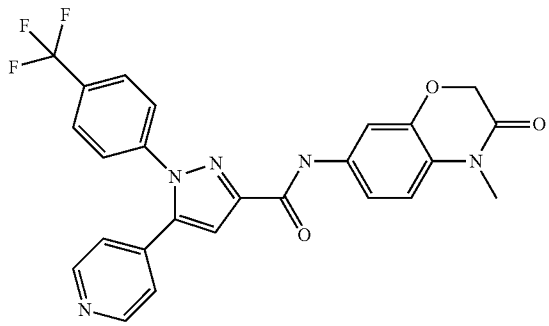 [SMILES: CN1C(=O)COc2cc(NC(=O)c3cc(-c4ccncc4)n(-c4ccc(C(F)(F)F)cc4)n3)ccc21] | 54% | 494.21 (M + H)$^+$, 95.76% | δ 10.33 (br s, 1H), 8.61 (m, 2H), 7.90-7.92 (m, 2H), 7.70 (m, 2H), 7.53-7.59 (m, 2H), 7.40 (s, 1H), 7.32 (m, 2H), 7.15 (m, 1H), 4.65 (s, 2H) and 3.27 (s, 3H) |
| 68 | 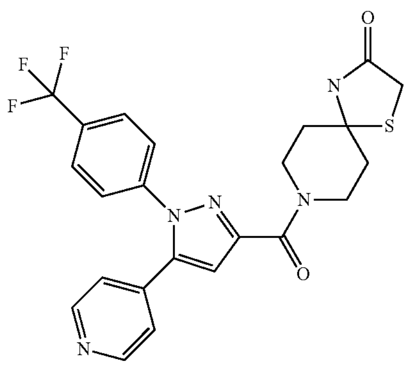 [SMILES: O=C1CSC2(CCN(C(=O)c3cc(-c4ccncc4)n(-c4ccc(C(F)(F)F)cc4)n3)CC2)N1] | 87% | 488.18 (M + H)$^+$, 98.83% | δ 8.92 (br s, 1H), 8.60 (d, J = 4.80 Hz, 2H), 7.88 (d, J = 8.0 Hz, 2H), 7.60 (d, J = 8.0 Hz, 2H), 7.30 (d, J = 5.60 Hz, 2H), 7.18 (s, 1H), 4.40 (m, 1H), 4.24 (m, 1H), 3.55 (m, 4H) and 1.94 (m, 4H) |
| 69 | 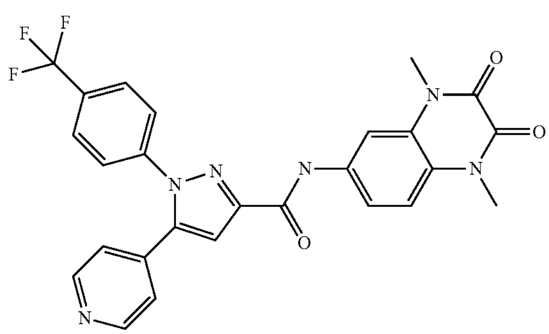 [SMILES: Cn1c(=O)c(=O)n(C)c2cc(NC(=O)c3cc(-c4ccncc4)n(-c4ccc(C(F)(F)F)cc4)n3)ccc21] | 51% | 521.13 (M + H)$^+$, 99.69% | δ 10.49 (s, 1H), 8.62 (d, J = 5.60 Hz, 2H), 7.97 (d, J = 1.60 Hz, 1H), 7.93 (d, J = 8.40 Hz, 2H), 7.87 (d, J = 8.80 Hz, 1H), 7.71 (d, J = 8.0 Hz, 2H), 7.42-7.44 (m, 2H), 7.34 (d, J = 6.00 Hz, 2H), 3.54 (s, 3H) and 3.52 (s, 3H) |
| 70 | 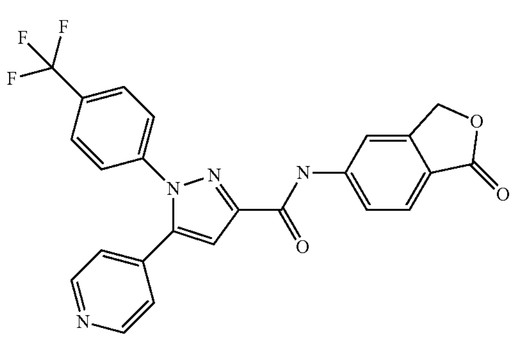 [SMILES: O=C(Nc1ccc2c(c1)COC2=O)c1cc(-c2ccncc2)n(-c2ccc(C(F)(F)F)cc2)n1] | 27% | 465.30 (M + H)$^+$, 98.41% | δ 10.80 (br s, 1H), 8.63 (d, J = 5.60 Hz, 2H), 8.27 (br s, 1H), 7.91-7.97 (m, 3H), 7.85 (m, 1H), 7.72 (d, J = 8.40 Hz, 2H), 7.47 (s, 1H), 7.34 (d, J = 6.0 Hz, 2H) and 5.41 (s, 2H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 71 | 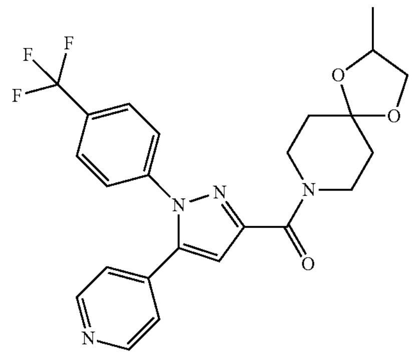 [SMILES: CC1COC2(CCN(C(=O)c3cc(-c4ccncc4)n(-c4ccc(C(F)(F)F)cc4)n3)CC2)O1] | 74% | 473.24 (M + H)$^+$, 98.86% | δ 8.60 (d, J = 4.40 Hz, 2H), 7.87 (d, J = 7.60 Hz, 2H), 7.60 (d, J = 7.60 Hz, 2H), 7.30 (d, J = 4.40 Hz, 2H), 7.18 (s, 1H), 4.22 (m, 1H), 4.07 (m, 1H), 3.86-3.94 (m, 2H), 3.67-3.75 (m, 2H), 1.70 (m, 4H) and 1.20 (m, 4H) |
| 72 | 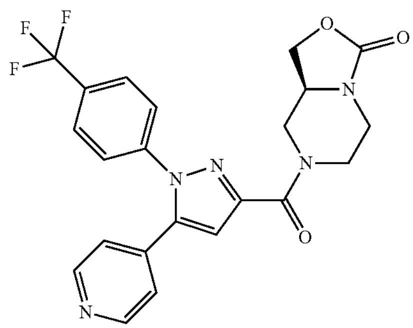 [SMILES: O=C(c1cc(-c2ccncc2)n(-c2ccc(C(F)(F)F)cc2)n1)N1CCN2C(=O)OC[C@@H]2C1] | 56% | 458.26 (M + H)$^+$, 97.18% | δ 8.61 (d, J = 6.0 Hz, 2H), 7.88 (d, J = 8.40 Hz, 2H), 7.62 (d, J = 8.40 Hz, 2H), 7.29 (m, 2H), 7.22 (s, 1H), 4.33-4.79 (m, 3H), 3.89-4.05 (m, 2H), 3.63-3.73 (m, 1H), 3.18-3.21 (m, 1H), 3.01-3.10 (m, 1H) and 2.78-2.84 (m, 1H) |
| 73 | 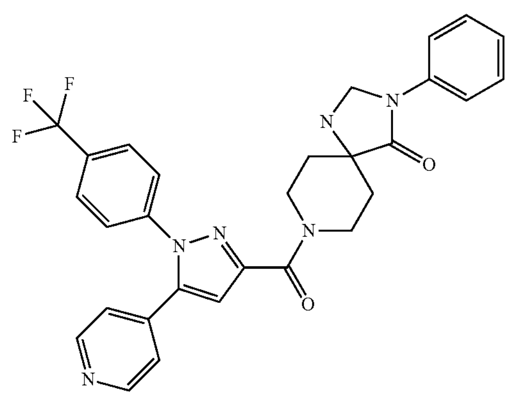 [SMILES: O=C(c1cc(-c2ccncc2)n(-c2ccc(C(F)(F)F)cc2)n1)N1CCC2(CC1)NCN(c1ccccc1)C2=O] | 38% | 547.44 (M + H)$^+$, 97.83% | δ 8.61 (d, J = 6.0 Hz, 2H), 7.87 (d, J = 8.40 Hz, 2H), 7.66 (d, J = 8.0 Hz, 2H), 7.61 (d, J = 8.40 Hz, 2H), 7.39 (m, 2H), 7.31 (d, J = 6.0 Hz, 2H), 7.20 (s, 1H), 7.13-7.16 (m, 1H), 4.73-4.76 (m, 2H), 4.42-4.50 (m, 2H), 3.61 (m, 1H), 3.49 (m, 1H), 3.16 (m, 1H) and 1.64-1.80 (m, 4H) |
| 74 | 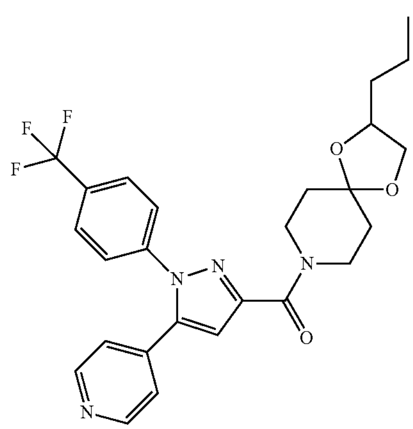 [SMILES: CCCC1COC2(CCN(C(=O)c3cc(-c4ccncc4)n(-c4ccc(C(F)(F)F)cc4)n3)CC2)O1] | 50% | 501.21 (M + H)$^+$, 96.25% | δ 8.60 (d, J = 6.0 Hz, 2H), 7.87 (d, J = 8.40 Hz, 2H), 7.60 (d, J = 8.0 Hz, 2H), 7.30 (d, J = 6.0 Hz, 2H), 7.18 (s, 1H), 4.05-4.12 (m, 2H), 3.95 (m, 1H), 3.77-3.86 (m, 2H), 3.62-3.67 (m, 1H), 3.51 (m, 1H), 1.69 (m, 4H), 1.28-1.54 (m, 4H) and 0.89 (t, J = 6.80 Hz, 3H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 75 | 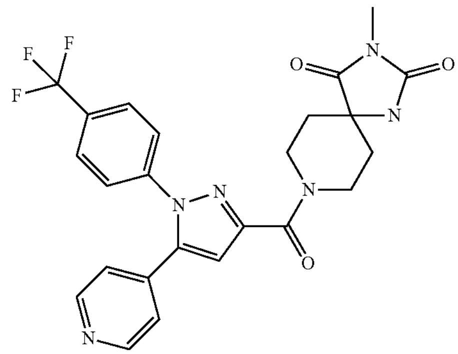 [SMILES: CN1C(=O)NC2(CCN(C(=O)c3cc(-c4ccncc4)n(-c4ccc(C(F)(F)F)cc4)n3)CC2)C1=O] | 71% | 499.21 (M + H)$^+$, 98.50% | δ 8.91 (br s, 1H), 8.61 (d, J = 5.60 Hz, 2H), 7.87 (d, J = 8.40 Hz, 2H), 7.61 (d, J = 8.40 Hz, 2H), 7.30 (d, J = 6.0 Hz, 2H), 7.21 (s, 1H), 4.44 (m, 1H), 4.34 (m, 1H), 3.62 (m, 1H), 3.39 (m, 1H), 2.84 (s, 3H), 1.82-1.88 (m, 2H) and 1.62-1.70 (m, 2H) |
| 76 | 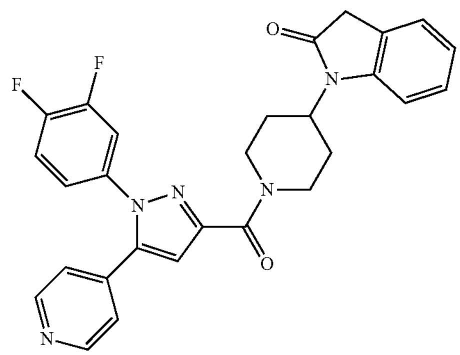 [SMILES: O=C(c1cc(-c2ccncc2)n(-c2ccc(F)c(F)c2)n1)N1CCC(N2C(=O)Cc3ccccc32)CC1] | 55% | 500.18 (M + H)$^+$, 99.18% | δ 8.59 (d, J = 6.0 Hz, 2H), 7.68-7.72 (m, 1H), 7.52-7.59 (m, 1H), 7.21-7.29 (m, 6H), 7.15-7.17 (m, 1H), 6.99 (m, 1H), 4.67-4.77 (m, 2H), 4.42 (m, 1H), 3.53 (s, 2H), 3.39 (m, 1H), 2.93 (m, 1H), 2.26-2.38 (m, 2H) and 1.69-1.79 (m, 2H) |
| 77 | 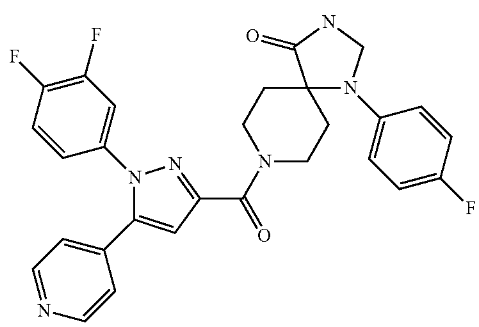 [SMILES: O=C(c1cc(-c2ccncc2)n(-c2ccc(F)c(F)c2)n1)N1CCC2(CC1)C(=O)NCN2c1ccc(F)cc1] | 34% | 533.37 (M + H)$^+$, 98.79% | δ 8.80 (br s, 1H), 8.59 (d, J = 6.0 Hz, 2H), 7.64-7.69 (m, 1H), 7.51-7.58 (m, 1H), 7.28 (d, J = 6.0 Hz, 2H), 7.20 (m, 2H), 7.08-7.12 (m, 2H), 6.83-6.87 (m, 2H), 4.58 (s, 2H), 4.41-4.50 (m, 2H), 3.86 (m, 1H), 3.53 (m, 1H), 2.18-2.31 (m, 2H) and 1.73-1.82 (m, 2H) |
| 78 | 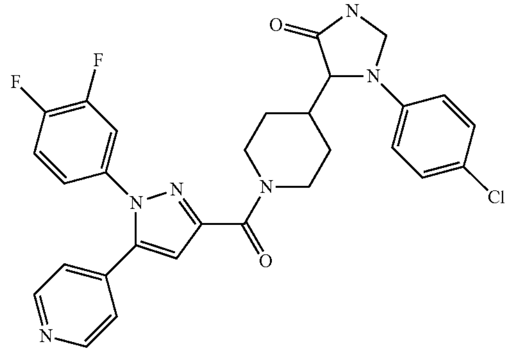 [SMILES: O=C1NCN(c2ccc(Cl)cc2)C1C1CCN(C(=O)c2cc(-c3ccncc3)n(-c3ccc(F)c(F)c3)n2)CC1] | 33% | 549.43 (M + H)$^+$, 97.25% | δ 8.87 (br s, 1H), 8.59 (br s, 2H), 7.68-7.70 (m, 1H), 7.51-7.57 (m, 1H), 7.23-7.29 (m, 6H), 6.74-6.77 (m, 2H), 4.60 (s, 2H), 4.47-4.53 (m, 2H), 3.82-3.88 (m, 1H), 3.50-3.56 (m, 1H), 2.35-2.41 (m, 2H) and 1.70-1.80 (m, 2H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 79 | 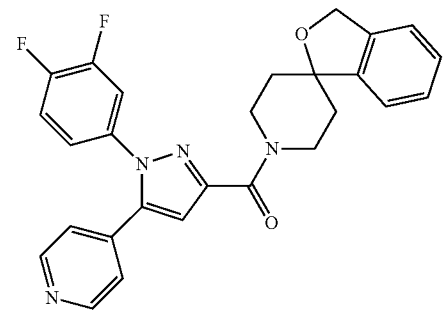 [SMILES: O=C(c1cc(-c2ccncc2)n(-c2ccc(F)c(F)c2)n1)N1CCC2(CC1)OCc1ccccc12] | 81% | 473.13 (M + H)$^+$, 93.47% | δ 8.59 (d, J = 5.60 Hz, 2H), 7.66-7.71 (m, 1H), 7.52-7.59 (m, 1H), 7.27-7.32 (m, 6H), 7.23 (m, 1H), 7.19 (s, 1H), 5.04 (s, 2H), 4.55-4.61 (m, 2H), 3.43-3.52 (m, 1H), 3.09-3.15 (m, 1H), 1.88-1.98 (m, 2H) and 1.68-1.76 (m, 2H) |
| 80 | 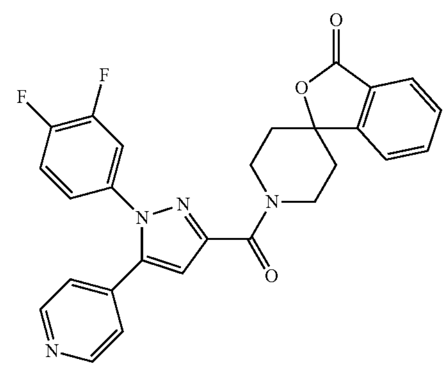 [SMILES: O=C1OC2(CCN(C(=O)c3cc(-c4ccncc4)n(-c4ccc(F)c(F)c4)n3)CC2)c2ccccc21] | 82% | 487.17 (M + H)$^+$, 95.38% | δ 8.60 (d, J = 4.80 Hz, 2H), 7.76-7.86 (m, 3H), 7.68-7.72 (m, 1H), 7.53-7.63 (m, 2H), 7.30 (d, J = 5.60 Hz, 2H), 7.22 (m, 2H), 4.77-4.80 (m, 1H), 4.66-4.69 (m, 1H), 3.50-3.56 (m, 1H), 3.13-3.20 (m, 1H), 2.24-2.28 (m, 2H) and 1.72-1.80 (m, 2H) |
| 82 | 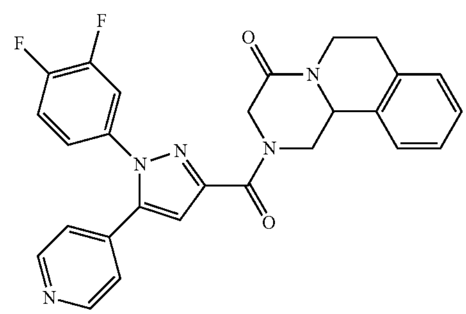 [SMILES: O=C(c1cc(-c2ccncc2)n(-c2ccc(F)c(F)c2)n1)N1CC(=O)N2CCc3ccccc3C2C1] | 71% | 486.58 (M + H)$^+$, 97.21% | δ 8.61 (m, 2H), 7.56-7.86 (m, 2H), 7.22-7.39 (m, 8H), 4.50-5.54 (m, 4H), 3.95-4.42 (m, 1H), 3.45 (m, 1H) and 2.79-2.91 (m, 3H) |
| 83 | 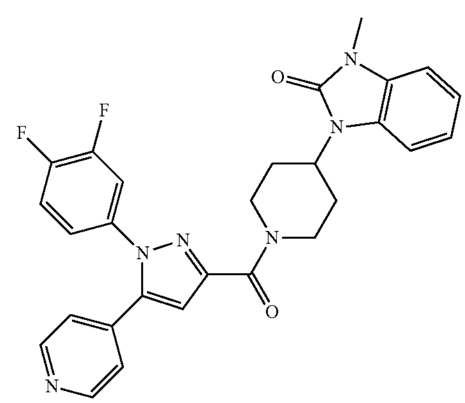 [SMILES: Cn1c(=O)n(C2CCN(C(=O)c3cc(-c4ccncc4)n(-c4ccc(F)c(F)c4)n3)CC2)c2ccccc21] | 58% | 515.19 (M + H)$^+$, 96.42% | δ 8.59 (d, J = 5.20 Hz, 2H), 7.68-7.72 (m, 1H), 7.52-7.59 (m, 1H), 7.28-7.29 (m, 3H), 7.22-7.24 (m, 2H), 7.15 (m, 1H), 7.02-7.08 (m, 2H), 4.69-4.79 (m, 2H), 4.55 (m, 1H), 3.30 (s, 3H), 2.92-2.98 (m, 2H), 2.28-2.37 (m, 2H) and 1.76-1.85 (m, 2H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 84 | 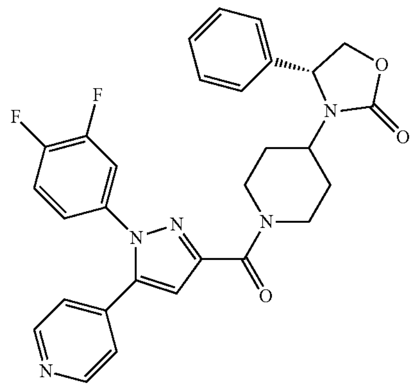 [SMILES: O=C(c1cc(-c2ccncc2)n(-c2ccc(F)c(F)c2)n1)N1CCC(N2C(=O)OC[C@H]2c2ccccc2)CC1] | 34% | 530.17 (M + H)$^+$, 92.49% | δ 8.58 (m, 2H), 7.54-7.71 (m, 2H), 7.40 (m, 5H), 7.23-7.26 (m, 3H), 7.05-7.11 (m, 1H), 5.01 (m, 1H), 4.52-4.66 (m, 2H), 4.43 (m, 1H), 3.98 (m, 1H), 3.60 (m, 1H), 3.03 (m, 1H), 2.66 (m, 1H), 1.90 (m, 1H), 1.56-1.76 (m, 2H) and 1.17 (m, 1H) |
| 85 | 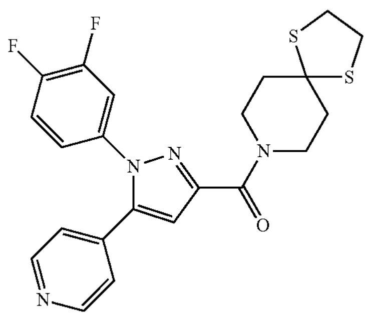 [SMILES: O=C(c1cc(-c2ccncc2)n(-c2ccc(F)c(F)c2)n1)N1CCC2(CC1)SCCS2] | 78% | 459.10 (M + H)$^+$, 99.41% | δ 8.59 (d, J = 4.80 Hz, 2H), 7.70 (m, 1H), 7.52-7.59 (m, 1H), 7.27 (d, J = 4.80 Hz, 2H), 7.22 (m, 1H), 7.17 (s, 1H), 3.94 (m, 2H), 3.73 (m, 2H), 3.34 (m, 4H) and 2.08 (m, 4H) |
| 87 | 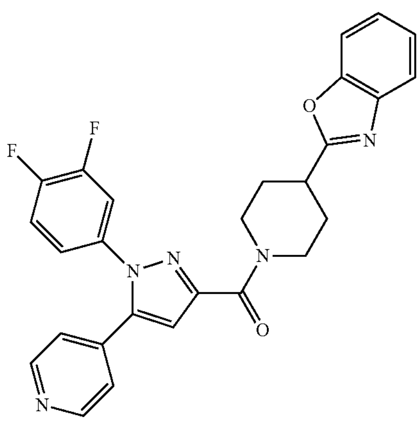 [SMILES: O=C(c1cc(-c2ccncc2)n(-c2ccc(F)c(F)c2)n1)N1CCC(c2nc3ccccc3o2)CC1] | 58% | 485.99 (M + H)$^+$, 97.66% | δ 8.59 (d, J = 6.0 Hz, 2H), 7.67-7.73 (m, 3H), 7.53-7.60 (m, 1H), 7.32-7.38 (m, 2H), 7.28 (m, 2H), 7.24 (m, 1H), 7.18 (s, 1H), 4.47-4.57 (m, 2H), 3.45 (m, 2H), 3.14 (m, 1H), 2.20 (m, 2H) and 1.79-1.90 (m, 2H) |
| 88 | 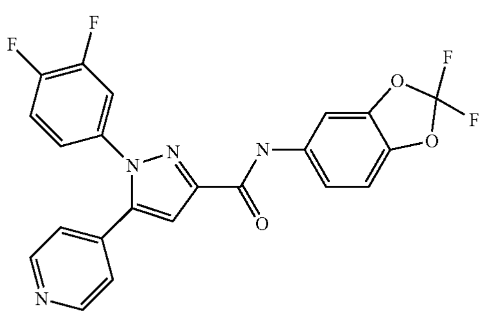 [SMILES: O=C(Nc1ccc2c(c1)OC(F)(F)O2)c1cc(-c2ccncc2)n(-c2ccc(F)c(F)c2)n1] | 57% | 457.27 (M + H)$^+$, 99.14% | δ 10.55 (br s, 1H), 8.60 (d, J = 6.0 Hz, 2H), 7.94 (m, 1H), 7.78-7.83 (m, 1H), 7.57-7.64 (m, 2H), 7.39-7.41 (m, 2H) and 7.32 (m, 3H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 89 | 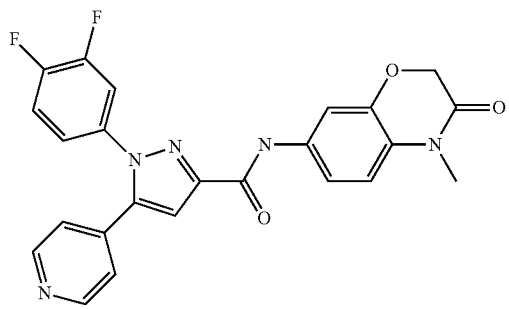 [SMILES: CN1C(=O)COc2cc(NC(=O)c3cc(-c4ccncc4)n(-c4ccc(F)c(F)c4)n3)ccc21] | 88% | 462.31 (M + H)$^+$, 98.43% | δ 10.34 (br s, 1H), 8.60 (d, J = 6.0 Hz, 2H), 7.78-7.83 (m, 1H), 7.54-7.63 (m, 3H), 7.39 (s, 1H), 7.30-7.31 (m, 3H), 7.15 (d, J = 8.80 Hz, 1H), 4.65 (s, 2H) and 3.27 (s, 3H) |
| 90 | 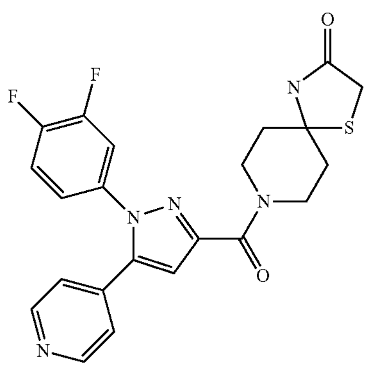 [SMILES: O=C1CSC2(CCN(C(=O)c3cc(-c4ccncc4)n(-c4ccc(F)c(F)c4)n3)CC2)N1] | 58% | 456.30 (M + H)$^+$, 99.11% | δ 8.92 (br s, 1H), 8.59 (d, J = 6.0 Hz, 2H), 7.67-7.72 (m, 1H), 7.53-7.60 (m, 1H), 7.28 (d, J = 6.0 Hz, 2H), 7.23 (m, 1H), 7.17 (s, 1H), 4.40 (m, 1H), 4.23 (m, 1H), 3.51-3.55 (m, 3H), 3.24 (m, 1H) and 1.93 (m, 4H) |
| 91 | 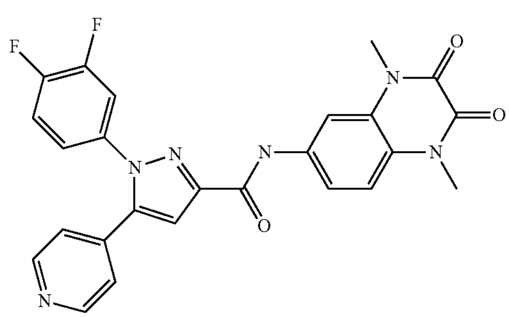 [SMILES: Cn1c(=O)c(=O)n(C)c2cc(NC(=O)c3cc(-c4ccncc4)n(-c4ccc(F)c(F)c4)n3)ccc21] | 49% | 489.11 (M + H)$^+$, 96.81% | δ 10.49 (s, 1H), 8.61 (d, J = 5.60 Hz, 2H), 7.95-7.98 (m, 1H), 7.81-7.89 (m, 2H), 7.59-7.65 (m, 1H), 7.41-7.44 (m, 2H), 7.32 (d, J = 6.0 Hz, 3H), 3.54 (s, 3H) and 3.52 (s, 3H) |
| 92 | 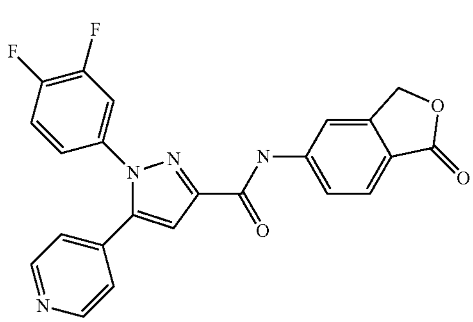 [SMILES: O=C(Nc1ccc2c(c1)COC2=O)c1cc(-c2ccncc2)n(-c2ccc(F)c(F)c2)n1] | 33% | 433.31 (M + H)$^+$, 99.88% | δ 10.80 (s, 1H), 8.61 (d, J = 6.0 Hz, 2H), 8.27 (s, 1H), 7.98 (d, J = 8.80 Hz, 1H), 7.80-7.84 (m, 2H), 7.57-7.64 (m, 1H), 7.44 (s, 1H), 7.31-7.33 (m, 3H) and 5.41 (s, 2H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 93 | 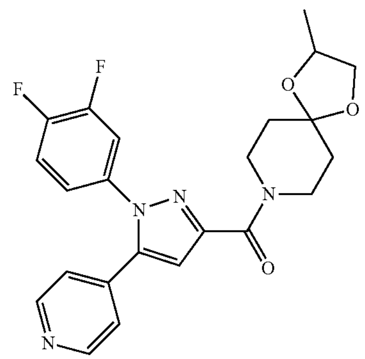 [SMILES: CC1COC2(CCN(C(=O)c3cc(-c4ccncc4)n(-c4ccc(F)c(F)c4)n3)CC2)O1] | 82% | 441.36 (M + H)$^+$, 98.16% | δ 8.59 (d, J = 5.60 Hz, 2H), 7.66-7.70 (m, 1H), 7.52-7.59 (m, 1H), 7.27 (d, J = 6.0 Hz, 2H), 7.22 (m, 1H), 7.16 (s, 1H), 4.22 (m, 1H), 4.06 (m, 1H), 3.86-3.94 (m, 2H), 3.65-3.74 (m, 2H), 1.70 (m, 4H) and 1.20 (m, 4H) |
| 94 | 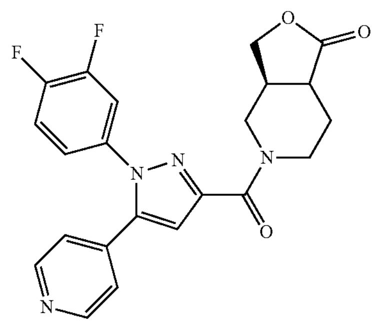 | 57% | 426.59 (M + H)$^+$, 98.12% | δ 8.59 (d, J = 6.0 Hz, 2H), 7.70-7.75 (m, 1H), 7.53-7.60 (m, 1H), 7.28 (d, J = 4.80 Hz, 2H), 7.20 (m, 2H), 4.50-4.81 (m, 2H), 4.34-4.44 (m, 1H), 3.96-4.06 (m, 1H), 3.87 (m, 1H), 3.63-3.72 (m, 1H), 3.18-3.21 (m, 1H), 3.0-3.09 (m, 1H) and 2.77-2.86 (m, 1H) |
| 95 | 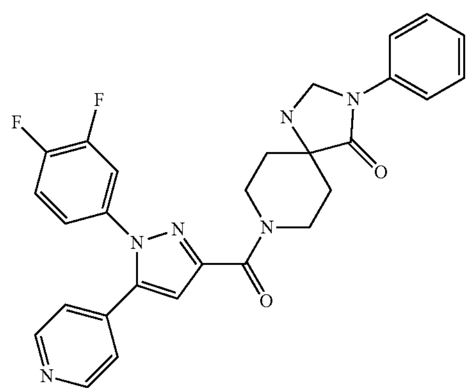 [SMILES: O=C(c1cc(-c2ccncc2)n(-c2ccc(F)c(F)c2)n1)N1CCC2(CC1)NCN(c1ccccc1)C2=O] | 43% | 515.03 (M + H)$^+$, 98.41% | δ 8.59 (m, 2H), 7.64-7.72 (m, 3H), 7.52-7.59 (m, 1H), 7.37-7.41 (m, 2H), 7.28 (m, 2H), 7.21 (m, 1H), 7.19 (s, 1H), 7.12-7.16 (m, 1H), 4.73-4.76 (m, 2H), 4.41-4.51 (m, 2H), 3.60 (m, 1H), 3.48 (m, 1H), 3.15 (m, 1H) and 1.66-1.80 (m, 4H) |
| 96 | 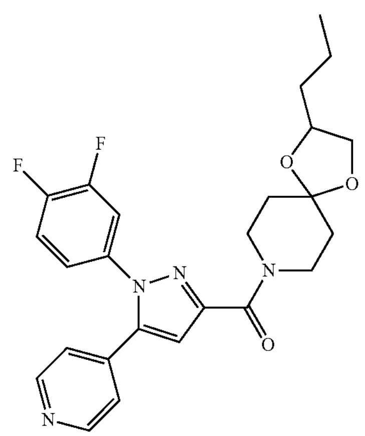 [SMILES: CCCC1COC2(CCN(C(=O)c3cc(-c4ccncc4)n(-c4ccc(F)c(F)c4)n3)CC2)O1] | 67% | 469.37 (M + H)$^+$, 98.48% | δ 8.59 (d, J = 6.0 Hz, 2H), 7.66-7.70 (m, 1H), 7.52-7.59 (m, 1H), 7.27 (d, J = 6.0 Hz, 2H), 7.21 (m, 1H), 7.16 (s, 1H), 4.05-4.08 (m, 2H), 3.94-3.98 (m, 1H), 3.76-3.88 (m, 2H), 3.63-3.66 (m, 1H), 3.50 (m, 1H), 1.69 (m, 4H), 1.23-1.52 (m, 4H) and 0.88 (t, J = 6.80 Hz, 3H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 97 | 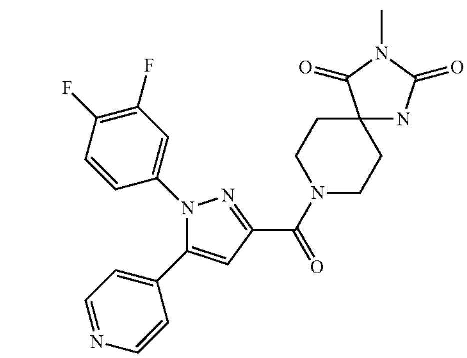 [SMILES: CN1C(=O)NC2(CCN(C(=O)c3cc(-c4ccncc4)n(-c4ccc(F)c(F)c4)n3)CC2)C1=O] | 34% | 465.29 (M − H)$^+$, 99.18% | δ 8.93 (br s, 1H), 8.60 (d, J = 5.60 Hz, 2H), 7.69-7.73 (m, 1H), 7.54-7.61 (m, 1H), 7.29 (d, J = 5.60 Hz, 2H), 7.24 (m, 1H), 7.21 (s, 1H), 4.46 (m, 1H), 4.34 (m, 1H), 3.62 (m, 1H), 3.29 (m, 1H), 2.85 (s, 3H), 1.82-1.88 (m, 2H) and 1.61-1.67 (m, 2H) |
| 98 | 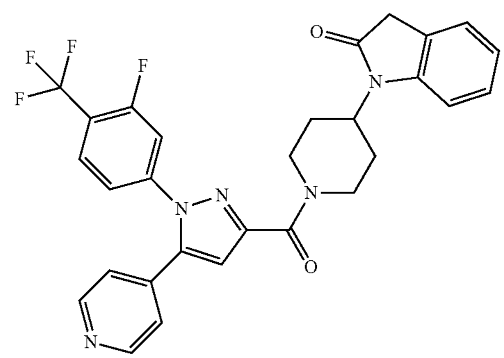 [SMILES: O=C(c1cc(-c2ccncc2)n(-c2ccc(C(F)(F)F)c(F)c2)n1)N1CCC(N2C(=O)Cc3ccccc32)CC1] | 65% | 550.40 (M + H)$^+$, 95.71% | δ 8.63 (m, 2H), 7.87-7.91 (m, 1H), 7.69-7.72 (m, 1H), 7.34-7.36 (m, 3H), 7.23-7.26 (m, 3H), 7.15-7.17 (m, 1H), 6.97-7.01 (m, 1H), 4.70 (m, 2H), 4.42 (m, 1H), 3.54 (s, 2H), 3.37 (m, 1H), 2.94 (m, 1H), 2.30-2.38 (m, 2H) and 1.71-1.79 (m, 2H) |
| 99 | 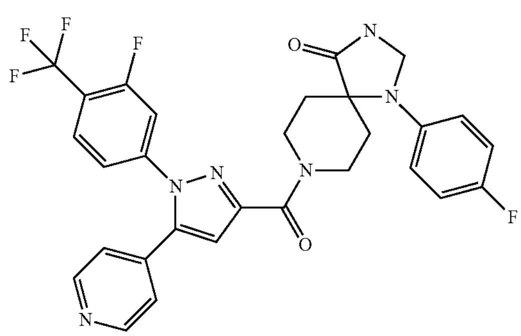 [SMILES: O=C(c1cc(-c2ccncc2)n(-c2ccc(C(F)(F)F)c(F)c2)n1)N1CCC2(CC1)C(=O)NCN2c1ccc(F)cc1] | 43% | 581.34 (M − H)$^+$, 98.78% | δ 8.82 (br s, 1H), 8.63 (d, J = 5.60 Hz, 2H), 7.85-7.89 (m, 1H), 7.67-7.69 (m, 1H), 7.30-7.35 (m, 3H), 7.22 (s, 1H), 7.08-7.12 (m, 2H), 6.84-6.87 (m, 2H), 4.59 (s, 2H), 4.42-4.45 (m, 2H), 3.87 (m, 1H), 3.54 (m, 1H), 2.20-2.36 (m, 2H) and 1.73-1.80 (m, 2H) |
| 100 | 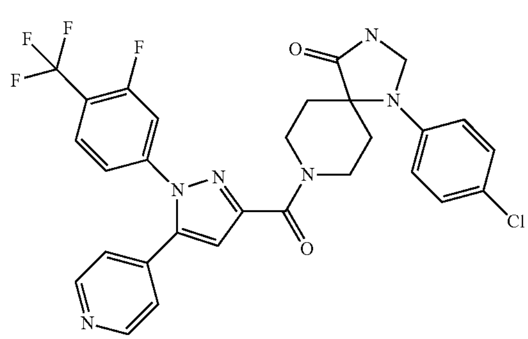 [SMILES: O=C(c1cc(-c2ccncc2)n(-c2ccc(C(F)(F)F)c(F)c2)n1)N1CCC2(CC1)C(=O)NCN2c1ccc(Cl)cc1] | 50% | 599.40 (M + H)$^+$, 96.20% | δ 8.88 (br s, 1H), 8.64 (d, J = 4.40 Hz, 2H), 7.84-7.88 (m, 1H), 7.67-7.70 (m, 1H), 7.25-7.36 (m, 6H), 6.78 (d, J = 8.80 Hz, 2H), 4.61 (br s, 2H), 4.44-4.49 (m, 2H), 3.84-3.90 (m, 1H), 3.50-3.57 (m, 1H), 2.35-2.42 (m, 2H) and 1.71-1.81 (m, 2H) |

TABLE 5-continued

| | | Yield | | NMR data (DMSO-d$_6$, 400 MHz), |
|---|---|---|---|---|
| Cpd ID | Structure | (%) | LCMS | unless otherwise specified |
| 101 | | 68% | 523.33 (M + H)$^+$, 95.04% | δ 8.63 (d, J = 6.0 Hz, 2H), 7.86-7.91 (m, 1H), 7.71 (m, 1H), 7.29-7.36 (m, 7H), 7.22 (s, 1H), 5.04 (s, 2H), 4.55-4.58 (m, 2H), 3.47-3.54 (m, 1H), 3.10-3.17 (m, 1H), 1.90-2.01 (m, 2H) and 1.68-1.77 (m, 2H) |
| 102 | | 53% | 537.35 (M + H)$^+$, 95.01% | δ 8.64 (d, J = 5.60 Hz, 2H), 7.78-7.91 (m, 4H), 7.70-7.73 (m, 1H), 7.60-7.64 (m, 1H), 7.33-7.36 (m, 3H), 7.25 (s, 1H), 4.66-4.76 (m, 2H), 3.54-3.57 (m, 1H), 3.14-3.21 (m, 1H), 2.29-2.36 (m, 2H) and 1.72-1.80 (m, 2H) |
| 103 | | 31% | 571.31 (M + H)$^+$, 99.71% | δ 8.64 (d, J = 5.20 Hz, 2H), 7.85-7.91 (m, 4H), 7.70-7.73 (m, 1H), 7.33-7.36 (m, 3H), 7.24 (s, 1H), 4.66-4.76 (m, 2H), 3.49-3.55 (m, 1H), 3.12-3.19 (m, 1H), 2.30-2.37 (m, 2H) and 1.74-1.83 (m, 2H) |
| 104 | | 67% | 536.36 (M + H)$^+$, 96.92% | δ 8.64-8.65 (m, 2H), 7.70-7.97 (m, 2H), 7.18-7.42 (m, 8H), 5.13-5.52 (m, 1H), 3.48-5.0 (m, 4H), 3.30 (m, 1H) and 2.79-2.91 (m, 3H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 105 | 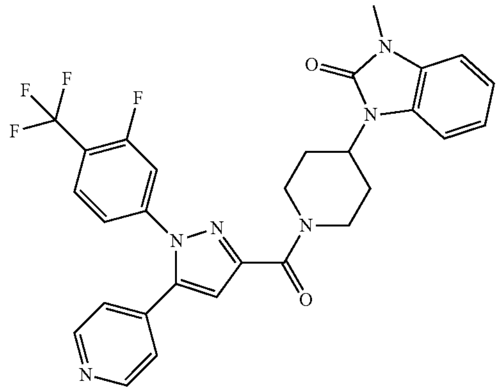 [SMILES: Cn1c(=O)n(C2CCN(C(=O)c3cc(-c4ccncc4)n(-c4ccc(C(F)(F)F)c(F)c4)n3)CC2)c2ccccc21] | 70% | 565.37 (M + H)$^+$, 94.01% | δ 8.63 (d, J = 6.0 Hz, 2H), 7.87-7.91 (m, 1H), 7.69-7.72 (m, 1H), 7.34-7.36 (m, 4H), 7.24 (s, 1H), 7.13-7.16 (m, 1H), 7.04-7.08 (m, 2H), 4.70-4.74 (m, 2H), 4.53-4.59 (m, 1H), 3.37 (m, 1H), 3.30 (s, 3H), 2.94-3.0 (m, 1H), 2.30-2.38 (m, 2H) and 1.77-1.86 (m, 2H) |
| 106 | 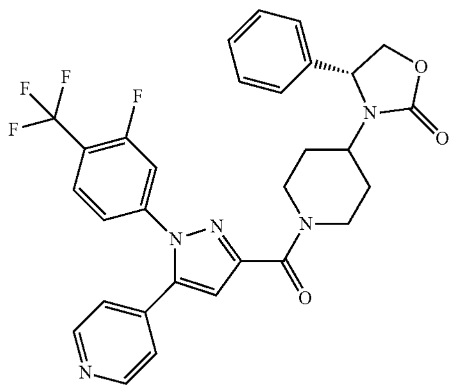 [SMILES: O=C(c1cc(-c2ccncc2)n(-c2ccc(C(F)(F)F)c(F)c2)n1)N1CCC(N2C(=O)OC[C@H]2c2ccccc2)CC1] | 86% | 580.35 (M + H)$^+$, 95.40% | δ 8.62 (m, 2H), 7.85-7.91 (m, 1H), 7.59-7.71 (m, 1H), 7.24-7.40 (m, 8H), 7.07-7.14 (m, 1H), 5.01 (m, 1H), 4.57-4.62 (m, 2H), 4.43 (m, 1H), 3.98 (m, 1H), 3.59 (m, 1H), 3.03 (m, 1H), 2.72 (m, 1H), 1.85-1.94 (m, 1H), 1.56-1.77 (m, 2H) and 1.23 (m, 1H) |
| 107 | 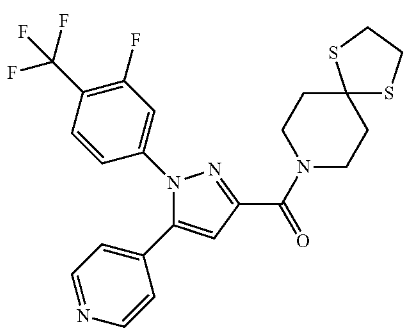 [SMILES: O=C(c1cc(-c2ccncc2)n(-c2ccc(C(F)(F)F)c(F)c2)n1)N1CCC2(CC1)SCCS2] | 76% | 509.31 (M + H)$^+$, 95.64% | δ 8.63 (d, J = 6.0 Hz, 2H), 7.88 (m, 1H), 7.70-7.72 (m, 1H), 7.32-7.34 (m, 3H), 7.19 (s, 1H), 3.94 (m, 2H), 3.74 (m, 2H), 3.35 (m, 4H) and 2.09 (m, 4H) |
| 108 | 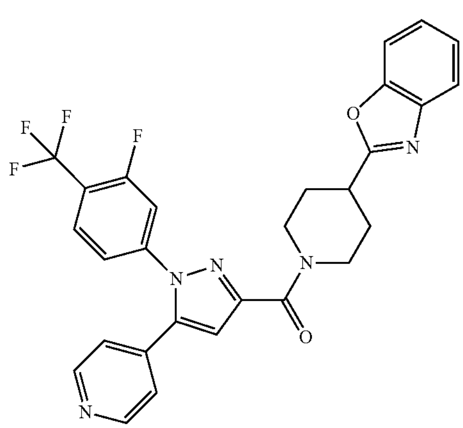 [SMILES: O=C(c1cc(-c2ccncc2)n(-c2ccc(C(F)(F)F)c(F)c2)n1)N1CCC(c2nc3ccccc3o2)CC1] | 31% | 536.36 (M + H)$^+$, 95.15% | δ 8.63 (d, J = 5.60 Hz, 2H), 7.89 (t, J = 8.40 Hz, 1H), 7.67-7.73 (m, 3H), 7.35 (m, 5H), 7.21 (s, 1H), 4.47-4.54 (m, 2H), 3.39-3.52 (m, 2H), 3.13-3.19 (m, 1H), 2.18-2.25 (m, 2H) and 1.18-1.23 (m, 2H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 109 | 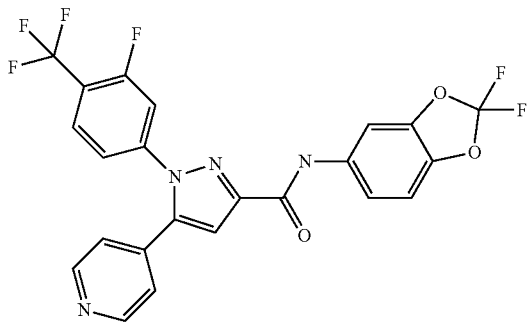 [SMILES: O=C(Nc1ccc2c(c1)OC(F)(F)O2)c1cc(-c2ccncc2)n(-c2ccc(C(F)(F)F)c(F)c2)n1] | 57% | 507.27 (M + H)$^+$, 97.62% | δ 10.56 (s, 1H), 8.64-8.65 (m, 2H), 7.94-7.90 (m, 2H), 7.85 (m, 1H), 7.62 (dd, J = 8.80 & 2.00 Hz, 1H) and 7.39-7.43 (m, 5H) |
| 110 | 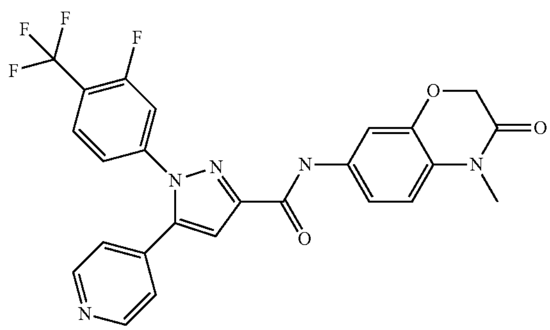 [SMILES: CN1C(=O)COc2cc(NC(=O)c3cc(-c4ccncc4)n(-c4ccc(C(F)(F)F)c(F)c4)n3)ccc21] | 77% | 510.23 (M − H)$^+$, 97.05% | δ 10.35 (s, 1H), 8.65 (d, J = 6.00 Hz, 2H), 7.93 (d, J = 8.00 Hz, 1H), 7.86 (m, 1H), 7.59 (d, J = 2.40 Hz, 1H), 7.54 (dd, J = 8.80 & 2.40 Hz, 1H), 7.38-7.41 (m, 4H), 7.16 (d, J = 8.8 Hz, 1H), 4.66 (s, 2H) and 3.28 (s, 3H) |
| 111 | 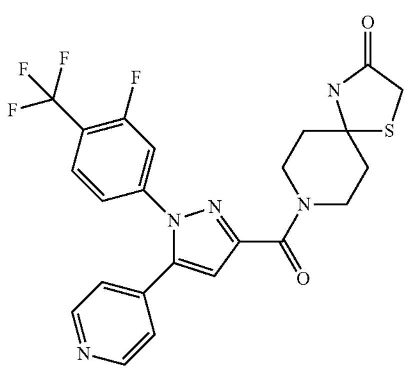 [SMILES: O=C1CSC2(CCN(C(=O)c3cc(-c4ccncc4)n(-c4ccc(C(F)(F)F)c(F)c4)n3)CC2)N1] | 58% | 504.25 (M − H)$^+$, 98.75% | δ 8.62-8.63 (m, 2H), 8.40 (s, 1H), 7.89 (t, J = 8.00 Hz, 1H), 7.72 (m, 1H), 7.33-7.35 (m, 3H), 7.20 (s, 1H), 4.35-4.39 (m, 1H), 4.21-4.24 (m, 1H), 3.69 (m, 4H), 3.30 (m, 1H) and 2.08-2.11 (m, 3H) |
| 112 | 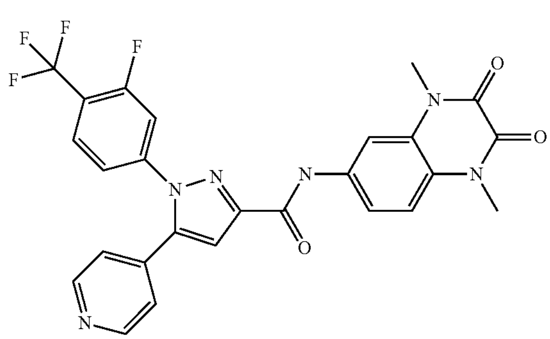 [SMILES: Cn1c(=O)c(=O)n(C)c2cc(NC(=O)c3cc(-c4ccncc4)n(-c4ccc(C(F)(F)F)c(F)c4)n3)ccc21] | 54% | 539.14 (M + H)$^+$, 98.59% | δ 10.43 (s, 1H), 8.65 (d, J = 6.0 Hz, 2H), 7.91-7.96 (m, 2H), 7.85 (d, J = 8.0 Hz, 2H), 7.38-7.45 (m, 5H), 3.55 (s, 3H) and 3.54 (s, 3H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 113 | 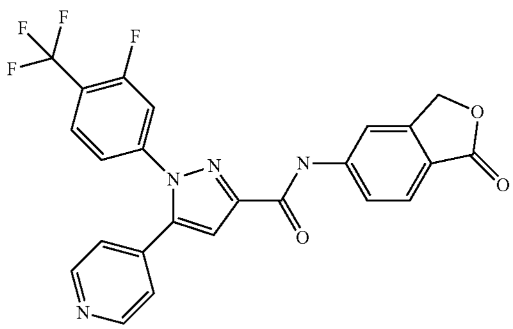 [SMILES: O=C(Nc1ccc2c(c1)COC2=O)c1cc(-c2ccncc2)n(-c2ccc(C(F)(F)F)c(F)c2)n1] | 38% | 481.20 (M − H)$^+$, 99.50% | δ 10.80 (s, 1H), 8.65 (d, J = 6.0 Hz, 2H), 8.27 (s, 1H), 7.92-7.98 (m, 2H), 7.84-7.89 (m, 2H), 7.48 (s, 1H), 7.39-7.43 (m, 3H) and 5.42 (s, 2H) |
| 114 | 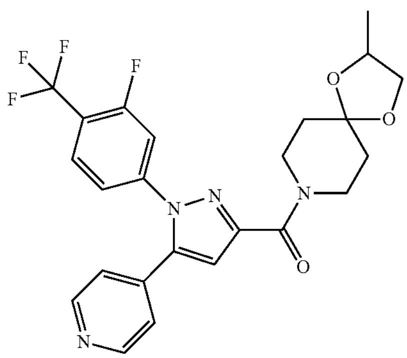 [SMILES: CC1COC2(CCN(C(=O)c3cc(-c4ccncc4)n(-c4ccc(C(F)(F)F)c(F)c4)n3)CC2)O1] | 67% | 491.36 (M + H)$^+$, 99.52% | δ 8.62 (d, J = 6.00 Hz, 2H), 7.89 (d, J = 8.40 Hz, 1H), 7.71 (m, 1H), 7.32-7.35 (m, 3H), 7.19 (s, 1H), 4.19-4.22 (m, 1H), 4.05-4.10 (m, 1H), 3.76-3.95 (m, 4H), 3.40-3.46 (m, 1H), 1.69-1.70 (m, 4H) and 1.19-1.22 (m, 3H) |
| 115 | 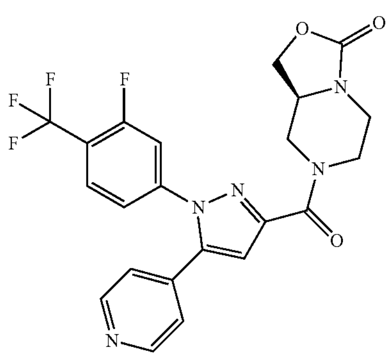 [SMILES: O=C(c1cc(-c2ccncc2)n(-c2ccc(C(F)(F)F)c(F)c2)n1)N1CCN2C(=O)OC[C@@H]2C1] | 81% | 476.11 (M + H)$^+$, 99.38% | δ 8.63 (d, J = 5.60 Hz, 2H), 7.89 (t, J = 8.00 Hz, 1H), 7.76 (d, J = 10.40 Hz, 1H), 7.35 (br s, 3H), 7.24 (s, 1H), 4.51-4.76 (m, 2H), 4.34-4.54 (m, 1H), 3.88-4.07 (m, 2H), 3.64-3.73 (m, 1H), 3.08-3.11 (m, 1H), 3.19-3.22 (m, 1H) and 2.82-2.87 (m, 1H) |
| 116 | 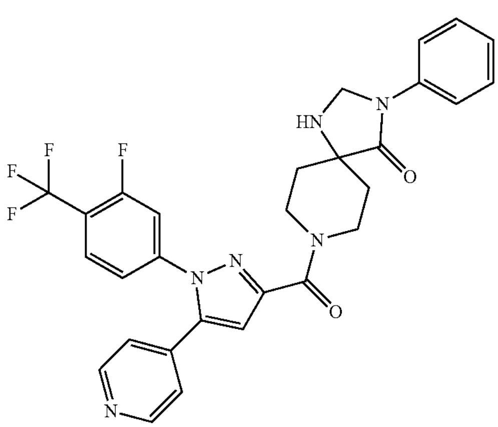 [SMILES: O=C(c1cc(-c2ccncc2)n(-c2ccc(C(F)(F)F)c(F)c2)n1)N1CCC2(CC1)NCN(c1ccccc1)C2=O] | 57% | 303.75 (M + H)$^+$, 99.72% | δ 8.62 (d, J = 6.40 Hz, 2H), 7.89 (t, J = 8.40 Hz, 1H), 7.65-7.72 (m, 3H), 7.35-7.41 (m, 5H), 7.22 (s, 1H), 7.15 (t, J = 7.20 Hz, 1H), 4.71-4.76 (m, 2H), 4.42-4.47 (m, 2H), 3.61-3.63 (m, 1H), 3.47-3.53 (m, 1H), 3.16-3.17 (m, 1H) and 1.68-1.79 (m, 4H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 117 | 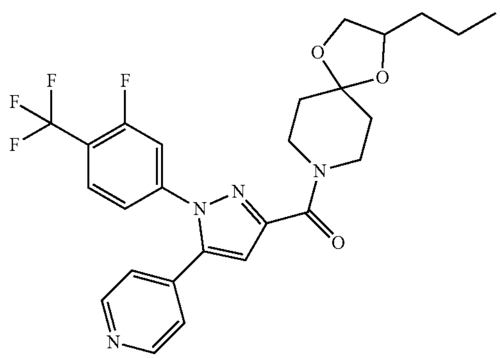 [SMILES: CCCC1COC2(CCN(C(=O)c3cc(-c4ccncc4)n(-c4ccc(C(F)(F)F)c(F)c4)n3)CC2)O1] | 39% | 519.17 (M + H)$^+$, 99.31% | δ 8.62 (d, J = 5.20 Hz, 2H), 7.89 (t, J = 8.4 Hz, 1H), 7.70 (d, J = 10.8 Hz, 1H), 7.32-7.35 (m, 3H), 7.19 (s, 1H), 4.07-4.09 (m, 2H), 3.76-3.96 (m, 3H), 3.62-3.65 (m, 1H), 3.50-3.51 (m, 1H), 1.74 (br s, 4H), 1.23-1.69 (m, 4H) and 0.88-0.92 (m, 3H) |
| 118 | 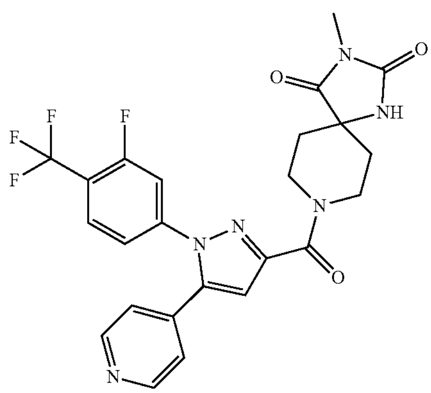 [SMILES: CN1C(=O)NC2(CCN(C(=O)c3cc(-c4ccncc4)n(-c4ccc(C(F)(F)F)c(F)c4)n3)CC2)C1=O] | 67% | 517.13 (M + H)$^+$, 99.26% | δ 8.94 (s, 1H), 8.63 (d, J = 4.80 Hz, 2H), 7.89 (t, J = 7.6 Hz, 1H), 7.72 (d, J = 12.0 Hz, 1H), 7.34-7.35 (m, 3H), 7.23 (s, 1H), 4.31-4.43 (m, 2H), 3.58-3.64 (m, 1H), 3.29 (m, 1H), 2.84 (s, 3H), 1.85-1.89 (m, 2H) and 1.64-1.70 (m, 2H) |
| 119 | 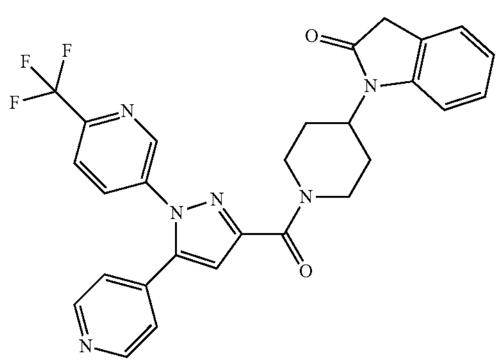 [SMILES: O=C(c1cc(-c2ccncc2)n(-c2ccc(C(F)(F)F)nc2)n1)N1CCC(N2C(=O)Cc3ccccc32)CC1] | 29% | 533.35 (M + H)$^+$, 96.97% | δ 8.84 (s, 1H), 8.63 (m, 2H), 8.04-8.10 (m, 2H), 7.38 (d, J = 6.0 Hz, 2H), 7.23-7.28 (m, 3H), 7.17 (d, J = 8.40 Hz, 1H), 6.99 (t, J = 7.2 Hz, 1H), 4.72 (m, 2H), 4.40-4.46 (m, 1H), 3.54 (s, 2H), 3.35-3.41 (m, 1H), 2.92-2.98 (m, 1H), 2.33-2.40 (m, 1H), 1.71-1.80 (m, 2H) and 1.07-1.11 (m, 1H) |
| 120 | 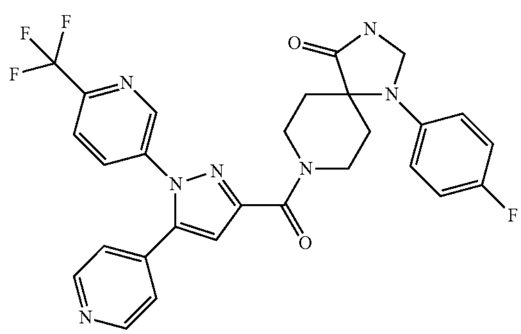 [SMILES: O=C(c1cc(-c2ccncc2)n(-c2ccc(C(F)(F)F)nc2)n1)N1CCC2(CC1)C(=O)NCN2c1ccc(F)cc1] | 38% | 564.37 (M − H)$^+$, 98.73% | δ 8.82 (br s, 2H), 8.63 (d, J = 6.0 Hz, 2H), 8.03 (s, 2H), 7.37 (d, J = 6.0 Hz, 2H), 7.26 (s, 1H), 7.10 (t, J = 8.80 Hz, 2H), 6.84 (m, 2H), 4.65 (s, 2H), 4.59-4.60 (m, 2H), 3.86-3.92 (m, 1H), 3.51-3.58 (m, 1H), 3.35-3.39 (m, 1H), 2.19-2.29 (m, 2H) and 1.07-1.11 (m, 1H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 121 | 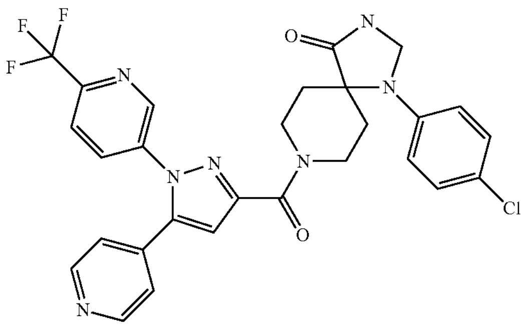 [SMILES: O=C(c1cc(-c2ccncc2)n(-c2ccc(C(F)(F)F)nc2)n1)N1CCC2(CC1)C(=O)NCN2c1ccc(Cl)cc1] | 46% | 582.41 (M + H)$^+$, 96.72% | δ 8.88 (br s, 2H), 8.83 (s, 1H), 8.64 (d, J = 5.60 Hz, 2H), 8.03 (br s, 2H), 7.38 (d, J = 5.60 Hz, 2H), 7.24-7.29 (m, 3H), 6.78 (d, J = 8.80 Hz, 2H), 4.61 (br s, 2H), 4.51 (m, 2H), 3.86-3.91 (m, 1H), 3.51-3.57 (m, 1H), 2.41 (m, 2H) and 1.72-1.81 (m, 2H) |
| 122 | 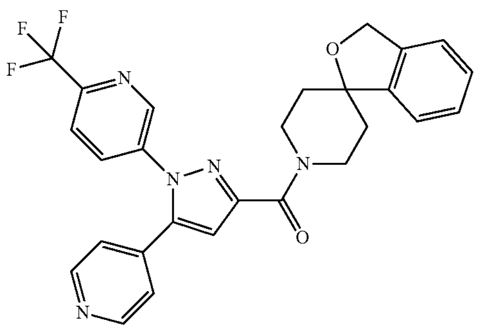 | 30% | 506.36 (M + H)$^+$, 98.17% | δ 8.84 (br s, 1H), 8.64 (d, J = 6.0 Hz, 2H), 8.03-8.09 (m, 2H), 7.37-7.39 (m, 2H), 7.29-7.33 (m, 5H), 5.05 (s, 2H), 4.58 (m, 2H), 3.48-3.55 (m, 1H), 3.12-3.15 (m, 1H), 1.90-1.99 (m, 2H) and 1.69-1.78 (m, 2H) |
| 123 | 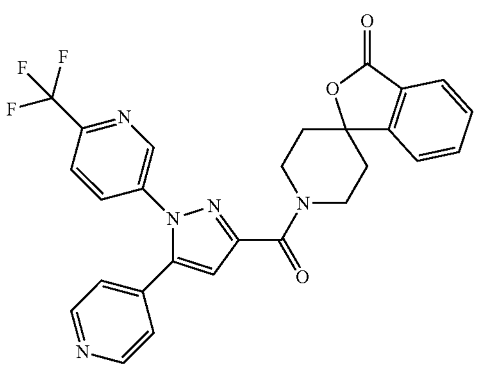 | 41% | 520.34 (M + H)$^+$, 95.11% | δ 8.86 (br s, 1H), 8.64 (d, J = 6.0 Hz, 2H), 8.04-8.10 (m, 2H), 7.77-7.87 (m, 3H), 7.62 (t, J = 7.20 Hz, 1H), 7.38 (d, J = 6.0 Hz, 2H), 7.29 (s, 1H), 4.67-4.76 (m, 2H), 3.56 (m, 1H), 3.19 (m, 1H) and 2.25-2.37 (m, 4H) |
| 124 | 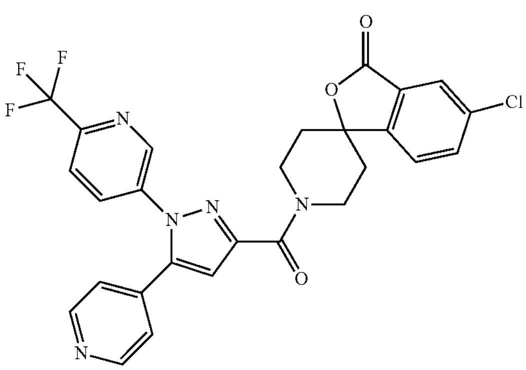 [SMILES: O=C1OC2(CCN(C(=O)c3cc(-c4ccncc4)n(-c4ccc(C(F)(F)F)nc4)n3)CC2)c2ccc(Cl)cc21] | 70% | 554.30 (M + H)$^+$, 97.55% | δ 8.85 (br s, 1H), 8.64 (d, J = 6.0 Hz, 2H), 8.04-8.10 (m, 2H), 7.84-7.92 (m, 3H), 7.38 (dd, J = 4.40 & 2.0 Hz, 2H), 7.28 (s, 1H), 4.67-4.77 (m, 2H), 3.53 (m, 1H), 3.16 (m, 1H), 2.69 (m, 1H) and 2.49-2.50 (m, 3H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 125 | 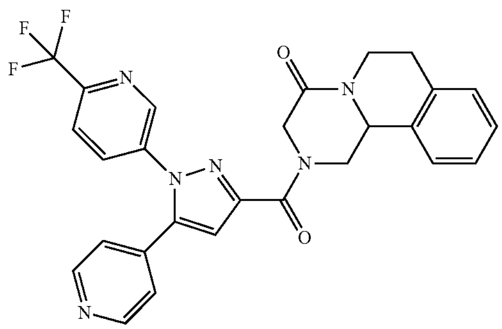 | 46% | 519.37 (M + H)$^+$, 98.55% | δ 8.83-8.95 (distorted s, 1H), 8.64 (m, 2H), 8.05-8.16 (m, 2H), 7.23-7.41 (m, 7H), 5.00-5.17 (m, 1H), 4.54-4.92 (m, 3H), 3.97-4.44 (m, 1H), 3.49-3.56 (m, 1H) and 2.67-2.89 (m, 3H) |
| 126 | 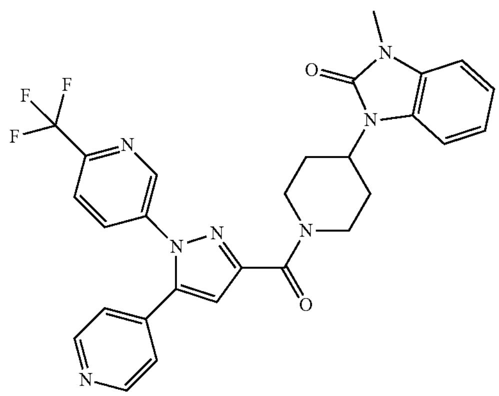 [SMILES: Cn1c(=O)n(C2CCN(C(=O)c3cc(-c4ccncc4)n(-c4ccc(C(F)(F)F)nc4)n3)CC2)c2ccccc21] | 59% | 548.35 (M + H)$^+$, 95.06% | δ 8.84 (s, 1H), 8.63 (d, J = 5.6 Hz, 2H), 8.04-8.09 (m, 2H), 7.38 (d, J = 5.6 Hz, 2H), 7.28-7.32 (m, 2H), 7.14-7.16 (m, 1H), 7.06-7.08 (m, 2H), 4.73 (m, 2H), 4.54-4.60 (m, 1H), 3.43 (m, 1H), 3.31 (s, 3H), 2.95-3.04 (m, 1H), 2.33-2.39 (m, 2H) and 1.78-1.86 (m, 2H) |
| 127 | 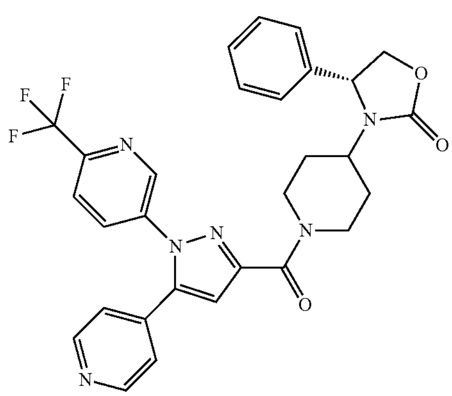 [SMILES: O=C(c1cc(-c2ccncc2)n(-c2ccc(C(F)(F)F)nc2)n1)N1CCC(N2C(=O)OC[C@H]2c2ccccc2)CC1] | 46% | 563.38 (M + H)$^+$, 98.89% | δ 8.76-8.83 (two signals due to rotational isomer, 1H), 8.62 (br s, 2H), 7.98-8.05 (m, 2H), 7.32-7.40 (m, 7H), 7.11-7.17 (two signals due to rotational isomer, 1H), 4.99-5.03 (m, 1H), 4.53-4.62 (m, 2H), 4.40-4.43 (m, 1H), 3.97-4.01 (m, 1H), 3.60-3.62 (m, 1H), 3.06-3.09 (m, 1H), 2.67-2.73 (m, 1H), 1.83-1.95 (m, 1H), 1.55-1.78 (m, 2H) and 1.24-1.30 (m, 1H) |
| 128 | 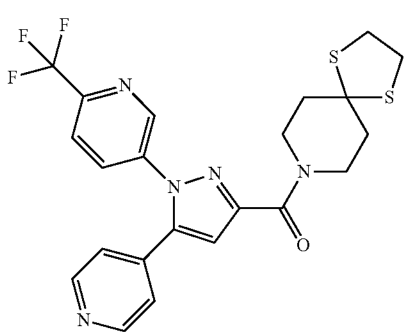 [SMILES: O=C(c1cc(-c2ccncc2)n(-c2ccc(C(F)(F)F)nc2)n1)N1CCC2(CC1)SCCS2] | 88% | 492.30 (M + H)$^+$, 97.31% | δ 8.83 (s, 1H), 8.63 (d, J = 6.0 Hz, 2H), 8.06-8.07 (m, 2H), 7.36 (d, J = 6.4 Hz, 2H), 7.23 (s, 1H), 3.94 (m, 2H), 3.74 (m, 2H), 3.33-3.35 (m, 4H) and 2.10 (m, 4H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 129 | 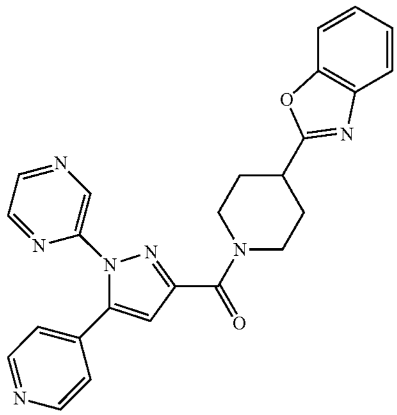 [SMILES: O=C(c1cc(-c2ccncc2)n(-c2cnccn2)n1)N1CCC(c2nc3ccccc3o2)CC1] | 71% | 452.36 (M + H)$^+$, 98.30% | δ 9.18 (s, 1H), 8.73 (d, J = 2.8 Hz, 1H), 8.58 (d, J = 5.6 Hz, 2H), 8.42 (s, 1H), 7.68-7.72 (m, 2H), 7.33-7.38 (m, 4H), 7.21 (s, 1H), 4.50 (m, 2H), 3.37-3.54 (m, 2H), 3.15-3.21 (m, 1H), 2.20-2.23 (m, 2H) and 1.82-1.91 (m, 2H) |
| 130 | 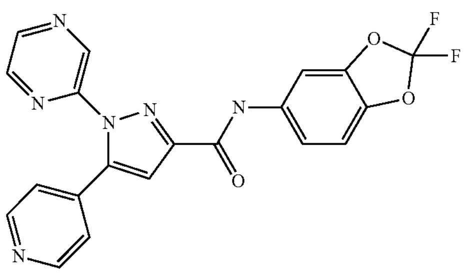 [SMILES: O=C(Nc1ccc2c(c1)OC(F)(F)O2)c1cc(-c2ccncc2)n(-c2cnccn2)n1] | 46% | 421.24 (M − H)$^+$, 99.49% | δ 10.60 (s, 1H), 9.33 (s, 1H), 8.78 (d, J = 2.4 Hz, 1H), 8.60 (d, J = 6.0 Hz, 2H), 8.46-8.47 (m, 1H), 7.95 (d, J = 2.0 Hz, 1H), 7.61-7.64 (m, 1H) and 7.39-7.44 (m, 4H) |
| 131 | 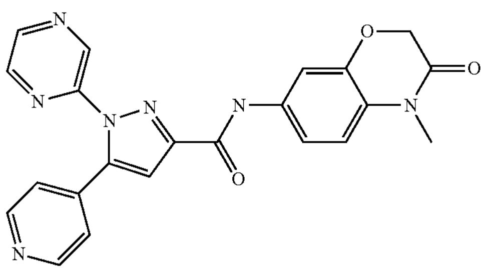 [SMILES: CN1C(=O)COc2cc(NC(=O)c3cc(-c4ccncc4)n(-c4cnccn4)n3)ccc21] | 93% | 426.26 (M − H)$^+$, 95.02% | δ 10.39 (s, 1H), 9.35 (s, 1H), 8.77 (d, J = 2.4 Hz, 1H), 8.60 (d, J = 6.0 Hz, 2H), 8.45 (s, 1H), 7.55-7.60 (m, 2H), 7.40-7.41 (m, 3H), 7.17 (d, J = 8.8 Hz, 1H), 4.67 (s, 2H) and 3.33 (s, 3H) |
| 132 | 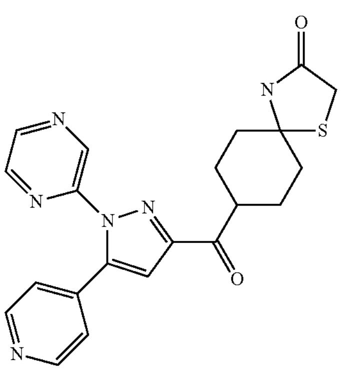 [SMILES: O=C1CSC2(CCC(C(=O)c3cc(-c4ccncc4)n(-c4cnccn4)n3)CC2)N1] | 29% | 422.30 (M + H)$^+$, 98.86% | δ 9.17 (s, 1H), 8.94 (br s, 1H), 8.73 (d, J = 2.4 Hz, 1H), 8.57-8.59 (m, 2H), 8.41-8.42 (m, 1H), 7.35-7.37 (m, 2H), 7.19 (s, 1H), 4.22-4.38 (m, 2H), 3.55-3.60 (m, 3H), 3.28 (m, 1H) and 1.90-1.97 (m, 4H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 133 | 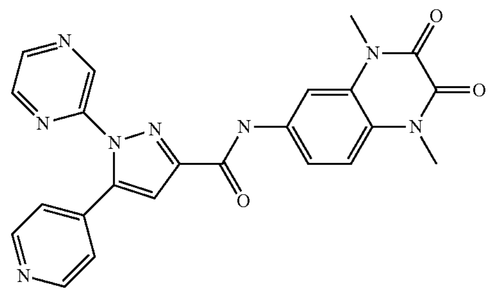 [SMILES: Cn1c(=O)c(=O)n(C)c2cc(NC(=O)c3cc(-c4ccncc4)n(-c4cnccn4)n3)ccc21] | 31% | 455.11 (M + H)$^+$, 98.49% | δ 10.55 (s, 1H), 9.36 (s, 1H), 8.79 (d, J = 2.40 Hz, 1H), 8.61 (d, J = 5.60 Hz, 2H), 8.47 (br s, 1H), 8.00 (br s, 1H), 7.85-7.89 (m, 1H), 7.40-7.47 (m, 4H), 3.55 (s, 3H) and 3.54 (s, 3H) |
| 134 | 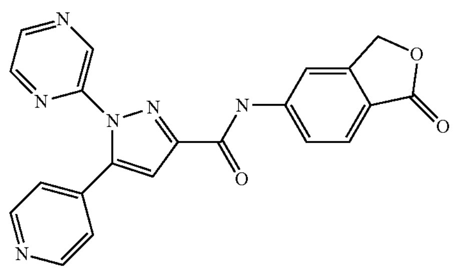 [SMILES: O=C(Nc1ccc2c(c1)COC2=O)c1cc(-c2ccncc2)n(-c2cnccn2)n1] | 31% | 399.10 (M + H)$^+$, 92.75% | δ 10.85 (s, 1H), 9.36 (s, 1H), 8.79 (d, J = 2.40 Hz, 1H), 8.60 (d, J = 5.60 Hz, 2H), 8.47 (br s, 1H), 8.28 (s, 1H), 7.98 (d, J = 8.0 Hz, 1H), 7.86 (d, J = 8.40 Hz, 1H), 7.47 (s, 1H), 7.41 (d, J = 6.0 Hz, 2H) and 5.42 (s, 2H) |
| 135 | 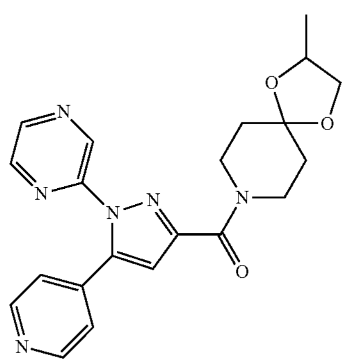 [SMILES: CC1COC2(CCN(C(=O)c3cc(-c4ccncc4)n(-c4cnccn4)n3)CC2)O1] | 44% | 407.37 (M + H)$^+$, 99.68% | δ 9.16 (s, 1H), 8.73 (d, 2.8 Hz, 1H), 8.57-8.58 (m, 2H), 8.40-8.41 (m, 1H), 7.35-7.36 (m, 2H), 7.19 (s, 1H), 4.21-4.25 (m, 1H), 4.05-4.10 (m, 1H), 3.63-3.98 (m, 4H), 3.40-3.46 (m, 1H), 1.72 (m, 4H) and 1.20 (m, 3H) |
| 136 | 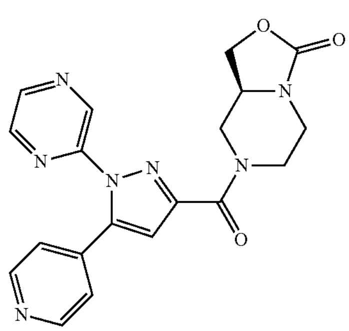 [SMILES: O=C(c1cc(-c2ccncc2)n(-c2cnccn2)n1)N1CCN2C(=O)OC[C@@H]2C1] | 37% | 392.29 (M + H)$^+$, 97.02% | δ 9.23 (d, J = 9.2 Hz, 1H), 8.74 (d, J = 2.4 Hz, 1H), 8.58 (d, J = 6.0 Hz, 2H), 8.41 (s, 1H), 7.36 (br s, 2H), 7.23 (d, J = 2.4 Hz, 1H), 4.52-4.78 (m, 2H), 4.37-4.43 (m, 1H), 3.90-4.08 (m, 2H), 3.66-3.74 (m, 1H), 3.12-3.33 (m, 2H) and 2.83-2.89 (m, 1H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 137 | 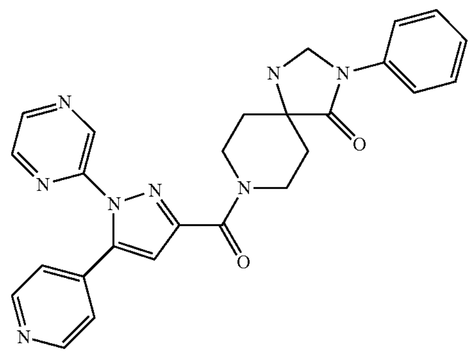 [SMILES: O=C(c1cc(-c2ccncc2)n(-c2cnccn2)n1)N1CCC2(CC1)NCN(c1ccccc1)C2=O] | 79% | 481.39 (M + H)$^+$, 97.37% | δ 9.17 (s, 1H), 8.73 (d, J = 2.4 Hz, 1H), 8.57-8.59 (m, 2H), 8.41-8.42 (m, 1H), 7.66 (d, J = 8.0 Hz, 2H), 7.36-7.41 (m, 4H), 7.21 (s, 1H), 7.15 (t, J = 7.2 Hz, 1H), 4.17-4.79 (m, 2H), 4.44-4.46 (m, 2H), 3.63 (t, J = 9.2 Hz, 1H), 3.49-3.55 (m, 1H), 3.18-3.22 (m, 1H) and 1.70-1.75 (m, 4H) |
| 138 | 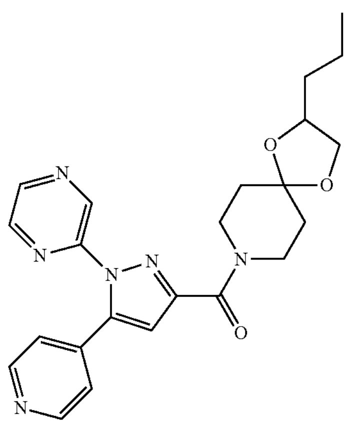 [SMILES: CCCC1COC2(CCN(C(=O)c3cc(-c4ccncc4)n(-c4cnccn4)n3)CC2)O1] | 33% | 435.38 (M + H)$^+$, 99.02% | δ 9.16 (s, 1H), 8.72 (d, J = 2.4 Hz, 1H), 8.58 (d, J = 2.4 Hz, 2H), 8.41 (s, 1H), 7.36 (d, J = 5.6 Hz, 2H), 7.19 (s, 1H), 4.05-4.09 (m, 2H), 3.66-3.96 (m, 4H), 3.49-3.51 (m, 1H), 1.71 (m, 4H), 1.23-1.57 (m, 4H) and 0.90 (t, J = 6.8 Hz, 3H) |
| 139 | 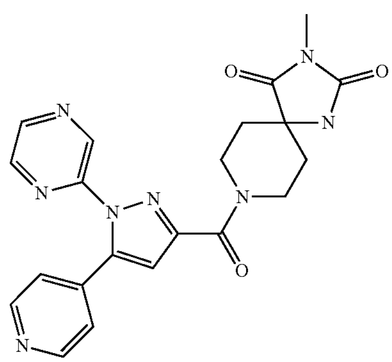 [SMILES: CN1C(=O)NC2(CCN(C(=O)c3cc(-c4ccncc4)n(-c4cnccn4)n3)CC2)C1=O] | 37% | 431.28 (M − H)$^+$, 99.81% | δ 9.16 (s, 1H), 8.93 (s, 1H), 8.73 (d, J = 2.4 Hz, 1H), 8.58 (d, J = 6.0 Hz, 2H), 8.42 (s, 1H), 7.36 (d, J = 5.6 Hz, 2H), 7.22 (s, 1H), 4.31-4.43 (m, 2H), 3.61-3.72 (m, 1H), 2.85 (s, 3H), 1.83-1.94 (m, 2H), 1.69 (m, 2H) and 1.23-1.27 (m, 1H) |
| 140 | 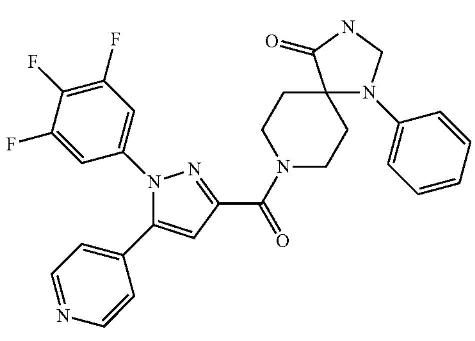 [SMILES: O=C(c1cc(-c2ccncc2)n(-c2cc(F)c(F)c(F)c2)n1)N1CCC2(CC1)C(=O)NCN2c1ccccc1] | 36% | 531.32 (M − H)$^+$, 99.38% | δ 8.84 (br s, 1H), 8.60 (d, J = 6.4 Hz, 2H), 7.51-7.55 (m, 2H), 7.31-7.32 (m, 2H), 7.20-7.24 (m, 3H), 6.74-6.78 (m, 3H), 4.62 (s, 2H), 4.47-4.53 (m, 2H), 3.83-3.89 (m, 1H), 3.49-3.56 (m, 1H) and 1.69-1.88 (m, 4H) |

TABLE 5-continued

Exemplary Compounds

| Cpd ID | Structure | Yield (%) | LCMS | NMR data (DMSO-d$_6$, 400 MHz), unless otherwise specified |
|---|---|---|---|---|
| 141 | 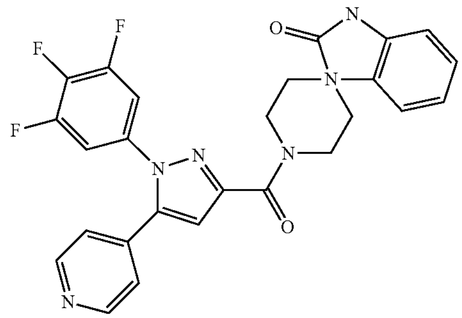 | 28% | 517.31 (M − H)$^+$, 98.75% | δ 8.60 (d, J = 6.0 Hz, 2H), 7.55-7.58 (m, 2H), 7.32 (d, J = 6.0 Hz, 2H), 7.23-7.24 (m, 2H), 6.97 (m, 3H), 4.69-4.76 (m, 2H), 4.47-4.53 (m, 1H), 3.29-3.60 (m, 2H), 2.92-2.98 (m, 1H), 2.29-2.36 (m, 2H) and 1.75-1.81 (m, 2H) |
| 142 | 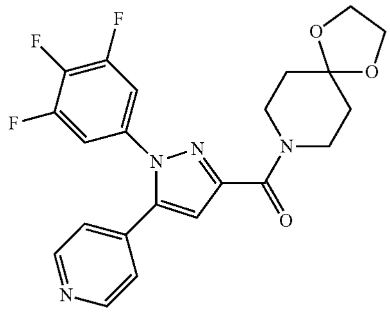 [SMILES: O=C(c1cc(-c2ccncc2)n(-c2cc(F)c(F)c(F)c2)n1)N1CCC2(CC1)OCCO2] | 47% | 445.30 (M + H)$^+$, 99.52% | δ 8.59-8.60 (m, 2H), 7.53-7.57 (m, 2H), 7.29-7.31 (m, 2H), 7.19 (s, 1H), 3.92 (m, 6H), 3.71 (m, 2H) and 1.75-1.88 (m, 4H) |
| 175 | 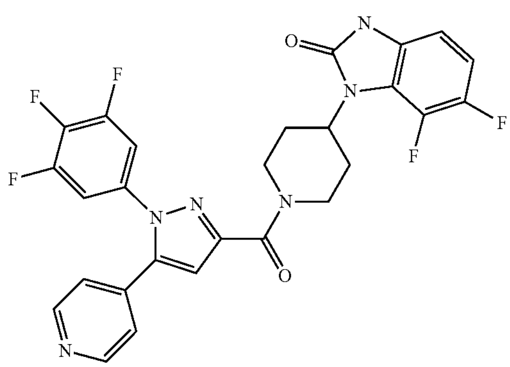 [SMILES: O=C(c1cc(-c2ccncc2)n(-c2cc(F)c(F)c(F)c2)n1)N1CCC(n2c(=O)[nH]c3ccc(F)c(F)c32)CC1] | 29% | 555.43 (M + H)$^+$, 99.51% | δ 11.25 (br s, 1H), 8.60 (d, J = 6.0 Hz, 2H), 7.54-7.58 (m, 2H), 7.32 (d, J = 6.0 Hz, 2H), 7.23 (s, 1H), 7.0-7.07 (m, 1H), 6.77-6.80 (m, 1H), 4.78-4.81 (m, 1H), 4.66-4.69 (m, 2H), 3.30 (m, 1H), 2.92-2.98 (m, 1H), 2.13-2.19 (m, 2H) and 1.84-1.90 (m, 2H) |
| 176 | 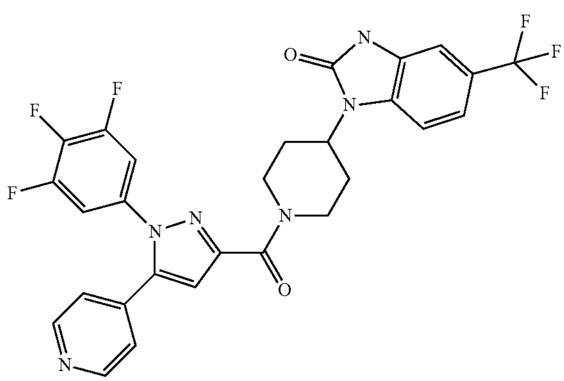 [SMILES: O=C(c1cc(-c2ccncc2)n(-c2cc(F)c(F)c(F)c2)n1)N1CCC(n2c(=O)[nH]c3cc(C(F)(F)F)ccc32)CC1] | 22% | 587.40 (M + H)$^+$, 99.83% | δ 11.26 (br s, 1H), 8.61 (d, J = 6.0 Hz, 2H), 7.54-7.58 (m, 2H), 7.45-7.47 (m, 1H), 7.35-7.37 (m, 1H), 7.32 (d, J = 6.0 Hz, 2H), 7.21-7.24 (m, 2H), 4.70-4.78 (m, 2H), 4.53-4.59 (m, 1H), 3.30 (m, 1H), 2.92-2.98 (m, 1H), 2.25-2.35 (m, 2H) and 1.79-1.90 (m, 2H) |

TABLE 5-continued
Exemplary Compounds
| Cpd ID | Structure | Yield (%) | LCMS | NMR data (DMSO-d$_6$, 400 MHz), unless otherwise specified |
|---|---|---|---|---|
| 179 | 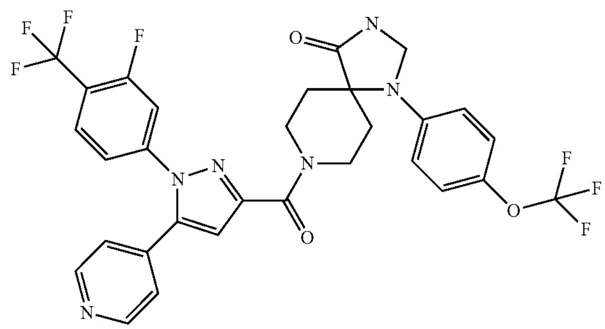 [SMILES: O=C(c1cc(-c2ccncc2)n(-c2ccc(C(F)(F)F)c(F)c2)n1)N1CCC2(CC1)C(=O)NCN2c1ccc(OC(F)(F)F)cc1] | 10% | 649.53 (M + H)$^+$, 96.93% | δ 8.90 (s, 1H), 8.60-8.64 (m, 2H), 7.85 (t, J = 7.2 Hz, 1H), 7.69 (d, J = 10.8 Hz, 1H), 7.30-7.36 (m, 3H), 7.20-7.25 (m, 3H), 6.82 (d, J = 8.0 Hz, 2H), 6.54 (s, 1H), 4.63 (s, 2H), 4.44-4.51 (m, 2H), 3.84-3.86 (m, 1H), 3.51-3.57 (m, 1H), 2.59 (m, 1H) and 1.71-1.87 (m, 2H) |
In another embodiment, compounds of the disclosure are made according to Scheme F.
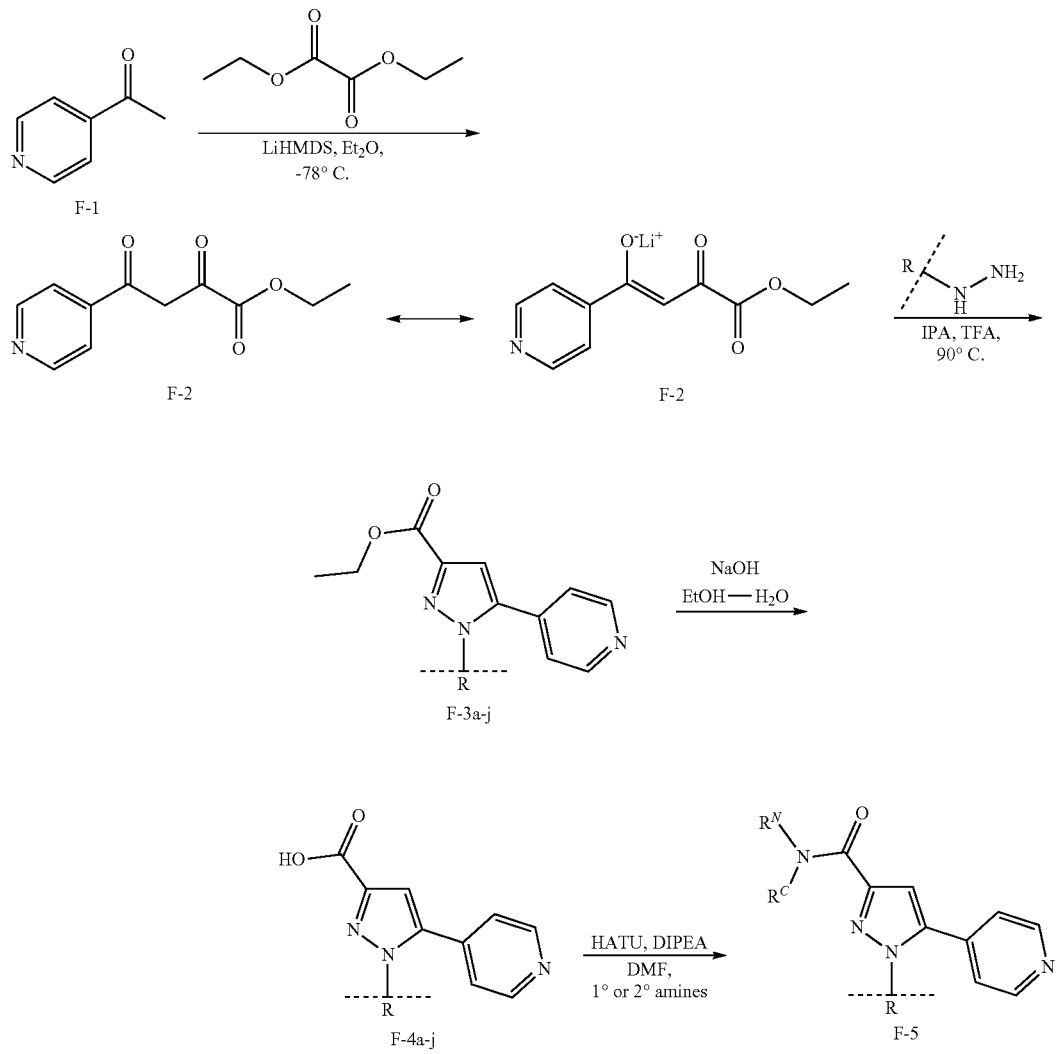
Scheme F -continued

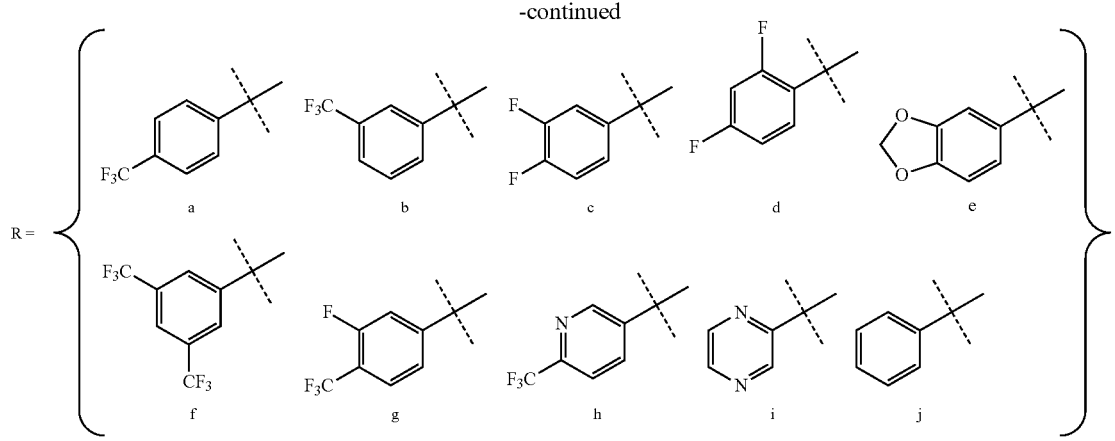

Preparation of ethyl 2,4-dioxo-4-(pyridin-4-yl)butanoate (F-2)

A solution of 4-acetyl pyridine (10.0 g, 82.55 mmol) in diethyl ether (160 mL) was cooled to −78° C. followed by addition of LiHMDS (15.16 g, 90.80 mmol). The resulting reaction mixture was stirred at −78° C. for 45 min followed by dropwise addition of diethyl oxalate (13.5 mL, 98.92 mmol) in about 30 min. The reaction mixture was then left to stir at room temperature for 16 h. After completion of the reaction (TLC and MS monitoring), the solution was then cooled 0° C. and the resulting precipitate was filtered to get the desired product as an off-white solid (18.0 g, 98%), which was carried forward to the next step without purification. $^1$H-NMR (400 MHz, DMSO-$d_6$): δ 8.66 (d, J=4.80 Hz, 2H), 7.70 (d, J=5.20 Hz, 2H), 6.43 (s, 1H), 4.15 (q, J=7.20 Hz, 2H) and 1.25 (t, J=7.20 Hz, 3H).

General Procedure for the Preparation of Compounds F-3a-j:

To an ice-cold solution of ethyl 2,4-dioxo-4-(pyridin-4-yl)butanoate F-2 (1.0 eq) in IPA was added a respective hydrazine (1.10 eq) and TFA (2.0 eq). The resulting reaction mixture was warmed up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 Mesh, 10-15% EtOAc-hexane) to get the desired product.

Ethyl 5-(pyridin-4-yl)-1-(4-(trifluoromethyl)phenyl)-1H-pyrazole-3-carboxylate (F-3a)

$^1$H-NMR (400 MHz, CDCl$_3$): δ 8.61 (d, J=6.0 Hz, 2H), 7.66 (d, J=8.4 Hz, 2H), 7.47 (d, J=8.4 Hz, 2H), 7.17 (s, 1H), 7.11 (m, 2H), 4.44 (q, J=7.20 Hz, 2H) and 1.41 (t, J=7.20 Hz, 3H). LCMS: 362.21 (M+H)$^+$, 99.95%. Yield: 50%.

Ethyl 5-(pyridin-4-yl)-1-(3-(trifluoromethyl)phenyl)-1H-pyrazole-3-carboxylate (F-3b)

$^1$H-NMR (400 MHz, CDCl$_3$): δ 8.60 (d, J=6.0 Hz, 2H), 7.73 (s, 1H), 7.67 (d, J=8.0 Hz, 1H), 7.49 (m, 1H), 7.35 (m, 1H), 7.23 (s, 1H), 7.14 (m, 2H), 4.29 (q, J=7.20 Hz, 2H) and 1.42 (t, J=7.20 Hz, 3H). LCMS: 362.22 (M+H)$^+$, 91.70%. Yield: 62%.

Ethyl 1-(3,4-difluorophenyl)-5-(pyridin-4-yl)-1H-pyrazole-3-carboxylate (F-3c)

$^1$H-NMR (400 MHz, CDCl$_3$): δ 8.61 (d, J=6.0 Hz, 2H), 7.31 (m, 1H), 7.30 (s, 1H), 7.19 (m, 1H), 7.04 (m, 2H), 7.01 (m, 1H), 4.43 (q, J=7.20 Hz, 2H) and 1.39 (t, J=7.20 Hz, 3H). LCMS: 330.14 (M+H)$^+$, 93.07%. Yield: 55%.

Ethyl 1-(2,4-difluorophenyl)-5-(pyridin-4-yl)-1H-pyrazole-3-carboxylate (F-3d)

$^1$H-NMR (400 MHz, CDCl$_3$): δ 8.62 (d, J=6.4 Hz, 2H), 7.82 (m, 1H), 7.55 (m, 1H), 7.53 (s, 1H), 7.34 (m, 3H), 4.32 (q, J=7.20 Hz, 2H) and 1.30 (t, J=7.20 Hz, 3H). LCMS: 330.21 (M+H)+, 91.46%. Yield: 65%.

Ethyl 1-(benzo[d][1,3]dioxol-5-yl)-5-(pyridin-4-yl)-1H-pyrazole-3-carboxylate (F-3e)

$^1$H-NMR (400 MHz, CDCl$_3$): δ 8.57 (d, J=6.0 Hz, 2H), 7.10 (m, 3H), 6.81 (s, 1H), 6.72 (m, 2H), 6.04 (s, 2H), 4.42 (q, J=7.20 Hz, 2H) and 1.40 (t, J=7.20 Hz, 3H). LCMS: 338.20 (M+H)+, 77.49%. Yield: 20%.

Ethyl 1-(3,5-bis(trifluoromethyl)phenyl)-5-(pyridin-4-yl)-1H-pyrazole-3-carboxylate (F-3f)

$^1$H-NMR (400 MHz, CDCl$_3$): δ 8.56 (dd, J=1.6 & 4.40 Hz, 2H), 7.90 (s, 1H), 7.82 (s, 2H), 7.20 (s, 1H), 7.12 (dd, J=1.6 & 4.40 Hz, 2H), 4.45 (q, J=7.20 Hz, 2H) and 1.42 (t, J=7.20 Hz, 3H). LCMS: 430.26 (M+H)$^+$, 93.03%. Yield: 32%.

Ethyl 1-(3-fluoro-4-(trifluoromethyl)phenyl)-5-(pyridin-4-yl)-1H-pyrazole-3-carboxylate (F-3g)

$^1$H-NMR (400 MHz, CDCl$_3$): δ 8.68 (dd, J=1.6 & 4.40 Hz, 2H), 7.60 (m, 1H), 7.36 (m, 1H), 7.14 (m, 4H), 4.44 (q, J=7.20 Hz, 2H) and 1.39 (t, J=6.80 Hz, 3H). MS: 380.0 (M+H)$^+$. Yield: 45%.

Ethyl 5-(pyridin-4-yl)-1-(6-(trifluoromethyl)pyridin-3-yl)-1H-pyrazole-3-carboxylate (F-3h)

$^1$H-NMR (400 MHz, CDCl$_3$): δ 8.67 (m, 3H), 7.92 (dd, J=2.0 & 8.40 Hz, 1H), 7.76 (s, 1H), 7.18 (m, 3H), 4.45 (q, J=7.20 Hz, 2H) and 1.42 (t, J=6.80 Hz, 3H). LCMS: 362.89 (M+H)$^+$, 98.45%. Yield: 50%.

Ethyl 1-(pyrazin-2-yl)-5-(pyridin-4-yl)-1H-pyrazole-3-carboxylate (F-3i)

$^1$H-NMR (400 MHz, CDCl$_3$): δ 9.21 (d, J=1.20 Hz, 1H), 8.62 (m, 2H), 8.60 (m, 1H), 8.23 (dd, J=1.2 & 2.40 Hz, 1H), 7.17 (d, J=6.0 Hz, 2H), 7.14 (s, 1H), 4.45 (q, J=7.20 Hz, 2H) and 1.42 (t, J=6.80 Hz, 3H). LCMS: 296.18 (M+H)$^+$, 96.22%. Yield: 30%.

Ethyl 1-phenyl-5-(pyridin-4-yl)-1H-pyrazole-3-carboxylate (F-3j)

$^1$H-NMR (400 MHz, DMSO-d$_6$): δ 8.55 (d, J=6.0 Hz, 2H), 7.51 (m, 3H), 7.38 (m, 3H), 7.24 (m, 2H), 4.35 (q, J=7.20 Hz, 2H) and 1.32 (t, J=7.20 Hz, 3H). Yield: 33%.

General Procedure for the Preparation of Compounds F-4a-j:

To an ice-cold solution of compound (F-3a-j) (1.0 eq) in EtOH was added dropwise an aqueous solution of sodium hydroxide (3.0 eq). The resulting solution was stirred at room temperature for 4 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~6 by adding 1N HCl. The resulting precipitate was filtered and dried under vacuum to get the desired product (60-80%) as a white solid.

5-(Pyridin-4-yl)-1-(4-(trifluoromethyl)phenyl)-1H-pyrazole-3-carboxylic Acid (F-4a)

$^1$H-NMR (400 MHz, DMSO-d$_6$): δ 12.84 (br s, 1H), 8.58 (d, J=5.60 Hz, 2H), 7.87 (d, J=8.4 Hz, 2H), 7.59 (d, J=8.4 Hz, 2H), 7.28 (m, 3H). LCMS: 334.13 (M+H)$^+$, 97.98%. Yield: 95%.

5-(Pyridin-4-yl)-1-(3-(trifluoromethyl)phenyl)-1H-pyrazole-3-carboxylic Acid (F-4b)

$^1$H-NMR (400 MHz, DMSO-d$_6$): δ 8.58 (d, J=6.00 Hz, 2H), 7.85 (d, J=8.0 Hz, 1H), 7.79 (s, 1H), 7.69 (m, 1H), 7.62 (d, J=8.0 Hz, 1H), 7.31 (s, 1H), 7.26 (m, 2H). LCMS: 334.13 (M+H)+, 98.62%. Yield: 94%.

1-(3,4-Difluorophenyl)-5-(pyridin-4-yl)-1H-pyrazole-3-carboxylic Acid (F-4c)

$^1$H-NMR (400 MHz, DMSO-d$_6$): δ 13.17 (br s, 1H), 8.57 (d, J=5.60 Hz, 2H), 7.69 (m, 1H), 7.54 (m, 1H), 7.22 (m, 4H). MS: 302.18 (M+H)$^+$. Yield: 78%.

1-(2,4-Difluorophenyl)-5-(pyridin-4-yl)-1H-pyrazole-3-carboxylic Acid (F-4d)

$^1$H-NMR (400 MHz, DMSO-d$_6$): δ 13.20 (br s, 1H), 8.56 (d, J=5.60 Hz, 2H), 7.80 (m, 1H), 7.51 (m, 1H), 7.32 (m, 2H), 7.25 (m, 2H). LCMS: 301.80 (M+H)$^+$, 98.31%. Yield: 85%.

1-(Benzo[d][1,3]dioxol-5-yl)-5-(pyridin-4-yl)-1H-pyrazole-3-carboxylic Acid (F-4e)

$^1$H-NMR (400 MHz, DMSO-d$_6$): δ 13.12 (br s, 1H), 8.56 (m, 2H), 7.25-7.27 (m, 3H), 7.04 (m, 1H), 6.97 (d, J=8.0 Hz, 1H), 6.79-6.81 (m, 1H) and 6.14 (s, 2H). LCMS: 310.10 (M+H)$^+$, 99.56%. Yield: 82%.

1-(3,5-Bis(trifluoromethyl)phenyl)-5-(pyridin-4-yl)-1H-pyrazole-3-carboxylic Acid (F-4f)

$^1$H-NMR (400 MHz, DMSO-d$_6$): δ 13.17 (br s, 1H), 8.59 (d, J=6.0 Hz, 2H), 8.26 (s, 1H), 8.07 (s, 2H), 7.32 (m, 3H). LCMS: 402.15 (M+H)$^+$, 91.73%. Yield: 94%.

1-(3-Fluoro-4-(trifluoromethyl)phenyl)-5-(pyridin-4-yl)-1H-pyrazole-3-carboxylic Acid (F-4g)

$^1$H-NMR (400 MHz, DMSO-d$_6$): δ 8.60 (d, J=5.6 Hz, 2H), 7.88 (m, 1H), 7.67 (s, 1H), 7.32 (m, 4H). LCMS: 352.17 (M+H)$^+$, 98.60%. Yield: 92%.

5-(Pyridin-4-yl)-1-(6-(trifluoromethyl)pyridin-3-yl)-1H-pyrazole-3-carboxylic Acid (F-4h)

$^1$H-NMR (400 MHz, DMSO-d$_6$): δ 13.07 (br s, 1H), 8.81 (s, 1H), 8.60 (d, J=6.0 Hz, 2H), 8.05 (m, 2H), 7.34 (m, 3H). LCMS: 335.13 (M+H)$^+$, 97.97%. Yield: 75%.

1-(Pyrazin-2-yl)-5-(pyridin-4-yl)-1H-pyrazole-3-carboxylic Acid (F-4i)

$^1$H-NMR (400 MHz, DMSO-d$_6$): δ 13.40 (br s, 1H), 9.15 (s, 1H), 8.75 (d, J=6.4 Hz, 1H), 8.56 (m, 2H), 8.43 (s, 1H), 7.33 (s, 3H). LCMS: 268.17 (M+H)$^+$, 99.0%. Yield: 74%.

1-Phenyl-5-(pyridin-4-yl)-1H-pyrazole-3-carboxylic Acid (F-4j)

$^1$H-NMR (400 MHz, DMSO-d$_6$): δ 13.11 (br s, 1H), 8.55 (d, J=5.60 Hz, 2H), 7.50 (m, 3H), 7.38 (m, 2H), 7.31 (s, 1H) and 7.23 (d, J=6.0 Hz, 2H). Yield: 61%.

General Procedure for the Preparation of Final Compounds (F-5):

To an ice-cold solution of carboxylic acids F-4(a-j) (1.0 eq), in DMF (2.0 mL) was added DIPEA (3.0 eq) and HATU (1.50 eq). The resulting mixture was stirred under nitrogen atmosphere at 0° C. for 15 min followed by addition of the respective amine (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-TLC using the solvent systems 3-5% MeOH-DCM. The final step was performed on 75-100 mg scale.

Amines used in the preparation of the final compounds illustrated in Table 6 according to Scheme F are commercially available or can be synthesized by one of ordinary skill.

TABLE 6

Additional compounds of the disclosure prepared according the general method disclosed in Scheme F.

| Cpd. ID | Structure | Yield (%) | LCMS | NMR data (DMSO-d$_6$, 400 MHz), unless otherwise specified |
|---|---|---|---|---|
| 143 | 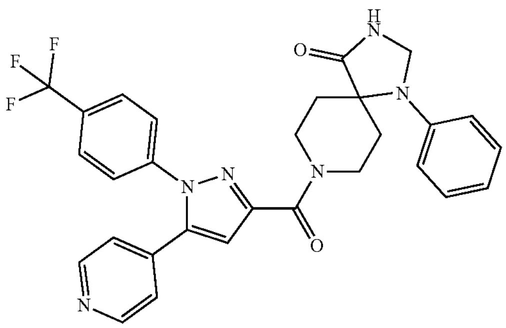 [SMILES: O=C(c1cc(-c2ccncc2)n(-c2ccc(C(F)(F)F)cc2)n1)N1CCC2(CC1)C(=O)NCN2c1ccccc1] | 43% | 547.16 (M + H)$^+$, 96.32% | δ 8.84 (br s, 1H), 8.61 (d, J = 6.0 Hz, 2H), 7.85 (d, J = 8.40 Hz, 2H), 7.59 (d, J = 8.0 Hz, 2H), 7.31 (d, J = 6.0 Hz, 2H), 7.19-7.23 (m, 3H), 6.73-6.78 (m, 3H), 4.61 (s, 2H), 4.51 (t, J = 13.20 Hz, 2H), 3.88 (t, J = 13.20 Hz, 1H), 3.54 (t, J = 12.40 Hz, 1H), 2.60 (m, 2H) and 1.71-1.80 (m, 2H) |
| 144 | 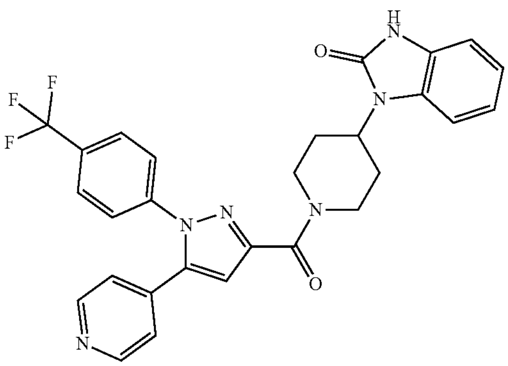 | 58% | 533.16 (M + H)$^+$, 95.43% | δ 10.86 (br s, 1H), 8.61 (d, J = 6.0 Hz, 2H), 7.87 (d, J = 8.80 Hz, 2H), 7.61 (d, J = 8.40 Hz, 2H), 7.32 (d, J = 5.60 Hz, 2H), 7.23 (m, 2H), 6.97 (m, 3H), 4.74 (t, J = 15.20 Hz, 2H), 4.51 (m, 1H), 3.30 (m, 1H), 2.95 (m, 1H), 2.26-2.37 (m, 2H) and 1.76-1.85 (m, 2H) |
| 145 | 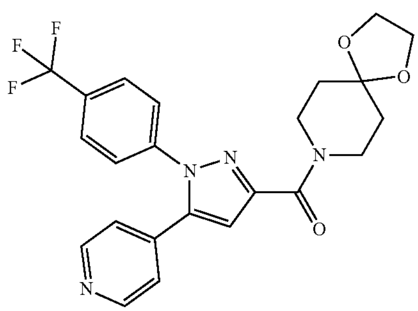 [SMILES: O=C(c1cc(-c2ccncc2)n(-c2ccc(C(F)(F)F)cc2)n1)N1CCC2(CC1)OCCO2] | 60% | 459.09 (M + H)$^+$, 95.06% | δ 8.60 (d, J = 6.0 Hz, 2H), 7.87 (d, J = 8.40 Hz, 2H), 7.60 (d, J = 8.40 Hz, 2H), 7.30 (d, J = 6.0 Hz, 2H), 7.18 (s, 1H), 3.92 (br s, 6H), 3.71 (m, 2H), and 1.68 (t, J = 5.20 Hz, 4H) |
| 146 | 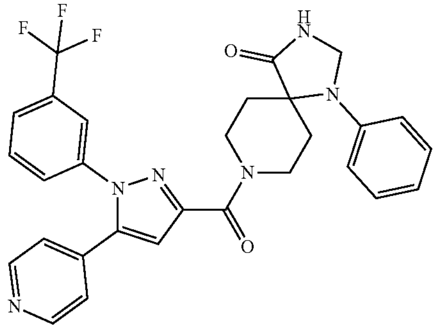 [SMILES: O=C(c1cc(-c2ccncc2)n(-c2cccc(C(F)(F)F)c2)n1)N1CCC2(CC1)C(=O)NCN2c1ccccc1] | 49% | 547.23 (M + H)$^+$, 92.28% | δ 8.83 (br s, 1H), 8.59 (d, J = 5.60 Hz, 2H), 7.82 (d, J = 7.20 Hz, 1H), 7.75 (s, 1H), 7.63-7.70 (m, 2H), 7.29 (d, J = 6.0 Hz, 2H), 7.19-7.22 (m, 3H), 6.73-6.78 (m, 3H), 4.61 (s, 2H), 4.51 (m, 2H), 3.86 (t, J = 6.0 Hz, 1H), 3.53 (t, J = 13.20 Hz, 1H), 2.59 (m, 2H) and 1.70-1.80 (m, 2H) |

TABLE 6-continued

Additional compounds of the disclosure prepared according the general method disclosed in Scheme F.

| Cpd. ID | Structure | Yield (%) | LCMS | NMR data (DMSO-d$_6$, 400 MHz), unless otherwise specified |
|---|---|---|---|---|
| 147 | 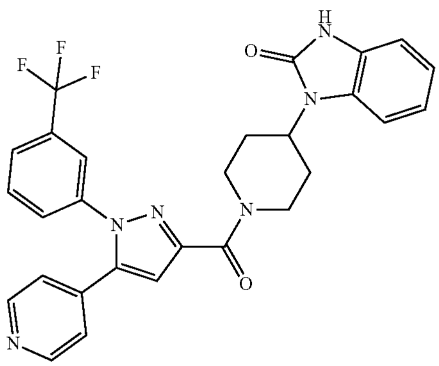 [SMILES: O=C(c1cc(-c2ccncc2)n(-c2cccc(C(F)(F)F)c2)n1)N1CCC(n2c(=O)[nH]c3ccccc32)CC1] | 57% | 533.16 (M + H)$^+$, 99.17% | δ 10.86 (br s, 1H), 8.59 (d, J = 6.0 Hz, 2H), 7.84 (d, J = 7.20 Hz, 1H), 7.76 (s, 1H), 7.66-7.71 (m, 2H), 7.30 (d, J = 6.0 Hz, 2H), 7.23-7.24 (m, 2H), 6.97-6.99 (m, 3H), 4.72 (m, 2H), 4.50 (m, 1H), 3.36 (m, 1H), 2.95 (m, 1H), 2.29-2.36 (m, 2H) and 1.76-1.85 (m, 2H) |
| 148 | 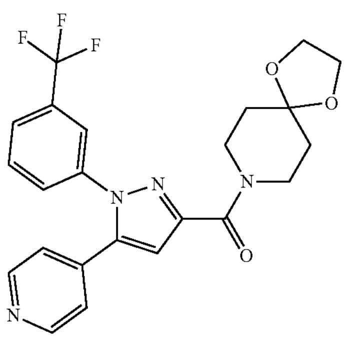 [SMILES: O=C(c1cc(-c2ccncc2)n(-c2cccc(C(F)(F)F)c2)n1)N1CCC2(CC1)OCCO2] | 58% | 459.11 (M + H)$^+$, 97.12% | δ 8.59 (d, J = 6.0 Hz, 2H), 7.85 (d, J = 7.60 Hz, 1H), 7.75 (s, 1H), 7.64-7.73 (m, 2H), 7.28 (d, J = 6.0 Hz, 2H), 7.18 (s, 1H), 3.92 (br s, 6H), 3.71 (m, 2H), and 1.68 (t, J = 5.20 Hz, 4H) |
| 149 | 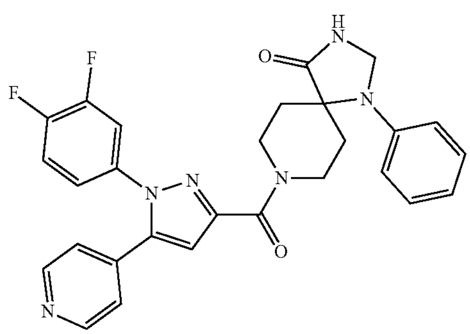 [SMILES: O=C(c1cc(-c2ccncc2)n(-c2ccc(F)c(F)c2)n1)N1CCC2(CC1)C(=O)NCN2c1ccccc1] | 35% | 515.34 (M +H)$^+$, 95.94% | CDCl$_3$: δ 8.59 (d, J = 5.60 Hz, 2H), 7.12-7.28 (m, 6H), 7.06 (s, 1H), 6.97 (m, 1H), 6.90 (m, 1H), 6.82 (d, J = 8.0 Hz, 2H), 6.13 (br s, 1H), 4.76-4.78 (m, 4H), 4.03 (m, 1H), 3.68 (m, 1H), 2.63-2.72 (m, 2H) and 1.80-2.0 (m, 2H) |
| 150 | 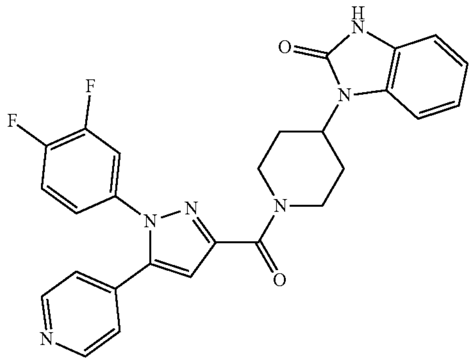 [SMILES: O=C(c1cc(-c2ccncc2)n(-c2ccc(F)c(F)c2)n1)N1CCC(n2c(=O)[nH]c3ccccc32)CC1] | 36% | 501.30 (M + H)$^+$ 99.02% | δ 10.86 (br s, 1H), 8.59 (d, J = 6.0 Hz, 2H), 7.70-7.72 (m, 1H), 7.52-7.59 (m, 1H), 7.29 (d, J = 6.0 Hz, 2H), 7.22-7.24 (m, 3H), 6.97-7.0 (m, 3H), 4.69-4.79 (m, 2H), 4.50 (t, J = 12.0 Hz, 1H), 3.27 (m, 1H), 2.94 (t, J = 12.0 Hz, 1H), 2.28-2.36 (m, 2H) and 1.76-1.84 (m, 2H) |

TABLE 6-continued

Additional compounds of the disclosure prepared according the general method disclosed in Scheme F.

| Cpd. ID | Structure | Yield (%) | LCMS | NMR data (DMSO-d$_6$, 400 MHz), unless otherwise specified |
|---|---|---|---|---|
| 151 | 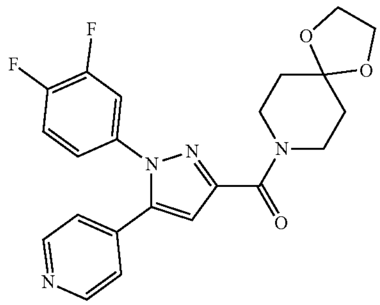 [SMILES: O=C(c1cc(-c2ccncc2)n(-c2ccc(F)c(F)c2)n1)N1CCC2(CC1)OCCO2] | 78% | 427.32 (M + H)$^+$, 98.52% | CDCl$_3$: δ 8.62 (d, J = 6.0 Hz. 2H), 7.18-7.21 (m, 2H), 7.28 (d, J = 6.0 Hz, 2H), 7.13 (m, 2H), 7.02 (s, 1H), 6.96-6.98 (m, 1H), 4.09 (t, J = 6.0 Hz, 2H), 4.0 (m, 4H), 3.89 (t, J = 6.80 Hz, 2H) and 1.81 (m, 4H) |
| 152 | 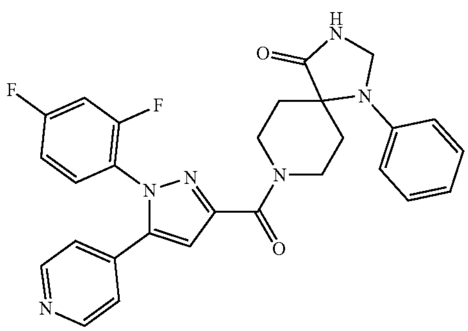 [SMILES: O=C(c1cc(-c2ccncc2)n(-c2ccc(F)cc2F)n1)N1CCC2(CC1)C(=O)NCN2c1ccccc1] | 56% | 515.16 (M + H)$^+$, 94.94% | δ 8.83 (br s, 1H), 8.58 (d, J = 5.60 Hz, 2H), 7.77-7.83 (m, 1H), 7.46-7.53 (m, 1H), 7.18-7.33 (m, 6H, 6.73-6.76 (m, 3H), 4.61 (s, 2H), 4.49 (m, 2H), 3.85 (m, 1H), 3.52 (m, 1H), 2.59 (m, 2H) and 1.69-1.79 (m, 2H) |
| 153 | 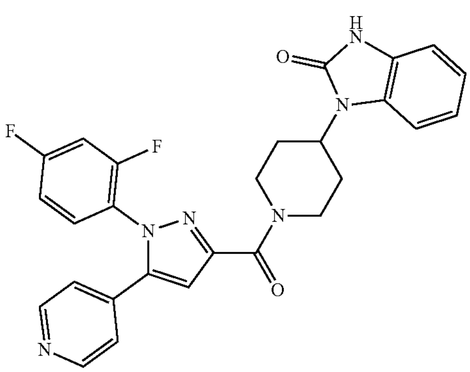 [SMILES: O=C(c1cc(-c2ccncc2)n(-c2ccc(F)cc2F)n1)N1CCC(n2c(=O)[nH]c3ccccc32)CC1] | 59% | 501.12 (M + H)$^+$, 98.92% | δ 10.86 (br s, 1H), 8.58 (d, J = 5.60 Hz, 2H), 7.80-86 (m, 1H), 7.52 (t, J = 8.40 Hz, 1H), 7.23-7.34 (m, 5H), 6.96 (m, 3H), 4.73 (m, 2H), 4.49 (m, 1H), 3.36 (m, 1H), 2.94 (m, 1H), 2.28-2.37 (m, 2H) and 1.75-1.84 (m, 2H) |
| 154 | 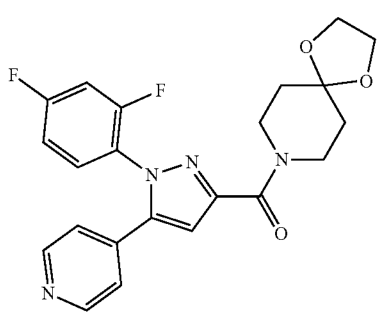 [SMILES: O=C(c1cc(-c2ccncc2)n(-c2ccc(F)cc2F)n1)N1CCC2(CC1)OCCO2] | 46% | 427.07 (M + H)$^+$, 97.93% | δ 8.57 (d, J = 6.0 Hz, 2H), 7.86-7.84 (m, 1H), 7.52 (d, J = 8.0 Hz, 1H), 7.33 (d, J = 8.40 Hz, 1H), 7.23-7.26 (m, 3H), 3.88-3.91 (m, 6H), 3.71 (m, 2H) and 1.67 (m, 4H) |

TABLE 6-continued

Additional compounds of the disclosure prepared according the general method disclosed in Scheme F.

| Cpd. ID | Structure | Yield (%) | LCMS | NMR data (DMSO-$d_6$, 400 MHz), unless otherwise specified |
|---|---|---|---|---|
| 155 | 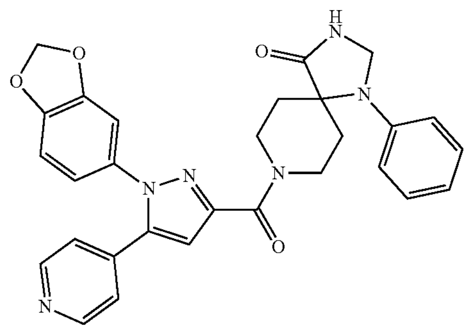 [SMILES: O=C(c1cc(-c2ccncc2)n(-c2ccc3c(c2)OCO3)n1)N1CCC2(CC1)C(=O)NCN2c1ccccc1] | 47% | 523.29 (M + H)$^+$, 94.27% | δ 8.83 (br s, 1H), 8.57 (d, J = 5.60 Hz, 2H), 7.27 (d, J = 5.60 Hz, 2H), 7.18-7.23 (m, 3H), 7.05 (d, J = 2.0 Hz, 1H), 6.95 (d, J = 8.0 Hz, 1H), 6.73-6.77 (m, 4H), 6.11 (s, 2H), 4.58-4.61 (m, 3H), 4.49 (m, 1H), 3.84 (m, 1H), 3.52 (m, 1H), 2.50 (m, 2H) and 1.70-1.78 (m, 2H) |
| 156 | 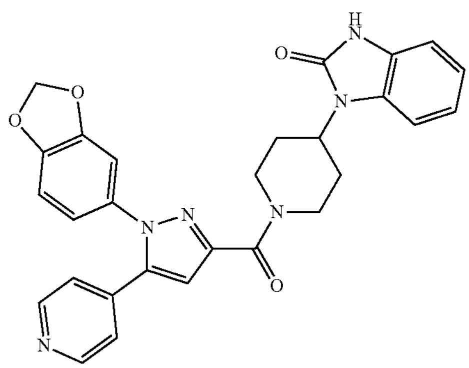 [SMILES: O=C(c1cc(-c2ccncc2)n(-c2ccc3c(c2)OCO3)n1)N1CCC(n2c(=O)[nH]c3ccccc32)CC1] | 39% | 507.02 (M − H)$^+$, 99.10% | δ 10.86 (br s, 1H), 8.58 (d, J = 6.0 Hz, 2H), 7.28 (d, J = 6.0 Hz, 2H), 7.22 (m, 1H), 7.18 (s, 1H), 7.08 (d, J = 1.60 Hz, 1H), 6.95-7.0 (m, 4H), 6.80 (dd, J = 2.0 and 8.40 Hz respectively, 1H), 6.12 (s, 2H), 4.85 (d, J = 13.20 Hz, 1H), 4.72 (d, J = 11.20 Hz, 1H), 4.49 (t, J = 12.80 Hz, 1H), 3.26 (m, 1H), 2.93 (m, 1H), 2.27-2.36 (m, 2H) and 1.76-1.83 (m, 2H) |
| 157 | 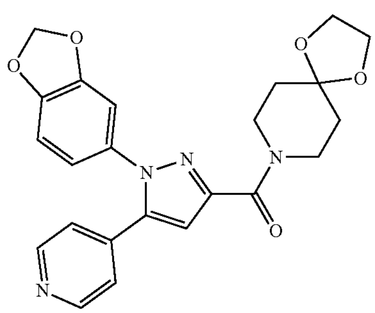 [SMILES: O=C(c1cc(-c2ccncc2)n(-c2ccc3c(c2)OCO3)n1)N1CCC2(CC1)OCCO2] | 38% | 435.06 (M + H)$^+$, 98.73% | δ 8.57 (d, J = 6.0 Hz, 2H), 7.26 (d, J = 6.40 Hz, 2H), 7.13 (s, 1H), 7.06 (d, J = 2.0 Hz, 1H), 6.98 (d, J = 8.40 Hz, 1H), 6.79 (dd, J = 2.0 and 8.0 Hz respectively, 1H), 6.13 (s, 2H), 3.92-3.96 (m, 6H), 3.70 (m, 2H) and 1.67 (m, 4H) |
| 158 | 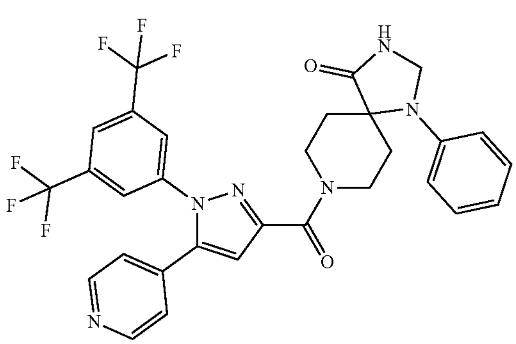 [SMILES: O=C(c1cc(-c2ccncc2)n(-c2cc(C(F)(F)F)cc(C(F)(F)F)c2)n1)N1CCC2(CC1)C(=O)NCN2c1ccccc1] | 43% | 615.16 (M + H)$^+$, 96.93% | δ 8.84 (br s, 1H), 8.61 (d, J = 6.0 Hz, 2H), 8.20 (s, 1H), 8.04 (m, 2H), 7.34 (d, J = 5.60 Hz, 2H), 7.20-7.25 (m, 3H), 6.73-6.79 (m, 3H), 4.62 (s, 2H), 4.40-4.50 (m, 2H), 3.86 (m, 1H), 3.54 (m, 1H), 2.56 (m, 2H) and 1.70-1.80 (m, 2H) |

TABLE 6-continued

Additional compounds of the disclosure prepared according the general method disclosed in Scheme F.

| Cpd. ID | Structure | Yield (%) | LCMS | NMR data (DMSO-$d_6$, 400 MHz), unless otherwise specified |
|---|---|---|---|---|
| 159 | 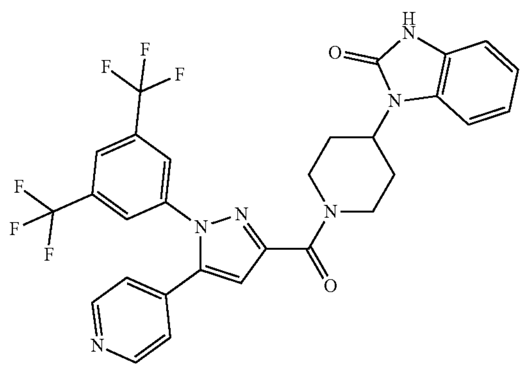 [SMILES: O=C(c1cc(-c2ccncc2)n(-c2cc(C(F)(F)F)cc(C(F)(F)F)c2)n1)N1CCC(n2c(=O)[nH]c3ccccc32)CC1] | 70% | 601.12 (M + H)$^+$, 99.75% | δ 10.86 (br s, 1H), 8.61 (d, J = 6.0 Hz, 2H), 8.23 (s, 1H), 8.07 (m, 2H), 7.35 (d, J = 6.0 Hz, 2H), 7.24 (m, 2H), 6.97-6.99 (m, 3H), 4.64-4.73 (m, 2H), 4.51 (t, J = 12.40 Hz, 1H), 3.36 (m, 1H), 2.97 (t, J = 12.0 Hz, 1H), 2.33 (t, J = 13.60 Hz, 2H) and 1.76-1.85 (m, 2H) |
| 160 | 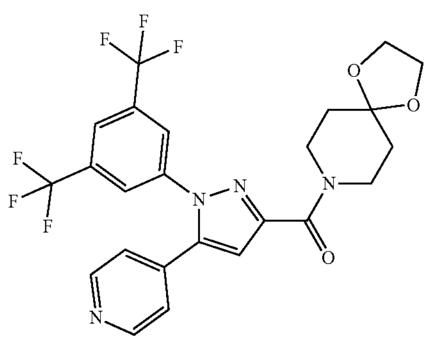 [SMILES: O=C(c1cc(-c2ccncc2)n(-c2cc(C(F)(F)F)cc(C(F)(F)F)c2)n1)N1CCC2(CC1)OCCO2] | 61% | 527.07 (M + H)$^+$, 95.45% | δ 8.61 (d, J = 6.0 Hz, 2H), 8.23 (s, 1H), 8.06 (s, 2H), 7.33 (d, J = 6.0 Hz, 2H), 7.20 (s, 1H), 3.88-3.92 (m, 6H), 3.72 (m, 2H) and 1.68 (m, 4H) |
| 161 | 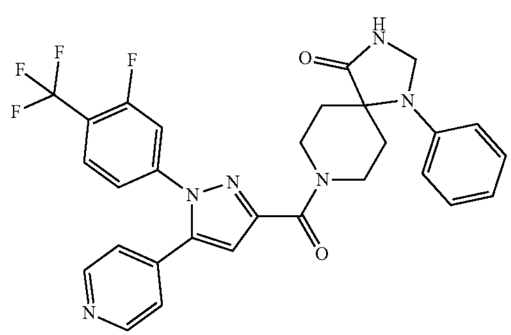 [SMILES: O=C(c1cc(-c2ccncc2)n(-c2ccc(C(F)(F)F)c(F)c2)n1)N1CCC2(CC1)C(=O)NCN2c1ccccc1] | 37% | 565.17 (M + H)$^+$, 96.70% | δ 8.84 (br s, 1H), 8.63 (d, J = 6.0 Hz, 2H), 7.86 (t, J = 8.0 Hz, 1H), 7.69 (d, J = 11.60 Hz, 1H), 7.30-7.36 (m, 3H), 7.20-7.24 (m, 3H), 6.73-6.78 (m, 3H), 4.62 (s, 2H), 4.48-4.50 (m, 2H), 3.87 (t, J = 11.20 Hz, 1H), 3.54 (t, J = 11.60 Hz, 1H), 2.56 (m, 2H) and 1.71-1.86 (m, 2H) |
| 162 | 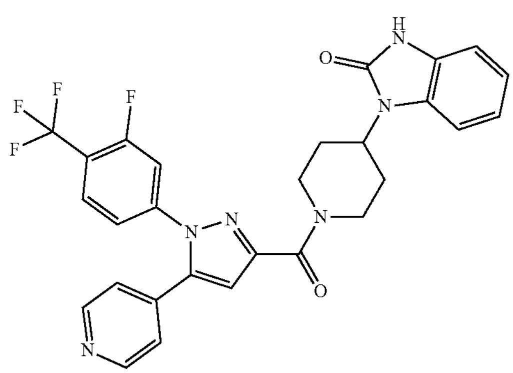 [SMILES: O=C(c1cc(-c2ccncc2)n(-c2ccc(C(F)(F)F)c(F)c2)n1)N1CCC(n2c(=O)[nH]c3ccccc32)CC1] | 51% | 551.12 (M + H)$^+$, 98.94% | δ 10.86 (br s, 1H), 8.63 (d, J = 5.60 Hz, 2H), 7.89 (t, J = 8.0 Hz, 1H), 7.72 (d, J = 11.20 Hz, 1H), 7.35 (m, 3H), 7.24 (m, 2H), 6.97-6.99 (m, 3H), 4.72 (m, 2H), 4.51 (t, J = 12.40 Hz, 1H), 3.35 (m, 1H), 2.96 (t, J = 13.20 Hz, 1H), 2.29-2.40 (m, 2H) and 1.76-1.85 (m, 2H) |

TABLE 6-continued

Additional compounds of the disclosure prepared according the general method disclosed in Scheme F.

| Cpd. ID | Structure | Yield (%) | LCMS | NMR data (DMSO-d$_6$, 400 MHz), unless otherwise specified |
|---|---|---|---|---|
| 163 | 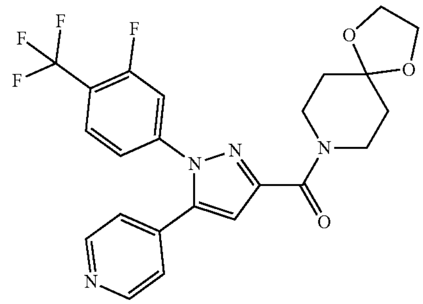 [SMILES: O=C(c1cc(-c2ccncc2)n(-c2ccc(C(F)(F)F)c(F)c2)n1)N1CCC2(CC1)OCCO2] | 56% | 477.11 (M + H)$^+$, 96.46% | δ 8.62 (d, J = 4.80 Hz, 2H), 7.88 (t, J = 8.0 Hz, 1H), 7.71 (d, J = 11.20 Hz, 1H), 7.33 (m, 3H), 7.19 (s, 1H), 3.92 (m, 6H), 3.71 (m, 2H) and 1.69 (m, 4H) |
| 164 | 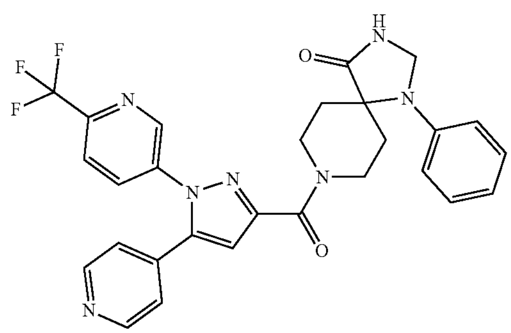 [SMILES: O=C(c1cc(-c2ccncc2)n(-c2ccc(C(F)(F)F)nc2)n1)N1CCC2(CC1)C(=O)NCN2c1ccccc1] | 40% | 548.20 (M + H)$^+$, 96.66% | δ 8.84 (m, 2H), 8.64 (d, J = 6.0 Hz, 2H), 8.03 (s, 2H), 7.38 (d, J = 6.0 Hz, 2H), 7.28 (s, 1H), 7.21 (t, J = 8.0 Hz, 2H), 6.73-6.78 (m, 3H), 4.62 (s, 2H), 4.49-4.51 (m, 2H), 3.88 (t, J = 11.60 Hz, 1H), 3.54 (t, J = 11.60 Hz, 1H), 2.56 (m, 2H) and 1.72-1.80 (m, 2H) |
| 165 | 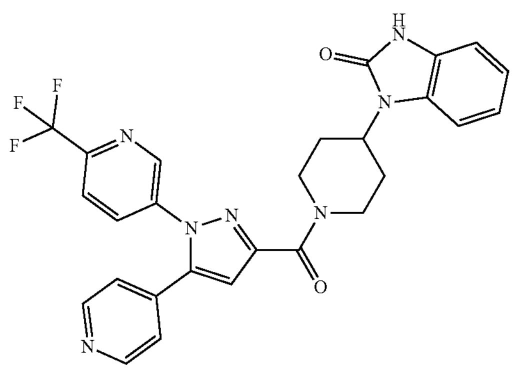 [SMILES: O=C(c1cc(-c2ccncc2)n(-c2ccc(C(F)(F)F)nc2)n1)N1CCC(n2c(=O)[nH]c3ccccc32)CC1] | 44% | 534.13 (M + H)$^+$, 99.22% | δ 10.86 (br s, 1H), 8.40 (s, 1H), 8.64 (d, J = 6.0 Hz, 2H), 8.03-8.09 (m, 2H), 7.38 (d, J = 6.0 Hz, 2H), 7.28 (s, 1H), 7.24 (m, 1H), 6.97 (m, 3H), 4.72 (m, 2H), 4.51 (t, J = 12.0 Hz, 1H), 3.35 (m, 1H), 2.97 (t, J = 12.0 Hz, 1H), 2.29-2.38 (m, 2H) and 1.77-1.86 (m, 2H) |
| 166 | 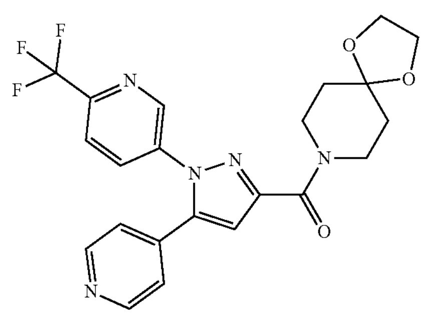 | 41% | 460.15 (M + H)$^+$, 98.30% | δ 8.82 (br s, 1H), 8.63 (d, J = 5.20 Hz, 2H), 8.05 (s, 1H), 7.36 (d, J = 6.0 Hz, 2H), 7.22 (s, 1H), 3.92 (m, 6H), 3.72 (m, 2H) and 1.69 (m, 4H) |

TABLE 6-continued

Additional compounds of the disclosure prepared according the general method disclosed in Scheme F.

| Cpd. ID | Structure | Yield (%) | LCMS | NMR data (DMSO-d$_6$, 400 MHz), unless otherwise specified |
|---|---|---|---|---|
| 167 | 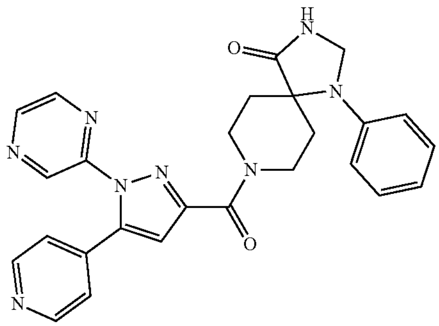 [SMILES: O=C(c1cc(-c2ccncc2)n(-c2cnccn2)n1)N1CCC2(CC1)C(=O)NCN2c1ccccc1] | 28% | 481.28 (M + H)$^+$, 97.91% | δ 9.12 (s, 1H), 8.85(s, 1H), 8.69 (d, J = 2.40 Hz, 1H), 8.59 (d, J = 5.60 Hz, 2H), 8.39 (s, 1H), 7.38 (d, J = 6.0 Hz, 2H), 7.20-7.24 (m, 3H), 6.73-6.80 (m, 3H), 4.63 (s, 2H), 4.45-4.51 (m, 2H), 3.89 (t, J = 12.40 Hz, 1H), 3.54 (t, J = 12.0 Hz, 1H), 2.62 (m, 1H), 2.44 (m, 1H) and 1.74-1.81 (m, 2H) |
| 168 | 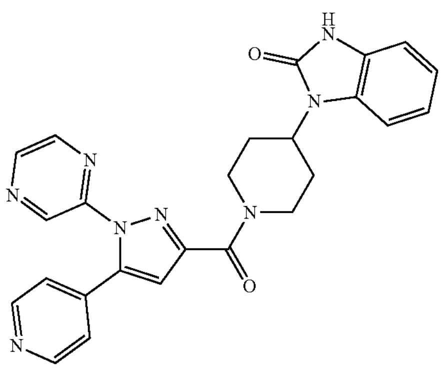 [SMILES: O=C(c1cc(-c2ccncc2)n(-c2cnccn2)n1)N1CCC(n2c(=O)[nH]c3ccccc32)CC1] | 43% | 467.24 (M + H)$^+$, 99.30% | δ 10.87 (br s, 1H), 9.17 (s, 1H), 8.72 (s, 1H), 8.59 (d, J = 5.20 Hz, 2H), 8.41 (s, 1H), 7.38 (d, J = 5.20 Hz, 2H), 7.24-7.26 (m, 2H), 6.97 (m, 3H), 4.73 (d, J = 13.20 Hz, 2H), 4.55 (m, 1H), 3.39 (m, 1H), 2.97 (m, 1H), 2.37 (m, 2H) and 1.78-1.85 (m, 2H) |
| 169 | 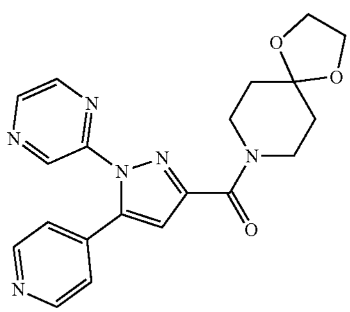 [SMILES: O=C(c1cc(-c2ccncc2)n(-c2cnccn2)n1)N1CCC2(CC1)OCCO2] | 37% | 393.34 (M + H)$^+$, 99.28% | δ 9.15 (s, 1H), 8.72 (m, 1H), 8.58 (d, J = 6.0 Hz, 2H), 8.41 (s, 1H), 7.36 (d, J = 6.0 Hz, 2H), 7.18 (s, 1H), 3.93 (m, 6H), 3.73 (m, 2H) and 1.71 (m, 4H) |
| 170 | 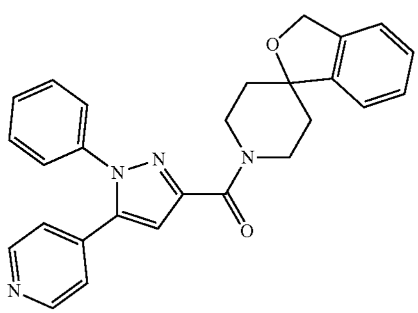 [SMILES: O=C(c1cc(-c2ccncc2)n(-c2ccccc2)n1)N1CCC2(CC1)OCc1ccccc12] | 48% | 437.24 (M + H)$^+$, 96.34% | δ 8.56 (m, 2H), 7.47 (m, 3H), 7.38 (m, 2H), 7.19-7.28 (m, 7H), 5.03 (s, 2H), 4.56-4.67 (m, 2H), 3.49 (t, J = 12.0 Hz, 1H), 3.12 (t, J = 12.0 Hz, 1H), 1.89-1.96 (m, 2H) and 1.67-1.76 (m, 2H) |

TABLE 6-continued

Additional compounds of the disclosure prepared according the general method disclosed in Scheme F.

| Cpd. ID | Structure | Yield (%) | LCMS | NMR data (DMSO-d$_6$, 400 MHz), unless otherwise specified |
|---|---|---|---|---|
| 171 | 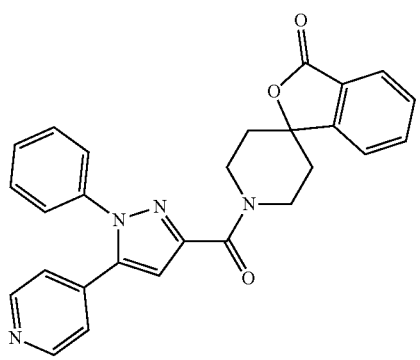 [SMILES: O=C1OC2(CCN(C(=O)c3cc(-c4ccncc4)n(-c4ccccc4)n3)CC2)c2ccccc21] | 51% | 451.15 (M + H)$^+$, 95.28% | δ 8.57 (d, J = 6.0 Hz, 2H), 7.76-7.86 (m, 3H), 7.61 (t, J = 8.40 Hz, 1H), 7.48-7.50 (m, 3H), 7.37-7.39 (m, 2H), 7.22-7.25 (m, 3H), 4.85 (d, J = 10.40 Hz, 1H), 4.70 (m, 1H), 3.53 (m, 1H), 3.16 (t, J = 10.80 Hz, 1H), 2.25-2.32 (m, 2H) and 1.71-1.79 (m, 2H) |
| 172 | 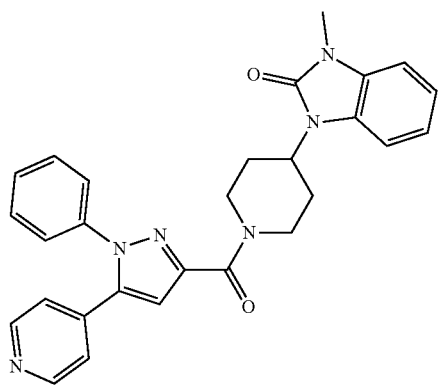 [SMILES: Cn1c(=O)n(C2CCN(C(=O)c3cc(-c4ccncc4)n(-c4ccccc4)n3)CC2)c2ccccc21] | 52% | 479.12 (M + H)$^+$, 98.91% | δ 8.56 (d, J = 6.0 Hz, 2H), 7.47-7.50 (m, 3H), 7.37-7.39 (m, 2H), 7.28-7.31 (m, 1H), 7.21-7.25 (m, 3H), 7.13-7.15 (m, 1H), 7.02-7.07 (m, 2H), 4.84 (d, J = 13.20 Hz, 1H), 4.73 (d, J = 12.40 Hz, 1H), 4.53 (m, 1H), 3.70 (s, 3H), 3.36 (m, 1H), 2.95 (m, 1H), 2.26-2.40 (m, 2H) and 1.77-1.85 (m, 2H) |
| 173 | 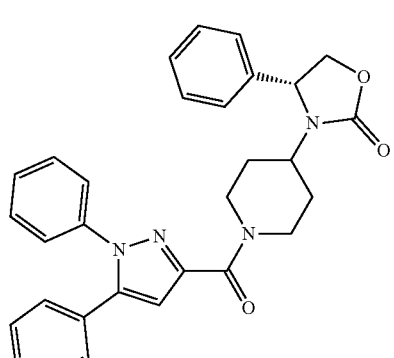 | 68% | 494.39 (M + H)$^+$, 97.19% | δ 8.54 (d, J = 4.80 Hz, 2H), 7.48 (m, 3H), 7.31-7.39 (m, 7H), 7.21 (m, 2H), 7.04-7.11 (m, 1H), 5.01 (t, J = 8.0 Hz, 1H), 4.41-4.71 (m, 3H), 3.98 (m, 1H), 3.59 (m, 1H), 3.03 (m, 1H), 2.68 (m, 1H), 1.90 (m, 1H), 1.56-1.76 (m, 2H) and 1.23-1.27 (m, 1H) |
| 174 | 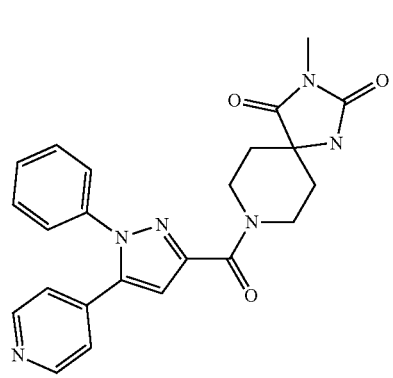 [SMILES: CN1C(=O)NC2(CCN(C(=O)c3cc(-c4ccncc4)n(-c4ccccc4)n3)CC2)C1=O] | 59% | 431.10 (M + H)$^+$, 99.54% | δ 8.91 (br s, 1H), 8.56 (d, J = 5.60 Hz, 2H), 7.48-7.49 (m, 3H), 7.36-7.38 (m, 2H), 7.19-7.24 (m, 3H), 4.47 (d, J = 13.60 Hz, 1H), 4.33 (d, J = 12.80 Hz, 1H), 3.63 (t, J = 12.0 Hz, 1H), 3.25 (m, 1H), 2.84 (s, 3H), 1.81-1.98 (m, 2H) and 1.66 (m, 2H) |

Experimental Procedures:

For the numbered schemes (e.g., Scheme 1), yields reported herein refer to purified products (unless specified) and are not optimised. Analytical TLC was performed on Merck silica gel 60 F$_{254}$ aluminium-backed plates. Compounds were visualised by UV light and/or stained with either 1$_2$ or potassium permanganate solution followed by heating. Flash column chromatography was performed on silica gel. $^1$H-NMR spectra were recorded on a Bruker Avance-400 MHz spectrometer with a BBO (Broad Band Observe) and BBFO (Broad Band Fluorine Observe) probe. Chemical shifts (3) are expressed in parts per million (ppm) downfield by reference to tetramethylsilane as the internal standard. Splitting patterns are designated as s (singlet), d (doublet), t (triplet), q (quartet), m (multiplet) and br s (broad singlet). Coupling constants (J) are given in hertz (Hz). LCMS analyses were performed either on an Acquity BEH C-18 column (2.10×100 mm, 1.70 μm) or Acquity HSS-T3 (2.1×100 mm, 1.8 μm) using the Electrospray Ionisation (ESI) technique.

The final compounds were purified via reverse-phase prep-HPLC employing either of the 2 methods mentioned below.

1. Column: SUNFIRE C 18 (19×250) mm, 5μ particle size, Mobile phase: A 0.1% TFA in Water, B ACN

| Flow mode: | | |
|---|---|---|
| Time | % A | % B |
| 1.00 | 50 | 50 |
| 15.00 | 36 | 74 |
| 15.10 | 10 | 90 |
| 17.00 | 10 | 90 |
| 17.10 | 50 | 50 |
| 20.00 | 50 | 50 |

Or

2. Column: X TERRA C 18 (19×250) mm, 5μ particle size, Mobile phase: A 5 mM Ammonium Acetate n water, B ACN

| Flow mode: | | |
|---|---|---|
| Time | % A | % B |
| 1.00 | 60 | 40 |
| 10.00 | 35 | 65 |
| 11.00 | 35 | 65 |
| 11.10 | 60 | 40 |
| 14.00 | 60 | 40 |

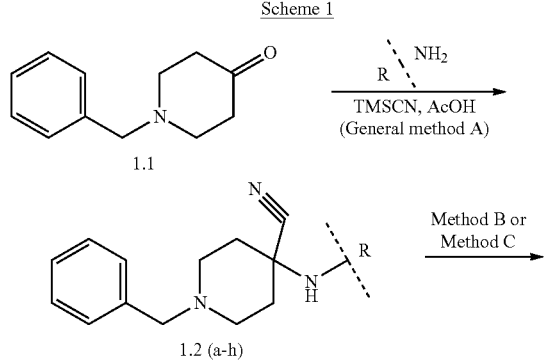

Scheme 1

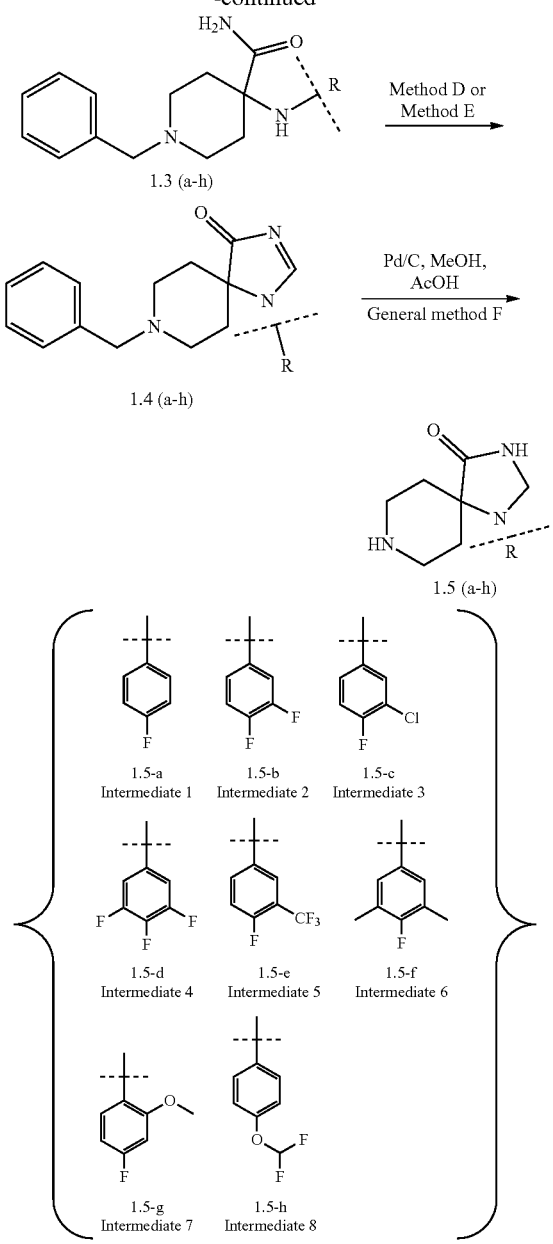

Reference: WO 2005/040166 and Tett. Lett; 2007, 55, 501-502

General Procedure for the Preparation of 1.5 (a-h):

General Method A:

To an ice-cold solution of 1-benzylpiperidin-4-one 1.1 (5.0-7.0 g, 1.0 eq) in acetic acid was added respective amines (1.1 eq) and trimethylsilyl cyanide (1.5 eq). The resulting reaction mass was stirred at RT for 18 h. After completion of the reaction (TLC monitoring), the reaction mass was cooled to 0° C. and the pH adjusted to ~10 using 5.0 N sodium hydroxide solution. The aqueous part was extracted with DCM (3×250 mL). The combined organics were dried over anhydrous Na$_2$SO$_4$, filtered and concentrated. The crude was triturated with diethyl ether to get the desired product 1.2 (a-h) as off white solid.

1-Benzyl-4-((4-fluorophenyl)amino)piperidine-4-carbonitrile (1.2-a)

¹H-NMR (400 MHz, CDCl₃): δ 7.35-7.38 (m, 5H), 6.90-6.95 (m, 4H), 3.54 (s, 2H), 3.48 (br s, 1H), 2.80-2.84 (m, 2H), 2.38-2.41 (m, 2H), 2.22-2.24 (m, 2H) and 1.89-1.94 (m, 2H). LC-MS: 310.23 (M+H)+, 95.66%. Yield: 58%.

1-Benzyl-4-((3,4-difluorophenyl)amino)piperidine-4-carbonitrile (1.2-b)

¹H-NMR (400 MHz, CDCl₃): δ 7.27-7.31 (m, 5H), 7.03-7.08 (m, 1H), 6.75-6.79 (m, 1H), 6.60-6.63 (m, 1H), 3.59 (br s, 1H), 3.55 (s, 2H), 2.80-2.84 (m, 2H), 2.41-2.47 (m, 2H), 2.26-2.39 (m, 2H) and 1.87-1.89 (m, 2H). LC-MS: 328.42 (M+H)⁺, 94.27%. Yield: 40%.

1-Benzyl-4-((3-chloro-4-fluorophenyl)amino)piperidine-4-carbonitrile (1.2-c)

¹H-NMR (400 MHz, CDCl₃): δ 7.28-7.34 (m, 5H), 7.01-7.05 (m, 1H), 6.95-6.97 (m, 1H), 6.79-6.82 (m, 1H), 3.57 (s, 3H), 2.80-2.83 (m, 2H), 2.41-2.46 (m, 2H), 2.24-2.27 (m, 2H) and 1.87-1.92 (m, 2H). LC-MS: 344.28 (M+H)⁺, 99.52%. Yield: 32%.

1-Benzyl-4-((3,4,5-trifluorophenyl)amino)piperidine-4-carbonitrile (1.2-d)

¹H-NMR (400 MHz, CDCl₃): δ 7.31-7.34 (m, 5H), 6.48-6.51 (m, 2H), 3.73 (s, 1H), 3.56 (s, 2H), 2.75-2.80 (m, 2H), 2.45-2.48 (m, 2H), 2.29-2.32 (m, 2H) and 1.86-1.88 (m, 2H). MS: 346.00 (M+H)⁺, 99.52%. Yield: 25%.

1-Benzyl-4-((4-fluoro-3-(trifluoromethyl)phenyl)amino)piperidine-4-carbonitrile (1.2-e)

¹H-NMR (400 MHz, CDCl₃): δ 7.29-7.31 (m, 5H), 7.10-7.11 (m, 3H), 3.69 (s, 1H), 3.56 (s, 2H), 2.82-2.85 (m, 2H), 2.45-2.48 (m, 2H), 2.19-2.22 (m, 2H) and 1.92-1.92 (m, 2H). LC-MS: 378.33 (M+H)⁺, 94.03%. Yield: 45%.

1-Benzyl-4-((4-fluoro-3,5-dimethylphenyl)amino)piperidine-4-carbonitrile (1.2-f)

¹H-NMR (400 MHz, CDCl₃): δ 7.26-7.31 (m, 5H), 6.55-6.57 (m, 1H), 6.37-6.38 (m, 1H), 3.60 (s, 1H), 3.53 (s, 2H), 2.76-2.81 (m, 2H), 2.45-2.50 (m, 2H), 2.28-2.32 (m, 2H), 2.09 (m, 6H), and 1.88-1.93 (m, 2H). MS: 338.33 (M+H)⁺, Yield: 60%.

1-Benzyl-4-((4-fluoro-2-methoxyphenyl)amino)piperidine-4-carbonitrile (1.2-g)

¹H-NMR (400 MHz, CDCl₃): δ 7.31-7.35 (m, 5H), 6.99-7.03 (m, 1H), 6.58-6.62 (m, 2H), 4.09 (s, 1H), 3.82 (s, 3H), 3.55 (s, 2H), 2.73-2.76 (m, 2H), 2.44-2.47 (m, 2H), 2.27-2.31 (m, 2H) and 1.90-1.93 (m, 2H). MS: 340.25 (M+H)⁺. Yield: 60%.

1-Benzyl-4-((4-(difluoromethoxy)phenyl)amino)piperidine-4-carbonitrile (1.2-h)

¹H-NMR (400 MHz, CDCl₃): δ 7.25-7.34 (m, 5H), 7.02 (d, J=8.8 Hz, 2H), 6.89 (d, J=8.8 Hz, 2H), 3.61 (br s, 1H), 3.49 (s, 3H), 2.80-2.83 (m, 2H), 2.43-2.47 (m, 2H), 2.17-2.22 (m, 2H) and 1.88-1.94 (m, 2H). LC-MS: 358.0 (M+H)⁺, 96.98%. Yield: 52.23%.

General Procedure for the Preparation of 1.3 (a-h): General Method B:

An ice-cold solution of 1.2 (a-g) (3.0-4.0 g, 1.0 eq) in 90% aqueous sulphuric acid was stirred at 0° C. for 30.0 min, then warm up to RT and stirred for 16 h. After completion of the reaction (TLC monitoring), the reaction mass was cooled to 0° C. and the pH adjusted to ~10 using 5.0 N sodium hydroxide solution. The aqueous part was extracted with DCM. The combined organics were dried over anhydrous sodium sulphate, filtered and concentrated. The crude was triturated with diethyl ether to get the desired products 1.3 (a-g) as off-white solids.

General Method C:

To an ice-cold solution of 1-benzyl-4-((4-(difluoromethoxy)phenyl)amino)piperidine-4-carbonitrile 1.2-h (2.5 g, 7.0 mmol, 1.0 eq) in DMSO was added H₂O₂ (30% aqueous solution, 1.5 eq) and K₂CO₃ (0.2 eq). The resulting reaction mixture was stirred at RT for 30.0 min. After completion of reaction (TLC mentoring), H₂O was added and extracted with DCM (3 times). The combined organics were dried over anhydrous sodium sulphate, filtered and concentrated. The crude was triturated with diethyl ether to get the desired product 1.3-h as an off-white solid.

1-Benzyl-4-(4-fluorophenylamino)piperidine-4-carboxamide (1.3-a)

¹H-NMR (400 MHz, CDCl₃): δ 7.23-7.25 (m, 5H), 6.85-6.87 (m, 3H), 6.54-6.55 (m, 2H), 5.47 (br s, 1H), 3.93 (s, 1H), 3.48 (s, 2H), 2.72-2.74 (m, 2H), 2.28-2.29 (m, 2H), 2.04-2.07 (m, 2H) and 1.86-1.89 (m, 2H). LCMS: 328.22 (M+H)⁺, 98.42%. Yield: 84%.

1-Benzyl-4-((3,4-difluorophenyl)amino)piperidine-4-carboxamide (1.3-b)

¹H-NMR (400 MHz, CDCl₃): δ 7.31-7.33 (m, 5H), 6.89-6.92 (m, 1H), 6.79 (br s, 1H), 6.45-6.48 (m, 1H), 6.29-6.31 (m, 1H), 5.51 (br s, 1H), 3.98 (s, 1H), 3.49 (s, 2H), 2.74-2.75 (m, 2H), 2.28-2.31 (m, 2H), 2.04-2.07 (m, 2H) and 1.85-1.87 (m, 2H). LCMS: 346.14 (M+H)⁺, 94.52%. Yield: 85%.

1-Benzyl-4-((3-chloro-4-fluorophenyl)amino)piperidine-4-carboxamide (1.3-c)

¹H-NMR (400 MHz, CDCl₃): δ 7.28-7.32 (m, 6H), 7.07-7.00 (m, 2H), 6.68 (br s, 1H), 6.50 (br s, 1H), 5.75 (br s, 1H), 3.42 (s, 2H), 2.50-2.52 (m, 2H), 2.22-2.24 (m, 2H), 1.98-2.00 (m, 2H) and 1.76-1.79 (m, 2H). LCMS: 362.05 (M+H)⁺, 90.00%. Yield: 79%.

1-Benzyl-4-((3,4,5-trifluorophenyl)amino)piperidine-4-carboxamide (1.3-d)

¹H-NMR (400 MHz, CDCl₃): δ 7.28-7.34 (m, 6H), 7.11 (br s, 1H), 6.31-6.35 (m, 2H), 6.11 (br s, 1H), 3.48 (s, 2H), 2.50-2.53 (m, 2H), 2.22-2.25 (m, 2H), 1.95-1.97 (m, 2H) and 1.77-1.80 (m, 2H). LCMS: 364.00 (M+H)⁺, 91.64%. Yield: 40%.

1-Benzyl-4-((4-fluoro-3-(trifluoromethyl)phenyl)amino)piperidine-4-carboxamide (1.3-e)

¹H-NMR (400 MHz, CDCl₃): δ 7.28-7.35 (m, 5H), 7.17-7.22 (m, 2H), 7.08 (br s, 1H), 6.94-6.95 (m, 1H), 6.73-6.75

(m, 1H), 6.00 (br s, 1H), 3.42 (s, 2H), 2.49-2.53 (m, 2H), 2.23-2.28 (m, 2H), 1.97-2.02 (m, 2H) and 1.76-1.80 (m, 2H). LCMS: 396.20 (M+H)$^+$, 95.56%. Yield: 45%.

1-Benzyl-4-((4-fluoro-3,5-dimethylphenyl)amino) piperidine-4-carboxamide (1.3-f)

$^1$H-NMR (400 MHz, CDCl$_3$): δ 7.28-7.34 (m, 6H), 7.15 (br s, 1H), 7.01 (s, 1H), 6.21-6.27 (m, 2H), 3.48 (s, 2H), 2.50-2.51 (m, 2H), 2.22-2.24 (m, 2H), 2.06 (d, J=6.0 Hz, 6H), 1.96-1.99 (m, 2H) and 1.77-1.81 (m, 2H). MS: 356.37 (M+H)$^+$. Yield: 56.6%.

1-Benzyl-4-((4-fluoro-2-methoxyphenyl)amino)piperidine-4-carboxamide (1.3-g)

$^1$H-NMR (400 MHz, CDCl$_3$): δ 7.22-7.30 (m, 6H), 7.05 (br s, 1H), 6.80-6.83 (m, 1H), 6.54-6.58 (m, 1H), 6.25-6.28 (m, 1H), 4.55 (s, 1H), 3.82 (s, 3H), 3.33-3.38 (m, 2H), 2.54-2.56 (m, 2H), 1.94-2.08 (m, 4H) and 1.80-1.83 (m, 2H). LCMS: 358.40 (M+H)$^+$, 99.78%. Yield: 61.38%.

1-Benzyl-4-((4-(difluoromethoxy)phenyl)amino) piperidine-4-carboxamide (1.3-h)

$^1$H-NMR (400 MHz, CDCl$_3$): δ 7.21-7.29 (m, 6H), 7.02 (br s, 1H), 6.90-6.95 (m, 3H), 6.56 (d, J=8.8 Hz, 2H), 3.42 (s, 3H), 2.53-2.59 (m, 2H), 2.32-2.36 (m, 2H), 1.99-2.11 (m, 2H) and 1.82-1.90 (m, 2H). MS: 376.30 (M+H)$^+$. Yield: 30%.

General Procedure for the Preparation of 1.4 (a-h):

General Method D:

A solution of compounds 1.3 (a-c) (2.0-4.0 g, 1.0 eq), in triethylorthoformate and AcOH (3:1) was irradiated by microwave in a sealed tube to 190° C. for 2 h. The reaction mixture was diluted with water and extracted with EtOAc. The combined organics were washed with brine, dried over anhydrous Na$_2$SO$_4$, filtered and concentrated. The residue was purified over silica gel (100-200 M, 2-4% MeOH-DCM) to get the desired products 1.4 (a-c) as off-white solids.

General Method E:

To a solution of compounds 1.3 (a-h) (1.0-2.5 g, 1.0 eq) in methanol was added DMF-DMA (3.0 eq). The resulting reaction mass was heated at 65° C. for h. After completion of reaction (TLC monitoring), the solvent was evaporated to dryness. The resulting crude residue was triturated with diethyl ether to get the desired product as an off-white solid product 1.4 (a-h).

8-Benzyl-1-(4-fluorophenyl)-1,3,8-triazaspiro[4.5] dec-2-en-4-one (1.4-a)

H-NMR (400 MHz, DMSO-d$_6$): δ 8.65 (s, 1H), 7.44-7.46 (m, 2H), 7.31-7.34 (m, 2H), 7.13-7.16 (m, 5H), 3.41 (s, 2H), 2.66-2.69 (m, 2H), 2.41-2.44 (m, 2H) and 1.75-1.78 (m, 4H). MS: 338.22 (M+H)$^+$. Yield: 48% with method D and 89% with method E.

8-Benzyl-1-(3,4-difluorophenyl)-1,3,8-triazaspiro [4.5]dec-2-en-4-one (4-b)

$^1$H-NMR (400 MHz, DMSO-d$_6$): δ 8.69 (s, 1H), 7.66-7.71 (m, 1H), 7.56-7.61 (m, 1H), 7.19-7.30 (m, 6H), 3.47 (s, 2H), 2.72-2.78 (m, 2H), 2.43-2.46 (m, 2H) and 1.72-1.80 (m, 4H). LCMS: 356.40 (M+H)$^+$, 87.67%. Yield: 22% with method D and 85% with method E.

8-Benzyl-1-(3-chloro-4-fluorophenyl)-1,3,8-triazaspiro[4.5]dec-2-en-4-one (1.4-c)

LCMS: 372.40 (M+H)+, 75.07%. Yield: 20% with method D.

8-Benzyl-1-(3,4,5-trifluorophenyl)-1,3,8-triazaspiro [4.5]dec-2-en-4-one (1.4-d)

$^1$H-NMR (400 MHz, DMSO-d$_6$): δ 8.71 (s, 1H), 7.57-7.60 (m, 2H), 7.24-7.28 (m, 5H), 3.49 (s, 2H), 2.73-2.75 (m, 2H), 2.48-2.49 (m, 2H), 1.83-1.85 (m, 2H) and 1.71-1.77 (m, 2H). MS: 373.96 (M+H)$^+$. Yield: 65% with method E.

8-benzyl-1-(4-fluoro-3-(trifluoromethyl)phenyl)-1,3,8-triazaspiro[4.5]dec-2-en-4-one (1.4-e)

$^1$H-NMR (400 MHz, DMSO-d$_6$): δ 8.22 (s, 1H), 7.33-7.42 (m, 8H), 3.50 (s, 2H), 2.92-2.95 (m, 2H), 2.68-2.70 (m, 2H), 1.90-1.91 (m, 2H) and 1.72-1.73 (m, 2H). MS: 406.56 (M+H)$^+$. Yield: 63% with method E.

8-Benzyl-1-(4-fluoro-3,5-dimethylphenyl)-1,3,8-triazaspiro[4.5]dec-2-en-4-one (1.4-f)

$^1$H-NMR (400 MHz, DMSO-d$_6$): δ 8.15 (s, 1H), 7.48-7.49 (m, 4H), 7.26-7.28 (m, 1H), 7.80-7.81 (m, 2H), 3.60 (s, 2H), 2.87-2.91 (m, 2H), 2.59-2.61 (m, 2H), 2.28 (s, 6H), 1.88-1.89 (m, 2H) and 1.56-1.58 (m, 2H). MS: 366.35 (M+H)$^+$. Yield: 79% with method E.

8-Benzyl-1-(4-fluoro-2-methoxyphenyl)-1,3,8-triazaspiro[4.5]dec-2-en-4-one (1.4-g)

$^1$H-NMR (400 MHz, DMSO-d$_6$): δ 8.01 (s, 1H), 7.22-7.26 (m, 5H), 7.08-7.12 (m, 1H), 6.70-6.74 (m, 2H), 3.77 (s, 3H), 3.55 (s, 2H), 2.87-2.95 (m, 2H), 2.59-2.62 (m, 2H) and 1.83-1.98 (m, 4H). LCMS: 368.00 (M+H)$^+$, 90.91%. Yield: 78% with method E.

8-Benzyl-1-(4-(difluoromethoxy)phenyl)-1,3,8-triazaspiro[4.5]dec-2-en-4-one (1.4-h)

$^1$H-NMR (400 MHz, DMSO-d$_6$): δ 8.67 (s, 1H), 7.45 (d, J=8.8 Hz, 2H), 7.30 (d, J=8.8 Hz, 2H), 7.21-7.26 (m, 5H), 3.46 (s, 2H), 3.28-3.32 (m, 1H), 2.67-2.72 (m, 2H), 2.45-2.49 (m, 2H) and 1.74-1.75 (m, 4H). MS: 386.0 (M+H)$^+$. Yield: 53% with method E.

General Procedure for the Preparation of 1.5 (a-h):

General Method F:

To a solution of compounds 1.4 (a-h) (0.50-1.5 g, 1.0 eq) in MeOH and AcOH (40:1, 20 mL) were added Pd—C (10 mol % w/w) and the resulting solution was stirred under hydrogen atmosphere (1 atm) at ambient temperature for 16 h. The reaction mixture was filtered through diatomaceous earth (Celite) bed and the filtrate was concentrated under reduced pressure. The residue was purified over silica gel (basic alumina, 2-4% MeOH-DCM) to get the desired products 1.5 (a-h) as off white solids.

1-(4-Fluorophenyl)-1,3,8-triazaspiro[4.5]dec-2-en-4-one (1.5-a): Intermediate 1

$^1$H-NMR (400 MHz, DMSO-d$_6$): δ 8.81 (br s, 1H), 7.05-7.08 (m, 2H), 6.95-6.96 (m, 2H), 4.58 (s, 2H), 3.34-

3.37 (m, 3H), 2.97-2.99 (m, 2H), 2.35-2.36 (m, 2H) and 1.61-1.63 (m, 2H). LCMS: 250.23 (M+H)$^+$, 88.25%. Yield: 90%

1-(3,4-Difluorophenyl)-1,3,8-triazaspiro[4.5]dec-2-en-4-one (1.5-b): Intermediate 2

$^1$H-NMR (400 MHz, DMSO-d$_6$): δ 8.77 (br s, 1H), 7.17-7.28 (m, 2H), 6.90-6.94 (m, 1H), 6.68-6.71 (m, 1H), 4.55 (s, 2H), 3.22-3.25 (m, 2H), 2.94-2.97 (m, 2H), 2.37-2.40 (m, 2H) and 1.54-1.57 (m, 2H). MS: 268.25 (M+H)$^+$. Yield: 86%

1-(3-Chloro-4-fluorophenyl)-1,3,8-triazaspiro[4.5]decan-4-one (1.5-c): Intermediate 3

MS: 284.12 (M+H)$^+$. Yield: 50%.

1-(3,4,5-Trifluorophenyl)-1,3,8-triazaspiro[4.5]decan-4-one (1.5-d): Intermediate 4

$^1$H-NMR (400 MHz, DMSO-d$_6$): δ 9.27 (s, 1H), 9.07 (s, 1H), 6.90-6.92 (m, 1H), 4.59 (s, 2H), 3.28-3.33 (m, 2H), 2.74-2.76 (m, 2H), 2.50-2.52 (m, 2H) and 1.82-1.85 (m, 2H). MS: 286.24 (M+H)$^+$. Yield: 60%.

1-(4-Fluoro-3-(trifluoromethyl)phenyl)-1,3,8-triazaspiro[4.5]decan-4-one (1.5-e): Intermediate 5

$^1$H-NMR (400 MHz, DMSO-d$_6$): δ 8.77 (br s, 1H), 7.33-7.35 (m, 2H), 6.92-6.93 (m, 1H), 6.70-6.71 (m, 1H), 4.62 (s, 2H), 3.17-3.20 (m, 2H), 2.88-2.90 (m, 2H), 2.33-2.39 (m, 2H) and 1.53-1.56 (m, 2H). LCMS: 318.29 (M+H)$^+$, 90.82%. Yield: 64%.

1-(4-Fluoro-3,5-dimethylphenyl)-1,3,8-triazaspiro[4.5]decan-4-one (1.5-f): Intermediate-6

$^1$H-NMR (400 MHz, DMSO-d$_6$): δ 8.83 (s, 1H), 7.66-7.68 (m, 1H), 6.60-6.66 (m, 2H), 4.54 (s, 2H), 3.38-3.41 (m, 2H), 3.12-3.16 (m, 2H), 2.50-2.53 (m, 2H), 2.19 (s, 6H) and 1.67-1.70 (m, 2H). MS: 278.32 (M+H)$^+$. Yield: 80%.

1-(4-Fluoro-2-methoxyphenyl)-1,3,8-triazaspiro[4.5]decan-4-one (1.5-g): Intermediate 7

$^1$H-NMR (400 MHz, DMSO-d$_6$): δ 8.51 (s, 1H), 7.62-7.69 (m, 1H), 7.22-7.26 (m, 1H), 6.92-6.98 (m, 1H), 6.72-6.76 (m, 1H), 4.66 (s, 2H), 3.76 (s, 3H), 3.19-3.26 (m, 2H), 2.90-3.01 (m, 2H), 2.50-2.54 (m, 2H) and 1.50-1.52 (m, 2H). MS: 280.26 (M+H)$^+$. Yield: 71%.

1-(4-(Difluoromethoxy)phenyl)-1,3,8-triazaspiro[4.5]decan-4-one (1.5-h): Intermediate 8

$^1$H-NMR (400 MHz, DMSO-d$_6$): δ 9.05 (br s, 1H), 7.10-7.13 (m, 3H), 6.93-6.96 (m, 2H), 4.57 (s, 2H), 3.25-3.28 (m, 3H), 2.97-2.99 (m, 2H), 2.40-2.42 (m, 2H) and 1.59-1.64 (m, 2H). MS: 298.34 (M+H)$^+$. Yield: 78%.

Scheme 2

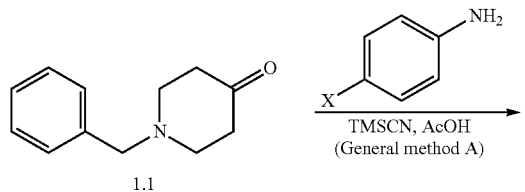

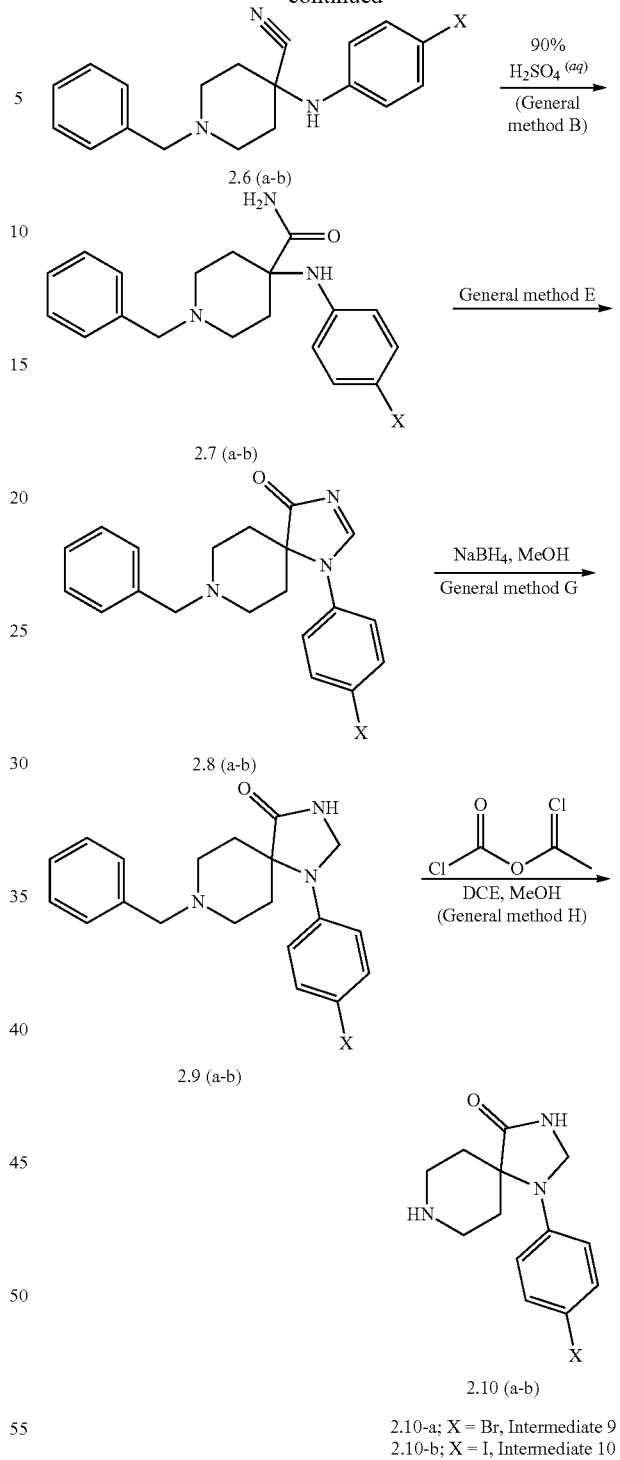

2.10-a; X = Br, Intermediate 9
2.10-b; X = I, Intermediate 10

General Procedure for the Preparation of 2.6 (a-b):
Prepared following general method A.

1-Benzyl-4-((4-bromophenyl)amino)piperidine-4-carbonitrile (2.6-a)

$^1$H-NMR (400 MHz, CDCl$_3$): δ 7.35-7.38 (m, 7H), 6.79 (d, J=8.4 Hz, 2H), 6.30 (br s, 1H), 3.51 (s, 2H), 2.74-2.76 (m, 2H), 2.28-2.31 (m, 4H) and 1.81-1.83 (m, 2H). MS: 369.98 (M+H)$^+$. Yield: 52%.

1-Benzyl-4-((4-iodophenyl)amino)piperidine-4-carbonitrile (2.6-b)

$^1$H-NMR (400 MHz, CDCl$_3$): δ 7.45 (d, J=7.6 Hz, 2H), 7.26-7.30 (m, 5H), 6.68 (d, J=2.0 Hz, 2H), 6.32 (br s, 1H), 3.51 (s, 2H), 2.73-2.75 (m, 2H), 2.28-2.34 (m, 4H) and 1.81-1.83 (m, 2H). MS: 418.35 (M+H)$^+$. Yield: 40%.

General Procedure for the Preparation of 2.7 (a-b):
Prepared following general method B.

1-Benzyl-4-(4-bromophenylamino)piperidine-4-carboxamide (2.7-a)

$^1$H-NMR (400 MHz, CDCl$_3$): δ 7.34-7.56 (m, 10H), 6.51-6.53 (m, 2H), 3.41 (s, 2H), 2.66-2.72 (m, 2H), 2.23-2.26 (m, 2H), 1.96-1.98 (m, 2H) and 1.78-1.82 (m, 2H). MS: 388.26 (M+H)$^+$. Yield: 60%.

1-Benzyl-4-(iodophenylamino)piperidine-4-carboxamide (2.7-b)

$^1$H-NMR (400 MHz, CDCl$_3$): δ 7.26-7.37 (m, 8H), 7.01 (s, 1H), 6.41 (d, J=8.4 Hz, 2H), 5.72 (br s, 1H), 3.41 (s, 2H), 2.49-2.52 (m, 2H), 2.20-2.25 (m, 2H), 1.95-2.00 (m, 2H) and 1.78-1.81 (m, 2H). LCMS: 436.32 (M+H)$^+$, 93.67%. Yield: 41%.

General Procedure for the Preparation of 2.8 (a-b):
Prepared following general method E.

8-Benzyl-1-(4-bromophenyl)-1,3,8-triazaspiro[4.5]dec-2-en-4-one (2.8-a)

$^1$H-NMR (400 MHz, DMSO-d$_6$): δ 8.25 (s, 1H), 7.60 (d, J=8.4 Hz, 2H), 7.26-7.31 (m, 5H), 7.08 (d, J=7.2 Hz, 2H), 3.59 (s, 2H), 2.86-2.88 (m, 2H), 2.30-2.35 (m, 2H), 2.02-2.06 (m, 2H) and 1.65-1.68 (m, 2H). LCMS: 398.31 (M+H)+, 83.8%. Yield: 89%.

8-Benzyl-1-(4-iodophenyl)-1,3,8-triazaspiro[4.5]dec-2-en-4-one (2.8-b)

$^1$H-NMR (400 MHz, DMSO-d$_6$): δ 8.70 (s, 1H), 7.86 (d, J=8.4 Hz, 2H), 7.19-7.30 (m, 7H), 3.47 (s, 2H), 2.72-2.78 (m, 2H), 2.46-2.49 (m, 2H) and 1.70-1.79 (m, 4H). MS: 446.18 (M+H)$^+$. Yield: 59%.

General Procedure for the Preparation of 2.9 (a-b):
General Method G:

To an ice-cold solution of compound 2.8 (a-b) (1.0-1.5 g, 1.0 eq) in methanol was added NaBH$_4$ (2.5 eq) portion-wise. The resulting reaction mixture was stirred at RT for 2 h. After completion of reaction (TLC monitoring), cooled to 0° C. added water and extracted with EtOAc (3 times). The combined organics were washed with brine, dried over anhydrous Na$_2$SO$_4$, filtered and concentrated. The crude was triturated with diethyl ether to get desired products 2.9 (a-b) as off white solids.

8-Benzyl-1-(4-bromophenyl)-1,3,8-triazaspiro[4.5]decan-4-one (2.9-a)

$^1$H-NMR (400 MHz, DMSO-d$_6$): δ 8.66 (s, 1H), 7.39 (d, J=8.8 Hz, 2H), 7.31-7.34 (m, 4H), 7.24-7.26 (m, 1H), 6.79 (d, J=8.8 Hz, 2H), 4.55 (s, 2H), 3.52-3.54 (m, 2H), 2.66-2.71 (m, 4H) and 1.54-1.58 (m, 4H). LCMS: 400.32 (M+H)$^+$, 98.11%. Yield: 83%.

8-Benzyl-1-(4-iodophenyl)-1,3,8-triazaspiro[4.5]decan-4-one (2.9-b)

$^1$H-NMR (400 MHz, DMSO-d$_6$): δ 8.66 (s, 1H), 7.53 (d, J=8.8 Hz, 2H), 7.31-7.34 (m, 4H), 7.24 (br s, 1H), 6.67 (d, J=8.4 Hz, 2H), 4.50 (s, 2H), 3.52-3.53 (m, 2H), 2.66-2.69 (m, 4H) and 1.53-1.57 (m, 4H). LCMS: 448.20 (M+H)$^+$, 96.28%. Yield: 91%.

General Procedure for the Preparation of 2.10 (a-b):
General Method H:

To an ice-cold solution of 2.9 (a-b) (0.50-1.0 g, 1.0 eq) in DCE was added 1-chloroethyl chloroformate (2.0 eq). The resulting reaction mixture was refluxed for 5 h. After completion of reaction (TLC monitoring), solvent was evaporated to dryness. The crude residue was dissolved in MeOH and heated at 65° C. for 16 h. After completion of reaction (TLC monitoring), solvent was evaporated. The crude was purified over silica gel (100-200M), and eluted with 3-5% MeOH/DCM to get the desired products 2.10 (a-b) as off-white solids.

1-(4-Bromophenyl)-1,3,8-triazaspiro[4.5]decan-4-one (2.10-a): Intermediate 9

LCMS: 310.16 (M+H)$^+$, 87.90%. Yield: 43%.

1-(4-Iodophenyl)-1,3,8-triazaspiro[4.5]decan-4-one (2.10-b): Intermediate 10

$^1$H-NMR (400 MHz, DMSO-d$_6$): δ 9.34 (br s, 1H), 8.99 (s, 1H), 7.45 (d, J=8.8 Hz, 2H), 6.89 (d, J=8.8 Hz, 2H), 4.61 (s, 2H), 3.51-3.53 (m, 2H), 3.28-3.33 (m, 2H), 2.79-2.83 (m, 2H) and 1.75-1.79 (m, 2H). LCMS: 358.17 (M+H)$^+$, 89.37%. Yield: 68%.

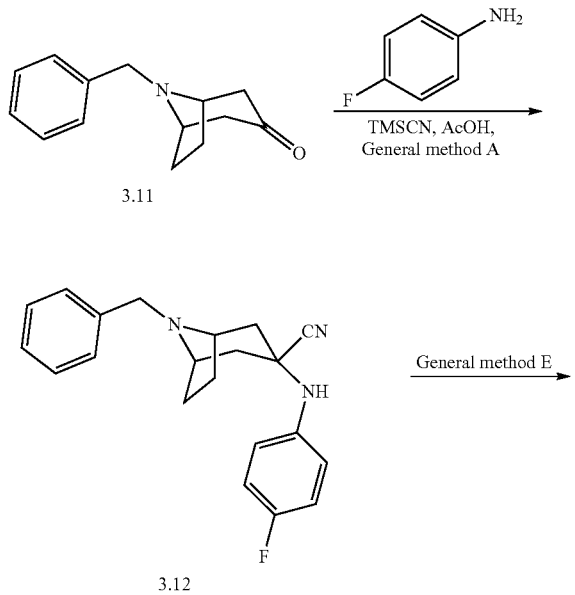

Scheme 3

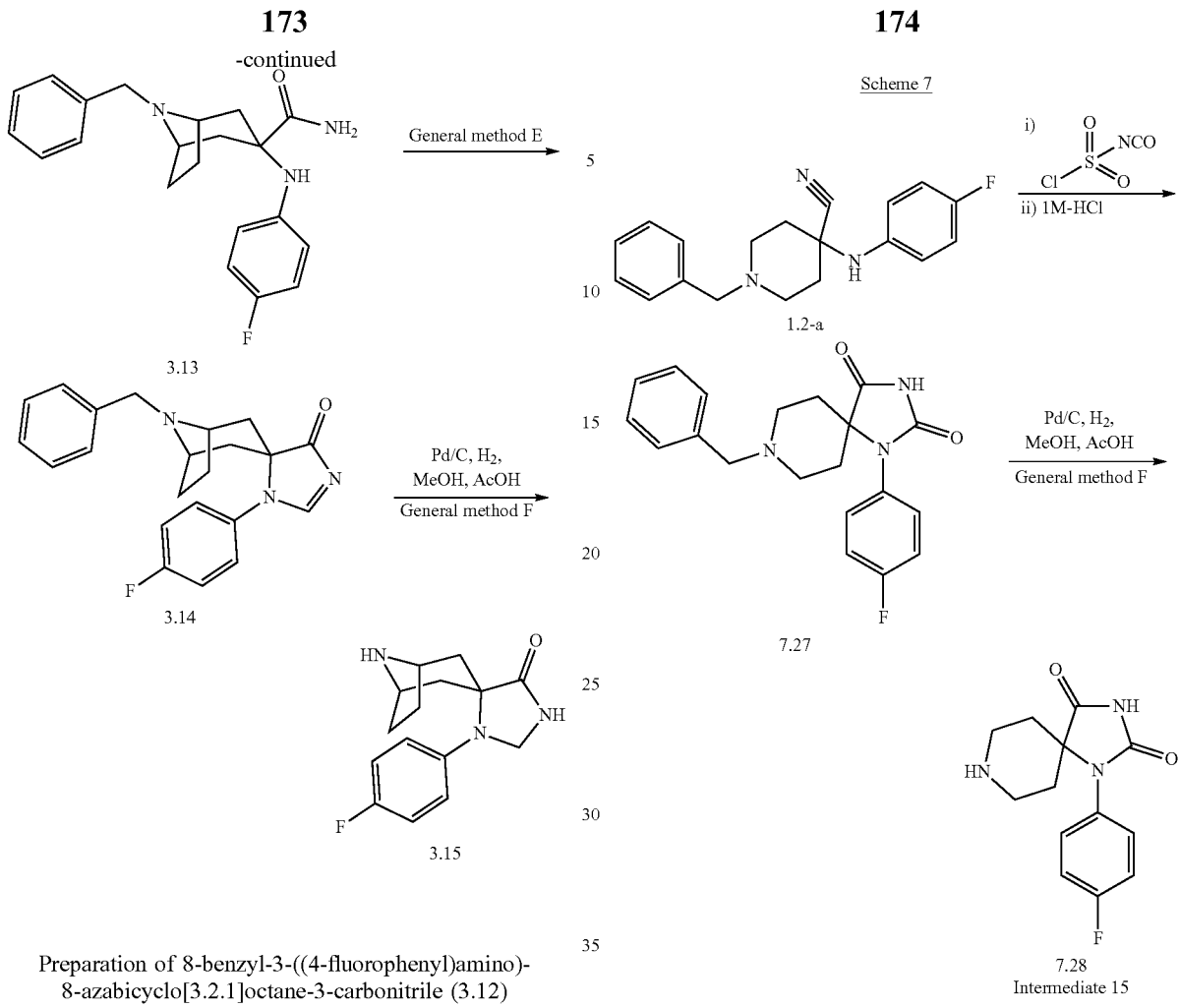

Preparation of 8-benzyl-3-((4-fluorophenyl)amino)-8-azabicyclo[3.2.1]octane-3-carbonitrile (3.12)

Prepared following general method A. MS: 336.14 (M+H)⁺. Yield: 32%.

Preparation of 8-benzyl-3-((4-fluorophenyl)amino)-8-azabicyclo[3.2.1]octane-3-carboxamide (3.13)

Prepared following general method B. ¹H-NMR (400 MHz, DMSO-d₆): δ 7.63 (br s, 1H), 7.46-7.52 (m, 2H), 7.41-7.46 (m, 2H), 7.26-7.30 (m, 3H), 6.87-6.91 (m, 2H), 6.59 (br s, 2H), 5.44 (m, 1H), 4.15 (m, 1H), 3.83-3.85 (s, 2H), 3.37-3.40 (m, 2H), 2.72-2.78 (m, 2H), 2.12-2.17 (m, 2H) and 1.80-1.90 (m, 2H). LCMS: 354.36 (M+H)⁺, 93.06%. Yield: 45%.

Preparation of 8-benzyl-3'-(4-fluorophenyl)-8-azaspiro[bicycle[3.2.1]octane-3,4'-imidazol]-5'(3'H)-one (3.14)

The compound was prepared following general method E. MS: 363.98 (M+H)⁺. Yield: 50%.

Preparation of 3'-(4-fluorophenyl)-8-azaspiro[bicyclo[3.2.1]octane-3,4'-imidazolidin]-5'-one (3.15)

Intermediate 11: The compound was prepared following the general method F. MS: 276.18 (M+H)⁺. Yield: 29%.

Preparation of 8-benzyl-1-(4-fluorophenyl)-1,3,8-triazaspiro[4.5]decane-2,4-dione (7.27)

To an ice-cold solution of 1-benzyl-4-((4-fluorophenyl)amino)piperidine-4-carbonitrile 1.2-a (1.0 g, 3.23 mmol) in CHCl₃ (50 mL) was added chlorosulfonyl isocyanate (0.56 mL, 6.47 mmol). The reaction mass was stirred at RT for 1 h. After completion of the reaction (TLC monitoring), the reaction mass was concentrated to get off white solid product, which was dissolved in 1M-HCl (100 mL) and heated at 100° C. for 2 h. After completion of the reaction (TLC monitoring), reaction mass was cooled to 0° C. and adjusted the pH~10 using 5N—NaOH solution. The resulting solid was filtered and washed with diethyl ether to get desired product 7.27 (1.0 g, 87%) as an off-white solid. ¹H-NMR (400 MHz, DMSO-d₆): δ 11.08 (br s, 1H), 7.19-7.32 (m, 9H), 3.31-3.37 (m, 2H), 2.55-2.65 (m, 4H), 1.94-1.97 (m, 2H) and 1.58-1.63 (m, 2H). LCMS: 354.36 (M+H)⁺, 98.93%.

Preparation of 1-(4-fluorophenyl)-1,3,8-triazaspiro[4.5]decane-2,4-dione (7.28)

Intermediate 15 was prepared following the general method F: ¹H-NMR (400 MHz, DMSO-d₆): δ 8.61 (br s, 1H), 7.30-7.32 (m, 4H), 5.75-5.77 (m, 1H), 2.55-2.58 (m, 4H) and 1.84-1.92 (m, 4H). MS: 264.27 (M+H)⁺. Yield: 94%.

Scheme 8

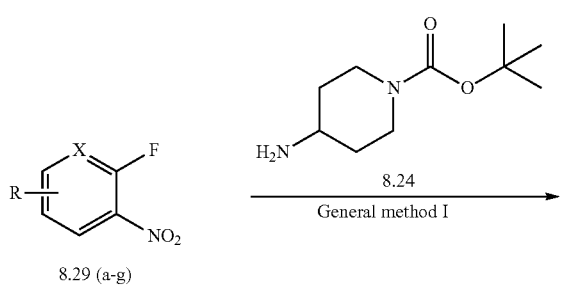

8.29 (a-g)

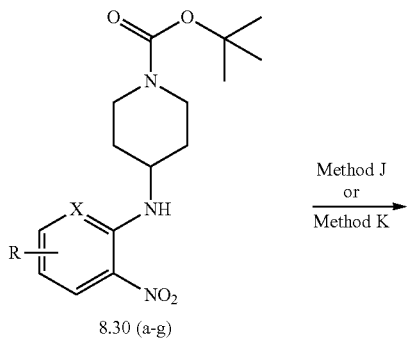

8.30 (a-g)

Method J or Method K

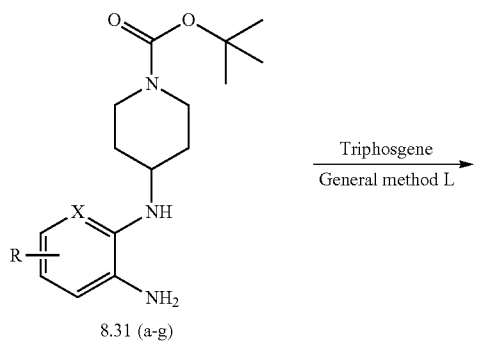

8.31 (a-g)

Triphosgene
General method L

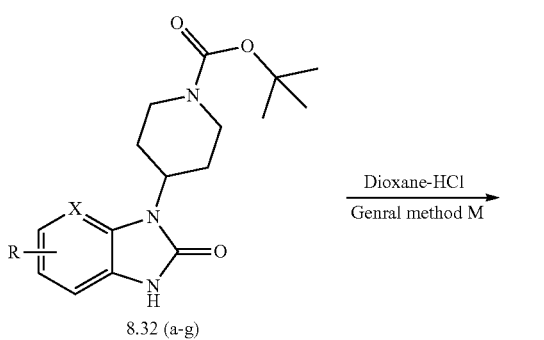

8.32 (a-g)

Dioxane-HCl
General method M

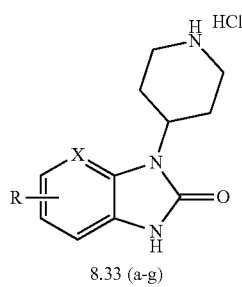

8.33 (a-g)

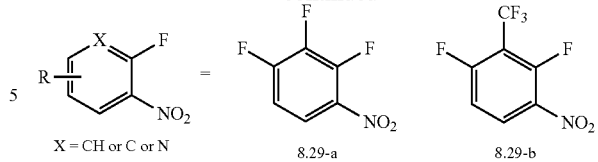

X = CH or C or N

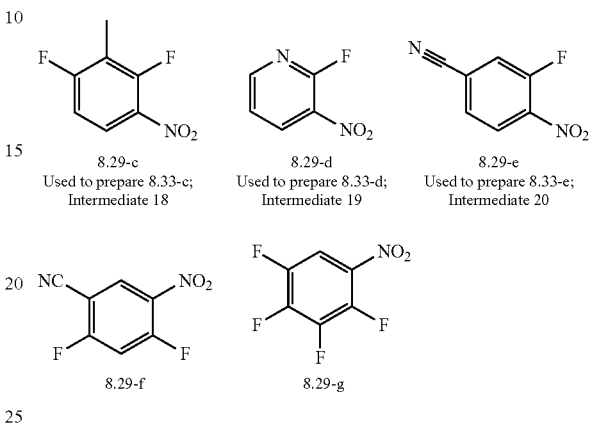

8.29-a
Used to prepare 8.33-a;
Intermediate 16

8.29-b
Used to prepare 8.33-b;
Intermediate 17

8.29-c
Used to prepare 8.33-c;
Intermediate 18

8.29-d
Used to prepare 8.33-d;
Intermediate 19

8.29-e
Used to prepare 8.33-e;
Intermediate 20

8.29-f 8.29-g

General Procedure for the Preparation of 8.30 (a-g):

General Method I:

To an ice-cold solution of tert-butyl 4-aminopiperidine-1-carboxylate 8.24 (1.0-2.5 g, 1.0 eq) in DMF was added DIPEA (1.5 eq) and respective nitro compounds 8.29 (a-g) (1.0 eq). The resulting reaction mixture was stirred at RT for 2-3 h. After completion of the reaction (TLC monitoring), the reaction mass was diluted with ice-cold water and extracted with EtOAc (3 times). The combined organics were washed with brine, dried over anhydrous $Na_2SO_4$, filtered and concentrated. The crude was purified over silica gel (100-200 M, 10-15% EtOAc-hexane) to get the desired product 8.30 (a-g).

tert-Butyl 4-((2,3-difluoro-6-nitrophenyl)amino)piperidine-1-carboxylate (8.30-a)

$^1$H-NMR (400 MHz, $CDCl_3$): δ 8.00-8.04 (m, 1H), 7.94 (d, J=8.0 Hz, 1H), 6.48-6.54 (m, 1H), 4.01-4.02 (m, 3H), 2.94-2.99 (m, 2H), 2.04-2.06 (m, 2H) and 1.46-1.49 (m, 11H). LCMS: 356.52 (M−H)$^+$, 99.10%. Yield: 56%.

tert-Butyl 4-((3-fluoro-6-nitro-2-(trifluoromethyl)phenyl)amino)piperidine-1-carboxylate (8.30-b)

$^1$H-NMR (400 MHz, $CDCl_3$): δ 8.25-8.28 (m, 1H), 7.03 (m, 1H), 6.67-6.71 (m, 1H), 4.01-4.04 (m, 2H), 3.39-3.42 (m, 1H), 2.78-2.84 (m, 2H), 1.91-1.93 (m, 2H), 1.45 (s, 9H) and 1.40-1.41 (m, 2H). LCMS: 406.19 (M−H)$^+$, 88.60%. Yield: 78%.

tert-Butyl 4-((3-fluoro-2-methyl-6-nitrophenyl)amino)piperidine-1-carboxylate (8.30-c)

$^1$H-NMR (400 MHz, $CDCl_3$): δ 7.98-8.02 (m, 1H), 8.62-8.67 (m, 1H), 3.97-4.02 (m, 2H), 2.48 (s, 1H), 3.38-3.40 (m, 1H), 2.80-2.86 (m, 2H), 2.24 (s, 3H), 1.85-188 (m, 2H), 1.44 (s, 9H) and 1.34-1.37 (m, 2H). LCMS: 352.28 (M−H)$^+$, 99.33%. Yield: 40%.

tert-Butyl 4-((3-nitropyridin-2-yl)amino)piperidine-1-carboxylate (8.30-d)

$^1$H-NMR (400 MHz, CDCl$_3$): δ 8.38-8.41 (m, 2H), 8.15-8.16 (m, 1H), 6.63-6.66 (m, 1H), 4.32-4.39 (m, 1H), 2.48 (s, 1H), 4.05-4.07 (m, 1H), 2.96-3.02 (m, 2H), 2.04-2.07 (m, 2H), 1.55-1.62 (m, 2H) and 1.48 (s, 9H). LCMS: 321.24 (M–H)$^+$, 95.81%. Yield: 80%.

tert-Butyl 4-((5-cyano-2-nitrophenyl)amino)piperidine-1-carboxylate (8.30-e)

$^1$H-NMR (400 MHz, CDCl$_3$): δ 8.25 (d, J=8.8 Hz, 1H), 8.25 (m, J=7.2 Hz, 1H), 7.17 (s, 1H), 6.86 (d, J=8.8 Hz, 1H), 4.04-4.10 (m, 2H), 3.60-3.67 (m, 1H), 3.03-3.08 (m, 2H), 2.03-2.07 (m, 2H), 1.57-1.63 (m, 2H) and 1.51 (s, 9H). LCMS: 345.22 (M–H)$^+$, 99.0%. Yield: 75.3%.

tert-Butyl 4-((4-cyano-5-fluoro-2-nitrophenyl)amino)piperidine-1-carboxylate (8.30-f)

$^1$H-NMR (400 MHz, CDCl$_3$): δ 8.51-8.56 (m, 2H), 6.60-6.63 (m, 1H), 4.05-4.12 (m, 2H), 3.57-3.61 (m, 1H), 3.01-3.06 (m, 2H), 2.04-2.06 (m, 2H), 1.54-1.63 (m, 2H) and 1.47 (s, 9H). LCMS: 363.20 (M–H)$^+$, 87.37%. Yield: 82% tert-Butyl 4-((2,3,4-trifluoro-6-nitrophenyl)amino)piperidine-1-carboxylate (8.30-g)

$^1$H-NMR (400 MHz, CDCl$_3$): δ 7.77-7.93 (m, 2H), 3.94-4.04 (m, 3H), 2.92-2.98 (m, 2H), 2.01-2.04 (m, 2H) and 1.25-1.30 (m, 11H). MS: 376.12 (M+H)$^+$. Yield: 47%

General Procedure for the Preparation of 8.31 (a-d, f, g):

General Method J:

To a solution of compound 8.30 (a-d, f, g) (1.0-2.5 g, 1.0 eq) in EtOAc were added Pd—C (w/w, 10 mol %) and the resulting solution was stirred under hydrogen atmosphere (1 atm) at ambient temperature for 16 h. The reaction mixture was filtered through diatomaceous earth (Celite) bed and the filtrate was concentrated under reduced pressure to get the desired product 8.31 (a-d, f, g).

tert-Butyl 4-((6-amino-2,3-difluorophenyl)amino)piperidine-1-carboxylate (8.31-a)

$^1$H-NMR (400 MHz, DMSO-d$_6$): δ 6.58-6.65 (m, 1H), 6.33-6.36 (m, 1H), 4.80 (br s, 1H), 3.87-4.05 (m, 3H), 3.17-3.20 (m, 1H), 2.73-2.75 (m, 2H), 1.73-1.76 (m, 2H), 1.39 (s, 9H) and 1.23-1.25 (m, 2H). LCMS: 328.41 (M+H)$^+$, 97.70%. Yield: 97%.

tert-Butyl 4-((6-amino-3-fluoro-2-(trifluoromethyl)phenyl)amino)piperidine-1-carboxylate (8.31-b)

$^1$H-NMR (400 MHz, DMSO-d$_6$): δ 6.85-6.89 (m, 1H), 6.70-6.79 (m, 1H), 4.90 (br s, 2H), 3.92-3.99 (m, 3H), 3.09-3.11 (m, 1H), 2.64-2.68 (m, 2H), 1.69-1.73 (m, 2H), 1.38 (s, 9H) and 1.26-1.27 (m, 2H). LCMS: 356.30 (M–H)$^+$, 96.01%. Yield: 75%.

tert-Butyl 4-((6-amino-3-fluoro-2-methylphenyl)amino)piperidine-1-carboxylate (8.31-c)

$^1$H-NMR (400 MHz, DMSO-d$_6$): δ 6.62-6.64 (m, 1H), 6.51-6.53 (m, 1H), 4.10-4.12 (m, 3H), 3.41-3.45 (m, 2H), 3.11-3.14 (m, 1H), 2.66-2.69 (m, 2H), 2.14 (s, 3H), 1.85-1.86 (m, 2H), 1.42 (s, 9H) and 1.27-1.29 (m, 2H). LCMS: 324.31 (M–H)$^+$, 88.69%. Yield: 80%.

tert-Butyl 4-((3-aminopyridin-2-yl)amino)piperidine-1-carboxylate (8.31-d)

$^1$H-NMR (400 MHz, CDCl$_3$): δ 6.68-6.69 (m, 1H), 7.86-7.88 (m, 1H), 6.51-6.55 (m, 1H), 4.49-4.53 (br s, 1H), 3.98-4.12 (m, 3H), 3.45-3.48 (m, 2H), 2.97-2.99 (m, 2H), 2.04-2.09 (m, 2H), 1.48 (s, 9H) and 1.30-1.32 (m, 2H). LCMS: 293.23 (M+H)$^+$, 98.28%. Yield: 85%.

Tert-butyl 4-((2-amino-4-cyano-5-fluorophenyl)amino)piperidine-1-carboxylate (8.31-f)

$^1$H-NMR (400 MHz, CDCl$_3$): δ 6.84 (d, J=6.4 Hz, 1H), 6.31 (d, J=7.2 Hz, 1H), 4.38-4.40 (m, 1H), 4.06 (br s, 2H), 3.38-3.41 (m, 1H), 2.92-3.06 (m, 4H), 2.01-2.04 (m, 2H) and 1.46 (s, 11H). LCMS: 333.0 (M–H)$^+$, 98.21%. Yield: 76%.

Tert-butyl 4-((6-amino-2,3,4-trifluorophenyl)amino)piperidine-1-carboxylate (8.31-g)

$^1$H-NMR (400 MHz, DMSO-d$_6$): δ 6.37-6.42 (m, 1H), 5.16 (br s, 2H), 3.84-3.89 (m, 3H), 3.01 (br s. 1H), 2.71-2.73 (m, 2H), 1.71-1.74 (m, 2H) and 1.38 (s, 11H). MS: 346.18 (M+H)$^+$. Yield: 96%.

General Method K:

To a solution of compound 8.30-e (1.0-2.0 g, 1.0 eq) in MeOH was added ammonium formate (5.0 eq) and Pd—C (w/w, 10 mol %) and the resulting solution was stirred under at RT for 3-4 h. The reaction mixture was filtered through diatomaceous earth (Celite) bed and the filtrate was concentrated under reduced pressure to get the desired product 8.31-e.

Tert-butyl 4-((2-amino-5-cyanophenyl)amino)piperidine-1-carboxylate (8.31-e)

$^1$H-NMR (400 MHz, CDCl$_3$): δ 7.01 (d, J=8.8 Hz, 1H), 6.87 (s, 1H), 6.68 (d, J=8.8 Hz, 1H), 4.05-4.10 (br s, 3H), 3.36-3.39 (m, 1H), 2.91-2.94 (m, 2H), 2.00-2.03 (m, 4H) and 1.40 (s, 11H). MS: 317.39 (M+H)$^+$. Yield: 85%.

General Procedure for the Preparation of 8.32 (a-g):

General Method L:

To an ice-cold solution of compound 8.31 (a-g) (0.50-1.50 g, 1.0 eq) in THF was added Et$_3$N (2.0 eq) and triphosgene (1.5 eq). The resulting reaction mixture was stirred at RT for 4 h. After completion of the reaction (TLC monitoring), the solvent was evaporated and the residue was diluted with water and extracted with ethyl acetate (3 times). The combined organics were washed with brine, dried over anhydrous Na$_2$SO$_4$, filtered and concentrated. The crude was purified over silica gel (100-200 M, 30-40% EtOAc-hexane) to get the desired product 8.32 (a-g).

Tert-butyl 4-(6,7-difluoro-2-oxo-2,3-dihydro-1H-benzo[d]imidazol-1-yl)piperidine-1-carboxylate (8.32-a)

$^1$H-NMR (400 MHz, DMSO-d$_6$): δ 11.24 (br s, 1H), 7.02-7.06 (m, 1H), 6.76-6.79 (m, 1H), 4.47-4.52 (m, 1H), 3.99-4.05 (m, 2H), 2.87-2.89 (m, 2H), 1.90-1.98 (m, 2H), 1.71-1.74 (m, 2H) and 1.42 (s, 9H). LCMS: 354.55 (M+H)$^+$, 86.20%. Yield: 92%.

Tert-butyl 4-(6-fluoro-2-oxo-7-(trifluoromethyl)-2,3-dihydro-1H-benzo[d]imidazol-1-yl)piperidine-1-carboxylate (8.32-b)

$^1$H-NMR (400 MHz, CDCl$_3$): δ 10.27 (br s, 1H), 7.17-7.21 (m, 1H), 6.91-6.99 (m, 1H), 3.70-3.73 (m, 3H), 2.68-2.74 (m, 4H), 1.71-1.73 (m, 2H) and 1.46 (s, 9H). LCMS: 354.55 (M+H)$^+$, 86.20%. Yield: 72%.

Tert-butyl 4-(6-fluoro-7-methyl-2-oxo-2,3-dihydro-1H-benzo[d]imidazol-1-yl)piperidine-1-carboxylate (8.32-c)

$^1$H-NMR (400 MHz, CDCl$_3$): δ 9.02 (br s, 1H), 6.75-6.82 (m, 2H), 4.49 (s, 1H), 4.30-4.32 (m, 2H), 2.73 (s, 3H), 2.44-2.48 (m, 2H), 1.79-1.80 (m, 2H), 1.60-1.62 (m, 2H) and 1.48 (s, 9H). LCMS: 350.36 (M+H)$^+$, 90.82%. Yield: 80%.

Tert-butyl 4-(2-oxo-1,2-dihydro-3H-imidazo[4,5-b]pyridin-3-yl)piperidine-1-carboxylate (8.32-d)

LCMS: 319.33 (M+H)$^+$, 87.69%. Yield: 85%.

Tert-butyl 4-(6-cyano-2-oxo-2,3-dihydro-1H-benzo[d]imidazol-1-yl)piperidine-1-carboxylate (8.32-e)

$^1$H-NMR (400 MHz, CDCl$_3$): δ 10.01 (br s, 1H), 7.38-7.41 (m, 2H), 7.16 (d, J=8.0 Hz, 1H), 4.37-4.45 (m, 3H), 2.84-2.90 (m, 2H), 2.30-2.35 (m, 2H), 1.83-1.85 (m, 2H) and 1.52 (s, 9H). LCMS: 343.37 (M+H)$^+$, 86.18%. Yield: 60%.

Tert-butyl 4-(5-cyano-6-fluoro-2-oxo-2,3-dihydro-1H-benzo[d]imidazol-1-yl)piperidine-1-carboxylate (8.32-f)

$^1$H-NMR (400 MHz, CDCl$_3$): δ 9.87 (br s, 1H), 7.25-7.27 (m, 1H), 6.98 (d, J=8.8 Hz, 1H), 4.37-4.44 (m, 3H), 2.84-2.86 (m, 2H), 2.22-2.27 (m, 2H), 1.84-1.84 (m, 2H) and 1.51 (s, 9H). LCMS: 359.11 (M−H)$^+$, 98.18%. Yield: 56%.

Tert-butyl 4-(5,6,7-trifluoro-2-oxo-2,3-dihydro-1H-benzo[d]imidazol-1-yl)piperidine-1-carboxylate (8.32-g)

$^1$H-NMR (400 MHz, DMSO-d$_6$): δ 11.28 (br s, 1H), 6.95-6.99 (m, 1H), 4.47-4.50 (m, 1H), 3.99-4.05 (m, 2H), 2.86-2.89 (m, 2H), 1.90-1.98 (m, 2H), 1.70-1.73 (m, 2H) and 1.42 (s, 9H). MS: 370.20 (M−H)$^+$, Yield: 93%.

General Procedure for the Preparation of 8.33 (a-g):
General Method M:
An ice-cold solution of compound 8.32 (a-e) (0.5 g-1.0 g, 1.0 eq) in dioxane-HCl (~4N) was stirred at RT for 2 h. After completion of the reaction (TLC monitoring), the reaction mass was dried under reduced pressure. The crude was triturated with diethyl ether to get desired product 8.33 (a-e) as off-white solids.

6,7-Difluoro-1-(piperidin-4-yl)-1,3-dihydro-2H-benzo[d]imidazol-2-one Hydrochloride (8.33-a): Intermediate 16

$^1$H-NMR (400 MHz, DMSO-d$_6$): δ 11.38 (br s, 1H), 9.44 (br s, 1H), 8.65 (br s, 1H), 7.01-7.07 (m, 1H), 6.78-6.79 (m, 1H), 4.58-4.60 (m, 1H), 3.63-3.65 (m, 2H), 2.45-3.49 (m, 2H), 3.03-3.12 (m, 2H) and 2.35-2.38 (m, 2H). LCMS: 254.11 (M+H)$^+$, 95.61%. Yield: quantitative.

6-Difluoro-1-(piperidin-4-yl)-7-(trifluoromethyl)-1,3-dihydro-2H-benzo[d]imidazol-2-one Hydrochloride (8.33-b): Intermediate 17

$^1$H-NMR (400 MHz, DMSO-d$_6$): δ 11.66 (br s, 1H), 9.40 (br s, 1H), 8.57 (br s, 1H), 7.28-7.28 (m, 1H), 7.04-7.08 (m, 1H), 4.43-4.45 (m, 3H), 2.82-2.90 (m, 4H) and 1.88-1.98 (m, 2H). LCMS: 304.21 (M+H)$^+$, 92.41%. Yield: 92%.

6-Fluoro-7-methyl-1-(piperidin-4-yl)-1,3-dihydro-2H-benzo[d]imidazol-2-one Hydrochloride (8.33-c): Intermediate 18

$^1$H-NMR (400 MHz, DMSO-d$_6$): δ 10.94 (br s, 1H), 9.44 (br s, 1H), 8.48 (br s, 1H), 6.76-6.83 (m, 2H), 4.44-4.48 (m, 1H), 3.32-3.38 (m, 2H), 3.01-3.07 (m, 2H), 2.77-2.83 (m, 2H), 2.46 (s, 3H) and 1.93-1.96 (m, 2H). MS: 250.29 (M+H)$^+$. Yield: 93%.

3-(piperidin-4-yl)-1,3-dihydro-2H-imidazo[4,5-b]pyridin-2-one Hydrochloride (8.33-d): Intermediate 19

$^1$H-NMR (400 MHz, DMSO-d$_6$): δ 10.25 (br s, 1H), 9.36 (br s, 1H), 8.57 (br s, 1H), 7.92 (d, J=7.6 Hz, 1H), 7.31 (d, J=7.6 Hz, 1H), 7.00 (t, J=7.6 Hz, 1H), 4.55-4.61 (m, 1H), 3.35-3.38 (m, 2H), 3.03-3.11 (m, 2H), 2.69-2.78 (m, 2H) and 1.86-1.89 (m, 2H). LCMS: 219.14 (M+H)$^+$, 90.67%. Yield: 90%.

2-oxo-3-(piperidin-4-yl)-2,3-dihydro-1H-benzo[d]imidazole-5-carbonitrile Hydrochloride (8.33-e): Intermediate 20

$^1$H-NMR (400 MHz, DMSO-d$_6$): δ 11.55 (br s, 1H), 8.93 (br s, 1H), 8.75 (br s, 1H), 7.86 (s, 1H), 7.47 (d, J=7.2 Hz, 1H), 7.14 (d, J=8.8 Hz, 1H), 4.57-4.60 (m, 1H), 3.35-3.40 (m, 2H), 3.04-3.08 (m, 2H), 2.55-2.61 (m, 2H) and 1.85-1.88 (m, 2H). LCMS: 243.32 (M+H)$^+$, 98.82%. Yield: 85%.

6-Fluoro-2-oxo-1-(piperidin-4-yl)-2,3-dihydro-1H-benzo[d]imidazole-5-carbonitrile Hydrochloride (8.33-f)

$^1$H-NMR (400 MHz, DMSO-d$_6$): δ 11.49 (br s, 1H), 8.86 (br s, 2H), 7.68-7.71 (m, 1H), 7.41-7.43 (s, 1H), 4.53-4.60 (m, 2H), 3.56-3.61 (m, 1H), 3.04-3.16 (m, 2H), 2.55-2.58 (m, 2H) and 1.84-1.88 (m, 2H). LCMS: 261.13 (M+H)$^+$, 99.60%. Yield: 93%.

5,6,7-Trifluoro-1-(piperidin-4-yl)-1,3-dihydro-2H-benzo[d]imidazol-2-one Hydrochloride (8.33-g)

Intermediate-6: $^1$H-NMR (400 MHz, DMSO-d$_6$): δ 11.50 (br s, 1H), 9.26 (br s, 1H), 8.59-8.61 (m, 1H), 6.97-7.01 (m, 1H), 4.52-4.58 (m, 1H), 3.25-3.40 (m, 2H), 3.07-3.13 (m, 2H), 2.33-2.41 (m, 2H) and 1.90-1.97 (m, 2H). MS: 272.31 (M+H)$^+$. Yield: 95%.

Scheme 9

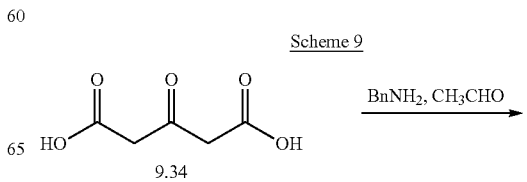

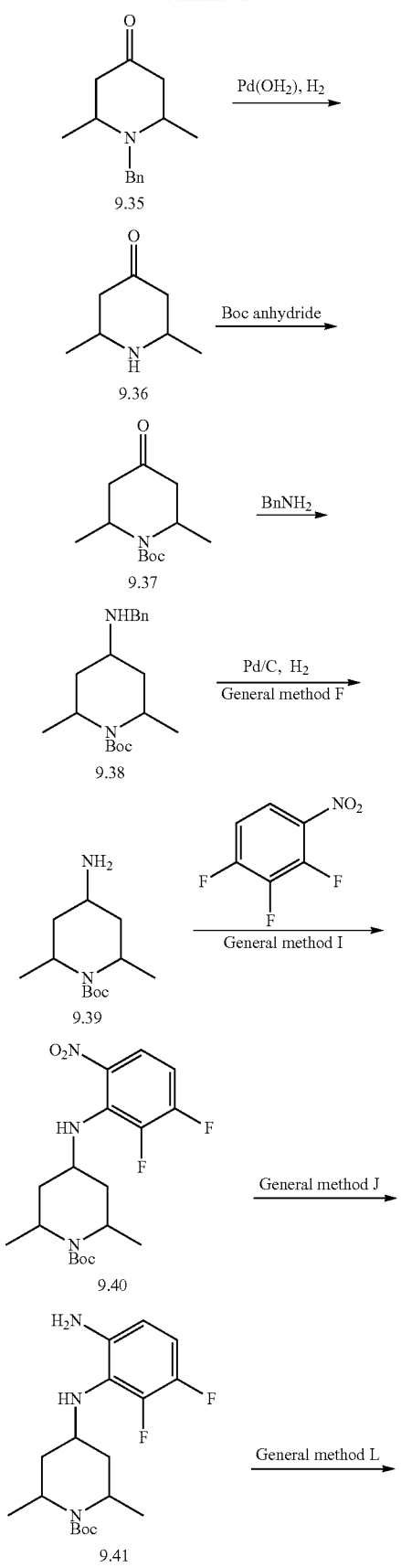

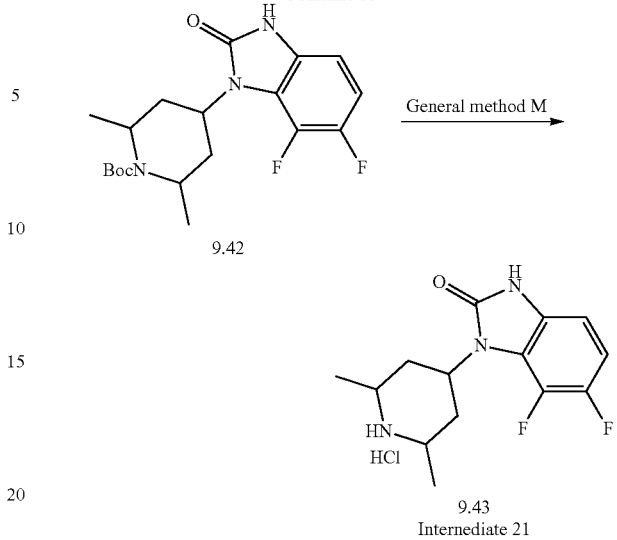

9.43
Internediate 21

Preparation of 1-benzyl-2,6-dimethylpiperidin-4-one (9.35)

To an ice-cold solution of 3-oxopentanedioic acid 9.34 (10 g, 64.49 mmol) in water (30 mL) was added acetaldehyde (6 g, 137 mmol) and benzyl amine (7.50 mL, 64.49 mmol). The resulting yellow solution was stirred at RT for 78 h. After completion of reaction (TLC monitoring), cooled the reaction mass, adjust pH~2 using 1N HCl and stirred for 1 h at RT. The resulting mixture was neutralized with aq. $NaHCO_3$ solution and extracted with DCM (2×100 ml). Combined organics were washed with brine, dried with $Na_2SO_4$ and evaporated to get a brown liquid. The crude was purified by flash chromatography using 10% EtOAc/hexane to get product 9.35 (10 g, Yield: 68%) as a viscous liquid. NMR (400 MHz, $CDCl_3$): δ 7.26-7.40 (m, 5H), 3.90-3.94 (m, 1H), 3.51-3.53 (m, 1H), 3.24-3.30 (m, 2H), 2.42-2.51 (m, 2H), 2.12-2.21 (m, 2H) and 1.05 (m, 6H). MS: 218.10 $(M+H)^+$.

Preparation of 2,6-dimethylpiperidin-4-one (9.36)

To a solution of 1-benzyl-2,6-dimethylpiperidin-4-one 9.35 (8.0 g, 36.78 mmol) in IPA (100 mL) was added $Pd(OH)_2$ (10% w/w, 0.8 g, 3.67 mmol). The resulting mixture was stirred at RT for 16 h under $H_2$ atmosphere. After completion of reaction (TLC monitoring), reaction mass filtered through diatomaceous earth (Celite) bed, washed with EtOAc (100 mL). The filtrate was concentrated under reduced pressure to get desired product 9.36 (3.6 g, Yield: 77%) as a viscous liquid. The crude was used for the next step without purification. MS: 128.14 $(M+H)^+$.

Preparation of tert-butyl 2,6-dimethyl-4-oxopiperidine-1-carboxylate (9.37)

To an ice-cold solution of 2,6-dimethylpiperidin-4-one 9.36 (3.6 g, 28.34 mmol) in DCM (50 mL) was added $Et_3N$ (9.8 mL, 70.8 mmol) and boc anhydride (12.1 mL, 56.6 mmol). The resulting reaction mixture was stirred at RT for 16 h. After completion of the reaction (TLC monitoring), the reaction mass was diluted with water and extracted with DCM (3 times). The combined organics were washed with brine, dried over anhydrous $Na_2SO_4$, filtered and concentrated. The crude was purified over silica gel (100-200 M, 10-15% EtOAc-hexane) to get the desired product 9.37 (3.9 g, Yield: 60.9%). $^1$H-NMR (400 MHz, $CDCl_3$): δ 2.85 (d, J=6.4 Hz, 1H), 2.81 (d, J=6.4 Hz, 1H), 2.38-2.39 (m, 2H), 2.34-2.36 (m, 2H), 1.48 (s, 9H) and 1.25-1.27 (m, 6H). MS: 228.08 $(M+H)^+$.

Preparation of tert-butyl 4-(benzylamino)-2,6-dimethylpiperidine-1-carboxylate (9.38)

To an ice-cold solution of tert-butyl 2,6-dimethyl-4-oxopiperidine-1-carboxylate 9.37 (3.4 g, 14.9 mmol) in DCM (50 mL) was added benzyl amine (2.13 mL, 17.9 mmol) and AcOH (1.02 mL, 17.9 mmol). The resulting mixture was stirred at 0° C. for 2 h followed by addition of sodium tri-acetoxyborohydride (6.3 g, 29.8 mmol). The resulting reaction mixture was stirred at RT for 16 h. After completion of the reaction (TLC monitoring), the reaction mass was diluted with water and extracted with DCM (3 times). The combined organics were washed with brine, dried over anhydrous $Na_2SO_4$, filtered and concentrated. The crude was purified over silica gel (100-200 M, 20% EtOAc-hexane) to get the desired product 9.38 (1.8 g, Yield: 37.8%). MS: 319.34 $(M+H)^+$.

Preparation of tert-butyl 4-amino-2,6-dimethylpiperidine-1-carboxylate (9.39)

Prepared following the general method F. MS: 229.20 $(M+H)^+$. Yield: Quantitative.

Preparation of tert-butyl 4-((2,3-difluoro-6-nitrophenyl)amino)-2,6-dimethylpiperidine-1-carboxylate (9.40)

Prepared following the general method I. $^1$H-NMR (400 MHz, $CDCl_3$): δ 7.95-8.04 (m, 2H), 6.47-6.54 (m, 1H), 4.30-4.35 (m, 2H), 3.88-3.89 (m, 1H), 2.31-2.34 (m, 1H), 2.18-2.20 (m, 1H), 1.88-1.90 (m, 2H), 1.62 (s, 9H) and 1.31-1.33 (m, 6H). MS: 386.31 $(M+H)^+$. Yield: 35%.

Preparation of tert-butyl 4-((6-amino-2,3-difluorophenyl)amino)-2,6-dimethylpiperidine-1-carboxylate (9.41)

Prepared following the general method J. $^1$H-NMR (400 MHz, DMSO-$d_6$): δ 6.57-6.64 (m, 1H), 6.34-6.36 (m, 1H), 4.78 (s, 2H), 4.16 (s, 1H), 4.01-4.03 (m, 1H), 3.89-3.91 (m, 1H), 3.62 (br s, 1H), 1.88-1.89 (m, 1H), 1.72-1.74 (m, 2H), 1.35-1.39 (m, 1H), 1.39 (s, 9H) and 1.31-1.33 (m, 6H). MS: 356.38 $(M+H)^+$. Yield: 35%.

Preparation of tert-butyl 4-(6,7-difluoro-2-oxo-2,3-dihydro-1H-benzo[d]imidazol-1-yl)-2,6-dimethylpiperidine-1-carboxylate (9.42)

Prepared following the general method L. LCMS: 380.28 $(M-H)^+$, 84.35%. Yield: 80%.

Preparation of 1-(2,6-dimethylpiperidin-4-yl)-6,7-difluoro-1,3-dihydro-2H-benzo[d]imidazol-2-one Hydrochloride (9.43): Intermediate 21

Prepared following the general method M. $^1$H-NMR (400 MHz, DMSO-$d_6$): δ 11.33 (br s, 1H), 9.20-9.25 (m, 1H), 8.89-8.99 (m, 1H), 7.01-7.04 (m, 1H), 6.75-6.78 (m, 1H), 4.73-4.79 (m, 1H), 3.61-3.64 (m, 2H), 3.35-3.38 (m, 1H), 2.19-2.25 (m, 1H), 2.00-2.03 (m, 1H), 1.81-1.84 (m, 1H) and 1.29-1.35 (m, 6H). LCMS: 280.13 $(M-H)^+$, 84.65%. Yield: 90%.

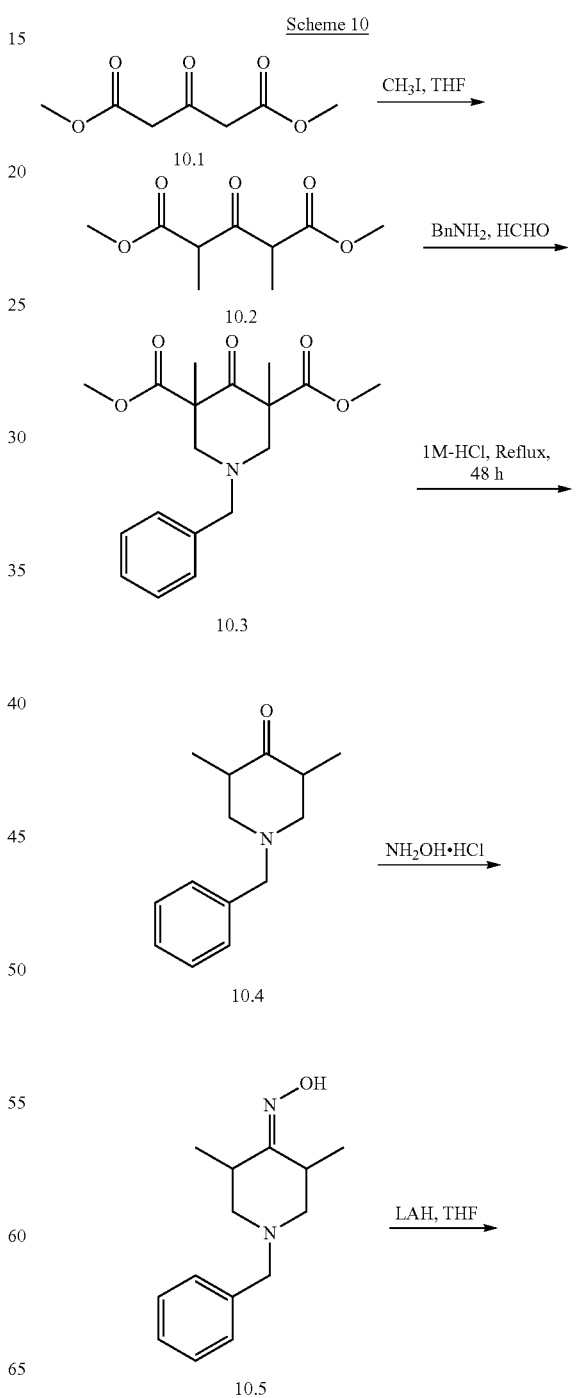

Scheme 10

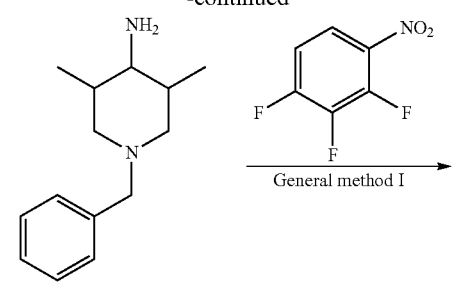

10.6

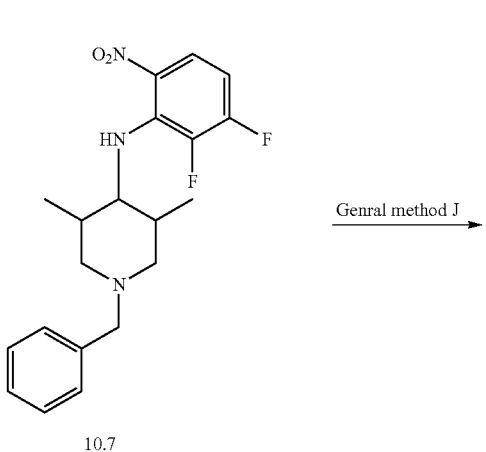

10.7

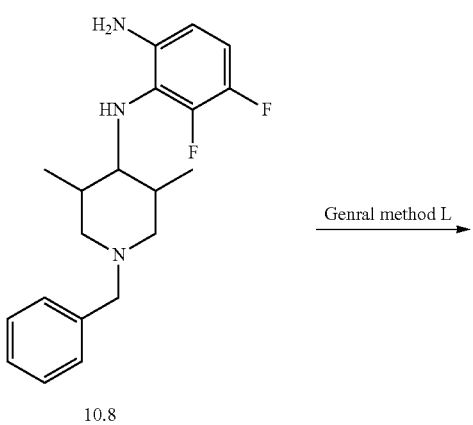

10.8

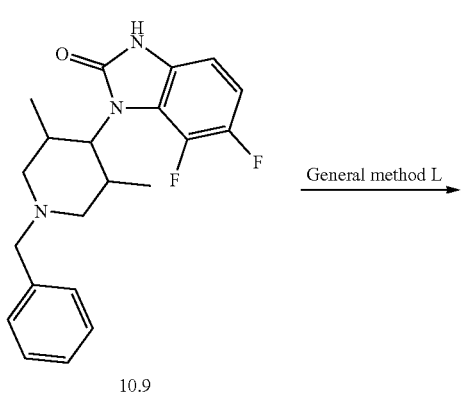

10.9

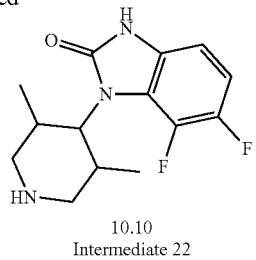

10.10
Intermediate 22

Preparation of dimethyl 2,4-dimethyl-3-oxopentanedioate (10.2)

To an ice-cold solution of dimethyl 3-oxopentanedioate 10.1 (10.0 g, 57.47 mmol) in THF (150 mL) was added $K_2CO_3$ (11.8 g, 86.2 mmol) and methyl iodide (9.0 mL, 143.67 mmol). The resulting reaction mixture was stirred at RT for 16 h. After completion of the reaction (TLC monitoring), the reaction mass was diluted with water and extracted with DCM (3 times). The combined organics were washed with brine, dried over anhydrous $Na_2SO_4$, filtered and concentrated to get desired product 10.2 (10.0 g, Yield: 86%) as viscous liquid. $^1$H-NMR (400 MHz, $CDCl_3$): δ 5.09-5.16 (m, 2H), 3.85-3.87 (m, 6H) and 3.51-3.54 (m, 6H). MS: 203.10 $(M+H)^+$.

Preparation of dimethyl 1-benzyl-3,5-dimethyl-4-oxopiperidine-3,5-dicarboxylate (10.3)

To an ice-cold solution of dimethyl 2,4-dimethyl-3-oxopentanedioate 10.2 (10.0 g, 49.3 mmol) in $CH_3OH$ (100 mL) was added 1M-HCl (15.0 mL), benzylamine (5.4 mL, 49.3 mmol) and formaldehyde (37% in $H_2O$, 9.0 mL, 108.46 mmol). The resulting reaction mixture was stirred at RT for 72 h. After completion of the reaction (TLC monitoring), the reaction mass was diluted with water and extracted with EtOAc (3 times). The combined organics were washed with brine, dried over anhydrous $Na_2SO_4$, filtered and concentrated to get desired product 10.3 (12.0 g, Yield: 73%) as a viscous liquid. The crude was used for the next step without purification. MS: 334.18 $(M+H)^+$.

Preparation of 1-benzyl-3,5-dimethylpiperidin-4-one (10.4)

A solution of dimethyl 1-benzyl-3,5-dimethyl-4-oxopiperidine-3,5-dicarboxylate 10.3 (12.0 g, 36.01 mmol) in 1N—HCl (100 mL) was heated at 100° C. for 16 h. After completion of the reaction (TLC monitoring), the reaction mass was cooled to 0° C., adjust pH~10 using ammonium hydroxide solution and extracted with DCM (3 times). The combined organics were washed with brine, dried over anhydrous $Na_2SO_4$, filtered and concentrated to get desired product 10.4 (7.5 g, Yield: quantitative) as viscous liquid. The crude was used for next step without purification. $^1$H-NMR (400 MHz, $CDCl_3$): δ 7.32-7.35 (m, 5H), 3.64-3.66 (m, 2H), 3.10-3.13 (m, 2H), 2.66-2.69 (m, 2H), 2.02-2.07 (m, 2H) and 0.95 (d, J=6.4 Hz, 6H). MS: 203.10 $(M+H)^+$.

Preparation of 1-benzyl-3,5-dimethylpiperidin-4-one Oxime (10.5)

To a solution of hydroxylamine hydrochloride (2.4 g, 34.56 mmol) in $H_2O$ (30 mL) was added $CH_3COONa$ (5.6 g, 69.12 mmol). The reaction mixture was heat at 60° C. and followed by addition of 1-benzyl-3,5-dimethylpiperidin-4-one 10.4 (5.0 g, 23.04 mmol). The resulting reaction mixture was heated at 60° C. for 2 h. After completion of the reaction (TLC monitoring), the reaction mass was cooled to RT and extracted with DCM (3 times). The combined organics were washed with brine, dried over anhydrous Na$_2$SO$_4$, filtered and concentrated to get desired product 10.5 (5.0 g, Yield: quantitative). $^1$H-NMR (400 MHz, CDCl$_3$): δ 10.28 (s, 1H), 7.44-7.58 (m, 5H), 3.40-3.50 (m, 2H), 3.20-3.22 (m, 2H), 2.56-2.59 (m, 2H), 2.03-2.10 (m, 2H) and 1.17 (d, J=7.2 Hz, 6H). MS: 233.20 (M+H)$^+$.

Preparation of 1-benzyl-3,5-dimethylpiperidin-4-amine (10.6)

To an ice-cold solution of 1-benzyl-3,5-dimethylpiperidin-4-one oxime 10.5 (2.0 g, 8.62 mmol) was added LAH (2.0 M in THF, 13.0 mL). The resulting reaction mixture was heated at 65° C. for 3 h. After completion of the reaction (TLC monitoring), the reaction mass was cooled to 0° C., added dropwise 15% NaOH solution (10 mL). The reaction mass was filtered through a diatomaceous earth (Celite) bed, and washed with EtOAc (100 mL). The filtrate was dried over anhydrous Na$_2$SO$_4$, filtered and concentrated to get desired product 10.6 (1.4 g, Yield: 70%). MS: 219.21 (M+H)$^+$.

Preparation of 1-benzyl-N-(2,3-difluoro-6-nitrophenyl)-3,5-dimethylpiperidin-4-amine (10.7)

This compound was prepared following the general Method I. $^1$H-NMR (400 MHz, CDCl$_3$): δ 8.02-8.05 (m, 1H), 7.38-7.50 (m, 5H), 6.44-6.51 (m, 1H), 4.29-4.30 (m, 1H), 3.70-3.73 (m, 2H), 2.81-2.84 (m, 2H), 2.11-2.17 (m, 2H), 1.55-1.57 (m, 2H), 1.31-1.32 (m, 1H) and 0.86 (d, J=6.4 Hz, 6H). LCMS: 376.06 (M+H)$^+$, 96.22%. Yield: 25%.

Preparation of N1-(1-benzyl-3,5-dimethylpiperidin-4-yl)-5,6-difluorobenzene-1,2-diamine (10.8)

This compound was prepared following the general Method J. LCMS: 344.39 (M–H)$^+$, 81.10%. Yield: 80%.

Preparation of 1-(1-benzyl-3,5-dimethylpiperidin-4-yl)-6,7-difluoro-1,3-dihydro-2H-benzo[d]imidazol-2-one (10.9)

This compound was prepared following the general Method L. MS: 370.36 (M–H)$^+$. Yield: 60%.

Preparation of 1-(3,5-dimethylpiperidin-4-yl)-6,7-difluoro-1,3-dihydro-2H-benzo[d]imidazol-2-one (10.10): Intermediate 22

This compound was prepared following the general Method F. $^1$H-NMR (400 MHz, CDCl$_3$): δ 10.25 (br s, 1H), 7.02-7.09 (m, 1H), 6.75-6.79 (m, 1H), 4.58 (br s, 1H), 3.48-3.51 (m, 2H), 3.38-3.40 (m, 2H), 3.00-3.02 (m, 2H), 1.22-1.25 (m, 1H) and 0.80 (d, J=6.4 Hz, 6H). LCMS: 282.25 (M+H)$^+$, 88.77%. Yield: 90%.

Synthesis of Final Compounds

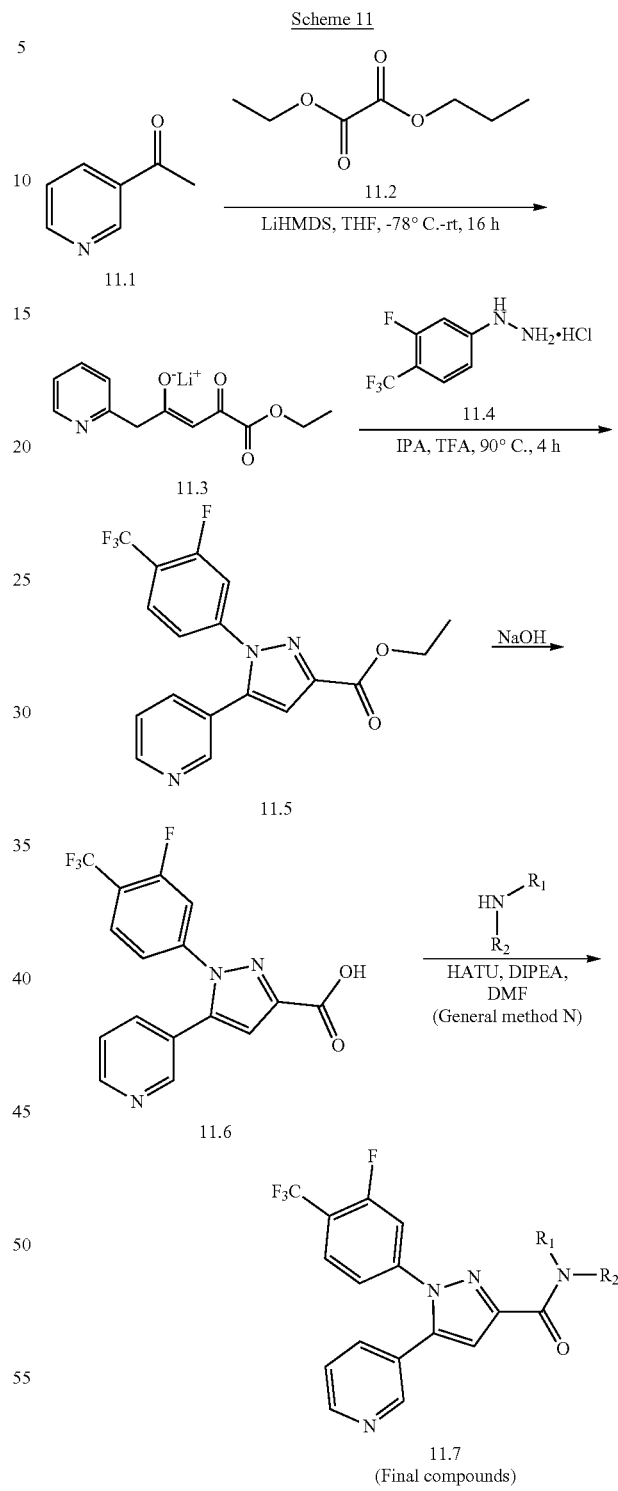

Scheme 11

Preparation of 4-ethoxy-3,4-dioxo-1-(pyridin-3-yl) but-1-en-1-olate Lithium Salt (11.3)

A solution of 3-acetyl pyridine 11.1 (20 g, 165.09 mmol) in di-ethyl ether (250 mL) was cooled to −78° C. followed by addition of LiHMDS (1.0 M in THF, 181.60 mL, 181.60 mmol). The resulting reaction mixture was stirred at −78° C. for 45 min followed by dropwise addition of diethyl oxalate 11.2 (27.03 mL, 198.10 mmol) in about 20 min. The reaction mixture was then left to stir at room temperature for 16 h. After completion of the reaction (TLC and MS monitoring), the solution was then cooled to 0° C. and the resulting precipitate was filtered to get the desired product 11.3 as an off-white solid (30 g), which was carried forward to the next step without purification. $^1$H-NMR (400 MHz, DMSO-$d_6$): δ 8.95 (s, 1H), 8.61 (d, J=4.0 Hz, 1H), 8.14 (m, 1H), 7.44 (m, 1H), 6.40 (m, 1H), 4.12 (q, J=7.20 Hz, 2H) and 1.21 (t, J=7.2 Hz, 3H). MS: 221.95 (M+H)$^+$. Yield: 82%.

Preparation of ethyl 1-(3-fluoro-4-(trifluoromethyl)phenyl)-5-(pyridin-3-yl)-1H-pyrazole-3-carboxylate (11.5)

To an ice-cold solution of 4-ethoxy-3,4-dioxo-1-(pyridin-3-yl)but-1-en-1-olate lithium salt 11.3 (10 g, 45.23 mmol) in IPA (60 mL) was added (3-fluoro-4-(trifluoromethyl)phenyl)hydrazine hydrochloride 11.4 (10.5 g, 54.28 mmol) and TFA (7.25 mL, 90.46 mL). The resulting reaction mixture was warmed to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 11.5 (8.0 g, 47%). $^1$H-NMR (400 MHz, CDCl$_3$): δ 8.72 (m, 2H), 7.74 (m, 3H), 7.51 (d, J=7.6 Hz, 1H), 7.48 (d, J=7.6 Hz, 1H), 7.15 (s, 1H), 4.48 (q, J=6.8 Hz, 2H) and 1.40 (t, J=7.2 Hz, 3H). MS: 379.90 (M+H)$^+$.

Preparation of 1-(3-fluoro-4-(trifluoromethyl)phenyl)-5-(pyridin-3-yl)-1H-pyrazole-3-carboxylic Acid (11.6)

To an ice-cold solution of ethyl 1-(3-fluoro-4-(trifluoromethyl)phenyl)-5-(pyridin-3-yl)-1H-pyrazole-3-carboxylate 11.5 (8.0 g, 21.09 mmol) in EtOH (60 mL) was added dropwise an aqueous solution of sodium hydroxide (1.68 g, 42.18 mmol) in 8 mL H$_2$O. The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 11.6 (4.5 g, 61%) as a white solid. $^1$H-NMR (400 MHz, DMSO-$d_6$): δ 13.10 (br s, 1H), 8.59 (m, 2H), 7.88 (t, J=8.0 Hz, 1H), 7.72 (d, J=7.6 Hz, 1H), 7.65 (m, 1H), 7.45 (m, 1H), 7.35 (d, J=8.4 Hz, 1H) and 7.26 (s, 1H). LCMS: 351.96 (M+H)$^+$, 93.37%.

General Procedure for the Preparation of Final Compounds (General Structure 11.7):

General Method N:

To an ice-cold solution of 1-(3-fluoro-4-(trifluoromethyl)phenyl)-5-(pyridin-3-yl)-1H-pyrazole-3-carboxylic acid 11.6 (0.150 g, 0.43 mmol), in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC.

Please refer to Table 6.1 for individual yields and the analytical data of the final compounds.

TABLE 6.1

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 180 | 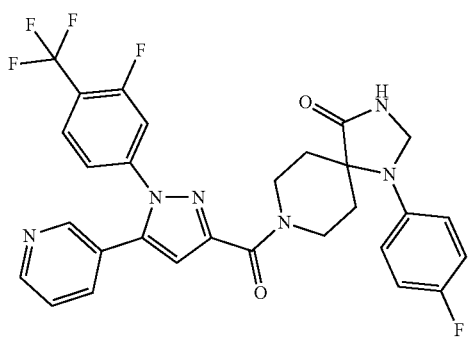 | 1 | 42 | 581.52 (M − H)$^+$, 99.91% | δ 8.81 (s, 1H), 8.59-8.62 (m, 2H), 7.83 (t, J = 8.0 Hz, 1H), 7.72 (d, J = 8.0 Hz, 1H), 7.61-7.64 (m, 1H), 7.44-7.47 (m, 1H), 7.28 (d, J = 8.0 Hz, 1H), 7.16 (s, 1H), 7.08-7.13 (m, 2H), 6.86-6.88 (m, 2H), 4.48-4.62 (m, 2H), 4.43-4.45 (m, 2H), 3.85-3.91 (m, 1H), 3.51-3.57 (m, 1H), 2.20-2.24 (m, 2H) and 1.74-1.78 (m, 2H) |

TABLE 6.1-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 181 | 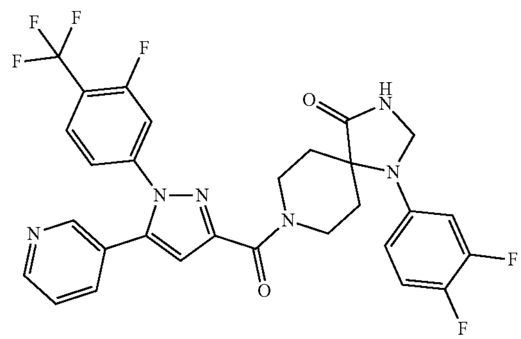 [SMILES: O=C(c1cc(-c2cccnc2)n(-c2ccc(C(F)(F)F)c(F)c2)n1)N1CCC2(CC1)C(=O)NCN2c1ccc(F)c(F)c1] | 2 | 10 | 599.35 (M − H)$^+$, 99.71% | δ 8.89 (s, 1H), 8.60-8.62 (m, 2H), 7.82 (t, J = 8.0 Hz, 1H), 7.73 (d, J = 8.0 Hz, 1H), 7.61 (d, J = 7.2 Hz, 1H), 7.44-7.47 (m, 1H), 7.28-7.34 (m, 2H), 7.16 (s, 1H), 6.75-6.79 (m, 1H), 6.57-6.60 (m, 1H), 4.60 (s, 2H), 4.47-4.49 (m, 2H), 3.83-3.89 (m, 1H), 3.50-3.55 (m, 1H), 2.32-2.40 (m, 2H) and 1.73-1.82 (m, 2H) |
| 182 | 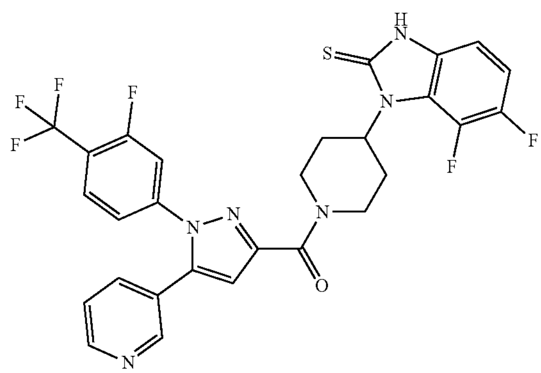 [SMILES: O=C(c1cc(-c2cccnc2)n(-c2ccc(C(F)(F)F)c(F)c2)n1)N1CCC(n2c(=S)[nH]c3ccc(F)c(F)c32)CC1] | Commercial | 9 | 603.44 (M + H)$^+$, 95.32% | δ 8.61 (s, 2H), 7.82 (t, J = 8.64 Hz, 1H), 7.73 (d, J = 7.68 Hz, 1H), 7.64 (m, 1H), 7.44-7.47 (m, 1H), 7.33-7.35 (m, 1H), 7.24-7.31 (m, 2H), 7.19 (s, 1H), 6.99-7.01 (m, 1H), 5.64 (s, 1H), 4.85-4.89 (m, 1H), 4.71-4.74 (m, 1H), 3.40 (s, 1H), 2.05-2.09 (m, 2H) and 1.86 (s, 2H) |
| 183 | 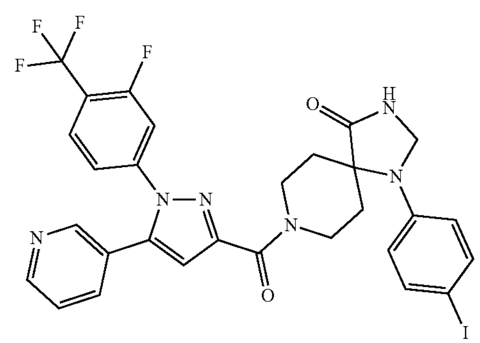 | 10 | 30 | 691.46 (M + H)$^+$, 96.07% | δ 8.87 (s, 1H), 8.62-8.63 (m, 2H), 7.82 (t, J = 8.2 Hz, 1H), 7.73 (d, J = 8.4 Hz, 1H), 7.62-7.64 (m, 1H), 7.45-7.52 (m, 3H), 7.30 (d, J = 8.6 Hz, 1H), 7.08 (s, 1H), 6.59-6.61 (m, 2H), 4.59-4.60 (m, 2H), 4.48-4.50 (m, 2H), 3.84-3.90 (m, 1H), 3.47-3.56 (m, 1H), 2.38-2.42 (m, 2H) and 1.71-1.77 (m, 2H) |
| 184 | 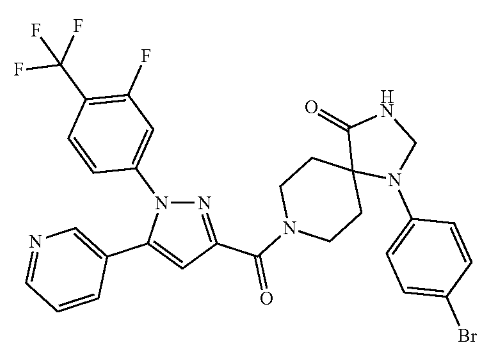 [SMILES: O=C(c1cc(-c2cccnc2)n(-c2ccc(C(F)(F)F)c(F)c2)n1)N1CCC2(CC1)C(=O)NCN2c1ccc(Br)cc1] | 9 | 26 | 641.34 (M − H)$^+$, 99.54% | δ 8.88 (s, 1H), 8.61-8.62 (m, 2H), 7.84 (t, J = 8.24 Hz, 1H), 7.73 (d, J = 7.88 Hz, 1H), 7.62-7.65 (m, 1H), 7.44-7.48 (m, 1H), 7.36 (d, J = 8.76 Hz, 2H), 7.29 (d, J = 8.6 Hz, 1H), 7.19 (s, 1H), 6.70-6.73 (m, 2H), 4.61 (s, 2H), 4.48-4.51 (m, 2H), 3.84-3.90 (m, 1H), 3.51-3.57 (m, 1H), 2.42-2.49 (m, 2H) and 1.71-1.81 (m, 2H) |

TABLE 6.1-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 185 | 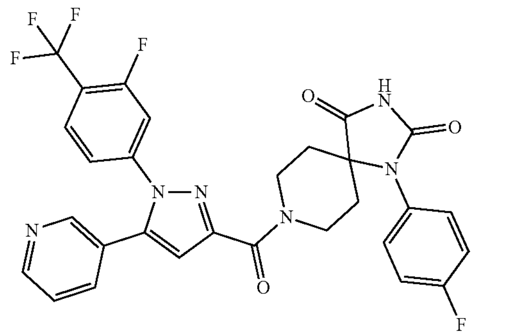 [SMILES: O=C(c1cc(-c2cccnc2)n(-c2ccc(C(F)(F)F)c(F)c2)n1)N1CCC2(CC1)C(=O)NC(=O)N2c1ccc(F)cc1] | 15 | 18 | 595.34 (M − H)$^+$, 99.29% | δ 11.29 (br s, 1H), 8.60-8.62 (m, 1H), 8.56 (d, J = 1.52 Hz, 1H), 7.84 (t, J = 8.28 Hz, 1H), 7.70 (d, J = 8.12 Hz, 1H), 7.59 (d, J = 11.04 Hz, 1H), 7.44-7.48 (m, 1H), 7.27-7.37 (m, 5H), 7.07 (s, 1H), 4.48-4.51 (m, 1H), 4.32-4.36 (m, 1H), 3.78-3.84 (m, 1H), 3.42-3.48 (m, 1H), 2.13-2.22 (m, 2H) and 1.55-1.62 (m, 2H) |
| 186 | 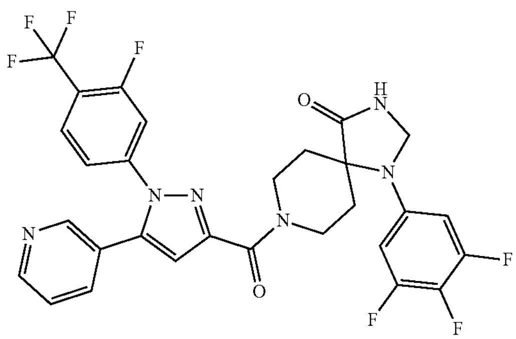 [SMILES: O=C(c1cc(-c2cccnc2)n(-c2ccc(C(F)(F)F)c(F)c2)n1)N1CCC2(CC1)C(=O)NCN2c1cc(F)c(F)c(F)c1] | 4 | 40 | 617.48 (M − H)$^+$, 95.47% | δ 8.95 (s, 1H), 8.63-8.64 (m, 2H), 7.85 (t, J = 8.24 Hz, 1H), 7.78-7.80 (m, 1H), 7.60-7.63 (m, 1H), 7.48-7.51 (m, 1H), 7.27 (d, J = 8.76 Hz, 1H), 7.08 (s, 1H), 6.56-6.61 (m, 2H), 4.60 (s, 2H), 4.47-4.47 (m, 2H), 3.82-3.88 (m, 1H), 3.48-3.54 (m, 1H), 2.38-2.44 (m, 2H) and 1.73-1.81 (m, 2H) |
| 187 | 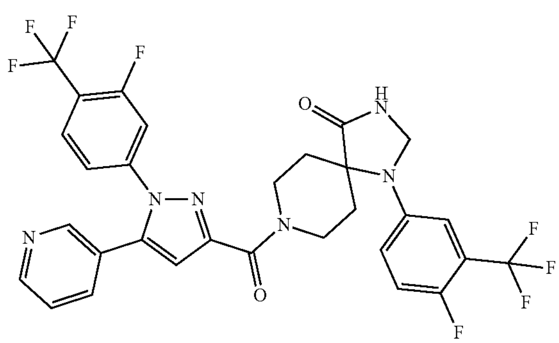 [SMILES: O=C(c1cc(-c2cccnc2)n(-c2ccc(C(F)(F)F)c(F)c2)n1)N1CCC2(CC1)C(=O)NCN2c1ccc(F)c(C(F)(F)F)c1] | 5 | 18 | 651.54 (M − H)$^+$, 95.32% | δ 8.93 (s, 1H), 8.62-8.64 (m, 2H), 7.82-7.86 (m, 1H), 7.75-7.77 (m, 1H), 7.60-7.63 (m, 1H), 7.47-7.50 (m, 1H), 7.38-7.42 (m, 1H), 7.27-7.29 (m, 1H), 7.15 (s, 1H), 7.06-7.08 (m, 1H), 6.94-6.97 (m, 1H), 4.68 (s, 2H), 4.47-4.51 (m, 2H), 3.75-3.80 (m, 1H), 3.49-3.55 (m, 1H), 2.32-2.41 (m, 2H) and 1.76-1.84 (m, 2H) |
| 188 | 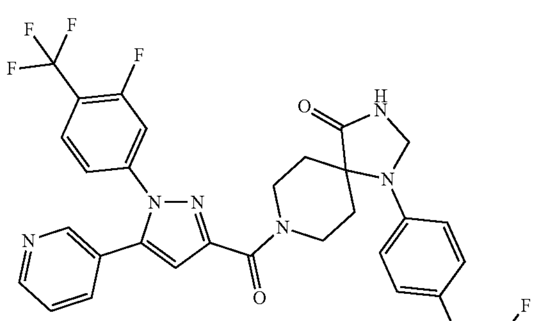 | 8 | 14 | 629.46 (M − H)$^+$, 99.56% | δ 8.84 (s, 1H), 8.60-8.63 (m, 2H), 7.82 (t, J = 8.28 Hz, 1H), 7.72 (d, J = 8.28 Hz, 1H), 7.61-7.64 (m, 1H), 7.44-7.47 (m, 1H), 7.29-7.32 (m, 1H), 7.17 (s, 1H), 6.82-7.09 (m, 4H), 4.61 (s, 2H), 4.46-4.49 (m, 2H), 3.85-3.91 (m, 1H), 3.51-3.57 (m, 1H), 2.32-2.39 (m, 2H) and 1.74-1.82 (m, 2H) |

TABLE 6.1-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 189 | 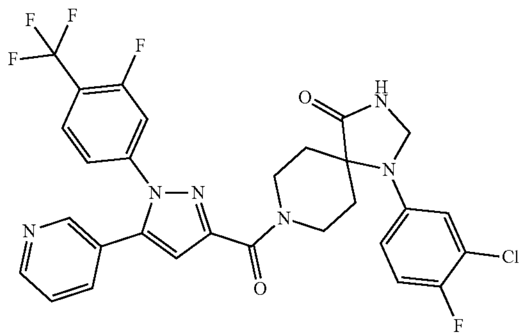 [SMILES: O=C(c1cc(-c2cccnc2)n(-c2ccc(C(F)(F)F)c(F)c2)n1)N1CCC2(CC1)C(=O)NCN2c1ccc(F)c(Cl)c1] | 3 | 8 | 617.26 (M + H)$^+$, 93.55% | δ 8.88 (s, 1H), 8.60-8.62 (m, 2H), 7.82 (t, J = 8.4 Hz, 1H), 7.72 (d, J = 7.88 Hz, 1H), 7.62 (d, J = 7.6 Hz, 1H), 7.44-7.47 (m, 1H), 7.28-7.32 (m, 2H), 7.16 (s, 1H), 6.85-6.89 (m, 1H), 6.78-6.80 (m, 1H), 4.62 (s, 2H), 4.46-4.49 (m, 2H), 3.49-3.55 (m, 2H), 2.38-2.42 (m, 2H) and 1.74-1.79 (m, 2H) |
| 190 | 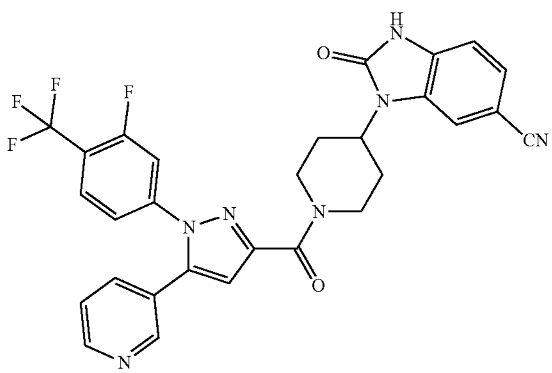 [SMILES: N#Cc1ccc2[nH]c(=O)n(C3CCN(C(=O)c4cc(-c5cccnc5)n(-c5ccc(C(F)(F)F)c(F)c5)n4)CC3)c2c1] | 20 | 13 | 574.46 (M − H)$^+$, 99.75% | δ 11.46 (br s, 1H), 8.62-8.64 (m, 2H), 7.85-7.89 (m, 2H), 7.76 (d, J = 8.08 Hz, 1H), 7.64-7.67 (m, 1H), 7.43-7.50 (m, 2H), 7.33 (d, J = 8.12 Hz, 1H), 7.18 (s, 1H), 7.10-7.12 (m, 1H), 4.71-4.75 (m, 2H), 4.52-4.58 (m, 1H), 3.28-3.35 (m, 1H), 2.90-2.97 (m, 1H), 2.29-2.36 (m, 2H) and 1.78-1.86 (m, 2H) |
| 191 | 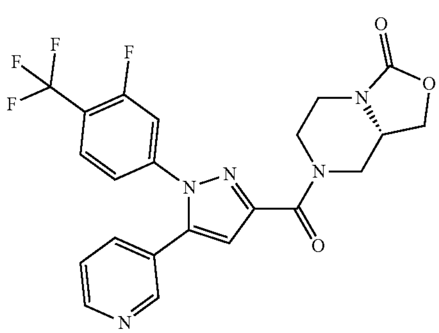 [SMILES: O=C(c1cc(-c2cccnc2)n(-c2ccc(C(F)(F)F)c(F)c2)n1)N1CCN2C(=O)OC[C@@H]2C1] | Commercial | 30 | 476.43 (M + H)$^+$, 99.89% | δ 8.59-8.62 (m, 2H), 7.85 (t, J = 8.08 Hz, 1H), 7.69-7.73 (m, 2H), 7.44-7.47 (m, 1H), 7.31 (d, J = 7.88 Hz, 1H), 7.16 (s, 1H), 4.67-4.81 (m, 2H), 4.35-4.42 (m, 1H), 4.01-4.07 (m, 2H), 3.66-3.73 (m, 1H), 3.19-3.21 (m, 1H), 3.08-3.12 (m, 1H) and 2.78-2.84 (m, 1H) |
| 192 | 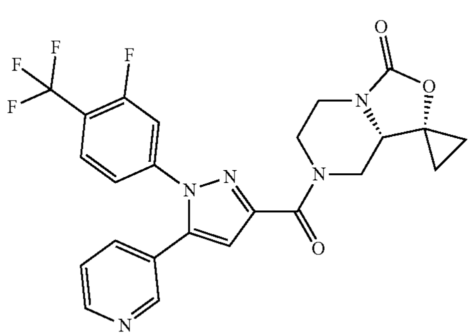 | Commercial | 48 | 502.44 (M + H)$^+$, 99.81% | δ 8.59-8.63 (m, 2H), 7.87 (s, 1H), 7.63-7.72 (m, 2H), 7.44-7.47 (m, 1H), 7.29-7.34 (m, 1H), 7.16 (s, 1H), 4.70-4.72 (m, 1H), 4.52-4.56 (m, 1H), 3.74-3.84 (m, 2H), 3.12-3.18 (m, 2H), 2.85-2.94 (m, 1H) and 0.94-1.08 (m, 4H) |

TABLE 6.1-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 193 | 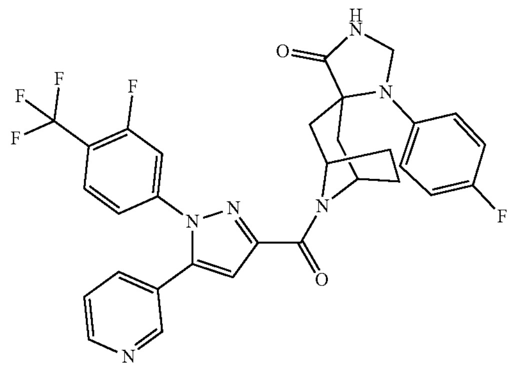 [SMILES: O=C(c1cc(-c2cccnc2)n(-c2ccc(C(F)(F)F)c(F)c2)n1)N1C2CCC1CC1(C2)C(=O)NCN1c1ccc(F)cc1] | 11 | 5 | 609.52 (M + H)$^+$, 99.73% | δ 8.79 (br s, 1H), 8.63 (s, 2H), 7.81 (t, J = 8.4 Hz, 1H), 7.74 (d, J = 8.0 Hz, 1H), 7.57-7.60 (m, 1H), 7.45-7.48 (m, 1H), 7.33 (s, 1H), 7.27-7.29 (m, 1H), 6.90-6.94 (m, 2H), 6.72-6.75 (m, 2H), 5.24 (s, 1H), 4.92 (s, 1H), 4.54 (s, 2H), 3.31-3.33 (m, 2H), 2.71-2.75 (m, 1H), 2.49-2.50 (m, 1H), 2.33-2.38 (m, 2H) and 1.82-1.92 (m, 2H) |
| 194 | 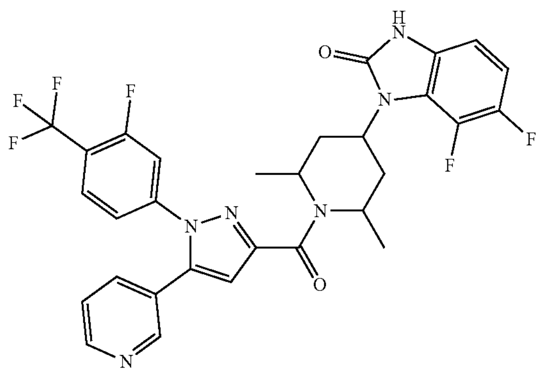 [SMILES: CC1CC(n2c(=O)[nH]c3ccc(F)c(F)c32)CC(C)N1C(=O)c1cc(-c2cccnc2)n(-c2ccc(C(F)(F)F)c(F)c2)n1] | 21 | 15 | 613.23 (M − H)$^+$, 96.59% | δ 11.25 (br s, 1H), 8.60-8.62 (m, 2H), 8.58 (t, J = 8.4 Hz, 1H), 7.73 (d, J = 8.0 Hz, 1H), 7.60-7.63 (m, 1H), 7.44-7.47 (m, 1H), 7.32 (d, J = 8.0 Hz, 1H), 7.12 (s, 1H), 7.00-7.06 (m, 1H), 6.76-6.79 (m, 1H), 4.82 (s, 1H), 4.67 (s, 1H), 3.91 (s, 1H), 2.22-2.27 (m, 2H), 1.88-1.91 (m, 1H), 1.78-1.81 (m, 1H), 1.52 (d, J = 6.4 Hz, 3H) and 1.44 (d, J = 6.8 Hz, 3H) |
| 195 | 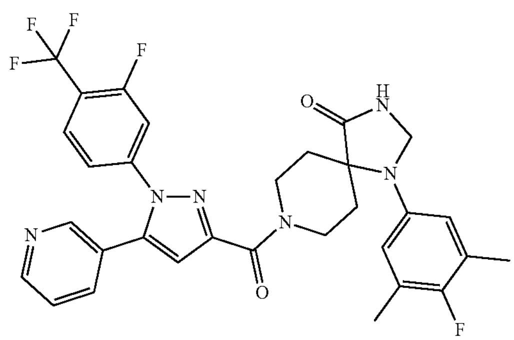 [SMILES: Cc1cc(N2CNC(=O)C23CCN(C(=O)c2cc(-c4cccnc4)n(-c4ccc(C(F)(F)F)c(F)c4)n2)CC3)cc(C)c1F] | 6 | 20 | 609.18 (M − H)$^+$, 99.41% | δ 8.75 (s, 1H), 8.59-8.62 (m, 2H), 7.84 (t, J = 8.4 Hz, 1H), 7.72 (d, J = 8.0 Hz, 1H), 7.58-7.61 (m, 1H), 7.41-7.47 (m, 1H), 7.27 (d, J = 8.8 Hz, 1H), 7.12 (s, 1H), 6.58-6.59 (m, 2H), 4.55 (s, 2H), 4.39 (s, 2H), 3.81-3.87 (m, 2H), 2.28-2.32 (m, 1H), 2.18-2.21 (m, 1H), 2.08 (s, 6H) and 1.72-1.80 (m, 2H) |
| 196 | 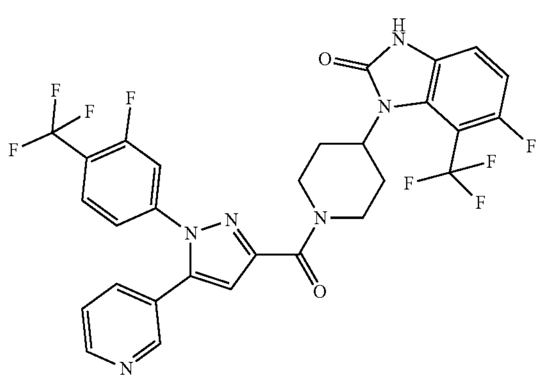 [SMILES: O=C(c1cc(-c2cccnc2)n(-c2ccc(C(F)(F)F)c(F)c2)n1)N1CCC(n2c(=O)[nH]c3ccc(F)c(C(F)(F)F)c32)CC1] | 17 | 35 | 635.45 (M − H)$^+$, 99.92% | δ 11.25 (br s, 1H), 8.60-8.62 (m, 2H), 7.85 (t, J = 8.0 Hz, 1H), 7.73 (d, J = 8.0 Hz, 1H), 7.65-7.68 (m, 1H), 7.44-7.47 (m, 1H), 7.33 (d, J = 8.0 Hz, 1H), 7.22-7.25 (m, 1H), 7.16 (s, 1H), 7.04-7.09 (m, 1H), 4.82-4.85 (m, 1H), 4.70-4.73 (m, 1H), 4.21-4.27 (m, 1H), 3.16-3.22 (m, 1H), 2.77-2.80 (m, 1H), 2.58-2.64 (m, 2H) and 1.75-1.84 (m, 2H) |

TABLE 6.1-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 197 | 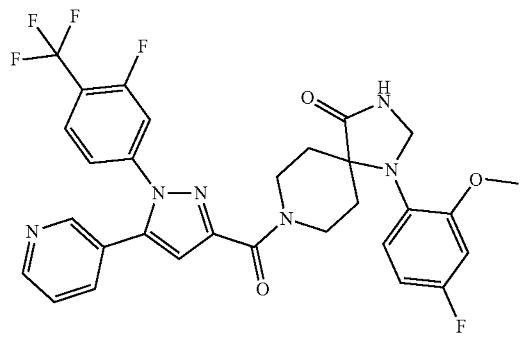 [SMILES: COc1cc(F)ccc1N1CNC(=O)C12CCN(C(=O)c1cc(-c3cccnc3)n(-c3ccc(C(F)(F)F)c(F)c3)n1)CC2] | 7 | 14 | 612.90 (M + H)$^+$, 97.83% | δ 8.59-8.60 (m, 1H), 8.56 (s, 1H), 8.50 (s, 1H), 7.83 (t, J = 8.4 Hz, 1H), 7.68 (d, J = 8.0 Hz, 1H), 7.58-7.61 (m, 1H), 7.42-7.45 (m, 1H), 7.27 (d, J = 6.4 Hz, 2H), 7.05 (s, 1H), 6.93-6.97 (m, 1H), 6.71-6.75 (m, 1H), 4.47-4.52 (m, 2H), 4.00-4.08 (m, 1H), 3.91-3.96 (m, 2H), 3.76 (s, 3H), 3.62-3.68 (m, 1H), 1.83-1.89 (m, 2H) and 1.40-1.46 (m, 2H) |

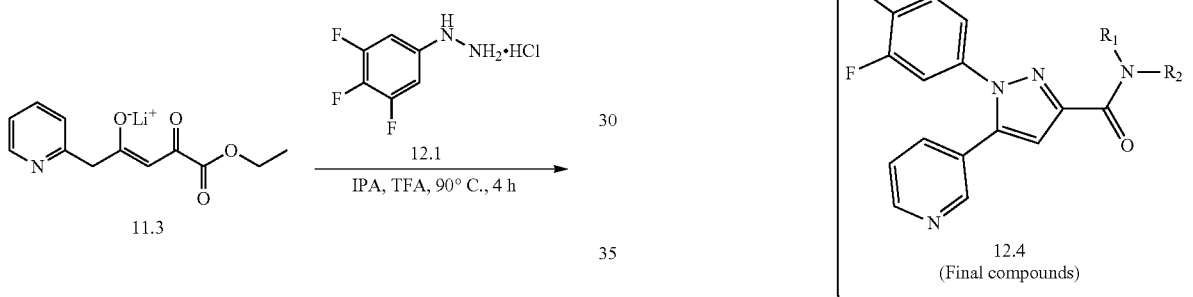

Scheme 12

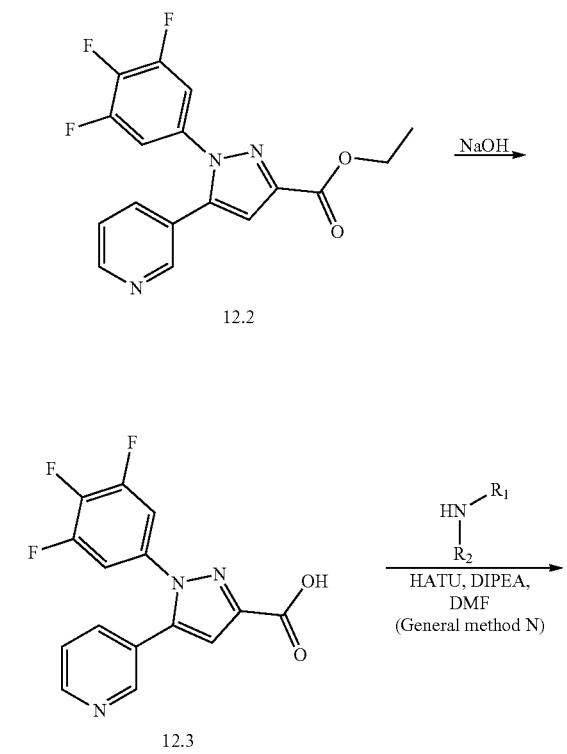

Preparation of ethyl 5-(pyridin-3-yl)-1-(3,4,5-trifluorophenyl)-1H-pyrazole-3-carboxylate (12.2)

To an ice-cold solution of 4-ethoxy-3,4-dioxo-1-(pyridin-3-yl)but-1-en-1-olate lithium salt 11.3 (10.0 g, 45.23 mmol) in IPA (50 mL) was added (3,4,5-trifluorophenyl)hydrazine hydrochloride 12.1 (10.77 g, 54.28 mmol) and TFA (6.9 mL, 90.46 mmol). The resulting reaction mixture was warmed to room temperature and then stirred at 90° C. for 4 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 12.2 (5.50 g, 35%). $^1$H-NMR (400 MHz, CDCl$_3$): δ 8.68 (m, 1H), 8.61 (s, 1H), 7.61 (d, J=8.0 Hz, 1H), 7.42 (m, 1H), 7.14 (s, 1H), 7.03 (m, 2H), 4.48 (q, J=7.2 Hz, 2H) and 1.41 (t, J=7.2 Hz, 3H). MS: 348.15 (M+H)$^+$.

Preparation of 5-(pyridin-3-yl)-1-(3,4,5-trifluorophenyl)-1H-pyrazole-3-carboxylic Acid (12.3)

To an ice-cold solution of ethyl 5-(pyridin-3-yl)-1-(3,4,5-trifluorophenyl)-1H-pyrazole-3-carboxylate 12.2 (5.50 g, 15.82 mmol) in EtOH (40 mL) was added dropwise an aqueous solution of sodium hydroxide (1.26 g, 31.64 mmol). The resulting solution was stirred at room temperature for 2 h. After completion of the reaction (TLC monitoring), the solvent was evaporated, added H₂O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 12.3 (3.0 g, 59%) as a white solid. $^{1}$H-NMR (400 MHz, DMSO-$d_6$): δ 13.13 (br s, 1H), 8.59 (s, 2H), 7.65 (d, J=8.4 Hz, 1H), 7.52 (m, 2H), 7.41 (m, 1H) and 7.25 (s, 1H). LCMS: 320.14 (M+H)$^{+}$, 95.20%.

General Procedure for the Preparation of Final Compounds (General Structure 12.4):

The final compounds were prepared following the general method N. To an ice-cold solution of carboxylic acid 12.3 (125-150 mg), in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na₂SO₄, filtered and concentrated under reduced pressure. The crude residue was purified via prep-HPLC.

Please refer to Table 6.2 for individual yields and the analytical data of the final compounds.

TABLE 6.2

Tabulated data of the final compounds including the individual yields

| No. | Structure | Amine Intermediate used | Yield (%) | LCMS | NMR data (DMSO-$d_6$, 400 MHz) |
|---|---|---|---|---|---|
| 198 | 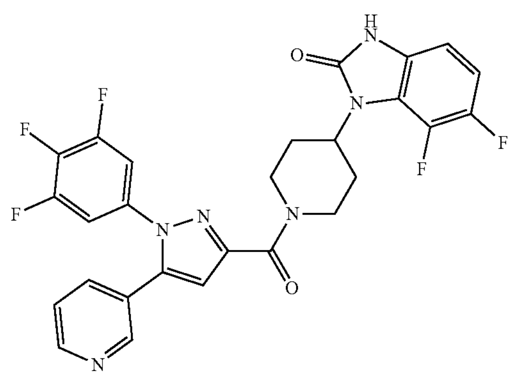 | 16 | 32 | 555.11 (M + H)$^{+}$, 95.55% | δ 11.25 (br s, 1H), 8.60 (s, 2H), 7.67 (d, J = 8.0 Hz, 1H), 7.50-7.53 (m, 2H), 7.39-7.42 (m, 1H), 7.14 (s, 1H), 7.00-7.05 (m, 1H), 6.77-6.80 (m, 1H), 4.80-4.84 (m, 1H), 4.67-4.70 (m, 2H), 3.32 (s, 1H), 2.92-2.98 (m, 1H), 2.11-2.16 (m, 2H) and 1.85-1.88 (m, 2H) |
| 199 | 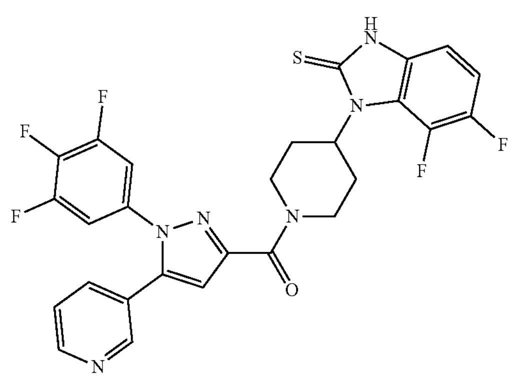 [SMILES: O=C(c1cc(-c2cccnc2)n(-c2cc(F)c(F)c(F)c2)n1)N1CCC(n2c(=O)[nH]c3ccc(F)c(F)c32)CC1] | Commercial | 10 | 569.31 (M − H)$^{+}$, 88.55% | δ 13.11 (br s, 1H), 8.60 (s, 2H), 7.70 (d, J = 8.56 Hz, 1H), 7.50-7.53 (m, 2H), 7.41-7.44 (m, 1H), 7.24-7.29 (m, 1H), 7.16 (s, 1H), 7.00-7.01 (m, 1H), 4.87-4.90 (m, 1H), 4.72-4.74 (m, 2H), 3.32 (s, 1H), 2.92-2.98 (m, 1H), 2.07-2.11 (m, 2H) and 1.86-1.90 (m, 2H) |
| 200 | 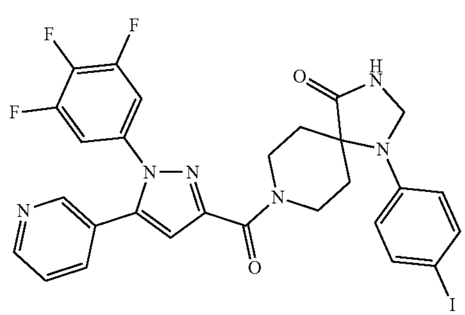 [SMILES: O=C(c1cc(-c2cccnc2)n(-c2cc(F)c(F)c(F)c2)n1)N1CCC2(CC1)C(=O)NCN2c1ccc(I)cc1] | 10 | 22 | 659.50 (M + H)$^{+}$, 97.37% | δ 8.87 (s, 1H), 8.62-8.63 (m, 2H), 7.71 (t, J = 8.2 Hz, 1H), 7.44-7.51 (m, 5H), 7.17 (s, 1H), 6.58-6.60 (m, 2H), 4.59-4.60 (m, 2H), 4.49-4.50 (m, 2H), 3.82-3.87 (m, 2H), 3.49-3.55 (m, 1H), 2.42-2.45 (m, 1H) and 1.70-1.79 (m, 2H) |

TABLE 6.2-continued

Tabulated data of the final compounds including the individual yields

| No. | Structure | Amine Intermediate used | Yield (%) | LCMS | NMR data (DMSO-$d_6$, 400 MHz) |
|---|---|---|---|---|---|
| 201 | 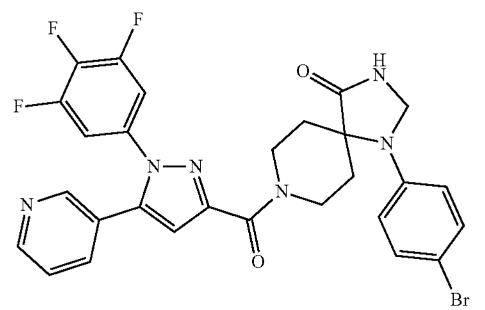 [SMILES: O=C(c1cc(-c2cccnc2)n(-c2cc(F)c(F)c(F)c2)n1)N1CCC2(CC1)C(=O)NCN2c1ccc(Br)cc1] | 9 | 25 | 609.29 (M − H)+, 99.91 | δ 8.88 (s, 1H), 8.60-8.61 (m, 2H), 7.66 (t, J = 8.04 Hz, 1H), 7.36-7.50 (m, 5H), 7.17 (s, 1H), 6.69-6.72 (m, 2H), 4.59-4.60 (m, 2H), 4.47-4.50 (m, 2H), 3.82-3.88 (m, 1H), 3.50-3.55 (m, 1H), 2.42-2.49 (m, 2H) and 1.70-1.80 (m, 2H) |
| 202 | 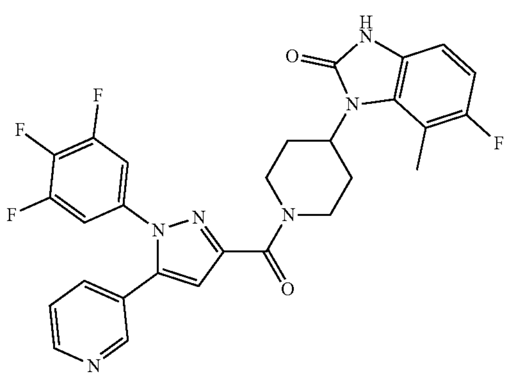 [SMILES: Cc1c(F)ccc2[nH]c(=O)n(C3CCN(C(=O)c4cc(-c5cccnc5)n(-c5cc(F)c(F)c(F)c5)n4)CC3)c12] | 18 | 18 | 551.37 (M + H)+, 99.88% | δ 10.84 (br s, 1H), 8.60 (s, 2H), 7.68 (t, J = 7.92 Hz, 1H), 7.50-7.56 (m, 2H), 7.42-7.45 (m, 1H), 7.13 (s, 1H), 6.74-6.82 (m, 2H), 4.76-4.79 (m, 1H), 4.66-4.69 (m, 2H), 3.25-3.28 (m, 1H), 2.88-2.94 (m, 1H), 2.55-2.58 (m, 2H), 2.50 (s, 3H) and 1.84-1.90 (m, 2H) |
| 203 | 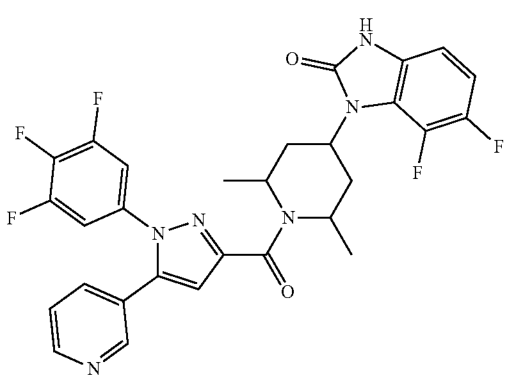 [SMILES: CC1CC(n2c(=O)[nH]c3ccc(F)c(F)c32)CC(C)N1C(=O)c1cc(-c2cccnc2)n(-c2cc(F)c(F)c(F)c2)n1] | 21 | 5 | 583.21 (M + H)+, 97.96% | δ 11.25 (br s, 1H), 8.59-8.60 (m, 2H), 7.67 (d, J = 8.0 Hz, 1H), 7.47-7.50 (m, 2H), 7.41-7.44 (m, 1H), 7.10 (s, 1H), 7.00-7.07 (m, 1H), 6.76-6.79 (m, 1H), 4.80 (s, 1H), 4.67 (s, 1H), 3.90 (s, 1H), 2.23-2 30 (m, 2H), 1.80-1.90 (m, 2H), 1.51 (d, J = 6.4 Hz, 3H) and 1.42 (d, J = 6.8 Hz, 3H) |
| 204 | 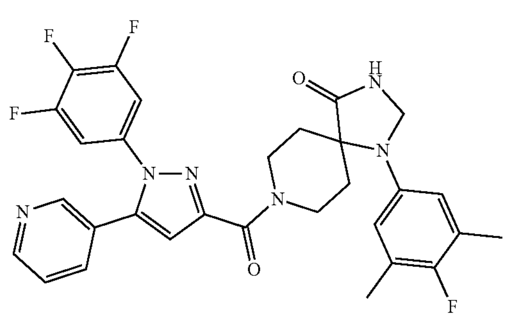 [SMILES: Cc1cc(N2CNC(=O)C23CCN(C(=O)c2cc(-c4cccnc4)n(-c4cc(F)c(F)c(F)c4)n2)CC3)cc(C)c1F] | 6 | 18 | 579.13 (M + H)+, 99.12% | δ 8.74 (s, 1H), 8.58-8.60 (m, 2H), 7.66 (d, J = 8.0 Hz, 1H), 7.41-7.48 (m, 3H), 7.10 (s, 1H), 6.58-6.59 (m, 2H), 4.55 (s, 2H), 4.38-4.41 (s, 2H), 3.79-3.85 (m, 1H), 3.47-3.53 (m, 1H), 2.21-2.25 (m, 2H), 2.12 (s, 6H) and 1.72-1.79 (m, 2H) |

TABLE 6.2-continued
Tabulated data of the final compounds including the individual yields
| No. | Structure | Amine Intermediate used | Yield (%) | LCMS | NMR data (DMSO-d$_6$, 400 MHz) |
|---|---|---|---|---|---|
| 207 | 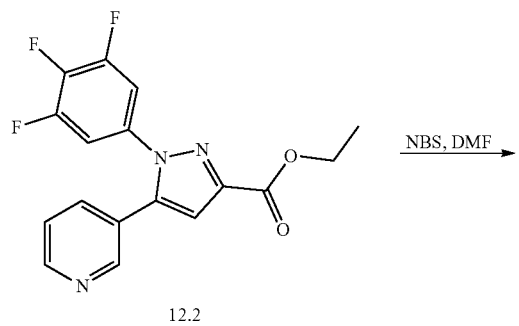 | 22 | 6 | 583.37 (M + H)$^+$, 97.90% | δ 11.31 (br s, 1H), 8.60-8.61 (m, 2H), 7.69 (d, J = 8.4 Hz, 1H), 7.43-7.52 (m, 3H), 7.10 (s, 1H), 6.99-7.07 (m, 1H), 6.77-6.79 (m, 1H), 4.65 (s, 1H), 431-4.34 (m, 2H), 3.87-3.90 (m, 1H), 3.51-3.54 (m, 1H), 2.26-2.33 (m, 2H), 0.85 (d, J = 6.4 Hz, 3H) and 0.77 (d, J = 6.8 Hz, 3H) |
| 208 | 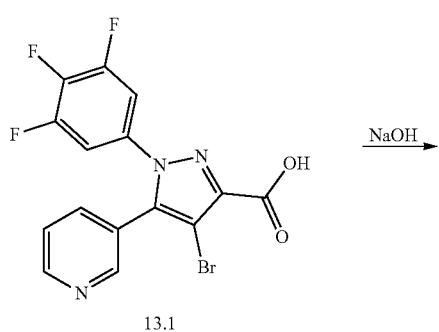 | 19 | 12 | 518.13 (M − H)$^+$, 97.02% | δ 11.12 (br s, 1H), 8.59-8.60 (m, 2H), 7.92 (d, J = 4.4 Hz, 1H), 7.67 (d, J = 8.0 Hz, 1H), 7.50-7.54 (m, 2H), 7.41-7.44 (m, 1H), 7.28 (d J = 6.8 Hz, 1H), 7.15 (s, 1H), 6.97 (t, J = 7.6 Hz, 1H), 4.79-4.82 (m, 1H), 4.69-4.72 (m, 1H), 4.55-4.57 (m, 1H), 3.28-3.32 (m, 1H), 2.90-2.96 (m, 1H), 2.50-2.55 (m, 2H) and 1.76-1.84 (m, 2H) |
Scheme 13
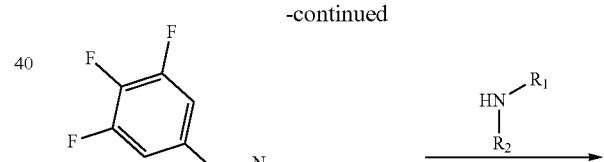
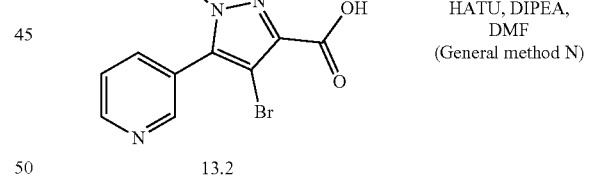
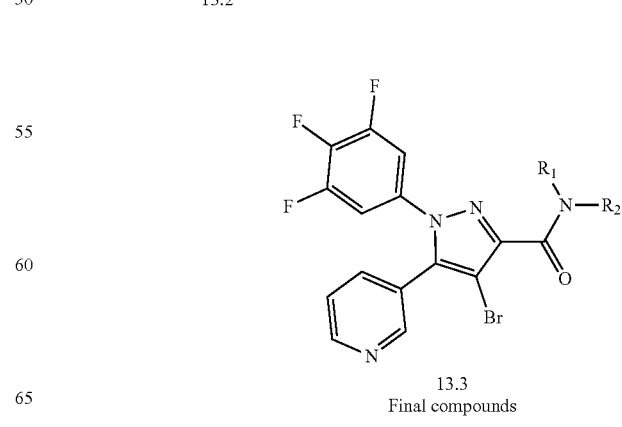
13.3
Final compounds Preparation of Ethyl 4-bromo-5-(pyridin-3-yl)-1-(3,4,5-trifluorophenyl)-1H-pyrazole-3-carboxylate (13.1)

To a solution of ethyl 5-(pyridin-3-yl)-1-(3,4,5-trifluorophenyl)-1H-pyrazole-3-carboxylate 12.2 (1.0 g, 2.88 mmol) in DMF (15 mL) was added NBS (0.77 g, 4.32 mmol). The resulting reaction mixture was heated at 50° C. for 4 h. After completion of the reaction (TLC monitoring), the solvent was ice-cold water and extracted with ethyl acetate (3 times). The combined organics were washed with ice-cold water, brine, dried over anhydrous sodium sulfate, filtered and concentrated. The crude was purified over silica gel (100-200 M, 3-5% EtOAc-hexane) to get the desired product 13.1 (0.99 g, yield: 81%). $^1$H-NMR (400 MHz, CDCl$_3$): δ 8.71-8.72 (m, 1H), 8.53 (s, 1H), 7.66 (d, J=7.88 Hz, 1H), 7.42-7.45 (m, 1H), 6.93-6.99 (m, 2H), 4.50 (q, J=7.12 Hz, 2H) and 1.39 (t, J=7.2 Hz, 3H). MS: 426.18 (M+H)$^+$.

4-Bromo-5-(pyridin-3-yl)-1-(3,4,5-trifluorophenyl)-1H-pyrazole-3-carboxylic Acid (13.2)

To an ice-cold solution of ethyl 4-bromo-5-(pyridin-3-yl)-1-(3,4,5-trifluorophenyl)-1H-pyrazole-3-carboxylate 13.1 (0.99 g, 2.33 mmol) in EtOH (20 mL) was added dropwise an aqueous solution of sodium hydroxide (0.19 g, 4.66 mmol). The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 13.2 (0.35 g, yield: 39%) as a white solid. $^1$H-NMR (400 MHz, DMSO-d$_6$): δ 13.45 (br s, 1H), 8.64-8.65 (m, 1H), 8.57 (s, 1H), 7.77 (d, J=7.96 Hz, 1H) and 7.48-7.52 (m, 3H). LCMS: 397.94 (M+H)$^+$, 86.45%.

General Procedure for the Preparation of Final Compounds (General Structure 13.3):

The final compounds were prepared following the general method N on 100-150 mg scale. Please refer to Table 6.3 for individual yields and the analytical data of the final compounds.

TABLE 6:3

Tabulated data of the final compounds including the individual yields

| No. | Structure | Amine Intermediate Used | Yield (%) | LCMS | NMR data (DMSO-d$_6$, 400 MHz) |
| --- | --- | --- | --- | --- | --- |
| 210 | 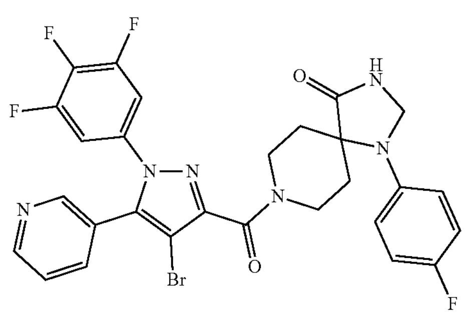 [SMILES: O=C(c1nn(-c2cc(F)c(F)c(F)c2)c(-c2cccnc2)c1Br)N1CCC2(CC1)C(=O)NCN2c1ccc(F)cc1] | 1 | 13 | 629.42 (M + H)$^+$, 99.53% | δ 8.84 (s, 1H), 8.65-8.66 (m, 1H), 8.58 (s, 1H), 7.77 (d, J = 7.84 Hz, 1H), 7.50-7.53 (m, 1H), 7.42-7.45 (m, 2H), 7.10-7.14 (m, 2H), 6.83-6.86 (m, 2H), 4.58-4.61 (m, 2H), 4.45-4.48 (m, 1H), 3.80-3.90 (m, 2H), 3.52-3.58 (m, 1H), 2.27-2.32 (m, 2H), 1.80-1.84 (m, 1H) and 1.71-1.75 (m, 1H) |
| 211 | 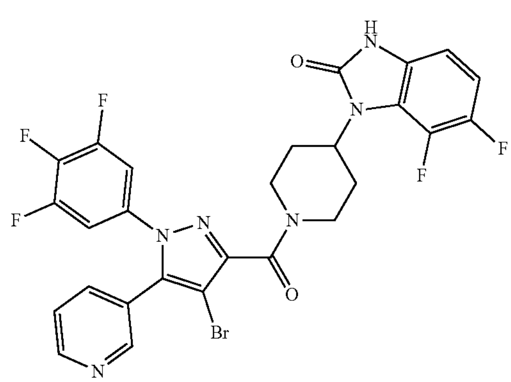 [SMILES: O=C(c1nn(-c2cc(F)c(F)c(F)c2)c(-c2cccnc2)c1Br)N1CCC(n2c(=O)[nH]c3ccc(F)c(F)c32)CC1] | 16 | 26 | 633.38 (M + H)$^+$, 97.73% | δ 10.50 (br s, 1H), 8.65-8.66 (m, 1H), 8.59 (s, 1H), 7.78 (d, J = 7.88 Hz, 1H), 7.44-7.52 (m, 3H), 7.00-7.07 (m, 1H), 6.78-6.80 (m, 1H), 4.60-4.70 (m, 2H), 4.10-4.13 (m, 1H), 3.32 (s, 1H), 2.97-3.03 (m, 1H), 2.12-2.18 (m, 2H) and 1.75-1.90 (m, 2H) |

Scheme 14

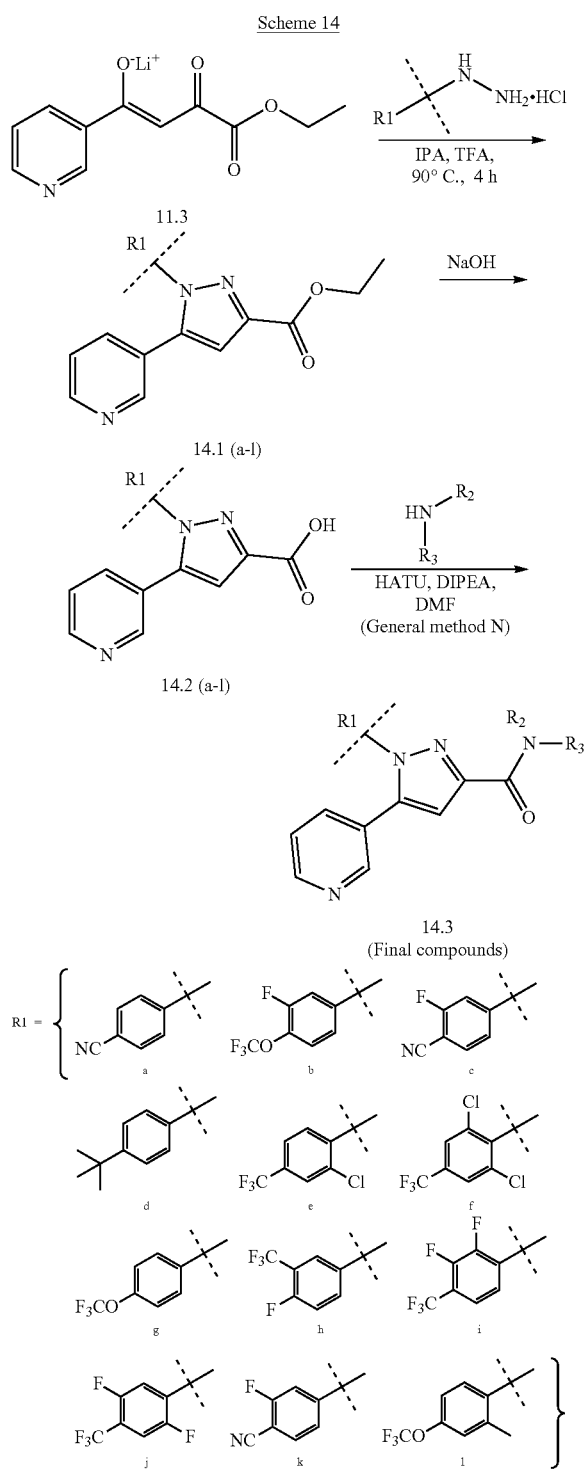

General Procedure for the Preparation of Compounds 14.1 (a-l):

To an ice-cold solution of 4-ethoxy-2-methyl-3,4-dioxo-1-(pyridin-3-yl)but-1-en-1-olate lithium salt 11.3 (3.0 g, 13.21 mmol) in IPA was added respective hydrazine hydrochloride (1.2 eq) and TFA (2.0 eq). The resulting reaction mixture was warmed to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 14.1 (a-l).

Ethyl 1-(4-cyanophenyl)-5-(pyridin-3-yl)-1H-pyrazole-3-carboxylate (14.1-a)

$^1$H-NMR (400 MHz, CDCl$_3$): δ 9.17 (m, 1H), 8.80-8.81 (m, 1H), 8.22-8.24 (m, 1H), 7.61-7.63 (m, 2H), 7.42-7.45 (m, 2H), 7.14 (s, 1H), 7.05-7.09 (m, 1H), 4.44 (q, J=7.2 Hz, 2H) and 1.35 (t, J=7.2 Hz, 3H). MS: 319.03 (M+H)$^+$. Yield: 13%.

Ethyl 1-(3-fluoro-4-(trifluoromethoxy)phenyl)-5-(pyridin-3-yl)-1H-pyrazole-3-carboxylate (14.1-b)

$^1$H-NMR (400 MHz, CDCl$_3$): δ 8.62-8.68 (m, 2H), 7.61-7.63 (m, 1H), 7.41-7.44 (m, 1H), 7.29-7.34 (m, 2H), 7.14 (s, 1H), 7.07-7.10 (m, 1H), 4.44 (q, J=7.6 Hz, 2H) and 1.38 (t, J=7.2 Hz, 3H). MS: 396.14 (M+H)$^+$. Yield: 41%.

Ethyl 1-(4-cyano-3-fluorophenyl)-5-(pyridin-3-yl)-1H-pyrazole-3-carboxylate (14.1-c)

$^1$H-NMR (400 MHz, CDCl$_3$): δ 8.71-8.72 (m, 1H), 8.62 (s, 1H), 7.61-7.64 (m, 2H), 7.44-7.47 (m, 1H), 7.35-7.38 (m, 1H), 7.19 (s, 1H), 7.15-7.17 (m, 1H), 4.42 (q, J=7.6 Hz, 2H) and 1.36 (t, J=7.6 Hz, 3H). LCMS: 337.13 (M+H)$^+$, 96.65%. Yield: 26%.

Ethyl 1-(4-(tert-butyl)phenyl)-5-(pyridin-3-yl)-1H-pyrazole-3-carboxylate (14.1-d)

$^1$H-NMR (400 MHz, CDCl$_3$): δ 8.58-8.62 (m, 1H), 8.54-8.58 (m, 1H), 7.52-7.54 (m, 1H), 7.39-7.41 (m, 2H), 7.22-7.28 (m, 3H), 7.11 (s, 1H), 4.44 (q, J=7.2 Hz, 2H), 1.37 (t, J=7.6 Hz, 3H) and 1.25 (s, 9H). MS: 350.23 (M+H)$^+$. Yield: 23%.

Ethyl 1-(2-chloro-4-(trifluoromethyl)phenyl)-5-(pyridin-3-yl)-1H-pyrazole-3-carboxylate (14.1-e)

$^1$H-NMR (400 MHz, CDCl$_3$): δ 8.57-8.58 (m, 1H), 8.48 (s, 1H), 7.65-7.70 (m, 3H), 7.48-7.50 (m, 1H), 7.24-7.27 (m, 1H), 7.14 (s, 1H), 4.44 (q, J=7.2 Hz, 2H) and 1.36 (t, J=7.2 Hz, 3H). MS: 396.27 (M+H)$^+$. Yield: 30%.

Ethyl 1-(2,6-dichloro-4-(trifluoromethyl)phenyl)-5-(pyridin-3-yl)-1H-pyrazole-3-carboxylate (14.1-f)

$^1$H-NMR (400 MHz, CDCl$_3$): δ 8.71-8.76 (m, 1H), 8.62-8.65 (m, 1H), 7.74 (d, J=8.0 Hz, 1H), 7.69 (s, 2H), 7.46-7.49 (m, 1H), 7.21 (s, 1H), 4.45 (q, J=7.6 Hz, 2H) and 1.38 (t, J=7.2 Hz, 3H). MS: 430.08 (M+H)$^+$. Yield: 31%.

Ethyl 5-(pyridin-3-yl)-1-(4-(trifluoromethoxy)phenyl)-1H-pyrazole-3-carboxylate (14.1-g)

$^1$H-NMR (400 MHz, CDCl$_3$): δ 8.73-8.81 (m, 2H), 8.39-8.41 (m, 1H), 7.72-7.74 (m, 1H), 7.52-7.54 (m, 1H), 7.45-7.47 (m, 2H), 7.33-7.35 (m, 2H), 4.52 (q, J=7.6 Hz, 2H) and 1.51 (t, J=7.2 Hz, 3H). LC-MS: 378.28 (M+H)$^+$, 88.27% Yield: 40%.

Ethyl 1-(4-fluoro-3-(trifluoromethyl)phenyl)-5-(pyridin-3-yl)-1H-pyrazole-3-carboxylate (14.1-h)

$^1$H-NMR (400 MHz, CDCl$_3$): δ 8.59-8.66 (m, 1H), 7.77-7.78 (m, 1H), 7.56 (d, J=8.04 Hz, 1H) 7.38-7.41 (m, 2H), 7.23-7.25 (m, 1H), 7.21 (s, 1H), 7.07-7.10 (m, 1H), 4.48 (q, J=7.2 Hz, 2H) and 1.38 (t, J=7.6 Hz, 3H). MS: 380.22 (M+H)$^+$. Yield: 35%.

Ethyl 1-(2,3-difluoro-4-(trifluoromethyl)phenyl)-5-(pyridin-3-yl)-1H-pyrazole-3-carboxylate (14.1-i)

$^1$H-NMR (400 MHz, CDCl$_3$): δ 8.75-8.79 (m, 1H), 8.50-8.51 (m, 1H), 7.52-7.57 (m, 3H), 7.26 (s, 1H), 7.15 (s, 1H), 4.44 (q, J=6.92 Hz, 2H) and 1.39 (t, J=7.16 Hz, 3H). MS: 397.94 (M+H)$^+$. Yield: 16%.

Ethyl 1-(2,5-difluoro-4-(trifluoromethyl)phenyl)-5-(pyridin-3-yl)-1H-pyrazole-3-carboxylate (14.1-j)

$^1$H-NMR (400 MHz, CDCl$_3$): δ 8.66-8.73 (m, 2H), 7.80 (d, J=8.0 Hz, 1H), 7.62-7.66 (m, 1H), 7.55-7.58 (m, 1H), 7.35-7.35 (m, 1H), 7.21 (s, 1H), 4.48 (q, J=7.20 Hz, 2H) and 1.42 (t, J=7.20 Hz, 3H). MS: 398.15 (M+H)$^+$. Yield: 35%.

Ethyl 1-(4-cyano-3-fluorophenyl)-5-(pyridin-3-yl)-1H-pyrazole-3-carboxylate (14.1-k)

$^1$H-NMR (400 MHz, CDCl$_3$): δ 8.71-8.72 (m, 1H), 8.62 (s, 1H), 7.61-7.64 (m, 2H), 7.44-7.47 (m, 1H), 7.36 (d, J=7.6 Hz, 1H), 7.26 (s, 1H), 7.15-7.17 (m, 1H), 4.50 (q, J=7.16 Hz, 2H) and 1.43 (t, J=7.24 Hz, 3H). MS: 337.14 (M+H)$^+$. Yield: 26%.

Ethyl 1-(2-methyl-4-(trifluoromethoxy)phenyl)-5-(pyridin-3-yl)-1H-pyrazole-3-carboxylate (14.1-l)

$^1$H-NMR (400 MHz, CDCl$_3$): δ 8.51-8.55 (m, 2H), 8.40-8.42 (m, 1H), 7.32-7.34 (m, 1H), 7.20-7.24 (m, 1H), 7.17 (s, 1H), 6.94-6.99 (m, 2H), 4.43 (q, J=7.20 Hz, 2H), 1.98 (s, 3H) and 1.42 (t, J=7.24 Hz, 3H). MS: 392.54 (M+H)$^+$. Yield: 29%.

General Procedure for the Preparation of Compounds 14.2 (a-l):

To an ice-cold solution of compound 14.1 (a-l) (0.80-1.5 g, 1.0 eq) in EtOH was added dropwise an aqueous solution of sodium hydroxide (3.0 eq). The resulting solution was stirred at room temperature for 2-3 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 69 (a-l) as a white solid.

1-(4-Cyanophenyl)-5-(pyridin-3-yl)-1H-pyrazole-3-carboxylic Acid (14.2-a)

LC-MS: 291.27 (M+H)$^+$, 85.5%. Yield: 66%.

1-(3-Fluoro-4-(trifluoromethoxy)phenyl)-5-(pyridin-3-yl)-1H-pyrazole-3-carboxylic Acid (14.2-b)

$^1$H-NMR (400 MHz, DMSO-d$_6$): δ 13.15 (br s, 1H), 8.56-8.59 (m, 2H), 7.68-7.71 (m, 3H), 7.41-7.44 (m, 1H), 7.25-7.29 (m, 1H) and 7.17 (s, 1H). LCMS: 368.29 (M+H)+, 94.25%. Yield: 61%.

1-(4-Cyano-3-fluorophenyl)-5-(pyridin-3-yl)-1H-pyrazole-3-carboxylic Acid (14.2-c)

$^1$H-NMR (400 MHz, DMSO-d$_6$): δ 13.18 (br s, 1H), 8.59-8.91 (m, 2H), 7.67-7.68 (m, 2H), 7.41-7.44 (m, 1H), 7.25-7.27 (m, 2H) and 7.22 (s, 1H). MS: 309.11 (M+H)$^+$. Yield: 30%.

1-(4-(tert-Butyl)phenyl)-5-(pyridin-3-yl)-1H-pyrazole-3-carboxylic Acid (14.2-d)

$^1$H-NMR (400 MHz, DMSO-d$_6$): δ 13.0 (br s, 1H), 8.54-8.55 (m, 1H), 8.48 (s, 1H), 7.66-7.68 (m, 1H), 7.47-7.49 (m, 2H), 7.39-7.42 (m, 1H), 7.26-7.28 (m, 2H), 7.20 (s, 1H) and 1.29 (s, 9H). LCMS: 322.0 (M+H)$^+$, 98.33%. Yield: 30%.

1-(2-Chloro-4-(trifluoromethyl)phenyl)-5-(pyridin-3-yl)-1H-pyrazole-3-carboxylic Acid (14.2-e)

$^1$H-NMR (400 MHz, DMSO-d$_6$): δ 13.19 (br s, 1H), 8.50-8.54 (m, 2H), 8.14 (s, 1H), 8.04 (d, J=8.16 Hz, 1H), 7.96 (d, J=8.20 Hz, 1H), 7.62-7.63 (m, 1H), 7.37-7.43 (m, 1H) and 7.33 (s, 1H). LCMS: 368.12 (M+H)$^+$, 97.38%. Yield: 81%.

1-(2,6-Dichloro-4-(trifluoromethyl)phenyl)-5-(pyridin-3-yl)-1H-pyrazole-3-carboxylic Acid (14.2-f)

$^1$H-NMR (400 MHz, DMSO-d$_6$): δ 13.33 (br s, 1H), 8.57 (d, J=1.6 Hz, 1H), 8.52 (s, 1H), 8.28 (s, 2H), 7.60-7.62 (m, 1H) and 7.41-7.44 (m, 2H). LCMS: 402.08 (M+H)$^+$, 96.28%. Yield: 84%.

5-(Pyridin-3-yl)-1-(4-(trifluoromethoxy)phenyl)-1H-pyrazole-3-carboxylic Acid (14.2-g)

$^1$H-NMR (400 MHz, DMSO-d$_6$): δ 13.09 (br s, 1H), 8.52-8.57 (m, 2H), 7.66-7.70 (m, 1H), 7.40-7.43 (m, 5H) and 7.23 (s, 1H). LCMS: 350.27 (M+H)$^+$, 91.79%. Yield: 63%.

1-(4-Fluoro-3-(trifluoromethyl)phenyl)-5-(pyridin-3-yl)-1H-pyrazole-3-carboxylic Acid (14.2-h)

$^1$H-NMR (400 MHz, DMSO-d$_6$): δ 13.15 (br s, 1H), 8.57-8.58 (m, 2H), 7.84-7.86 (m, 1H), 7.60-7.69 (m, 3H), 7.40-7.45 (m, 1H) and 7.24 (s, 1H). LCMS: 352.24 (M+H)+, 95.84%. Yield: 73%.

1-(2,3-Difluoro-4-(trifluoromethyl)phenyl)-5-(pyridin-3-yl)-1H-pyrazole-3-carboxylic Acid (14.2-i)

$^1$H-NMR (400 MHz, DMSO-d$_6$): δ 13.30 (br s, 1H), 8.60-8.61 (m, 2H), 7.80-7.83 (m, 1H), 7.63-7.73 (m, 2H), 7.41-7.44 (m, 1H) and 7.25 (s, 1H). MS: 370.08 (M+H)$^+$, Yield: 86%.

1-(2,5-Difluoro-4-(trifluoromethyl)phenyl)-5-(pyridin-3-yl)-1H-pyrazole-3-carboxylic Acid (14.2-j)

$^1$H-NMR (400 MHz, DMSO-d$_6$): δ 13.34 (br s, 1H), 8.60 (s, 2H), 7.99-8.10 (m, 2H), 7.72 (d, J=7.0 Hz, 1H), 7.43 (s, 1H) and 7.33 (s, 1H). LCMS: 370.27 (M+H)+, 97.55%. Yield: 68%.

1-(4-Cyano-3-fluorophenyl)-5-(pyridin-3-yl)-1H-pyrazole-3-carboxylic Acid (14.2-k)

$^1$H-NMR (400 MHz, DMSO-d$_6$): δ 13.18 (br s, 1H), 8.59 (s, 2H), 8.01-8.05 (m, 1H), 7.81 (d, J=8.32 Hz, 1H), 7.67-7.70 (m, 2H), 7.25-7.27 (m, 1H) and 7.22 (s, 1H). MS: 309.11 (M+H)$^+$. Yield: 30%.

1-(2-Methyl-4-(trifluoromethoxy)phenyl)-5-(pyridin-3-yl)-1H-pyrazole-3-carboxylic Acid (14.2-l)

$^1$H-NMR (400 MHz, DMSO-d$_6$): δ 13.08 (br s, 1H), 8.51-8.57 (m, 1H), 8.47 (s, 1H), 7.55-7.62 (m, 2H), 7.44 (s, 1H), 7.34-7.38 (m, 2H), 7.29 (s, 1H) and 1.93 (s, 3H). LCMS: 364.26 (M+H)$^+$, 92.06%. Yield: 75%.

General Procedure for the Preparation of Final Compounds (General Structure 14.3)

The final compounds were prepared following the general method N. To an ice-cold solution of carboxylic acids 14.2 (a-l) (125-150 mg), in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The final compounds were purified via prep-HPLC.

Please refer to Table 6.4 for individual yields and the analytical data of the final compounds.

TABLE 6.4

Tabulated data of the final compounds including the individual yields

| No. | Structure | Amine intermediate used | Yield (%) | LCMS | NMR data (DMSO-d$_6$, 400 MHz) |
|---|---|---|---|---|---|
| 212 | 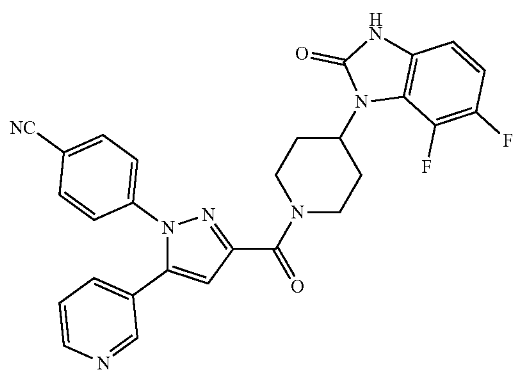 [SMILES: N#Cc1ccc(-n2nc(C(=O)N3CCC(n4c(=O)[nH]c5ccc(F)c(F)c54)CC3)cc2-c2cccnc2)cc1] | 16 | 15 | 524.35 (M − H)$^+$, 99.78% | δ 11.15 (br s, 1H), 8.60 (d, J = 1.12 Hz, 1H), 8.56 ((d, J = 1.68 Hz, 1H), 7.93 (d, J = 8.52 Hz, 2H), 7.68 ((d, J = 8.0 Hz, 1H), 7.54 ((d, J = 8.52 Hz, 2H), 7.41-7.45 (m, 1H), 7.15 (s, 1H), 7.00-7.07 (m, 1H), 6.77-6.80 (m, 1H), 4.80-4.83 (m, 1H), 4.63-4.71 (m, 2H), 3.32 (s, 1H), 2.93-2.99 (m, 1H), 2.07-2.17 (m, 2H) and 1.85-1.88 (m, 2H) |
| 213 | 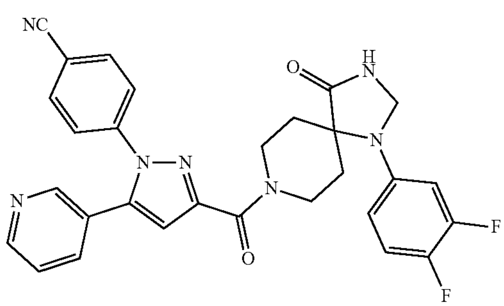 [SMILES: N#Cc1ccc(-n2nc(C(=O)N3CCC4(CC3)C(=O)NCN4c3ccc(F)c(F)c3)cc2-c2cccnc2)cc1] | 2 | 13 | 538.35 (M − H)$^+$, 98.24% | δ 8.89 (s, 1H), 8.56-8.61 (m, 2H), 7.91 (t, J = 8.52 Hz, 1H), 7.73 (d, J = 8.0 Hz, 1H), 7.67 (d, J = 8.12 Hz, 1H), 7.51-7.54 (m, 2H), 7.42-7.45 (m, 1H), 7.26-7.31 (m, 1H), 7.15 (s, 1H), 6.74-6.79 (m, 1H), 6.57-6.59 (m, 1H), 4.59 (s, 2H), 4.47-4.52 (m, 2H), 3.84-3.90 (m, 1H), 3.49-3.55 (m, 1H), 2.35-2.39 (m, 2H) and 1.73-1.81 (m, 2H) |
| 214 | 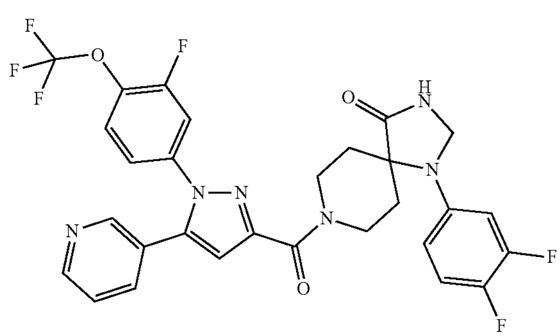 [SMILES: O=C(c1cc(-c2cccnc2)n(-c2ccc(OC(F)(F)F)c(F)c2)n1)N1CCC2(CC1)C(=O)NCN2c1ccc(F)c(F)c1] | 2 | 31 | 615.38 (M − H)$^+$, 99.36% | δ 8.88 (s, 1H), 8.58-8.61 (m, 2H), 7.63-7.72 (m, 3H), 7.47-7.47 (m, 1H), 7.24-7.34 (m, 2H), 7.15 (s, 1H), 6.74-6.79 (m, 1H), 6.57-6.59 (m, 1H), 4.60 (s, 2H), 4.47-4.52 (m, 2H), 3.83-3.89 (m, 1H), 3.45-3.55 (m, 1H), 2.33-2.44 (m, 2H) and 1.73-1.77 (m, 2H) |

TABLE 6.4-continued

Tabulated data of the final compounds including the individual yields

| No. | Structure | Amine intermediate used | Yield (%) | LCMS | NMR data (DMSO-d$_6$, 400 MHz) |
|---|---|---|---|---|---|
| 215 | 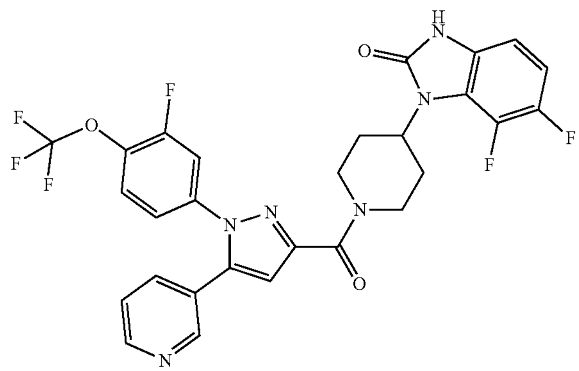 [SMILES: O=C(c1cc(-c2cccnc2)n(-c2ccc(OC(F)(F)F)c(F)c2)n1)N1CCC(n2c(=O)[nH]c3ccc(F)c(F)c32)CC1] | 16 | 22 | 603.42 (M + H)$^+$, 96.04% | δ 11.25 (br s, 1H), 8.57-8.59 (m, 2H), 7.68-7.72 (m, 3H), 7.42-7.45 (m, 1H), 7.28 (d, J = 8.6 Hz, 1H), 7.14 (s, 1H), 7.00-7.04 (m, 1H), 6.77-6.80 (m, 1H), 4.82-4.85 (m, 1H), 4.67-4.71 (m, 2H), 3.32 (s, 1H), 2.92-2.98 (m, 1H), 2.11-2.17 (m, 2H) and 1.85-1.92 (m, 2H) |
| 216 | 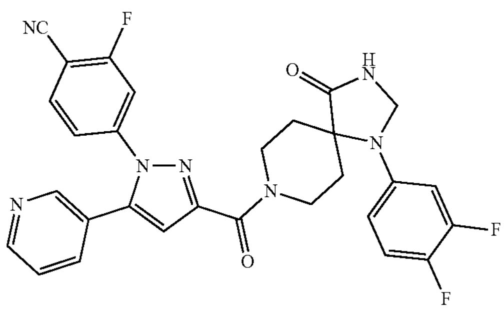 [SMILES: N#Cc1ccc(-n2nc(C(=O)N3CCC4(CC3)C(=O)NCN4c3ccc(F)c(F)c3)cc2-c2cccnc2)cc1F] | 2 | 6 | 556.41 (M − H)$^+$, 99.04% | δ 8.89 (s, 1H), 8.61-8.63 (m, 2H), 7.97 (d, J = 7.92 Hz, 1H), 7.71 (d, J = 7.92 Hz, 1H), 7.62-7.65 (m, 1H), 7.43-7.47 (m, 1H), 7.28-7.33 (m, 2H), 7.17 (s, 1H), 6.74-6.78 (m, 1H), 6.57-6.59 (m, 1H), 4.60 (s, 2H), 4.45-4.49 (m, 2H), 3.83-3.89 (m, 1H), 3.50-3.55 (m, 1H), 2.36-2.43 (m, 2H) and 1.73-1.82 (m, 2H) |
| 217 | 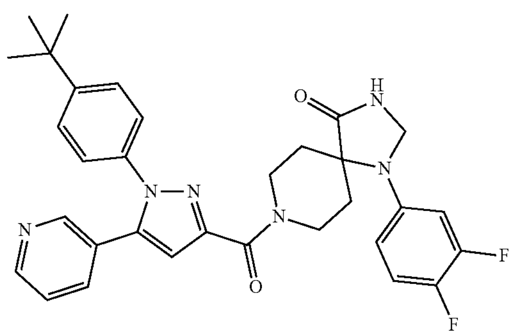 [SMILES: CC(C)(C)c1ccc(-n2nc(C(=O)N3CCC4(CC3)C(=O)NCN4c3ccc(F)c(F)c3)cc2-c2cccnc2)cc1] | 2 | 27 | 571.51 (M + H)$^+$, 99.10% | δ 8.87 (s, 1H), 8.51-8.57 (m, 2H), 7.70 (d, J = 8.0 Hz, 1H), 7.43-7.46 (m, 3H), 7.20-7.26 (m, 3H), 7.11 (s, 1H), 6.74-6.78 (m, 1H), 6.56-6.59 (m, 1H), 4.59 (s, 3H), 4.47-4.49 (m, 1H), 3.78-3.82 (m, 1H), 3.48-3.54 (m, 1H), 2.38-2.40 (m, 2H), 1.72-1.80 (m, 2H) and 1.27 (s, 9H) |
| 218 | 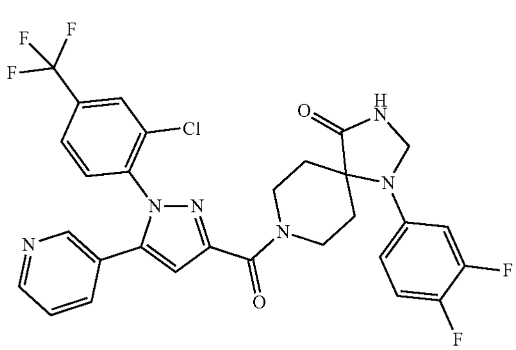 [SMILES: O=C(c1cc(-c2cccnc2)n(-c2ccc(C(F)(F)F)cc2Cl)n1)N1CCC2(CC1)C(=O)NCN2c1ccc(F)c(F)c1] | 2 | 40 | 617.47 (M + H)$^+$, 99.59% | δ 8.87 (s, 1H), 8.54 (d, J = 4.44 Hz, 1H), 8.50 (s, 1H), 8.13 (s, 1H), 7.96-7.98 (m, 1H), 7.90-7.92 (m, 1H), 7.61-7.63 (m, 1H), 7.38-7.41 (m, 1H), 7.23-7.27 (m, 2H), 6.71-6.76 (m, 1H), 6.54-6.56 (m, 1H), 4.58 (s, 2H), 4.47-4.50 (m, 2H), 3.81-3.87 (m, 1H), 3.49-3.54 (m, 1H), 2.32-2.40 (m, 2H) and 1.70-1.81 (m, 2H) |

TABLE 6.4-continued

Tabulated data of the final compounds including the individual yields

| No. | Structure | Amine intermediate used | Yield (%) | LCMS | NMR data (DMSO-$d_6$, 400 MHz) |
|---|---|---|---|---|---|
| 219 | 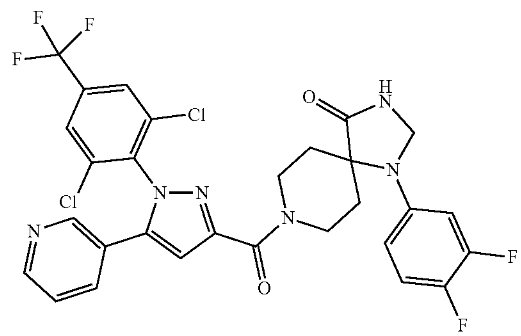 [SMILES: O=C(c1cc(-c2cccnc2)n(-c2c(Cl)cc(C(F)(F)F)cc2Cl)n1)N1CCC2(CC1)C(=O)NCN2c1ccc(F)c(F)c1] | 2 | 42 | 649.35 (M − H)$^+$, 98.81% | δ 8.87 (s, 1H), 8.57 (d, J = 4.16 Hz, 1H), 8.52 (s, 1H), 8.24 (d, J = 7.56 Hz, 2H), 7.60-7.62 (m, 1H), 7.41-7.44 (m, 1H), 7.28 (s, 1H), 7.21-7.25 (m, 1H), 6.71-6.75 (m, 1H), 6.53-6.55 (m, 1H), 4.58 (s, 2H), 4.46-4.49 (m, 1H), 4.46-4.54 (m, 1H), 3.80-3.86 (m, 1H), 3.49-3.54 (m, 1H), 2.32-2.40 (m, 2H) and 1.69-1.81 (m, 2H) |
| 220 | 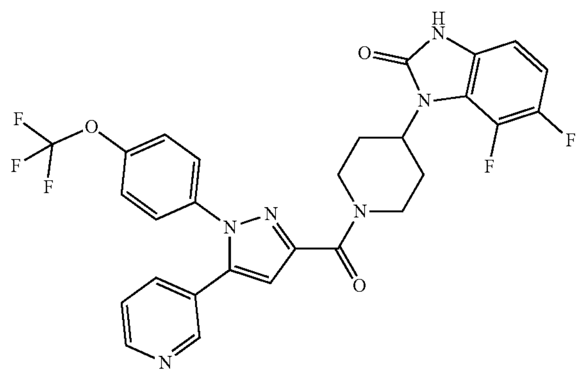 [SMILES: O=C(c1cc(-c2cccnc2)n(-c2ccc(OC(F)(F)F)cc2)n1)N1CCC(n2c(=O)[nH]c3ccc(F)c(F)c32)CC1] | 16 | 58 | 583.39 (M − H)$^+$, 99.73% | δ 11.18 (br s, 1H), 8.56 (d, J = 4.08 Hz, 1H), 8.54 (s, 1H), 7.67 (d, J = 7.84 Hz, 1H), 7.40-7.52 (m, 5H), 7.13 (s, 1H), 6.99-7.06 (m, 1H), 6.77-6.80 (m, 1H), 4.85-4.89 (m, 1H), 4.65-4.71 (m, 2H), 3.31 (s, 1H), 2.92-2.98 (m, 1H), 2.07-2.17 (m, 2H) and 1.84-1.91 (m, 2H) |
| 221 | 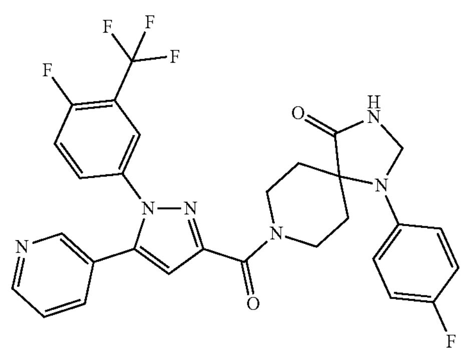 [SMILES: O=C(c1cc(-c2cccnc2)n(-c2ccc(F)c(C(F)(F)F)c2)n1)N1CCC2(CC1)C(=O)NCN2c1ccc(F)cc1] | 1 | 23 | 581.12 (M − H)$^+$, 98.65% | δ 8.80 (s, 1H), 8.57 (s, 2H), 7.81 (s, 1H), 7.57-7.68 (m, 3H), 7.42 (s, 1H), 7.09-7.13 (m, 3H), 6.86-6.91 (m, 2H), 4.59 (s, 2H), 4.45 (s, 2H), 3.86-3.89 (m, 1H), 3.50-3.56 (m, 1H), 2.23-2.32 (m, 2H) and 1.72-1.82 (m, 2H) |
| 222 | 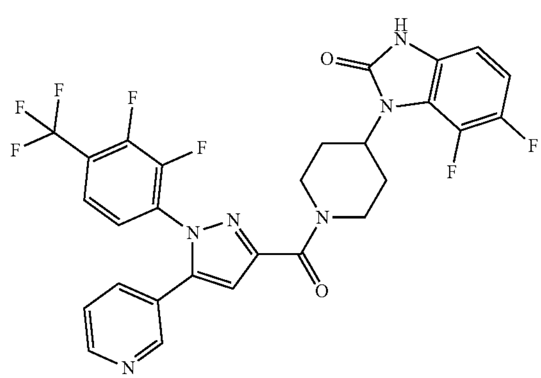 [SMILES: O=C(c1cc(-c2cccnc2)n(-c2ccc(C(F)(F)F)c(F)c2F)n1)N1CCC(n2c(=O)[nH]c3ccc(F)c(F)c32)CC1] | 16 | 28 | 603.10 (M − H)$^+$, 99.06% | δ 11.22 (br s, 1H), 8.59-8.63, (m, 2H), 7.75-7.81 (m, 2H), 7.64 (t, J = 7.6 Hz, 1H), 7.41-7.44 (m, 1H), 7.24 (s, 1H), 7.00-7.07 (m, 1H), 6.77-6.80 (m, 1H), 4.85-4.89 (m, 1H), 4.65-4.71 (m, 2H), 3.31 (s, 1H), 2.92-2.98 (m, 1H), 2.07-2.17 (m, 2H) and 1.84-1.91 (m, 2H) |

TABLE 6.4-continued

Tabulated data of the final compounds including the individual yields

| No. | Structure | Amine intermediate used | Yield (%) | LCMS | NMR data (DMSO-d$_6$, 400 MHz) |
|---|---|---|---|---|---|
| 223 | 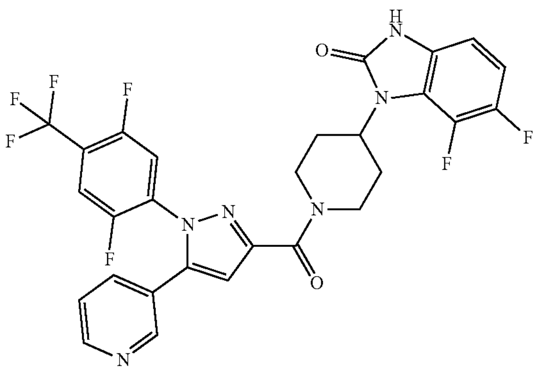 [SMILES: O=C(c1cc(-c2cccnc2)n(-c2cc(F)c(C(F)(F)F)cc2F)n1)N1CCC(n2c(=O)[nH]c3ccc(F)c(F)c32)CC1] | 16 | 34 | 603.10 (M − H)$^+$, 98.00% | δ 11 24 (br s, 1H), 8.59-8.62 (m, 2H), 8.07-8.11 (m, 1H), 7.99-8.03 (m, 1H), 7.74 (t, J = 8.0 Hz, 1H), 7.42-7.45 (m, 1H), 7.22 (s, 1H), 7.00-7.07 (m, 1H), 6.77-6.80 (m, 1H), 4.65-4.77 (m, 3H), 3.32-3.37 (m, 1H), 2.93-2.99 (m, 1H), 2.12-2.20 (m, 2H) and 1.84-1.92 (m, 2H) |
| 224 | 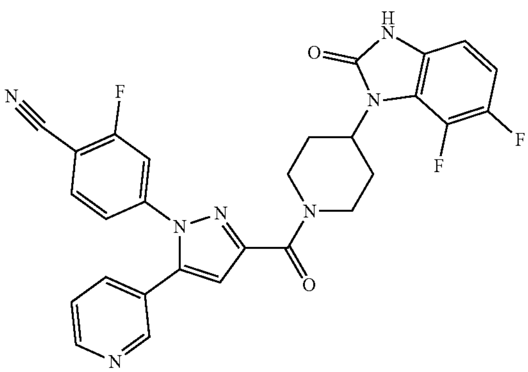 [SMILES: N#Cc1ccc(-n2nc(C(=O)N3CCC(n4c(=O)[nH]c5ccc(F)c(F)c54)CC3)cc2-c2cccnc2)cc1F] | 16 | 26 | 544.34 (M + H)$^+$, 97.34% | δ 10.60 (br s, 1H), 8.61-8.62 (m, 2H), 7.99-8.02 (m, 1H), 7.71-7.33 (m, 1H), 7.65-7.68 (m, 1H), 7.43-7.46 (m, 1H), 7.32-7.34 (m, 1H), 7.17 (s, 1H), 7.00-7.07 (m, 1H), 6.76-6.79 (m, 1H), 4.61-4.70 (m, 2H), 3.32-3.33 (m, 1H), 2.93-2.99 (m, 1H), 2.07-2.21 (m, 2H) and 1.85-1.92 (m, 2H) |
| 225 | 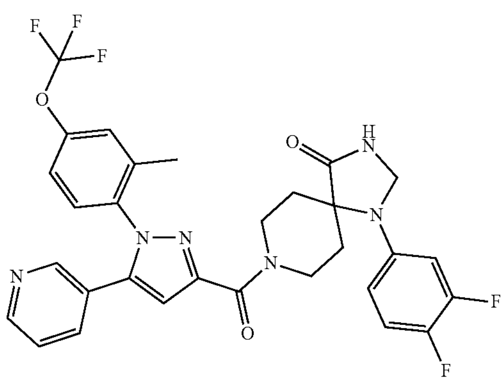 [SMILES: Cc1cc(OC(F)(F)F)ccc1-n1nc(C(=O)N2CCC3(CC2)C(=O)NCN3c2ccc(F)c(F)c2)cc1-c1cccnc1] | 2 | 19 | 613.18 (M + H)$^+$, 96.25% | δ 8.87 (s, 1H), 8.51-8.53 (m, 1H), 8.46-8.47 (m, 1H), 7.59 (d, J = 6.4 Hz, 1H), 7.44-7.49 (m, 2H), 7.36-7.39 (m, 1H), 7.23-7.30 (m, 2H), 7.19 (s, 1H), 6.70-6.75 (m, 1H), 6.54-6.56 (m, 1H), 4.47-4.59 (m, 4H), 3.81-3.86 (m, 1H), 3.48-3.54 (m, 1H), 2.32-2.36 (m, 2H), 2.00 (s, 3H) and 1.71-1.80 (m, 2H) |
| 226 | 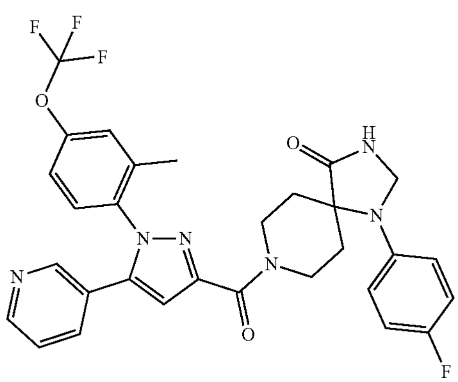 [SMILES: Cc1cc(OC(F)(F)F)ccc1-n1nc(C(=O)N2CCC3(CC2)C(=O)NCN3c2ccc(F)cc2)cc1-c1cccnc1] | 1 | 10 | 595.38 (M + H)$^+$, 93.90% | δ 8.79 (s, 1H), 8.51-8.52 (m, 1H), 8.46-8.47 (m, 1H), 7.59 (d, J = 6.4 Hz, 1H), 7.47 (d, J = 8.8 Hz, 1H), 7.44 (s, 1H), 7.35-7.38 (m, 1H), 7.29-7.31 (m, 1H), 7.18 (s, 1H), 7.05-7.09 (m, 2H), 6.82-6.85 (m, 2H), 4.57-4.58 (m, 2H), 4.42-4.48 (m, 2H), 3.82-3.85 (m, 1H), 3.50-3.55 (m, 1H), 2.18-2.22 (m, 2H), 2.00 (s, 3H) and 1.73-1.78 (m, 2H) |

TABLE 6.4-continued

Tabulated data of the final compounds including the individual yields

| No. | Structure | Amine intermediate used | Yield (%) | LCMS | NMR data (DMSO-$d_6$, 400 MHz) |
|---|---|---|---|---|---|
| 227 | 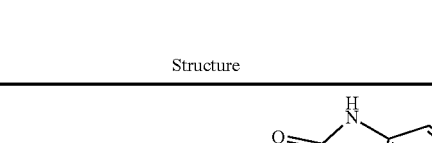 | 16 | 38 | 599.17 (M + H)+, 96.76% | δ 11.24 (br s, 1H), 8.47-8.53 (m, 2H), 7.61 (d, J = 8.0 Hz, 1H), 7.51 (d, J = 6.8 Hz, 1H), 7.44 (s, 1H), 7.36 (t, J = 8.0 Hz, 1H), 7.30-7.32 (m, 1H), 7.18 (s, 1H), 6.99-7.06 (m, 1H), 6.76-6.79 (m, 1H), 4.81-4.84 (m, 1H), 4.61-4.68 (m, 2H), 3.29-3.32 (m, 1H), 2.91-2.97 (m, 1H), 2.07-2.20 (m, 2H) and 1.82-1.91 (m, 2H) |

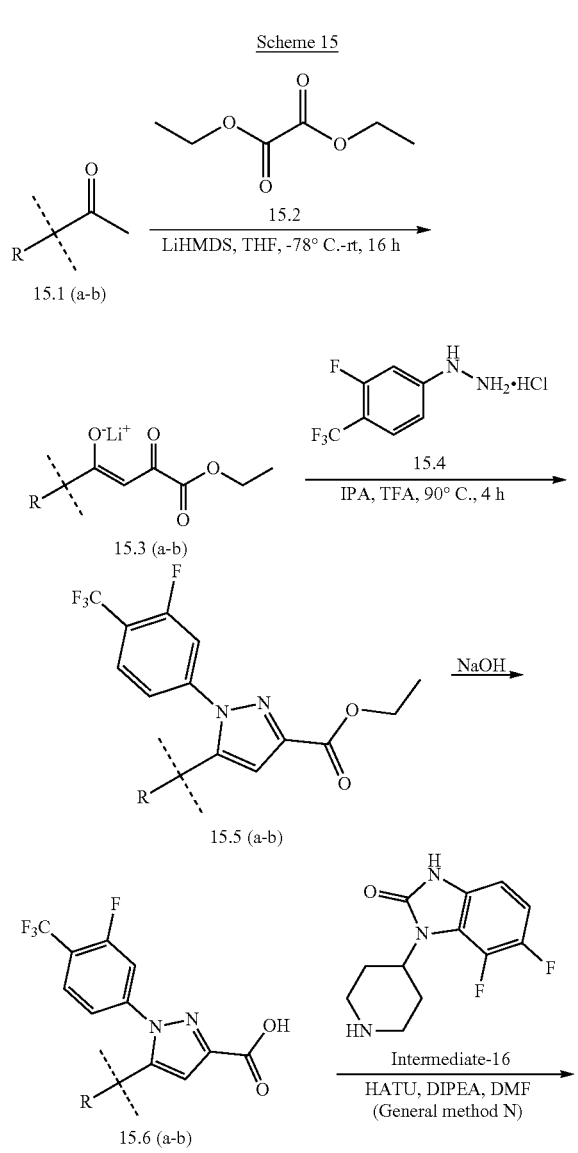

Scheme 15

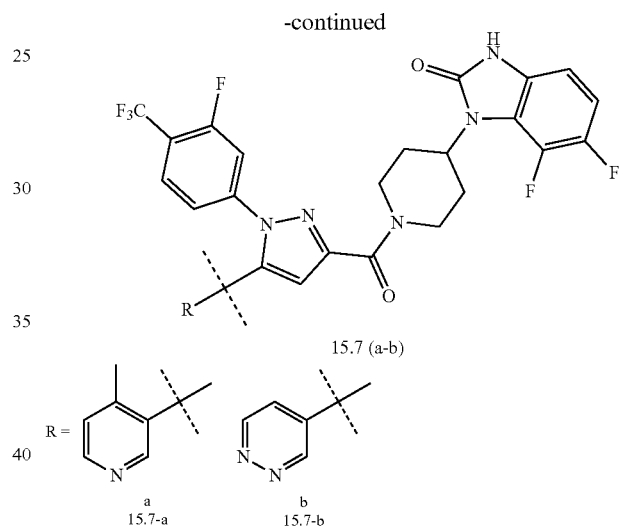

General Procedure for the Preparation of Compounds 15.3 (a-b):

A solution of compound 15.1 (a-b) (2.5 g) in di-ethyl ether was cooled to −78° C. followed by addition of LiHMDS (1.10 eq). The resulting reaction mixture was stirred at −78° C. for 45 min followed by dropwise addition of diethyl oxalate 15.2 (1.20 eq) in about 30 min. The reaction mixture was then left to stir at room temperature for 16 h. After completion of the reaction (TLC and MS monitoring), the solution was then cooled 0° C. and the resulting precipitate was filtered to get the desired product 15.3 (a-b) as an off-white solid, which was carried forward to the next step without purification.

4-Ethoxy-1-(4-methylpyridin-3-yl)-3,4-dioxobut-1-en-1-olate Lithium Salt (15.3-a)

$^1$H-NMR (400 MHz, DMSO-$d_6$): δ 8.44 (s, 1H), 8.38-8.39 (m, 1H), 7.21-7.22 (m, 1H), 5.93 (s, 1H), 4.10 (q, J=7.16 Hz, 2H), 2.36 (s, 3H) and 1.20 (t, J=7.6 Hz, 3H). MS: 236.0 (M+H)+. Yield: quantitative.

4-Ethoxy-3,4-dioxo-1-(pyridazin-4-yl)but-1-en-1-olate Lithium Salt (15.3-b)

$^1$H-NMR (400 MHz, DMSO-d$_6$): δ 9.48-9.56 (m, 2H), 9.20-9.21 (m, 1H), 6.46 (s, 1H), 4.10 (q, J=7.20 Hz, 2H) and 1.21 (t, J=7.6 Hz, 3H). MS: 223.04 (M+H)$^+$. Yield: 76%.

General Procedure for the Preparation of Compounds 15.5 (a-b):

To an ice-cold solution of compound 15.3 (a-b) (2.50-3.0 g, 1.0 eq) in IPA was added (3-fluoro-4-(trifluoromethyl)phenyl)hydrazine hydrochloride 15.4 (1.10 eq) and TFA (2.0 eq). The resulting reaction mixture was warmed to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 15.5 (a-b).

Ethyl 1-(3-fluoro-4-(trifluoromethyl)phenyl)-5-(4-methylpyridin-3-yl)-1H-pyrazole-3-carboxylate (15.5-a)

$^1$H-NMR (400 MHz, CDCl$_3$): δ 8.60-8.66 (m, 2H), 7.53-7.55 (m, 1H), 7.46-7.47 (m, 1H), 7.21-7.28 (m, 1H), 7.08 (s, 1H), 6.99-7.05 (m, 1H), 4.45 (q, J=7.2 Hz, 2H), 2.15 (s, 3H) and 1.42 (t, J=7.6 Hz, 3H). MS: 394.33 (M+H)$^+$. Yield: 22%.

Ethyl 1-(3-fluoro-4-(trifluoromethyl)phenyl)-5-(pyridazin-4-yl)-1H-pyrazole-3-carboxylate (15.5-b)

$^1$H-NMR (400 MHz, CDCl$_3$): δ 7.61-7.71 (m, 2H), 7.41-7.55 (m, 4H), 7.11 (s, 1H), 4.46 (q, J=7.16 Hz, 2H) and 1.42 (t, J=7.24 Hz, 3H). MS: 381.25 (M+H)$^+$. Yield: 27%.

General Procedure for the Preparation of Compounds 15.6(a-b):

To an ice-cold solution of compound 15.5 (a-b), (1.0-1.2 g) (1.0 eq) in EtOH was added dropwise an aqueous solution of sodium hydroxide (3.0 eq). The resulting solution was stirred at room temperature for 2-3 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 15.6 (a-b) as a white solid.

1-(3-fluoro-4-(trifluoromethyl)phenyl)-5-(4-methylpyridin-3-yl)-1H-pyrazole-3-carboxylic Acid (15.6-a)

$^1$H-NMR (400 MHz, DMSO-d$_6$): δ 13.20 (br s, 1H), 8.50 (d, J=4.12 Hz, 1H), 8.39 (s, 1H), 7.82 (t, J=7.88 Hz, 1H), 7.51-7.53 (m, 1H), 7.35-7.37 (m, 1H), 7.24-7.26 (m, 1H), 7.17 (s, 1H) and 2.08 (s, 3H). LCMS: 366.22 (M+H)$^+$, 99.72%. Yield: 60%.

1-(3-fluoro-4-(trifluoromethyl)phenyl)-5-(pyridazin-4-yl)-1H-pyrazole-3-carboxylic Acid (15.6-b)

$^1$H-NMR (400 MHz, DMSO-d$_6$): δ 13.20 (br s, 1H), 9.24-9.27 (m, 2H), 7.89-7.90 (m, 1H), 7.75-7.77 (m, 1H), 7.53-7.54 (m, 1H) and 7.40-7.46 (m, 2H). LCMS: 353.19 (M+H)+, 93.39%. Yield: 70%.

General Procedure for the Preparation of Final Compounds (15.7-a and 15.7-b):

The final compounds were prepared following the general method N. To an ice-cold solution of carboxylic acids 74 (a-b), (125 mg, 1.0 eq), in DMF (2.0 mL) was added DIPEA (3.0 eq) and HATU (1.50 eq). The resulting mixture was stirred under nitrogen atmosphere at 0° C. for 15 min followed by addition of 6,7-difluoro-1-(piperidin-4-yl)-1,3-dihydro-2H-benzo[d]imidazol-2-one Intermediate 16 (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC.

6,7-difluoro-1-(1-(1-(3-fluoro-4-(trifluoromethyl)phenyl)-5-(4-methylpyridin-3-yl)-1H-pyrazole-3-carbonyl)piperidin-4-yl)-1,3-dihydro-2H-benzo[d]imidazol-2-one (15.7-a)

$^1$H-NMR (400 MHz, DMSO-d$_6$): δ 11.25 (br s, 1H), 8.50-8.52 (m, 1H), 8.42 (s, 1H), 7.80 (t, J=8.12 Hz, 1H), 7.51-7.53 (m, 1H), 7.37 (d, J=4.92 Hz, 1H), 7.22 (d, J=8.92 Hz, 1H), 7.07 (s, 1H), 7.00-7.05 (m, 1H), 6.77-6.80 (m, 1H), 4.81-4.84 (m, 1H), 4.64-4.72 (m, 2H), 3.38-3.41 (m, 1H), 2.94-3.00 (m, 1H), 2.10-2.22 (m, 5H), and 1.87-1.90 (m, 2H). LCMS: 601.17 (M+H)$^+$, 99.94%. Yield: 24%.

6,7-difluoro-1-(1-(1-(3-fluoro-4-(trifluoromethyl)phenyl)-5-(pyridazin-4-yl)-1H-pyrazole-3-carbonyl)piperidin-4-yl)-1,3-dihydro-2H-benzo[d]imidazol-2-one (15.7-b)

$^1$H-NMR (400 MHz, DMSO-d$_6$): δ 11.25 (br s, 1H), 9.26-9.29 (m, 2H), 7.89-7.93 (m, 1H), 7.75-7.78 (m, 1H), 7.57 (d, J=4.04 Hz, 1H), 7.42-7.44 (m, 2H), 7.00-7.06 (m, 1H), 6.78-6.79 (m, 1H), 4.67-4.77 (m, 3H), 3.32 (s, 1H), 2.95-3.00 (m, 1H), 2.08-2.15 (m, 2H) and 1.85-1.92 (m, 2H). LCMS: 588.26 (M+H)$^+$, 99.30%. Yield: 32%.

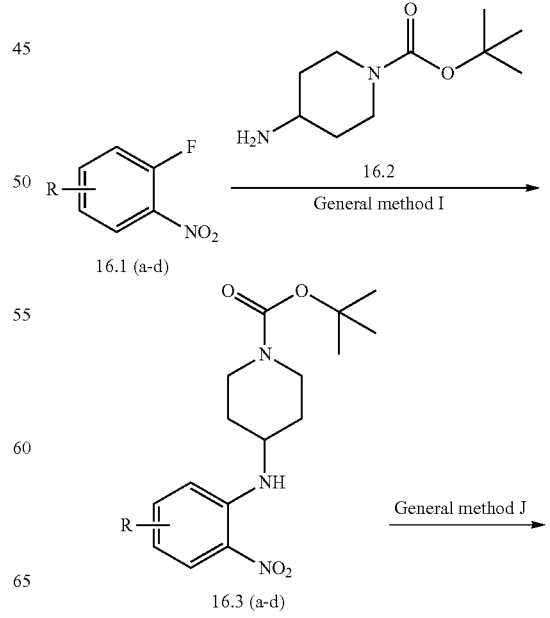

Scheme 16

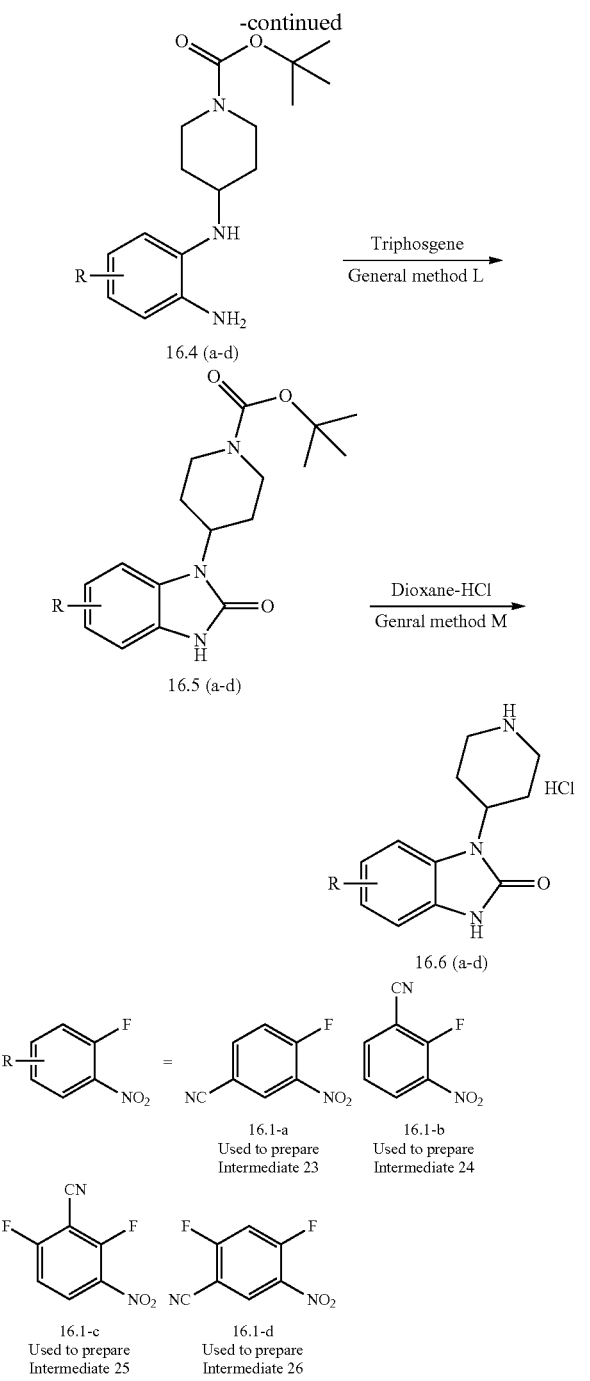

General Procedure for the Preparation of 16.6 (a-d):

General Method I:

To an ice-cold solution of tert-butyl 4-aminopiperidine-1-carboxylate 16.2 (1.0-2.5 g, 1.0 eq) in DMF was added DIPEA (1.5 eq) and respective nitro compounds 16.1 (a-d) (1.0 eq). The resulting reaction mixture was stirred at RT for 2-3 h. After completion of the reaction (TLC monitoring), the reaction mass was diluted with ice-cold water and extracted with EtOAc (3 times). The combined organics were washed with brine, dried over anhydrous $Na_2SO_4$, filtered and concentrated. The crude was purified over silica gel (100-200 M, 10-15% EtOAc-hexane) to get the desired product 16.3 (a-d).

tert-Butyl 4-((4-cyano-2-nitrophenyl)amino)piperidine-1-carboxylate (16.3-a)

$^1$H-NMR (400 MHz, CDCl$_3$): δ 8.42 (d, J=6.8 Hz, 1H), 7.58 (dd, J=2.0 & 8.8 Hz, 1H), 6.92 (d, J=8.8 Hz, 1H), 4.04-4.06 (m, 2H), 3.67-3.74 (m, 1H), 3.01-3.06 (m, 2H), 2.04-2.07 (m, 2H), 1.59-1.63 (m, 3H) and 1.47 (s, 9H). LCMS: 345.53 (M–H)$^+$, 92.45%. Yield: 57%.

tert-Butyl 4-((2-cyano-6-nitrophenyl)amino)piperidine-1-carboxylate (16.3-b)

$^1$H-NMR (400 MHz, CDCl$_3$): δ 8.37-8.40 (m, 1H), 7.73-7.75 (m, 1H), 6.72-6.76 (m, 1H), 4.47-4.54 (m, 1H), 4.04-4.06 (m, 2H), 3.01-3.03 (m, 2H), 2.12-2.15 (m, 2H), 1.50-1.56 (m, 3H) and 1.44 (s, 9H). LCMS: 345.28 (M–H)$^+$, 95.79%. Yield: 77%.

tert-Butyl 4-((2-cyano-3-fluoro-6-nitrophenyl)amino)piperidine-1-carboxylate (16.3-c)

$^1$H-NMR (400 MHz, CDCl$_3$): δ 8.81-8.83 (m, 1H), 8.44-8.48 (m, 1H), 6.49-6.54 (m, 1H), 4.53-4.60 (m, 1H), 4.07-4.10 (m, 2H), 3.00-3.06 (m, 2H), 2.14-2.17 (m, 2H), 1.62-1.67 (m, 2H) and 1.40 (s, 9H). LCMS: 363.32 (M–H)$^+$, 97.61%. Yield: 59%.

tert-Butyl 4-((4-cyano-5-fluoro-2-nitrophenyl)amino)piperidine-1-carboxylate (16.3-d)

$^1$H-NMR (400 MHz, CDCl$_3$): δ 8.51-8.56 (m, 2H), 8.60-8.63 (m, 1H), 4.04-4.07 (m, 2H), 3.57-3.61 (m, 1H), 3.01-3.07 (m, 2H), 2.03-2.06 (m, 2H), 1.56-1.60 (m, 2H) and 1.47 (s, 9H). MS: 363.37 (M–H)$^+$. Yield: 77%.

General Procedure for the Preparation of 16.4 (a-d):

General Method J:

To a solution of compound 16.3 (a-d) (1.0-2.5 g, 1.0 eq) in EtOAc were added Pd—C (w/w, 10 mol %) and the resulting solution was stirred under hydrogen atmosphere (1 atm) at ambient temperature for 16 h. The reaction mixture was filtered through diatomaceous earth (Celite) bed and the filtrate was concentrated under reduced pressure to get the desired product 16.4 (a-d).

tert-Butyl 4-((2-amino-4-cyanophenyl)amino)piperidine-1-carboxylate (16.4-a)

$^1$H-NMR (400 MHz, DMSO-d$_6$): δ 6.89 (d, J=6.8 Hz, 1H), 6.77 (s, 1H), 6.54-6.56 (m, 1H), 5.11-5.12 (m, 1H), 4.98 (br s, 2H), 3.89-3.91 (m, 2H), 3.52 (br s, 1H), 2.89 (s, 2H), 1.88-1.90 (m, 2H) and 1.17-1.29 (m, 11H). MS: 315.18 (M–H)$^+$. Yield: 78%.

tert-Butyl 4-((2-amino-6-cyanophenyl)amino)piperidine-1-carboxylate (16.4-b)

$^1$H-NMR (400 MHz, DMSO-d$_6$): δ 6.95-6.96 (m, 1H), 6.88-6.91 (m, 2H), 4.11-4.12 (m, 2H), 3.48-3.49 (m, 1H), 3.34-3.37 (m, 1H), 2.73-2.79 (m, 2H), 1.89-1.92 (m, 2H), 1.59-1.61 (m, 2H) and 1.45-1.49 (m, 11H). MS: 315.55 (M–H)$^+$. Yield: 40%.

tert-Butyl 4-((6-amino-2-cyano-3-fluorophenyl)amino)piperidine-1-carboxylate (16.4-c)

$^1$H-NMR (400 MHz, DMSO-d$_6$): δ 6.81-6.84 (m, 1H), 6.54-6.58 (m, 1H), 4.09-4.14 (m, 2H), 3.78-3.82 (m, 1H), 3.66-3.68 (m, 1H), 3.44-3.48 (m, 2H), 2.80-2.85 (m, 2H), 1.95-1.98 (m, 2H) and 1.43-1.48 (m, 11H). LCMS: 333.56 (M–H)⁺, 82.07%. Yield: 88%.

tert-Butyl 4-((2-amino-4-cyano-5-fluorophenyl)amino)piperidine-1-carboxylate (16.4-d)

¹H-NMR (400 MHz, CDCl₃): δ 6.92-6.94 (m, 1H), 6.30-6.36 (m, 1H), 4.39-4.41 (br s, 1H), 4.06-4.10 (m, 2H), 3.38-3.40 (m, 2H), 2.91-2.97 (m, 2H), 2.00-2.03 (m, 2H) and 1.48 (s, 12H). MS: 333.56 (M–H)⁺. Yield: 62%.

General Procedure for the Preparation of 16.5 (a-d): General Method L:

To an ice-cold solution of compound 16.4 (a-d) (0.50-1.50 g, 1.0 eq) in THF was added Et₃N (2.0 eq) and triphosgene (1.5 eq). The resulting reaction mixture was stirred at RT for 4 h. After completion of the reaction (TLC monitoring), the solvent was evaporated and the residue was diluted with water and extracted with ethyl acetate (3 times). The combined organics were washed with brine, dried over anhydrous Na₂SO₄, filtered and concentrated. The crude was purified over silica gel (100-200 M, 30-40% EtOAc-hexane) to get the desired product 16.5 (a-d).

Tert-butyl 4-(5-cyano-2-oxo-2,3-dihydro-1H-benzo[d]imidazol-1-yl)piperidine-1-carboxylate (16.5-a)

¹H-NMR (400 MHz, DMSO-d₆): δ 10.08 (br s, 1H), 7.38-7.40 (m, 2H), 7.18-7.20 (m, 1H), 4.43-4.46 (m, 1H), 4.32-4.36 (m, 2H), 2.87-2.87 (m, 2H), 2.25-2.28 (m, 2H), 1.83-1.85 (m, 2H) and 1.44 (s, 9H). LCMS: 343.41 (M+H)⁺, 93.09%. Yield: 90%.

Tert-butyl 4-(7-cyano-2-oxo-2,3-dihydro-1H-benzo[d]imidazol-1-yl)piperidine-1-carboxylate (16.5-b)

LCMS: 341.14 (M–H)⁺, 83.61%. Yield: 75%.

Tert-butyl 4-(7-cyano-6-fluoro-2-oxo-2,3-dihydro-1H-benzo[d]imidazol-1-yl)piperidine-1-carboxylate (16.5-c)

LCMS: 359.32 (M–H)⁺, 83.11%. Yield: 48%.

Tert-butyl 4-(5-cyano-6-fluoro-2-oxo-2,3-dihydro-1H-benzo[d]imidazol-1-yl)piperidine-1-carboxylate (16.5-d)

LCMS: 359.57 (M–H)⁺, 81.30%. Yield: 82%.

General Procedure for the Preparation of 16.6 (a-d): General Method M:

An ice-cold solution of compound 16.5 (a-d) (0.5 g-1.0 g, 1.0 eq) in dioxane-HCl (~4N) was stirred at RT for 2 h. After completion of the reaction (TLC monitoring), the reaction mass was dried under reduced pressure. The crude was triturated with diethyl ether to get desired product 16.6 (a-d) as off solid.

2-Oxo-1-(piperidin-4-yl)-2,3-dihydro-1H-benzo[d]imidazole-5-carbonitrile Hydrochloride (16.6-a): Intermediate 23

¹H-NMR (400 MHz, DMSO-d₆): δ 11.45 (br s, 1H), 9.11 (br s, 2H), 7.64 (d, J=8.0 Hz, 1H), 7.50-7.52 (m, 1H), 7.40-7.41 (m, 1H), 4.56-4.62 (m, 1H), 3.34-3.41 (m, 2H), 3.03-3.08 (m, 2H), 2.58-2.64 (m, 2H) and 1.83-1.90 (m, 2H). LCMS: 243.16 (M+H)⁺, 98.94%. Yield: 89%.

2-Oxo-3-(piperidin-4-yl)-2,3-dihydro-1H-benzo[d]imidazole-4-carbonitrile Hydrochloride (16.6-b): Intermediate 24

¹H-NMR (400 MHz, DMSO-d₆): δ 11.50 (br s, 1H), 9.13 (br s, 1H), 8.62 (br s, 1H), 7.40-7.42 (m, 1H), 7.32-7.36 (m, 1H), 7.28-7.30 (m, 1H), 4.72-4.78 (m, 1H), 3.35-3.48 (m, 2H), 2.86-2.95 (m, 2H), 2.67-2.72 (m, 2H) and 2.06-2.09 (m, 2H). LCMS: 241.05 (M–H)⁺, 89.68%. Yield: 95%.

5-Fluoro-2-oxo-3-(piperidin-4-yl)-2,3-dihydro-1H-benzo[d]imidazole-4-carbonitrile Hydrochloride (16.6-c): Intermediate 25

¹H-NMR (400 MHz, DMSO-d₆): δ 11.58 (br s, 1H), 9.35 (br s, 1H), 8.76 (br s, 1H), 7.20-7.25 (m, 1H), 7.06-7.11 (m, 1H), 4.65-4.71 (m, 1H), 3.56-3.63 (m, 2H), 2.85-2.90 (m, 2H), 2.67-2.73 (m, 2H) and 2.08-2.11 (m, 2H). LCMS: 260.96 (M+H)⁺, 95.41%. Yield: 28%.

6-Fluoro-2-oxo-1-(piperidin-4-yl)-2,3-dihydro-1H-benzo[d]imidazole-5-carbonitrile Hydrochloride (16.6-d): Intermediate 26

¹H-NMR (400 MHz, DMSO-d₆): δ 10.51 (br s, 1H), 9.13-9.24 (m, 2H), 7.76 (d, J=8.8 Hz, 1H), 7.40 (d, J=5.2 Hz, 1H), 4.55-4.61 (m, 1H), 3.31-3.35 (m, 2H), 3.04-3.07 (m, 2H), 2.60-2.66 (m, 2H) and 1.84-1.87 (m, 2H). LCMS: 259.2 (M–H)⁺, 97.74%. Yield: 91%.

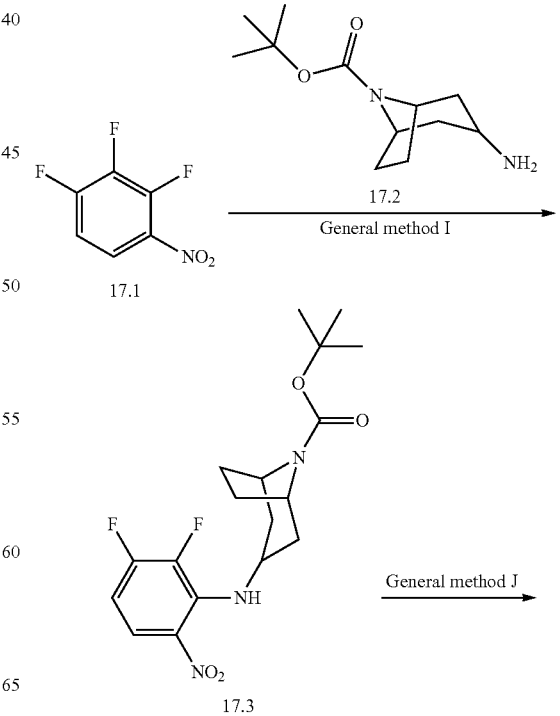

Scheme 17

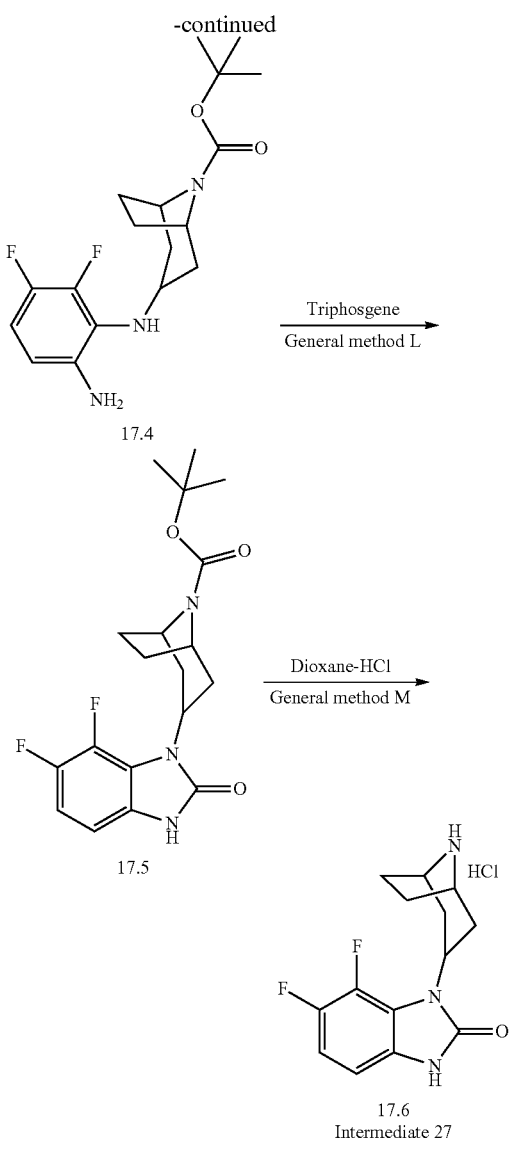

Preparation of tert-butyl 3-((2,3-difluoro-6-nitrophenyl)amino)-8-azabicyclo[3.2.1]octane-8-carboxylate (17.3)

This compound was prepared following the general method I. $^1$H-NMR (400 MHz, CDCl$_3$): δ 8.61 (d, J=6.0 Hz, 1H), 8.01-8.04 (m, 1H), 6.45-6.51 (m, 1H), 4.21-4.31 (m, 3H), 2.29-2.35 (m, 2H), 2.07-2.09 (m, 2H), 1.94-1.96 (m, 2H), 1.68-1.73 (m, 2H) and 1.47 (s, 9H). LCMS: 384.36 (M+H)+, 99.35%. Yield: 78%.

Preparation of tert-butyl 3-((6-amino-2,3-difluorophenyl)amino)-8-azabicyclo[3.2.1]octane-8-carboxylate (17.4)

This compound was prepared following the general method J. $^1$H-NMR (400 MHz, DMSO-d$_6$): δ 6.57-6.60 (m, 1H), 6.39-6.41 (m, 1H), 4.70 (br s, 2H), 4.17-4.19 (m, 1H), 4.01-4.08 (m, 2H), 3.64 (br s, 1H), 1.98-2.06 (m, 4H), 1.84-1.86 (m, 2H), 1.61-1.64 (m, 2H) and 1.38 (s, 9H). MS: 354.13 (M+H)$^+$. Yield: 95%.

Preparation of tert-butyl 3-(6,7-difluoro-2-oxo-2,3-dihydro-1H-benzo[d]imidazol-1-yl)-8-azabicyclo[3.2.1]octane-8-carboxylate (17.5)

This compound was prepared following the general method L. $^1$H-NMR (400 MHz, CDCl$_3$): δ 10.03 (br s, 1H), 6.85-6.97 (m, 1H), 6.74-6.75 (m, 1H), 4.52-4.59 (m, 1H), 4.34-4.46 (m, 2H), 2.52-2.54 (m, 2H), 2.06-2.10 (m, 2H), 1.80-1.89 (m, 4H) and 1.52 (s, 9H). LCMS: 378.13 (M−H)$^+$, 96.51%. Yield: 85%.

Preparation of 1-(8-azabicyclo[3.2.1]octan-3-yl)-6,7-difluoro-1,3-dihydro-2H-benzo[d]imidazol-2-one Hydrochloride (17.6): Intermediate 27

This compound was prepared following the general method M. $^1$H-NMR (400 MHz, DMSO-d$_6$): δ 11.34 (br s, 1H), 9.02 (br s, 1H), 8.87 (br s, 1H), 7.03-7.10 (m, 1H), 6.80-6.81 (m, 1H), 4.89-4.93 (m, 1H), 4.08-4.10 (m, 2H), 2.49-2.52 (m, 2H), 2.08-2.09 (m, 2H) and 1.90-1.97 (m, 4H). LCMS: 278.06 (M−H)$^+$, 99.73%. Yield: 94%.

TABLE 6.5

Tabulated data of the final compounds including the individual yields

| No. | Structure | Amine intermediate used | Yield (%) | LCMS | $^1$H-NMR data (DMSO-d$_6$, 400 MHz), unless otherwise specified |
|---|---|---|---|---|---|
| 228 | 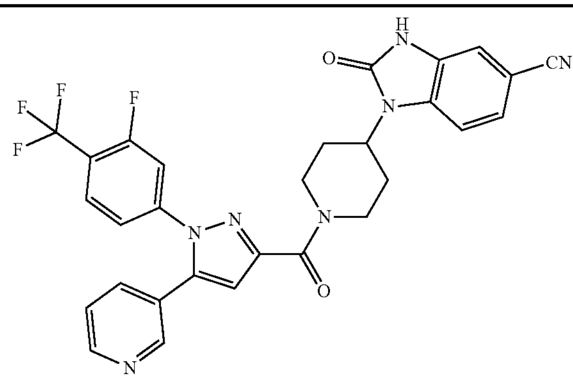 | 23 | 38 | 573.86 (M − H)$^+$, 98.22% | δ 11.31 (br s, 1H), 8.60-8.62 (m, 2H), 7.85 (t, J = 8.40 Hz, 1H), 7.73 (d, J = 8.0 Hz, 1H), 7.64-7.67 (m, 1H), 7.44-7.47 (m, 3H), 7.37 (s, 1H), 7.32 (d, J = 8.4 Hz, 1H), 7.17 (s, 1H), 4.70-4.78 (m, 2H), 4.54-4.57 (m, 1H), 3.28-3.32 (m, 1H), 2.92-2.98 (m, 1H), 2.25-2.28 (m, 2H) and 1.79-1.83 (m, 2H) |

TABLE 6.5-continued

Tabulated data of the final compounds including the individual yields

| No. | Structure | Amine intermediate used | Yield (%) | LCMS | ¹H-NMR data (DMSO-d$_6$, 400 MHz), unless otherwise specified |
|---|---|---|---|---|---|
| 229 | 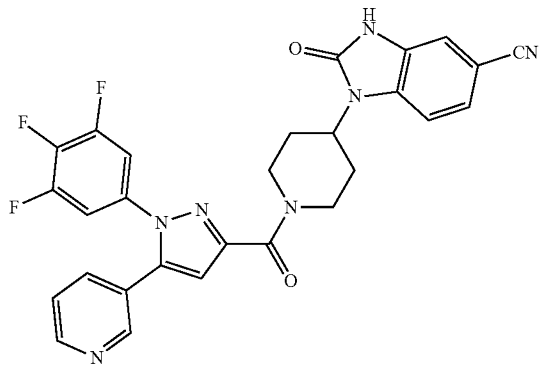 [SMILES: N#Cc1ccc2c(c1)[nH]c(=O)n2C1CCN(C(=O)c2cc(-c3cccnc3)n(-c3cc(F)c(F)c(F)c3)n2)CC1] | 23 | 35 | 541.85 (M − H)⁺, 98.34% | δ 11.36 (br s, 1H), 8.60-8.61 (m, 2H), 7.67-7.69 (m, 1H), 7.41-7.53 (m, 5H), 7.37 (s, 1H), 7.15 (s, 1H), 4.69-4.77 (m, 2H), 4.53-4.56 (m, 1H), 3.29-3.32 (m, 1H), 2.92-2.97 (m, 1H), 2.25-2.29 (m, 2H) and 1.79-1.87 (m, 2H) |
| 230 | 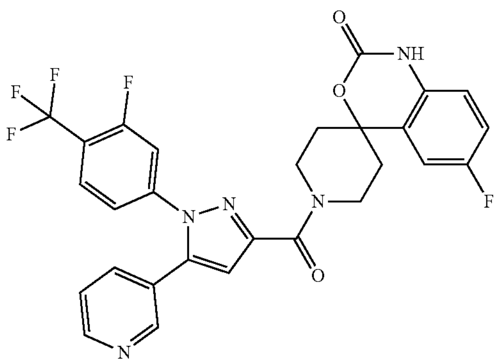 [SMILES: O=C1Nc2ccc(F)cc2C2(CCN(C(=O)c3cc(-c4cccnc4)n(-c4ccc(C(F)(F)F)c(F)c4)n3)CC2)O1] | Commercial 23 | | 569.82 (M + H)⁺, 98.81% | δ 10.36 (br s, 1H), 8.61-8.63 (m, 2H), 7.84 (t, J = 8.0 Hz, 1H), 7.73 (d, J = 7.6 Hz, 1H), 7.66-7.69 (m, 1H), 7.44-7.48 (m, 1H), 7.30-7.34 (m, 2H), 7.17 (s, 1H), 7.10-7.15 (m, 1H), 6.90-6.93 (m, 1H), 4.58-4.68 (m, 2H), 3.50-3.56 (m, 1H), 3.11-3.18 (m, 1H) and 2.02-2.18 (m, 4H) |
| 231 | 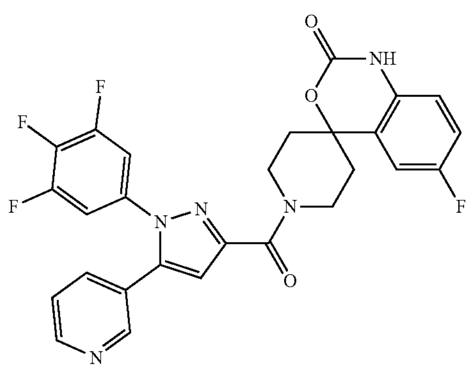 [SMILES: O=C1Nc2ccc(F)cc2C2(CCN(C(=O)c3cc(-c4cccnc4)n(-c4cc(F)c(F)c(F)c4)n3)CC2)O1] | Commercial 21 | | 537.86 (M + H)⁺, 97.64% | δ 10.36 (br s, 1H), 8.60-8.61 (m, 2H), 7.67 (d, J = 8.0 Hz, 1H), 7.49-7.53 (m, 2H), 7.42-7.45 (m, 1H), 7.29-7.31 (m, 1H), 7.14 (s, 1H), 7.11-7.13 (m, 1H), 6.89-6.93 (m, 1H), 4.57-4.67 (m, 2H), 3.48-3.52 (m, 1H), 3.10-3.17 (m, 1H) and 2.01-2.13 (m, 4H) |
| 232 | 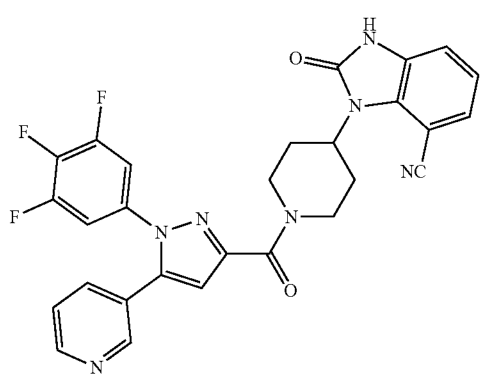 [SMILES: N#Cc1cccc2[nH]c(=O)n(C3CCN(C(=O)c4cc(-c5cccnc5)n(-c5cc(F)c(F)c(F)c5)n4)CC3)c12] | 24 | 10 | 542.41 (M − H)⁺, 97.92% | δ 11.25 (br s, 1H), 8.60-8.61 (m, 2H), 7.68 (d, J = 7.6 Hz, 1H), 7.51 (t, J = 8.4 Hz, 2H), 7.39-7.45 (m, 2H), 7.26 (d, J = 8.0 Hz, 1H), 7.11-7.13 (m, 2H), 4.85-4.85 (m, 2H), 4.74-4.77 (m, 1H), 3.78-3.81 (m, 1H), 3.22-3.26 (m, 2H), 2.76-2.77 (m, 1H) and 1.94-1.96 (m, 2H) |

TABLE 6.5-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 233 | 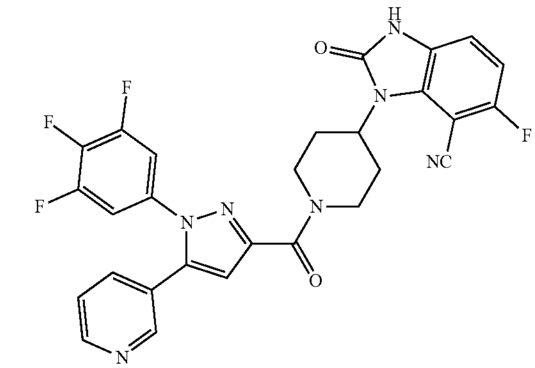 [SMILES: N#Cc1c(F)ccc2[nH]c(=O)n(C3CCN(C(=O)c4cc(-c5cccnc5)n(-c5cc(F)c(F)c(F)c5)n4)CC3)c12] | 25 | 11 | 560.43 (M − H)$^+$, 95.31% | δ 11.48 (br s, 1H), 8.61-8.62 (m, 2H), 7.70 (d, J = 7.6 Hz, 1H), 7.47-7.55 (m, 2H), 7.44-7.46 (m, 1H), 7.23-7.27 (m, 1H), 7.13 (s, 1H), 7.05-7.08 (m, 1H), 4.83-4.85 (m, 2H), 4.73-4.80 (m, 1H), 3.76-3.81 (m, 1H), 3.22-3.26 (m, 2H), 2.80-2.86 (m, 1H) and 1.96-1.99 (m, 2H) |
| 234 | 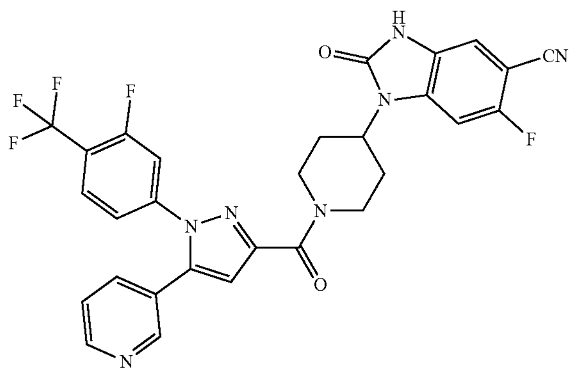 [SMILES: N#Cc1cc2[nH]c(=O)n(C3CCN(C(=O)c4cc(-c5cccnc5)n(-c5ccc(C(F)(F)F)c(F)c5)n4)CC3)c2cc1F] | 26 | 19 | 592.11 (M − H)$^+$, 98.27% | δ 11.45 (br s, 1H), 8.60-8.62 (m, 2H), 7.85 (t, J = 8.0 Hz, 1H), 7.75 (d, J = 8.00 Hz, 1H), 7.62-7.67 (m, 2H), 7.46-7.49 (m, 1H), 7.33-7.38 (m, 2H), 7.17 (s, 1H), 4.70-4.78 (m, 2H), 4.50-4.56 (m, 1H), 3.27-3.33 (m, 1H), 2.89-2.92 (m, 1H), 2.30-2.35 (m, 2H) and 1.78-1.86 (m, 2H) |
| 235 | 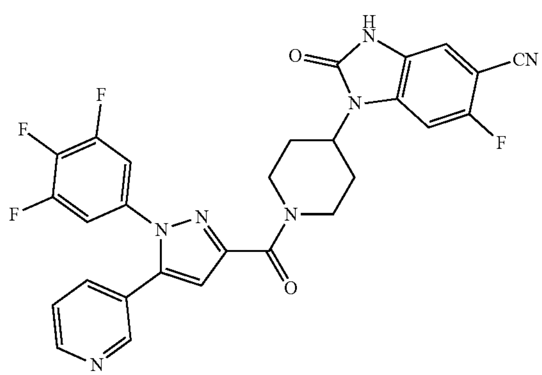 [SMILES: N#Cc1cc2[nH]c(=O)n(C3CCN(C(=O)c4cc(-c5cccnc5)n(-c5cc(F)c(F)c(F)c5)n4)CC3)c2cc1F] | 26 | 48 | 560.42 (M − H)$^+$, 98.73% | δ 11.39 (br s, 1H), 8.59-8.60 (m, 2H), 7.67 (d, J = 8.0 Hz, 1H), 7.61-7.64 (m, 1H), 7.49 (t, J = 8.4 Hz, 2H), 7.41-7.43 (m, 1H), 7.37 (d, J = 5.6 Hz, 1H), 7.14 (s, 1H), 4.69-4.80 (m, 2H), 4.49-4.55 (m, 1H), 2.87-2.94 (m, 1H), 2.25-2.36 (m, 3H) and 1.78-1.86 (m, 2H) |
| 236 | 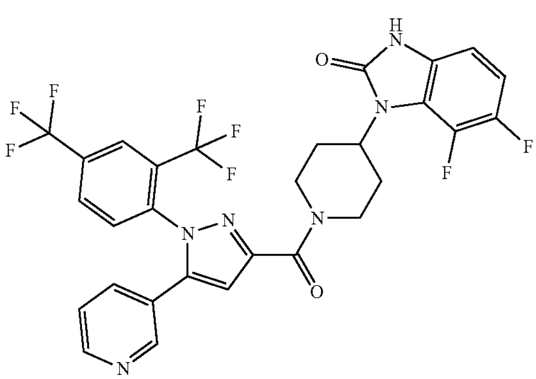 [SMILES: O=C(c1cc(-c2cccnc2)n(-c2ccc(C(F)(F)F)cc2C(F)(F)F)n1)N1CCC(n2c(=O)[nH]c3ccc(F)c(F)c32)CC1] | 16 | 28 | 635.45 (M − H)$^+$, 99.95% | δ 11.21 (br s, 1H), 8.51-8.54 (m, 2H), 8.33 (s, 1H), 8.20 (d, J = 8.40 Hz, 1H), 7.90 (d, J = 8.40 Hz, 1H), 7.59 (d, J = 8.0 Hz, 1H), 7.36-7.40 (m, 1H), 7.25 (s, 1H), 6.98-7.05 (m, 1H), 6.76-6.79 (m, 1H), 4.62-4.76 (m, 3H), 3.21-3.25 (m, 1H), 2.92-2.98 (m, 1H), 2.07-2.12 (m, 2H) and 1.79-1.91 (m, 2H) |

TABLE 6.5-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 237 | 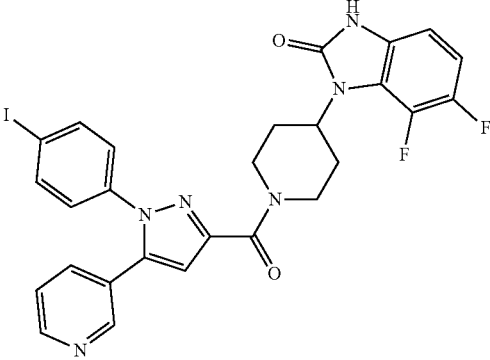 [SMILES: O=C(c1cc(-c2cccnc2)n(-c2ccc(I)cc2)n1)N1CCC(n2c(=O)[nH]c3ccc(F)c(F)c32)CC1] | 16 | 20 | 627.09 (M + H)$^+$, 99.86% | δ 11.25 (br s, 1H), 8.56-8.60 (m, 2H), 7.80 (d, J = 8.40 Hz, 2H), 7.71-7.73 (m, 1H), 7.45-7.48 (m, 1H), 7.18 (d, J = 8.4 Hz, 1H), 1H), 7.13 (s, 1H), 7.06-7.09 (m, 1H), 7.01-7.03 (m, 1H), 6.77-6.80 (m, 1H), 4.83-4.86 (m, 1H), 4.62-4.70 (m, 2H), 3.33-3.36 (m, 1H), 2.94-2.97 (m, 1H), 2.13-2.17 (m, 2H) and 1.83-1.90 (m, 2H) |
| 238 | 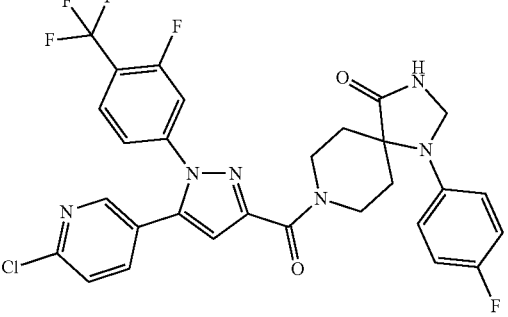 | 1 | 13 | 617.16 (M + H)$^+$, 95.05% | δ 8.83-8.85 (m, 1H), 8.44-8.47 (m, 1H), 7.86 (t, J = 8.4 Hz, 1H), 7.75-7.77 (m, 1H), 7.66-7.69 (m, 1H), 7.58 (d, J = 7.6 Hz, 1H), 7.30-7.32 (m, 1H), 7.16 (s, 1H), 7.08-7.12 (m, 2H), 6.84-6.88 (m, 2H), 4.59-4.60 (m, 2H), 4.38-4.44 (m, 2H), 3.88-3.90 (m, 1H), 3.51-3.54 (m, 1H), 2.26-2.30 (m, 2H) and 1.78-1.83 (m, 2H) |
| 239 | 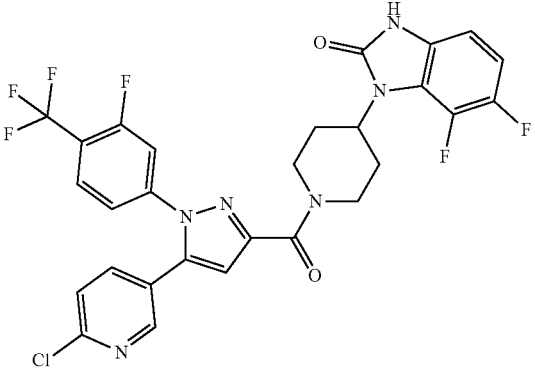 [SMILES: O=C(c1cc(-c2ccc(Cl)nc2)n(-c2ccc(C(F)(F)F)c(F)c2)n1)N1CCC(n2c(=O)[nH]c3ccc(F)c(F)c32)CC1] | 16 | 8 | 621.24 (M + H)$^+$, 98.56% | δ 11.25 (br s, 1H), 8.48-4.49 (m, 1H), 7.88 (t, J = 8.0 Hz, 1H), 7.78 (d, J = 8.4 Hz, 1H), 7.76-7.77 (m, 1H), 7.58 (d, J = 8.0 Hz, 1H), 7.36 (d, J = 7.20 Hz, 1H), 7.21 (s, 1H), 7.02-7.05 (m, 1H), 6.77-6.80 (m, 1H), 4.77-4.80 (m, 1H), 4.66-4.70 (m, 2H), 3.33-3.36 (m, 1H), 2.94-2.97 (m, 1H), 2.11-2.17 (m, 2H) and 1.85-1.88 (m, 2H) |
| 240 | 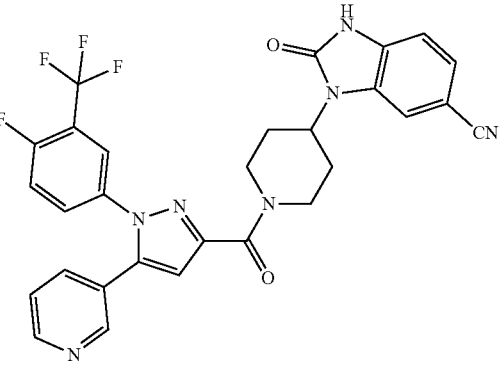 | 20 | 9 | 576.41 (M + H)$^+$, 99.91% | δ 11.45 (br s, 1H), 8.58-8.59 (m, 2H), 7.81-7.84 (m, 2H), 7.73-7.76 (m, 2H), 7.60-7.64 (m, 1H), 7.43-7.45 (m, 2H), 7.10-7.14 (m, 2H), 4.71-4.79 (m, 2H), 4.51-4.54 (m, 1H), 3.23-3.27 (m, 1H), 2.89-2.95 (m, 1H), 2.32-2.35 (m, 2H) and 1.77-1.85 (m, 2H) |

TABLE 6.5-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 241 | 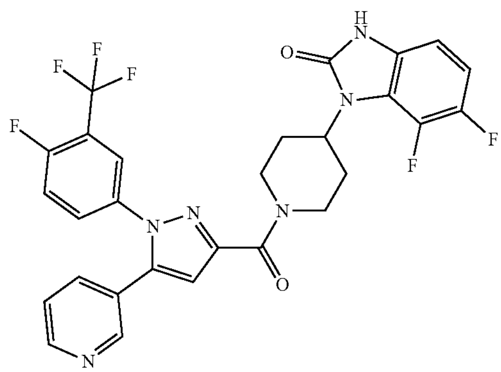 [SMILES: O=C(c1cc(-c2cccnc2)n(-c2ccc(F)c(C(F)(F)F)c2)n1)N1CCC(n2c(=O)[nH]c3ccc(F)c(F)c32)CC1] | 16 | 18 | 587.46 (M + H)$^+$, 97.82% | δ 11.25 (br s, 1H), 8.58-8.59 (m, 2H), 7.82-7.83 (m, 1H), 7.72-7.75 (m, 2H), 7.59 (t, J = 8.4 Hz, 1H), 7.43-7.46 (m, 1H), 7.14 s, 1H), 7.04-7.07 (m, 1H), 6.77-6.80 (m, 1H), 4.78-4.81 (m, 1H), 4.67-4.80 (m, 2H), 3.31-3.34 (m, 1H), 2.92-2.99 (m, 1H), 2.11-2.17 (m, 2H) and 1.84-1.87 (m, 2H) |
| 242 | 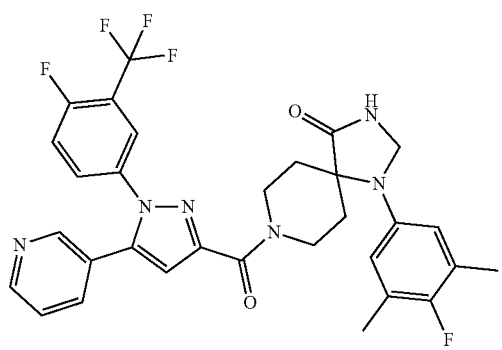 [SMILES: Cc1cc(N2CNC(=O)C23CCN(C(=O)c2cc(-c4cccnc4)n(-c4ccc(F)c(C(F)(F)F)c4)n2)CC3)cc(C)c1F] | 6 | 16 | 611.24 (M + H)$^+$, 96.86% | δ 8.74 (br s, 1H), 8.60-8.61 (m, 2H), 7.79-7.80 (m, 1H), 7.58-7.73 (m, 3H), 7.44-7.47 (m, 1H), 7.10 (s, 1H), 6.57 (d, J = 5.6 Hz, 2H), 4.55 (s, 2H), 4.36-4.39 (m, 2H), 3.79-3.85 (m, 1H), 3.47-3.53 (m, 1H), 2.29-2.32 (m, 1H), 2.17-2.20 (m, 1H), 2.10 (s, 6H) and 1.70-1.76 (m, 2H) |
| 243 | 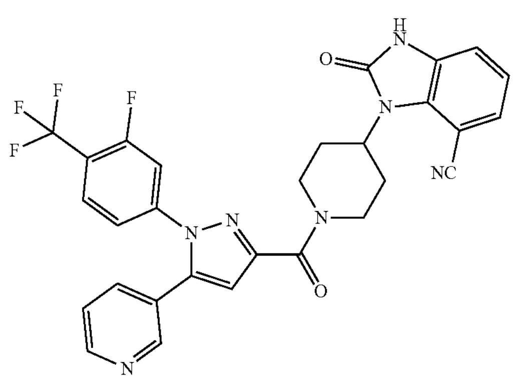 [SMILES: N#Cc1cccc2[nH]c(=O)n(C3CCN(C(=O)c4cc(-c5cccnc5)n(-c5ccc(C(F)(F)F)c(F)c5)n4)CC3)c12] | 24 | 12 | 576.15 (M + H)$^+$, 91.27% | δ 11.24 (br s, 1H), 8.61-8.62 (m, 2H), 7.85 (t, J = 8.4 Hz, 1H), 7.74 (d, J = 7.6 Hz, 1H), 7.66-7.69 (m, 1H), 7.40-7.46 (m, 2H), 7.28-7.35 (m, 2H), 7.15 (s, 1H), 7.10-7.11 (m, 1H), 4.83-4.86 (m, 2H), 4.74-4.77 (m, 1H), 3.32-3.40 (m, 1H), 3.21-3.27 (m, 2H), 2.95-3.00 (m, 1H) and 1.98-2.01 (m, 2H) |
| 244 | 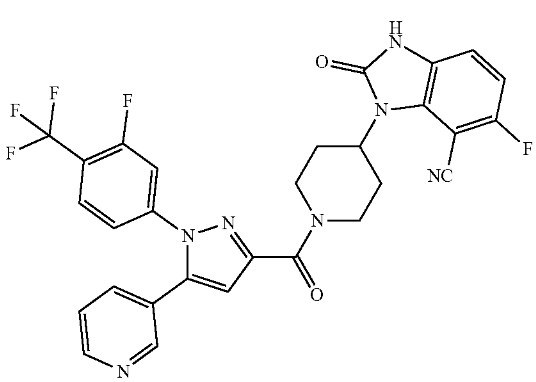 [SMILES: N#Cc1c(F)ccc2[nH]c(=O)n(C3CCN(C(=O)c4cc(-c5cccnc5)n(-c5ccc(C(F)(F)F)c(F)c5)n4)CC3)c12] | 25 | 10 | 592.04 (M − H)$^+$, 97.13% | δ 11.24 (br s, 1H), 8.60-8.62 (m, 2H), 7.85 (t, J = 8.80 Hz, 1H), 7.73 (d, J = 7.2 Hz, 1H), 7.66-7.69 (m, 1H), 7.44-7.47 (m, 1H), 7.33 (d, J = 8.0 Hz, 1H), 7.23-7.27 (m, 1H), 7.15 (s, 1H), 7.05-7.10 (m, 1H), 4.73-4.87 (m, 3H), 3.15-3.20 (m, 2H), 2.81-2.84 (m, 1H) and 1.92-2.02 (m, 3H) |

TABLE 6.5-continued

Tabulated data of the final compounds including the individual yields

| No. | Structure | Amine intermediate used | Yield (%) | LCMS | $^1$H-NMR data (DMSO-$d_6$, 400 MHz), unless otherwise specified |
|---|---|---|---|---|---|
| 245 | 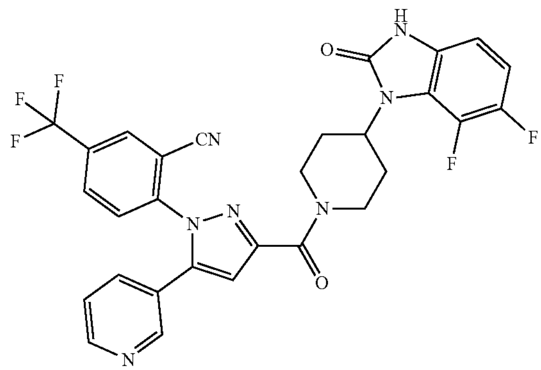 [SMILES: N#Cc1cc(C(F)(F)F)ccc1-n1nc(C(=O)N2CCC(n3c(=O)[nH]c4ccc(F)c(F)c43)CC2)cc1-c1cccnc1] | 16 | 12 | 594.16 (M + H)$^+$, 95.67% | δ 11.25 (br s, 1H), 9.41 (s, 1H), 8.84-8.85 (m, 1H), 8.70-8.72 (m, 1H), 8.65 (s, 1H), 8.07-8.10 (m, 2H), 7.91-7.93 (m, 1H), 7.72-7.75 (m, 1H), 7.03-7.08 (m, 1H), 6.79-6.81 (m, 1H), 4.69-4.76 (m, 2H), 4.09-4.13 (m, 1H), 3.07-3.15 (m, 2H), 1.97-2.00 (m, 2H) and 1.74-1.82 (m, 2H) |
| 246 | 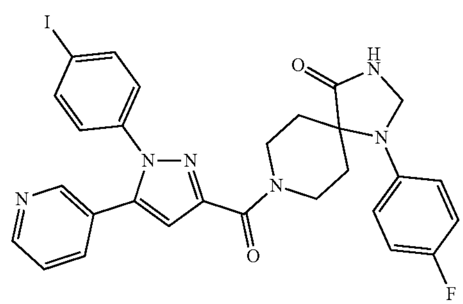 [SMILES: O=C(c1cc(-c2cccnc2)n(-c2ccc(I)cc2)n1)N1CCC2(CC1)C(=O)NCN2c1ccc(F)cc1] | 1 | 10 | 623.08 (M + H)$^+$, 90.04% | δ 8.79 (br s, 1H), 8.56-8.57 (m, 1H), 8.51 (s, 1H), 7.78-7.80 (m, 2H), 7.64-7.66 (m, 1H), 7.40-7.43 (m, 1H), 7.07-7.14 (m, 5H), 6.84-6.86 (m, 2H), 4.53 (s, 2H), 4.41-4.43 (m, 2H), 3.84-3.89 (m, 1H), 3.49-3.55 (m, 1H), 2.14-2.21 (m, 2H) and 1.73-1.77 (m, 2H) |
| 247 | 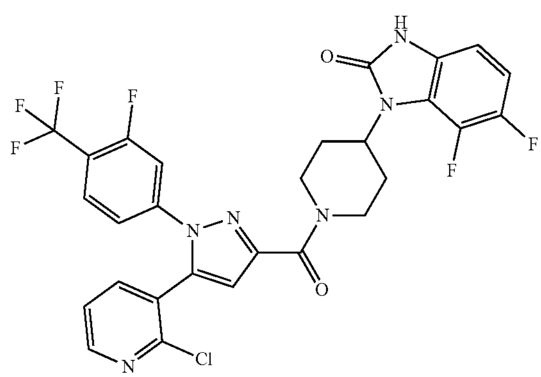 [SMILES: O=C(c1cc(-c2cccnc2Cl)n(-c2ccc(C(F)(F)F)c(F)c2)n1)N1CCC(n2c(=O)[nH]c3ccc(F)c(F)c32)CC1] | 16 | 13 | 619.03 (M − H)$^+$, 95.97% | δ 11.10 (br s, 1H), 8.55-8.56 (m, 1H), 8.13-8.15 (m, 1H), 7.83 (t, J = 8.0 Hz, 1H), 7.56-7.63 (m, 2H), 7.22 (d, J = 8.8 Hz, 1H), 7.12 (s, 1H), 7.01-7.05 (m, 1H), 6.77-6.81 (m, 1H), 4.79-4.82 (m, 1H), 4.68-4.71 (m, 2H), 3.37-3.41 (m, 1H), 2.95-3.01 (m, 1H), 2.12-2.21 (m, 2H) and 1.91-1.99 (m, 2H) |
| 248 | 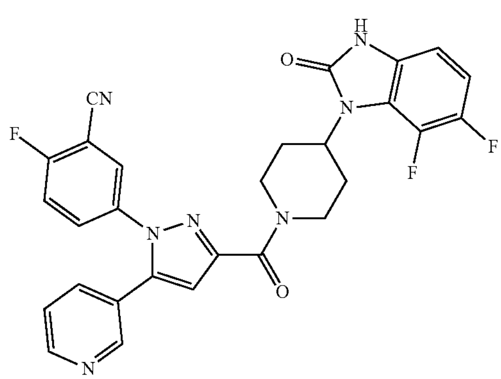 [SMILES: N#Cc1cc(-n2nc(C(=O)N3CCC(n4c(=O)[nH]c5ccc(F)c(F)c54)CC3)cc2-c2cccnc2)ccc1F] | 16 | 20 | 544.12 (M + H)$^+$, 98.99% | δ 11.25 (br s, 1H), 8.58-8.59 (m, 2H), 8.11-8.13 (m, 1H), 7.75-7.80 (m, 1H), 7.60-7.67 (m, 2H), 7.40-7.43 (m, 1H), 7.15 (s, 1H), 6.96-7.03 (m, 1H), 6.75-6.78 (m, 1H), 4.82-4.85 (m, 1H), 4.68-4.70 (m, 2H), 3.33 (s, 1H), 2.91-2.98 (m, 1H), 2.13-2.15 (m, 2H) and 1.83-1.90 (m, 2H) |

TABLE 6.5-continued
Tabulated data of the final compounds including the individual yields
| No. | Structure | Amine intermediate used | Yield (%) | LCMS | ¹H-NMR data (DMSO-d₆, 400 MHz), unless otherwise specified |
|---|---|---|---|---|---|
| 249 | 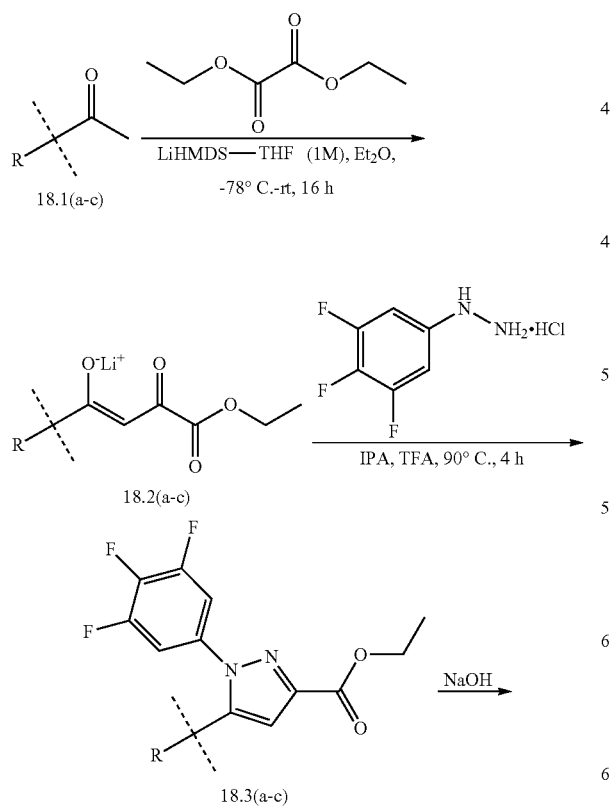 | 6 | 10 | 566.08 (M − H)⁺, 99.21% | δ 8.76 (br s, 1H), 8.56-8.59 (m, 2H), 8.05-8.07 (m, 1H), 7.70-7.74 (m, 1H), 7.59-7.66 (m, 2H), 7.40-7.43 (m, 1H), 7.10 (s, 1H), 6.57 (d, J = 6.4 Hz, 2H), 4.55 (s, 2H), 4.38-4.40 (m, 2H), 3.79-3.86 (m, 1H), 3.47-3.53 (m, 1H), 2.27-2.29 (m, 1H), 2.17-2.18 (m, 1H), 2.11 (s, 6H) and 1.71-1.79 (m, 2H) |
| 250 | 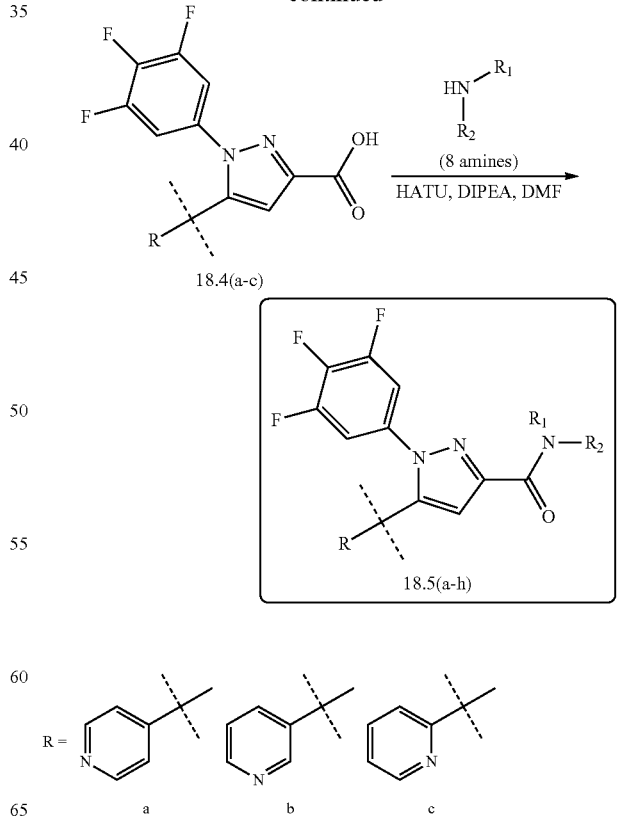 | 27 | 25 | 581.12 (M + H)⁺, 95.59% | δ 11.20 (br s, 1H), 8.58-8.60 (m, 2H), 7.69-7.70 (m, 1H), 7.52-7.55 (m, 2H), 7.42-7.45 (m, 1H), 7.22 (s, 1H), 7.01-7.08 (m, 1H), 6.77-6.79 (m, 1H), 5.34 (m, 1H), 4.86 (m, 1H), 4.36-4.38 (m, 1H), 2.49 (m, 1H), 2.00-2.11 (m, 2H) and 1.84-1.92 (m, 5H) |
Scheme 18:

General Procedure for the Preparation of Compounds 18.2 (a-c):

A solution of compound 18.1 (a-c) (1 eq) in di-ethyl ether was cooled to −78° C. followed by addition of LiHMDS-THF (1M solution, 1.10 eq). The resulting reaction mixture was stirred at −78° C. for 45 min followed by dropwise addition of diethyl oxalate (1.20 eq) in about 30 min. The reaction mixture was then left to stir at room temperature for 16 h. After completion of the reaction (TLC and MS monitoring), the solution was then cooled 0° C. and the resulting precipitate was filtered to get the desired product as an off-white solid 18.2 (a-c), which was carried forward to the next step without purification.

4-Ethoxy-3,4-dioxo-1-(pyridin-4-yl)but-1-en-1-olate Lithium Salt (18.2a)

$^1$H-NMR (400 MHz, DMSO-d$_6$): δ 8.93 (s, 1H), 8.62 (m, 1H), 8.10 (m, 1H), 7.40 (m, 1H), 6.38 (m, 1H), 4.11 (q, J=7.20 Hz, 2H) and 1.22 (t, J=7.2 Hz, 3H). MS: 221.96 (M+H)$^+$. Yield: 90%.

4-Ethoxy-3,4-dioxo-1-(pyridin-3-yl)but-1-en-1-olate Lithium Salt (18.2b)

$^1$H-NMR (400 MHz, DMSO-d$_6$): δ 8.97 (s, 1H), 8.63 (d, J=4.0 Hz, 1H), 8.14 (m, 1H), 7.43 (m, 1H), 6.41 (m, 1H), 4.13 (q, J=7.20 Hz, 2H) and 1.23 (t, J=7.2 Hz, 3H). MS: 221.92 (M+H)$^+$. Yield: 76%.

4-Ethoxy-3,4-dioxo-1-(pyridin-2-yl)but-1-en-1-olate Lithium Salt (18.2c)

$^1$H-NMR (400 MHz, DMSO-d$_6$): δ 8.60 (d, J=4.4 Hz, 1H), 7.98 (m, 1H), 7.87 (m, 1H), 7.45 (m, 1H), 6.48 (s, 1H), 4.15 (q, J=7.20 Hz, 2H) and 1.19 (t, J=6.8 Hz, 3H). MS: 221.97 (M+H)$^+$. Yield: 96%.

General Procedure for the Preparation of Compounds 18.3 (a-c):

To an ice-cold solution of compound 18.2 (a-c), (1.0 eq) in IPA was added 3,4,5-trifluorophenyl hydrazine HCl (1.10 eq) and TFA (2.0 eq). The resulting reaction mixture was warmed to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired products 18.3 (a-c).

Ethyl 5-(pyridin-4-yl)-1-(3,4,5-trifluorophenyl)-1H-pyrazole-3-carboxylate (18.3a)

$^1$H-NMR (400 MHz, CDCl$_3$): δ 8.70 (m, 1H), 8.65 (s, 1H), 7.62 (d, J=8.0 Hz, 1H), 7.42 (m, 1H), 7.15 (s, 1H), 7.03 (m, 2H), 4.49 (q, J=7.2 Hz, 2H) and 1.45 (t, J=7.2 Hz, 3H). MS: 348.09 (M+H)$^+$. Yield: 28%.

Ethyl 5-(pyridin-3-yl)-1-(3,4,5-trifluorophenyl)-1H-pyrazole-3-carboxylate (18.3b)

$^1$H-NMR (400 MHz, CDCl$_3$): δ 8.67 (m, 1H), 8.60 (s, 1H), 7.59 (d, J=8.0 Hz, 1H), 7.41 (m, 1H), 7.12 (s, 1H), 7.00 (m, 2H), 4.47 (q, J=7.2 Hz, 2H) and 1.43 (t, J=7.2 Hz, 3H). MS: 348.15 (M+H)$^+$. Yield: 22%.

Ethyl 5-(pyridin-2-yl)-1-(3,4,5-trifluorophenyl)-1H-pyrazole-3-carboxylate (18.3c)

$^1$H-NMR (400 MHz, CDCl$_3$): δ 8.53 (m, 1H), 7.75 (m, 1H), 7.45 (d, J=8.0 Hz, 1H), 7.30 (m, 1H), 7.23 (s, 1H), 7.03 (m, 2H), 4.39 (q, J=6.8 Hz, 2H) and 1.41 (t, J=7.2 Hz, 3H). MS: 347.88 (M+H)$^+$. Yield: 23%.

General Procedure for the Preparation of Compounds 18.4 (a-c):

To an ice-cold solution of compound 18.3 (a-c) (1.0 eq) in EtOH was added dropwise an aqueous solution of sodium hydroxide (3.0 eq). The resulting solution was stirred at room temperature for 2-3 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired products 18.4 (a-c) as a white solid.

5-(pyridin-4-yl)-1-(3,4,5-trifluorophenyl)-1H-pyrazole-3-carboxylic Acid (18.4a)

$^1$H-NMR (400 MHz, DMSO-d$_6$): δ 13.40 (br s, 1H), 8.62 (m, 2H), 7.68 (d, J=8.0 Hz, 1H), 7.56 (m, 2H), 7.45 (m, 1H) and 7.22 (s, 1H). LCMS: 320.17 (M+H)$^+$, 96.12%. Yield: 65%.

5-(pyridin-3-yl)-1-(3,4,5-trifluorophenyl)-1H-pyrazole-3-carboxylic Acid (18.4b)

$^1$H-NMR (400 MHz, DMSO-d$_6$): δ 13.12 (br s, 1H), 8.58 (s, 2H), 7.64 (d, J=8.4 Hz, 1H), 7.50 (m, 2H), 7.40 (m, 1H) and 7.24 (s, 1H). LCMS: 320.14 (M+H)$^+$, 94.25%. Yield: 61%.

5-(pyridin-2-yl)-1-(3,4,5-trifluorophenyl)-1H-pyrazole-3-carboxylic Acid (18.4c)

$^1$H-NMR (400 MHz, DMSO-d$_6$): 6.8.45 (d, J=5.4 Hz, 1H), 7.87 (m, 1H), 7.72 (d, J=8.0 Hz, 1H), 7.35 (m, 3H) and 7.25 (s, 1H). LCMS: 320.12 (M+H)$^+$, 98.46%. Yield: 55%.

General Procedure for the Preparation of Final Compounds 5 (18.a-h):

To an ice-cold solution of carboxylic acids 18.4 (a-c) (1.0 eq), in DMF (2.0 mL) was added DIPEA (3.0 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC.

Individual yields and the analytical data of the final compounds synthesized via scheme 18 are set forth in Table 6.6.

TABLE 6.6

Tabulated data of the final compounds including the individual yields obtained via scheme 18.

| Compound No. | Structure | Yield (%) | LCMS | NMR data (DMSO-d$_6$, 400 MHz), unless otherwise specified |
|---|---|---|---|---|
| 251 | 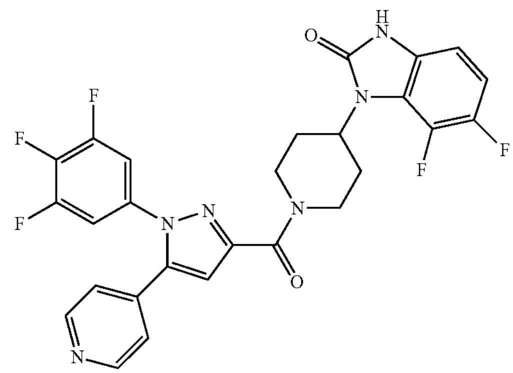 [SMILES: O=C(c1cc(-c2ccncc2)n(-c2cc(F)c(F)c(F)c2)n1)N1CCC(n2c(=O)[nH]c3ccc(F)c(F)c32)CC1] | 23 | 555.11 (M + H)$^+$, 99.32% | δ 11.9 (br s, 1H), 8.59 (d, J = 6.0 Hz, 2H), 7.54 (t, J = 7.6 Hz, 2H), 7.31 (d, J = 5.6 Hz, 2H), 7.23 (s, 1H), 7.00-7.07 (m, 1H), 6.77-6.80 (m, 1H), 4.78-4.81 (m, 1H), 4.67-4.70 (m, 2H), 3.29 (s, 1H), 2.92-2.98 (m, 1H), 2.07-2.13 (m, 2H) and 1.84-1.87 (m, 2H) |
| 252 | 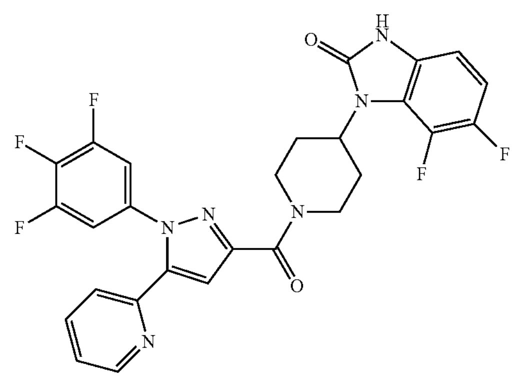 [SMILES: O=C(c1cc(-c2ccccn2)n(-c2cc(F)c(F)c(F)c2)n1)N1CCC(n2c(=O)[nH]c3ccc(F)c(F)c32)CC1] | 15 | 555.09 (M + H)$^+$, 99.89% | δ 11.25 (br s, 1H), 8.47 (s, 1H), 7.91 (s, 1H), 7.71 (s, 1H), 7.48 (s, 2H), 7.38 (s, 1H), 7.25 (s, 1H), 7.04-7.09 (m, 1H), 6.79 (s, 1H), 4.81-4.83 (m, 1H), 4.67-4.74 (m, 2H), 3.17 (s, 1H), 2.94-2.98 (m, 1H), 2.14-2.16 (m, 2H) and 1.83-1.87 (m, 2H) |
| 253 | 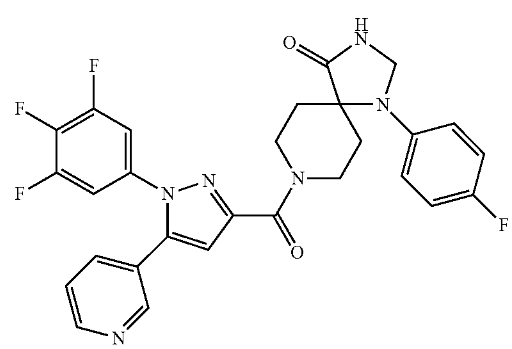 [SMILES: O=C(c1cc(-c2cccnc2)n(-c2cc(F)c(F)c(F)c2)n1)N1CCC2(CC1)C(=O)NCN2c1ccc(F)cc1] | 20 | 551.13 (M + H)$^+$, 99.86% | δ 8.80 (s, 1H), 8.59-8.60 (m, 2H), 7.66 (d, J = 7.6 Hz, 1H), 7.41-7.48 (m, 3H), 7.08-7.15 (m, 3H), 6.84-6.87 (m, 2H), 4.59 (s, 2H), 4.41-4.49 (m, 2H), 3.83-3.89 (m, 1H), 3.50-3.56 (m, 1H), 2.20-2.28 (m, 2H) and 1.74-1.83 (m, 2H) |
| 254 | 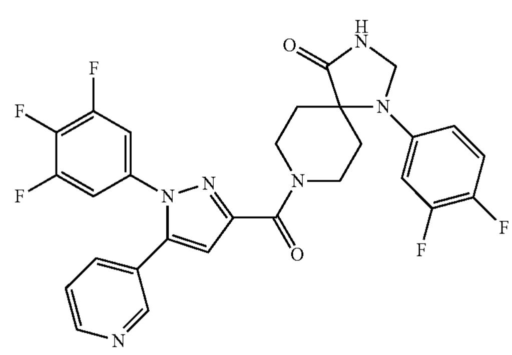 [SMILES: O=C(c1cc(-c2cccnc2)n(-c2cc(F)c(F)c(F)c2)n1)N1CCC2(CC1)C(=O)NCN2c1ccc(F)c(F)c1] | 19 | 567.12 (M − H)$^+$, 98.45% | δ 8.89 (s, 1H), 8.62 (s, 2H), 7.70-7.72 (m, 1H), 7.45-7.50 (m, 3H), 7.28-7.31 (m, 1H), 7.15 (s, 1H), 6.74-6.79 (m, 1H), 6.57-6.59 (m, 1H), 4.59 (s, 2H), 4.47-4.49 (m, 2H), 3.82-3.85 (m, 1H), 3.49-3.53 (m, 1H), 2.33-2.36 (m, 2H) and 1.72-1.76 (m, 2H) |

TABLE 6.6-continued

Tabulated data of the final compounds including the individual yields obtained via scheme 18.

| Compound No. | Structure | Yield (%) | LCMS | NMR data (DMSO-$d_6$, 400 MHz), unless otherwise specified |
|---|---|---|---|---|
| 255 | 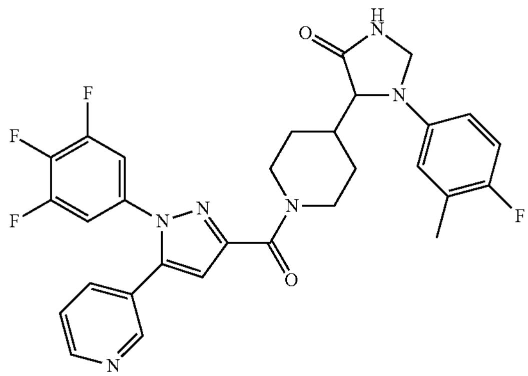 | 23 | 565.34 (M + H)$^+$, 97.49% | δ 8.78 (s, 1H), 8.59-8.60 (m, 2H), 7.66 (d, J = 7.6 Hz, 1H), 7.41-7.48 (m, 3H), 7.12 (s, 1H), 7.01-7.05 (m, 1H), 6.68-6.74 (m, 2H), 4.57 (s, 2H), 4.40-4.43 (m, 2H), 3.81-3.84 (m, 1H), 3.49-3.51 (m, 1H), 2.23-2.26 (m, 2H), 2.14 (s, 3H) and 1.72-1.76 (m, 2H) |
| 256 | 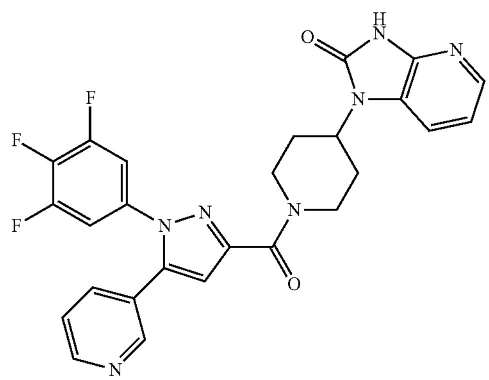 [SMILES: O=C(c1cc(-c2cccnc2)n(-c2cc(F)c(F)c(F)c2)n1)N1CCC(n2c(=O)[nH]c3ncccc32)CC1] | 9.8 | 520.10 (M + H)$^+$, 99.67% | δ 11.55 (br s, 1H), 8.60 (s, 2H), 7.89 (d, J = 4.4 Hz, 1H), 7.67 (d, J = 7.6 Hz, 1H), 7.57 (d, J = 7.6 Hz, 1H), 7.50 (d, J = 7.6 Hz, 2H), 7.41-7.45 (m, 1H), 7.15 (s, 1H), 6.97-7.01 (m, 1H), 4.70-4.79 (m, 2H), 4.49-4.55 (m, 1H), 2.90-2.96 (m, 1H), 2.22-2.26 (m, 3H) and 1.80-1.84 (m, 2H) |
| 257 | 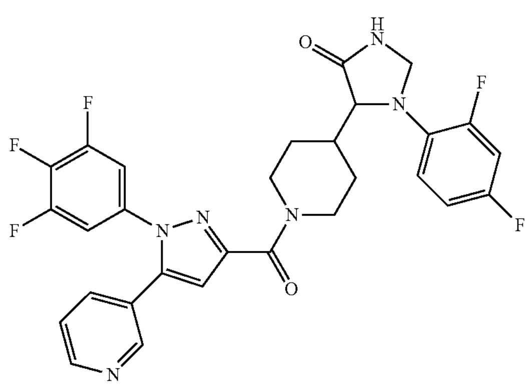 [SMILES: O=C1NCN(c2ccc(F)cc2F)C1C1CCN(C(=O)c2cc(-c3cccnc3)n(-c3cc(F)c(F)c(F)c3)n2)CC1] | 15 | 569.31 (M + H)$^+$, 99.50% | δ 8.65 (s, 1H), 8.59-8.60 (m, 2H), 7.62 (d, J = 8.0 Hz, 1H), 7.43-7.48 (m, 4H), 7.27-7.30 (m, 1H), 7.07-7.10 (m, 1H), 7.04 (s, 1H), 4.53-4.57 (m, 2H), 4.22-4.26 (m, 1H), 4.10-4.14 (m, 1H), 3.87-3.93 (m, 1H), 3.55-3.61 (m, 1H), 1.87-1.94 (m, 2H) and 1.37-1.42 (m, 2H) |

Scheme 19:

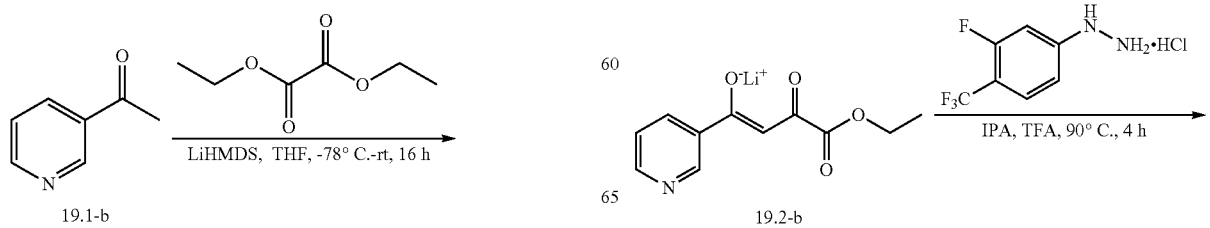

249
-continued

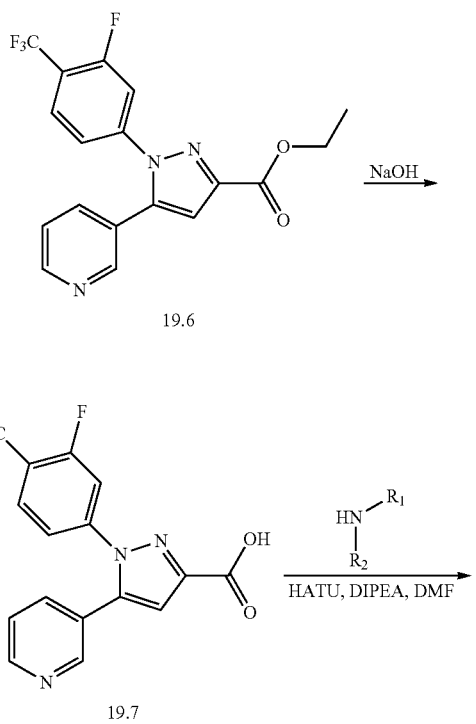

Preparation of 4-ethoxy-3,4-dioxo-1-(pyridin-3-yl)but-1-en-1-olate Lithium Salt (19.2-b)

A solution of 3-acetyl pyridine 19.1-b (25 g, 206.37 mmol) in di-ethyl ether (300 mL) was cooled to −78° C. followed by addition of LiHMDS (1.0 M in THF, 250 mL, 227.01 mmol). The resulting reaction mixture was stirred at −78° C. for 45 min followed by dropwise addition of diethyl oxalate (33.8 mL, 247.64 mL) in about 30 min. The reaction mixture was then left to stir at room temperature for 16 h. After completion of the reaction (TLC and MS monitoring), the solution was then cooled to 0° C. and the resulting precipitate was filtered to get the desired product as an off-white solid 2 (34 g, 76%), which was carried forward to the next step without purification. $^1$H-NMR (400 MHz, DMSO-$d_6$): δ 8.97 (s, 1H), 8.63 (d, J=4.0 Hz, 1H), 8.14 (m, 1H), 7.43 (m, 1H), 6.41 (m, 1H), 4.13 (q, J=7.20 Hz, 2H) and 1.23 (t, J=7.2 Hz, 3H). MS: 221.92 (M+H)$^+$.

Preparation of ethyl 1-(3-fluoro-4-(trifluoromethyl)phenyl)-5-(pyridin-3-yl)-1H-pyrazole-3-carboxylate (19.6)

To an ice-cold solution of 4-ethoxy-3,4-dioxo-1-(pyridin-3-yl)but-1-en-1-olate lithium salt 19.2-b (10 g, 45.23 mmol) in IPA (60 mL) was added (3-fluoro-4-(trifluoromethyl)phenyl)hydrazine hydrochloride 10.5 g, 54.28 mmol) and TFA (7.25 mL, 90.46 mL). The resulting reaction mixture was warmed to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 19.6 (7.5 g, 41%). $^1$H-NMR (400 MHz, CDCl$_3$): δ 8.70 (m, 2H), 7.73 (m, 3H), 7.48 (d, J=7.6 Hz, 1H), 7.46 (d, J=7.6 Hz, 1H), 7.13 (s, 1H), 4.47 (q, J=6.8 Hz, 2H) and 1.43 (t, J=7.2 Hz, 3H). MS: 379.88 (M+H)$^+$.

Preparation of 1-(3-fluoro-4-(trifluoromethyl)phenyl)-5-(pyridin-3-yl)-1H-pyrazole-3-carboxylic Acid 19.7

To an ice-cold solution of ethyl 1-(3-fluoro-4-(trifluoromethyl)phenyl)-5-(pyridin-3-yl)-1H-pyrazole-3-carboxylate 19.6 (7.5 g, 19.77 mmol) in EtOH (50 mL) was added dropwise an aqueous solution of sodium hydroxide (1.6 g in 5 mL H$_2$O). The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 19.7 (4.0 g, 58%) as a white solid. $^1$H-NMR (400 MHz, DMSO-$d_6$): 6.8.58 (m, 2H), 7.86 (t, J=8.0 Hz, 1H), 7.70 (d, J=7.6 Hz, 1H), 7.63 (m, 1H), 7.43 (m, 1H), 7.33 (d, J=8.4 Hz, 1H) and 7.24 (s, 1H). LCMS: 351.96 (M+H)$^+$, 90.40%.

General Procedure for the Preparation of Final Compounds 19.8 (a-f):

To an ice-cold solution of 1-(3-fluoro-4-(trifluoromethyl)phenyl)-5-(pyridin-3-yl)-1H-pyrazole-3-carboxylic acid 19.7 (1.0 eq), in DMF (2.0 mL) was added DIPEA (3.0 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC.

Yields and the analytical data of the final compounds synthesized via scheme 19 are set forth in Table 6.7.

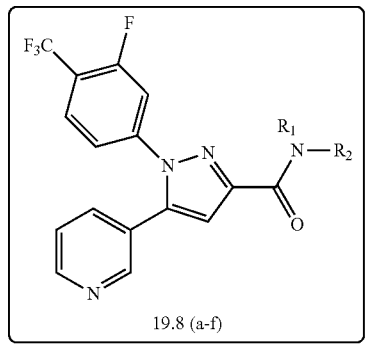

TABLE 6.7

Tabulated data of the final compounds including the individual yields obtained via scheme 19.

| Compound No. | Structure | Yield (%) | LCMS | NMR data (DMSO-d$_6$, 400 MHz), unless otherwise specified |
|---|---|---|---|---|
| 258 | 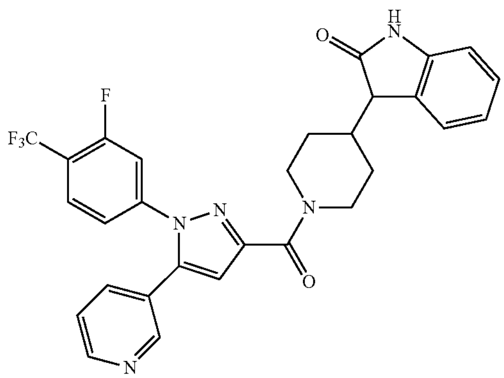 [SMILES: O=C1Nc2ccccc2C1C1CCN(C(=O)c2cc(-c3cccnc3)n(-c3ccc(C(F)(F)F)c(F)c3)n2)CC1] | 20 | 551.15 (M + H)$^+$, 98.86% | δ 10.39 (br s, 1H), 8.58-8.61 (m, 2H), 7.83 (t, J = 8.4 Hz, 1H), 7.70 (d, J = 8.0 Hz, 1H), 7.65-7.67 (m, 1H), 7.43-7.46 (m, 1H), 7.29-7.32 (m, 2H), 7.19 (d, J = 7.6 Hz, 1H), 7.12 (s, 1H), 6.96 (t, J = 7.6 Hz, 1H), 6.78 (d, J = 7.6 Hz, 1H), 4.43 (s, 1H), 3.96-3.98 (m, 2H), 3.65-3.67 (m, 2H), 2.81-2.86 (m, 2H) and 2.67-2.68 (m, 2H) |
| 259 | 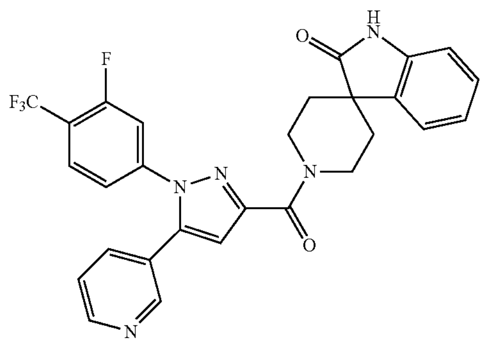 [SMILES: O=C(c1cc(-c2cccnc2)n(-c2ccc(C(F)(F)F)c(F)c2)n1)N1CCC2(CC1)C(=O)Nc1ccccc12] | 21 | 536.12 (M + H)$^+$, 96.33% | δ 10.48 (br s, 1H), 8.61-8.62 (m, 2H), 7.85 (t, J = 8.4 Hz, 1H), 7.73 (d, J = 8.0 Hz, 1H), 7.64-7.67 (m, 1H), 7.50 (d, J = 7.6 Hz, 1H), 7.44-7.46 (m, 1H), 7.32-7.34 (m, 1H), 7.18-7.22 (m, 2H), 7.95 (t, J = 8.4 Hz, 1H), 6.86 (t, J = 8.0 Hz, 1H), 4.22-4.23 (m, 2H), 4.00-4.05 (m, 2H) and 1.81-1.83 (m, 4H) |
| 260 | 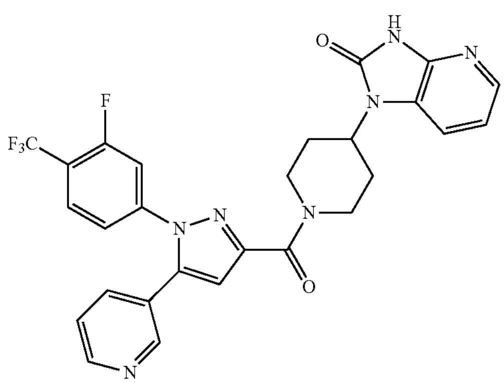 [SMILES: O=C(c1cc(-c2cccnc2)n(-c2ccc(C(F)(F)F)c(F)c2)n1)N1CCC(n2c(=O)[nH]c3ncccc32)CC1] | 12 | 552.11 (M + H)$^+$, 95.74% | δ 10.57 (br s, 1H), 8.61-8.62 (m, 2H), 7.85-7.89 (m, 2H), 7.73 (d, J = 8.0 Hz, 1H), 7.64-7.67 (m, 1H), 7.58 (d, J = 8.0 Hz, 1H), 7.44-7.46 (m, 1H), 7.32-7.35 (m, 1H), 7.17 (s, 1H), 6.97-7.01 (m, 1H), 4.70-4.74 (m, 2H), 4.50-4.53 (m, 1H), 3.35-3.37 (m, 1H), 2.92-2.95 (m, 1H), 2.23-2.28 (m, 2H) and 1.81-1.86 (m, 2H) |
| 261 | 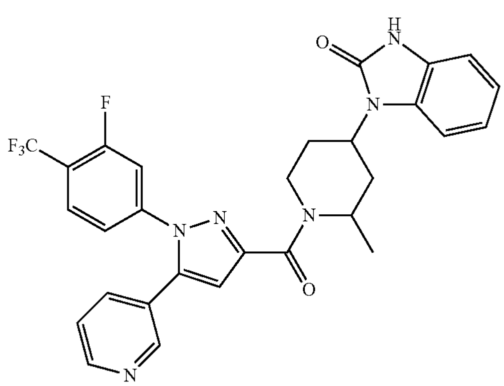 [SMILES: CC1CC(n2c(=O)[nH]c3ccccc32)CCN1C(=O)c1cc(-c2cccnc2)n(-c2ccc(C(F)(F)F)c(F)c2)n1] | 19 | 565.21 (M + H)$^+$, 99.87% | δ 10.87 (br s, 1H), 8.61-8.62 (m, 2H), 7.84-7.88 (m, 1H), 7.73 (d, J = 8.0 Hz, 1H), 7.64-7.68 (m, 1H), 7.44-7.48 (m, 1H), 7.32-7.34 (m, 2H), 7.18 (s, 1H), 6.98-7.01 (m, 3H), 4.37-4.42 (m, 3H), 3.70 (s, 1H), 2.11-2.15 (m, 2H), 1.88-1.90 (m, 2H) and 1.31-1.33 (d, J = 6.0 Hz, 3H) |

Scheme 20:

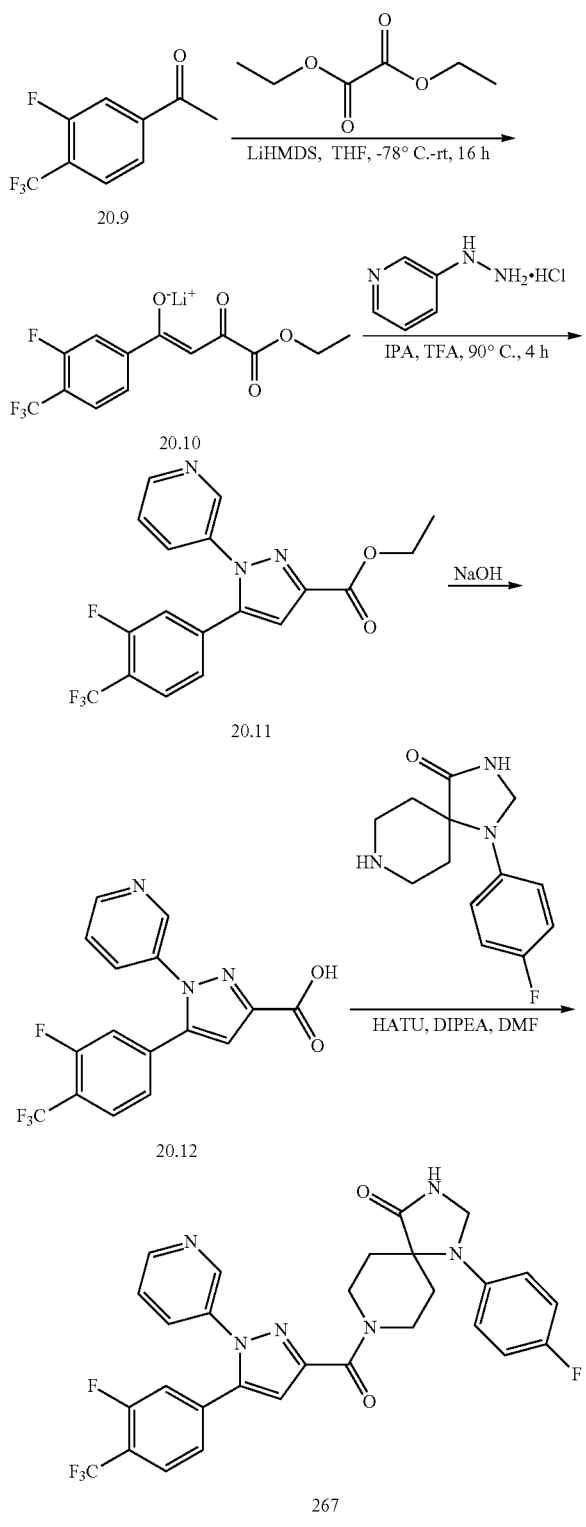

Preparation of 4-ethoxy-1-(3-fluoro-4-(trifluoromethyl)phenyl)-3,4-dioxobut-1-en-1-olate Lithium Salt (20.10)

A solution of 1-(3-fluoro-4-(trifluoromethyl)phenyl)ethan-1-one 20.9 (5 g, 24.25 mmol) in diethyl ether (60 mL) was cooled to −78° C. followed by addition of LiHMDS (1.0 M in THF, 27 mL, 26.68 mmol). The resulting reaction mixture was stirred at −78° C. for 45 min followed by dropwise addition of diethyl oxalate (4.0 mL, 29.10 mmol) in about 30 min. The reaction mixture was then left to stir at room temperature for 16 h. After completion of the reaction (TLC and MS monitoring), the solution was then cooled 0° C. and the resulting precipitate was filtered to get the desired product as an off-white solid 20.10 (7.4 g, 99%), which was carried forward to the next step without purification. $^1$H-NMR (400 MHz, DMSO-d$_6$): δ 7.76 (m, 3H), 6.44 (s, 1H), 4.14 (q, J=7.20 Hz, 2H) and 1.23 (t, J=7.2 Hz, 3H). MS: 306.98 (M+H)$^+$.

Preparation of ethyl 5-(3-fluoro-4-(trifluoromethyl)phenyl)-1-(pyridin-3-yl)-1H-pyrazole-3-carboxylate (20.11)

To an ice-cold solution of 4-ethoxy-1-(3-fluoro-4-(trifluoromethyl)phenyl)-3,4-dioxobut-1-en-1-olate lithium salt 20.10 (2.5 g, 8.01 mmol) in IPA (20 mL) was added 3-hydrazinylpyridine hydrochloride 1.5 g, 8.01 mmol) and TFA (1.2 mL, 16.03 mmol). The resulting reaction mixture was warmed up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 20.11 (1.0 g, 34%). $^1$H-NMR (400 MHz, CDCl$_3$): δ 8.65 (m, 1H), 8.56 (s, 1H), 7.74 (d, J=7.6 Hz, 1H), 7.56 (t, J=7.6 Hz, 1H), 7.39 (m, 1H), 7.14 (s, 1H), 7.00 (m, 2H), 4.39 (q, J=7.6 Hz, 2H) and 1.42 (t, J=7.2 Hz, 3H). MS: 380.17 (M+H)$^+$.

Preparation of 5-(3-fluoro-4-(trifluoromethyl)phenyl)-1-(pyridin-3-yl)-1H-pyrazole-3-carboxylic Acid (20.12)

To an ice-cold solution of ethyl 5-(3-fluoro-4-(trifluoromethyl)phenyl)-1-(pyridin-3-yl)-1H-pyrazole-3-carboxylate 20.11 (1.0 g, 2.63 mmol) in EtOH (30 mL) was added dropwise an aqueous solution of sodium hydroxide (0.22 g in 3 mL H$_2$O). The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 20.12 (0.8 g, 86%) as a white solid. $^1$H-NMR (400 MHz, DMSO-d$_6$): δ 13.23 (br s, 1H), 8.66 (t, J=4.0 Hz, 1H), 8.60 (m, 1H), 7.84 (d, J=8.4 Hz, 1H), 7.77 (t, J=7.6 Hz, 1H), 7.54 (m, 2H), 7.34 (s, 1H) and 7.23 (d, J=8.0 Hz, 1H). LCMS: 352.00 (M+H)$^+$, 95.49%.

Preparation of 8-(5-(3-fluoro-4-(trifluoromethyl)phenyl)-1-(pyridin-3-yl)-1H-pyrazole-3-carbonyl)-1-(4-fluorophenyl)-1,3,8-triazaspiro[4.5]decan-4-one (Compound 267)

To an ice-cold solution of 5-(3-fluoro-4-(trifluoromethyl)phenyl)-1-(pyridin-3-yl)-1H-pyrazole-3-carboxylic acid 20.12 (0.15 g, 0.43 mmol) in DMF (2.0 mL) was added DIPEA (0.22 mL, 1.29 mmol) and HATU (0.25 g, 0.65 mmol). The resulting mixture was stirred under nitrogen atmosphere at 0° C. for 15 min followed by addition of 1-(4-fluorophenyl)-1,3,8-triazaspiro[4.5]decan-4-one (0.11 g, 0.43 mmol). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous $Na_2SO_4$, filtered and concentrated under reduced pressure. The crude residue was purified via prep-HPLC (0.045 g, 18%). $^1$H-NMR (400 MHz, DMSO-$d_6$): δ 8.80 (s, 1H), 8.60-8.63 (m, 2H), 7.78-7.83 (m, 2H), 7.53-7.56 (m, 1H), 7.50-7.52 (m, 1H), 7.24 (d, J=8.0 Hz, 1H), 7.22 (s, 1H), 7.07 (d, J=8.8 Hz, 2H), 6.84-6.87 (m, 2H), 4.58-4.59 (m, 2H), 4.42-4.48 (m, 2H), 3.84-3.87 (m, 1H), 3.51-3.56 (m, 1H), 2.19-2.23 (m, 2H) and 1.74-1.79 (m, 2H). LCMS: 583.14 (M+H)$^+$, 96.73%.

Scheme 21:

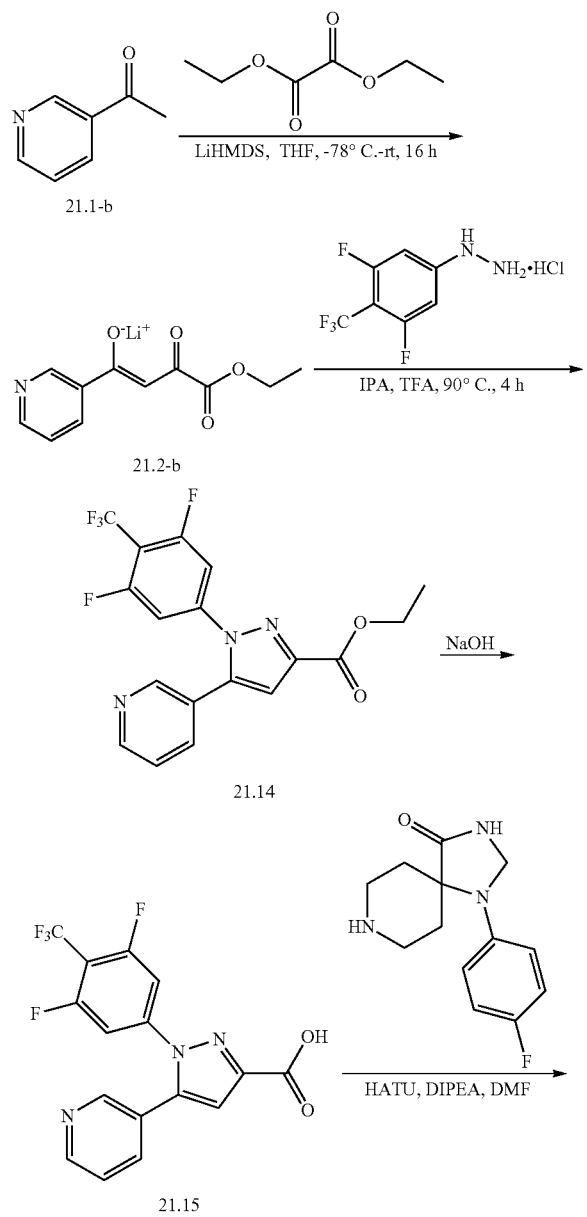

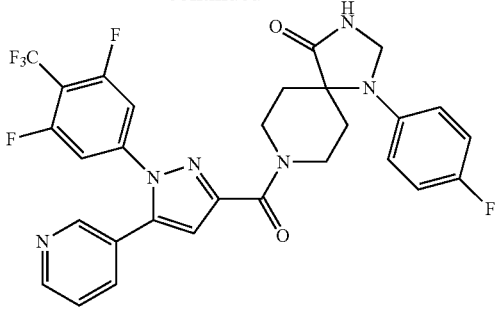

268

Preparation of 4-ethoxy-3,4-dioxo-1-(pyridin-3-yl) but-1-en-1-olate lithium salt (21.2-b)

Intermediate 21.2-b was prepared as per the procedure mentioned in Scheme 19.

Preparation of ethyl 1-(3,5-difluoro-4-(trifluoromethyl)phenyl)-5-(pyridin-3-yl)-1H-pyrazole-3-carboxylate (21.14)

To an ice-cold solution of 4-ethoxy-3,4-dioxo-1-(pyridin-3-yl)but-1-en-1-olate lithium salt 21.2-b (1.5 g, 6.78 mmol) in IPA (20 mL) was added (3,5-difluoro-4-(trifluoromethyl)phenyl)hydrazine hydrochloride (1.68 g, 6.78 mmol) and TFA (1.0 mL, 13.56 mL). The resulting reaction mixture was warmed to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 21.14 (0.66 g, 25%). $^1$H-NMR (400 MHz, CDCl$_3$): δ 8.70 (m, 1H), 8.58 (m, 1H), 7.57 (m, 1H), 7.38 (m, 1H), 7.08 (s, 1H), 7.03 (m, 2H), 4.44 (q, J=6.8 Hz, 2H) and 1.41 (t, J=6.8 Hz, 3H). MS: 398.16 (M+H)$^+$.

Preparation of 1-(3,5-difluoro-4-(trifluoromethyl) phenyl)-5-(pyridin-3-yl)-1H-pyrazole-3-carboxylic Acid (2.15)

To an ice-cold solution of ethyl 1-(3,5-difluoro-4-(trifluoromethyl)phenyl)-5-(pyridin-3-yl)-1H-pyrazole-3-carboxylate 2.14 (0.60 g, 1.65 mmol) in EtOH (20 mL) was added dropwise an aqueous solution of sodium hydroxide (0.13 g in 3 mL H$_2$O). The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 2.15 (0.3 g, 51%) as a white solid. $^1$H-NMR (400 MHz, DMSO-$d_6$): δ 13.31 (br s, 1H), 8.59 (m, 2H), 7.73 (m, 1H), 7.45 (m, 2H), 7.38 (m, 1H) and 7.04 (m, 1H). MS: 368.14 (M−H)$^+$.

Preparation of 8-(1-(3,5-difluoro-4-(trifluoromethyl)phenyl)-5-(pyridin-3-yl)-1H-pyrazole-3-carbonyl)-1-(4-fluorophenyl)-1,3,8-triazaspiro[4.5]decan-4-one (Compound 268)

To an ice-cold solution of 1-(3,5-difluoro-4-(trifluoromethyl)phenyl)-5-(pyridin-3-yl)-1H-pyrazole-3-carboxylic acid 2.15 (0.10 g, 0.27 mmol) in DMF (2.0 mL) was added DIPEA (0.14 mL, 0.81 mmol) and HATU (0.154 g, 0.41 mmol). The resulting mixture was stirred under nitrogen atmosphere at 0° C. for 15 min followed by addition of 1-(4-fluorophenyl)-1,3,8-triazaspiro[4.5]decan-4-one (0.067 g, 0.27 mmol). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous $Na_2SO_4$, filtered and concentrated under reduced pressure. The crude residue was purified via prep-HPLC (0.035 g, 21%). $^1$H-NMR (400 MHz, DMSO-$d_6$+$D_2O$): δ 8.59-8.60 (m, 1H), 8.54-8.55 (m, 1H), 7.75 (d, J=8.0 Hz, 1H) 7.46-7.47 (m, 1H), 7.30-7.32 (m, 2H), 7.05-7.09 (m, 3H), 6.84-6.88 (m, 2H), 4.56 (s, 2H), 4.31-4.35 (m, 2H), 3.79-3.81 (m, 1H), 3.48-3.51 (m, 1H), 2.15-2.19 (m, 2H) and 1.71-1.75 (m, 2H). LCMS: 601.10 (M+H)$^+$, 99.21%.

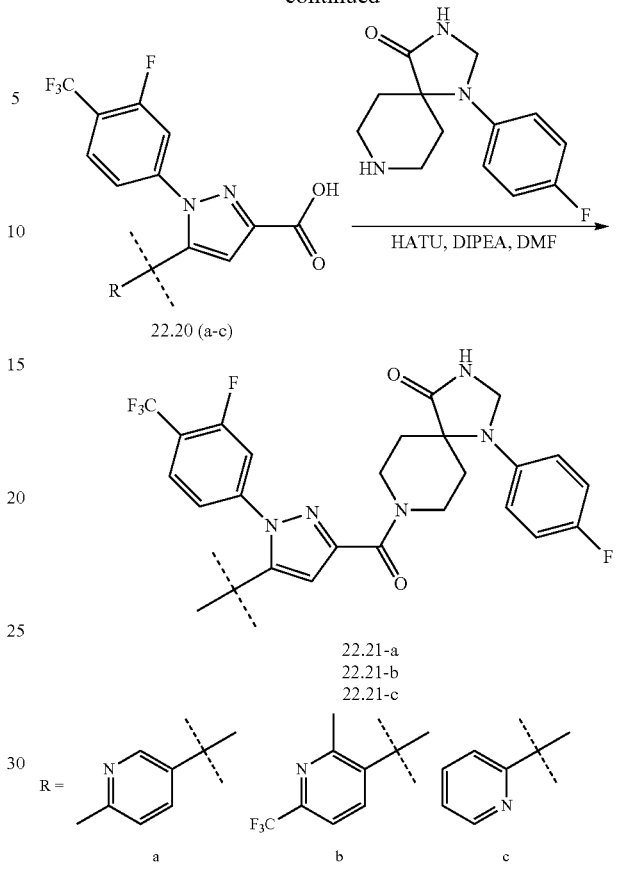

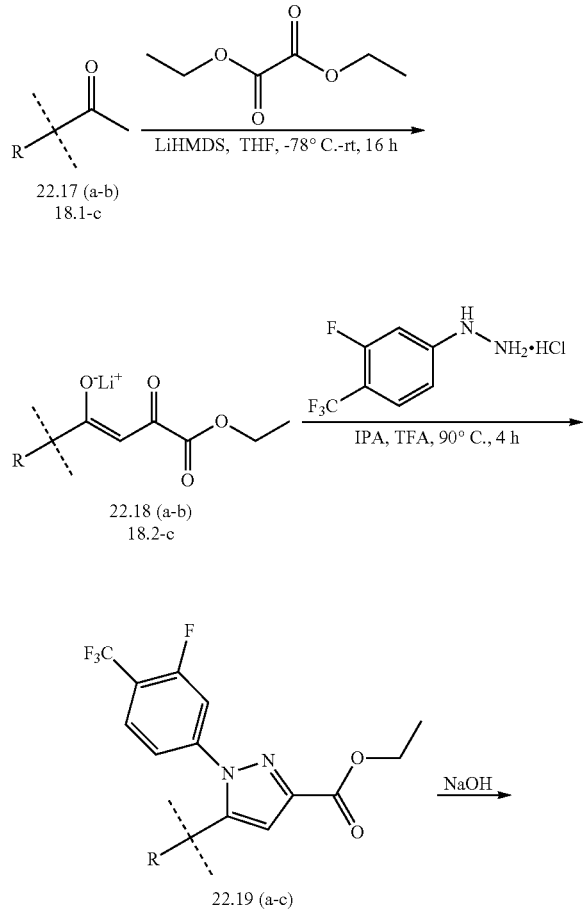

Preparation of 22.18 (a-b) and 18.1-c:
These intermediates were prepared following the general procedure mentioned in Scheme 18.

4-Ethoxy-1-(6-methylpyridin-3-yl)-3,4-dioxobut-1-en-1-olate Lithium Salt (22.18-a)

$^1$H-NMR (400 MHz, DMSO-$d_6$): δ 8.85 (s, 1H), 8.03 (d, J=7.2 Hz, 1H), 7.28 (d, J=8.0 Hz, 1H), 6.40 (s, 1H), 4.14 (q, J=6.8 Hz, 2H), 2.45 (s, 3H) and 1.25 (t, J=7.2 Hz, 3H). MS: 236.14 (M+H)$^+$. Yield: 80%.

4-Ethoxy-1-(2-methyl-6-(trifluoromethyl)pyridin-3-yl)-3,4-dioxobut-1-en-1-olate Lithium Salt (22.18-b)

$^1$H-NMR (400 MHz, DMSO-$d_6$): δ 7.87 (d, J=7.6 Hz, 1H), 7.70 (d, J=7.2 Hz, 1H), 5.91 (s, 1H), 4.17 (q, J=7.6 Hz, 2H), 2.58 (s, 3H) and 1.16 (t, J=7.2 Hz, 3H). MS: 304.12 (M+H)$^+$. Yield: 93%.

4-Ethoxy-3,4-dioxo-1-(pyridin-2-yl)but-1-en-1-olate Lithium Salt (18.2-c)

$^1$H-NMR (400 MHz, DMSO-$d_6$): δ 8.60 (d, J=4.4 Hz, 1H), 7.98 (m, 1H), 7.87 (m, 1H), 7.45 (m, 1H), 6.48 (s, 1H), 4.15 (q, J=7.20 Hz, 2H) and 1.19 (t, J=6.8 Hz, 3H). MS: 221.97 (M+H)$^+$. Yield: 96%.

Preparation of 22.19 (a-c):
These intermediates were prepared following the general procedure mentioned in Scheme 18.

Ethyl 1-(3-fluoro-4-(trifluoromethyl)phenyl)-5-(6-methylpyridin-3-yl)-1H-pyrazole-3-carboxylate (22.19-a)

¹H-NMR (400 MHz, CDCl₃): δ 8.61 (m, 1H), 7.60 (t, J=8.0 Hz, 1H), 7.53 (d, J=8.0 Hz, 1H), 7.32 (m, 2H), 7.13 (m, 2H), 4.44 (q, J=7.2 Hz, 2H), 2.68 (s, 3H) and 1.41 (t, J=7.2 Hz, 3H). MS: 394.17 (M+H)⁺. Yield: 57%.

Ethyl 1-(3-fluoro-4-(trifluoromethyl)phenyl)-5-(2-methyl-6-(trifluoromethyl)pyridin-3-yl)-1H-pyrazole-3-carboxylate (22.19-b)

¹H-NMR (400 MHz, CDCl₃): δ 7.69 (d, J=7.6 Hz, 1H), 7.60 (t, J=6.8 Hz, 1H), 7.53 (t, J=8.0 Hz, 1H), 7.30 (m, 2H), 7.03 (s, 1H), 4.46 (q, J=6.8 Hz, 2H), 2.37 (s, 3H) and 1.38 (t, J=6.8 Hz, 3H). MS: 462.25 (M+H)⁺. Yield: 26%.

Ethyl 1-(3-fluoro-4-(trifluoromethyl)phenyl)-5-(pyridin-2-yl)-1H-pyrazole-3-carboxylate (22.19-c)

¹H-NMR (400 MHz, CDCl₃): δ 8.52 (d, J=4.4 Hz, 1H), 7.77 (t, J=8.0 Hz, 1H), 7.55 (t, J=7.6 Hz, 1H), 7.47 (d, J=7.6 Hz, 1H), 7.29 (m, 2H), 7.25 (m, 1H), 7.19 (m, 1H), 4.43 (q, J=7.2 Hz, 2H) and 1.39 (t, J=7.2 Hz, 3H). MS: 380.20 (M+H)⁺. Yield: 40%.

Preparation of 22.20 (a-c):

These intermediates were prepared following the general procedure mentioned in Scheme 18.

1-(3-fluoro-4-(trifluoromethyl)phenyl)-5-(6-methylpyridin-3-yl)-1H-pyrazole-3-carboxylic Acid (22.20-a)

¹H-NMR (400 MHz, DMSO-d₆): δ 8.44 (s, 1H), 7.87 (m, 1H), 7.64 (d, J=7.2 Hz, 1H), 7.57 (m, 1H), 7.29 (m, 2H), 7.19 (m, 1H) and 2.50 (s, 3H). MS: 366.15 (M+H)⁺. Yield: 59%.

1-(3-Fluoro-4-(trifluoromethyl)phenyl)-5-(2-methyl-6-(trifluoromethyl)pyridin-3-yl)-1H-pyrazole-3-carboxylic Acid (22.20-b)

¹H-NMR (400 MHz, DMSO-d₆): δ 7.93 (d, J=8.0 Hz, 1H), 7.80 (d, J=8.0 Hz, 1H), 7.76 (m, 1H), 7.62 (m, 1H), 7.27 (m, 1H), 7.08 (m, 1H) and 2.63 (s, 3H). MS: 432.09 (M−H)⁺. Yield: 83%.

1-(3-Fluoro-4-(trifluoromethyl)phenyl)-5-(pyridin-2-yl)-1H-pyrazole-3-carboxylic Acid (22.20-c)

¹H-NMR (400 MHz, DMSO-d₆): δ 8.45 (d, J=4.0 Hz, 1H), 7.90 (t, J=8.0 Hz, 1H), 7.76 (m, 2H), 7.54 (d, J=7.2 Hz, 1H), 7.37 (m, 1H), 7.27 (d, J=8.0 Hz, 1H) and 7.20 (s, 1H): LC-MS: 351.97 (M+H)⁺, 99.57%. Yield: 47%.

Preparation of 22.21 (a-c):

These intermediates were prepared following the general procedure mentioned in Scheme 18.

Yields and the analytical data of the final compounds are set forth in Table 6.8.

TABLE 6.8

Tabulated data of the final compounds including the individual yields

| Comound No. | Structure | Yield (%) | LCMS | NMR data (DMSO-d₆, 400 MHz), unless otherwise specified |
|---|---|---|---|---|
| 262 | 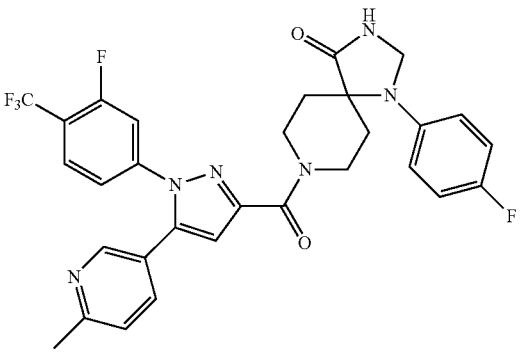 [SMILES: Cc1ccc(-c2cc(C(=O)N3CCC4(CC3)C(=O)NCN4c3ccc(F)cc3)nn2-c2ccc(C(F)(F)F)c(F)c2)cn1] | 22 | 597.18 (M + H)⁺, 97.44% | δ 8.81 (s, 1H), 8.45-8.46 (m, 1H), 7.83-7.87 (m, 1H), 7.58-7.65 (m, 2H), 7.28-7.32 (m, 2H), 7.08-7.12 (m, 3H), 6.84-6.87 (m, 2H), 4.58-4.59 (m, 2H), 4.42-4.45 (m, 2H), 3.84-3.87 (m, 1H), 3.50-3.54 (m, 1H), 2.50 (s, 3H), 2.20-2.23 (m, 2H) and 1.74-1.79 (m, 2H) |
| 263 | 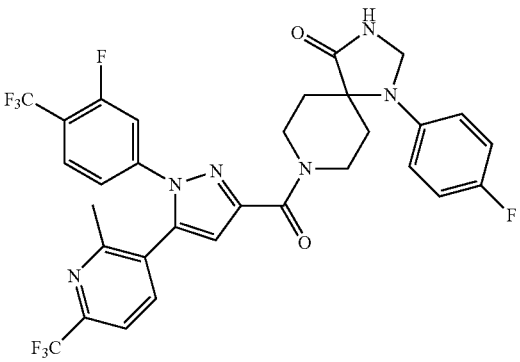 [SMILES: Cc1nc(C(F)(F)F)ccc1-c1cc(C(=O)N2CCC3(CC2)C(=O)NCN3c2ccc(F)cc2)nn1-c1ccc(C(F)(F)F)c(F)c1] | 26 | 663.10 (M − H)⁺, 98.09% | δ 8.82 (s, 1H), 7.94-7.96 (m, 1H), 7.80-7.83 (m, 2H), 7.60-7.63 (m, 1H), 7.17-7.19 (m, 2H), 7.09-7.11 (m, 2H), 6.85-6.89 (m, 2H), 4.60 (s, 2H), 4.44-4.45 (m, 2H), 3.86-3.89 (m, 1H), 3.53-3.55 (m, 1H), 2.40 (s, 3H), 2.22-2.25 (m, 2H) and 1.75-1.81 (m, 2H) |

TABLE 6.8-continued

Tabulated data of the final compounds including the individual yields

| Compound No. | Structure | Yield (%) | LCMS | NMR data (DMSO-$d_6$, 400 MHz), unless otherwise specified |
|---|---|---|---|---|
| 264 | 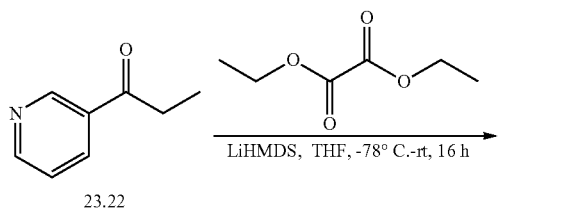 | 25 | 583.14 (M + H)$^+$, 96.24% | δ 8.81 (s, 1H), 8.47-8.48 (m, 1H), 7.92-7.96 (m, 1H), 7.79-7.81 (m, 2H), 7.57-7.60 (m, 1H), 7.39-7.42 (m, 1H), 7.27-7.30 (m, 2H), 7.08-7.12 (m, 2H), 6.84-6.87 (m, 2H), 4.58-4.59 (m, 2H), 4.44-4.45 (m, 2H), 3.84-3.88 (m, 1H), 3.50-3.54 (m, 1H), 2.17-2.21 (m, 2H) and 1.74-1.77 (m, 2H) |

Scheme 23:

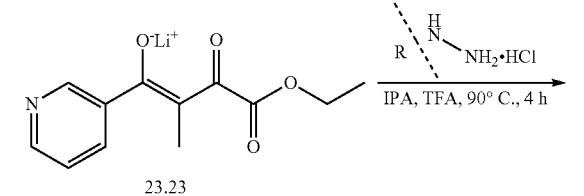

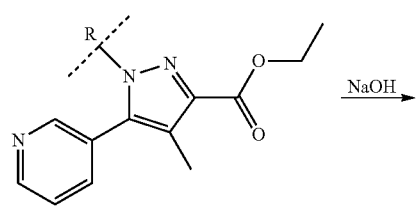

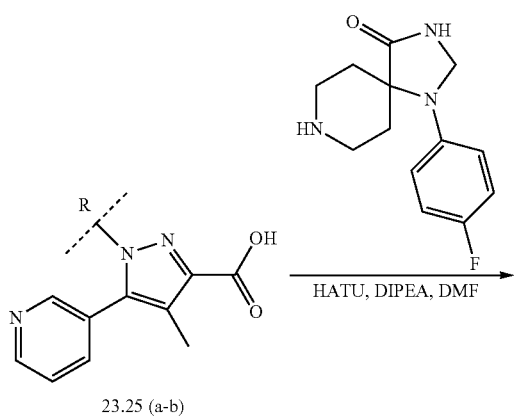

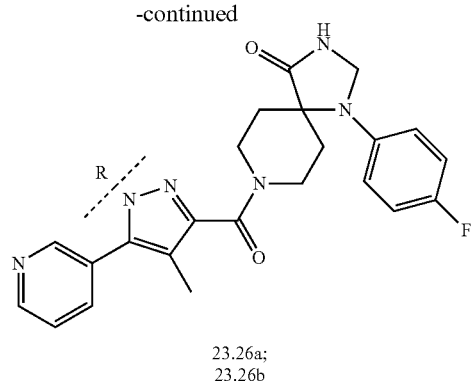

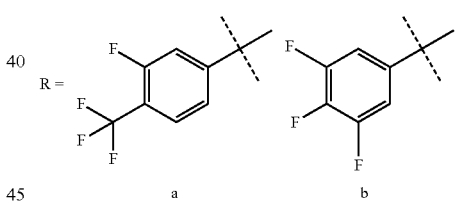

Preparation of 4-ethoxy-2-methyl-3,4-dioxo-1-(pyridin-3-yl)but-1-en-1-olate Lithium Salt (23.23)

A solution of 3-propionylpyridine 23.22 (2 g, 14.8 mmol) in diethyl ether (20 mL) was cooled to −78° C. followed by addition of LiHMDS (1.0 M in THF, 17 mL, 17.0 mmol). The resulting reaction mixture was stirred at −78° C. for 45 min followed by dropwise addition of diethyl oxalate (2.32 mL, 17.0 mmol) in about 30 min. The reaction mixture was then left to stir at room temperature for 16 h. After completion of the reaction (TLC and MS monitoring), the solution was then cooled 0° C. and the resulting precipitate was filtered to get the desired product as an off-white solid 23.23 (3.4 g, 98%), which was carried forward to the next step without purification. $^1$H-NMR (400 MHz, DMSO-$d_6$): δ 8.41 (m, 2H), 7.56 (d, J=7.60 Hz, 1H), 7.25 (d, J=7.60 Hz, 1H), 3.65 (q, J=7.20 Hz, 2H), 3.36 (s, 3H) and 1.08 (t, J=6.8 Hz, 3H). MS: 236.10 (M+H)$^+$.

General Procedure for the Preparation of Compounds 23.24 (a-b):

To an ice-cold solution of 4-ethoxy-2-methyl-3,4-dioxo-1-(pyridin-3-yl)but-1-en-1-olate lithium salt 23.23 (1 eq) in IPA was added respective hydrazine hydrochloride (1 eq) and TFA (2 eq). The resulting reaction mixture was warmed to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 23.24 (a-b).

Ethyl 1-(3-fluoro-4-(trifluoromethyl)phenyl)-4-methyl-5-(pyridin-3-yl)-1H-pyrazole-3-carboxylate (23.24-a)

$^1$H-NMR (400 MHz, CDCl$_3$): δ 8.73 (m, 1H), 8.57 (s, 1H), 7.68 (m, 1H), 7.60 (m, 3H), 7.02 (m, 1H), 4.45 (q, J=7.2 Hz, 2H), 2.33 (s, 3H) and 1.18 (t, J=7.6 Hz, 3H). MS: 394.08 (M+H)$^+$. Yield: 25%.

Ethyl 4-methyl-5-(pyridin-3-yl)-1-(3,4,5-trifluorophenyl)-1H-pyrazole-3-carboxylate (23.24-b)

$^1$H-NMR (400 MHz, CDCl$_3$): δ 8.62 (m, 1H), 8.49 (s, 1H), 7.69 (m, 1H), 7.49 (m, 1H), 7.40 (m, 2H), 4.36 (q, J=6.8 Hz, 2H), 2.22 (s, 3H) and 1.17 (t, J=6.8 Hz, 3H). MS: 362.13 (M+H)$^+$. Yield: 22%.

General Procedure for the Preparation of Compounds 23.25 (a-b):

To an ice-cold solution of compound 23.24 (a-b) (1.0 eq) in EtOH was added dropwise an aqueous solution of sodium hydroxide (3.0 eq). The resulting solution was stirred at room temperature for 4 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 23.25 (a-b) as a white solid.

1-(3-Fluoro-4-(trifluoromethyl)phenyl)-4-methyl-5-(pyridin-3-yl)-1H-pyrazole-3-carboxylic Acid (23.25-a)

$^1$H-NMR (400 MHz, DMSO-d$_6$): δ 13.12 (br s, 1H), 8.64 (m, 1H), 8.50 (s, 1H), 7.81 (t, J=8.0 Hz, 1H), 7.74 (d, J=7.6 Hz, 1H), 7.48 (m, 2H), 7.23 (d, J=8.0 Hz, 1H) and 2.21 (s, 3H). MS: 366.17 (M+H)$^+$. Yield: 65%.

4-Methyl-5-(pyridin-3-yl)-1-(3,4,5-trifluorophenyl)-1H-pyrazole-3-carboxylic Acid (23.25-b)

$^1$H-NMR (400 MHz, DMSO-d$_6$): δ 13.07 (br s, 1H), 8.62 (m, 1H), 8.49 (s, 1H), 7.69 (d, J=7.6 Hz, 1H), 7.46 (m, 1H), 7.36 (m, 2H) and 2.20 (s, 3H). LCMS: 334.13 (M+H)$^+$, 99.66%. Yield: 55%.

General Procedure for the Preparation of Final Compounds 23.26 (a-b):

To an ice-cold solution of carboxylic acids 23.25 (a-b) (1.0 eq), in DMF (2.0 mL) was added DIPEA (3.0 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC.

The yields and analytical data of the final compounds are set forth in Table 6.9.

TABLE 6.9

Tabulated data of the final compounds including the individual yields

| Compound No. | Structure | Yield (%) | LCMS | NMR data (DMSO-d$_6$, 400 MHz), unless otherwise specified |
|---|---|---|---|---|
| 265 | 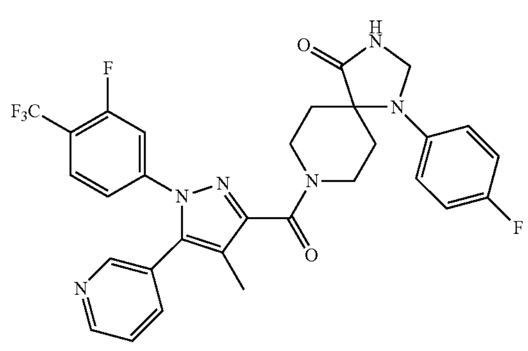 [SMILES: Cc1c(C(=O)N2CCC3(CC2)C(=O)NCN3c2ccc(F)cc2)nn(-c2ccc(C(F)(F)F)c(F)c2)c1-c1cccnc1] | 13 | 597.18 (M + H)$^+$, 99.21% | δ 8.82 (s, 1H), 8.64-8.66 (m, 1H), 8.53-8.54 (m, 1H), 7.75-7.80 (m, 2H), 7.46-7.53 (m, 2H), 7.07-7.16 (m, 3H), 6.85-6.88 (m, 2H), 4.59-4.60 (m, 2H), 4.45-4.48 (m, 1H), 4.10-4.13 (m, 1H), 3.79-3.85 (m, 1H), 3.51-3.57 (m, 1H), 2.36-2.38 (m, 1H), 2.27-2.29 (m, 1H), 2.09 (s, 3H), 1.80-1.84 (m, 1H) and 1.72-1.75 (m, 1H) |

TABLE 6.9-continued

Tabulated data of the final compounds including the individual yields

| Compound No. | Structure | Yield (%) | LCMS | NMR data (DMSO-$d_6$, 400 MHz), unless otherwise specified |
|---|---|---|---|---|
| 266 | 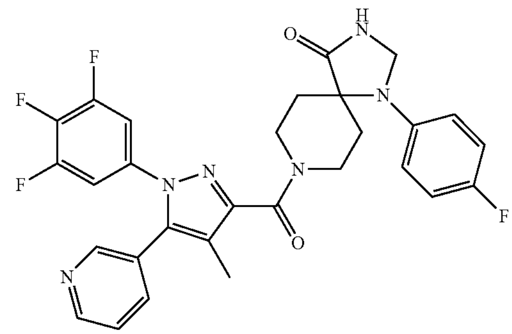 [SMILES: Cc1c(C(=O)N2CCC3(CC2)C(=O)NCN3c2ccc(F)cc2)nn(-c2cc(F)c(F)c(F)c2)c1-c1cccnc1] | 12 | 565.14 (M + H)$^+$, 99.90% | δ 8.81 (s, 1H), 8.62-8.63 (m, 1H), 8.50-8.51 (m, 1H), 7.70 (d, J = 8.0 Hz, 1H), 7.47-7.49 (m, 1H), 7.29-7.31 (m, 2H), 7.07-7.12 (m, 2H), 6.84-6.87 (m, 2H), 4.59 (s, 2H), 4.43-4.46 (m, 1H), 4.12-4.15 (m, 1H), 3.78-3.83 (m, 1H), 3.50-3.53 (m, 1H), 2.26-2.30 (m, 2H), 2.08 (s, 3H) and 1.71-1.83 (m, 2H) |

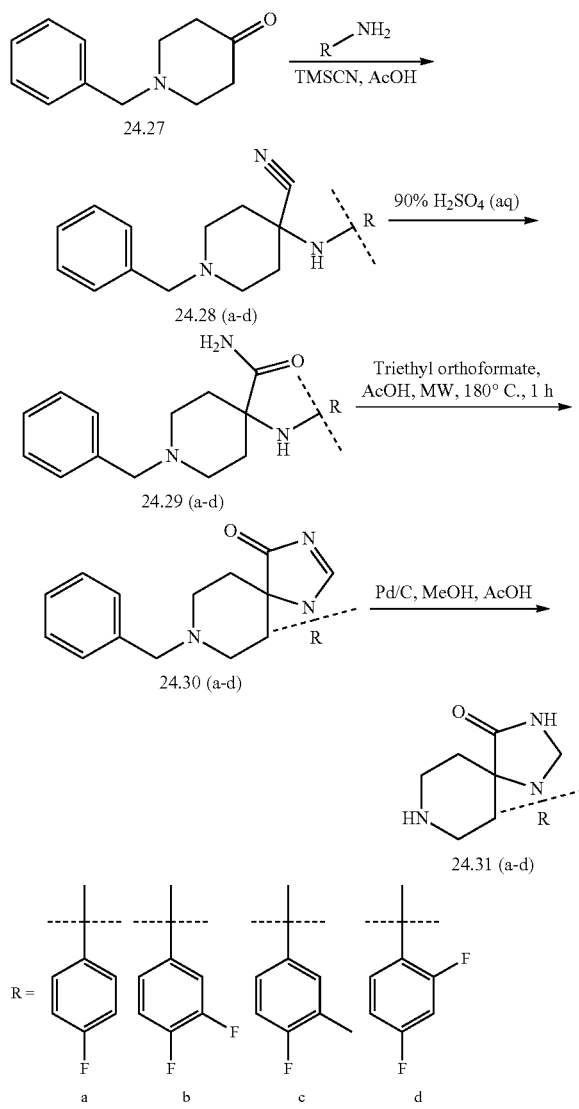

Scheme 24:

General Procedure for the Preparation of 24.28 (a-d):

To an ice-cold solution of 1-benzylpiperidin-4-one 24.27 (1 eq) in acetic acid was added respective aryl amines (1.1 eq) and trimethylsilyl cyanide (1.5 eq). The resulting reaction mass was stirred at RT for 18 h. After completion of the reaction (TLC monitoring), the reaction mass was cooled to 0° C. and the pH adjusted to ~10 using 5.0 N sodium hydroxide solution. The aqueous part was extracted with DCM (3×250 mL). The combined organics were dried over anhydrous $Na_2SO_4$, filtered and concentrated. The crude was triturated with diethyl ether to get the desired product 24.28 (a-d) as off white solid.

1-Benzyl-4-((4-fluorophenyl)amino)piperidine-4-carbonitrile (24.28-a)

$^1$H-NMR (400 MHz, CDCl$_3$): δ 7.32 (m, 5H), 6.91-6.94 (m, 4H), 3.55 (s, 2H), 3.47 (br s, 1H), 2.81-2.84 (m, 2H), 2.39 (m, 2H), 2.21-2.24 (m, 2H) and 1.87-1.94 (m, 2H). LC-MS: 310.13 (M+H)$^+$, 96.16%. Yield: 84%

1-Benzyl-4-((3,4-difluorophenyl)amino)piperidine-4-carbonitrile (24.28-b)

$^1$H-NMR (400 MHz, CDCl$_3$): δ 7.28 (m, 5H), 7.00 (m, 1H), 6.73 (m, 1H), 6.61 (m, 1H), 3.58 (br s, 1H), 3.55 (s, 2H), 2.80 (m, 2H), 2.41 (m, 2H), 2.26 (m, 2H) and 1.87 (m, 2H). LC-MS: 328.42 (M+H)+, 94.27%. Yield: 50%

1-Benzyl-4-((4-fluoro-3-methylphenyl)amino)piperidine-4-carbonitrile (24.28-c)

$^1$H-NMR (400 MHz, CDCl$_3$): δ 7.31 (m, 5H), 6.87 (m, 1H), 6.74 (m, 2H), 3.55 (s, 2H), 3.40 (s, 1H), 2.81-2.84 (m, 2H), 2.39 (m, 2H), 2.23 (s, 3H), 2.21 (m, 2H) and 1.87 (m, 2H). LC-MS: 324.40 (M+H)$^+$, 92.13%. Yield: 77%

1-Benzyl-4-((2,4-difluorophenyl)amino)piperidine-4-carbonitrile (24.28-d)

$^1$H-NMR (400 MHz, CDCl$_3$): δ 7.28 (m, 5H), 7.12 (m, 1H), 6.69 (m, 2H), 3.71 (br s, 1H), 3.62 (s, 2H), 2.81 (m, 2H), 2.41 (m, 2H), 2.19 (m, 2H) and 1.91 (m, 2H). LC-MS: 328.26 (M+H)$^+$, 95.96%. Yield: 36%

General Procedure for the Preparation of 24.29 (a-d):

To an ice-cold solution of 24.28 (a-d) (1.0 eq) was added 90% aqueous sulphuric acid and the resulting reaction mixture was stirred at room temperature for 16 h. After completion of the reaction (TLC monitoring), the reaction mass was cooled to 0° C. and the pH adjusted to ~10 using 5.0 N sodium hydroxide solution. The aqueous part was extracted with DCM. The combined organics were dried over anhydrous sodium sulphate, filtered and concentrated. The crude was triturated with diethyl ether to get the desired product 24.29 (a-d) as off-white solid.

1-Benzyl-4-(4-fluorophenylamino)piperidine-4-carboxamide (24.29-a)

$^1$H-NMR (400 MHz, CDCl$_3$): δ 7.23 (m, 5H), 6.87 (m, 3H), 6.55 (m, 2H), 5.47 (br s, 1H), 3.93 (s, 1H), 3.48 (s, 2H), 2.72 (m, 2H), 2.28 (m, 2H), 2.04 (m, 2H) and 1.86 (m, 2H). LCMS: 328.12 (M+H)+, 99.60%. Yield: 84%

1-Benzyl-4-((3,4-difluorophenyl)amino)piperidine-4-carboxamide (24.29-b)

$^1$H-NMR (400 MHz, CDCl$_3$): δ 7.30 (m, 5H), 6.88 (m, 1H), 6.78 (br s, 1H), 6.42 (m, 1H), 6.29 (m, 1H), 5.51 (br s, 1H), 3.98 (s, 1H), 3.48 (s, 2H), 2.73 (m, 2H), 2.28 (m, 2H), 2.04 (m, 2H) and 1.85 (m, 2H). LCMS: 346.14 (M+H)$^+$, 92.24%. Yield: 66%

1-Benzyl-4-((3-fluoro-4-methylphenyl)amino)piperidine-4-carboxamide (24.29-c)

$^1$H-NMR (400 MHz, DMSO-d$_6$): δ 7.24 (m, 5H), 7.18 (s, 1H), 7.02 (br s, 1H), 6.81 (m, 1H), 6.45 (m, 1H), 6.35 (m, 1H), 5.34 (br s, 1H), 3.41 (s, 2H), 2.50 (m, 2H), 2.24 (m, 2H), 2.09 (s, 3H), 1.95 (m, 2H) and 1.81 (m, 2H). LCMS: 342.33 (M+H)$^+$, 97.83%. Yield: 59%

1-Benzyl-4-((2,4-difluorophenyl)amino)piperidine-4-carboxamide (24.29-d)

$^1$H-NMR (400 MHz, DMSO-d$_6$): δ 7.20 (m, 6H), 7.10 (m, 1H), 7.07 (br s, 1H), 6.82 (m, 1H), 6.46 (m, 1H), 4.78 (s, 1H), 3.41 (s, 2H), 2.52 (m, 2H), 2.13 (m, 2H), 1.98 (m, 2H) and 1.83 (m, 2H). LCMS: 346.25 (M+H)$^+$, 96.72%. Yield: 46.9%

General Procedure for the Preparation of 24.30 (a-d):

A solution of compounds 24.29 (a-d) in triethylorthoformate and AcOH (3:1) was irradiated by microwave in a sealed tube to 190° C. for 2 h. The reaction mixture was diluted with water and extracted with EtOAc. The combined organics were washed with brine, dried over anhydrous Na$_2$SO$_4$, filtered and concentrated. The residue was purified over silica gel (100-200 M, 2-4% MeOH-DCM) to get the desired product 24.30 (a-d) as off-white solid.

8-Benzyl-1-(4-fluorophenyl)-1,3,8-triazaspiro[4.5]dec-2-en-4-one (24.30-a)

$^1$H-NMR (400 MHz, DMSO-d$_6$): δ 8.65 (s, 1H), 7.44 (m, 2H), 7.34 (m, 2H), 7.13 (m, 5H), 3.41 (s, 2H), 2.66 (m, 2H), 2.41 (m, 2H) and 1.75 (m, 4H). MS: 338.22 (M+H)$^+$. Yield: 48%.

8-Benzyl-1-(3,4-difluorophenyl)-1,3,8-triazaspiro[4.5]dec-2-en-4-one (24.30-b)

LCMS: 356.29 (M+H)+, 82.22%. Yield: 22%.

8-Benzyl-1-(4-fluoro-3-methylphenyl)-1,3,8-triazaspiro[4.5]dec-2-en-4-one (24.30-c)

MS: 352.13 (M+H)$^+$. Yield: 31%.

8-benzyl-1-(2,4-difluorophenyl)-1,3,8-triazaspiro[4.5]dec-2-en-4-one (24.30-d)

MS: 356.19 (M+H)$^+$. Yield: 18%.

General Procedure for the Preparation of 24.31 (a-d):

To a solution of compounds 24.30 (a-d) (1.0 eq) in MeOH and AcOH (40:1, 20 mL) was added Pd—C (w/w, 10 mol %) and the resulting solution was stirred under hydrogen atmosphere (1 atm) at ambient temperature for 16 h. The reaction mixture was filtered through diatomaceous earth (Celite) bed and the filtrate was concentrated under reduced pressure. The residue was purified over silica gel (basic alumina, 2-4% MeOH-DCM) to get the desired product 24.31 (a-d) as off-white solid.

1-(4-Fluorophenyl)-1,3,8-triazaspiro[4.5]dec-2-en-4-one (24.31-a)

$^1$H-NMR (400 MHz, DMSO-d$_6$): δ 8.79 (br s, 1H), 7.03 (m, 2H), 6.95 (m, 2H), 4.56 (s, 2H), 3.37 (m, 3H), 2.95 (m, 2H), 2.33 (m, 2H) and 1.62 (m, 2H). LCMS: 250.13 (M+H)$^+$, 81.19%. Yield: 70%

1-(3,4-Difluorophenyl)-1,3,8-triazaspiro[4.5]dec-2-en-4-one (24.31-b)

MS: 268.20 (M+H)$^+$. Yield: 25%

1-(4-Fluoro-3-methylphenyl)-1,3,8-triazaspiro[4.5]dec-2-en-4-one (24.31-c)

$^1$H-NMR (400 MHz, DMSO-d$_6$): δ 8.58 (br s, 1H), 6.96 (m, 1H), 6.83 (m, 2H), 4.52 (s, 2H), 3.40 (m, 1H), 3.17 (m, 2H), 2.83 (m, 2H), 2.15 (m, 3H), 2.09 (m, 2H) and 1.49 (m, 2H). MS: 264.14 (M+H)$^+$. Yield: 50%

1-(2,4-Difluorophenyl)-1,3,8-triazaspiro[4.5]dec-2-en-4-one (24.31-d)

$^1$H-NMR (400 MHz, DMSO-d$_6$): δ 8.66 (br s, 1H), 7.47 (m, 1H), 7.27 (m, 1H), 7.08 (m, 1H), 4.51 (s, 2H), 3.12 (m, 1H), 2.81 (m, 2H), 1.83 (m, 4H) and 1.40 (m, 2H). LCMS: 268.12 (M+H)$^+$, 92.83%. Yield: 90%

Scheme 25:

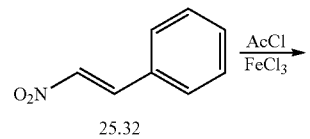

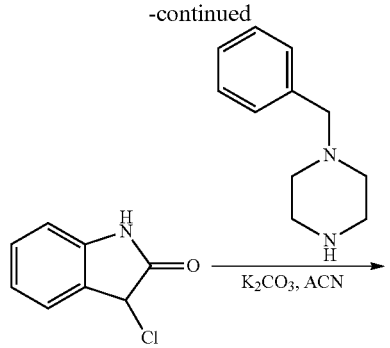

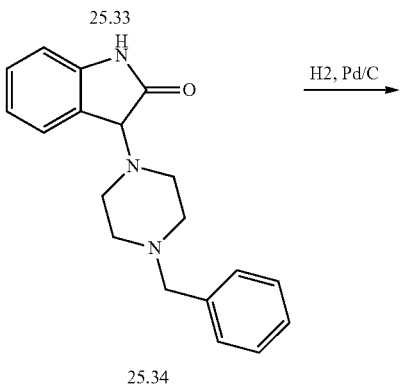

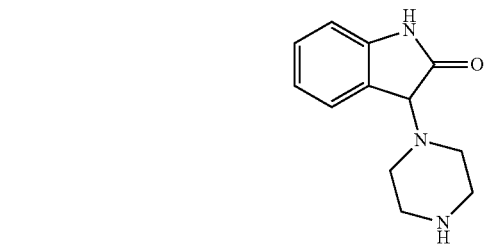

Preparation of 3-chloroindolin-2-one (25.33)

To an ice-cold solution of nitrostyrene 25.32 (5.0 g, 335.55 mmol) in DCM was added acetyl chloride (5.0 mL, 67.11 mmol) and FeCl$_3$ (13.0 g, 67.11 mmol). The resulting reaction mass was stirred at 0° C. for 5 h. After completion of reaction (TLC monitoring), added 0.1M HCl (100 mL) and stirred at RT for 16 h. The resulting reaction mixture was extracted with DCM (3×100 mL). The combined organics were washed with brine, dried over anhydrous Na$_2$SO$_4$, filtered and concentrated. The residue was purified over silica gel (100-200 M, 25% EtOAc/hexane) to get the desired product 25.33 (2.4 g, 43%) as off-white solid. $^1$H-NMR (400 MHz, DMSO-d$_6$): δ 10.76 (br s, 1H), 7.35 (d, J=7.6 Hz, 1H), 7.27 (t, J=7.6 Hz, 1H), 7.03 (t, J=7.2 Hz, 1H), 6.86 (d, J=7.6 Hz, 1H) and 5.57 (s, 1H). LCMS: 166.07 (M−H)$^+$, 99.70%.

Preparation of 3-(4-benzylpiperazin-1-yl) indolin-2-one (25.34)

To a solution of 3-chloroindolin-2-one 25.33 (1.0 g, 5.97 mmol) in ACN (10 mL) was added potassium carbonate (1.23 g, 8.96 mmol) and 1-benzylpiperazine (1.16 g, 6.57 mmol). The resulting reaction mixture was heated at 80° C. for 16 h. After completion of the reaction (TLC monitoring), the solvent was evaporated and the residue was diluted with water and extracted with ethyl acetate (3 times). The combined organics were washed with brine, dried over anhydrous Na$_2$SO$_4$, filtered and concentrated. The crude was purified over silica gel (100-200 M, 40% EtOAc-hexane) to get the desired product 25.34 (0.62 g, 31%). $^1$H-NMR (400 MHz, DMSO-d$_6$): δ 7.84 (br s, 1H), 7.36 (d, J=7.6 Hz, 1H), 7.20 (m, 6H), 7.01 (t, J=7.6 Hz, 1H), 6.80 (d, J=7.6 Hz, 1H), 4.29 (s, 1H), 3.51 (s, 2H), 2.88 (m, 2H), 2.65 (m, 2H) and 2.49 (m, 4H). MS: 308.21 (M+H)$^+$.

Preparation of 3-(piperazin-1-yl) indolin-2-one (25.35)

To a solution of 3-(4-benzylpiperazin-1-yl) indolin-2-one 25.34 (0.30 g, 0.98 mmol) in MeOH and AcOH (40:1, 10 mL) was added Pd—C (w/w, 10 mol %) and the resulting solution was stirred under hydrogen atmosphere (1 atm) at ambient temperature for 16 h. The reaction mixture was filtered through diatomaceous earth (Celite) bed and the filtrate was concentrated under reduced pressure to get the desired product 25.35 (0.16 g, 76%) as off-white solid. $^1$H-NMR (400 MHz, DMSO-d$_6$): δ 10.32 (br s, 1H), 7.23 (d, J=7.2 Hz, 1H), 7.17 (m, 1H), 6.93 (t, J=6.8 Hz, 1H), 6.71 (d, J=8.0 Hz, 1H), 4.25 (s, 1H), 2.53 (m, 1H), 2.50 (m, 4H), 2.38 (m, 2H) and 1.87 (m, 2H). MS: 218.16 (M+H)$^+$.

Scheme 26:

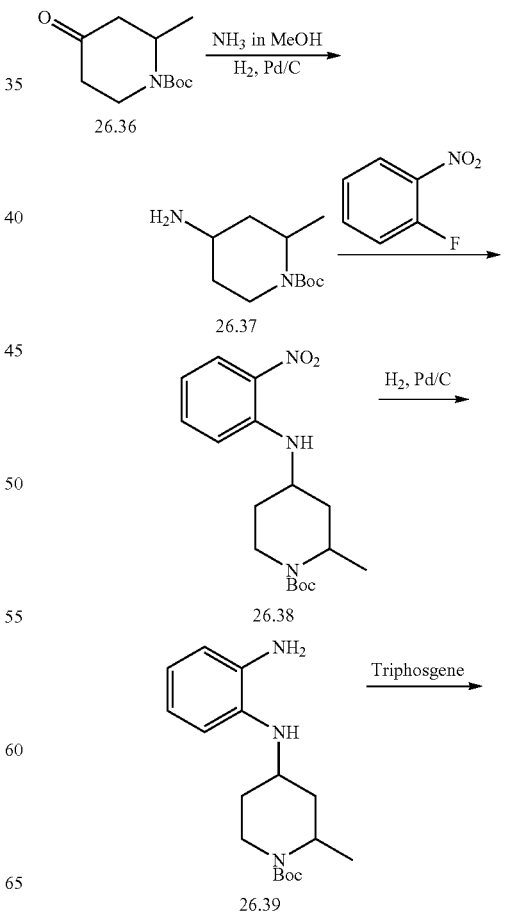

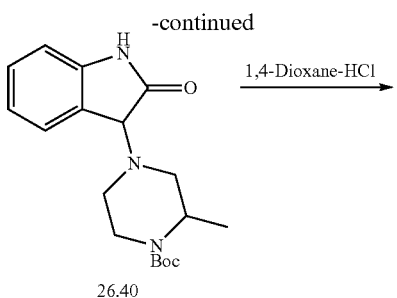

26.40

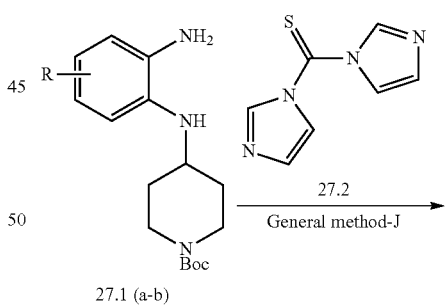

26.41

Preparation of tert-butyl 4-amino-2-methylpiperidine-1-carboxylate (26.37)

To a solution of tert-butyl 2-methyl-4-oxopiperidine-1-carboxylate 26.36 (2.0 g, 9.38 mmol) in methanolic ammonia (~4N, 200 mL) was added Pd/C (10 mol %, 0.2 g). The resulting reaction mixture was stirred at 50 PSI for 60 h under hydrogen atmosphere. After completion of the reaction (TLC monitoring), the reaction mass was filtered through diatomaceous earth (Celite) bed. The filtrate was dried under reduced pressure to get desired product 26.37 (2.0 g, quantitative yield) as semi solid. MS: 215.17 (M+H)$^+$.

Preparation of tert-butyl 2-methyl-4-((2-nitrophenyl)amino)piperidine-1-carboxylate (26.38)

To an ice-cold solution of tert-butyl 4-amino-2-methylpiperidine-1-carboxylate 26.37 (1.7 g, 7.93 mmol) in DMF (10 mL) was added DIPEA (2.0 mL, 11.89 mmol) and 1-fluoro-2-nitrobenzene (1.2 g, 7.93 mmol). The resulting reaction mixture was heated at 80° C. for 16 h. After completion of the reaction (TLC monitoring), the solvent was evaporated and the residue was diluted with water and extracted with ethyl acetate (3 times). The combined organics were washed with brine, dried over anhydrous Na$_2$SO$_4$, filtered and concentrated. The crude was purified over silica gel (100-200 M, 10% EtOAc-hexane) to get the desired product 26.38 (1.3 g, 50%). $^1$H-NMR (400 MHz, CDCl$_3$): δ 8.38 (m, 1H), 8.18 (d, J=8.8 Hz, 1H), 7.42 (t, J=7.2 Hz, 1H), 6.82 (d, J=8.8 Hz, 1H), 6.40 (t, J=7.6 Hz, 1H), 4.30 (m, 1H), 3.90 (m, 1H), 3.21 (m, 2H), 1.95 (m, 2H), 1.77 (m, 2H), 1.47 (s, 9H) and 1.30 (d, J=6.8 Hz, 3H). LCMS: 334.21 (M−H)$^+$, 89.85%.

Preparation of tert-butyl 4-((2-aminophenyl)amino)-2-methylpiperidine-1-carboxylate (26.39)

To a solution of tert-butyl 2-methyl-4-((2-nitrophenyl)amino)piperidine-1-carboxylate 26.38 (1.30 g, 3.87 mmol) in MeOH (10 mL) was added Pd—C (w/w, 10 mol %) and the resulting solution was stirred under hydrogen atmosphere (1 atm) at ambient temperature for 16 h. The reaction mixture was filtered through diatomaceous earth (Celite) bed and the filtrate was concentrated under reduced pressure to get the desired product 26.39 (1.15 g, quantitative) as off-white solid. MS: 306.20 (M+H)$^+$.

Preparation of tert-butyl 2-methyl-4-(2-oxo-2,3-dihydro-1H-benzo[d]imidazol-1-yl)piperidine-1-carboxylate (26.40)

To an ice-cold solution of tert-butyl 4-((2-aminophenyl)amino)-2-methylpiperidine-1-carboxylate 26.39 (0.50 g, 1.64 mmol) in THF (20 mL) was added Et$_3$N (0.34 mL, 2.46 mmol) and triphosgene (0.59 g, 1.96 mmol). The resulting reaction mixture was heated at RT for 4 h. After completion of the reaction (TLC monitoring), the solvent was evaporated and the residue was diluted with water and extracted with ethyl acetate (3 times). The combined organics were washed with brine, dried over anhydrous Na$_2$SO$_4$, filtered and concentrated. The crude was purified over silica gel (100-200 M, 40% EtOAc-hexane) to get the desired product 26.40 (0.5 g, 90%). $^1$H-NMR (400 MHz, DMSO-d$_6$): δ 10.86 (br s, 1H), 7.23 (m, 1H), 6.97 (m, 3H), 4.34 (m, 1H), 3.64 (m, 2H), 2.27 (m, 1H), 1.94 (m, 2H), 1.72 (m, 2H), 1.43 (s, 9H) and 1.35 (m, 3H). MS: 330.22 (M−H)$^+$.

Preparation of 1-(2-methylpiperidin-4-yl)-1,3-dihydro-2H-benzo[d]imidazol-2-one Hydrochloride Salt (26.41)

An ice-cold solution of tert-butyl 2-methyl-4-(2-oxo-2,3-dihydro-1H-benzo[d]imidazol-1-yl)piperidine-1-carboxylate 26.40 (0.25 g, 0.75 mmol) in 1,4-dioxane-HCl (~4N, 10 mL) was stirred at RT for 2 h. After completion of the reaction (TLC monitoring), the reaction mass was dried under reduced pressure to get desired product 26.41 (0.2 g, quantitative) as off-white solid. MS: 232.12 (M+H)$^+$.

Scheme 27:

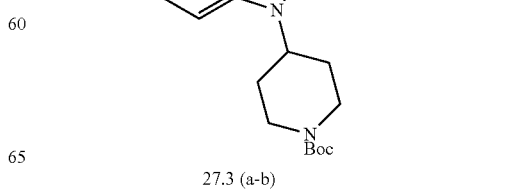

27.1 (a-b)

27.3 (a-b)

273
-continued

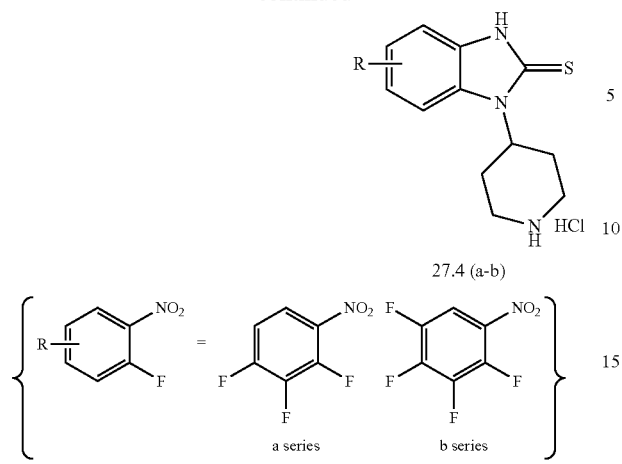

27.4 (a-b)

General Procedure for the Preparation of 27.3 (a-b):

General Method J:

To an ice-cold solution of compound 27.1-a or b (1.0 eq) in THF was added Et$_3$N (2.0 eq) and 1,1'-thiocarbonyldiimidazole 27.2 (1.5 eq). The resulting reaction mixture was stirred at RT for 4 h. After completion of the reaction (TLC monitoring), the solvent was evaporated and the residue was diluted with water and extracted with ethyl acetate (3 times). The combined organics were washed with brine, dried over anhydrous Na$_2$SO$_4$, filtered and concentrated. The crude was purified over silica gel (100-200 M, 40-45% EtOAc-hexane) to get the desired product 27.3 (a-b).

tert-Butyl 4-(6,7-difluoro-2-thioxo-2,3-dihydro-1H-benzo[d]imidazol-1-yl)piperidine-1-carboxylate (27.3a)

LCMS: 268.29 (M−H)$^+$, 93.54%. Yield: 47% tert-Butyl 4-(5,6,7-trifluoro-2-thioxo-2,3-dihydro-1H-benzo[d]imidazol-1-yl)piperidine-1-carboxylate (27.3b)

$^1$H-NMR (400 MHz, DMSO-d$_6$): δ 12.14 (br s, 1H), 6.37-6.42 (m, 1H), 4.01-4.07 (m, 1H), 3.84-3.89 (m, 2H), 2.67-2.71 (m, 2H), 1.71-1.74 (m, 2H), 1.42-1.43 (m, 2H) and 1.38 (s, 9H). MS: 386.05 (M−H)$^+$, Yield: 72%.

General Procedure for the Preparation of 27.4 (a-b):

This compound was prepared following the general method M (Scheme 8).

6,7-Difluoro-1-(piperidin-4-yl)-1,3-dihydro-2H-benzo[d]imidazole-2-thione Hydrochloride (27.4a)

$^1$H-NMR (400 MHz, DMSO-d$_6$): δ 13.24 (br s, 1H), 9.06 (br s, 1H), 8.48 (br s, 1H), 7.27-7.34 (m, 1H), 7.01-7.02 (s, 1H), 5.45-5.55 (m, 1H), 3.56-3.61 (m, 4H), 3.14-3.17 (m, 2H) and 1.93-1.96 (m, 2H). LCMS: 260.30 (M+H)$^+$, 91.35%. Yield: 98%.

274

5,6,7-Trifluoro-1-(piperidin-4-yl)-1,3-dihydro-2H-benzo[d]imidazole-2-thione Hydrochloride (27.4b)

MS: 287.99 (M+H)$^+$. Yield: 58%.

Scheme 28

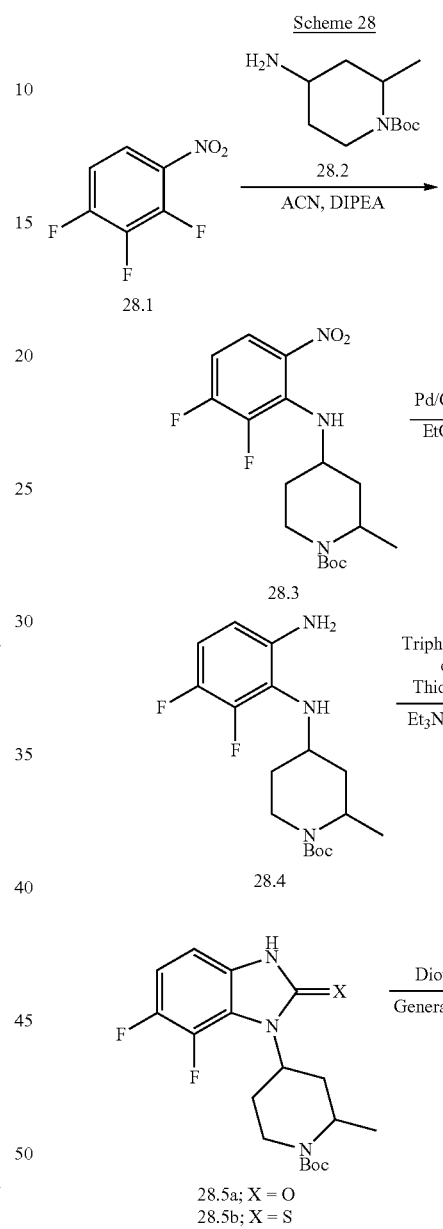

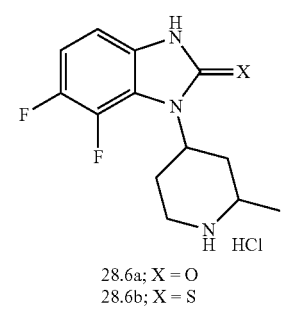

28.6a; X = O
28.6b; X = S

Preparation of tert-butyl 4-((2,3-difluoro-6-nitrophenyl)amino)-2-methylpiperidine-1-carboxylate (28.3)

To an ice-cold solution of tert-butyl 4-amino-2-methylpiperidine-1-carboxylate 28.2 (1.06 g, 4.97 mmol) in acetonitrile (15 mL) was added DIPEA (1.0 mL, 5.65 mmol) and 1,2,3-trifluoro-4-nitrobenzene 28.1 (0.8 g, 4.52 mmol). The resulting reaction mixture was stirred at RT for 3 h. After completion of the reaction (TLC monitoring), the reaction mass was diluted with ice-cold water (100 mL) and extracted with EtOAc (100 mL×3 times). The combined organics were washed with brine, dried over anhydrous $Na_2SO_4$, filtered and concentrated. The crude was purified over silica gel (100-200 M, 10-15% EtOAc-hexane) to get the desired product 28.3 (1.4 g, Yield: 85%) as pale yellow solid. $^1$H-NMR (400 MHz, CDCl$_3$): δ 8.26 (br s, 1H), 8.01-8.05 (m, 1H), 6.47-6.54 (m, 1H), 4.20-4.24 (m, 2H), 3.87-3.93 (m, 1H), 3.18-3.25 (m, 1H), 2.00-2.09 (m, 2H), 1.71-1.76 (m, 2H), 1.46 (s, 9H) and 1.22 (d, J=7.2 Hz, 3H). LCMS: 370.34 (M–H)$^+$, 93.68%.

Preparation of tert-butyl 4-((6-amino-2,3-difluorophenyl)amino)-2-methylpiperidine-1-carboxylate (28.4)

To a solution of tert-butyl 4-((2,3-difluoro-6-nitrophenyl)amino)-2-methylpiperidine-1-carboxylate 28.3 (1.4 g, 3.78 mmol) in EtOAc (40 mL) was added Pd—C (0.14 g, 0.38 mmol, w/w, 10 mol %) and the resulting solution was stirred under hydrogen atmosphere (1 atm) at ambient temperature for 16 h. The reaction mixture was filtered through a diatomaceous earth (Celite) bed and the filtrate was concentrated under reduced pressure to get the desired product 28.4 (1.1 g, Yield: 91.0%) as viscous liquid. $^1$H-NMR (400 MHz, DMSO-d$_6$): δ 6.57-6.64 (m, 1H), 6.32-6.36 (m, 1H), 4.76 (br s, 2H), 3.94-3.96 (m, 1H), 3.74-3.78 (m, 1H), 3.48-3.51 (m, 1H), 3.30-3.34 (m, 1H), 3.20-3.24 (m, 1H), 1.71-1.82 (m, 2H), 1.45-1.48 (m, 2H), 1.37 (s, 9H) and 1.14 (d, J=6.8 Hz, 3H). LCMS: 342.11 (M+H)$^+$, 94.16%. Yield: 92%.

General Procedure for the Preparation of 28.5 (a-b):

To an ice-cold solution of compound 17 (1.0 eq) in THF was added Et$_3$N (2.0 eq) and triphosgene (1.5 eq, for 18a) or 1,1'-thiocarbonyldiimidazole (1.5 eq, for 18b). The resulting reaction mixture was stirred at RT for 4 h. After completion of the reaction (TLC monitoring), the solvent was evaporated and the residue was diluted with water and extracted with ethyl acetate (3 times). The combined organics were washed with brine, dried over anhydrous $Na_2SO_4$, filtered and concentrated. The crude was purified over silica gel (100-200 M, 40-45% EtOAc-hexane) to get the desired product 18 (a-b).

tert-Butyl 4-(6,7-difluoro-2-oxo-2,3-dihydro-1H-benzo[d]imidazol-1-yl)-2-methylpiperidine-1-carboxylate (28.5-a)

$^1$H-NMR (400 MHz, CDCl$_3$): δ 9.45 (br s, 1H), 7.06-7.08 (m, 1H), 6.99-7.04 (m, 1H), 4.70-4.72 (m, 1H), 3.99-4.02 (m, 1H), 3.85-3.89 (m, 1H), 3.73-3.74 (m, 1H), 3.35-3.43 (m, 1H), 2.19-2.26 (m, 2H), 1.84-1.90 (m, 1H), 1.30-1.33 (m, 9H) and 1.24 (d, J=6.4 Hz, 3H). MS: 366.33 (M–H)$^+$. Yield: 56%.

tert-Butyl 4-(6,7-difluoro-2-thioxo-2,3-dihydro-1H-benzo[d]imidazol-1-yl)-2-methylpiperidine-1-carboxylate (28.5-b)

LCMS: 384.15 (M+H)$^+$, 89.21%. Yield: 71%.

General Procedure for the Preparation of 28.6 (a-b):

These compounds were prepared following the general method M (Scheme 8).

6,7-Difluoro-1-(2-methylpiperidin-4-yl)-1,3-dihydro-2H-benzo[d]imidazol-2-one Hydrochloride (28.6-a)

$^1$H-NMR (400 MHz, DMSO-d$_6$): δ 11.33 (br s, 1H), 9.41-9.43 (m, 1H), 8.64 (br s, 1H), 7.01-7.05 (m, 1H), 6.78-6.81 (m, 1H), 4.58-4.64 (m, 1H), 3.52-3.56 (m, 2H), 2.42-3.49 (m, 1H), 2.17-2.20 (m, 1H), 1.90-1.99 (m, 3H) and 1.27 (d, J=6.4 Hz, 3H). MS: 266.0 (M–H)$^+$. Yield: 92%.

6,7-Difluoro-1-(2-methylpiperidin-4-yl)-1,3-dihydro-2H-benzo[d]imidazole-2-thione Hydrochloride (28-6b)

$^1$H-NMR (400 MHz, DMSO-d$_6$): δ 13.35 (br s, 1H), 9.26 (br s, 1H), 8.60 (br s, 1H), 7.26-7.33 (m, 1H), 7.01-7.03 (s, 1H), 5.48-5.55 (m, 1H), 3.28-3.38 (m, 4H), 3.22-3.24 (m, 1H), 1.92-1.95 (m, 2H) and 1.24 (d, J=6.4 Hz, 3H). MS: 284.0 (M+H)$^+$. Yield: 67%.

Scheme 29

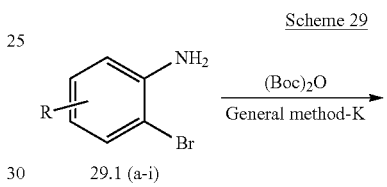

29.1 (a-i)

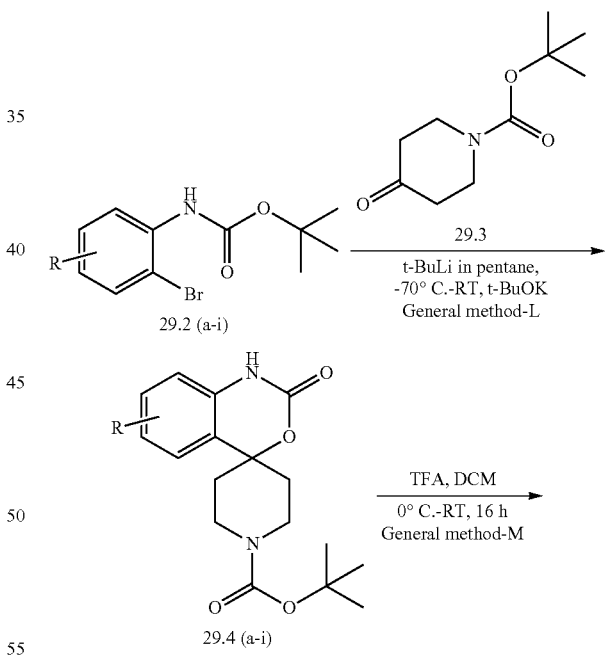

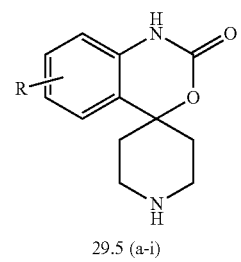

29.5 (a-i)

-continued

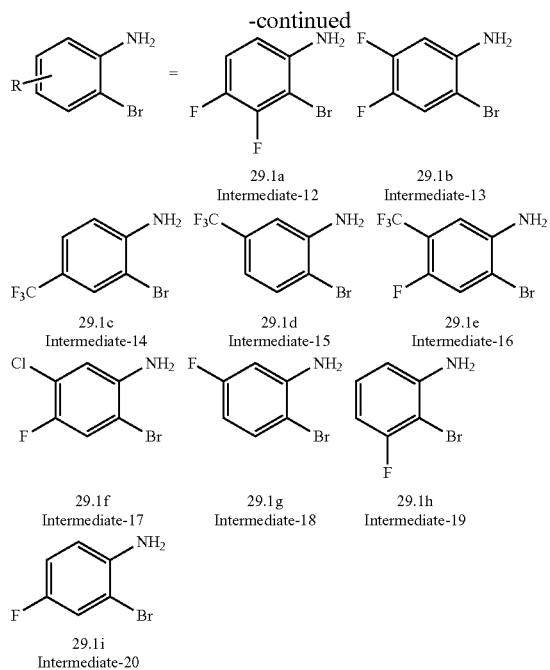

General Procedure for the Preparation of 29.2 (a-i)

General Method K:

To an ice-cold solution of compound 29.1 (a-i) (1.0 eq) in THF was added LiHMDS (1.0 M in THF, 2.5 eq) dropwise. The resulting reaction mixture was stirred at 0° C. for 15 min, followed by addition of boc anhydride (1.1 eq). The reaction mixture was warmed to RT and stirred for 4-5 h. After completion of reaction (TLC monitoring), reaction mass cooled to 0° C. and diluted with brine solution. The organic layer was extracted with EtOAc (3 times). The combined layer was dried over anhydrous $Na_2SO_4$, filtered and concentrated under reduced pressure. The crude was purified over silica gel (100-200M), elution with 5% EtOAc/hexane to get desired product 29.2 (a-i).

tert-Butyl (2-bromo-3,4-difluorophenyl)carbamate (29.2a)

$^1$H-NMR (400 MHz, CDCl$_3$): δ 7.91-7.92 (m, 1H), 7.11-7.18 (m, 1H), 6.87-6.95 (m, 1H) and 1.53 (s, 9H). MS: 306.06 (M–H)$^+$. Yield: 41%.

tert-Butyl (2-bromo-4,5-difluorophenyl)carbamate (29.2b)

$^1$H-NMR (400 MHz, CDCl$_3$): δ 8.12-8.17 (m, 2H), 7.32-7.36 (m, 1H) and 1.54 (s, 9H). LCMS: 306.09 (M–H)$^+$, 94.59%. Yield: 82%.

tert-Butyl (2-bromo-4-(trifluoromethyl)phenyl)carbamate (29.2c)

$^1$H-NMR (400 MHz, CDCl$_3$): δ 8.31-8.36 (m, 1H), 7.76-7.78 (m, 1H), 7.52-7.54 (m, 1H), 7.12-7.16 (m, 1H) and 1.54 (s, 9H). MS: 338.03 (M–H)$^+$. Yield: 71%.

tert-Butyl (2-bromo-5-(trifluoromethyl)phenyl)carbamate (29.2d)

$^1$H-NMR (400 MHz, CDCl$_3$): δ 8.51 (s, 1H), 7.61 (d, J=8.4 Hz, 1H), 7.10-7.15 (m, 2H) and 1.54 (s, 9H). LCMS: 338.10 (M–H)$^+$, 99.23%. Yield: 85%.

tert-Butyl (2-bromo-4-fluoro-5-(trifluoromethyl)phenyl)carbamate (29.2e)

$^1$H-NMR (400 MHz, CDCl$_3$): δ 8.47-8.48 (m, 1H), 7.39 (d, J=8.8 Hz, 1H), 6.64-6.96 (m, 1H) and 1.54 (s, 9H). LCMS: 356.05 (M–H)$^+$, 98.92%. Yield: 82%.

tert-Butyl (2-bromo-5-chloro-4-fluorophenyl)carbamate (29.2f)

$^1$H-NMR (400 MHz, CDCl$_3$): δ 8.29-8.31 (m, 1H), 7.26-7.33 (m, 1H), 6.86 (s, 1H) and 1.53 (s, 9H). LCMS: 322.01 (M–H)$^+$, 96.73%. Yield: 97%.

tert-Butyl (2-bromo-5-fluorophenyl)carbamate (29.2g)

$^1$H-NMR (400 MHz, CDCl$_3$): δ 8.00-8.03 (m, 1H), 7.41-7.45 (m, 1H), 7.03 (br s, 1H), 6.63-6.65 (m, 1H) and 1.53 (s, 9H). LCMS: 288.16 (M–H)$^+$, 99.03%. Yield: 40%.

tert-Butyl (2-bromo-3-fluorophenyl)carbamate (29.2h)

$^1$H-NMR (400 MHz, CDCl$_3$): δ 7.96 (d, J=8.4 Hz, 1H), 7.25-7.29 (m, 1H), 7.02 (br s, 1H), 6.79 (d, J=7.2 Hz, 1H) and 1.53 (s, 9H). LCMS: 287.93 (M–H)$^+$, 95.02%. Yield: 15%.

tert-Butyl (2-bromo-4-fluorophenyl)carbamate (29.2i)

$^1$H-NMR (400 MHz, CDCl$_3$): δ 7.97-8.01 (m, 1H), 7.48-7.52 (m, 1H), 7.06 (br s, 1H), 7.80-7.85 (m, 1H) and 1.54 (s, 9H). LCMS: 288.20 (M–H)$^+$, 96.13%. Yield: 25%.

General Procedure for the Preparation of 29.4 (a-i):

General Method L:

To an ice-cold solution of compound 29.2 (a-i) (1.0 eq) in THF was added MeLi (1.6 M in diethyl ether, 1.2 eq) dropwise under argon atmosphere. The resulting reaction mixture was stirred at 0° C. for 30 min. After cooling the reaction mass at −78° C., tert-BuLi (2.0 eq, 1.5 M in THF) was added dropwise and stirring continued for 1 h. A solution of tert-butyl 4-oxopiperidine-1-carboxylate 29.3 (1.0 eq) in THF was added and the resulting reaction mixture was allowed to warm-up to RT. Potassium tert-butoxide (0.05 eq) was added and stirred for 16 h at RT. After completion of reaction (TLC monitoring), reaction mass cooled to 0° C. and diluted with brine solution. The organic layer was extracted with EtOAc (3 times). The combined layer was dried over anhydrous $Na_2SO_4$, filtered and concentrated under reduced pressure. The crude was purified over silica gel (100-200M), elution with 15-20% EtOAc/hexane to get desired product 29.4 (a-i).

tert-Butyl 5,6-difluoro-2-oxo-1,2-dihydrospiro[benzo[d][1,3]oxazine-4,4'-piperidine]-1'-carboxylate (29.4a)

$^1$H-NMR (400 MHz, CDCl$_3$): δ 8.12 (s, 1H), 7.25 (s, 1H), 7.03-7.07 (m, 1H), 3.70-3.73 (m, 2H), 3.09-3.15 (m, 2H), 2.84-2.86 (m, 2H), 1.72-1.77 (m, 2H) and 1.52 (s, 9H). MS: 353.10 (M−H)$^+$. Yield: 34%.

tert-Butyl 6,7-difluoro-2-oxo-1,2-dihydrospiro[benzo[d][1,3]oxazine-4,4'-piperidine]-1'-carboxylate (29.4b)

$^1$H-NMR (400 MHz, CDCl$_3$): δ 7.84 (s, 1H), 6.93-6.98 (m, 1H), 6.65-6.69 (m, 1H), 4.05-4.10 (m, 2H), 3.29-3.30 (m, 2H), 2.04-2.10 (m, 2H), 1.83-1.90 (m, 2H) and 1.56 (s, 9H). MS: 353.18 (M−H)$^+$. Yield: 50%.

tert-Butyl 2-oxo-6-(trifluoromethyl)-1,2-dihydrospiro[benzo[d][1,3]oxazine-4,4'-piperidine]-1'-carboxylate (29.4c)

$^1$H-NMR (400 MHz, CDCl$_3$): δ 8.09 (br s, 1H), 7.53 (d, J=8.4 Hz, 1H), 7.37 (s, 1H), 6.90 (d, J=8.4 Hz, 1H), 4.09-4.13 (m, 2H), 3.30-3.33 (m, 2H), 2.11-2.14 (m, 2H), 1.94-1.98 (m, 2H) and 1.55 (s, 9H). LCMS: 385.23 (M−H)$^+$, 94.97%. Yield: 32%.

tert-Butyl 2-oxo-7-(trifluoromethyl)-1,2-dihydrospiro[benzo[d][1,3]oxazine-4,4'-piperidine]-1'-carboxylate (29.4d)

$^1$H-NMR (400 MHz, CDCl$_3$): δ 8.25 (br s, 1H), 7.34 (d, J=8.4 Hz, 1H), 7.23-7.26 (m, 1H), 7.08 (s, 1H), 4.00-4.12 (m, 2H), 3.26-3.34 (m, 2H), 2.10-2.14 (m, 2H), 1.97-1.99 (m, 2H) and 1.48 (s, 9H). LCMS: 385.33 (M−H)$^+$, 89.02%. Yield: 62%.

tert-Butyl 6-fluoro-2-oxo-7-(trifluoromethyl)-1,2-dihydrospiro[benzo[d][1,3]oxazine-4,4'-piperidine]-1'-carboxylate (29.4e)

$^1$H-NMR (400 MHz, CDCl$_3$): δ 8.90 (br s, 1H), 7.08 (d, J=5.6 Hz, 1H), 6.99-7.01 (m, 1H), 4.09-4.12 (m, 2H), 3.49-3.42 (m, 2H), 2.10-2.13 (m, 2H), 1.89-1.95 (m, 2H) and 1.54 (s, 9H). LCMS: 403.32 (M−H)$^+$, 94.74%. Yield: 22%.

tert-Butyl 7-chloro-6-fluoro-2-oxo-1,2-dihydrospiro[benzo[d][1,3]oxazine-4,4'-piperidine]-1'-carboxylate (29.4f)

$^1$H-NMR (400 MHz, CDCl$_3$): δ 8.40 (br s, 1H), 6.87-6.99 (m, 2H), 4.09-4.12 (m, 2H), 3.18-3.24 (m, 2H), 2.04-2.11 (m, 2H), 1.84-1.92 (m, 2H) and 1.58 (s, 9H). LCMS: 369.32 (M−H)$^+$, 99.36%. Yield: 47%.

tert-Butyl 7-fluoro-2-oxo-1,2-dihydrospiro[benzo[d][1,3]oxazine-4,4'-piperidine]-1'-carboxylate (29.4g)

$^1$H-NMR (400 MHz, CDCl$_3$): δ 7.53 (br s, 1H), 7.06-7.09 (m, 1H), 6.76-6.80 (m, 1H), 6.52-6.55 (m, 1H), 4.09-4.13 (m, 2H), 3.28-3.30 (m, 2H), 2.04-2.07 (m, 2H), 1.91-1.94 (m, 2H) and 1.49 (s, 9H). MS: 335.30 (M−H)$^+$. Yield: 8%.

tert-Butyl 5-fluoro-2-oxo-1,2-dihydrospiro[benzo[d][1,3]oxazine-4,4'-piperidine]-1'-carboxylate (29.4h)

MS: 335.30 (M−H)$^+$. Yield: 10%.

tert-Butyl 6-fluoro-2-oxo-1,2-dihydrospiro[benzo[d][1,3]oxazine-4,4'-piperidine]-1'-carboxylate (29.4i)

MS: 335.17 (M−H)$^+$. Yield: 12%.

General Procedure for the Preparation of 29.5 (a-i):
General Method-M:

An ice-cold solution of compound 28 (a-i) in 10% TFA-DCM was stirred at RT for 2 h. After completion of the reaction (TLC monitoring), the reaction mass was dried under reduced pressure. The crude was triturated with diethyl ether to get desired product 29 (a-i) as off solid.

5,6-Difluorospiro[benzo[d][1,3]oxazine-4,4'-piperidin]-2(1H)-one (29.5a): Intermediate-12

$^1$H-NMR (400 MHz, DMSO-d$_6$): δ 10.64 (s, 1H), 8.53-8.66 (m, 1H), 7.39-7.46 (m, 1H), 6.74-6.76 (m, 1H), 3.32-3.35 (m, 2H), 3.19-3.22 (m, 2H), 2.39-2.43 (m, 2H) and 2.26-2.30 (m, 2H). LCMS: 253.99 (M−H)$^+$, 91.53%. Yield: 90%.

6,7-Difluorospiro[benzo[d][1,3]oxazine-4,4'-piperidin]-2(1H)-one (29.5b): Intermediate-13

$^1$H-NMR (400 MHz, DMSO-d$_6$): δ 10.56 (s, 1H), 8.72-8.79 (m, 1H), 7.31-7.40 (m, 1H), 6.69-6.94 (m, 1H), 3.32-3.35 (m, 2H), 3.16-3.22 (m, 2H) and 2.15-2.25 (m, 4H). MS: 255.21 (M+H)$^+$. Yield: 78%.

6-(Trifluoromethyl)spiro[benzo[d][1,3]oxazine-4,4'-piperidin]-2(1H)-one (29.5c): Intermediate-14

$^1$H-NMR (400 MHz, DMSO-d$_6$): δ 10.82 (s, 1H), 8.46 (br s, 1H), 7.69-7.71 (m, 1H), 7.49 (s, 1H), 7.10-7.12 (m, 1H), 3.33-3.37 (m, 2H), 3.16-3.18 (m, 2H) and 2.21-2.31 (m, 4H). LCMS: 285.24 (M−H)$^+$, 99.24%. Yield: 95%.

7-(Trifluoromethyl)spiro[benzo[d][1,3]oxazine-4,4'-piperidin]-2(1H)-one (29.5d): Intermediate-15

$^1$H-NMR (400 MHz, DMSO-d$_6$): δ 10.91 (s, 1H), 9.13-9.14 (m, 1H), 7.43-7.52 (m, 2H), 7.22 (s, 1H), 3.34-3.38 (m, 2H), 3.18-3.22 (m, 2H) and 2.23-2.24 (m, 4H). LCMS: 286.91 (M+H)$^+$, 97.48%. Yield: 95%.

6-Fluoro-7-(trifluoromethyl)spiro[benzo[d][1,3]oxazine-4,4'-piperidin]-2(1H)-one (29.5e): Intermediate-16

$^1$H-NMR (400 MHz, DMSO-d$_6$): δ 10.70 (s, 1H), 8.60 (br s, 1H), 7.48-7.51 (m, 1H), 7.24-7.25 (m, 1H), 3.34-3.37 (m, 2H), 3.16-3.20 (m, 2H) and 2.23-2.28 (m, 4H). LCMS: 304.91 (M+H)$^+$, 97.69%. Yield: 83%.

7-Chloro-6-fluorospiro[benzo[d][1,3]oxazine-4,4'-piperidin]-2(1H)-one (29.5f): Intermediate-17

$^1$H-NMR (400 MHz, DMSO-d$_6$): δ 10.56 (s, 1H), 8.38-8.48 (m, 1H), 7.37-7.39 (m, 1H), 7.05-7.07 (m, 1H), 3.35-3.38 (m, 2H), 3.13-3.15 (m, 2H) and 2.19-2.21 (m, 4H). LCMS: 269.04 (M−H)$^+$, 99.39%. Yield: 93%.

7-Fluorospiro[benzo[d][1,3]oxazine-4,4'-piperidin]-2(1H)-one (29.5g): Intermediate-18

$^1$H-NMR (400 MHz, DMSO-d$_6$): δ 10.55 (s, 1H), 8.34-8.38 (m, 1H), 7.22-7.24 (m, 1H), 6.92-6.93 (m, 1H), 6.71-6.73 (m, 1H), 3.35-3.40 (m, 2H), 3.13-3.16 (m, 2H) and 2.17-2.21 (m, 4H). MS: 237.0 (M+H)$^+$. Yield: 96%.

5-Fluorospiro[benzo[d][1,3]oxazine-4,4'-piperidin]-2(1H)-one (29.5h): Intermediate-19

MS: 235.04 (M–H)$^+$. Yield: 80%.

6-Fluorospiro[benzo[d][1,3]oxazine-4,4'-piperidin]-2(1H)-one (29.5i): Intermediate-20

MS: 235.10 (M–H)$^+$. Yield: 78%.

8.31-8.36 (m, 1H), 7.76-7.78 (m, 1H), 7.52-7.54 (m, 1H), 7.12-7.16 (m, 1H) and 1.54 (s, 9H). MS: 338.03 (M–H)$^+$. Yield: 71%

Preparation of tert-butyl 2'-methyl-2-oxo-6-(trifluoromethyl)-1,2-dihydrospiro[benzo[d][1,3]oxazine-4,4'-piperidine]-1'-carboxylate (30.2)

This compound was prepared following the general method L (Scheme 29). MS: 399.38 (M–H)$^+$. Yield: 12%.

Preparation of 2'-methyl-6-(trifluoromethyl)spiro[benzo[d][1,3]oxazine-4,4'-piperidin]-2(1H)-one (30.3)

This compound was prepared following the general method-M (Scheme 29). $^1$H-NMR (400 MHz, DMSO-d$_6$): δ 10.84 (s, 1H), 8.58 (br s, 1H), 7.70-7.72 (m, 1H), 7.49-7.53 (m, 1H), 7.11-7.13 (m, 1H), 3.35-3.38 (m, 2H), 3.16-3.22 (m, 2H), 2.28-2.30 (m, 1H), 2.21-2.23 (m, 2H) and 1.27 (d, J=6.4 Hz, 3H). LCMS: 299.13 (M–H)$^+$. Yield: 96%.

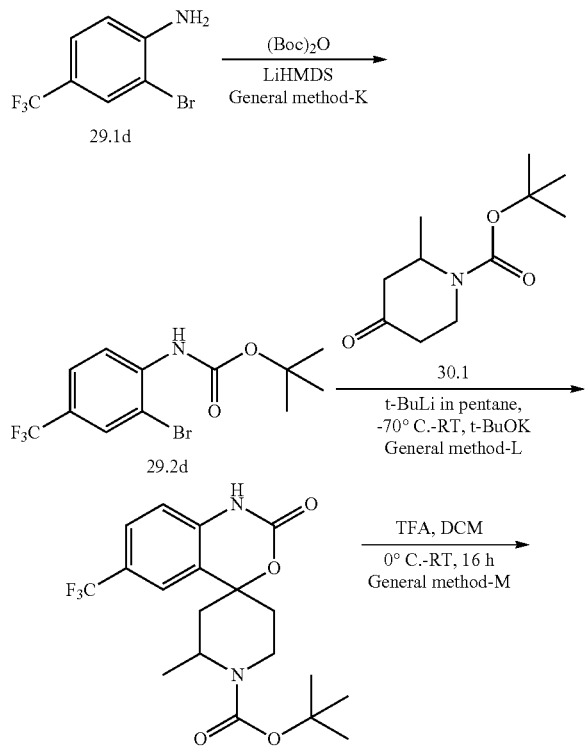

Scheme 30

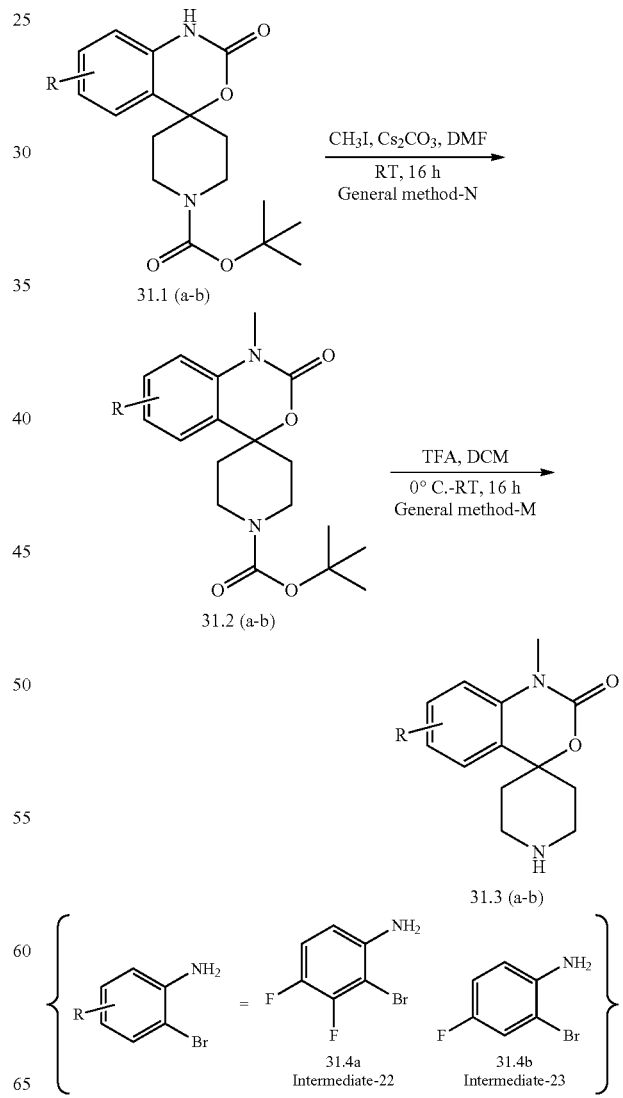

Scheme 31

Preparation of tert-butyl (2-bromo-4-(trifluoromethyl)phenyl)carbamate (29.2d)

This compound was prepared following the general method K (Scheme 29). $^1$H-NMR (400 MHz, CDCl$_3$): δ

General Procedure for the Preparation of 31.2 (a-b):

General Method N:

To a solution of compound 31.1 (a-b) (1.0 eq) in DMF was added $Cs_2CO_3$ (1.5 eq) and methyl iodide (1.5 eq). The resulting reaction mixture was stirred for 16 h at RT. After completion of reaction (TLC monitoring), reaction mass was diluted with ice-cold water and extracted with EtOAc (3 times). The combined layer was washed with ice-water and brine solution respectively and dried over anhydrous $Na_2SO_4$, filtered and concentrated under reduced pressure. The crude was purified over silica gel (100-200M), elution with 20-30% EtOAc/hexane to get desired product 31.2 (a-b).

tert-Butyl 5,6-difluoro-1-methyl-2-oxo-1,2-dihydrospiro[benzo[d][1,3]oxazine-4,4'-piperidine]-1'-carboxylate (31.2a)

$^1$H-NMR (400 MHz, $CDCl_3$): δ 7.08-7.18 (m, 1H), 6.64-6.66 (m, 1H), 4.06-4.14 (m, 2H), 3.37 (s, 3H), 3.19-3.25 (m, 2H), 2.25-2.31 (m, 2H), 2.02-2.06 (m, 2H) and 1.45 (s, 9H). MS: 369.12 $(M+H)^+$. Yield: 72%.

tert-Butyl 1-methyl-2-oxo-6-(trifluoromethyl)-1,2-dihydrospiro[benzo[d][1,3]oxazine-4,4'-piperidine]-1'-carboxylate (31.2b)

$^1$H-NMR (400 MHz, $CDCl_3$): δ 7.60-7.63 (m, 1H), 7.37 (s, 1H), 6.99-7.05 (m, 1H), 4.10-4.14 (m, 2H), 3.43 (s, 3H), 3.24-3.29 (m, 2H), 2.06-2.09 (m, 2H), 19.91-1.98 (m, 2H) and 1.48 (s, 9H). LCMS: 401.16 $(M+H)^+$, 96.95%. Yield: 70%.

General Procedure for the Preparation of 31.3 (a-b):

These compounds were prepared following the general method M (Scheme 29).

5,6-Difluoro-1-methylspiro[benzo[d][1,3]oxazine-4,4'-piperidin]-2(1H)-one (31.3a): Intermediate-22

$^1$H-NMR (400 MHz, DMSO-$d_6$): δ 8.74-8.84 (m, 1H), 7.53-7.55 (m, 1H), 7.01 (s, 1H), 3.74-4.02 (m, 3H), 2.88-3.30 (m, 5H), and 2.29-2.32 (m, 3H). MS: 269.06 $(M+H)^+$. Yield: 78%.

1-Methyl-6-(trifluoromethyl)spiro[benzo[d][1,3]oxazine-4,4'-piperidin]-2(1H)-one (31.3b): Intermediate-23

$^1$H-NMR (400 MHz, DMSO-$d_6$): δ 8.48 (br s, 1H), 7.80 (d, J=8.8 Hz, 1H), 7.55 (s, 1H), 7.34 (d, J=8.8 Hz, 1H), 3.35-3.45 (m, 5H), 3.16-3.18 (m, 2H) and 2.23-2.35 (m, 4H). LCMS: 301.07 $(M+H)^+$, 97.15%. Yield: 95%.

Scheme 32

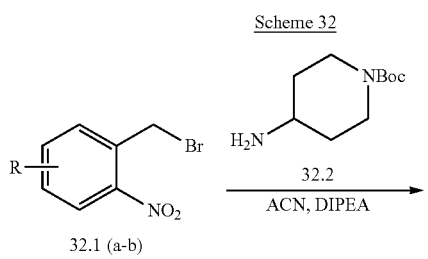

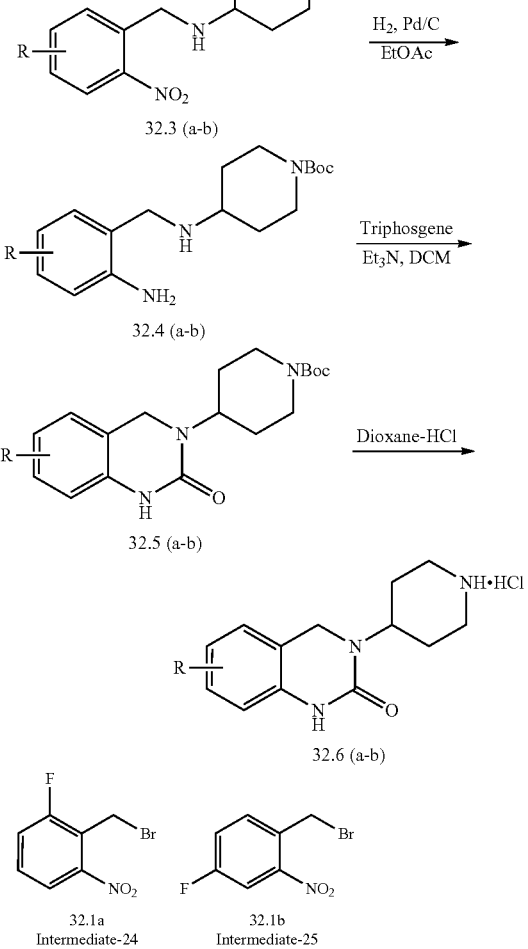

General Procedure for the Preparation of 32.3(a-b):

To an ice-cold solution of tert-butyl 4-aminopiperidine-1-carboxylate 32.2 (1.0 eq) in ACN was added DIPEA (1.5 eq) and the respective nitro compounds 32.1(a-b) (1.0 eq). The resulting reaction mixture was stirred at RT for 2-3 h. After completion of the reaction (TLC monitoring), the reaction mass was diluted with ice-cold water and extracted with EtOAc (3 times). The combined organics were washed with brine, dried over anhydrous $Na_2SO_4$, filtered and concentrated. The crude was purified over silica gel (100-200 M, 10-15% EtOAc-hexane) to get the desired product 32.3(a-b).

tert-Butyl 4-((2-fluoro-6-nitrobenzyl)amino)piperidine-1-carboxylate (32.3a)

$^1$H-NMR (400 MHz, $CDCl_3$): δ 7.69-7.71 (m, 1H), 7.32-7.43 (m, 2H), 4.01-4.02 (m, 4H), 2.83-2.89 (m, 2H), 2.60-2.65 (m, 1H), 1.83-1.85 (m, 2H), 1.44 (s, 9H) and 1.25-1.31 (m, 3H). LCMS: 354.33 $(M+H)^+$, 97.42%. Yield: 47%.

tert-Butyl 4-((4-fluoro-2-nitrobenzyl)amino)piperidine-1-carboxylate (32.3b)

$^1$H-NMR (400 MHz, $CDCl_3$): δ 7.65-7.68 (m, 2H), 7.28-7.32 (m, 1H), 4.00-4.02 (m, 4H), 2.78-2.84 (m, 2H), 2.62-

2.65 (m, 1H), 1.83-1.86 (m, 2H), 1.45 (s, 9H) and 1.25-1.29 (m, 3H). LCMS: 354.33 (M+H)⁺, 98.63%. Yield: 54%.

General Procedure for the Preparation of 32.4(a-b):

To a solution of compound 32.3(a-b) (1.0 eq) in EtOAc were added Pd—C (w/w, 10 mol %) and the resulting solution was stirred under hydrogen atmosphere (1 atm) at ambient temperature for 16 h. The reaction mixture was filtered through a diatomaceous earth (Celite) bed and the filtrate was concentrated under reduced pressure to get the desired product 32.4 (a-b).

tert-Butyl 4-((2-amino-6-fluorobenzyl)amino)piperidine-1-carboxylate (32.4a)

¹H-NMR (400 MHz, DMSO-d₆): δ 6.89-6.95 (m, 1H), 6.41-6.43 (m, 1H), 6.26-6.60 (m, 1H), 5.54 (br s, 2H), 3.77-3.80 (m, 2H), 3.68 (s, 2H), 2.78-2.81 (m, 2H), 2.63-2.65 (m, 1H), 1.77-1.79 (m, 2H), 1.38 (s, 9H) and 1.13-1.19 (m, 3H). LCMS: 324.12 (M+H)⁺, 85.32%. Yield: 78%.

tert-Butyl 4-((2-amino-4-fluorobenzyl)amino)piperidine-1-carboxylate (32.4b)

¹H-NMR (400 MHz, DMSO-d₆): δ 6.95-6.98 (m, 1H), 6.35-6.38 (m, 1H), 6.20-6.25 (m, 1H), 5.52 (br s, 2H), 3.78-3.81 (m, 2H), 3.60 (s, 2H), 2.66-2.83 (m, 3H), 1.77-1.80 (m, 2H), 1.38 (s, 9H) and 1.13-1.20 (m, 3H). LCMS: 324.22 (M+H)⁺, 84.74%. Yield: 91%.

General Procedure for the Preparation of 32.5(a-b):

To an ice-cold solution of compound 32.4 (a-b) (1.0 eq) in THF was added Et₃N (2.0 eq) and triphosgene (1.5 eq). The resulting reaction mixture was stirred at RT for 4 h. After completion of the reaction (TLC monitoring), the solvent was evaporated and the residue was diluted with water and extracted with ethyl acetate (3 times). The combined organics were washed with brine, dried over anhydrous Na₂SO₄, filtered and concentrated. The crude was purified over silica gel (100-200 M, 30-40% EtOAc-hexane) to get the desired product 32.5 (a-b).

tert-Butyl 4-(5-fluoro-2-oxo-1,4-dihydroquinazolin-3(2H)-yl)piperidine-1-carboxylate (32.5a)

¹H-NMR (400 MHz, CDCl₃): δ 7.62 (br s, 1H), 7.09-7.20 (m, 1H), 6.63 (t, J=8.8 Hz, 1H), 6.45 (d, J=7.6 Hz, 1H), 4.50-4.56 (m, 1H), 4.37 (s, 2H), 4.11-4.12 (m, 2H), 2.83-2.88 (m, 2H), 1.71-1.77 (m, 4H) and 1.47 (s, 9H). LCMS: 350.35 (M+H)⁺, 96.92%. Yield: 85%.

tert-Butyl 4-(7-fluoro-2-oxo-1,4-dihydroquinazolin-3(2H)-yl)piperidine-1-carboxylate (32.5b)

¹H-NMR (400 MHz, CDCl₃): δ 7.63 (br s, 1H), 6.96-7.00 (m, 1H), 6.61-6.65 (m, 1H), 6.43-6.46 (m, 1H), 4.48-4.56 (m, 1H), 4.27-4.33 (m, 4H), 2.83-2.88 (m, 2H), 1.69-1.72 (m, 4H) and 1.47 (s, 9H). LCMS: 350.39 (M+H)⁺, 92.96%. Yield: 55%.

General Procedure for the Preparation of 32.6(a-b):

An ice-cold solution of compound 32.5(a-b) in dioxane-HCl (~4N) was stirred at RT for 2 h. After completion of the reaction (TLC monitoring), the reaction mass was dried under reduced pressure. The crude was triturated with diethyl ether to get desired product 32.6(a-b) as an off-white solid.

5-Fluoro-3-(piperidin-4-yl)-3,4-dihydroquinazolin-2(1H)-one Hydrochloride (32.6a)

Intermediate-24: ¹H-NMR (400 MHz, DMSO-d₆): δ 9.54 (br s, 1H), 8.87 (br s, 1H), 8.61 (br s, 1H), 7.14-7.18 (m, 1H), 6.70-6.75 (m, 1H), 6.59-6.61 (m, 1H), 4.35-4.43 (m, 3H), 3.32-3.35 (m, 2H), 3.00-3.03 (m, 2H), 2.05-2.14 (m, 2H) and 1.72-1.75 (m, 2H). LCMS: 250.23 (M+H)⁺, 98.92%. Yield: 97%.

7-Fluoro-3-(piperidin-4-yl)-3,4-dihydroquinazolin-2(1H)-one Hydrochloride (32.6b)

Intermediate-25: ¹H-NMR (400 MHz, DMSO-d₆): δ 9.46 (br s, 1H), 8.94 (br s, 1H), 8.81 (br s, 1H), 7.16-7.22 (m, 1H), 6.68-6.71 (m, 1H), 6.55-6.58 (m, 1H), 4.32-4.38 (m, 1H), 4.27 (s, 2H), 3.83-3.85 (m, 2H), 3.32-3.38 (m, 2H), 2.01-2.07 (m, 2H) and 1.70-1.73 (m, 2H). LCMS: 250.10 (M+H)⁺, 96.20%. Yield: 98%.

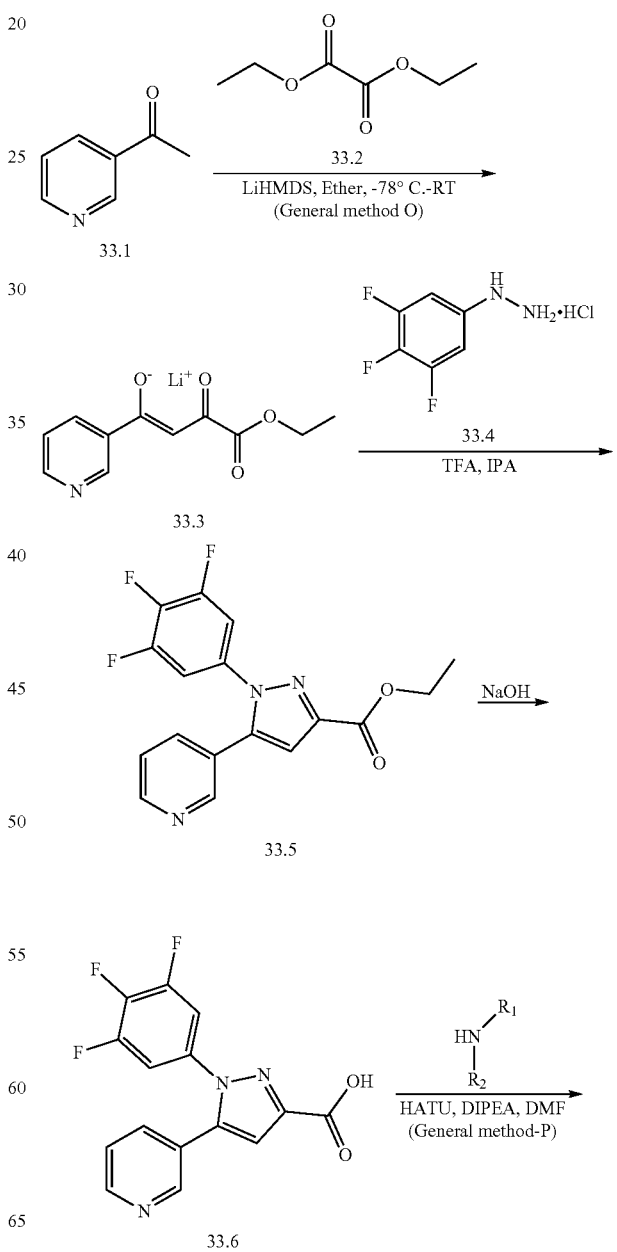

Scheme 33

287

-continued

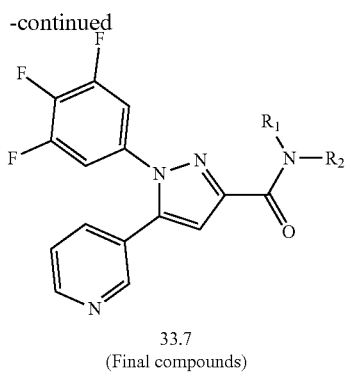

33.7
(Final compounds)

Preparation of 4-ethoxy-3,4-dioxo-1-(pyridin-3-yl) but-1-en-1-olate Lithium Salt (33.3) (General Method O)

A solution of 3-acetyl pyridine 33.1 (20 g, 165.09 mmol) in di-ethyl ether (250 mL) was cooled to −78° C. followed by addition of LiHMDS (1.0 M in THF, 181.60 mL, 181.60 mmol). The resulting reaction mixture was stirred at −78° C. for 45 min followed by drop wise addition of diethyl oxalate 33.2 (27.03 mL, 198.10 mmol) in about 20 min. The reaction mixture was then left to stir at room temperature for 16 h. After completion of the reaction (TLC and MS monitoring), the solution was then cooled to 0° C. and diluted with added diethyl ether (250 mL) and stirred for 30.0 min. The resulting precipitate was filtered to get the desired product 33.3 as an off-white solid (30 g, Yield: 82%), which was carried forward to the next step without purification. $^1$H-NMR (400 MHz, DMSO-$d_6$): δ 8.95 (s, 1H), 8.61 (d, J=4.0 Hz, 1H), 8.14 (m, 1H), 7.44 (m, 1H), 6.40 (m, 1H), 4.12 (q, J=7.20 Hz, 2H) and 1.21 (t, J=7.2 Hz, 3H). MS: 221.95 (M+H)$^+$.

Preparation of ethyl 5-(pyridin-3-yl)-1-(3,4,5-trifluorophenyl)-1H-pyrazole-3-carboxylate (33.5)

To an ice-cold solution of 4-ethoxy-3,4-dioxo-1-(pyridin-3-yl)but-1-en-1-olate lithium salt 33.3 (10.0 g, 45.23 mmol) in IPA (50 mL) was added (3,4,5-trifluorophenyl)hydrazine hydrochloride 33.4 (10.77 g, 54.28 mmol) and TFA (6.9 mL, 90.46 mmol). The resulting reaction mixture was warmed to room temperature and then stirred at 90° C. for 4 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 33.5 (5.50 g, 35%). $^1$H-NMR (400 MHz, CDCl$_3$): δ 8.68 (m, 1H), 8.61 (s, 1H), 7.61 (d, J=8.0 Hz, 1H), 7.42 (m, 1H), 7.14 (s, 1H), 7.03 (m, 2H), 4.48 (q, J=7.2 Hz, 2H) and 1.41 (t, J=7.2 Hz, 3H). MS: 348.15 (M+H)$^+$.

Preparation of 5-(pyridin-3-yl)-1-(3,4,5-trifluorophenyl)-1H-pyrazole-3-carboxylic Acid (33.6)

To an ice-cold solution of ethyl 5-(pyridin-3-yl)-1-(3,4,5-trifluorophenyl)-1H-pyrazole-3-carboxylate 33.5 (5.50 g, 15.82 mmol) in EtOH (40 mL) was added drop wise an aqueous solution of sodium hydroxide (1.26 g, 31.64 mmol). The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 33.6 (3.0 g, 59%) as a white solid. $^1$H-NMR (400 MHz, DMSO-$d_6$): δ 13.13 (br s, 1H), 8.59 (s, 2H), 7.65 (d, J=8.4 Hz, 1H), 7.52 (m, 2H), 7.41 (m, 1H) and 7.25 (s, 1H). LCMS: 320.14 (M+H)$^+$, 95.20%.

General Procedure for the Preparation of Final Compounds 33.7

General Method-P:

To an ice-cold solution of carboxylic acid 33.6 (125-150 mg), in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC.

The yields and analytical data of the compounds are set forth in Table 6.10.

TABLE 6.10

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 267 | ![structure] | Intermediate-5 | 23 | 560.13 (M − H)$^+$, 99.72% | δ 11.25 (br s, 1H), 8.59-8.60 (m, 2H), 7.67 (d, J = 8.0 Hz, 1H), 7.61-7.64 (m, 1H), 7.49-7.53 (m, 2H), 7.41-7.43 (m, 1H), 7.36-7.38 (m, 1H), 7.14 (s, 1H), 4.77-4.80 (m, 1H), 4.70-4.73 (m, 1H), 4.49-4.55 (m, 1H), 3.30-3.32 (m, 1H), 2.88-2.94 (m, 1H), 2.26-2.29 (m, 2H) and 1.77-1.80 (m, 2H) |

TABLE 6.10-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 268 | 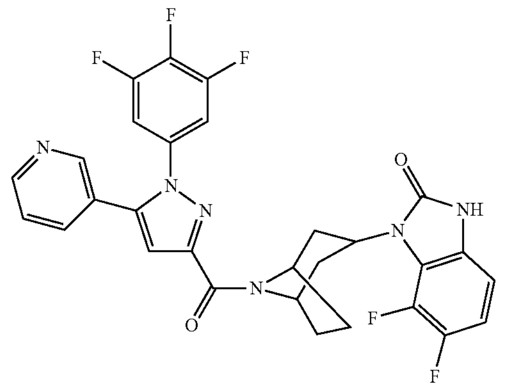 [SMILES: O=C(c1cc(-c2cccnc2)n(-c2cc(F)c(F)c(F)c2)n1)N1C2CCCC1CC(n1c(=O)[nH]c3ccc(F)c(F)c31)C2] | Intermediate-11 | 33 | 581.20 (M + H)$^+$ 97.77% | δ 11.27 (br s, 1H), 8.59-8.60 (m, 2H), 7.68-7.61 (m, 1H), 7.52-7.55 (m, 2H), 7.42-7.45 (m, 1H), 7.22 (s, 1H), 7.01-7.06 (m, 1H), 6.77-6.80 (m, 1H), 5.32-5.36 (m, 1H), 4.84-4.88 (m, 1H), 4.36-4.43 (m, 1H), 3.36-3.40 (m, 1H), 2.55-2.58 (m, 1H), 3.11-2.14 (m, 1H), 2.00-2.03 (m, 1H) and 1.84-1.89 (m, 4H). |

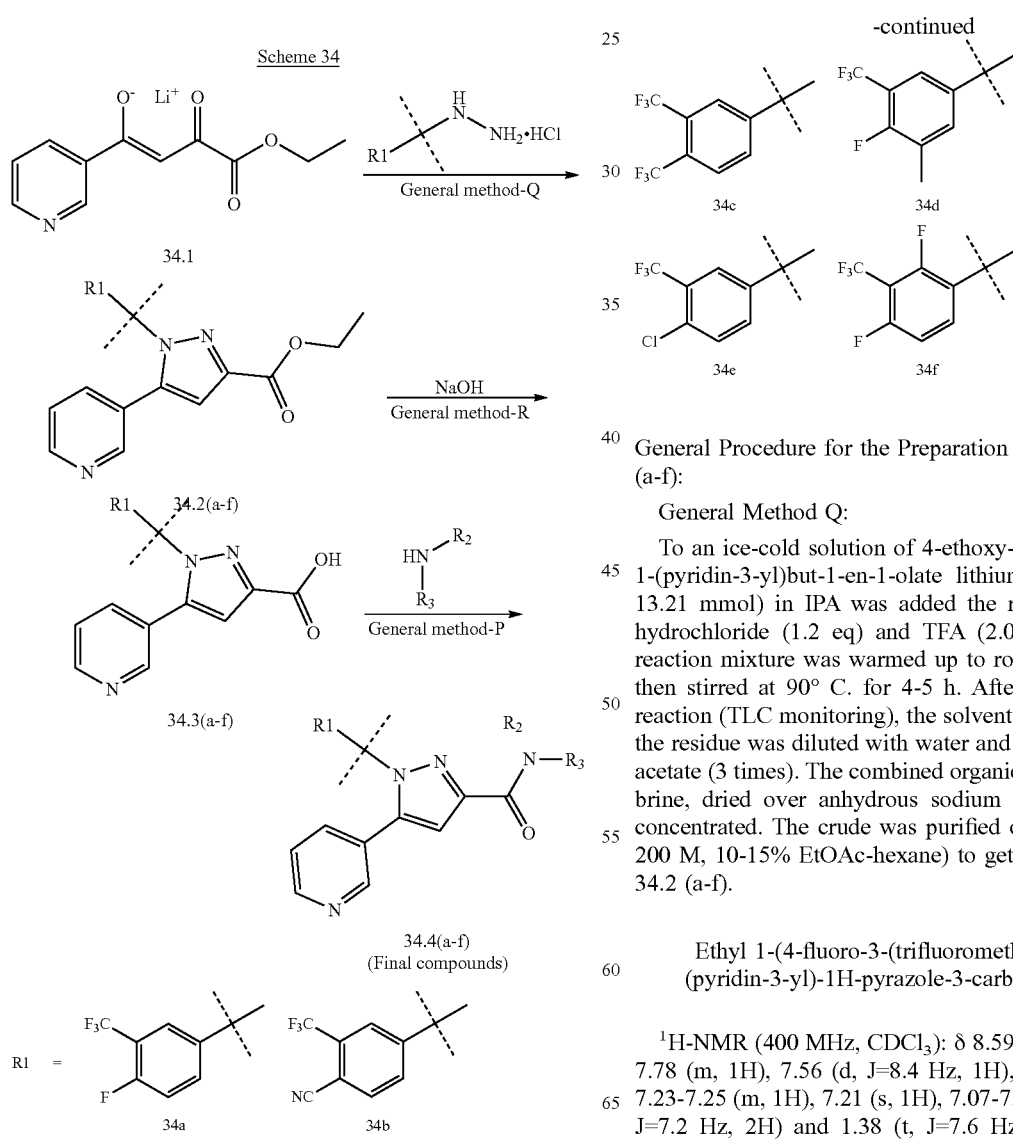

General Procedure for the Preparation of Compounds 34.2 (a-f):

General Method Q:

To an ice-cold solution of 4-ethoxy-2-methyl-3,4-dioxo-1-(pyridin-3-yl)but-1-en-1-olate lithium salt 34.1 (3.0 g, 13.21 mmol) in IPA was added the respective hydrazine hydrochloride (1.2 eq) and TFA (2.0 eq). The resulting reaction mixture was warmed up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to get the desired product 34.2 (a-f).

Ethyl 1-(4-fluoro-3-(trifluoromethyl)phenyl)-5-(pyridin-3-yl)-1H-pyrazole-3-carboxylate (34.2a)

$^1$H-NMR (400 MHz, CDCl$_3$): δ 8.59-8.66 (m, 1H), 7.77-7.78 (m, 1H), 7.56 (d, J=8.4 Hz, 1H), 7.38-7.41 (m, 2H), 7.23-7.25 (m, 1H), 7.21 (s, 1H), 7.07-7.10 (m, 1H), 4.48 (q, J=7.2 Hz, 2H) and 1.38 (t, J=7.6 Hz, 3H). MS: 380.22 (M+H)$^+$. Yield: 35%.

Ethyl 1-(4-cyano-3-(trifluoromethyl)phenyl)-5-(pyridin-3-yl)-1H-pyrazole-3-carboxylate (34.2b)

$^1$H-NMR (400 MHz, CDCl$_3$): δ 8.81-8.84 (m, 1H), 8.62 (s, 1H), 7.91 (s, 1H), 7.81-7.83 (m, 1H), 7.60-7.62 (m, 1H), 7.51-7.53 (m, 1H), 7.43-7.46 (m, 1H), 7.17 (s, 1H), 4.45 (q, J=7.2 Hz, 2H) and 1.44 (t, J=7.2 Hz, 3H). MS: 387.25 (M+H)$^+$. Yield: 47%.

Ethyl 1-(3,4-bis(trifluoromethyl)phenyl)-5-(pyridin-3-yl)-1H-pyrazole-3-carboxylate (34.2c)

$^1$H-NMR (400 MHz, CDCl$_3$): δ 8.70-8.71 (m, 1H), 8.64 (s, 1H), 7.93 (s, 1H), 7.84 (d, J=8.4 Hz, 1H), 7.63 (d, J=7.6 Hz, 1H), 7.55 (d, J=8.4 Hz, 1H), 7.45-7.49 (m, 1H), 7.18 (s, 1H), 4.39 (q, J=7.2 Hz, 2H) and 1.42 (t, J=7.2 Hz, 3H). LCMS: 430.21 (M+H)$^+$, 90.74%. Yield: 51%.

Ethyl 1-(4-fluoro-3-methyl-5-(trifluoromethyl)phenyl)-5-(pyridin-3-yl)-1H-pyrazole-3-carboxylate (34.2d)

$^1$H-NMR (400 MHz, CDCl$_3$): δ 8.54-8.64 (m, 2H), 7.55-7.57 (m, 1H), 7.38-7.45 (m, 3H), 7.13 (s, 1H), 4.44 (q, J=7.2 Hz, 2H), 2.30 (s, 3H) and 1.33 (t, J=7.2 Hz, 3H). LCMS: 394.23 (M+H)$^+$, 90.43%. Yield: 70%.

Ethyl 1-(4-chloro-3-(trifluoromethyl)phenyl)-5-(pyridin-3-yl)-1H-pyrazole-3-carboxylate (34.2e)

MS: 396.20 (M+H)$^+$. Yield: 48%.

Ethyl 1-(2,4-difluoro-3-(trifluoromethyl)phenyl)-5-(pyridin-3-yl)-1H-pyrazole-3-carboxylate (34.2f)

$^1$H-NMR (400 MHz, CDCl$_3$): δ 8.71-8.77 (m, 1H), 7.84-7.93 (m, 3H), 7.61-7.65 (m, 1H), 7.22-7.25 (m, 1H), 7.19 (s, 1H), 4.47 (q, J=6.8 Hz, 2H) and 1.43 (t, J=7.2 Hz, 3H). MS: 398.34 (M+H)$^+$. Yield: 15%.

General Procedure for the Preparation of Compounds 34.3 (a-f)

General Method R:

To an ice-cold solution of compound 34.3 (a-f) (0.80-1.5 g, 1.0 eq) in EtOH was added dropwise an aqueous solution of sodium hydroxide (3.0 eq). The resulting solution was stirred at room temperature for 2-3 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to get the desired product 34.3(a-f) as a white solid.

1-(4-Fluoro-3-(trifluoromethyl)phenyl)-5-(pyridin-3-yl)-1H-pyrazole-3-carboxylic Acid (34.3a)

$^1$H-NMR (400 MHz, DMSO-d$_6$): δ 13.15 (br s, 1H), 8.57-8.58 (m, 2H), 7.84-7.86 (m, 1H), 7.60-7.69 (m, 3H), 7.40-7.45 (m, 1H) and 7.24 (s, 1H). LCMS: 352.24 (M+H)$^+$, 95.84%. Yield: 73%.

1-(4-Cyano-3-(trifluoromethyl)phenyl)-5-(pyridin-3-yl)-1H-pyrazole-3-carboxylic Acid (34.3b)

LCMS: 359.26 (M+H)+, 99.29%. Yield: 96%.

1-(3,4-Bis(trifluoromethyl)phenyl)-5-(pyridin-3-yl)-1H-pyrazole-3-carboxylic Acid (34.3c)

$^1$H-NMR (400 MHz, DMSO-d$_6$): δ 13.28 (br s, 1H), 8.59-8.62 (m, 2H), 8.12-8.14 (m, 1H), 8.00 (s, 1H), 7.75-7.83 (m, 2H), 7.46-7.47 (m, 1H) and 7.29 (s, 1H). LCMS: 402.18 (M+H)$^+$, 95.09%. Yield: 70%.

1-(4-Fluoro-3-methyl-5-(trifluoromethyl)phenyl)-5-(pyridin-3-yl)-1H-pyrazole-3-carboxylic Acid (34.3d)

$^1$H-NMR (400 MHz, DMSO-d$_6$): δ 13.12 (br s, 1H), 8.53-8.57 (m, 2H), 7.74-7.75 (m, 1H), 7.66-7.68 (m, 1H), 7.56 (s, 1H), 7.40-7.43 (m, 1H), 7.24 (s, 1H) and 2.29 (s, 3H). LCMS: 366.22 (M+H)$^+$, 91.97%. Yield: 90%.

1-(4-Chloro-3-(trifluoromethyl)phenyl)-5-(pyridin-3-yl)-1H-pyrazole-3-carboxylic Acid (34.3e)

$^1$H-NMR (400 MHz, DMSO-d$_6$): δ 13.22 (br s, 1H), 8.57-8.60 (m, 2H), 7.87 (s, 1H), 7.80-7.82 (m, 1H), 7.70-7.72 (m, 1H), 7.60-7.62 (m, 1H), 7.41-7.44 (m, 1H) and 7.25 (s, 1H). LCMS: 368.15 (M+H)$^+$, 97.03%. Yield: 58%.

1-(2,4-Difluoro-3-(trifluoromethyl)phenyl)-5-(pyridin-3-yl)-1H-pyrazole-3-carboxylic Acid (34.3f)

$^1$H-NMR (400 MHz, DMSO-d$_6$): δ 13.20 (br s, 1H), 8.54-8.59 (m, 2H), 8.12-8.15 (m, 1H), 7.60-7.68 (m, 2H), 7.46-7.48 (m, 1H) and 7.32 (s, 1H). MS: 370.11 (M+H)$^+$. Yield: 42%.

General Procedure for the Preparation of Final Compounds:

The final compounds were prepared following the general method P (Scheme 10).

The yields and analytical data of the final compounds are set forth in Table 6.11.

TABLE 6.11

Tabulated data of the final compounds including the individual yields

| Compound ID | Structure | Amine intermediate used | Yield (%) | LCMS | $^1$H-NMR data (DMSO-d$_6$, 400 MHz), unless otherwise specified |
|---|---|---|---|---|---|
| 269 | (structure) | Intermediate-1 | 36 | 581.09 (M − H)$^+$, 99.77% | δ 8.81 (s, 1H), 8.57-8.59 (m, 2H), 7.80-7.82 (m, 1H), 7.67-7.70 (m, 2H), 7.58-7.62 (m, 1H), 7.41-7.44 (m, 1H), 7.09-7.13 (m, 3H), 6.84-6.87 (m, 2H), 4.59 (s, 2H), 4.45 (s, 2H), 3.83-3.88 (m, 1H), 3.50-3.56 (m, 1H), 2.23-2.32 (m, 2H) and 1.72-1.82 (m, 2H) |

TABLE 6.11-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 270 | 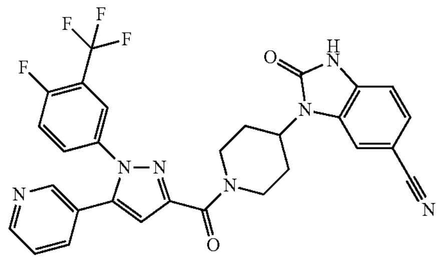 [SMILES: N#Cc1ccc2[nH]c(=O)n(C3CCN(C(=O)c4cc(-c5cccnc5)n(-c5ccc(F)c(C(F)(F)F)c5)n4)CC3)c2c1] | Intermediate-4 | 26 | 576.23 (M + H)$^+$ 98.97% | δ 11.24 (br s, 1H), 8.59-8.60 (m, 2H), 7.82-7.83 (m, 2H), 7.68-7.76 (m, 2H), 7.60-7.65 (m, 1H), 7.41-7.44 (m, 2H), 7.14 (s, 1H), 7.10 (d, J = 8.0 Hz, 1H), 4.71-4.74 (m, 2H), 4.51-4.57 (m, 1H), 3.28-3.32 (m, 1H), 2.89-2.95 (m, 1H), 2.29-2.35 (m, 2H) and 1.76-1.82 (m, 2H) |
| 271 | 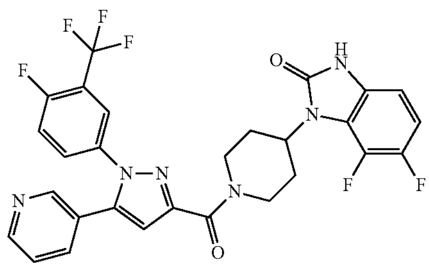 | Intermediate-3 | 45 | 587.17 (M + H)$^+$ 99.93% | δ 11.26 (br s, 1H), 8.57-8.59 (m, 2H), 7.82-7.83 (m, 1H), 7.69-7.73 (m, 2H), 7.60-7.64 (m, 1H), 7.41-7.44 (m, 1H), 7.14 (s, 1H), 7.00-7.05 (m, 1H), 6.77-6.80 (m, 1H), 4.78-4.81 (m, 1H), 4.68-4.70 (m, 2H), 3.30-3.32 (m, 1H), 2.92-2.96 (m, 1H), 2.07-2.14 (m, 2H) and 1.84-1.87 (m, 2H) |
| 272 | 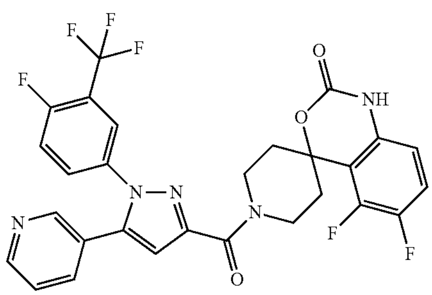 [SMILES: O=C1Nc2ccc(F)c(F)c2C2(CCN(C(=O)c3cc(-c4cccnc4)n(-c4ccc(F)c(C(F)(F)F)c4)n3)CC2)O1] | Intermediate-12 | 13 | 588.18 (M + H)$^+$ 99.73% | δ 10.54 (br s, 1H), 8.57-8.59 (m, 2H), 7.81-7.82 (m, 1H), 7.74-7.76 (m, 1H), 7.68-7.70 (m, 1H), 7.60-7.64 (m, 1H), 7.35-7.44 (m, 2H), 7.15 (s, 1H), 6.73-7.74 (m, 1H), 4.57-4.68 (m, 2H), 3.52-3.58 (m, 1H), 3.17-3.19 (m, 1H) and 2.16-2.22 (m, 4H). |
| 273 | 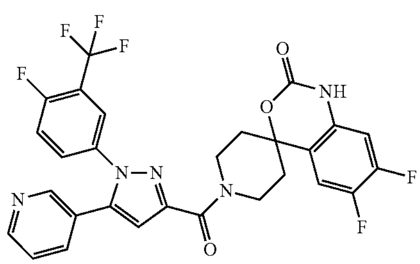 [SMILES: O=C1Nc2cc(F)c(F)cc2C2(CCN(C(=O)c3cc(-c4cccnc4)n(-c4ccc(F)c(C(F)(F)F)c4)n3)CC2)O1] | Intermediate-13 | 13 | 588.14 (M + H)$^+$ 99.88% | δ 10.44 (br s, 1H), 8.57-8.60 (m, 2H), 7.80-7.82 (m, 1H), 7.56-7.80 (m, 4H), 7.41-7.44 (m, 1H), 7.14 (s, 1H), 6.85-6.89 (m, 1H), 4.57-4.66 (m, 2H), 3.48-3.54 (m, 1H), 3.09-3.14 (m, 1H) and 2.00-2.09 (m, 4H). |
| 274 | 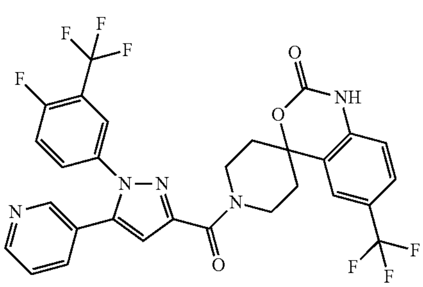 [SMILES: O=C1Nc2ccc(C(F)(F)F)cc2C2(CCN(C(=O)c3cc(-c4cccnc4)n(-c4ccc(F)c(C(F)(F)F)c4)n3)CC2)O1] | Intermediate-14 | 27 | 620.15 (M + H)$^+$ 99.87% | δ 10.71 (br s, 1H), 8.58-8.60 (m, 2H), 7.81-7.82 (m, 1H), 7.60-7.65 (m, 5H), 7.41-7.44 (m, 1H), 7.14 (s, 1H), 7.06-7.08 (d, J = 2.0 Hz, 1H), 4.59-4.67 (m, 2H), 3.50-3.56 (m, 1H), 3.11-3.17 (m, 1H) and 2.03-2.10 (m, 4H). |

TABLE 6.11-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 275 | 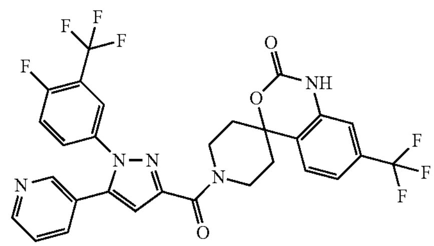 [SMILES: O=C1Nc2cc(C(F)(F)F)ccc2C2(CCN(C(=O)c3cc(-c4cccnc4)n(-c4ccc(F)c(C(F)(F)F)c4)n3)CC2)O1] | Intermediate-15 | 23 | 620.18 (M + H)$^+$ 99.42% | δ 10.70 (br s, 1H), 8.58-8.60 (m, 2H), 7.80-7.82 (m, 1H), 7.74-7.77 (m, 1H), 7.67-7.80 (m, 1H), 7.60-7.65 (m, 2H), 7.41-7.44 (m, 1H), 7.36-7.38 (m, 1H), 7.17-7.19 (m, 1H), 7.15 (s, 1H), 4.59-4.68 (m, 2H), 3.52-3.58 (m, 1H), 3.14-3.19 (m, 1H) and 2.07-2.14 (m, 4H). |
| 276 | 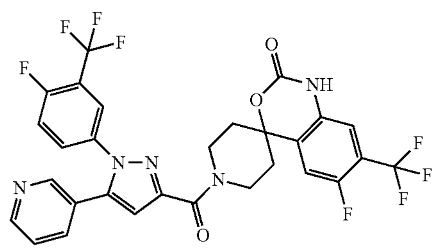 [SMILES: O=C1Nc2cc(C(F)(F)F)c(F)cc2C2(CCN(C(=O)c3cc(-c4cccnc4)n(-c4ccc(F)c(C(F)(F)F)c4)n3)CC2)O1] | Intermediate-16 | 31 | 638.19 (M + H)$^+$ 99.04% | δ 10.59 (br s, 1H), 8.58-8.59 (m, 2H), 7.81-7.82 (m, 1H), 7.73-7.76 (m, 1H), 7.60-7.70 (m, 3H), 7.41-7.44 (m, 1H), 7.20 (d, J = 8.4 Hz, 1H), 7.14 (s, 1H), 4.59-4.69 (m, 2H), 3.49-3.56 (m, 1H), 3.10-3.16 (m, 1H) and 2.05-2.13 (m, 4H). |
| 277 | 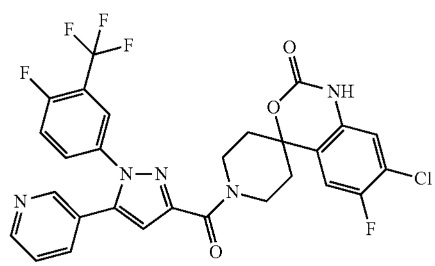 [SMILES: O=C1Nc2cc(Cl)c(F)cc2C2(CCN(C(=O)c3cc(-c4cccnc4)n(-c4ccc(F)c(C(F)(F)F)c4)n3)CC2)O1] | Intermediate-17 | 14 | 604.09 (M + H)$^+$ 97.81% | δ 10.47 (br s, 1H), 8.58-8.59 (m, 2H), 7.81-7.82 (m, 1H), 7.73-7.75 (m, 1H), 7.55-7.68 (m, 3H), 7.41-7.44 (m, 1H), 7.14 (s, 1H), 7.01 (d, J = 6.4 Hz, 1H), 4.57-4.66 (m, 2H), 3.48-3.55 (m, 1H), 3.13-3.16 (m, 1H) and 2.01-2.15 (m, 4H). |
| 278 | 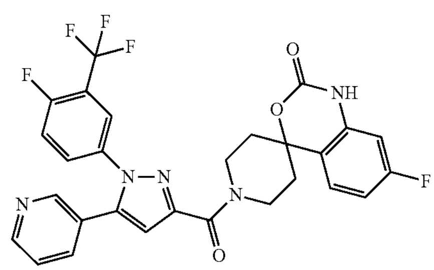 [SMILES: O=C1Nc2cc(F)ccc2C2(CCN(C(=O)c3cc(-c4cccnc4)n(-c4ccc(F)c(C(F)(F)F)c4)n3)CC2)O1] | Intermediate-18 | 7 | 570.21 (M + H)$^+$ 97.52% | δ 10.45 (br s, 1H), 8.57-8.59 (m, 2H), 7.80-7.81 (m, 1H), 7.60-7.79 (m, 3H), 7.32-7.44 (m, 2H), 7.14 (s, 1H), 6.82-6.87 (m, 1H), 6.68-6.71 (m, 1H), 4.57-4.64 (m, 2H), 3.50-3.56 (m, 1H), 3.12-3.17 (m, 1H) and 2.01-2.08 (m, 4H) |
| 279 | 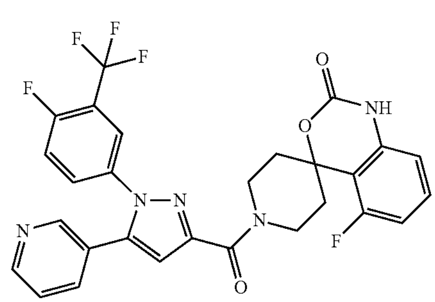 [SMILES: O=C1Nc2cccc(F)c2C2(CCN(C(=O)c3cc(-c4cccnc4)n(-c4ccc(F)c(C(F)(F)F)c4)n3)CC2)O1] | Intermediate-19 | 4 | 570.25 (M + H)$^+$ 97.65% | δ 10.56 (br s, 1H), 8.57-8.59 (m, 2H), 7.80-7.83 (m, 1H), 7.60-7.77 (m, 3H), 7.41-7.44 (m, 1H), 7.27-7.33 (m, 1H), 7.15 (s, 1H), 6.83-6.88 (m, 1H), 6.74 (d, J = 8.0 Hz, 1H), 4.55-4.67 (m, 2H), 3.52-3.58 (m, 1H), 3.13-3.18 (m, 1H) and 2.12-2.27 (m, 4H) |

TABLE 6.11-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 280 | 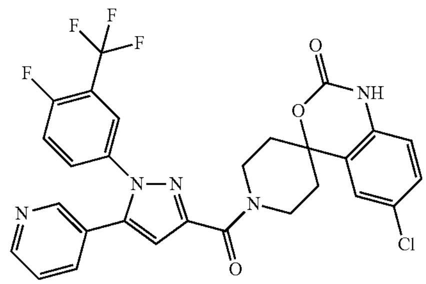 | Commercial | 33 | 586.13 (M + H)$^+$ 99.83% | δ 10.44 (br s, 1H), 8.58-8.60 (m, 2H), 7.80-7.81 (m, 1H), 7.68-7.76 (m, 2H), 7.60-7.64 (m, 1H), 7.47-7.48 (m, 1H), 7.41-7.44 (m, 1H), 7.31-7.34 (m, 1H), 7.14 (s, 1H), 6.90 (d, J = 8.4 Hz, 1H), 4.57-4.63 (m, 2H), 3.49-3.55 (m, 1H), 3.13-3.17 (m, 1H) and 2.00-2.16 (m, 4H) |
| 281 | 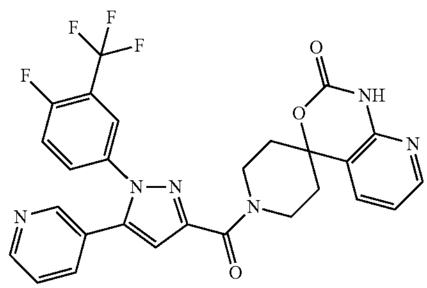 [SMILES: O=C1Nc2ncccc2C2(CCN(C(=O)c3cc(-c4cccnc4)n(-c4ccc(F)c(C(F)(F)F)c4)n3)CC2)O1] | Commercial | 34 | 553.15 (M + H)$^+$ 99.23% | δ 10.92 (br s, 1H), 8.57-8.60 (m, 2H), 8.20-8.21 (m, 1H), 7.60-7.81 (m, 5H), 7.41-7.44 (m, 1H), 7.14 (s, 1H), 7.06-7.09 (m, 1H), 4.59-4.67 (m, 2H), 3.50-3.57 (m, 1H), 3.13-3.18 (m, 1H) and 2.04-2.13 (m, 4H) |
| 282 | 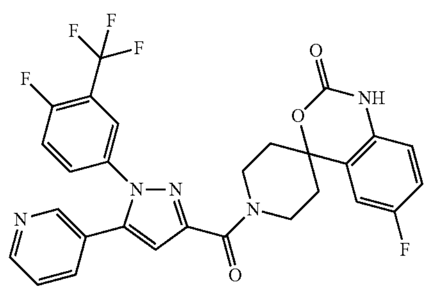 [SMILES: O=C1Nc2ccc(F)cc2C2(CCN(C(=O)c3cc(-c4cccnc4)n(-c4ccc(F)c(C(F)(F)F)c4)n3)CC2)O1] | Intermediate-20 | 10 | 570.18 (M + H)$^+$ 99.67% | δ 10.36 (br s, 1H), 8.58-8.59 (m, 2H), 7.80-7.82 (m, 1H), 7.60-7.77 (m, 3H), 7.41-7.44 (m, 1H), 7.30-7.33 (m, 1H), 7.15 (s, 1H), 7.10-7.13 (m, 1H), 6.89-6.93 (m, 1H), 4.57-4.65 (m, 2H), 3.49-3.55 (m, 1H), 3.10-3.17 (m, 1H) and 2.00-2.17 (m, 4H) |
| 283 | 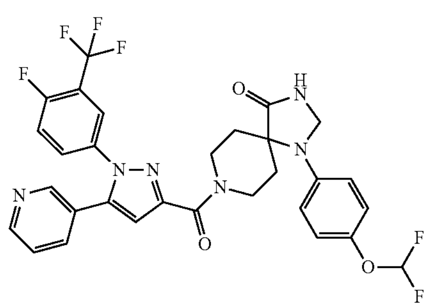 [SMILES: O=C(c1cc(-c2cccnc2)n(-c2ccc(F)c(C(F)(F)F)c2)n1)N1CCC2(CC1)C(=O)NCN2c1ccc(OC(F)F)cc1] | Intermediate-2 | 19 | 631.17 (M − H)$^+$ 97.58% | δ 8.83 (s, 1H), 8.57-8.59 (m, 2H), 7.79-7.81 (m, 1H), 7.67-7.73 (m, 2H), 7.57-7.62 (m, 1H), 7.41-7.44 (m, 1H), 6.81-7.20 (m, 6H), 4.60 (s, 2H), 4.48 (s, 2H), 3.84-3.90 (m, 1H), 3.50-3.56 (m, 1H), 2.33-2.37 (m, 2H) and 1.72-1.81 (m, 2H) |
| 284 | 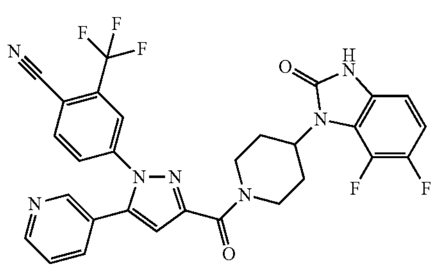 [SMILES: N#Cc1ccc(-n2nc(C(=O)N3CCC(n4c(=O)[nH]c5ccc(F)c(F)c54)CC3)cc2-c2cccnc2)cc1C(F)(F)F] | Intermediate-3 | 48 | 594.16 (M + H)$^+$ 98.92% | δ 11.25 (br s, 1H), 8.63 (s, 2H), 8.23 (d, J = 8.4 Hz, 1H), 7.94 (s, 1H), 7.75-7.82 (m, 2H), 7.44-7.47 (m, 1H), 7.18 (s, 1H), 7.00-7.07 (m, 1H), 6.77-6.80 (m, 1H), 4.68-4.70 (m, 3H), 3.36-3.39 (m, 1H), 2.94-3.0 (m, 1H), 2.12-2.16 (m, 2H) and 1.84-1.93 (m, 2H) |

TABLE 6.11-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 285 | 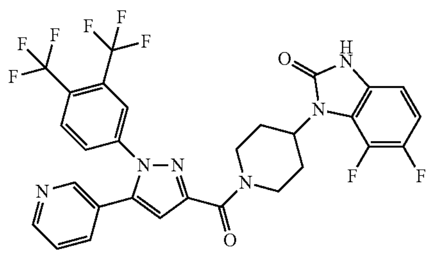 [SMILES: O=C(c1cc(-c2cccnc2)n(-c2ccc(C(F)(F)F)c(C(F)(F)F)c2)n1)N1CCC(n2c(=O)[nH]c3ccc(F)c(F)c32)CC1] | Intermediate-3 | 51 | 637.21 (M + H)+ 99.79% | δ 11.17 (br s, 1H), 8.62 (s, 2H), 8.11 (d, J = 8.4 Hz, 1H), 7.96 (s, 1H), 7.77-7.85 (m, 2H), 7.44-7.48 (m, 1H), 7.17 (s, 1H), 7.00-7.07 (m, 1H), 6.77-6.80 (m, 1H), 4.68-4.74 (m, 3H), 3.36-3.39 (m, 1H), 2.95-3.01 (m, 1H), 2.07-2.15 (m, 2H) and 1.85-1.93 (m, 2H) |
| 286 | 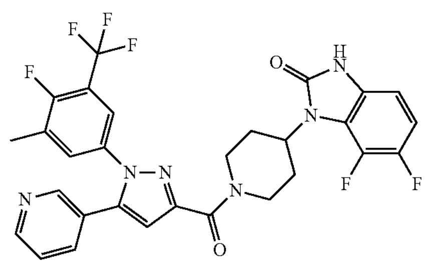 [SMILES: Cc1cc(-n2nc(C(=O)N3CCC(n4c(=O)[nH]c5ccc(F)c(F)c54)CC3)cc2-c2cccnc2)cc(C(F)(F)F)c1F] | Intermediate-3 | 17 | 601.21 (M + H)+ 99.44% | δ 11.14 (br s, 1H), 8.58 (s, 2H), 7.74-7.75 (m, 1H), 7.68 (d, J = 8.0 Hz, 1H), 7.56 (s, 1H), 7.40-7.43 (m, 1H), 7.13 (s, 1H), 6.99-7.08 (m, 1H), 6.77-6.79 (m, 1H), 4.77-4.80 (m, 1H), 4.56-4.70 (m, 2H), 3.33-3.36 (m, 1H), 2.92-2.98 (m, 1H), 2.28 (s, 3H), 2.08-2.14 (m, 2H) and 1.84-1.92 (m, 2H) |
| 287 | 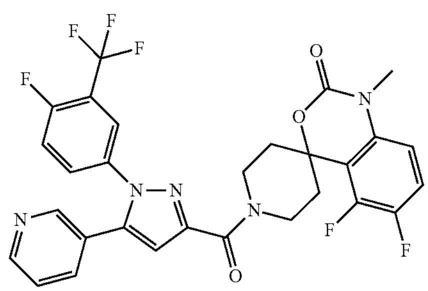 [SMILES: CN1C(=O)OC2(CCN(C(=O)c3cc(-c4cccnc4)n(-c4ccc(F)c(C(F)(F)F)c4)n3)CC2)c2c1ccc(F)c2F] | Intermediate-22 | 30 | 602.15 (M + H)+ 98.84% | δ 8.57-8.59 (m, 2H), 7.81-7.82 (m, 1H), 7.74-7.76 (m, 1H), 7.65-7.68 (m, 1H), 7.60-7.62 (m, 1H), 7.47-7.49 (m, 1H), 7.41-7.44 (m, 1H), 7.15 (s, 1H), 6.98-.700 (m, 1H), 4.67-4.71 (m, 1H), 4.57-4.60 (m, 1H), 3.51-3.55 (m, 1H), 3.30 (s, 3H), 3.16-3.19 (m, 1H) and 2.22-2.24 (m, 4H). |
| 288 | 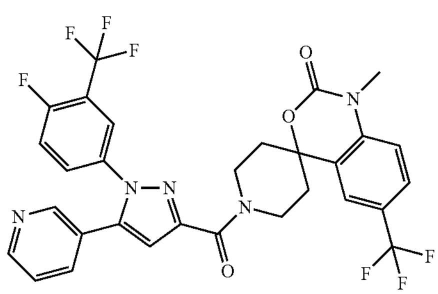 [SMILES: CN1C(=O)OC2(CCN(C(=O)c3cc(-c4cccnc4)n(-c4ccc(F)c(C(F)(F)F)c4)n3)CC2)c2cc(C(F)(F)F)ccc21] | Intermediate-23 | 22 | 634.19 (M + H)+ 99.86% | δ 8.58-8.60 (m, 2H), 7.81-7.82 (m, 1H), 7.59-7.68 (m, 5H), 7.41-7.44 (m, 1H), 7.30 (d, J = 8.4 Hz, 1H), 7.14 (s, 1H), 4.60-4.71 (m, 2H), 3.51-3.57 (m, 1H), 3.31 (s, 3H), 3.11-3.17 (m, 1H) and 2.06-2.16 (m, 4H). |
| 289 | 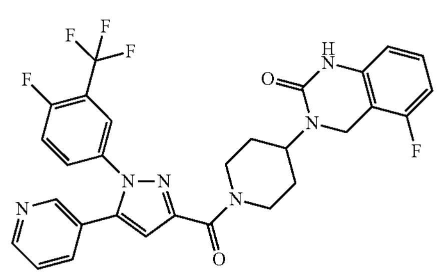 [SMILES: O=C(c1cc(-c2cccnc2)n(-c2ccc(F)c(C(F)(F)F)c2)n1)N1CCC(N2Cc3c(F)cccc3NC2=O)CC1] | Intermediate-24 | 6 | 583.25 (M + H)+ 99.25% | δ 9.47 (s, 1H), 8.57-8.59 (m, 2H), 7.80-7.82 (m, 1H), 7.60-7.76 (m, 3H), 7.41-7.44 (m, 1H), 7.12-7.18 (m, 1H), 7.11 (s, 1H), 6.67 (t, J = 8.8 Hz, 1H), 6.58 (d, J = 8.0 Hz, 1H), 4.65-4.68 (m, 2H), 4.43-4.49 (m, 1H), 4.37 (s, 2H), 3.16-3.21 (m, 1H), 2.83-2.89 (m, 1H), 1.81-1.86 (m, 2H) and 1.64-1.70 (m, 2H). |

TABLE 6.11-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 290 | 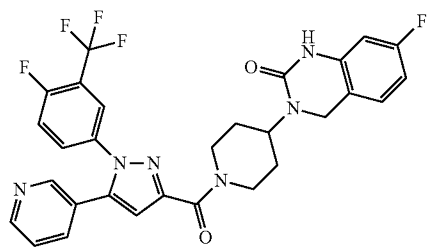 [SMILES: O=C(c1cc(-c2cccnc2)n(-c2ccc(F)c(C(F)(F)F)c2)n1)N1CCC(N2Cc3ccc(F)cc3NC2=O)CC1] | Intermediate-25 | 20 | 583.25 (M + H)$^+$ 98.71% | δ 9.36 (s, 1H), 8.57-8.59 (m, 2H), 7.80-7.82 (m, 1H), 7.60-7.75 (m, 3H), 7.41-7.44 (m, 1H), 7.12-7.15 (m, 1H), 7.10 (s, 1H), 6.65 (t, J = 8.4 Hz, 1H), 6.53-6.56 (m, 1H), 4.65-4.68 (m, 2H), 4.45-4.49 (m, 1H), 4.27 (s, 2H), 3.22-3.24 (m, 1H), 2.82-2.86 (m, 1H), and 1.62-1.80 (m, 4H). |
| 291 | 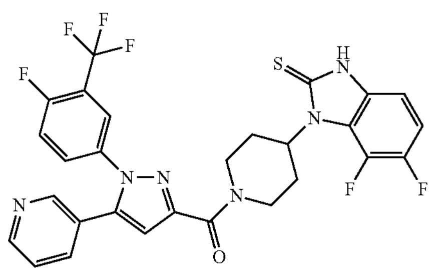 [SMILES: O=C(c1cc(-c2cccnc2)n(-c2ccc(F)c(C(F)(F)F)c2)n1)N1CCC(n2c(=S)[nH]c3ccc(F)c(F)c32)CC1] | Intermediate-7 | 7 | 603.20 (M + H)$^+$ 99.62% | δ 13.25 (br s, 1H), 8.58 (s, 2H), 7.81-7.83 (m, 1H), 7.70-7.75 (m, 2H), 7.59-7.64 (m, 1H), 7.41-7.44 (m, 1H), 7.24-7.31 (m, 1H), 7.17 (s, 1H), 6.99-7.02 (m, 1H), 5.63 (s, 1H), 4.84-4.87 (m, 1H), 4.71-4.74 (m, 1H), 3.39-3.42 (m, 1H), 2.97-3.03 (m, 1H), 2.07-2.11 (m, 2H) and 1.86-1.90 (m, 2H |
| 292 | 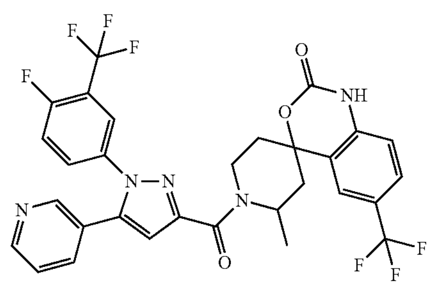 [SMILES: CC1CC2(CCN1C(=O)c1cc(-c3cccnc3)n(-c3ccc(F)c(C(F)(F)F)c3)n1)OC(=O)Nc1ccc(C(F)(F)F)cc12] | Intermediate-21 | 11 | 632.14 (M − H)$^+$ 99.65% | δ 10.71 (br s, 1H), 8.58-8.60 (m, 2H), 6.60-7.83 (m, 6H), 7.42-7.44 (m, 1H), 7.14 (s, 1H), 7.05-7.09 (m, 1H), 4.84-4.95 (m, 1H), 4.53-4.60 (m, 1H), 3.57-3.60 (m, 1H), 2.32-2.34 (m, 1H), 2.20-2.24 (m, 1H), 2.13-2.15 (m, 2H), and 1.50 (d, J = 6.4 Hz, 3H) |
| 293 | 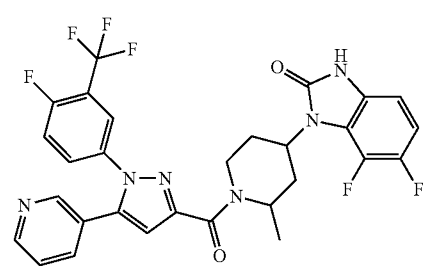 [SMILES: CC1CC(n2c(=O)[nH]c3ccc(F)c(F)c32)CCN1C(=O)c1cc(-c2cccnc2)n(-c2ccc(F)c(C(F)(F)F)c2)n1] | Intermediate-9 | 23 | 601.28 (M + H)$^+$ 99.91% | δ 10.27 (br s, 1H), 8.59-8.60 (m, 2H), 7.81-7.82 (m, 1H), 7.70-7.76 (m, 2H), 7.59-7.64 (m, 1H), 7.42-7.45 (m, 1H), 7.15 (s, 1H), 7.01-7.08 (m, 1H), 6.78-6.81 (m, 1H), 4.38-4.53 (m, 3H), 3.56-3.58 (m, 1H), 2.17-2.32 (m, 2H), 1.98-2.01 (m, 2H) and 1.30 (d, J = 6.0 Hz, 3H) |
| 294 | 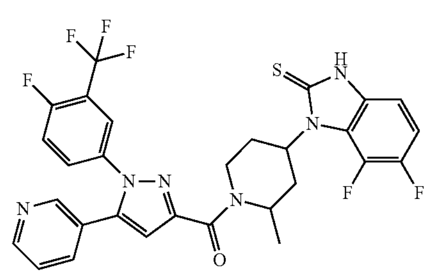 [SMILES: CC1CC(n2c(=S)[nH]c3ccc(F)c(F)c32)CCN1C(=O)c1cc(-c2cccnc2)n(-c2ccc(F)c(C(F)(F)F)c2)n1] | Intermediate-10 | 13 | 617.23 (M + H)$^+$ 97.62% | δ 13.24 (br s, 1H), 8.57-8.59 (m, 2H), 7.81-7.84 (m, 1H), 7.68-7.77 (m, 2H), 7.59-7.64 (m, 1H), 7.41-7.44 (m, 1H), 7.26-7.31 (m, 1H), 7.17 (s, 1H), 7.00-7.03 (m, 1H), 5.47 (s, 1H), 4.48-4.53 (m, 2H), 3.59-3.62 (m, 1H), 2.19-2.32 (m, 2H), 1.89-2.01 (m, 2H) and 1.32 (d, J = 6.0 Hz, 3H) |

TABLE 6.11-continued

Tabulated data of the final compounds including the individual yields

| Compound ID | Structure | Amine intermediate used | Yield (%) | LCMS | 1H-NMR data (DMSO-d6, 400 MHz), unless otherwise specified |
|---|---|---|---|---|---|
| 295 | 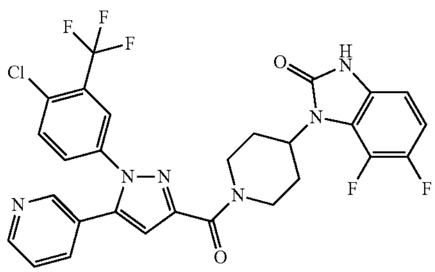 [SMILES: O=C(c1cc(-c2cccnc2)n(-c2ccc(Cl)c(C(F)(F)F)c2)n1)N1CCC(n2c(=O)[nH]c3ccc(F)c(F)c32)CC1] | Intermediate-3 | 22 | 601.07 (M − H)+ 99.74% | δ 11.22 (br s, 1H), 8.59-8.61 (m, 2H), 7.80-7.84 (m, 2H), 7.72-7.74 (m, 1H), 7.63-7.66 (m, 1H), 7.42-7.45 (m, 1H), 7.14 (s, 1H), 7.00-7.07 (m, 1H), 6.77-6.80 (m, 1H), 4.67-4.78 (m, 3H), 3.27-3.30 (m, 1H), 2.93-2.99 (m, 1H), 2.11-2.24 (m, 2H) and 1.84-1.92 (m, 2H) |
| 296 | 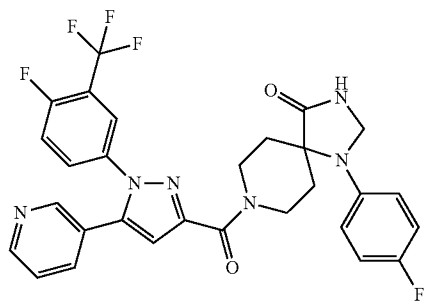 [SMILES: O=C(c1cc(-c2cccnc2)n(-c2ccc(F)c(C(F)(F)F)c2)n1)N1CCC2(CC1)C(=O)NCN2c1ccc(F)cc1] | Intermediate-1 | 11 | 599.23 (M + H)+ 96.98% | δ 8.80 (s, 1H), 8.58-8.61 (m, 2H), 7.78-7.82 (m, 2H), 7.70-7.72 (m, 1H), 7.58-7.61 (m, 1H), 7.42-7.45 (m, 1H), 7.15 (s, 1H), 7.07-7.13 (m, 2H), 6.84-6.88 (m, 2H), 4.59 (s, 2H), 4.42-4.45 (m, 2H), 3.83-3.89 (m, 1H), 3.50-3.56 (m, 1H), 2.19-2.29 (m, 2H) and 1.73-1.83 (m, 2H) |
| 297 | 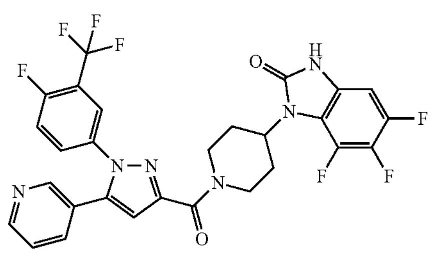 [SMILES: O=C(c1cc(-c2cccnc2)n(-c2ccc(F)c(C(F)(F)F)c2)n1)N1CCC(n2c(=O)[nH]c3cc(F)c(F)c(F)c32)CC1] | Intermediate-6 | 19 | 605.21 (M + H)+ 98.97% | δ 11.22 (br s, 1H), 8.58-8.59 (m, 2H), 7.81-7.83 (m, 1H), 7.68-7.76 (m, 2H), 7.59-7.64 (m, 1H), 7.40-7.44 (m, 1H), 7.13 (s, 1H), 6.96-7.00 (m, 1H), 4.77-4.81 (m, 1H), 4.60-4.67 (m, 2H), 3.31-3.32 (m, 1H), 2.92-2.97 (m, 1H), 2.08-2.14 (m, 2H) and 1.83-1.91 (m, 2H) |
| 298 | 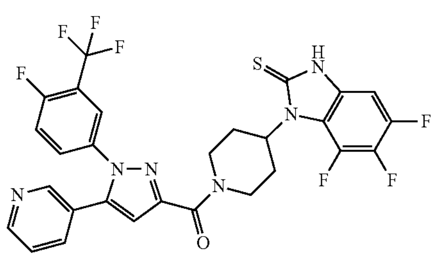 [SMILES: O=C(c1cc(-c2cccnc2)n(-c2ccc(F)c(C(F)(F)F)c2)n1)N1CCC(n2c(=S)[nH]c3cc(F)c(F)c(F)c32)CC1] | Intermediate-8 | 7 | 621.19 (M + H)+ 96.88% | δ 13.40 (br s, 1H), 8.58-8.59 (m, 2H), 7.82-7.84 (m, 1H), 7.69-7.76 (m, 2H), 7.59-7.64 (m, 1H), 7.41-7.44 (m, 1H), 7.11-7.15 (m, 2H), 5.62-5.64 (m, 1H), 4.84-4.87 (m, 1H), 4.71-4.74 (m, 1H), 3.39-3.42 (m, 1H), 2.97-3.03 (m, 1H), 2.03-2.07 (m, 2H) and 1.85-1.89 (m, 2H) |
| 299 | 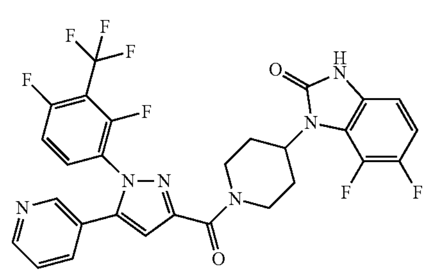 [SMILES: O=C(c1cc(-c2cccnc2)n(-c2ccc(F)c(C(F)(F)F)c2F)n1)N1CCC(n2c(=O)[nH]c3ccc(F)c(F)c32)CC1] | Intermediate-3 | 19 | 605.35 (M + H)+ 99.74% | δ 11.20 (br s, 1H), 8.58-8.59 (m, 2H), 8.12-8.18 (m, 1H), 7.69-7.72 (m, 1H), 7.57-7.62 (m, 1H), 7.40-7.43 (m, 1H), 7.21 (s, 1H), 6.99-7.06 (m, 1H), 6.76-6.79 (m, 1H), 4.62-4.75 (m, 3H), 3.30-3.32 (m, 1H), 2.92-2.98 (m, 1H), 2.07-2.16 (m, 2H) and 1.83-1.92 (m, 2H) |

TABLE 6.11-continued
Tabulated data of the final compounds including the individual yields
| Compound ID | Structure | Amine intermediate used | Yield (%) | LCMS | $^1$H-NMR data (DMSO-$d_6$, 400 MHz), unless otherwise specified |
|---|---|---|---|---|---|
| 300 | 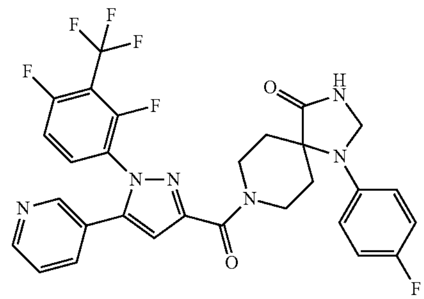 [SMILES: O=C(c1cc(-c2cccnc2)n(-c2ccc(F)c(C(F)(F)F)c2F)n1)N1CCC2(CC1)C(=O)NCN2c1ccc(F)cc1] | Intermediate-1 | 21 | 601.38 (M + H)$^+$ 98.66% | δ 8.79 (br s, 1H), 8.59 (d, J = 2.80 Hz, 2H), 8.08-8.14 (m, 1H), 7.67-7.69 (m, 1H), 7.56-7.61 (m, 1H), 7.40-7.43 (m, 1H), 7.22 (s, 1H), 7.06-7.10 (m, 2H), 6.83-6.87 (m, 2H), 4.58 (s, 2H), 4.43 (d, J = 12.40 Hz, 2H), 3.83-3.89 (m, 1H), 3.51-3.57 (m, 1H), 2.19-2.31 (m, 2H) and 1.72-1.83 (m, 2H) |
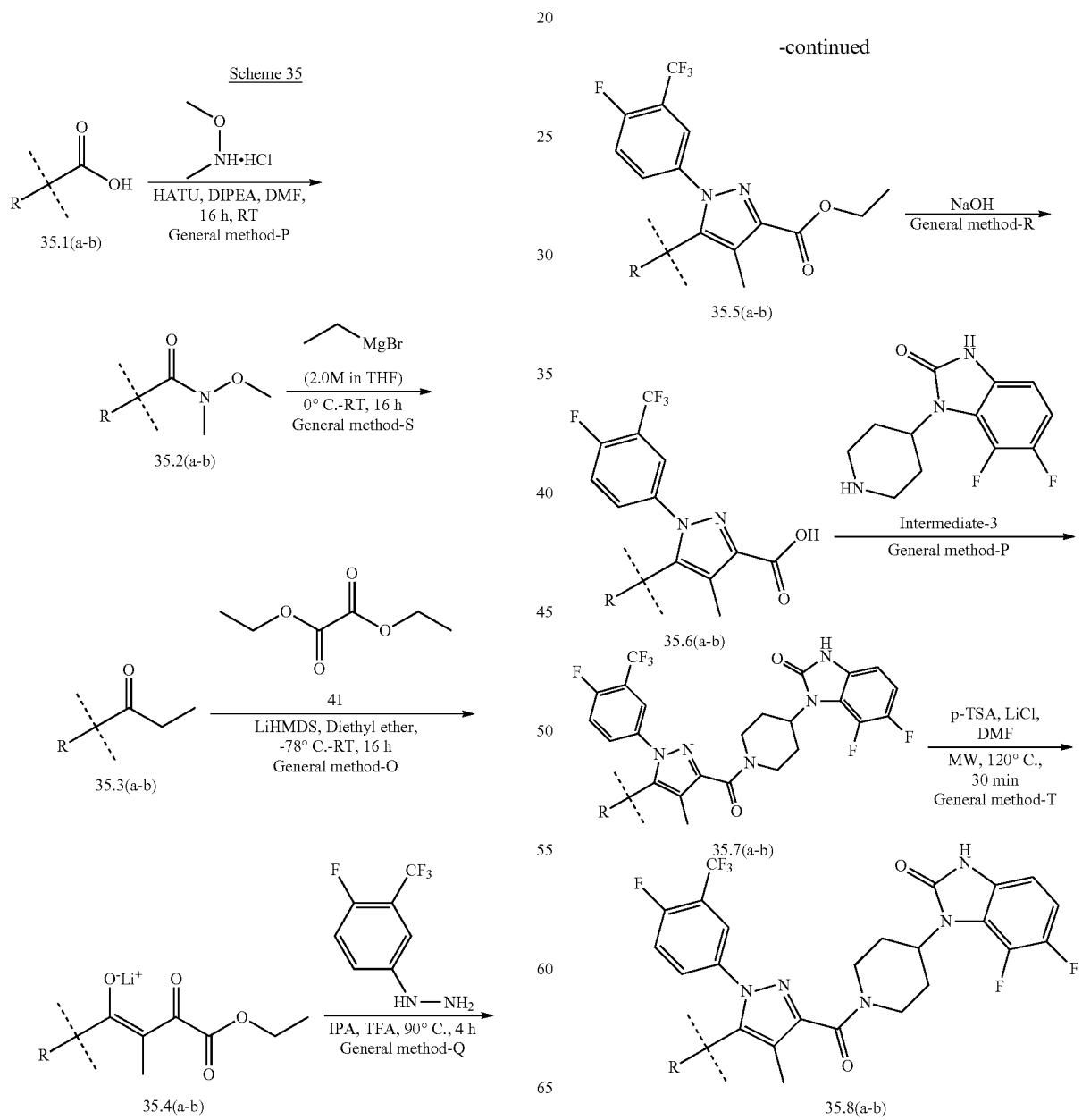
Scheme 35

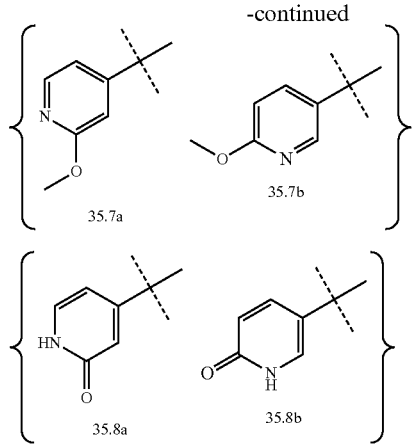

General Procedure for the Preparation of Compounds 35.2(a-b) (General Method P):

To an ice-cold solution of 2-methoxyisonicotinic acid 35.1a or 6-methoxynicotinic acid 35.1b (1.0 eq) in DMF was added DIPEA (1.5 eq) and HATU (1.50 eq). The resulting mixture was stirred under nitrogen atmosphere at 0° C. for 15 min followed by addition of N,O-dimethylhydroxylamine hydrochloride (1.1 eq). The reaction mixture was then stirred at room temperature for 16 h. After the completion of the reaction (TLC monitoring), the solution was diluted with ice-cold water followed by extraction with EtOAc (3 times). The combined organics were washed with brine, dried over anhydrous $Na_2SO_4$, filtered and concentrated under reduced pressure. The crude was purified by silica gel (100-200 M), elution with 2-3% MeOH/DCM to get desired product 35.2(a-b) as a viscous liquid.

N,2-Dimethoxy-N-methylisonicotinamide (35.2a)

$^1$H-NMR (400 MHz, DMSO-$d_6$): δ 8.24 (d, J=5.2 Hz, 1H), 7.07 (d, J=4.8 Hz, 1H), 6.91 (s, 1H), 3.89 (s, 3H), 3.24 (s, 3H) and 2.68 (s, 3H). MS: 197.09 (M+H)$^+$. Yield: 96%.

N,6-Dimethoxy-N-methylnicotinamide (35.2b)

$^1$H-NMR (400 MHz, DMSO-$d_6$): δ 8.76 (d, J=4.0 Hz, 1H), 7.50-7.53 (m, 1H), 6.86-6.91 (m, 1H), 3.90 (s, 3H), 3.26 (s, 3H) and 2.72 (s, 3H). MS: 197.19 (M+H)$^+$. Yield: 42%.

General Procedure for the Preparation of Compounds 35.3(a-b) (General Method S):

A solution of 35.2 (a-b) (1.0 eq) in THF was cooled to −78° C. followed by addition of ethyl magnesium bromide (1.5 eq, 2 M in THF) slowly under $N_2$ atmosphere. The reaction mixture was then left to stir at room temperature for 16 h. After completion of the reaction (TLC and MS monitoring), the solution was then cooled to 0° C. and diluted with saturated solution of $NH_4Cl$ and extracted with EtOAc (3 times). The combined organics were washed with brine, dried over anhydrous sodium sulfate, filtered and concentrated. The crude was purified over silica gel (100-200 M, 10-15% EtOAc-hexane) to get the desired product 35.3(a-b) as a viscous liquid.

1-(2-Methoxypyridin-4-yl)propan-1-one (35.3a)

$^1$H-NMR (400 MHz, CDCl$_3$): δ 8.29 (d, J=5.2 Hz, 1H), 7.30 (d, J=4.4 Hz, 1H), 7.18 (s, 1H), 3.97 (s, 3H), 2.93 (q, J=7.2 Hz, 2H) and 1.19 (t, J=7.2 Hz, 3H). LCMS: 165.98 (M+H)$^+$, 97.50%. Yield: 42%.

1-(6-Methoxypyridin-3-yl)propan-1-one (35.3b)

$^1$H-NMR (400 MHz, CDCl$_3$): δ 8.80 (s, 1H), 8.29 (dd, J=2.0 & 8.8 Hz, 1H), 6.78 (d, J=8.8 Hz, 1H), 4.10 (s, 3H), 2.92 (q, J=7.2 Hz, 2H) and 1.21 (t, J=7.2 Hz, 3H). LCMS: 166.25 (M+H)$^+$, 96.69%. Yield: 75%.

General Procedure for the Preparation of Compounds 35.4(a-b):

These compounds were prepared following the general method O (Scheme 33).

4-Ethoxy-1-(2-methoxypyridin-4-yl)-2-methyl-3,4-dioxobut-1-en-1-olate Lithium Salt (35.4a)

$^1$H-NMR (400 MHz, DMSO-$d_6$): δ 8.33-8.36 (m, 1H), 7.36-7.40 (m, 1H), 7.20-7.23 (m, 1H), 4.34 (q, J=7.20 Hz, 2H), 3.95 (s, 3H), 1.63 (s, 3H) and 1.09 (t, J=6.8 Hz, 3H). MS: 266.28 (M+H)$^+$. Yield: 90%.

4-Ethoxy-1-(6-methoxypyridin-3-yl)-2-methyl-3,4-dioxobut-1-en-1-olate (35.4b)

$^1$H-NMR (400 MHz, DMSO-$d_6$): δ 8.74 (s, 1H), 7.56-7.58 (m, 1H), 6.91-6.93 (m, 1H), 4.29 (q, J=7.20 Hz, 2H), 3.97 (s, 3H), 1.65 (s, 3H) and 1.09 (t, J=7.6 Hz, 3H). MS: 266.04 (M+H)$^+$. Yield: 72%.

General Procedure for the Preparation of Compounds 35.5 (a-b):

These compounds were prepared following the general method Q (Scheme 34).

Ethyl 1-(4-fluoro-3-(trifluoromethyl)phenyl)-5-(2-methoxypyridin-4-yl)-4-methyl-1H-pyrazole-3-carboxylate (35.5a)

$^1$H-NMR (400 MHz, CDCl$_3$): δ 8.25-8.27 (m, 1H), 7.70-7.71 (m, 1H), 7.26-7.30 (m, 1H), 7.14-7.18 (m, 1H), 6.65-6.69 (m, 2H), 4.44 (q, J=7.2 Hz, 2H), 4.00 (s, 3H), 2.36 (s, 3H) and 1.41 (t, J=7.2 Hz, 3H). MS: 424.04 (M+H)$^+$. Yield: 51%.

Ethyl 1-(4-fluoro-3-(trifluoromethyl)phenyl)-5-(6-methoxypyridin-3-yl)-4-methyl-1H-pyrazole-3-carboxylate (35.5b)

$^1$H-NMR (400 MHz, CDCl$_3$): δ 8.86 (s, 1H), 7.66-7.70 (m, 1H), 7.32-7.35 (m, 1H), 7.11-7.16 (m, 1H), 6.79-6.89 (m, 2H), 4.45 (q, J=7.2 Hz, 2H), 3.89 (s, 3H), 2.31 (s, 3H) and 1.42 (t, J=7.2 Hz, 3H). MS: 424.15 (M+H)$^+$. Yield: 38%.

General Procedure for the Preparation of Compounds 35.6(a-b):

These compounds were prepared following the general method R (Scheme 34).

1-(4-Fluoro-3-(trifluoromethyl)phenyl)-5-(2-methoxypyridin-4-yl)-4-methyl-1H-pyrazole-3-carboxylic Acid (35.6a)

$^1$H-NMR (400 MHz, DMSO-$d_6$): δ 13.01 (br s, 1H), 8.16-8.18 (m, 1H), 7.72-7.74 (m, 1H), 7.50-7.55 (m, 2H), 7.74-7.77 (m, 2H), 3.84 (s, 3H) and 2.21 (s, 3H). MS: 396.10 (M+H)$^+$. Yield: 77%.

1-(4-Fluoro-3-(trifluoromethyl)phenyl)-5-(6-methoxypyridin-3-yl)-4-methyl-1H-pyrazole-3-carboxylic Acid (35.6b)

$^1$H-NMR (400 MHz, DMSO-d$_6$): δ 13.86 (br s, 1H), 8.11 (s, 1H), 7.72-7.75 (m, 1H), 7.50-7.57 (m, 3H), 6.86-6.90 (m, 1H), 3.86 (s, 3H) and 2.19 (s, 3H). LCMS: 396.02 (M+H)$^+$, 95.80%. Yield: 58%.

General Procedure for the Preparation of Compounds 35.7(a-b):

These compounds were prepared following the general method P (Scheme 33). The final compounds 35.7a and 35.7b were purified via prep-HPLC.

General Procedure for the Preparation of Compounds 57 (a-b) (General Method T):

To a solution of compounds 35.7 (a-b) (1.0 eq) in DMF was added LiCl (5.0 eq) and p-TSA (5.0 eq). The resulting reaction mass was heated at 130° C. in microwave for 30 min. After the completion of the reaction (TLC monitoring), the solution was diluted with ice-cold water followed by extraction with EtOAc (3 times). The combined organics were washed with brine, dried over anhydrous Na$_2$SO$_4$, filtered and concentrated under reduced pressure. The final compounds 35.8a and 35.8b were purified via prep-HPLC.

The yields and analytical data of the final compounds are set forth in Table 6.12.

TABLE 6.12

Tabulated data of the final compounds including the individual yields

| Compound ID | Structure | Amine intermediate used | Yield (%) | LCMS | $^1$H-NMR data (DMSO-d$_6$, 400 MHz), unless otherwise specified |
|---|---|---|---|---|---|
| 301 | 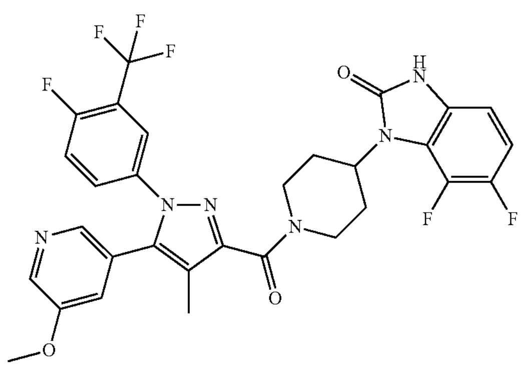 [SMILES: COc1cncc(-c2c(C)c(C(=O)N3CCC(n4c(=O)[nH]c5ccc(F)c(F)c54)CC3)nn2-c2ccc(F)c(C(F)(F)F)c2)c1] | Intermediate-3 | 37 | 631.27 (M + H)$^+$, 99.46% | δ 11.25 (br s, 1H), 8.19 (d, J = 5.2 Hz, 1H), 7.73-7.75 (m, 1H), 7.54-7.58 (m, 2H), 7.00-7.07 (m, 1H), 6.73-6.84 (m, 3H), 4.67-4.70 (m, 2H), 4.31-4.35 (m, 1H), 3.85 (s, 3H), 3.30-3.32 (m, 1H), 2.93-2.98 (m, 1H), 2.10-2.12 (m, 5H) and 1.81-1.91 (m, 2H) |
| 302 | 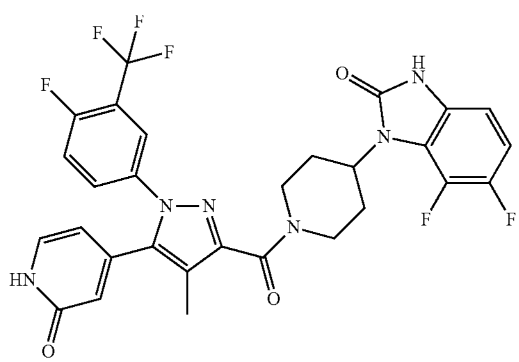 [SMILES: Cc1c(C(=O)N2CCC(n3c(=O)[nH]c4ccc(F)c(F)c43)CC2)nn(-c2ccc(F)c(C(F)(F)F)c2)c1-c1cc[nH]c(=O)c1] | Intermediate-3 | 44 | 617.30 (M + H)$^+$, 99.49% | δ 11.25-11.29 (m, 2H), 7.80-7.82 (m, 1H), 7.70-7.72 (m, 1H), 7.60-7.65 (m, 1H), 7.40 (d, J = 6.8 Hz, 1H), 7.00-7.08 (m, 1H), 6.78-6.81 (m, 1H), 6.36 (s, 1H), 5.93 (d, J = 6.8 Hz, 1H), 4.68-4.71 (m, 2H), 4.30-4.33 (m, 1H), 3.30-3.32 (m, 1H), 2.94-3.00 (m, 1H), 2.14-2.18 (m, 5H) and 1.82-1.92 (m, 2H) |
| 303 | 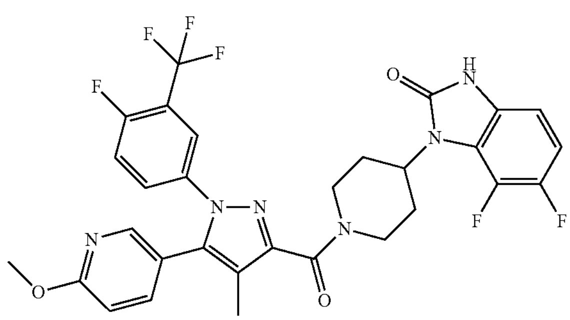 [SMILES: COc1ccc(-c2c(C)c(C(=O)N3CCC(n4c(=O)[nH]c5ccc(F)c(F)c54)CC3)nn2-c2ccc(F)c(C(F)(F)F)c2)cn1] | Intermediate-3 | 36 | 631.31 (M + H)$^+$, 99.90% | δ 11.25 (br s, 1H), 8.15 (d, J = 2.0 Hz, 1H), 7.70-7.72 (m, 1H), 7.53-7.62 (m, 3H), 7.00-7.07 (m, 1H), 6.87 (d, J = 8.4 Hz, 1H), 6.77-6.80 (m, 1H), 4.63-4.71 (m, 2H), 4.36-4.39 (m, 1H), 3.87 (s, 3H), 3.30-3.32 (m, 1H), 2.92-2.99 (m, 1H), 2.09-2.12 (m, 5H) and 1.81-1.91 (m, 2H) |

TABLE 6.12-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 304 | 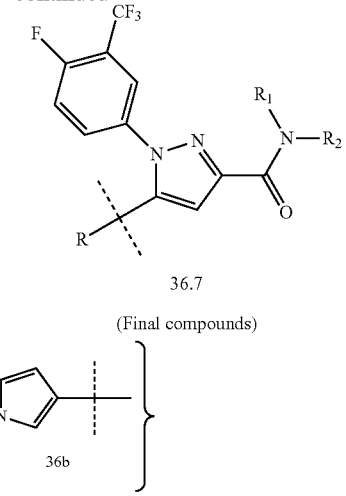 | Intermediate-3 | 15 | 617.27 (M + H)$^+$ 99.22% | δ 11.98 (br s, 1H), 11.25 (br s, 1H), 7.76-7.78 (m, 1H), 7.68-7.72 (m, 1H), 7.59-7.63 (m, 1H), 7.49 (s, 1H), 7.21-7.24 (m, 1H), 7.00-7.07 (m, 1H), 6.77-6.80 (m, 1H), 6.32-6.34 (m, 1H), 4.67-4.70 (m, 2H), 4.32-4.36 (m, 1H), 3.30-3.32 (m, 1H), 2.94-2.98 (m, 1H), 2.07-2.12 (m, 5H) and 1.80-1.90 (m, 2H) |

Scheme 36

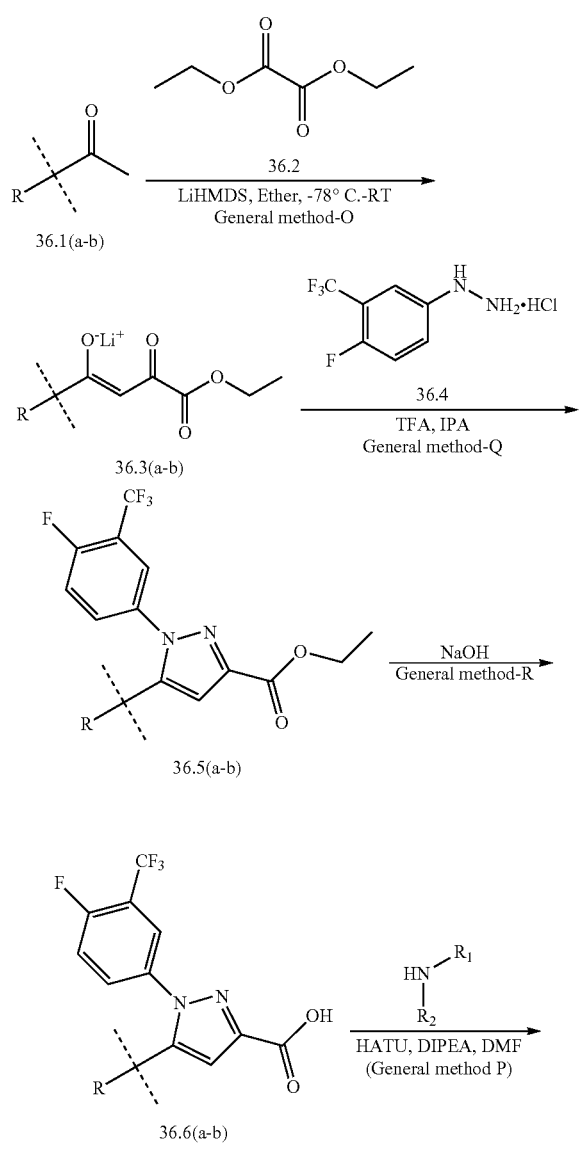

General Procedure for the Preparation of Compounds 36.3(a-b):

These compounds were prepared following the general method O (Scheme 33).

4-Ethoxy-3,4-dioxo-1-(pyrazin-2-yl)but-1-en-1-olate Lithium Salt (36.3a)

$^1$H-NMR (400 MHz, DMSO-$d_6$): δ 9.13-9.18 (m, 1H), 8.73-8.74 (m, 1H), 8.55-8.58 (m, 1H), 7.01 (s, 1H), 4.24 (q, J=6.8 Hz, 2H) and 1.23 (t, J=6.8 Hz, 3H). MS: 223.04 (M+H)$^+$. Yield: Quantitative.

4-Ethoxy-3,4-dioxo-1-(1H-pyrrol-3-yl)but-1-en-1-olate Lithium Salt (36.3b)

$^1$H-NMR (400 MHz, DMSO-$d_6$): δ 11.08 (br s, 1H), 7.24 (s, 1H), 6.70-6.80 (m, 1H), 6.35-6.41 (m, 1H), 6.13 (s, 1H), 4.18 (q, J=7.2 Hz, 2H) and 1.26 (t, J=6.8 Hz, 3H). MS: 210.19 (M+H)$^+$. Yield: Quantitative.

General Procedure for the Preparation of Compounds 36.5(a-b):

These compounds were prepared following the general method Q (Scheme 34).

Ethyl 1-(4-fluoro-3-(trifluoromethyl)phenyl)-5-(pyrazin-2-yl)-1H-pyrazole-3-carboxylate (36.5a)

$^1$H-NMR (400 MHz, CDCl$_3$): δ 8.80 (s, 1H), 8.54 (s, 1H), 8.37 (s, 1H), 7.71-7.72 (m, 1H), 7.50-7.53 (m, 1H), 7.38 (s, 1H), 7.20-7.22 (m, 1H), 4.50 (q, J=7.2 Hz, 2H) and 1.46 (t, J=7.2 Hz, 3H). MS: 381.31 (M+H)$^+$. Yield: 29%.

Ethyl 1-(4-fluoro-3-(trifluoromethyl)phenyl)-5-(1H-pyrrol-3-yl)-1H-pyrazole-3-carboxylate (36.5b)

$^1$H-NMR (400 MHz, CDCl$_3$): δ 8.27 (br s, 1H), 7.74-7.78 (m, 1H), 7.57-7.63 (m, 1H), 7.20-7.26 (m, 1H), 6.94-6.98 (m, 1H), 6.75 (s, 1H), 6.64 (s, 1H), 5.99 (s, 1H), 4.41 (q, J=7.2 Hz, 2H) and 1.40 (t, J=7.2 Hz, 3H). LCMS: 368.22 (M+H)$^+$, 96.13%. Yield: 45%.

General Procedure for the Preparation of Compounds 36.6(a-b):

These compounds were prepared following the general method R (Scheme 34).

1-(4-Fluoro-3-(trifluoromethyl)phenyl)-5-(pyrazin-2-yl)-1H-pyrazole-3-carboxylic Acid (36.6a)

$^1$H-NMR (400 MHz, DMSO-d$_6$): δ 13.24 (br s, 1H), 9.11 (s, 1H), 8.61 (d, J=2.0 Hz, 1H), 8.47 (s, 1H), 7.89-7.90 (m, 1H), 7.79-7.81 (m, 1H) and 7.69-7.64 (m, 2H). LCMS: 353.19 (M+H)+, 99.79%. Yield: 59%.

1-(4-Fluoro-3-(trifluoromethyl)phenyl)-5-(1H-pyrrol-3-yl)-1H-pyrazole-3-carboxylic Acid (36.6b)

$^1$H-NMR (400 MHz, DMSO-d$_6$): δ 12.88 (br s, 1H), 11.11 (br s, 1H), 7.81-7.86 (m, 2H), 7.65-7.69 (m, 1H), 6.90 (s, 1H), 6.75 (s, 2H) and 5.86 (s, 1H). LCMS: 340.07 (M+H)+, 99.90%. Yield: 71%.

General Procedure for the Preparation of Final Compounds 36.7:

The final compounds were prepared following the general method P (Scheme 33). To an ice-cold solution of carboxylic acid 61 (a-b) (125-150 mg), in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC. The final compounds were purified via prep-HPLC.

The yields and analytical data of the final compounds are set forth in Table 6.13.

TABLE 6.13

Tabulated data of the final compounds including the individual yields

| Compound ID | Structure | Amine intermediate used | Yield (%) | LCMS | $^1$H-NMR data (DMSO-d$_6$, 400 MHz), unless otherwise specified |
|---|---|---|---|---|---|
| 305 | 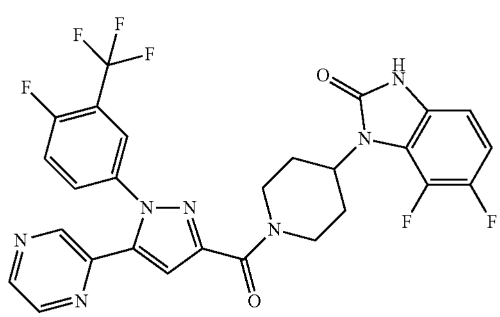 [SMILES: O=C(c1cc(-c2cnccn2)n(-c2ccc(F)c(C(F)(F)F)c2)n1)N1CCC(n2c(=O)[nH]c3ccc(F)c(F)c32)CC1] | Intermediate-3 | 24 | 588.29 (M + H)$^+$ 99.45% | δ 11.25 (br s, 1H), 9.11 (s, 1H), 8.61-8.62 (m, 1H), 8.48-8.49 (m, 1H), 7.88-7.90 (m, 1H), 7.80-7.84 (m, 1H), 7.58-7.63 (m, 1H), 7.50 (s, 1H), 7.00-7.06 (m, 1H), 6.77-6.80 (m, 1H), 4.76-4.79 (m, 1H), 4.63-4.68 (m, 2H), 3.31-3.32 (m, 1H), 2.93-2.99 (m, 1H), 2.12-2.17 (m, 2H) and 1.83-1.92 (m, 2H) |
| 306 | 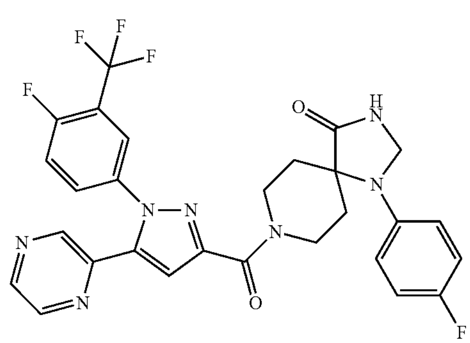 [SMILES: O=C(c1cc(-c2cnccn2)n(-c2ccc(F)c(C(F)(F)F)c2)n1)N1CCC2(CC1)C(=O)NCN2c1ccc(F)cc1] | Intermediate-1 | 28 | 584.33 (M + H)$^+$ 99.28% | δ 9.09 (s, 1H), 8.80 (s, 1H), 8.61-8.62 (m, 1H), 8.48-8.49 (m, 1H), 7.86-7.88 (m, 2H), 7.56-7.61 (m, 1H), 7.48 (s, 1H), 7.07-7.12 (m, 2H), 6.83-6.87 (m, 2H), 4.58 (s, 2H), 4.42-4.45 (m, 2H), 3.35-3.38 (m, 1H), 3.51-3.54 (m, 1H), 2.21-2.33 (m, 2H) and 1.72-1.83 (m, 2H) |

TABLE 6.13-continued
Tabulated data of the final compounds including the individual yields
| Compound ID | Structure | Amine intermediate used | Yield (%) | LCMS | 1H-NMR data (DMSO-d6, 400 MHz), unless otherwise specified |
|---|---|---|---|---|---|
| 307 | 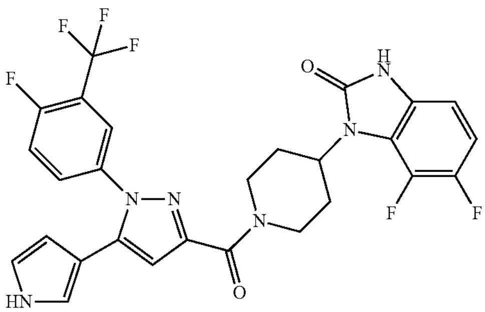 [SMILES: O=C(c1cc(-c2cc[nH]c2)n(-c2ccc(F)c(C(F)(F)F)c2)n1)N1CCC(n2c(=O)[nH]c3ccc(F)c(F)c32)CC1] | Intermediate-3 | 6 | 575.36 (M + H)+ 98.10% | δ 11.10 (br s, 2H), 7.83-7.86 (m, 2H), 7.63-7.65 (m, 1H), 6.99-7.06 (m, 1H), 6.76-6.79 (m, 4H), 5.86-5.88 (m, 1H), 4.82-4.86 (m, 1H), 4.60-4.68 (m, 2H), 3.25-3.28 (m, 1H), 2.88-2.93 (m, 1H), 2.11-2.17 (m, 2H) and 1.75-1.89 (m, 2H) |
| 308 | 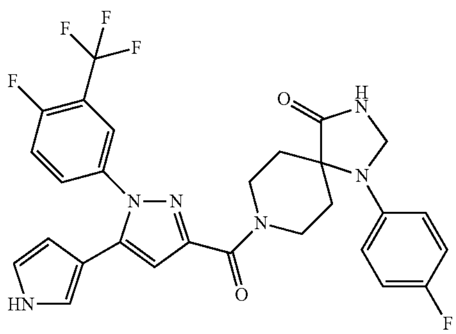 [SMILES: O=C(c1cc(-c2cc[nH]c2)n(-c2ccc(F)c(C(F)(F)F)c2)n1)N1CCC2(CC1)C(=O)NCN2c1ccc(F)cc1] | Intermediate-1 | 16 | 571.39 (M + H)+ 99.82% | δ 11.10 (br s, 1H), 8.78-8.81 (m, 1H), 7.79-7.83 (m, 2H), 7.61-7.66 (m, 1H), 7.06-7.11 (m, 2H), 6.82-6.86 (m, 2H), 6.76-6.79 (m, 3H), 5.86-5.88 (m, 1H), 4.58 (s, 2H), 4.39-4.50 (m, 2H), 3.79-3.84 (m, 1H), 3.47-3.52 (m, 1H), 2.17-2.25 (m, 2H) and 1.70-1.80 (m, 2H) |
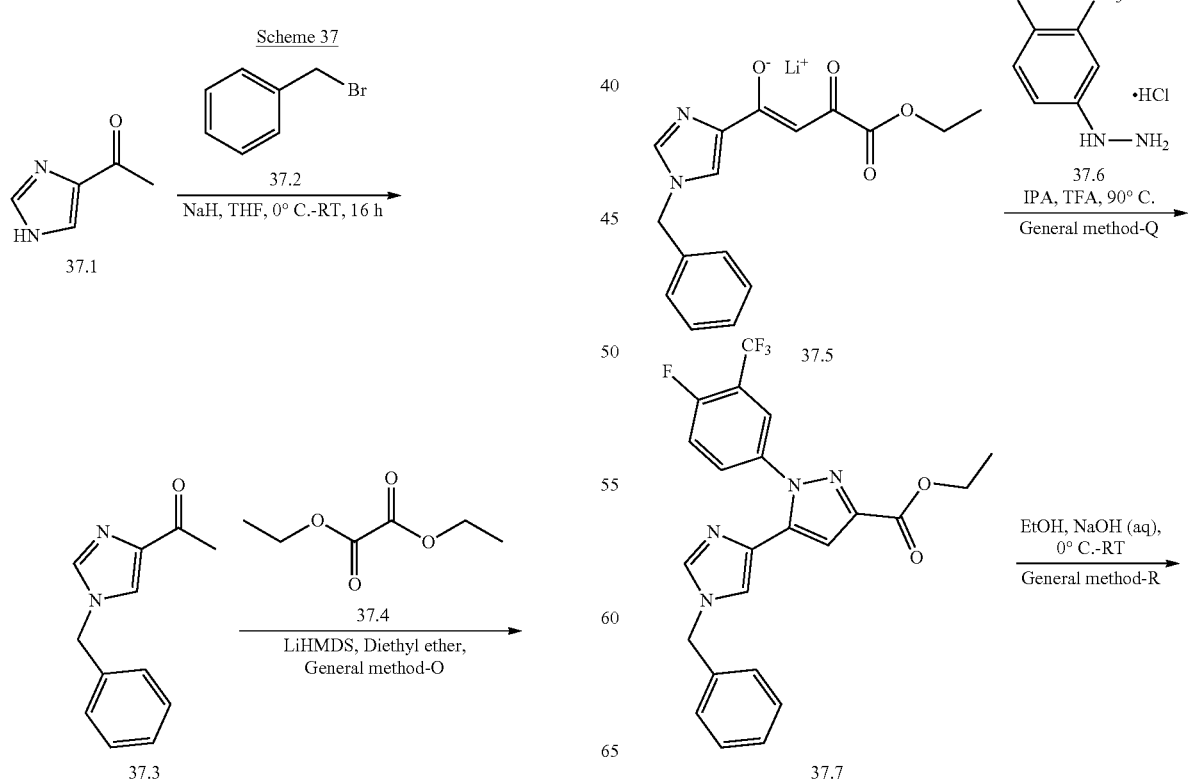
Scheme 37

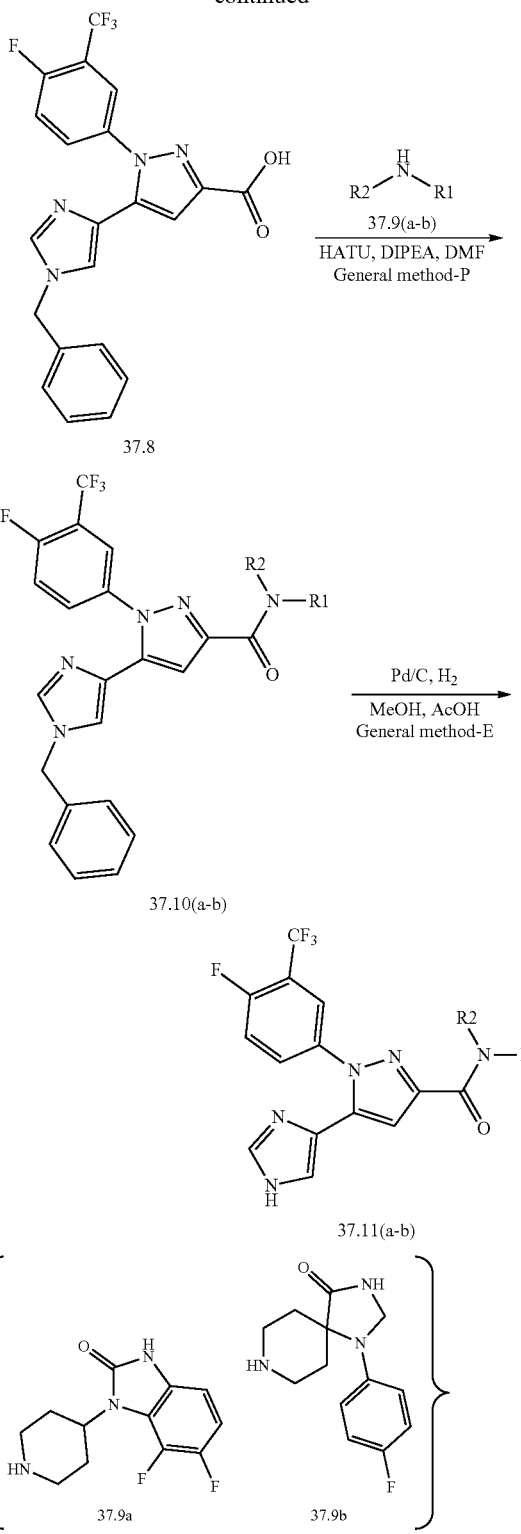

Preparation of 1-(1-benzyl-1H-imidazol-4-yl)ethan-1-one (37.3)

To an ice-cold solution of 1-(1H-imidazol-4-yl)ethan-1-one 37.1 (5.0 g, 45.43 mmol) in THF (50 mL) was added NaH (60% dispersion in mineral oil, 2.72 g, 68.15 mmol) portion-wise, followed by addition of benzyl bromide 37.2 (6.51 mL, 54.52 mmol). The resulting reaction mixture was stirred at RT for 16 h. After the completion of the reaction (TLC monitoring), the solution was diluted with ice-cold water (100 mL) followed by extraction with EtOAc (3×100 mL). The combined organics were washed with brine, dried over anhydrous $Na_2SO_4$, filtered and concentrated under reduced pressure. The crude was purified over silica gel (100-200 M), elution with 25% EtOAc/hexane to get desired product 37.3 (4.5 g, Yield: 49%) as off white solid. $^1$H-NMR (400 MHz, $CDCl_3$): δ 7.67 (s, 1H), 7.57 (s, 1H), 7.37-7.41 (m, 3H), 7.19-7.21 (m, 2H), 5.16 (s, 2H) and 2.56 (s, 3H). LCMS: 201.13 $(M+H)^+$, 98.80%.

Preparation of 1-(1-benzyl-1H-imidazol-4-yl)-4-ethoxy-3,4-dioxobut-1-en-1-olate Lithium Salt (37.5)

This compound was prepared following the general method O (Scheme 33). $^1$H-NMR (400 MHz, DMSO-$d_6$): δ 7.78 (s, 1H), 7.61 (s, 1H), 7.12-7.34 (m, 5H) and 6.58 (s, 1H), 5.20 (s, 2H), 4.12 (q, J=6.8 Hz, 2H) and 1.21 (t, J=7.2 Hz, 3H). MS: 301.13 $(M+H)^+$.

Preparation of ethyl 5-(1-benzyl-1H-imidazol-4-yl)-1-(4-fluoro-3-(trifluoromethyl)phenyl)-1H-pyrazole-3-carboxylate (37.7)

This compound was prepared following the general method Q (Scheme 34). $^1$H-NMR (400 MHz, $CDCl_3$): δ 7.85-7.93 (s, 2H), 7.81 (s, 1H), 7.61-7.66 (m, 1H), 7.30-7.38 (m, 4H), 7.20-7.25 (m, 2H), 7.06 (s, 1H), 5.17 (s, 2H), 4.31 (q, J=6.8 Hz, 2H) and 1.30 (t, J=7.2 Hz, 3H). MS: 459.15 $(M+H)^+$. Yield: 51%.

Preparation of 5-(1-benzyl-1H-imidazol-4-yl)-1-(4-fluoro-3-(trifluoromethyl)phenyl)-1H-pyrazole-3-carboxylic Acid (37.8)

This compound was prepared following the general method R (Scheme 11). $^1$H-NMR (400 MHz, DMSO-$d_6$): δ 13.14 (br s, 1H), 8.46 (s, 1H), 7.86-7.91 (m, 2H), 7.63-7.67 (m, 1H), 7.34-7.36 (m, 4H), 7.24-7.25 (m, 2H), 7.17 (s, 1H) and 5.26 (s, 2H). LCMS: 431.17 $(M+H)^+$, 93.47%. Yield: 64%.

General Procedure for the Preparation of Final Compounds 37.10(a-b):

The final compounds were prepared following the general method P (Scheme 33). The final compounds 37.10a and 37.10b were purified via prep-HPLC. Please refer to Table 14 for individual yields and the analytical data of the final compounds.

General Procedure for the Preparation of Compounds 37.11(a-b):

The final compounds were prepared following the general method E (Scheme 1). The final compounds 37.11a and 37.11b were purified via prep-HPLC.

The yields and analytical data of the final compounds are set forth in Table 6.14.

TABLE 6.14

Tabulated data of the final compounds including the individual yields

| Compound ID | Structure | Amine intermediate used | Yield (%) | LCMS | $^1$H-NMR data (DMSO-d$_6$, 400 MHz), unless otherwise specified |
|---|---|---|---|---|---|
| 309 | •xTFA | Intermediate-3 | 24 | 576.33 (M + H)$^+$ 95.60% | δ 11.25 (br s, 1H, D$_2$O exchangeable), 8.50 (br s, 1H), 8.79 (s, 1H), 7.87-7.93 (m, 2H), 7.63-7.68 (m, 1H), 7.37 (s, 1H), 7.02-7.07 (m, 2H), 6.77-6.80 (m, 1H), 4.80 (d, J = 14.0 Hz, 1H), 4.62-4.68 (m, 2H), 3.29-3.35 (m, 2H), 2.91-2.97 (m, 1H), 2.12-2.15 (m, 2H) and 1.82-1.91 (m, 2H) |
| 310 | 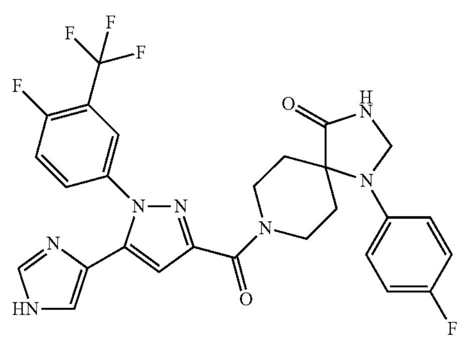 [SMILES: O=C(c1cc(-c2c[nH]cn2)n(-c2ccc(F)c(C(F)(F)F)c2)n1)N1CCC2(CC1)C(=O)NCN2c1ccc(F)cc1] | Intermediate-1 | 20 | 572.34 (M + H)$^+$ 98.43% | δ 12.37 (br s, 1H), 8.79 (s, 1H), 7.81-7.85 (m, 2H), 7.70 (s, 1H), 7.57-7.62 (m, 1H), 7.30 (m, 1H), 7.06-7.11 (m, 2H), 6.92 (s, 1H), 6.83-6.86 (m, 2H), 4.58 (s, 2H), 4.40-4.49 (m, 2H), 3.80-3.85 (m, 1H), 3.48-3.54 (m, 1H), 2.18-2.33 (m, 2H) and 1.70-1.81 (m, 2H) |
| 311 | 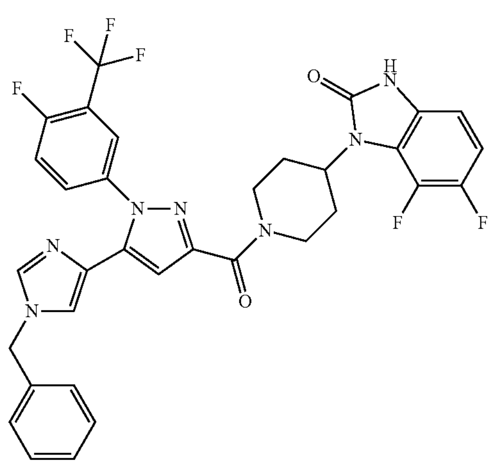 [SMILES: O=C(c1cc(-c2cn(Cc3ccccc3)cn2)n(-c2ccc(F)c(C(F)(F)F)c2)n1)N1CCC(n2c(=O)[nH]c3ccc(F)c(F)c32)CC1] | Intermediate-3 | 15 | 666.39 (M + H)$^+$ 99.81% | δ 11.20 (br s, 1H), 7.82-7.89 (m, 3H), 7.59-7.63 (m, 1H), 7.28-7.37 (m, 4H), 7.20-7.22 (m, 2H), 6.99-7.06 (m, 1H), 6.88 (s, 1H), 6.76-6.79 (m, 1H), 5.19 (s, 2H), 4.79 (d, J = 12.80 Hz, 1H), 4.60-4.67 (m, 2H), 3.25-3.29 (m, 1H), 2.88-2.95 (m, 1H), 2.11 (m, 2H) and 1.80-1.89 (m, 2H) |

TABLE 6.14-continued

Tabulated data of the final compounds including the individual yields

| Compound ID | Structure | Amine intermediate used | Yield (%) | LCMS | $^1$H-NMR data (DMSO-$d_6$, 400 MHz), unless otherwise specified |
|---|---|---|---|---|---|
| 312 | 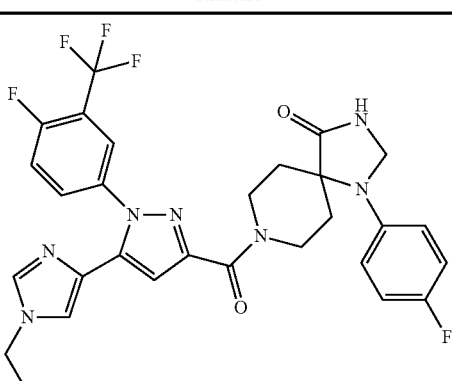 | Intermediate-1 | 13 | 662.44 (M + H)$^+$ 99.72% | δ 8.78 (br s, 1H), 7.81-7.85 (m, 3H), 7.57-7.61 (m, 1H), 7.28-7.37 (m, 4H), 7.20-7.22 (m, 2H), 7.06-7.10 (m, 2H), 6.88 (s, 1H), 6.84-6.86 (m, 2H), 5.19 (s, 2H), 4.57 (br s, 2H), 4.40-4.45 (m, 2H), 3.78-3.84 (m, 1H), 3.47-3.52 (m, 1H), 2.19-2.28 (m, 2H) and 1.69-1.80 (m, 2H) |

Scheme 38

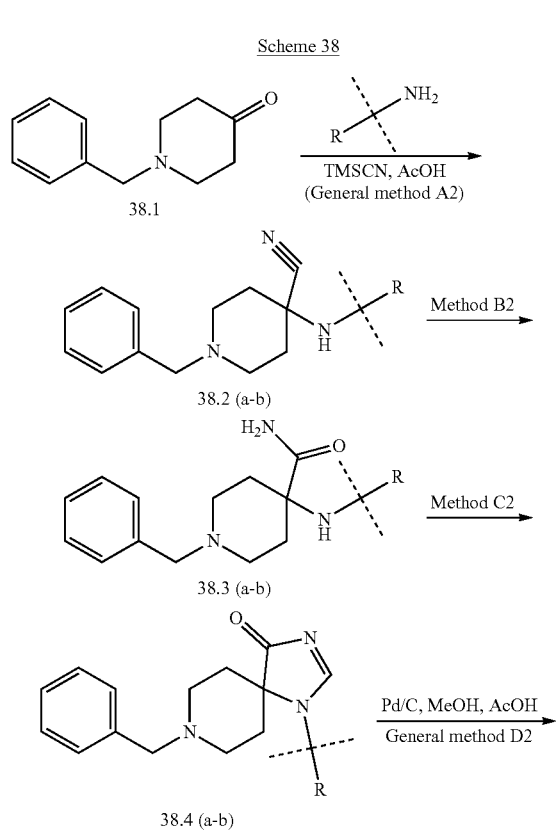

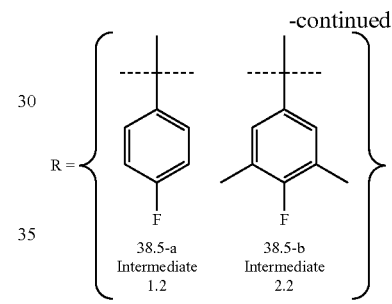

38.5-a Intermediate 1.2

38.5-b Intermediate 2.2

General Method A2 for the Preparation of Compounds 38.2 (a-b):

To an ice-cold solution of 1-benzylpiperidin-4-one 1 (5.0-7.0 g, 1.0 eq) in acetic acid was added respective amines (1.1 eq) and trimethylsilyl cyanide (1.5 eq). The resulting reaction mass was stirred at RT for 18 h. After completion of the reaction (TLC monitoring), the reaction mass was cooled to 0° C. and the pH adjusted to ~10 using 5.0 N sodium hydroxide solution. The aqueous part was extracted with DCM (3×250 mL). The combined organics were dried over anhydrous Na$_2$SO$_4$, filtered and concentrated. The crude was triturated with diethyl ether to obtain the desired product 38.2 (a-b) as off white solid.

1-Benzyl-4-((4-fluorophenyl)amino)piperidine-4-carbonitrile (38.2-a)

$^1$H-NMR (400 MHz, CDCl$_3$): δ 7.35-7.38 (m, 5H), 6.90-6.95 (m, 4H), 3.54 (s, 2H), 3.48 (br s, 1H), 2.80-2.84 (m, 2H), 2.38-2.41 (m, 2H), 2.22-2.24 (m, 2H) and 1.89-1.94 (m, 2H). LC-MS: 310.23 (M+H)+, 95.66%. Yield: 58%.

1-Benzyl-4-((4-fluoro-3,5-dimethylphenyl)amino) piperidine-4-carbonitrile (38.2-b)

$^1$H-NMR (400 MHz, CDCl$_3$): δ 7.26-7.31 (m, 5H), 6.55-6.57 (m, 1H), 6.37-6.38 (m, 1H), 3.60 (s, 1H), 3.53 (s, 2H), 2.76-2.81 (m, 2H), 2.45-2.50 (m, 2H), 2.28-2.32 (m, 2H), 2.09 (m, 6H), and 1.88-1.93 (m, 2H). MS: 338.33 (M+H)⁺, Yield: 60%.

General Method B2 for the Preparation of Compounds 38.3 (a-b):

An ice-cold solution of 38.2 (a-b) (3.0-4.0 g, 1.0 eq) in 90% aqueous sulphuric acid was stirred at 0° C. for 30.0 min, then warm up to RT and stirred for 16 h. After completion of the reaction (TLC monitoring), the reaction mass was cooled to 0° C. and the pH adjusted to ~10 using 5.0 N sodium hydroxide solution. The aqueous part was extracted with DCM. The combined organics were dried over anhydrous sodium sulphate, filtered and concentrated. The crude was triturated with diethyl ether to obtain the desired product 3 (a-b) as off-white solid.

1-Benzyl-4-(4-fluorophenylamino)piperidine-4-carboxamide (38.3-a)

¹H-NMR (400 MHz, CDCl₃): δ 7.23-7.25 (m, 5H), 6.85-6.87 (m, 3H), 6.54-6.55 (m, 2H), 5.47 (br s, 1H), 3.93 (s, 1H), 3.48 (s, 2H), 2.72-2.74 (m, 2H), 2.28-2.29 (m, 2H), 2.04-2.07 (m, 2H) and 1.86-1.89 (m, 2H). LCMS: 328.22 (M+H)⁺, 98.42%. Yield: 84%.

1-Benzyl-4-((4-fluoro-3,5-dimethylphenyl)amino)piperidine-4-carboxamide (38.3-b)

¹H-NMR (400 MHz, CDCl₃): δ 7.28-7.34 (m, 6H), 7.15 (br s, 1H), 7.01 (s, 1H), 6.21-6.27 (m, 2H), 3.48 (s, 2H), 2.50-2.51 (m, 2H), 2.22-2.24 (m, 2H), 2.06 (d, J=6.0 Hz, 6H), 1.96-1.99 (m, 2H) and 1.77-1.81 (m, 2H). MS: 356.37 (M+H)⁺. Yield: 56.6%.

General Method C2 for the Preparation of Compounds 38.4 (a-c):

To a solution of compounds 38.3 (a-b) (1.0-2.5 g, 1.0 eq) in methanol was added DMF-DMA (3.0 eq). The resulting reaction mass was heated at 65° C. for h. After completion of reaction (TLC monitoring), the solvent was evaporated to dryness. The resulting crude residue was triturated with diethyl ether to get off white solid product 38.4 (a-b).

8-Benzyl-1-(4-fluorophenyl)-1,3,8-triazaspiro[4.5]dec-2-en-4-one (38.4-a)

H-NMR (400 MHz, DMSO-d₆): δ 8.65 (s, 1H), 7.44-7.46 (m, 2H), 7.31-7.34 (m, 2H), 7.13-7.16 (m, 5H), 3.41 (s, 2H), 2.66-2.69 (m, 2H), 2.41-2.44 (m, 2H) and 1.75-1.78 (m, 4H). MS: 338.22 (M+H)⁺. Yield: 89%.

8-Benzyl-1-(4-fluoro-3,5-dimethylphenyl)-1,3,8-triazaspiro[4.5]dec-2-en-4-one (38.4-b)

¹H-NMR (400 MHz, DMSO-d₆): δ 8.15 (s, 1H), 7.48-7.49 (m, 4H), 7.26-7.28 (m, 1H), 7.80-7.81 (m, 2H), 3.60 (s, 2H), 2.87-2.91 (m, 2H), 2.59-2.61 (m, 2H), 2.28 (s, 6H), 1.88-1.89 (m, 2H) and 1.56-1.58 (m, 2H). MS: 366.35 (M+H)⁺. Yield: 79%.

General Method D2 for the Preparation of Compounds 38.5 (a-b):

To a solution of compounds 38.4 (a-b) (0.50-1.5 g, 1.0 eq) in MeOH and AcOH (40:1, 20 mL) were added Pd—C (10 mol % w/w) and the resulting solution was stirred under hydrogen atmosphere (1 atm) at ambient temperature for 16 h. The reaction mixture was filtered through a diatomaceous earth (Celite) bed and the filtrate was concentrated under reduced pressure. The residue was purified over silica gel (basic alumina, 2-4% MeOH-DCM) to obtain the desired product 38.5 (a-b) as off white solid.

1-(4-Fluorophenyl)-1,3,8-triazaspiro[4.5]dec-2-en-4-one (38.5-a; Intermediate 1.2)

¹H-NMR (400 MHz, DMSO-d₆): δ 8.81 (br s, 1H), 7.05-7.08 (m, 2H), 6.95-6.96 (m, 2H), 4.58 (s, 2H), 3.34-3.37 (m, 3H), 2.97-2.99 (m, 2H), 2.35-2.36 (m, 2H) and 1.61-1.63 (m, 2H). LCMS: 250.23 (M+H)⁺, 88.25%. Yield: 90%.

1-(4-Fluoro-3,5-dimethylphenyl)-1,3,8-triazaspiro[4.5]decan-4-one (38.5-b; Intermediate 2.2)

¹H-NMR (400 MHz, DMSO-d₆): δ 8.83 (s, 1H), 7.66-7.68 (m, 1H), 6.60-6.66 (m, 2H), 4.54 (s, 2H), 3.38-3.41 (m, 2H), 3.12-3.16 (m, 2H), 2.50-2.53 (m, 2H), 2.19 (s, 6H) and 1.67-1.70 (m, 2H). MS: 278.32 (M+H)⁺. Yield: 80%.

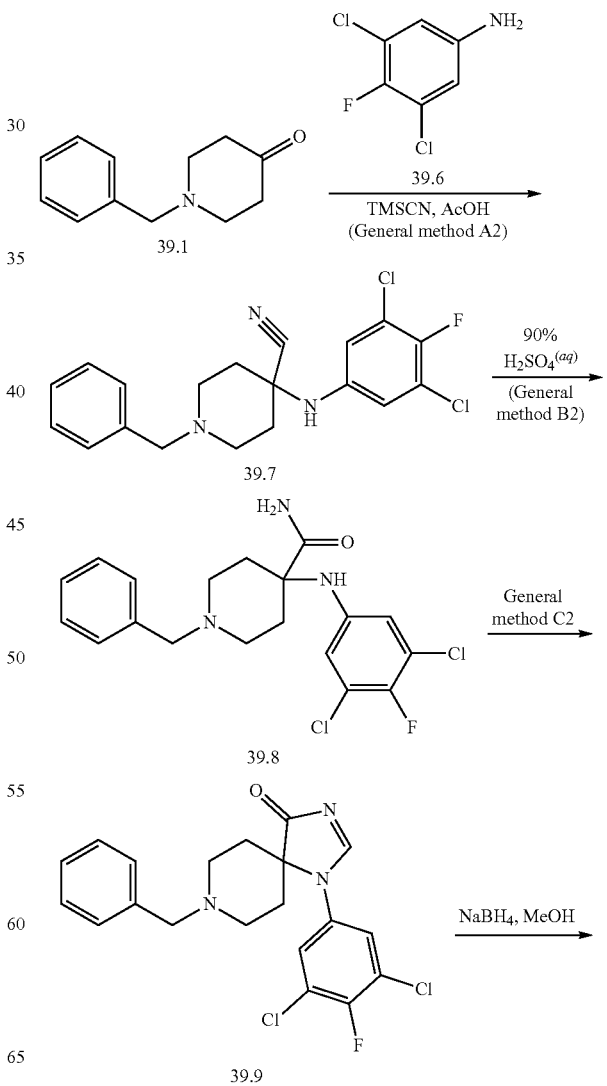

Scheme 39

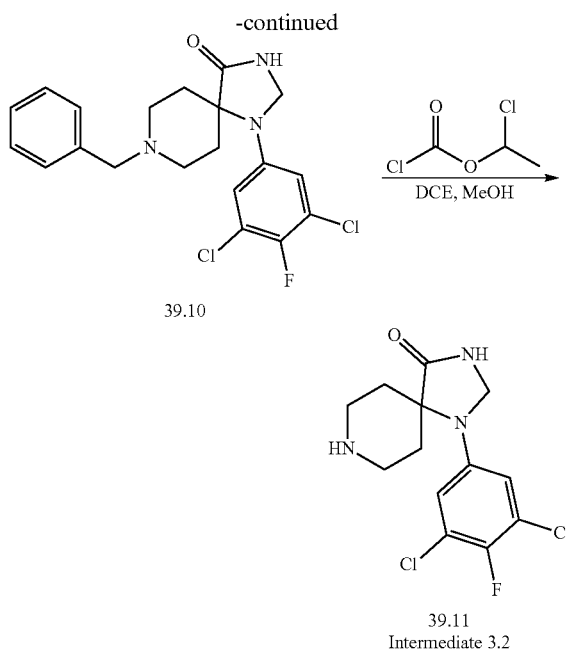

Preparation of 1-benzyl-4-((3,5-dichloro-4-fluorophenyl)amino)piperidine-4-carbonitrile 39.7

Prepared following general method A2. $^1$H-NMR (400 MHz, CDCl$_3$): δ 7.29-7.35 (m, 5H), 6.84-6.85 (m, 2H), 3.62 (s, 1H), 3.56 (s, 2H), 2.76-2.80 (m, 2H), 2.45-2.47 (m, 2H), 2.27-2.30 (m, 2H) and 1.86-1.91 (m, 2H). MS: 378.26 (M+H)$^+$, Yield: 47%.

Preparation of 1-benzyl-4-((3,5-dichloro-4-fluorophenyl)amino)piperidine-4-carboxamide 39.8

Prepared following general method B2. $^1$H-NMR (400 MHz, DMSO-d$_6$): δ 7.15-7.39 (m, 8H), 6.63-6.65 (m, 2H), 3.56-3.60 (m, 2H), 2.66-2.71 (m, 2H), 2.26-2.32 (m, 2H), 2.09-2.12 (m, 2H) and 1.80-1.90 (m, 2H). MS: 396.30 (M+H)$^+$, Yield: 68%.

Preparation of 8-benzyl-1-(3,5-dichloro-4-fluorophenyl)-1,3,8-triazaspiro[4.5]dec-2-en-4-one 39.9

Prepared following general method C2. MS: 405.99 (M+H)$^+$. Yield: 80%.

Preparation of 8-benzyl-1-(3,5-dichloro-4-fluorophenyl)-1,3,8-triazaspiro[4.5]decan-4-one 39.10

To an ice-cold solution of 8-benzyl-1-(3,5-dichloro-4-fluorophenyl)-1,3,8-triazaspiro[4.5]dec-2-en-4-one 39.9 (1.0 eq) in methanol was added NaBH$_4$ (2.5 eq) portionwise. The resulting reaction mixture was stirred at RT for 2 h. After completion of reaction (TLC monitoring), cooled to 0° C. added water and extracted with EtOAc (3 times). The combined organics were washed with brine, dried over anhydrous Na$_2$SO$_4$, filtered and concentrated. The crude was triturated with diethyl ether to get desired product 10 as off white solid. $^1$H-NMR (400 MHz, DMSO-d$_6$): δ 8.74 (br s, 1H), 7.31-7.35 (m, 4H), 7.24-7.26 (m, 1H), 6.95-6.96 (m, 2H), 4.58 (s, 2H), 3.53-3.54 (m, 2H), 2.73-2.74 (m, 2H), 2.63-2.68 (m, 2H), 2.32-2.40 (m, 2H) and 1.57-1.60 (m, 2H). LCMS: 408.29 (M+H)$^+$, 90.02%. Yield: 57%.

Preparation of 1-(3,5-dichloro-4-fluorophenyl)-1,3,8-triazaspiro[4.5]decan-4-one 39.11 (Intermediate 3.2)

To an ice-cold solution of 8-benzyl-1-(3,5-dichloro-4-fluorophenyl)-1,3,8-triazaspiro[4.5]decan-4-one 39.10 (1.0 eq) in DCE was added 1-chloroethyl chloroformate (2.0 eq). The resulting reaction mixture was refluxed for 5 h. After completion of reaction (TLC monitoring), solvent was evaporated to dryness. The crude residue was dissolved in MeOH and heated at 65° C. for 16 h. After completion of reaction (TLC monitoring), solvent was evaporated. The crude was purified over silica gel (100-200M), elution with 5% MeOH/DCM to get desired product 39.11 as an off-white solid. $^1$H-NMR (400 MHz, DMSO-d$_6$): δ 9.10 (s, 1H), 8.89-9.03 (m, 1H), 7.08-7.14 (m, 2H), 4.62 (s, 2H), 3.54-3.57 (m, 2H), 3.15-3.17 (m, 2H), 2.60-2.64 (m, 2H) and 1.81-1.90 (m, 2H). MS: 318.23 (M+H)$^+$. Yield: 60%.

Scheme 40

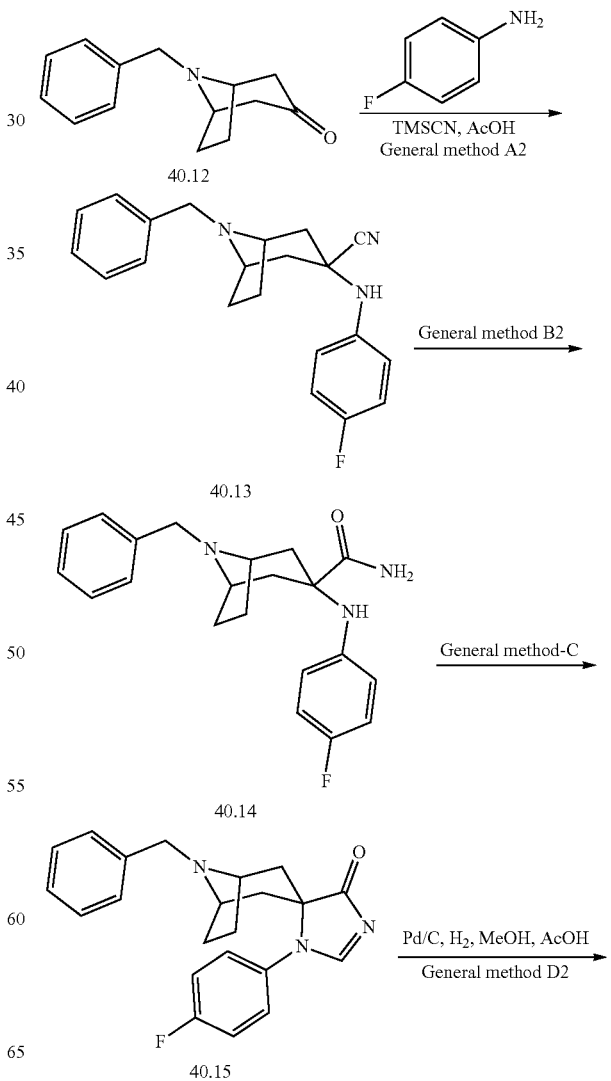

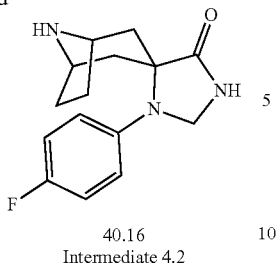

40.16
Intermediate 4.2

Preparation of 8-benzyl-3-((4-fluorophenyl)amino)-8-azabicyclo[3.2.1]octane-3-carbonitrile (40.13)

Prepared following general method A2. MS: 336.14 (M+H)+. Yield: 32%.

Preparation of 8-benzyl-3-((4-fluorophenyl)amino)-8-azabicyclo[3.2.1]octane-3-carboxamide (40.14)

Prepared following general method B2. $^1$H-NMR (400 MHz, DMSO-$d_6$): δ 7.63 (br s, 1H), 7.46-7.52 (m, 2H), 7.41-7.46 (m, 2H), 7.26-7.30 (m, 3H), 6.87-6.91 (m, 2H), 6.59 (br s, 2H), 5.44 (m, 1H), 4.15 (m, 1H), 3.83-3.85 (s, 2H), 3.37-3.40 (m, 2H), 2.72-2.78 (m, 2H), 2.12-2.17 (m, 2H) and 1.80-1.90 (m, 2H). LCMS: 354.36 (M+H)+, 93.06%. Yield: 45%.

Preparation of 8-benzyl-3'-(4-fluorophenyl)-8-azaspiro[bicycle[3.2.1]octane-3,4'-imidazol]-5'(3'H)-one (40.15)

Prepared following general method C2. MS: 363.98 (M+H)+. Yield: 50%.

Preparation of 3'-(4-fluorophenyl)-8-azaspiro[bicyclo[3.2.1]octane-3,4'-imidazolidin]-5'-one 40.16 (Intermediate 4.2)

Prepared following the general method D2. MS: 276.18 (M+H)+. Yield: 29%.

Scheme 41

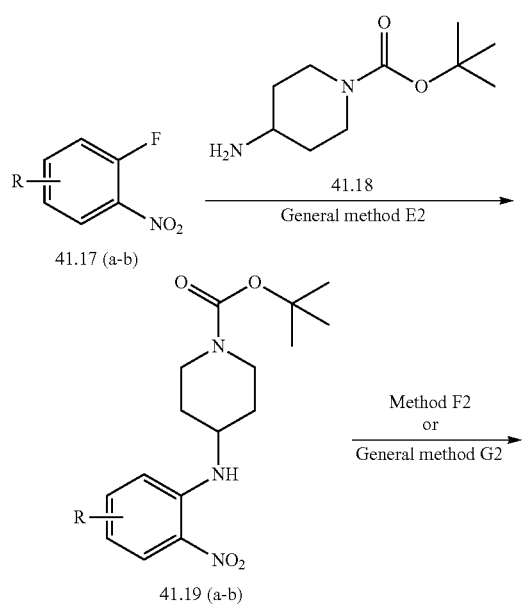

41.17 (a-b)

41.19 (a-b)

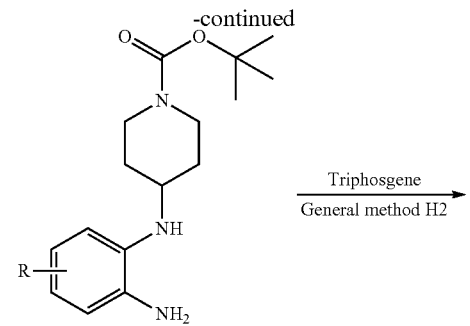

20 (a-b)

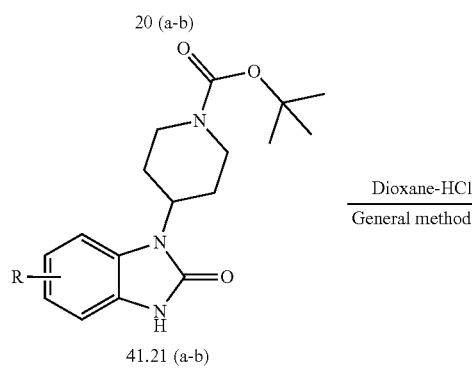

41.21 (a-b)

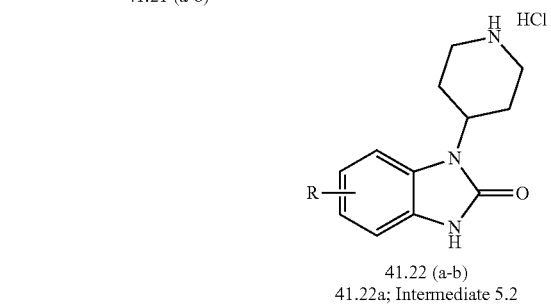

41.22 (a-b)
41.22a; Intermediate 5.2
41.22b; Intermediate 6.2

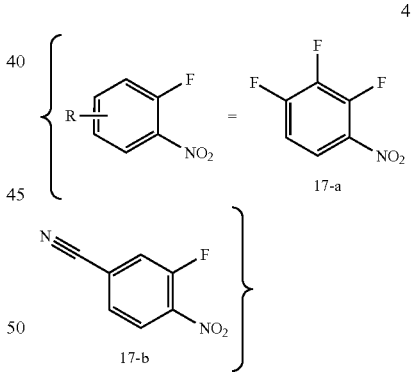

17-a 17-b

General Method E2: For the Preparation of Compounds 41.19 (a-b):

To an ice-cold solution of tert-butyl 4-aminopiperidine-1-carboxylate 41.18 (1.0-2.5 g, 1.0 eq) in DMF was added DIPEA (1.5 eq) and respective nitro compounds 41.17 (a-b) (1.0 eq). The resulting reaction mixture was stirred at RT for 2-3 h. After completion of the reaction (TLC monitoring), the reaction mass was diluted with ice-cold water and extracted with EtOAc (3 times). The combined organics were washed with brine, dried over anhydrous Na$_2$SO$_4$, filtered and concentrated. The crude was purified over silica gel (100-200 M, 10-15% EtOAc-hexane) to obtain the desired product 41.19 (a-b).

tert-Butyl 4-((2,3-difluoro-6-nitrophenyl)amino) piperidine-1-carboxylate (41.19-a)

$^1$H-NMR (400 MHz, CDCl$_3$): δ 8.00-8.04 (m, 1H), 7.94 (d, J=8.0 Hz, 1H), 6.48-6.54 (m, 1H), 4.01-4.02 (m, 3H), 2.94-2.99 (m, 2H), 2.04-2.06 (m, 2H) and 1.46-1.49 (m, 11H). LCMS: 356.52 (M−H)$^+$, 99.10%. Yield: 56%.

tert-Butyl 4-((5-cyano-2-nitrophenyl)amino)piperidine-1-carboxylate (41.19-b)

$^1$H-NMR (400 MHz, CDCl$_3$): δ 8.25 (d, J=8.8 Hz, 1H), 8.25 (m, J=7.2 Hz, 1H), 7.17 (s, 1H), 6.86 (d, J=8.8 Hz, 1H), 4.04-4.10 (m, 2H), 3.60-3.67 (m, 1H), 3.03-3.08 (m, 2H), 2.03-2.07 (m, 2H), 1.57-1.63 (m, 2H) and 1.51 (s, 9H). LCMS: 345.22 (M−H)$^+$, 99.0%. Yield: 75.3%.

General Method F2 for the Preparation of Compounds 41.20 (a-b):

To a solution of compound 41.19 a (1.0-2.5 g, 1.0 eq) in EtOAc were added Pd—C (w/w, 10 mol %) and the resulting solution was stirred under hydrogen atmosphere (1 atm) at ambient temperature for 16 h. The reaction mixture was filtered through a diatomaceous earth (Celite) bed and the filtrate was concentrated under reduced pressure to obtain the desired product 41.20a.

tert-Butyl 4-((6-amino-2,3-difluorophenyl)amino) piperidine-1-carboxylate (41.20-a)

$^1$H-NMR (400 MHz, DMSO-d$_6$): δ 6.58-6.65 (m, 1H), 6.33-6.36 (m, 1H), 4.80 (br s, 2H), 3.87-4.05 (m, 3H), 3.17-3.20 (m, 1H), 2.73-2.75 (m, 2H), 1.73-1.76 (m, 2H), 1.39 (s, 9H) and 1.23-1.25 (m, 2H). LCMS: 328.41 (M+H)$^+$, 97.70%. Yield: 97%.

General Method G2:

To a solution of compound 41.19-b (1.0-2.0 g, 1.0 eq) in MeOH were added ammonium formate (5.0 eq) and Pd—C (w/w, 10 mol %) and the resulting solution was stirred under at RT for 3-4 h. The reaction mixture was filtered through a diatomaceous earth (Celite) bed and the filtrate was concentrated under reduced pressure to obtain the desired product 41.20-b.

tert-Butyl 4-((2-amino-5-cyanophenyl)amino)piperidine-1-carboxylate (41.20-b)

$^1$H-NMR (400 MHz, CDCl$_3$): δ 7.01 (d, J=8.8 Hz, 1H), 6.87 (s, 1H), 6.68 (d, J=8.8 Hz, 1H), 4.05-4.10 (br s, 3H), 3.36-3.39 (m, 1H), 2.91-2.94 (m, 2H), 2.00-2.03 (m, 4H) and 1.40 (s, 11H). MS: 317.39 (M+H)$^+$. Yield: 85%.

General Method H2 for the Preparation of Compounds 41.21 (a-b):

To an ice-cold solution of compound 41.20 (a-b) (0.50-1.50 g, 1.0 eq) in THF was added Et$_3$N (2.0 eq) and triphosgene (1.5 eq). The resulting reaction mixture was stirred at RT for 4 h. After completion of the reaction (TLC monitoring), the solvent was evaporated and the residue was diluted with water and extracted with ethyl acetate (3 times). The combined organics were washed with brine, dried over anhydrous Na$_2$SO$_4$, filtered and concentrated. The crude was purified over silica gel (100-200 M, 30-40% EtOAc-hexane) to obtain the desired product 41.21 (a-b).

tert-Butyl 4-(6,7-difluoro-2-oxo-2,3-dihydro-1H-benzo[d]imidazol-1-yl)piperidine-1-carboxylate (41.21-a)

$^1$H-NMR (400 MHz, DMSO-d$_6$): δ 11.24 (br s, 1H), 7.02-7.06 (m, 1H), 6.76-6.79 (m, 1H), 4.47-4.52 (m, 1H), 3.99-4.05 (m, 2H), 2.87-2.89 (m, 2H), 1.90-1.98 (m, 2H), 1.71-1.74 (m, 2H) and 1.42 (s, 9H). LCMS: 354.55 (M+H)$^+$, 86.20%. Yield: 92%.

tert-Butyl 4-(6-cyano-2-oxo-2,3-dihydro-1H-benzo[d]imidazol-1-yl)piperidine-1-carboxylate (41.21-b)

$^1$H-NMR (400 MHz, CDCl$_3$): δ 10.01 (br s, 1H), 7.38-7.41 (m, 2H), 7.16 (d, J=8.0 Hz, 1H), 4.37-4.45 (m, 3H), 2.84-2.90 (m, 2H), 2.30-2.35 (m, 2H), 1.83-1.85 (m, 2H) and 1.52 (s, 9H). LCMS: 343.37 (M+H)$^+$, 86.18%. Yield: 60%.

General Method 12 for the Preparation of Compounds 41.22 (a-b):

An ice-cold solution of compound 41.21 (a-b) (0.5 g-1.0 g) in dioxane-HCl (~4N) was stirred at RT for 2 h. After completion of the reaction (TLC monitoring), the reaction mass was dried under reduced pressure. The crude was triturated with diethyl ether to get desired product 41.22 (a-b) as off solid.

6,7-Difluoro-1-(piperidin-4-yl)-1,3-dihydro-2H-benzo[d]imidazol-2-one Hydrochloride 41.22-a (Intermediate 5.2)

$^1$H-NMR (400 MHz, DMSO-d$_6$): δ 11.38 (br s, 1H), 9.44 (br s, 1H), 8.65 (br s, 1H), 7.01-7.07 (m, 1H), 6.78-6.79 (m, 1H), 4.58-4.60 (m, 1H), 3.63-3.65 (m, 2H), 2.45-3.49 (m, 2H), 3.03-3.12 (m, 2H) and 2.35-2.38 (m, 2H). LCMS: 254.11 (M+H)$^+$, 95.61%. Yield: quantitative.

2-Oxo-3-(piperidin-4-yl)-2,3-dihydro-1H-benzo[d]imidazole-5-carbonitrile Hydrochloride 41.22-b (Intermediate 6.2)

$^1$H-NMR (400 MHz, DMSO-d$_6$): δ 11.55 (br s, 1H), 8.93 (br s, 1H), 8.75 (br s, 1H), 7.86 (s, 1H), 7.47 (d, J=7.2 Hz, 1H), 7.14 (d, J=8.8 Hz, 1H), 4.57-4.60 (m, 1H), 3.35-3.40 (m, 2H), 3.04-3.08 (m, 2H), 2.55-2.61 (m, 2H) and 1.85-1.88 (m, 2H). LCMS: 243.32 (M+H)$^+$, 98.82%. Yield: 85%.

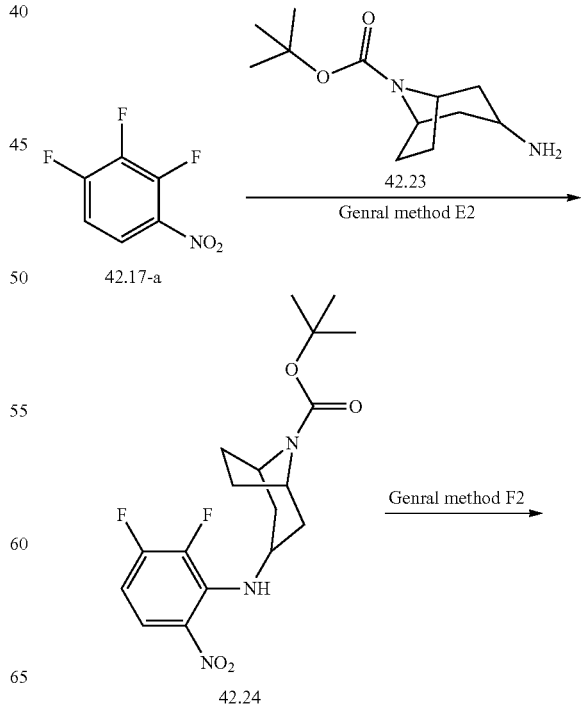

Scheme 42

331

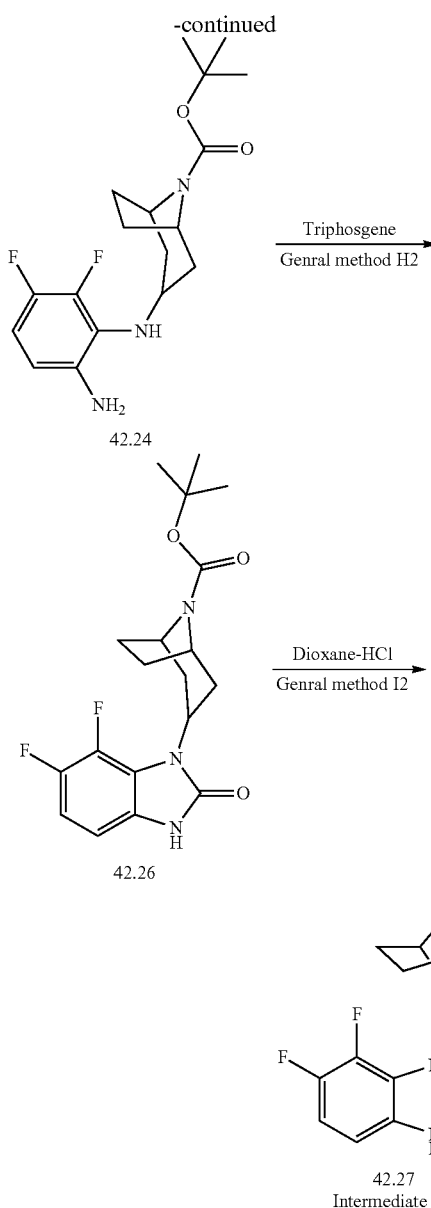

Preparation of tert-butyl 3-((2,3-difluoro-6-nitrophenyl)amino)-8-azabicyclo[3.2.1]octane-8-carboxylate (42.24)

Prepared following the general method E2. ¹H-NMR (400 MHz, CDCl₃): δ 8.61 (d, J=6.0 Hz, 1H), 8.01-8.04 (m, 1H), 6.45-6.51 (m, 1H), 4.21-4.31 (m, 3H), 2.29-2.35 (m, 2H), 2.07-2.09 (m, 2H), 1.94-1.96 (m, 2H), 1.68-1.73 (m, 2H) and 1.47 (s, 9H). LCMS: 384.36 (M+H)⁺, 99.35%. Yield: 78%.

Preparation of tert-butyl 3-((6-amino-2,3-difluorophenyl)amino)-8-azabicyclo[3.2.1]octane-8-carboxylate (42.25)

Prepared following the general method F2. ¹H-NMR (400 MHz, DMSO-d₆): δ 6.57-6.60 (m, 1H), 6.39-6.41 (m, 1H), 4.70 (br s, 2H), 4.17-4.19 (m, 1H), 4.01-4.08 (m, 2H), 3.64 (br s, 1H), 1.98-2.06 (m, 4H), 1.84-1.86 (m, 2H), 1.61-1.64 (m, 2H) and 1.38 (s, 9H). MS: 354.13 (M+H)⁺. Yield: 95%.

332

Preparation of tert-butyl 3-(6,7-difluoro-2-oxo-2,3-dihydro-1H-benzo[d]imidazol-1-yl)-8-azabicyclo[3.2.1]octane-8-carboxylate (42.26)

Prepared following the general method H2. ¹H-NMR (400 MHz, CDCl₃): δ 10.03 (br s, 1H), 6.85-6.97 (m, 1H), 6.74-6.75 (m, 1H), 4.52-4.59 (m, 1H), 4.34-4.46 (m, 2H), 2.52-2.54 (m, 2H), 2.06-2.10 (m, 2H), 1.80-1.89 (m, 4H) and 1.52 (s, 9H). LCMS: 378.13 (M−H)+, 96.51%. Yield: 85%.

Preparation of 1-(8-azabicyclo[3.2.1]octan-3-yl)-6,7-difluoro-1,3-dihydro-2H-benzo[d]imidazol-2-one Hydrochloride 42.27 (Intermediate 7.2)

Prepared following general method I2. ¹H-NMR (400 MHz, DMSO-d₆): δ 11.34 (br s, 1H), 9.02 (br s, 1H), 8.87 (br s, 1H), 7.03-7.10 (m, 1H), 6.80-6.81 (m, 1H), 4.89-4.93 (m, 1H), 4.08-4.10 (m, 2H), 2.49-2.52 (m, 2H), 2.08-2.09 (m, 2H) and 1.90-1.97 (m, 4H). LCMS: 278.06 (M−H)⁺, 99.73%. Yield: 94%.

Synthesis of Final Compounds

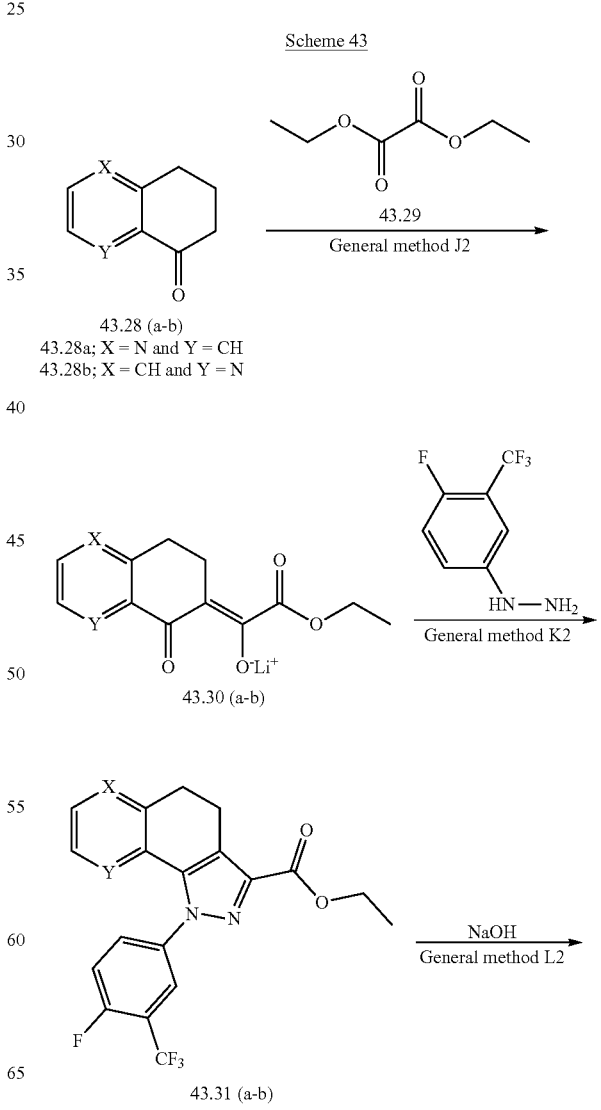

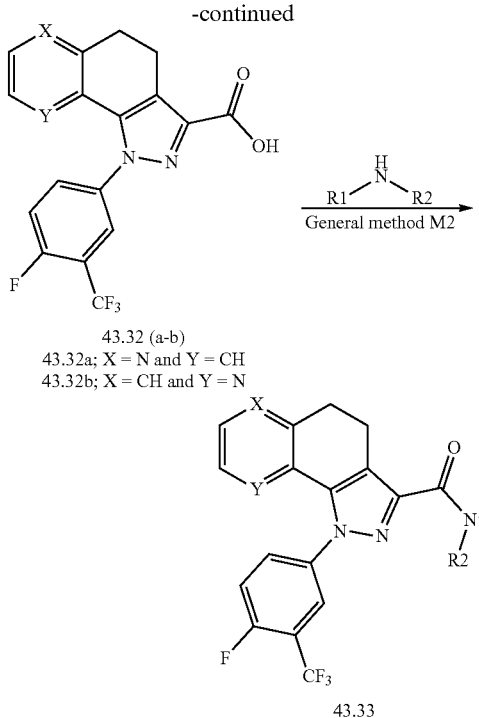

43.32 (a-b)
43.32a; X = N and Y = CH
43.32b; X = CH and Y = N 43.33

General Method J2 for the Preparation of Compounds 43.30 (a-b):

A solution of compound 43.28 (a-b) (1.0 eq) in di-ethyl ether was cooled to −78° C. followed by addition of LiHMDS (1.0 M in THF, 2.5 eq). The resulting reaction mixture was stirred at −78° C. for 45 min followed by drop wise addition of diethyl oxalate 43.29 (1.2 eq). The reaction mixture was then left to stir at room temperature for 16 h. After completion of the reaction (TLC and MS monitoring), the solution was then cooled to 0° C. and the resulting precipitate was filtered to obtain the desired product 43.30 (a-b) as an off-white solid, which was carried forward to the next step without purification.

2-Ethoxy-2-oxo-1-(5-oxo-7,8-dihydroquinolin-6 (5H)-ylidene)ethan-1-olate Lithium Salt (43.30-a)

MS: 248.24 (M+H)$^+$. Yield: 56%.

2-Ethoxy-2-oxo-1-(8-oxo-5,8-dihydroquinolin-7 (6H)-ylidene)ethan-1-olate Lithium Salt (43.30-b)

MS: 248.16 (M+H)$^+$. Yield: 60%.

General Method K2 for the Preparation of Compounds 43.31 (a-b):

To an ice-cold solution of lithium salt of compound 43.30 (a-b) (1.0 eq) in IPA was added (4-fluoro-3-(trifluoromethyl)phenyl)hydrazine (1.2 eq) and TFA (2.0 eq). The resulting reaction mixture was warm up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to obtain the desired product 43.31 (a-b).

Ethyl 1-(4-fluoro-3-(trifluoromethyl)phenyl)-4,5-dihydro-1H-pyrazolo[3,4-f]quinoline-3-carboxylate (43.31a)

$^1$H-NMR (400 MHz, CDCl$_3$): δ 8.40 (d, J=8.0 Hz, 1H), 8.08-8.09 (m, 1H), 7.99-8.01 (m, 1H), 7.72 (t, J=7.2 Hz, 1H), 7.18-7.21 (m, 1H), 7.06-7.14 (m, 1H), 4.36 (q, J=7.6 Hz, 2H), 3.09-3.17 (m, 4H) and 1.33 (t, J=7.2 Hz, 3H). MS: 406.32 (M+H)$^+$. Yield: 40%.

Ethyl 1-(4-fluoro-3-(trifluoromethyl)phenyl)-4,5-dihydro-1H-pyrazolo[4,3-h]quinoline-3-carboxylate (43.31b)

MS: 406.0 (M+H)$^+$. Yield: 7%.

General Method L2 for the Preparation of Compounds 43.32 (a-b):

To an ice-cold solution of ethyl 1-(3-fluoro-4-(trifluoromethyl)phenyl)-5-(pyridin-3-yl)-1H-pyrazole-3-carboxylate 43.31 (a-b) (8.0 g, 21.09 mmol) in EtOH (60 mL) was added drop wise an aqueous solution of sodium hydroxide (1.68 g, 42.18 mmol) in 8 mL H$_2$O. The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to obtain the desired product 43.32 (a-b) (4.5 g, 61%) as a white solid.

1-(4-fluoro-3-(trifluoromethyl)phenyl)-4,5-dihydro-1H-pyrazolo[3,4-f]quinoline-3-carboxylic Acid (43.32a)

$^1$H-NMR (400 MHz, DMSO-d$_6$): δ 13.05 (br s, 1H), 8.39 (s, 1H), 7.99-8.07 (m, 2H), 7.77 (s, 1H), 7.06-7.16 (m, 2H) and 3.07-3.14 (m, 4H). LCMS: 378.29 (M+H)$^+$, 88.67%. Yield: 45%.

1-(4-fluoro-3-(trifluoromethyl)phenyl)-4,5-dihydro-1H-pyrazolo[4,3-h]quinoline-3-carboxylic Acid (43.32b)

$^1$H-NMR (400 MHz, DMSO-d$_6$): δ 13.10 (br s, 1H), 7.96-8.16 (m, 2H), 7.62-7.74 (m, 2H), 7.21-7.24 (m, 1H), 7.02-7.07 (m, 1H) and 3.03-3.14 (m, 4H). MS: 378.20 (M+H)$^+$. Yield: 40%.

General Method M2 for the Preparation of Compounds of General Structure 43.33:

To an ice-cold solution of 1-(3-fluoro-4-(trifluoromethyl)phenyl)-5-(pyridin-3-yl)-1H-pyrazole-3-carboxylic acid 43.32 (a-b) (0.150 g, 0.43 mmol), in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC. The yields and analytical data of the final compounds are set forth in Table 16.15.

TABLE 6.15

Tabulated data of the final compounds including the individual yields

| Compound ID | Structure | Amine Intermediate used | Yield (%) | LCMS | ¹H-NMR data (DMSO-d$_6$, 400 MHz), unless otherwise specified |
|---|---|---|---|---|---|
| 313 | 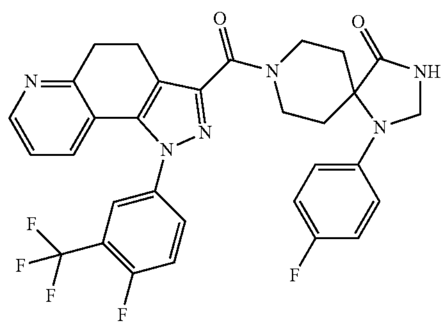 [SMILES: O=C(c1nn(-c2ccc(F)c(C(F)(F)F)c2)c2c1CCc1ncccc1-2)N1CCC2(CC1)C(=O)NCN2c1ccc(F)cc1] | Int 1.2 | 18% | 609.24 (M − H)$^+$, 95.20% | (DMSO-d$_6$ + D$_2$O): δ 8.29 (m, 1H), 7.92 (m, 1H), 7.84-7.86 (m, 1H), 7.60-7.64 (m, 1H), 7.09-7.11 (m, 1H), 7.01-7.05 (m, 3H), 6.83-6.84 (m, 2H), 4.59 (s, 2H), 4.32-4.44 (m, 2H), 3.70-3.76 (m, 1H), 3.47-3.51 (m, 1H), 3.02-3.13 (m, 2H), 2.80-2.88 (m, 2H), 2.18-2.25 (m, 2H) and 1.65-1.81 (m, 2H) |
| 314 | 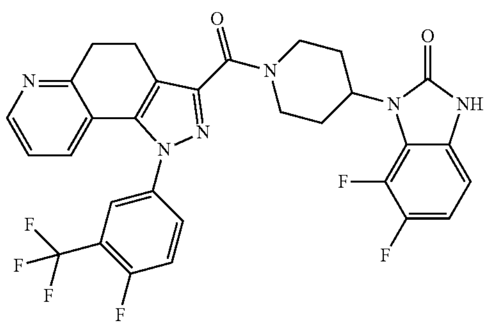 [SMILES: O=C(c1nn(-c2ccc(F)c(C(F)(F)F)c2)c2c1CCc1ncccc1-2)N1CCC(n2c(=O)[nH]c3ccc(F)c(F)c32)CC1] | Int 5.2 | 22% | 613.20 (M + H)$^+$, 99.50% | (DMSO-d$_6$ + D$_2$O): δ 8.38-8.40 (m, 1H), 7.97-7.99 (m, 1H), 7.91-7.94 (m, 1H), 7.64-7.69 (m, 1H), 7.27-7.34 (m, 2H), 6.99-7.06 (m, 1H), 6.84-6.83 (m, 1H), 4.62-4.64 (m, 2H), 4.49-4.52 (m, 1H), 3.19-3.30 (m, 3H), 2.89-2.96 (m, 3H), 2.0-2.08 (m, 2H) and 1.79-1.89 (m, 2H) |
| 315 | 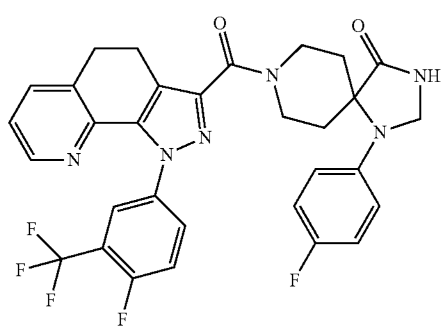 [SMILES: O=C(c1nn(-c2ccc(F)c(C(F)(F)F)c2)c2c1CCc1cccnc1-2)N1CCC2(CC1)C(=O)NCN2c1ccc(F)cc1] | Int 1.2 | 7% | 609.22 (M + H)$^+$, 99.48% | δ 8.80 (s, 1H), 8.17-8.18 (m, 1H), 7.93-7.98 (m, 2H), 7.78 (d, J = 7.60 Hz, 1H), 7.59-7.64 (m, 1H), 7.22-7.25 (m, 1H), 7.06-7.11 (m, 2H), 6.83-6.86 (m, 2H), 4.59 (s, 2H), 4.30-4.44 (m, 2H), 3.78-3.84 (m, 1H), 3.49-3.54 (m, 1H), 3.04-3.07 (m, 2H), 2.84-2.89 (m, 2H), 2.21-2.36 (m, 2H) and 1.69-1.82 (m, 2H) |
| 316 | 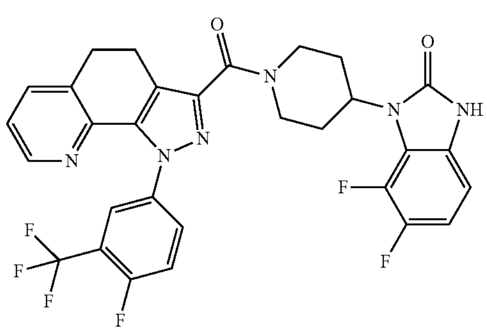 [SMILES: O=C(c1nn(-c2ccc(F)c(C(F)(F)F)c2)c2c1CCc1cccnc1-2)N1CCC(n2c(=O)[nH]c3ccc(F)c(F)c32)CC1] | Int 5.2 | 4% | 613.20 (M + H)$^+$, 96.24% | (MeOD): δ 8.17-8.18 (m, 1H), 7.86-7.92 (m, 2H), 7.72-7.74 (m, 1H), 7.41-7.46 (m, 1H), 7.19-7.22 (m, 1H), 6.94-7.01 (m, 1H), 6.80-6.83 (m, 1H), 3.34 (m, 1H), 2.97-3.13 (m, 4H), 2.35-2.40 (m, 2H), 1.87-2.03 (m, 2H) and 1.26-1.40 (m, 4H) |

Scheme 44

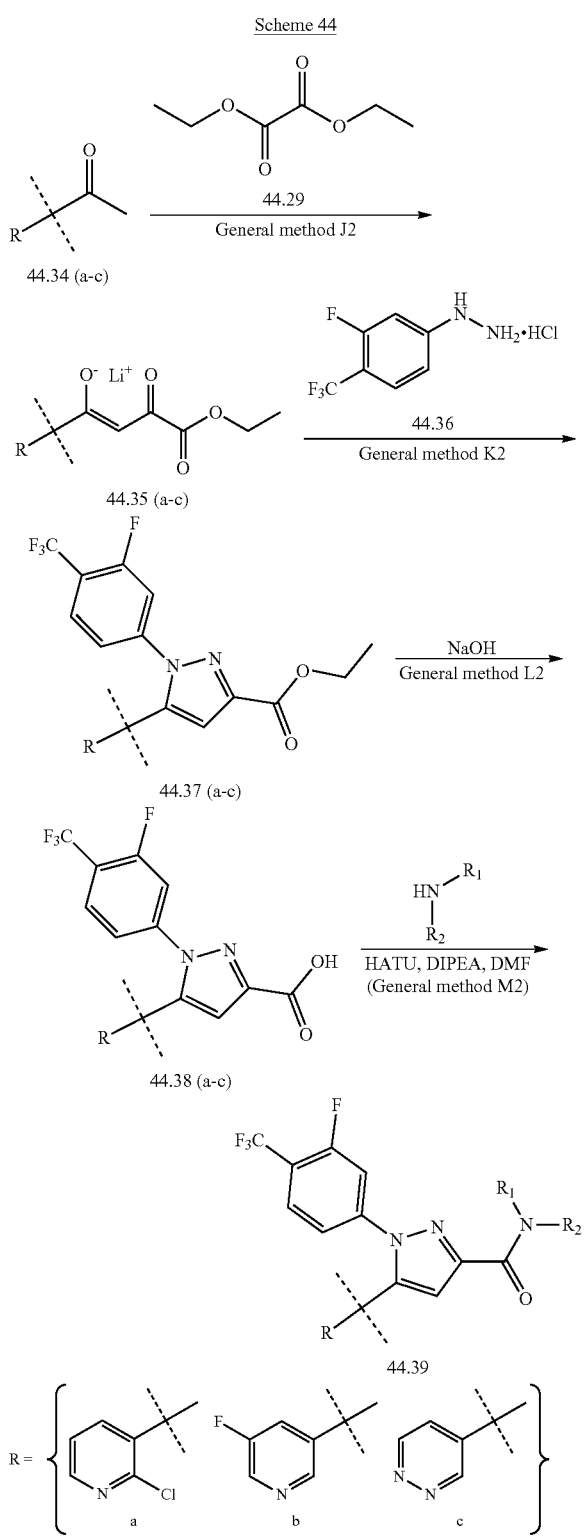

General Procedure for the Preparation of Compounds 44.35 (a-c):

A solution of compounds 44.34 (a-c) (1.0 eq) in di-ethyl ether (250 mL) was cooled to −78° C. followed by addition of LiHMDS (1.1 eq). The resulting reaction mixture was stirred at −78° C. for 45 min followed by drop wise addition of diethyl oxalate 29 (1.2 eq) in about 20 min. The reaction mixture was then left to stir at room temperature for 16 h. After completion of the reaction (TLC and MS monitoring), the solution was then cooled to 0° C. and the resulting precipitate was filtered to obtain the desired product 44.35 (a-c) as an off-white solid, which was carried forward to the next step without purification.

1-(2-chloropyridin-3-yl)-4-ethoxy-3,4-dioxobut-1-en-1-olate Lithium Salt (44.35-a)

$^1$H-NMR (400 MHz, DMSO-d$_6$): δ 8.85 (s, 1H), 8.58 (m, 1H), 7.38 (m, 1H), 6.43 (m, 1H), 4.15 (q, J=7.60 Hz, 2H) and 1.19 (t, J=7.2 Hz, 3H). MS: 256.10 (M+H)$^+$. Yield: 71%.

4-Ethoxy-1-(5-fluoropyridin-3-yl)-3,4-dioxobut-1-en-1-olate Lithium Salt (44.35-b)

$^1$H-NMR (400 MHz, DMSO-d$_6$): δ 8.84 (s, 1H), 8.64-8.65 (m, 1H), 7.84-7.98 (m, 1H), 6.39-6.43 (m, 1H), 4.13 (q, J=7.20 Hz, 2H) and 1.20 (t, J=7.2 Hz, 3H). MS: 240.29 (M+H)$^+$. Yield: quantitative.

4-Ethoxy-3,4-dioxo-1-(pyridazin-4-yl)but-1-en-1-olate Lithium Salt (44.35-c)

MS: 223.22 (M+H)$^+$. Yield: 40%.

General Method K2 for the Preparation of Compounds 44.37 (a-c):

To an ice-cold solution of compound 44.35 (a-c) (1.0 eq) in IPA (60 mL) was added (3-fluoro-4-(trifluoromethyl)phenyl)hydrazine hydrochloride 44.36 (1.2 eq) and TFA (2.0 eq). The resulting reaction mixture was warm up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to obtain the desired product 44.37 (a-c).

Ethyl 5-(2-chloropyridin-3-yl)-1-(3-fluoro-4-(trifluoromethyl)phenyl)-1H-pyrazole-3-carboxylate (44.37-a)

$^1$H-NMR (400 MHz, CDCl$_3$): δ 8.53-8.55 (m, 1H), 7.52-7.56 (m, 1H), 7.37-7.40 (m, 2H), 7.26-7.30 (m, 2H), 7.11 (s, 1H), 4.46 (q, J=7.2 Hz, 2H) and 1.41 (t, J=7.6 Hz, 3H). MS: 414.13 (M+H)$^+$. Yield: 90%.

Ethyl 1-(3-fluoro-4-(trifluoromethyl)phenyl)-5-(5-fluoropyridin-3-yl)-1H-pyrazole-3-carboxylate (44.37-b)

$^1$H-NMR (400 MHz, CDCl$_3$): δ 8.54 (s, 1H), 8.35 (s, 1H), 7.60-7.64 (m, 1H), 7.31-7.36 (m, 2H), 7.05-7.15 (m, 2H), 4.39 (q, J=7.2 Hz, 2H) and 1.42 (t, J=6.8 Hz, 3H). MS: 398.20 (M+H)$^+$. Yield: 22%.

Ethyl 1-(3-fluoro-4-(trifluoromethyl)phenyl)-5-(pyridazin-4-yl)-1H-pyrazole-3-carboxylate (44.37-c)

$^1$H-NMR (400 MHz, CDCl$_3$): δ 9.26-9.27 (m, 1H), 9.09-9.13 (m, 1H), 7.56-7.61 (m, 1H), 7.21-7.32 (m, 3H), 7.05-7.15 (m, 1H), 4.45 (q, J=7.2 Hz, 2H) and 1.42 (t, J=7.2 Hz, 3H). MS: 381.29 (M+H)$^+$. Yield: 15%.

General Procedure for the Preparation of Compounds 44.38 (a-c):

To an ice-cold solution of ethyl 1-(3-fluoro-4-(trifluoromethyl)phenyl)-5-(pyridin-3-yl)-1H-pyrazole-3-carboxylate 44.37 (a-c) (1.0 eq) in EtOH was added drop wise an aqueous solution of sodium hydroxide (2.0 eq) in H$_2$O. The resulting solution was stirred at room temperature for 2 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to obtain the desired products 44.38 (a-c) as white solids.

5-(2-Chloropyridin-3-yl)-1-(3-fluoro-4-(trifluoromethyl)phenyl)-1H-pyrazole-3-carboxylic Acid (44.38-a)

$^1$H-NMR (400 MHz, DMSO-d$_6$): δ 13.40 (br s, 1H), 8.53-8.54 (m, 1H), 8.09-8.11 (m, 1H), 7.85-7.86 (m, 1H), 7.55-7.61 (m, 2H), 7.21-7.23 (m, 1H) and 7.13 (s, 1H). LCMS: 386.19 (M+H)$^+$, 97.48%. Yield: 55%.

1-(3-Fluoro-4-(trifluoromethyl)phenyl)-5-(5-fluoropyridin-3-yl)-1H-pyrazole-3-carboxylic Acid (44.38-b)

$^1$H-NMR (400 MHz, DMSO-d$_6$): δ 13.16 (br s, 1H), 8.67 (s, 1H), 8.60 (s, 1H), 7.88-7.92 (m, 1H), 7.74-7.81 (m, 1H), 7.67-7.70 (m, 1H) and 7.27-7.34 (m, 2H). LCMS: 368.17 (M−H)$^+$, 93.75%. Yield: 90%.

1-(3-Fluoro-4-(trifluoromethyl)phenyl)-5-(pyridazin-4-yl)-1H-pyrazole-3-carboxylic Acid (44.38-c)

$^1$H-NMR (400 MHz, DMSO-d$_6$): δ 13.20 (br s, 1H), 9.26-9.28 (m, 2H), 7.95-7.99 (m, 1H), 7.75-7.78 (m, 1H), 7.55 (s, 2H) and 7.43-7.45 (m, 1H). MS: 353.24 (M+H)$^+$. Yield: 43%.

General Method M2 for the Preparation of Compounds of General Structure 44.39:

To an ice-cold solution of 1-(3-fluoro-4-(trifluoromethyl)phenyl)-5-(pyridin-3-yl)-1H-pyrazole-3-carboxylic acid 44.38 (a-c) (1.0 eq) in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude was purified via prep-HPLC. The yields and analytical data of the final compounds are set forth in Table 6.16.

TABLE 6.16

Tabulated data of the final compounds including the individual yields

| Compound ID | Structure | Amine Intermediate used | Yield (%) | LCMS | $^1$H-NMR data (DMSO-d$_6$, 400 MHz), unless otherwise specified |
|---|---|---|---|---|---|
| 317 | 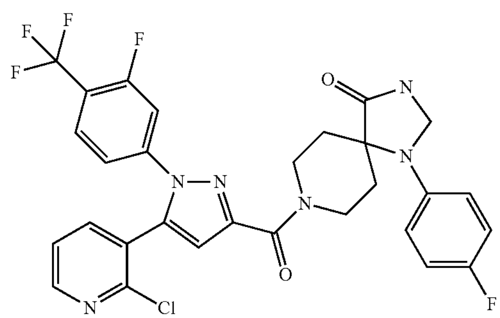 [SMILES: O=C(c1cc(-c2cccnc2Cl)n(-c2ccc(C(F)(F)F)c(F)c2)n1)N1CCC2(CC1)C(=O)NCN2c1ccc(F)cc1] | Int 1.2 | 6% | 617.37 (M + H)$^+$, 96.61% | δ 8.81 (m, 1H), 8.55 (m, 1H), 8.10 (m, 1H), 7.82 (m, 1H), 7.62-7.57 (m, 2H), 7.19 (m, 1H), 7.11 (m, 3H), 6.86 (m, 2H), 4.46 (m, 2H), 4.43 (m, 2H), 3.90 (m, 1H), 3.52 (m, 1H), 2.24 (m, 2H) and 1.80 (m, 2H) |
| 318 | 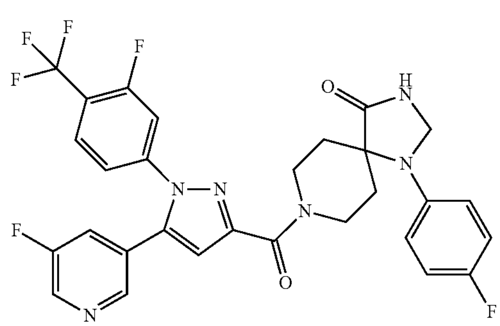 [SMILES: O=C(c1cc(-c2cncc(F)c2)n(-c2ccc(C(F)(F)F)c(F)c2)n1)N1CCC2(CC1)C(=O)NCN2c1ccc(F)cc1] | Int 1.2 | 10% | 601.17 (M + H)$^+$, 98.88% | δ 8.51 (m, 1H), 8.66 (m, 1H), 8.40 (m, 1H), 7.82 (m, 2H), 7.67 (m, 1H), 7.33 (m, 1H), 7.21 (s, 1H), 7.08 (m, 2H), 6.84 (m, 2H), 4.59 (m, 2H), 4.44 (m, 2H), 3.88 (m, 1H), 3.38 (m, 1H), 2.29 (m, 2H) and 1.80 (m, 2H) |

TABLE 6.16-continued
Tabulated data of the final compounds including the individual yields
| Compound ID | Structure | Amine Intermediate used | Yield (%) | LCMS | $^1$H-NMR data (DMSO-$d_6$, 400 MHz), unless otherwise specified |
|---|---|---|---|---|---|
| 319 | 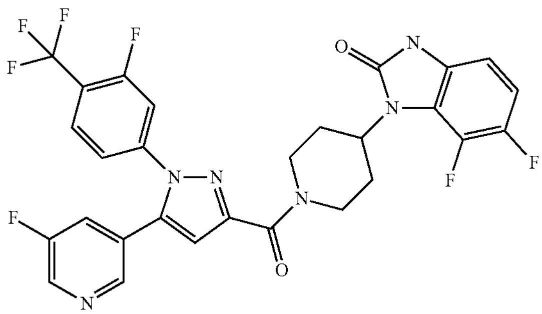 [SMILES: O=C(c1cc(-c2cncc(F)c2)n(-c2ccc(C(F)(F)F)c(F)c2)n1)N1CCC(n2c(=O)[nH]c3ccc(F)c(F)c32)CC1] | Int 5.2 | 25% | 605.17 (M − H)$^+$, 99.94% | δ 11.23 (br s, 1H), 8.65 (m, 1H), 8.40 (m, 1H), 7.86 (m, 2H), 7.70 (m, 1H), 7.37 (m, 1H), 7.23 (s, 1H), 7.04 (m, 1H), 6.79 (m, 1H), 4.80 (m, 1H), 4.70 (m, 2H), 3.35 (m, 1H), 2.97 (m, 1H), 2.14 (m, 2H) and 1.88 (m, 2H) |
| 320 | 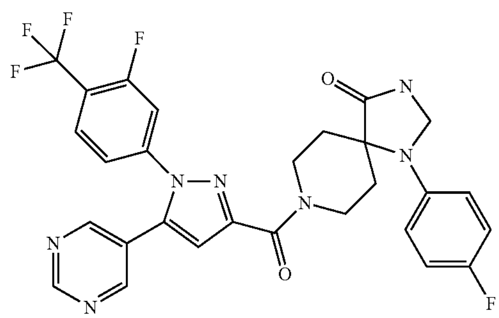 [SMILES: O=C(c1cc(-c2cncnc2)n(-c2ccc(C(F)(F)F)c(F)c2)n1)N1CCC2(CC1)C(=O)NCN2c1ccc(F)cc1] | Int 1.2 | 6% | 584.40 (M − H)$^+$, 95.72% | δ 9.28 (m, 2H), 8.81 (m, 1H), 7.91 (m, 1H), 7.89 (m, 1H), 7.57 (m, 1H), 7.42 (m, 2H), 7.01 (m, 2H), 6.85 (m, 2H), 4.62 (m, 2H), 4.43 (m, 2H), 3.90 (m, 1H), 3.52 (m, 1H), 2.24 (m, 2H) and 1.80 (m, 2H) |
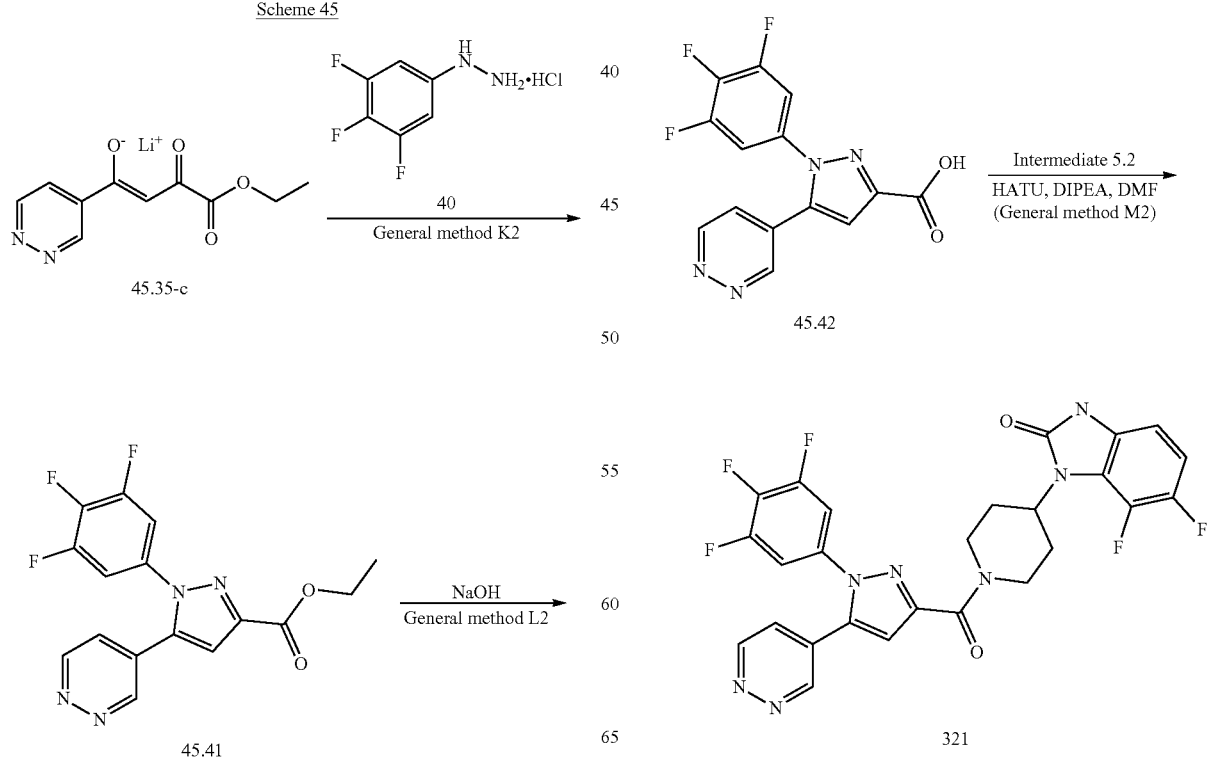
Scheme 45

Ethyl 5-(pyridazin-4-yl)-1-(3,4,5-trifluorophenyl)-1H-pyrazole-3-carboxylate (45.41)

The experimental procedure was similar to the one as mentioned in Scheme 43 above (general method K2). $^1$H-NMR (400 MHz, CDCl$_3$): δ 9.25-9.26 (m, 1H), 9.09-9.11 (m, 1H), 7.22-7.26 (m, 2H), 7.03-7.07 (m, 2H), 4.46 (q, J=6.8 Hz, 2H) and 1.43 (t, J=7.2 Hz, 3H). MS: 349.22 (M+H)$^+$. Yield: 18%.

5-(Pyridazin-4-yl)-1-(3,4,5-trifluorophenyl)-1H-pyrazole-3-carboxylic Acid (45.42)

The experimental procedure was similar to the one as mentioned in Scheme 43 above (General method L2). MS: 321.23 (M+H)$^+$. Yield: 68%.

General Method M2 for the Preparation of Final Compound 321:

To an ice-cold solution of 5-(pyridazin-4-yl)-1-(3,4,5-trifluorophenyl)-1H-pyrazole-3-carboxylic acid 45.42 (1.0 eq) in DMF (2.0 mL) was added DIPEA (2.5 eq) and HATU (1.50 eq). The resulting mixture was stirred under nitrogen atmosphere at 0° C. for 15 min followed by addition of Intermediate 5.2 (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The crude residue was purified via prep-HPLC. The yields and analytical data of the final compound are set forth in Table 6.17.

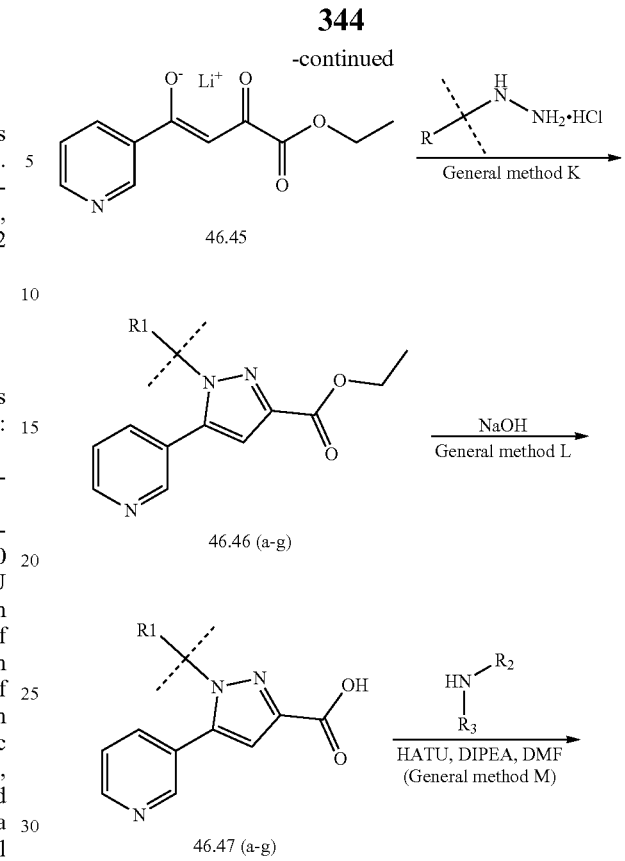

TABLE 6.17

Tabulated data of the final compounds including the individual yields

| Compound ID | Structure | Amine Intermediate used | Yield (%) | LCMS | $^1$H-NMR data (DMSO-d$_6$, 400 MHz), unless otherwise specified |
|---|---|---|---|---|---|
| 321 | 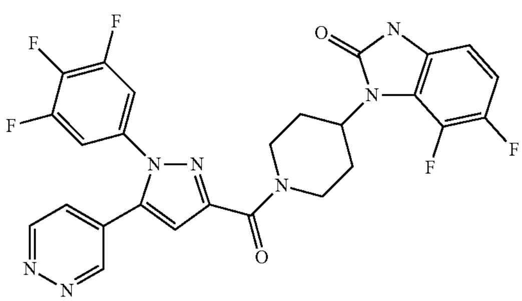 [SMILES: O=C(c1cc(-c2ccnnc2)n(-c2cc(F)c(F)c(F)c2)n1)N1CCC(n2c(=O)[nH]c3ccc(F)c(F)c32)CC1] | Int 5.2 | 13% | 554.01 (M + H)+, 99.55% | δ 11.23 (br s, 1H), 9.31 (m, 1H), 9.21 (m, 1H), 7.64 (m, 2H), 7.46 (m, 2H), 7.04 (m, 1H), 6.79 (m, 1H), 4.78 (m, 1H), 4.66 (m, 2H), 3.37 (m, 1H), 2.99 (m, 1H), 2.24 (m, 2H) and 1.84 (m, 2H) |

Scheme 46

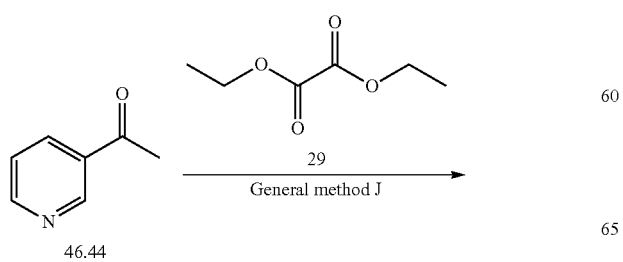

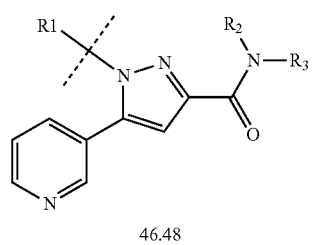

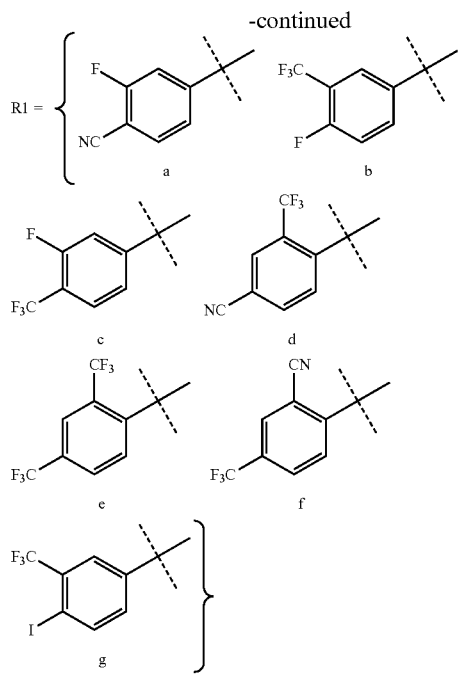

$R1 =$ a, b, c, d, e, f, g

Preparation of 4-ethoxy-3,4-dioxo-1-(pyridin-3-yl)but-1-en-1-olate Lithium Salt (46.45)

Prepared following the general method J2 (refer to scheme 43). $^1$H-NMR (400 MHz, DMSO-d$_6$): δ 8.95 (s, 1H), 8.61 (d, J=4.0 Hz, 1H), 8.14 (m, 1H), 7.44 (m, 1H), 6.40 (m, 1H), 4.12 (q, J=7.20 Hz, 2H) and 1.21 (t, J=7.2 Hz, 3H). MS: 221.95 (M+H)$^+$. Yield: 82%.

General Procedure for the Preparation of Compounds 46.46 (a-g):

To an ice-cold solution of 4-ethoxy-2-methyl-3,4-dioxo-1-(pyridin-3-yl)but-1-en-1-olate lithium salt 46.45 (1.0 eq) in IPA was added respective hydrazine hydrochloride (1.2 eq) and TFA (2.0 eq). The resulting reaction mixture was warm up to room temperature and then stirred at 90° C. for 4-5 h. After completion of the reaction (TLC monitoring), the solvent was evaporated and the residue was diluted with water and extracted with ethyl acetate (3 times). The combined organics were washed with brine, dried over anhydrous sodium sulfate, filtered and concentrated. The crude was purified over silica gel (100-200 M, 10-15% EtOAc-hexane) to obtain the desired products 46.46a-g.

Ethyl 1-(4-cyano-3-fluorophenyl)-5-(pyridin-3-yl)-1H-pyrazole-3-carboxylate (46.46-a)

$^1$H-NMR (400 MHz, CDCl$_3$): δ 8.71-8.72 (m, 1H), 8.62 (s, 1H), 7.61-7.64 (m, 2H), 7.44-7.47 (m, 1H), 7.35-7.38 (m, 1H), 7.19 (s, 1H), 7.15-7.17 (m, 1H), 4.42 (q, J=7.6 Hz, 2H) and 1.36 (t, J=7.6 Hz, 3H). LCMS: 337.13 (M+H)$^+$, 96.65%. Yield: 26%.

Ethyl 1-(4-fluoro-3-(trifluoromethyl)phenyl)-5-(pyridin-3-yl)-1H-pyrazole-3-carboxylate (46.46-b)

$^1$H-NMR (400 MHz, CDCl$_3$): δ 8.59-8.66 (m, 1H), 7.77-7.78 (m, 1H), 7.56 (d, J=8.04 Hz, 1H) 7.38-7.41 (m, 2H), 7.23-7.25 (m, 1H), 7.21 (s, 1H), 7.07-7.10 (m, 1H), 4.48 (q, J=7.2 Hz, 2H) and 1.38 (t, J=7.6 Hz, 3H). MS: 380.22 (M+H)$^+$. Yield: 35%.

Ethyl 1-(3-fluoro-4-(trifluoromethyl)phenyl)-5-(pyridin-3-yl)-1H-pyrazole-3-carboxylate (46.46-c)

$^1$H-NMR (400 MHz, CDCl$_3$): δ 8.57-8.61 (m, 1H), 7.73-7.75 (m, 1H), 7.60-7.63 (m, 1H) 7.37-7.40 (m, 2H), 7.23-7.27 (m, 1H), 7.20 (s, 1H), 7.03-7.09 (m, 1H), 4.45 (q, J=6.8 Hz, 2H) and 1.41 (t, J=7.2 Hz, 3H). MS: 380.13 (M+H)$^+$. Yield: 40%.

Ethyl 1-(4-cyano-2-(trifluoromethyl)phenyl)-5-(pyridin-3-yl)-1H-pyrazole-3-carboxylate (46.46-d)

$^1$H-NMR (400 MHz, CDCl$_3$): δ 8.58-8.59 (m, 1H), 8.46 (s, 1H), 8.13 (s, 1H), 7.92-7.94 (m, 1H), 7.51-7.57 (m, 2H), 7.31-7.35 (m, 1H), 7.19 (s, 1H), 4.44 (q, J=6.8 Hz, 2H) and 1.39 (t, J=7.2 Hz, 3H). MS: 387.12 (M+H)$^+$. Yield: 39%.

Ethyl 1-(2,4-bis(trifluoromethyl)phenyl)-5-(pyridin-3-yl)-1H-pyrazole-3-carboxylate (46.46-e)

$^1$H-NMR (400 MHz, CDCl$_3$): δ 8.56-8.57 (m, 1H), 8.47 (s, 1H), 8.04 (s, 1H), 7.77 (d, J=8.0 Hz, 1H), 7.50-7.59 (m, 2H), 7.26-7.32 (m, 1H), 7.18 (s, 1H), 4.40 (q, J=7.2 Hz, 2H) and 1.36 (t, J=7.6 Hz, 3H). MS: 430.12 (M+H)$^+$. Yield: 25%.

Ethyl 1-(2-cyano-4-(trifluoromethyl)phenyl)-5-(pyridin-3-yl)-1H-pyrazole-3-carboxylate (46.46-f)

$^1$H-NMR (400 MHz, CDCl$_3$): δ 8.56-8.60 (m, 1H), 8.48 (s, 1H), 8.15 (s, 1H), 7.88-7.95 (m, 1H), 7.53-7.58 (m, 2H), 7.30-7.36 (m, 1H), 7.18 (s, 1H), 4.41 (q, J=6.8 Hz, 2H) and 1.41 (t, J=7.6 Hz, 3H). MS: 387.09 (M+H)$^+$. Yield: 35%.

Ethyl 1-(4-iodo-3-(trifluoromethyl)phenyl)-5-(pyridin-3-yl)-1H-pyrazole-3-carboxylate (46.46-g)

MS: 487.90 (M+H)$^+$. Yield: 41%.

General Procedure for the Preparation of Compounds 46.47a-g:

To an ice-cold solution of compound 46.46a-g (0.80-1.5 g, 1.0 eq) in EtOH was added drop wise an aqueous solution of sodium hydroxide (3.0 eq). The resulting solution was stirred at room temperature for 2-3 h. After completion of the reaction (TLC monitoring), the solvent was evaporated, added H$_2$O to the residue followed by extraction with EtOAc (2×100 mL). The organic layer was discarded and the pH of the aqueous layer was adjusted to ~4 by adding 1N HCl. The resulting precipitate was filtered and dried under vacuum to obtain the desired product 46.47a-g as a white solid.

1-(4-Cyano-3-fluorophenyl)-5-(pyridin-3-yl)-1H-pyrazole-3-carboxylic Acid (46.47-a)

$^1$H-NMR (400 MHz, DMSO-d$_6$): δ 13.18 (br s, 1H), 8.59-8.91 (m, 2H), 7.67-7.68 (m, 2H), 7.41-7.44 (m, 1H), 7.25-7.27 (m, 2H) and 7.22 (s, 1H). MS: 309.11 (M+H)$^+$. Yield: 30%.

1-(4-Fluoro-3-(trifluoromethyl)phenyl)-5-(pyridin-3-yl)-1H-pyrazole-3-carboxylic Acid (46.47-b)

$^1$H-NMR (400 MHz, DMSO-d$_6$): δ 13.15 (br s, 1H), 8.57-8.58 (m, 2H), 7.84-7.86 (m, 1H), 7.60-7.69 (m, 3H), 7.40-7.45 (m, 1H) and 7.24 (s, 1H). LCMS: 352.24 (M+H)+, 95.84%. Yield: 73%.

1-(3-Fluoro-4-(trifluoromethyl)phenyl)-5-(pyridin-3-yl)-1H-pyrazole-3-carboxylic Acid (46.47-c)

LCMS: 352.10 (M+H)$^+$, 93.14%. Yield: 67%.

1-(4-Cyano-2-(trifluoromethyl)phenyl)-5-(pyridin-3-yl)-1H-pyrazole-3-carboxylic Acid (46.47-d)

MS: 357.10 (M−H)$^+$. Yield: 35%.

1-(2,4-Bis(trifluoromethyl)phenyl)-5-(pyridin-3-yl)-1H-pyrazole-3-carboxylic Acid (46.47-e)

$^1$H-NMR (400 MHz, DMSO-d$_6$): δ 13.16 (br s, 1H), 8.49-8.53 (m, 2H), 8.33 (s, 1H), 8.27 (d, J=8.4 Hz, 1H), 8.00 (d, J=8.4 Hz, 1H), 7.57-7.59 (m, 1H) and 7.35-7.38 (m, 2H). LCMS: 400.30 (M−H)$^+$, 99.38%. Yield: 44%.

1-(2-Cyano-4-(trifluoromethyl)phenyl)-5-(pyridin-3-yl)-1H-pyrazole-3-carboxylic Acid (46.47-f)

MS: 357.18 (M−H)$^+$. Yield: 28%.

1-(4-Iodo-3-(trifluoromethyl)phenyl)-5-(pyridin-3-yl)-1H-pyrazole-3-carboxylic Acid (46.47-g)

$^1$H-NMR (400 MHz, DMSO-d$_6$): δ 13.10 (br s, 1H), 9.03-9.06 (m, 2H), 8.65 (s, 1H), 7.70-7.73 (m, 2H), and 7.22-7.33 (m, 3H). LCMS: 460.05 (M+H)$^+$, 87.11%. Yield: 69%.

General Procedure for the Preparation of Compounds of General Structure 48:

To an ice-cold solution of carboxylic acids 46.47a-g (125-150 mg), in DMF (2.0 mL) was added DIPEA (2.5 eq) and HATU (1.50 eq). The resulting mixture was stirred under nitrogen atmosphere at 0° C. for 15 min followed by addition of respective amines (1.20 eq). The reaction mixture was then stirred at room temperature for 16 h. After the completion of the reaction (TLC monitoring), the solution was diluted with ice-cold water (30 mL) followed by extraction with EtOAc (3×50 mL). The combined organics were washed with brine, dried over anhydrous Na$_2$SO$_4$, filtered and concentrated under reduced pressure. The final compounds were purified via prep-HPLC. The yields and analytical data of the final compounds are set forth in Table 6.18.

TABLE 6.18

Tabulated data of the final compounds including the individual yields

| Compound ID | Structure | Amine Intermediate used | Yield (%) | LCMS | $^1$H-NMR data (DMSO-d$_6$, 400 MHz), unless otherwise specified |
|---|---|---|---|---|---|
| 322 | 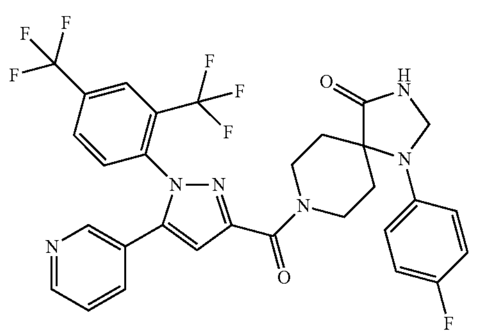 [SMILES: O=C(c1cc(-c2cccnc2)n(-c2ccc(C(F)(F)F)cc2C(F)(F)F)n1)N1CCC2(CC1)C(=O)NCN2c1ccc(F)cc1] | Int 1.2 | 16% | 633.14 (M + H)$^+$, 98.13% | δ 8.79 (m, 1H), 8.54-8.50 (m, 1H), 8.51 (m, 1H), 8.33 (s, 1H), 8.22 (m, 1H), 7.88-7.86 (m, 1H), 7.59-7.57 (m, 1H), 7.39-7.36 (m, 1H), 7.25 (s, 1H), 7.09-7.03 (m, 2H), 6.83-6.80 (m, 2H), 4.45 (m, 2H), 4.42 (m, 2H), 3.85 (m, 1H), 3.45 (m, 1H), 2.30-2.19 (m, 2H) and 1.82-1.69 (m, 2H) |
| 323 | 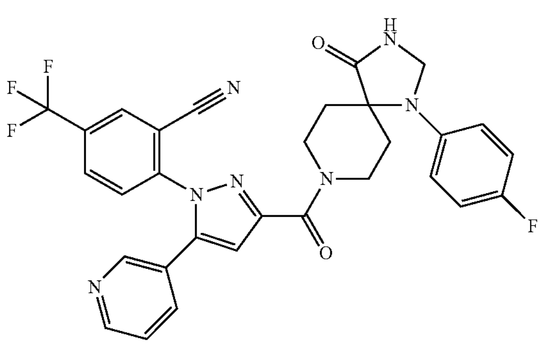 [SMILES: N#Cc1cc(C(F)(F)F)ccc1-n1nc(C(=O)N2CCC3(CC2)C(=O)NCN3c2ccc(F)cc2)cc1-c1cccnc1] | Int 1.2 | 14% | 590.19 (M + H)$^+$, 98.52% | δ 9.40 (m, 1H), 8.85 (m, 2H), 8.72-8.70 (m, 1H), 8.50 (m, 1H), 8.15 (s, 1H), 8.09-8.06 (m, 1H), 7.91 (m, 1H), 7.74 (m, 1H), 7.24-7.16 (m, 2H), 7.03-6.97 (m, 2H), 4.55 (m, 2H), 4.53 (m, 1H), 3.85 (m, 2H), 3.62 (m, 1H), 2.69 (m, 1H) 2.49 (m, 1H), 1.92 (m, 1H) and 1.69 (m, 1H) |

TABLE 6.18-continued

Tabulated data of the final compounds including the individual yields

| Compound ID | Structure | Amine Intermediate used | Yield (%) | LCMS | $^1$H-NMR data (DMSO-$d_6$, 400 MHz), unless otherwise specified |
|---|---|---|---|---|---|
| 324 | 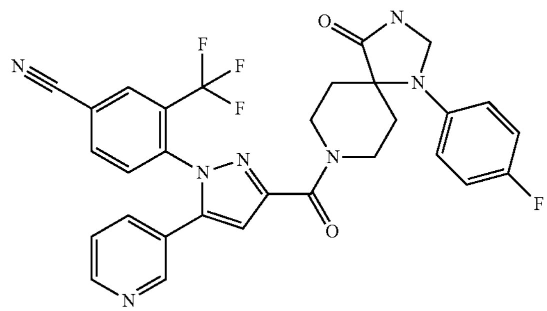 [SMILES: N#Cc1ccc(-n2nc(C(=O)N3CCC4(CC3)C(=O)NCN4c3ccc(F)cc3)cc2-c2cccnc2)c(C(F)(F)F)c1] | Int 1.2 | 5% | 590.21 (M + H)$^+$, 94.61% | δ 8.83 (m, 1H), 8.59 (m, 1H), 8.54-8.51 (m, 2H), 8.29-8.27 (m, 1H), 7.84 (m, 1H), 7.55 (m, 1H), 7.36 (m, 1H), 7.25 (s, 1H), 7.07-7.03 (m, 2H), 6.83-6.80 (m, 2H), 4.57 (m, 2H), 4.42 (m, 2H), 3.82 (m, 1H), 3.50 (m, 1H), 2.22 (m, 2H) 1.81 (m, 1H) and 1.72 (m, 1H) |
| 325 | 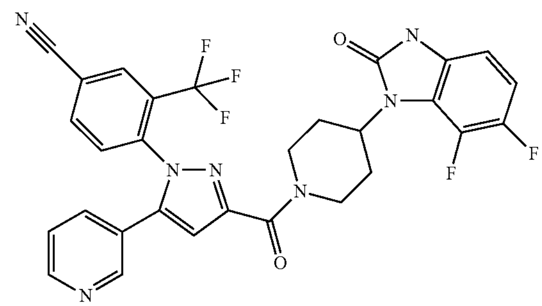 [SMILES: N#Cc1ccc(-n2nc(C(=O)N3CCC(n4c(=O)[nH]c5ccc(F)c(F)c54)CC3)cc2-c2cccnc2)c(C(F)(F)F)c1] | Int 5.2 | 5% | 594.38 (M + H)$^+$, 96.36% | δ 11.15 (br s, 1H), 8.59 (m, 1H), 8.54-8.48 (m, 2H), 8.30 (m, 1H), 7.87 (m, 1H), 7.58 (m, 1H), 7.37 (m, 1H), 7.25 (s, 1H), 7.03 (m, 1H), 6.78 (m, 1H), 4.70 (m, 2H), 3.57 (m, 2H), 3.23 (m, 1H), 2.94 (m, 1H), 2.14 (m, 1H) 1.90 (m, 1H) and 1.78 (m, 1H) |
| 326 | 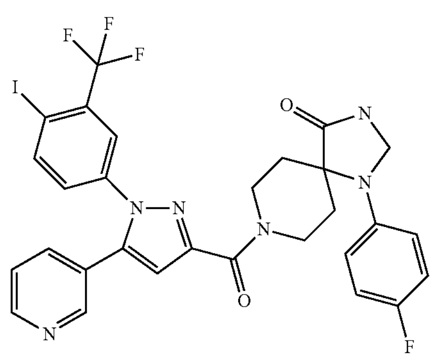 [SMILES: O=C(c1cc(-c2cccnc2)n(-c2ccc(I)c(C(F)(F)F)c2)n1)N1CCC2(CC1)C(=O)NCN2c1ccc(F)cc1] | Int 1.2 | 5% | 691.08 (M + H)$^+$, 92.90% | δ 8.81 (s, 1H), 8.60-8.57 (m, 2H), 8.16 (m, 1H), 7.70 (m, 2H), 7.44 (m, 1H), 7.28 (m, 1H), 7.12 (m, 3H), 6.86 (m, 2H), 4.59 (m, 2H), 4.44 (m, 2H), 3.88 (m, 1H), 3.53 (m, 1H), 2.27 (m, 2H) and 1.82 (m, 2H) |
| 327 | 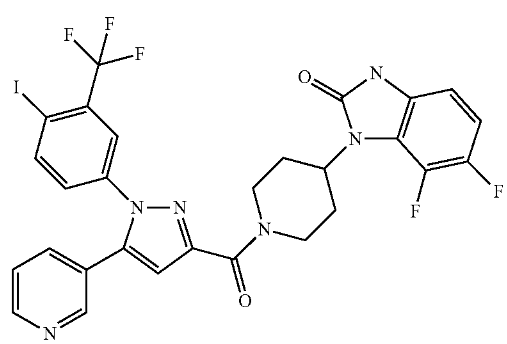 [SMILES: O=C(c1cc(-c2cccnc2)n(-c2ccc(I)c(C(F)(F)F)c2)n1)N1CCC(n2c(=O)[nH]c3ccc(F)c(F)c32)CC1] | Int 5.2 | 5% | 695.05 (M + H)$^+$, 99.83%. | δ 11.24 (br s, 1H), 8.63 (m, 2H), 8.19 (m, 1H), 7.79 (m, 1H), 7.72 (m, 1H), 7.48 (m, 1H), 7.32 (m, 1H), 7.14 (s, 1H), 7.03 (m, 1H), 6.79 (m, 1H), 4.77-4.67 (m, 3H), 3.35 (m, 1H), 2.96 (m, 1H), 2.14 (m, 2H) and 1.89 (m, 2H) |

TABLE 6.18-continued

Tabulated data of the final compounds including the individual yields

| Compound ID | Structure | Amine Intermediate used | Yield (%) | LCMS | ¹H-NMR data (DMSO-d$_6$, 400 MHz), unless otherwise specified |
|---|---|---|---|---|---|
| 328 | 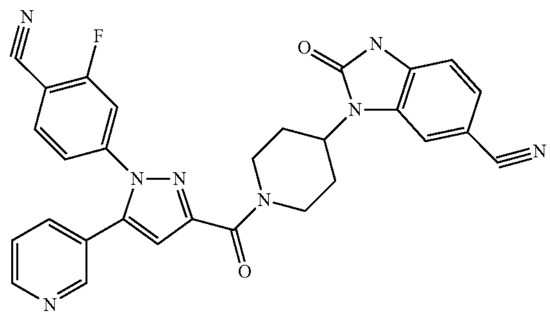 [SMILES: N#Cc1ccc2[nH]c(=O)n(C3CCN(C(=O)c4cc(-c5cccnc5)n(-c5ccc(C#N)c(F)c5)n4)CC3)c2c1] | Int 6.2 | 63% | 533.14 (M + H)⁺ 99.32% | δ 11.60 (br s, 1H), 8.64 (br s, 2H), 7.99-8.03 (m, 1H), 7.84 (s, 1H), 7.77 (d, J = 8.0 Hz, 1H), 7.66-7.69 (m, 1H), 7.43-7.50 (m, 2H), 7.35 (d, J = 8.40 Hz, 1H), 7.18 (s, 1H), 7.13 (d, J = 8.0 Hz, 1H), 4.71-4.85 (m, 2H), 4.54-4.63 (m, 1H), 3.28-3.35 (m, 1H), 2.90-2.96 (m, 1H), 2.32-2.39 (m, 2H) and 1.75-1.86 (m, 2H) |
| 329 | 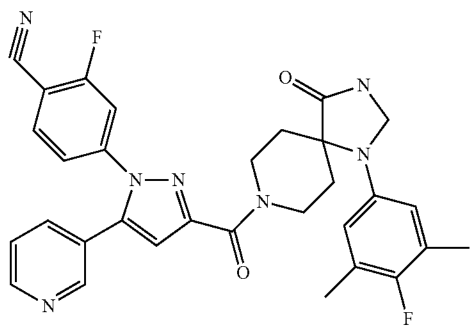 [SMILES: Cc1cc(N2CNC(=O)C23CCN(C(=O)c2cc(-c4cccnc4)n(-c4ccc(C#N)c(F)c4)n2)CC3)cc(C)c1F] | Int 2.2 | 15% | 568.24 (M + H)⁺ 98.81% | δ 8.83 (br s, 1H), 8.60-8.67 (m, 2H), 7.98-8.02 (m, 1H), 7.73 (d, J = 8.0 Hz, 1H), 7.59-7.62 (m, 1lH), 7.44-7.47 (m, 1H), 7.30 (m, 1H), 7.17 (s, 1H), 6.53-6.59 (m, 2H), 4.55 (s, 2H), 4.38 (br s, 2H), 3.48-3.86 (m, 2H), 2.30 (m, 1H), 2.11 (s, 6H), 2.15 (m, 1H) and 1.72-1.80 (m, 2H) |
| 330 | 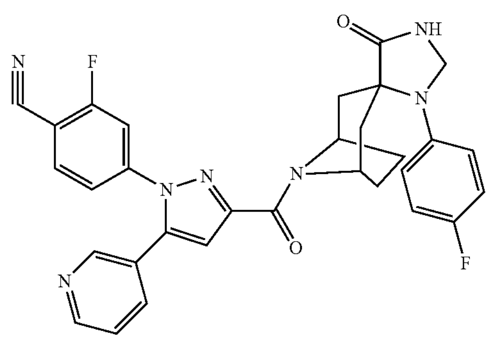 [SMILES: N#Cc1ccc(-n2nc(C(=O)N3C4CCCC3CC3(C4)C(=O)NCN3c3ccc(F)cc3)cc2-c2cccnc2)cc1F] | Int 4.2 | 34% | 566.18 (M + H)+ 97.01% | δ 8.81 (s, 1H), 8.64-8.65 (m, 2H), 7.96-8.0 (m, 1H), 7.76 (d, J = 8.40 Hz, 1H), 7.59-7.61 (m, 1H), 7.47-7.50 (m, 1H), 7.34 (s, 1H), 7.28-7.30 (m, 1H), 6.91-6.95 (m, 2H), 6.72-6.75 (m, 2H), 5.18 (m, 1H), 4.92 (m, 1H), 4.55 (s, 2H), 2.57-2.75 (m, 2H), 2.34-2.38 (m, 2H) and 1.83-1.82 (m, 4H) |
| 331 | 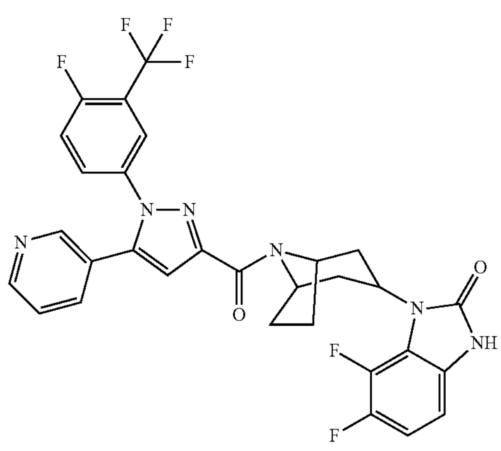 [SMILES: O=C(c1cc(-c2cccnc2)n(-c2ccc(F)c(C(F)(F)F)c2)n1)N1C2CCC1CC(n1c(=O)[nH]c3ccc(F)c(F)c31)C2] | Int 7.2 | 23% | 613.16 (M + H)+ 99.55% | δ 11.30 (br s, 1H), 8.58-8.60 (m, 2H), 7.78-7.82 (m, 2H), 7.70 (d, J = 8.0 Hz, 1H), 7.60-7.65 (m, 1H), 7.41-7.44 (m, 1H), 7.21 (s, 1H), 7.01-7.06 (m, 1H), 6.77-6.79 (m, 1H), 5.31 (t, J = 8 Hz, 1H), 4.87 (t, J = 8.40 Hz, 1H), 4.35-4.42 (m, 1H), 2.50 (m, 2H) and 1.84-2.14 (m, 6H) |

TABLE 6.18-continued

Tabulated data of the final compounds including the individual yields

| Compound ID | Structure | Amine Intermediate used | Yield (%) | LCMS | $^1$H-NMR data (DMSO-$d_6$, 400 MHz), unless otherwise specified |
|---|---|---|---|---|---|
| 332 | (structure) | Int 3.2 | 22% | 651.10 (M + H)+, 99.12% | δ 8.94 (s, 1H), 8.58-8.59 (m, 2H), 7.80-7.81 (m, 1H), 7.56-7.71 (m, 3H), 7.41-7.44 (m, 1H), 7.12 (s, 1H), 6.83 (m, 2H), 4.63 (s, 2H), 4.40-4.50 (m, 2H), 3.77-3.83 (m, 1H), 3.45-3.51 (m, 1H), 2.33-2.59 (m, 2H) and 1.71-1.81 (m, 2H) |
| 333 | (structure) | Int 4.2 | 16% | 609.16 (M + H)+, 99.85% | δ 8.79 (s, 1H), 8.60 (m, 2H), 7.76 (m, 1H), 7.66-7.71 (m, 2H), 7.56-7.61 (m, 1H), 7.41-7.44 (m, 1H), 7.28 (s, 1H), 6.92-6.96 (m, 2H), 6.74-6.77 (m, 2H), 5.16 (m, 1H), 4.92 (m, 1H), 4.54 (s, 2H), 2.49-2.75 (m, 2H), 2.32-2.34 (m, 2H) and 1.79-189 (m, 4H) |

Example 2. Biological Activity of Compounds of the Invention

Since TRPA1 functions as a ligand-gated ion channel which is a relatively non-selective cation channel that is calcium permeable, a cell-based functional assay that measured increases in intracellular calcium ($[Ca^{2+}]_i$) upon activation with agonist ligands was employed to test unknown compounds. A stable HEK293 cell line that expresses human TRPA1 in an inducible manner was employed in this assay. These HEK293 cells were grown in Dulbecco's minimal essential medium containing 4.5 mg/ml glucose supplemented with 10% heat-inactivated fetal bovine serum, 50 units/ml of penicillin, 50 µg/ml of streptomycin, supplemented with 5 µg/ml blasticidin and 50 µg/ml hygromycin B at 37° C. in 95% air 5% $CO_2$. The expression of TRPA1 was induced by including 1 µg/ml doxycycline in the culture medium. For the induced cells, ruthenium red (5 µM) was also added to minimize the constitutive TRPA1 channel activity and cells were used 14-18 hrs after induction. To measure $[Ca^{2+}]_i$ changes, cells were seeded in wells of 96-well plates at ~100,000 cells/well and grown for 14-18 hrs to reach confluency. To prevent cell loss from subsequent washing, the wells were treated with 20 µg/ml polyornithine (MW>30,000, Sigma, St Louis, Mo.) for >15 min and rinsed once with Hank's balanced salt solution without $Mg^{2+}$ and $Ca^{2+}$. To load the $Ca^{2+}$ indicator dye, cells were washed once with an extracellular solution (ECS) containing 140 mM NaCl, 5 mM KCl, 1 mM $MgCl_2$, 1.8 mM $CaCl_2$, 10 mM glucose, and 15 mM HEPES, pH 7.4 and then incubated in 50 µL ECS supplemented with 2 µM Fluo4-AM and 0.05% Pluronic F-127 at 37° C. for 60 min. In some experiments, Fluo-8-AM was used instead of Fluo-4-AM as the calcium-sensitive fluorescent probe. Probenecid (2 mM) was included in all solutions to prevent the leakage of Fluo-4 or Fluo-8 from the cells. At the end of the incubation, cells were washed three times with ECS and placed in 80 µL of the same solution. Fluorescence changes were measured using a fluid handling integrated fluorescence plate reader, FlexStation (Molecular Devices, Sunnyvale, Calif.). Stock solutions of test compounds were initially solubilized in 100% DMSO and then serially diluted to achieve the desired final concentration. The final concentration of DMSO in the assay did not exceed 0.3% (v/v). Drugs were diluted into ECS at 2× or 3× the desired final concentrations and delivered to the sample plate by an integrated robotic 8-channel pipettor at preprogrammed time points. The Fluo-4 or Fluo-8 fluorescence was read using the excitation wavelength of 494 nm and emission wavelength of 525 nm from the bottom of the plate at 0.67 Hz. Experiments were performed at 20-25° C. For certain experiments, 0.1% BSA was included with the cells and test compounds.

The kinetic data obtained at each test concentration of drug represents a series of fluorescent intensities as a function of time. Data were transferred from the Softmax Pro software to construct concentration-response curves for each active compound and curve fitting using the logistic equation (Prism, Graphpad, San Diego, Calif.) was used to obtain inhibition constants for antagonists ($IC_{50}$s) or activation constants for agonist ligands ($EC_{50}$s).

Using a sequential addition protocol, test compounds were initially applied to the cells loaded with Fluo-4 or Fluo-8 and fluorescence changes in each well monitored for 2.5 min. The plate was read again in a kinetic mode after a 15-30 min incubation with the test compounds after obtaining baseline values (about 30 s) and subsequent addition of challenge with a reference TRPA1 agonist. Reference TRPA1 agonists in testing each compound included at least one of flufenamic acid (FFA), allyl isothiocyanate (AITC) and 4-hydroxynonenal (4-HNE). Compounds that demonstrated antagonist activity showed a concentration dependent reduction in initial rate and/or reduction in the magnitude of activity stimulated by the reference agonist.

Antagonist activity can be expressed in terms of $IC_{50}$ with respect to TRPA1 and agonist activity can be expressed in terms of $EC_{50}$ with respect to TRPA1. Results for the TRPA1 modulatory activity of the disclosed compounds are found below in Table 7; the $IC_{50}$ values shown in Table 7 were determined from data collected during the time period initiated by addition of the reference TRPA1 agonist to the mixture containing TRPA1 and the test compound. For each compound, the activity is classified as A, B or C wherein A is an $IC_{50}$ of 0.001-5 µM; B is an $IC_{50}$ of 5-25 µM; and C is an $IC_{50}$ of >25 µM. One of skill in the art will appreciate that other analytical techniques (e.g., patch clamp experiments as described below) can be used to characterize compound activity, and that the $IC_{50}$ or the $EC_{50}$ value observed for a particular compound can vary depending on the technique employed

TABLE 7

TRPA1 modulatory activity of compounds of the disclosure.

| Cpd # | human TRPA1-HEK Activity |
|---|---|
| 6 | C |
| 31 | C |
| 4 | C |
| 12 | C |
| 16 | B |
| 25 | C |
| 28 | C |
| 13 | C |
| 18 | C |
| 29 | C |
| 30 | C |
| 8 | B |
| 143 | B |
| 144 | B |
| 145 | B |
| 146 | B |
| 147 | C |
| 148 | C |
| 152 | C |
| 153 | C |
| 154 | C |
| 155 | C |
| 156 | C |
| 157 | C |
| 158 | B |
| 159 | B |
| 160 | C |
| 161 | B |
| 162 | B |
| 163 | B |
| 164 | B |
| 165 | C |
| 166 | C |
| 170 | C |
| 171 | C |
| 172 | C |
| 174 | C |
| 149 | B |
| 150 | B |
| 151 | C |
| 167 | B |
| 168 | B |
| 169 | C |
| 173 | C |
| 54 | C |
| 55 | A |
| 56 | C |
| 57 | C |
| 58 | C |
| 61 | C |
| 62 | C |
| 63 | C |
| 66 | C |
| 67 | C |
| 68 | C |
| 71 | C |
| 74 | C |
| 75 | C |
| 76 | C |
| 79 | C |
| 80 | C |
| 83 | C |
| 84 | C |
| 85 | C |
| 60 | B |
| 65 | C |
| 70 | B |
| 72 | B |
| 73 | C |
| 77 | A |
| 78 | C |
| 82 | C |
| 87 | C |
| 88 | B |
| 89 | C |
| 90 | C |
| 92 | C |
| 93 | C |
| 94 | C |
| 95 | C |
| 96 | C |
| 98 | B |
| 100 | C |
| 101 | C |
| 105 | C |
| 106 | C |
| 107 | C |
| 97 | C |
| 99 | A |
| 102 | C |
| 103 | C |
| 104 | C |
| 108 | C |
| 109 | C |
| 110 | C |
| 111 | C |
| 114 | C |
| 119 | C |
| 120 | B |
| 121 | C |
| 122 | C |
| 123 | C |
| 124 | C |
| 125 | C |
| 126 | C |
| 127 | C |
| 128 | C |
| 129 | C |
| 130 | B |
| 131 | C |
| 132 | C |
| 135 | C |
| 136 | B |
| 137 | C |
| 138 | C |
| 139 | C |
| 140 | B |
| 141 | B |
| 142 | C |

TABLE 7-continued

TRPA1 modulatory activity of compounds of the disclosure.

| Cpd # | human TRPA1-HEK Activity |
|---|---|
| 69 | C |
| 91 | C |
| 112 | C |
| 113 | C |
| 115 | C |
| 116 | C |
| 117 | C |
| 118 | C |
| 133 | C |
| 134 | C |
| 177 | A |
| 178 | B |
| 175 | A |
| 176 | B |
| 49 | A |
| 45 | C |
| 52 | C |
| 32 | C |
| 33 | C |
| 34 | C |
| 35 | C |
| 37 | C |
| 38 | B |
| 39 | C |
| 40 | C |
| 179 | C |
| 180 | A |
| 264 | B |
| 259 | B |
| 260 | A |
| 262 | B |
| 198 | A |
| 252 | B |
| 253 | A |
| 256 | C |
| 267 | B |
| 268 | A |
| 266 | A |
| 263 | C |
| 181 | A |
| 254 | A |
| 255 | A |
| 258 | C |
| 261 | A |
| 257 | C |
| 265 | A |
| 182 | A |
| 199 | A |
| 212 | A |
| 213 | A |
| 218 | A |
| 219 | A |
| 220 | A |
| 189 | A |
| 185 | B |
| 202 | A |
| 217 | A |
| 184 | C |
| 201 | A |
| 214 | A |
| 215 | A |
| 183 | C |
| 186 | A |
| 187 | A |
| 200 | A |
| 190 | A |
| 188 | A |
| 191 | A |
| 192 | A |
| 193 | A |
| 205 | A |
| 216 | A |
| 196 | A |
| 206 | B |
| 210 | A |
| 211 | A |
| 194 | B |
| 195 | A |
| 204 | A |
| 221 | A |
| 197 | B |
| 209 | C |
| 203 | C |
| 208 | A |
| 222 | A |
| 223 | A |
| 224 | A |
| 207 | C |
| 75-b | A |
| 75-a | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | C |
| 244 | B |
| 245 | C |
| 246 | A |
| 247 | C |
| 248 | A |
| 249 | A |
| 250 | C |
| 280 | A |
| 281 | A |
| 282 | A |
| 283 | B |
| 284 | A |
| 272 | A |
| 273 | A |
| 274 | A |
| 285 | A |
| 286 | A |
| 278 | A |
| 289 | A |
| 290 | A |
| 291 | A |
| 292 | B |
| 295 | A |
| 296 | A |
| 293 | A |
| 301 | A |
| 297 | A |
| 294 | A |
| 298 | A |
| 305 | A |
| 306 | A |
| 328 | A |
| 324 | A |
| 322 | A |
| 323 | A |
| 331 | A |
| 325 | A |
| 317 | A |
| 320 | A |
| 321 | A |
| 329 | A |
| 330 | A |
| 333 | A |

TABLE 7-continued

TRPA1 modulatory activity of compounds of the disclosure.

| Cpd # | human TRPA1-HEK Activity |
|---|---|
| 318 | A |
| 319 | A |
| 326 | A |
| 327 | A |
| 332 | A |
| 313 | A |
| 314 | A |
| 315 | A |
| 316 | A |

Example 3. Electrophysiological Testing of Compounds of the Invention

Whole-cell patch clamp experiments permit the detection of currents through the TRPA1 channel in the cell line described above. A glass electrode is brought into contact with a single cell and the membrane is then ruptured, permitting control of the voltage of the cell membrane and measurement of currents flowing across the membrane using an amplifier attached to the electrode. A perfusion system permits control of the extracellular solution, including the rapid addition of TRPA1 agonists and antagonists that either induce or inhibit the current, respectively. The TRPA1 specific current is activated by application of a known agonist, selected from a group which consists of flufenamic acid, allyl isothiocyanate (AITC), or 15-deoxy-PGJ2 prostaglandin at the appropriate concentration to the solution. To determine the activity of compounds of the present invention, a compound is added before the addition of an agonist to determine the effects of pre-incubation on TRPA1 activity or alternatively the compound is added simultaneously with the agonist to determine the effects of simultaneous addition on TRPA1 activity. Alternatively, an agonist may be added first to activate TRPA1 and a test compound of the present invention added at a time interval and for a desired duration thereafter to determine the effect of the test compound on the TRPA1 response.

HEK293 cells expressing human TRPA1 are seeded on polyornithine-treated glass coverslips one day before patching. Recording pipettes are pulled from micropipette glass (World Precision Instruments Inc, Sarasota, Fla.) to 2-4 MΩ when filled with a pipette solution containing (in mM): 117 CsCl, 9 EGTA, 1.8 $MgCl_2$, 14 Tris-creatine phosphate, 4 Mg-ATP, 0.3 Tris-GTP, 9 HEPES, pH 7.4 and placed in the bath solution containing (in mM): 150 NaCl, 4 KCl, 2 $CaCl_2$, 2 $MgCl_2$, 10 glucose, 10 HEPES, pH 7.4. Isolated cells are voltage-clamped in the whole-cell mode using an EPC10 amplifier with data collected at a sampling rate of 5 kHz using an analog-to-digital converter under the control of PatchMaster (HEKA Instruments). Voltage ramps of 100 ms of −100 mV to +100 mV from the holding potential of −60 mV are applied every 0.5 s. The patched cell is continuously superfused by the bath solution through an 8-channel Smart-Squirt perfusion system (AutoMate Scientific, Inc., Berkeley, Calif., USA). Compounds are diluted in the final concentration and applied for 10-40 sec as desired. For either kinetic or concentration-response studies, the application of reference agonist is 10 sec and the maximal current densities at −100 and +100 mV are used for calculations. All recordings are performed at room temperature (~23° C.).

Example 4. Compound Activity in Freund's Complete Adjuvant Hyperalgesia Model

The efficacy of compounds of the disclosure in reducing or alleviating inflammatory pain is tested using an established animal model for testing potential analgesic activity of compounds that is widely known as the Freund's Complete Adjuvant (CFA) model of hyperalgesia. The CFA model is a well-established acute inflammatory pain model widely used by the pharmaceutical industry to evaluate the analgesic activity of compounds including TRPA1 antagonists (Eid, S R, et al. (2008) "HC-030031, a TRPA1 selective antagonist attenuates inflammatory- and neuropathy-induced mechanical hypersensitivity." Mol Pain 4:48-58.)

Testing employs the Randell-Selitto test or paw pressure test which is a technique for the measurement of the pain response in animals. For this inflammatory pain model, rats are injected with 200 µl of Complete Freund's Adjuvant (CFA), 1:1 in saline intraplantarly into their left paw (Colpaert, 1987). Animals are tested for hyperalgesia 3 days after CFA administration, using withdrawal threshold to paw pressure (Randal-Selitto test). To investigate whether the anti-hyperalgesic effect of the test compound are observed upon repeated dosing, the compound is administered for 3 days at a range of doses which include 0.3, 1, 3, 10 and 30 mg/kg by either oral or i.p. administration each day. Reversal of mechanical hyperalgesia is assessed at the time corresponding to the peak plasma levels of each drug (determined in separate pharmacokinetic experiments) after oral or i.p. dosing for the test compound (1-7 hrs) post-dose on day 1, 2 and 3. Either naproxen, indomethacin, and diclofenac (3-30 mg/kg PO) can be included as a positive control test agent. Compounds of the disclosure which have efficacy in this model diminish pain responses compared to responses in the absence of the compound.

Example 5. Compound Activity in Spinal Nerve Ligation Neuropathic Pain Model

This example describes the use of an animal model for testing compounds of the disclosure for their ability to reduce neuropathic pain. For the neuropathic pain model (spinal nerve ligation, SNL) also known as the Chung model, rats are anesthetized with isoflurane and placed on a heating pad. Using aseptic techniques, the L5 and L6 spinal nerves are exposed, ligated and transected (Kim, S. H. and Chung, J. M, (1992), Pain, 50 (3): 355-363). Muscle and skin are closed with 4-0 Polydiaxone and wound clips, respectively. Allodynia is assessed 2-4 weeks post SNL surgery and only rats that develop allodynia as defined by a significant decrease in their mechanical threshold using von Frey filaments are used. Tactile allodynia is assessed with calibrated von Frey filaments (Stoelting Co, Wood Dale, Ill.), using an up-down paradigm (Chaplan, S. R., et al. (1994) J. Neurosci. Methods, 53 (1): 55-63). Pregabalin (3-30 mg/kg PO) or gabapentin (50-100 mg/kg PO or 100-150 mg I.P) is included as a positive control.

Test compounds are administered to the surgically treated rats either orally or I.P, and pain measurements are assessed at post-dosing intervals that correspond to near-maximal peak plasma concentrations for the test compound and specific mode of administration.

Figure 2:
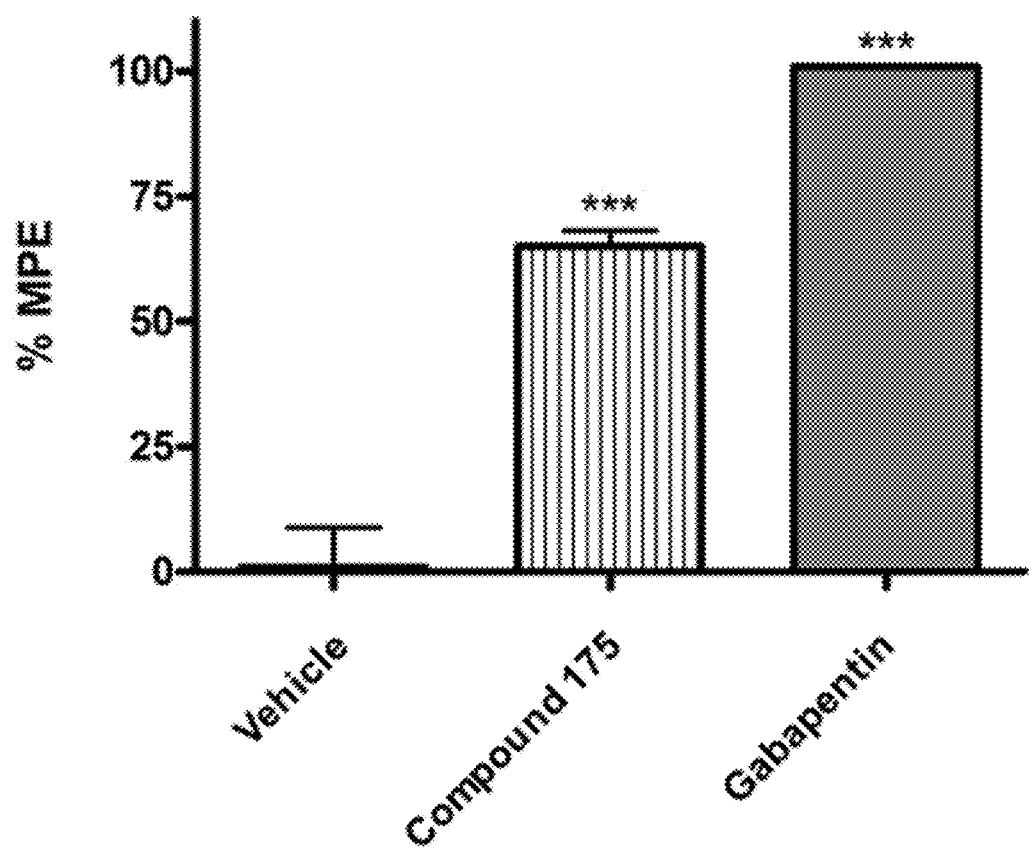
FIG. 2 shows the percentage of maximal possible effect (% MPE) of a compound of the invention in reducing neuropathic pain, as observed in rats treated with the compound after spinal nerve ligation.

The action of test compounds 175, 180, and 198 was evaluated in the Chung model after surgery to induce neuropathy. Test compounds were administered to the surgically treated rats 18 days after L5-L6 spinal nerve injury at 30 mg/kg i.p (10 ml/kg). Gabapentin at 150 mg/kg i.p. (10 ml/kg) was administered as a positive control group. Vehicle and test compounds were dissolved in 10% DMSO, 20% Tween-80 and 40% PEG-400. On the day before treatment, the neuropathic pain basal response was measured by von Frey test and the rats were randomized based on PWT responses. A cut-off of <4.0 g was considered before selection of animals for treatment. On the day of treatment, the test compounds were administered at 30 mg/kg i.p. (10 ml/kg) dissolved in 10% DMSO, 20% Tween-80, 40% PEG-400. Additional test groups included vehicle control and gabapentin at 150 mg/kg i.p. (10 ml/kg). The mechanical allodynia was measured at 2 hrs post-dose. Results for compound 175 are shown in FIGS. 1 and 2 where data are presented as paw withdrawal threshold (PWT in g) (FIG. 1) and percentage of maximal possible effect (% MPE) (FIG. 2). Each bar represents the mean±SEM of 8 rats. The test compounds demonstrated significant anti-allodynic effect on paw withdrawal threshold and % MPE (p<0.001). Statistical analysis was completed using one-way ANOVA followed by Dunnett's post-test. % MPE values exhibited by the test compounds are set forth in Table 8.

TABLE 8

Efficacy of Algomedix Compounds in the Spinal Nerve Ligation Model of Neuropathic Pain

| Compound No. | Dose | % MPE |
|---|---|---|
| 175 | 30 mg/kg, i.p | 59 ± 10 (3) |
| 180 | 30 mg/kg, i.p. | 65 (1) |
| 198 | 30 mg/kg, i.p. | 41 (1) |

% MPE = % Maximum Possible Effect
( ) number of experiments

The test compounds inhibited allodynia and hyperalgesia while the vehicle administered group did not show any improvement. Statistical analysis showed the differences between the vehicle and test compound group to be highly significant. From these results, the test compounds showed a high level of effectiveness (41-65% of maximal possible effect) for reducing neuropathic pain.

Example 6. Compound Activity in Incisional Pain Model

The effects of compounds of the disclosure on post-surgical pain are assessed using an incisional pain model, as described previously by Brennan et al. (1996). In the incisional pain model, Sprague-Dawley rats (weighing 200-300 g) undergo surgery by having a 1 cm longitudinal incision made through skin and fascia of the plantar aspect of the paw. Unoperated rats serve as controls. Hind paw withdrawal thresholds (PWTs) to a noxious mechanical stimulus are determined using an analgesimeter. Withdrawal responses to punctuate mechanical stimulation are determined by using calibrated von Frey filaments. Cut-off is set at 250 g and the endpoint is taken as complete paw withdrawal. Twenty-four hours following plantar incision, pre-drug PWTs are measured, and the rats (9-20/group) receive a single dose of 3, 10 or 30 mg/kg p.o. or i.p. the test compound, 30 mg/kg p.o. celecoxib as a positive control, or vehicle. PWTs are determined again at multiple intervals (eg. at 1, 3, 5 and 24 hours) postdrug administration. The percent reversal of hyperalgesia for each animal is calculated by (Postdose threshold−predose threshold)/(Baseline threshold−predose threshold)×100.

Example 7. Compound Activity in Iodoacetate Osteoarthritic Pain Model

An established animal model of osteoarthritis related pain has been termed the iodoacetate model since it is based upon the progressive joint destruction which occurs after injection of iodoacetate into the articular space of the knee of the rat (Marker and Pomonis, 2012). Pain related behaviors that can be measured include both hind limb weight bearing and primary mechanical hyperalgesia. In the rat model of osteoarthritis, iodoacetate (IOA, 2 mg/25 µL per rat in pH 7.4 saline) is administered under brief isoflurane anesthesia into the rat left knee joint and hypersensitivity to von Frey filaments and changes in weight bearing is assessed 6 weeks post-IOA administration. Rats receive a single dose of 1, 3, 10 or 30 mg/kg p.o. or i.p. of the test compound administered prior to testing at an interval determined by the time required to reach peak plasma levels for the individual test agent. Percent reversal of hypersensitivity is calculated as: (post-drug−post-IOA injection)/(pre-IOA injection−post-IOA injection)×100, where 100% is equivalent to complete reversibility.

Example 8. Compound Activity in Formalin Nociceptive Pain Model

The formalin model is widely used for evaluating the effects of analgesic compounds in laboratory animals. It is a useful model for nociceptive pain. In this test, a dilute (0.5-5%) formalin solution (in which formaldehyde is the active ingredient) is injected into the paw of a rodent, and pain-related behaviors are assessed over two temporally distinct phases, including an initial robust phase in which paw lifting, licking, and flinching are scored during the first 10 min, followed by a transient decline in these behaviors and a subsequent second phase of behavior lasting 30-60 min.

For the formalin-induced model, mice or rats are administered with formalin and/or one of the disclosed compounds. Test compounds are either injected intradermally, delivered orally or by i.p. administration 30-120 min prior to formalin injection. Formalin is then injected (50 µl of 2.5% formalin, diluted in saline) into the dorsal surface of the right hind paw of the rat, and the animal is put into a chamber of an apparatus where movement of the formalin-injected paw is recorded. The number of paw flinches or paw licking and biting is tallied by minute over the next 60 min. In some analyses of collected data, the 60 minute observation period is subdivided into various phases.

Example 9. Compound Activity in Chronic Constriction Injury Neuropathic Pain Model The rat chronic constriction injury (CCI) model of neuropathic pain developed by Bennett and Xie (1988) is a neuropathic pain model widely used to assess analgesic activity of test compounds. Subsequent to ligation of the sciatic nerve, eventual damage of peripheral nerves occurs in part due to production of several inflammatory mediators (e.g., proinflammatory cytokines and chemokines) which contribute to generation and maintenance of neuropathic pain.

The surgery protocol used for generating CCI rats is described by Bennett and Xie (Bennett, G J, Xie, Y K (1988) *Pain* 33(1): 87-107.). In brief, male Sprague-Dawley rats (175-250 g) are anesthetized, the middle third of the right sciatic nerve is exposed through a 1.5 cm longitudinal incision and three ligatures (5-0 chromic Catgut) are tied loosely around the sciatic nerve proximal to the sciatic trifurcation. Incisions are then sutured and closed, rats are administered antibiotic and general health is evaluated daily during the recovery. Two weeks post-nerve ligation, basal mechanical allodynia is measured as described for the rat Chung model and CCI rats using paw withdrawal thresholds (PWT)<4 g to qualify rats for inclusion in the study (Kim, S H, Chung, J M (1992). *Pain* 50(3): 355-363; Chaplin, S R, et al. (1994) *J Neurosci Methods* 53(1): 55-63).

On the following day, compounds of the invention are solubilized in a pre-validated vehicle and administered at doses of 1, 3, 10 and 30 mg/kg (oral or i.p.) and PWTs are measured during a period corresponding to peak plasma levels of the compound. Each experimental group consists of 8 rats. Gabapentin is used as a positive control group and the experimenter recording behavior is blinded to the treatment groups. The 50% PWT and % maximal possible effect data are analyzed using one-way ANOVA followed by the Dunnett post-test using Prism (Graphpad).

Example 10. Compound Activity in Streptozotocin Diabetic Neuropathic Pain Model

Diabetes related damage to sensory nerves (diabetic neuropathy) is a common complication of Type 1 and Type 2 diabetes and people with this neuropathy suffer from chronic pain. The injection of streptozotocin (STZ) into rats is a commonly used chemical method to induce a diabetic condition leading to diabetic neuropathic pain. The STZ neuropathic pain model is commonly used to evaluate the efficacy of anaglesic compounds, including TRPA1 antagonists (Courteix, C, et al. (1994) *Pain* 57(2): 153-160; Wei, H, et al. (2009) *Anesthesiology* 111: 147-154.) After STZ administration, hyperglycemia and hypoinsulinemia appear and persist due to irreversible toxicity.

The efficacy of compounds of the invention for inhibiting or reducing diabetic neuropathic pain and reducing pain hypersensitivity are determined in this model using the following established procedure. In brief, male Sprague-Dawley rats (175-200) grams are administered STZ (45 mg/kg i.v. in 0.1M citrate buffer) into the dorsal tail vein and, hyperglycemia is confirmed by measuring glucose levels 3, 10 and 17 days after STZ administration. Mechanical allodynia generally appears three weeks post injection of STZ and lasts for approximately seven weeks. On day 17 after STZ administration, basal mechanical allodynia is measured as described for the rat SNL model and rats displaying 50% PWT values of <5 g qualify for the investigation. The next day, compounds of the invention are solubilized in pre-validated vehicle and administered at doses of 1, 3, 10 and 30 mg/kg (oral or i.p.) to qualified rats. Mechanical allodynia is measured as described for the Chung model at time corresponding to the period when peak plasma levels for the study compound are observed. Each experimental group will include eight rats and tramadol (30 mg/kg, i.p.) will be used as a positive control. The 50% PWT and % MPE data are analyzed using one-way ANOVA and post-hoc Dunnett's test using the computer program, Prism (Graphpad).

Example 11. Compound Activity in Chemotherapy-Induced Neuropathic Pain Model

Chemotherapy-induced peripheral neuropathy is one of the most serious complications of anti-cancer drug therapy. For example, agents which include paclitaxel (Taxol) or oxaliplatin which are most effective and frequently used chemotherapeutics produce peripheral neurotoxicity with patients reporting neuropathic pain during and often persisting after chemotherapeutic treatment. The TRPA1 antagonist, AD_09, has been reported to reduce neuropathic pain in the oxaliplatin model (Nativi, C, et al. (2013) *Scientific Reports* 3, 2005, 1-10.)

The studies described below provide a method to test compounds of the present invention in the established rat model of paclitaxel-induced neuropathic pain (Flatters, S J and Bennett, G, *Pain* (2004) 109:150-161) and provide evidence for efficacy for one compound of the present invention. In this procedure, male Sprague-Dawley rats received i.p. injections of 1 mg/kg paclitaxel or vehicle solution every other day for a total of 4 injections (Day 0, 2, 4 and 6). After receiving injections on even-number experimental days, the rats were tested for mechanical and cold allodynia on odd-number experimental days. After the full development of allodynia after the last paclitaxel injection on day 11, one subgroup of the rats (7 rats per treatment group) received an oral dose or i.p. injection of compound of the present invention (e.g., 1, 3, 10 or 30 mg/kg) or its vehicle solution. On the day of treatment, the test compound was administered at 10 mg/kg i.p. (2 ml/kg) dissolved in 10% DMSO, 20% Tween-80, 40% PEG-400. Additional test groups included vehicle control and gabapentin at 10, 30 and 100 mg/kg i.p. (2 ml/kg). The mechanical allodynia was measured at 2 hrs post-dose for compound 271. Mechanical allodynia was measured using the Von Frey filaments to determine the paw withdrawal threshold for each animal and assess the effects of the test compound-s to reduce pain. Rats were tested for mechanical and/or cold allodynia 1 hour after dosing.

Rats can be tested at approximately 2 hour intervals thereafter (time interval dependent on the effect) as long as the effect of TRPA1 antagonist lasts. In some cases, more than one treatment of the compound of the present invention (TRPA1 antagonist) can be given before or after the effect of the previous dose subsides to provide repetitive dosing regimens.

The test compound #271 demonstrated significant anti-allodynic effect on paw withdrawal threshold and demonstrated a 49.1% MPE for reversing paclitaxel induced neuropathic pain. One-way ANOVA followed by Dunnet's post-test was used for statistical analysis of the data for Compound #271 and percentage change in the maximal possible effect was significant at the p<0.05. The magnitude of the effect on neuropathic pain in this model was greater than the gabapentin at the same dose, 34.8% MPE, at 10 mg/kg.

All publications and patent applications cited in this specification are herein incorporated by reference as if each individual publication or patent application were specifically and individually indicated to be incorporated by reference.

Although the foregoing has been described in some detail by way of illustration and example for purposes of clarity of understanding, it will be readily apparent to one of ordinary skill in the art in light of the disclosed teachings that certain changes and modifications may be made thereto without departing from the spirit or scope of the disclosure.

The invention claimed is:

1. A compound having the following formula,

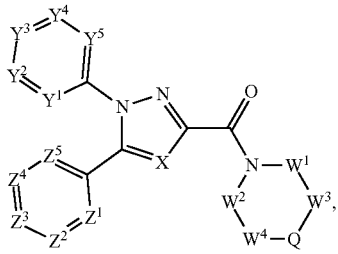

or a pharmaceutically acceptable salt thereof, or an isotopic variant thereof, wherein:

$Z^1$, $Z^2$, $Z^3$, $Z^4$, and $Z^5$ are each independently selected from the group consisting of N, CH, and $CR^a$;

or $Z^1$ and X, together with atoms in the rings to which they are attached, form an additional fused, five- to eight-membered cycloalkyl or heterocyclyl ring with from 0 to 4 $R^z$ substituents;

wherein at least one of $Z^2$, $Z^3$, and $Z^4$ is N wherein 0, 1, or 2 of $Z^2$, $Z^3$, and $Z^4$ is N;

$Y^1$, $Y^2$, $Y^3$, $Y^4$, and $Y^5$ are each independently selected from the group consisting of N, CH, and $CR^b$; wherein 0, 1, or 2 of $Y^1$, $Y^2$, $Y^3$, $Y^4$, and $Y^5$ is N each $R^a$ and $R^b$ is independently selected from the group consisting of cyano, carboxyl, $C_1$-$C_4$ alkyl, $C_1$-$C_4$ hydroxyalkyl, $C_3$-$C_8$ cycloalkyl, $C_1$-$C_4$ alkoxy, $C_1$-$C_4$ haloalkyl, $C_1$-$C_4$ haloalkoxy, halo, amino, $C_1$-$C_6$ alkylamino, $C_1$-$C_6$ amido, $C_1$-$C_4$ alkyloxycarbonyl, $C_1$-$C_6$ alkylsulfonyl, and hydroxyl; or, alternatively, two adjacent $R^a$ or two adjacent $R^b$, together with the atoms to which they are attached, form an additional fused aryl, heteroaryl, cycloalkyl, or heterocyclyl ring with from 0 to 4 $R^z$ substituents;

each $R^z$ is independently selected from the group consisting of halo, $C_1$-$C_3$ alkyl, $C_1$-$C_3$ haloalkyl, and $C_1$-$C_3$ alkoxy;

X is N or $CR^d$;

$R^d$ is selected from the group consisting of hydrogen, halo, cyano, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, and $C_3$-$C_6$ cycloalkoxy;

$W^1$, $W^2$, $W^3$, and $W^4$ are each $C(R^f)_2$;

each $R^f$ is independently selected from the group consisting of hydrogen, $C_1$-$C_3$ alkyl, $C_1$-$C_3$ fluoroalkyl, and halo;

or two axial $R_f$ substituents of a pair of $W^n$ selected from the group consisting of ($W^1$ and $W^2$), ($W^2$ and $W^3$), and ($W^3$ and $W^4$) join to form a —$(C(R^z)_2)_t$— bridge or a —$(CH_2)_t$— bridge;

t is an integer selected from 2 and 3;

Q is selected from the group consisting of $C(R^e)(D)$, F, and G;

$R^e$ is selected from the group consisting of hydrogen, $C_1$-$C_3$ alkyl, and $C_1$-$C_3$ fluoroalkyl;

D is a bicyclic group of Formula Id,

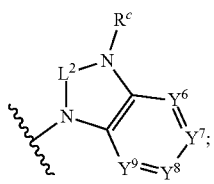

F is a spirocyclic group of Formula If,

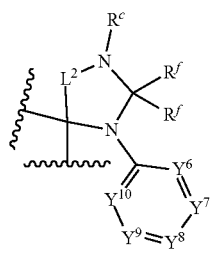 or 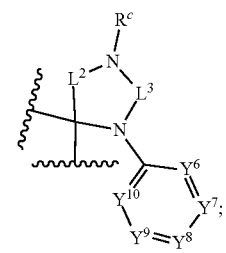

G is a bicyclic spirocyclic group of Formula Ig,

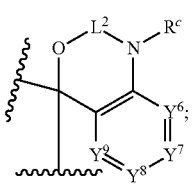

$L^2$ and $L^3$ are each independently selected from C=O and C=S;

$Y^6$, $Y^7$, $Y^8$, $Y^9$, and $Y^{10}$ are each independently selected from the group consisting of N, CH, and $CR^b$; wherein 0, 1, or 2 of $Y^6$, $Y^7$, $Y^8$, $Y^9$ and $Y^{10}$ is N and $R^c$ is selected from the group consisting of hydrogen, $C_1$-$C_4$ alkyl, $C_1$-$C_4$ haloalkyl, $C_3$-$C_6$ cycloalkyl, ($C_3$-$C_6$ cycloalkyl)$C_1$-$C_3$ alkyl, and $C_1$-$C_7$ acyl.

2. The compound of claim 1, or a pharmaceutically acceptable salt thereof, or an isotopic variant thereof, wherein:

each $R^f$ is independently selected from the group consisting of hydrogen, $C_1$-$C_3$ alkyl, $C_1$-$C_3$ fluoroalkyl, and halo.

3. The compound of claim 2, or a pharmaceutically acceptable salt thereof, or an isotopic variant thereof, wherein:

each $R^f$ is independently selected from the group consisting of hydrogen and $C_1$-$C_3$ alkyl.

4. The compound of claim 1, or a pharmaceutically acceptable salt thereof, or an isotopic variant thereof, wherein:

X is $CR^d$; and $R^d$ is selected from the group consisting of hydrogen, halo, and $C_1$-$C_4$ alkyl.

5. The compound of claim 1, or a pharmaceutically acceptable salt thereof, or an isotopic variant thereof, wherein:

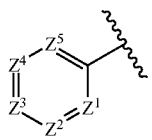

is a cyclic group selected from

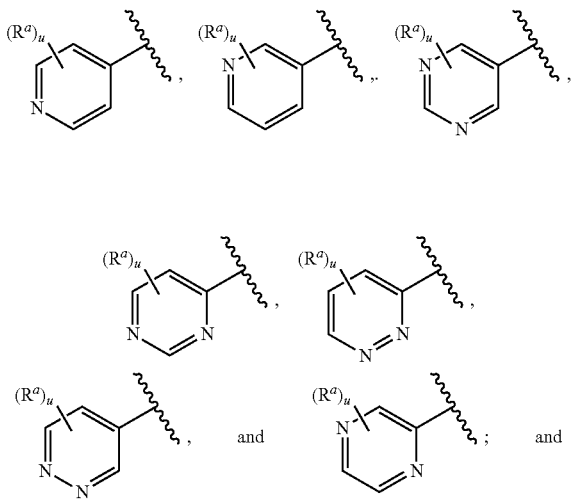

u is an integer from 0 to 4.

6. The compound of claim 5, or a pharmaceutically acceptable salt thereof, or an isotopic variant thereof, wherein:

each $R^a$ is independently selected from the group consisting of cyano, $C_1$-$C_4$ alkyl, $C_1$-$C_4$ alkoxy, $C_1$-$C_4$ haloalkyl, $C_1$-$C_4$ haloalkoxy, halo, $C_1$-$C_6$ amido, and hydroxyl.

7. The compound of claim 5, or a pharmaceutically acceptable salt thereof, or an isotopic variant thereof, wherein:

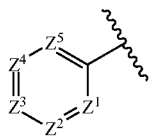

is a cyclic group selected from

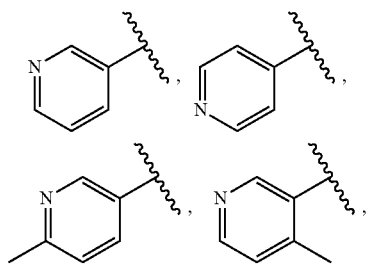

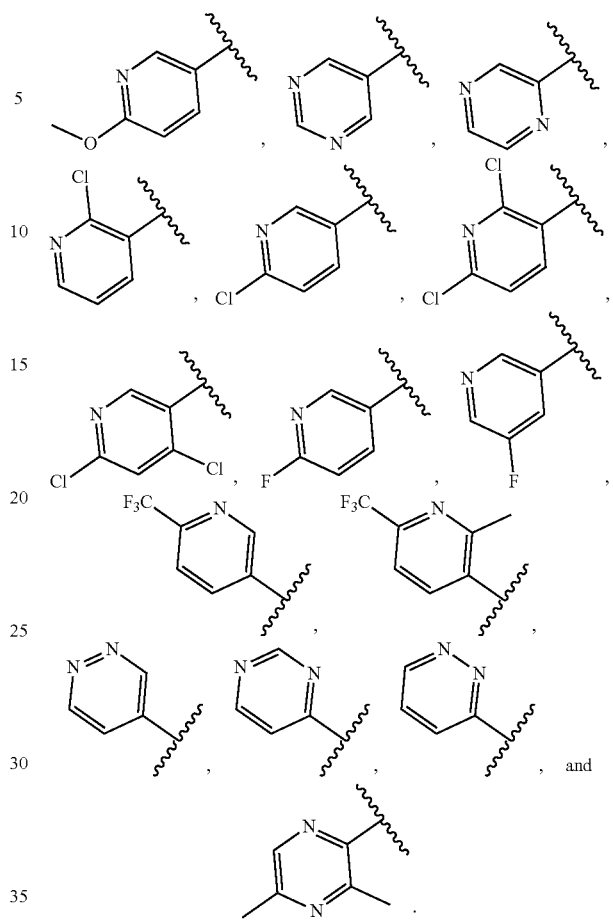

8. The compound of claim 1, or a pharmaceutically acceptable salt thereof, or an isotopic variant thereof, wherein:

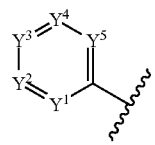

is a cyclic group selected from

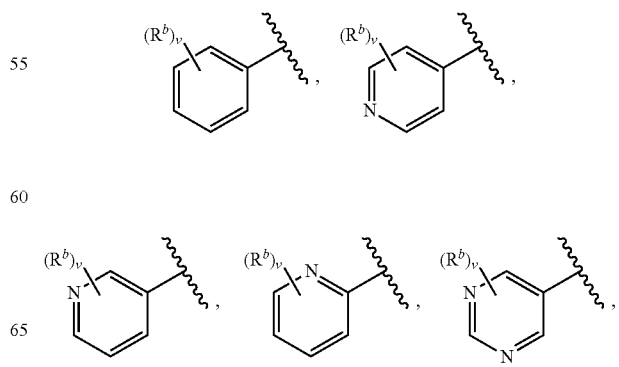

-continued

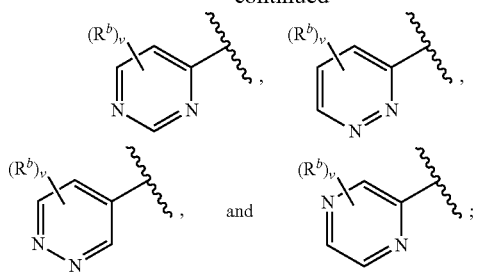

v is an integer from 0 to 5.

9. The compound of claim 8, or a pharmaceutically acceptable salt thereof, or an isotopic variant thereof, wherein:

each $R^b$ is independently selected from the group consisting of cyano, $C_1$-$C_4$ alkyl, $C_1$-$C_4$ alkoxy, $C_1$-$C_4$ haloalkyl, $C_1$-$C_4$ haloalkoxy, halo, $C_1$-$C_6$ alkylamino, amino, $C_1$-$C_6$ amido, and hydroxyl.

10. The compound of claim 8, or a pharmaceutically acceptable salt thereof, or an isotopic variant thereof, wherein:

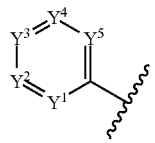

is a cyclic group selected from

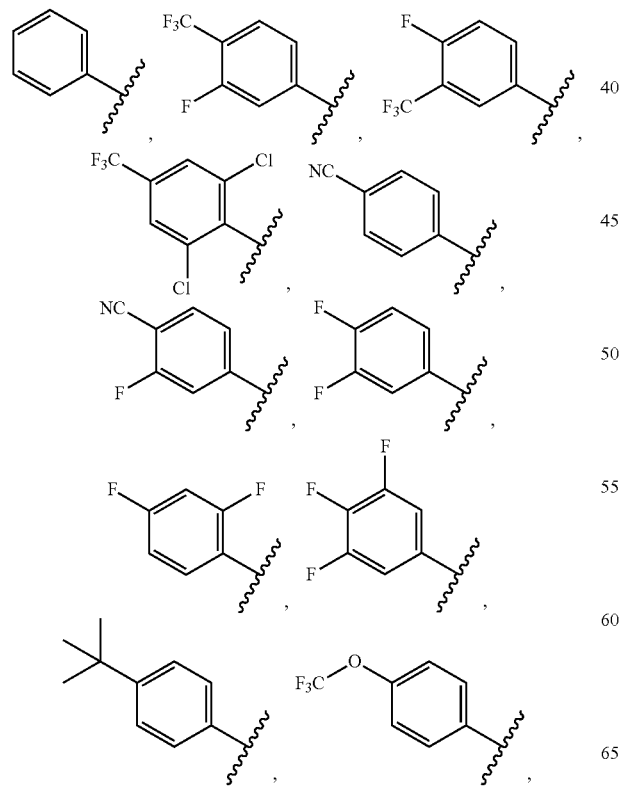

-continued

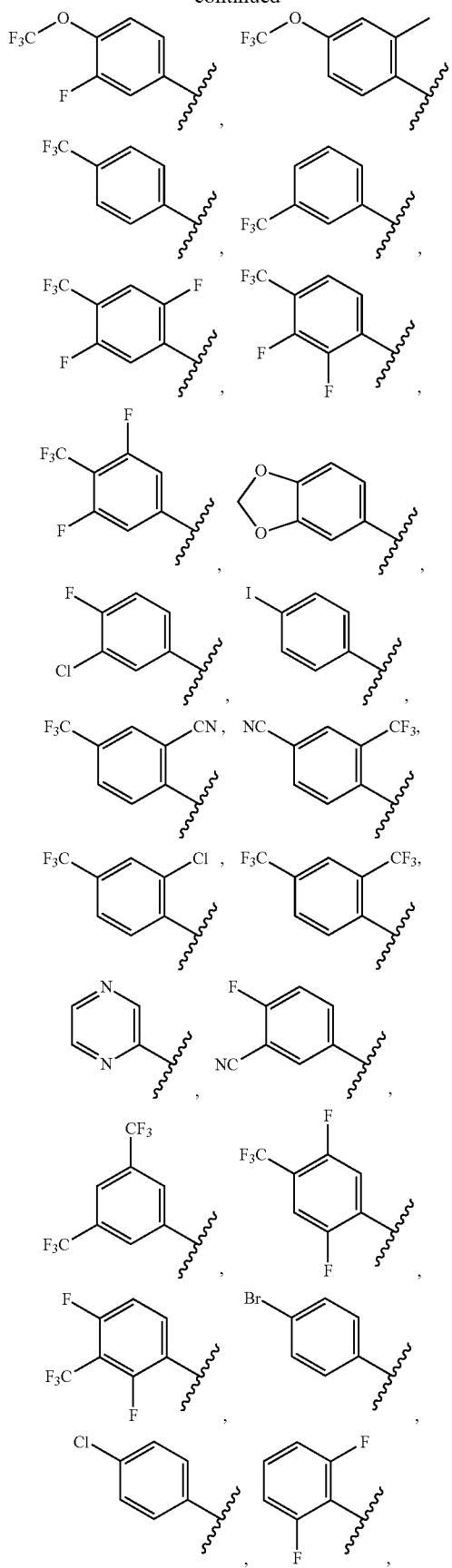

-continued

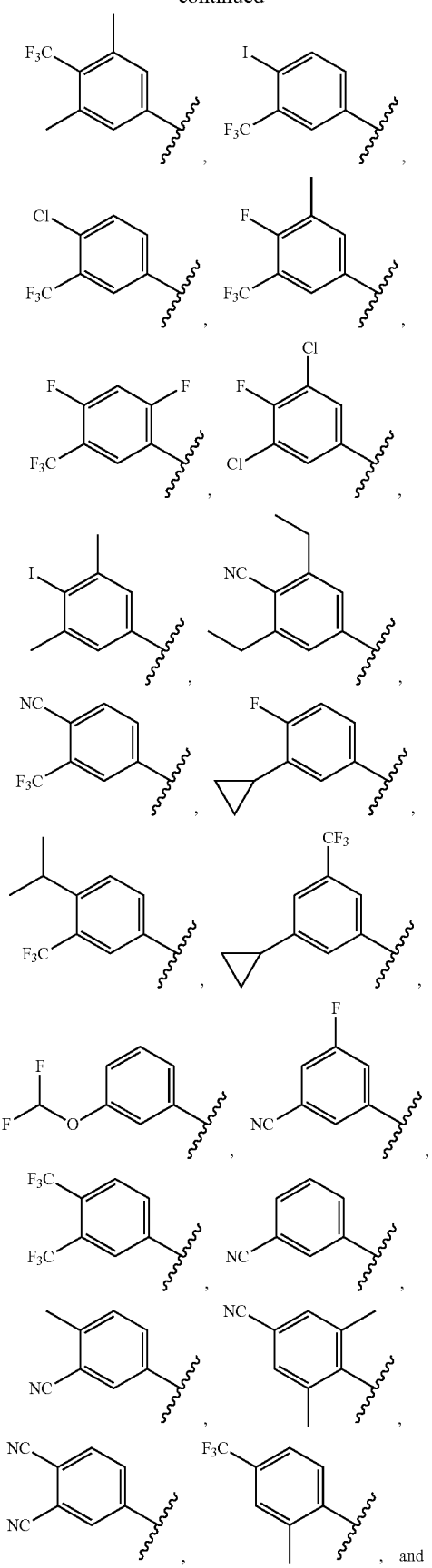

, and

-continued

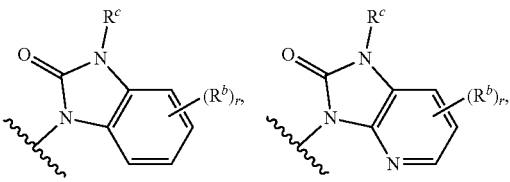

11. The compound of claim 1, or a pharmaceutically acceptable salt thereof, or an isotopic variant thereof, wherein:
Q is C(R$^e$)(D);
D is selected from the group consisting of

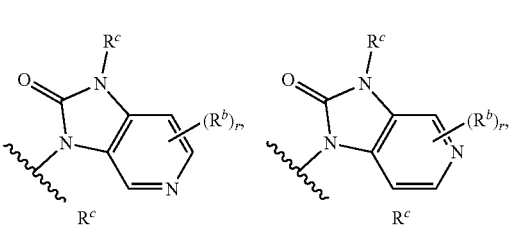

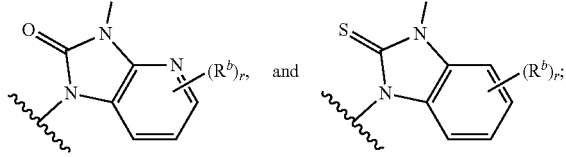

r is 0 to 4;
each R$^b$ is independently selected from the group consisting of cyano, $C_1$-$C_4$ alkyl, $C_1$-$C_4$ alkoxy, $C_1$-$C_4$ haloalkyl, $C_1$-$C_4$ haloalkoxy, and halo;
R$^e$ is hydrogen; and
R$^c$ is hydrogen or $C_1$-$C_4$ alkyl.

12. The compound of claim 11, or a pharmaceutically acceptable salt thereof, or an isotopic variant thereof, wherein:
D is selected from the group consisting o

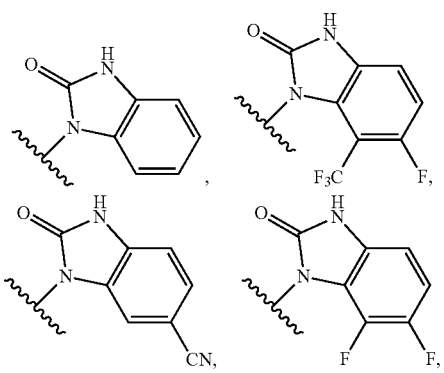

-continued

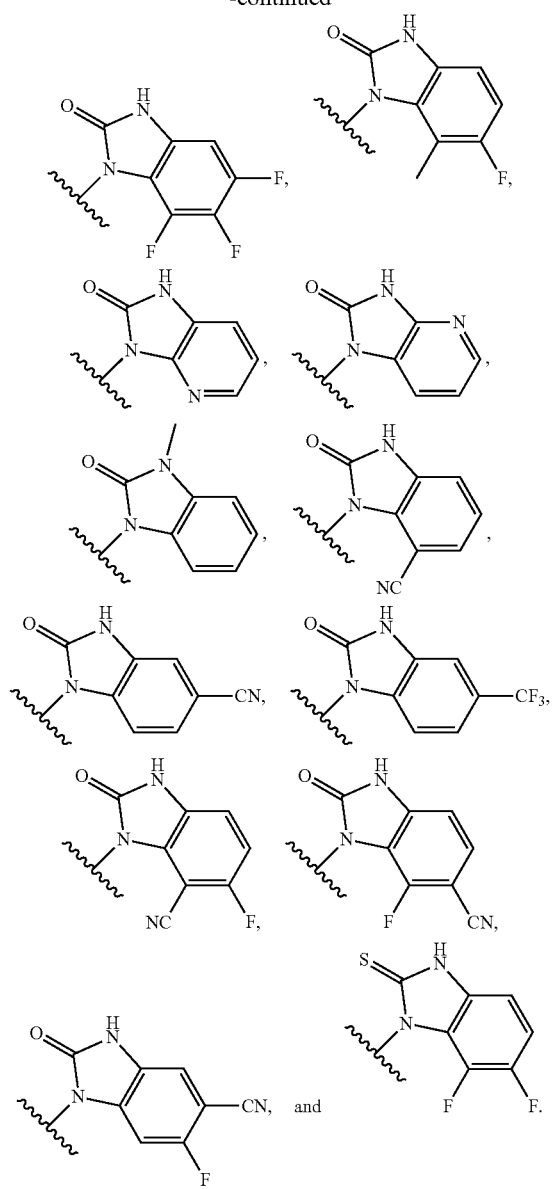

13. The compound of claim 1, or a pharmaceutically acceptable salt thereof, or an isotopic variant thereof, wherein:

Q is F;

F is a spirocyclic group selected from

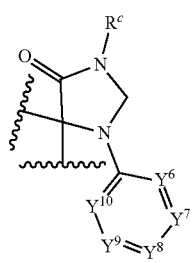

and

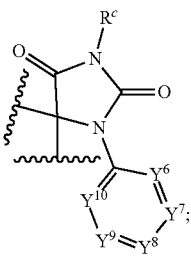

$Y^6$, $Y^7$, $Y^8$, $Y^9$, and $Y^{10}$ are each independently selected from the group consisting of N, CH, and $CR^b$ wherein 0, 1, or 2 of $Y^6$, $Y^7$, $Y^8$, $Y^9$ and $Y^{10}$ is N;

each $R^b$ is independently selected from the group consisting of cyano, $C_1$-$C_4$ alkyl, $C_1$-$C_4$ alkoxy, $C_1$-$C_4$ haloalkyl, $C_1$-$C_4$ haloalkoxy, and halo; and $R^c$ is selected from the group consisting of hydrogen and $C_1$-$C_4$ alkyl.

14. The compound of claim 13, or a pharmaceutically acceptable salt thereof, or an isotopic variant thereof, wherein:

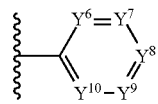

is selected from the group consisting of

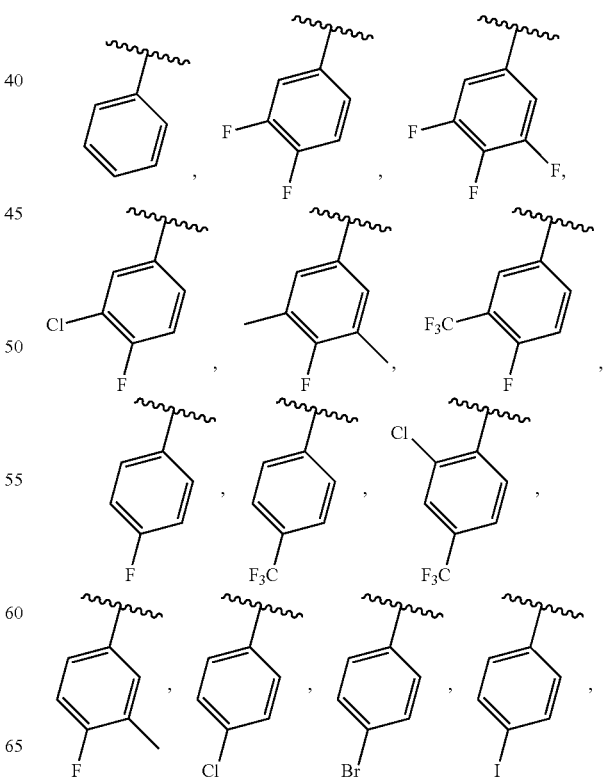

-continued

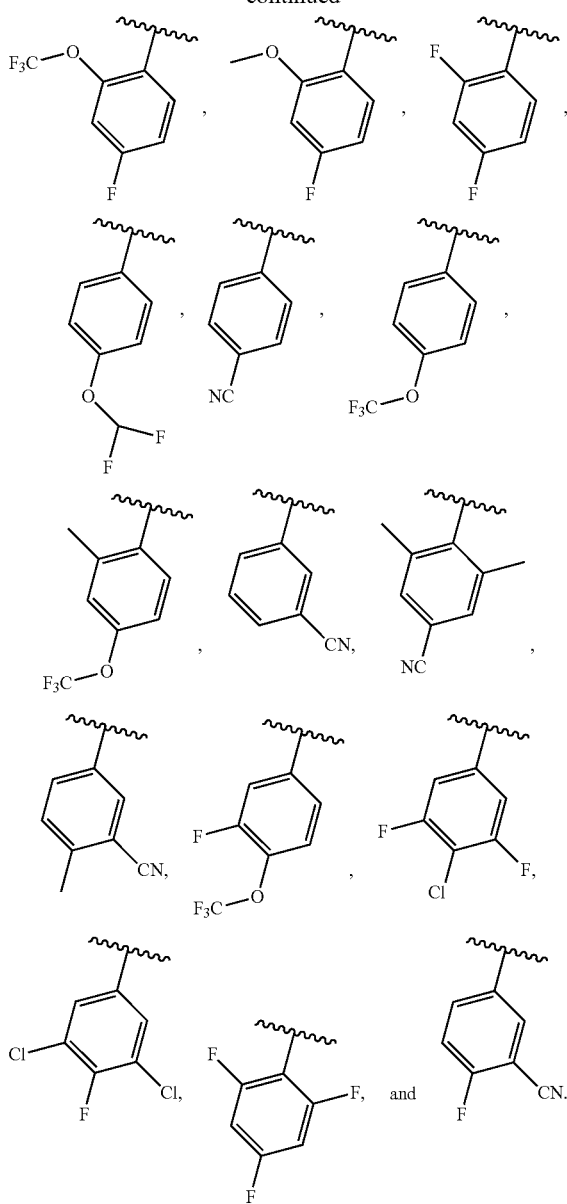

15. The compound of claim 1, or a pharmaceutically acceptable salt thereof, or an isotopic variant thereof, wherein:

Q is G;

G is

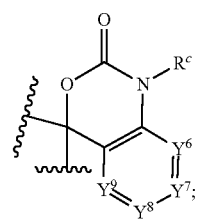

$Y^6$, $Y^7$, $Y^8$, and $Y^9$ are each independently selected from the group consisting of N, CH, and $CR^b$ wherein 0, 1, or 2 of $Y^6$, $Y^7$, $Y^8$, and $Y^9$ is N;

each $R^b$ is independently selected from the group consisting of cyano, $C_1$-$C_4$ alkyl, $C_1$-$C_4$ alkoxy, $C_1$-$C_4$ haloalkyl, $C_1$-$C_4$ haloalkoxy, and halo; and $R^c$ is selected from the group consisting of hydrogen and $C_1$-$C_4$ alkyl.

16. The compound of claim 15, or a pharmaceutically acceptable salt thereof, or an isotopic variant thereof, wherein:

G is selected from the group consisting of

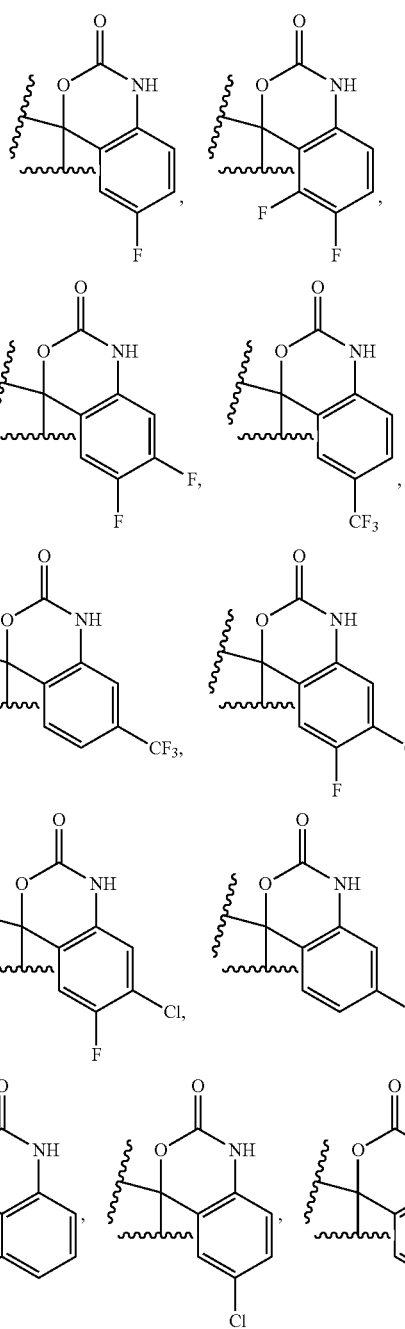

-continued
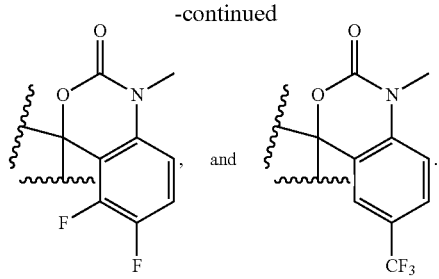 and 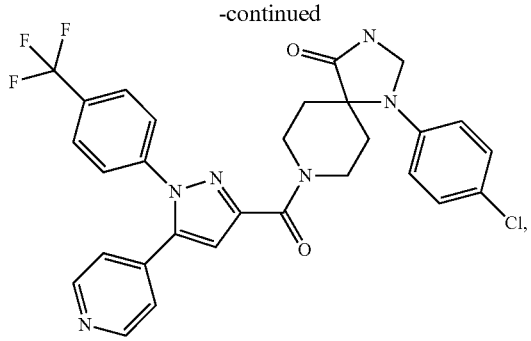
17. The compound of claim 1, or a pharmaceutically acceptable salt thereof, or an isotopic variant thereof, wherein the compound is selected from:
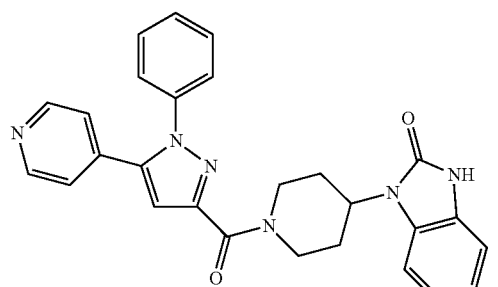,
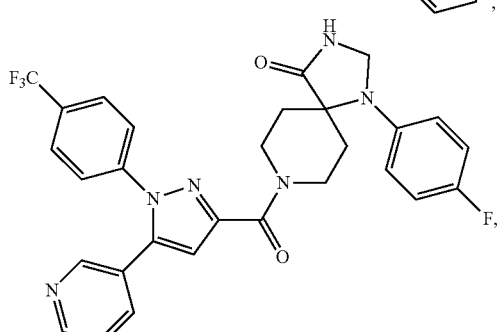,
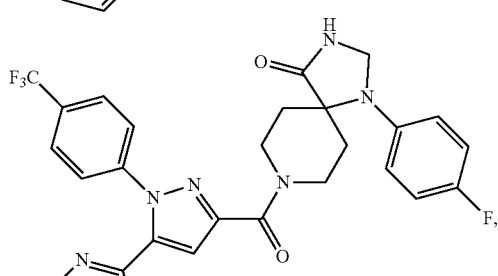,
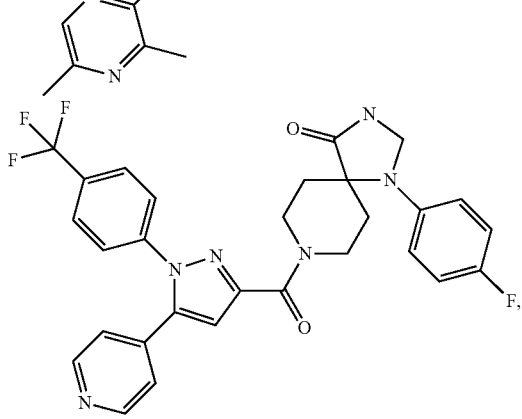,
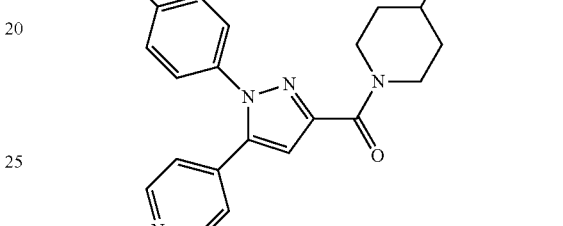,
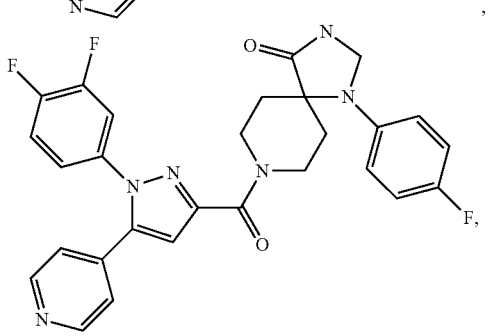,
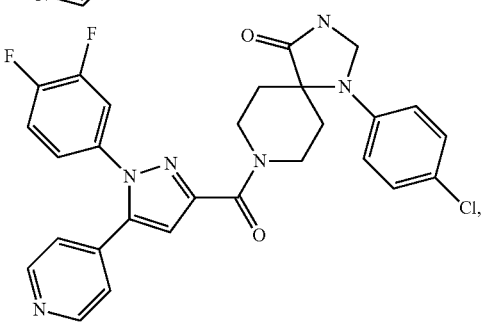,
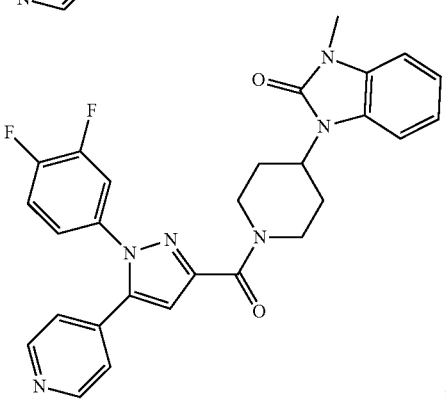, 419
-continued
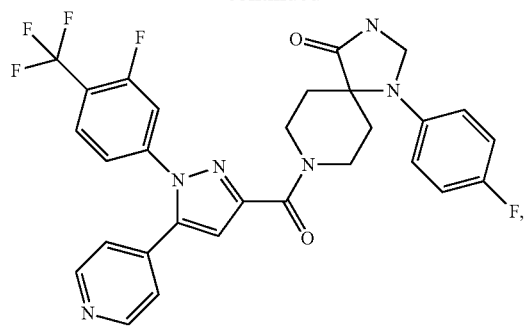
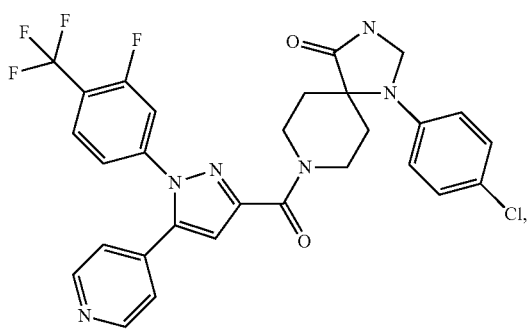
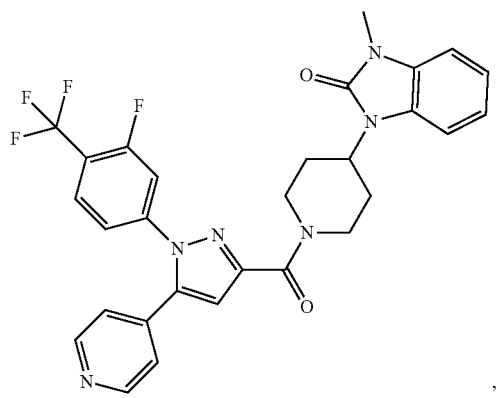
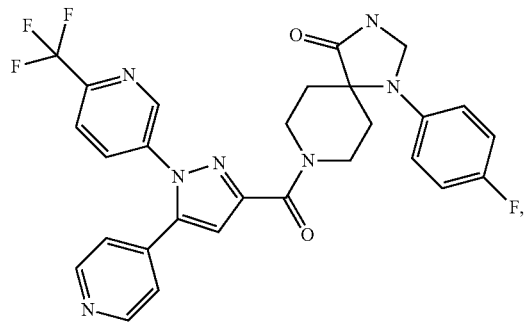
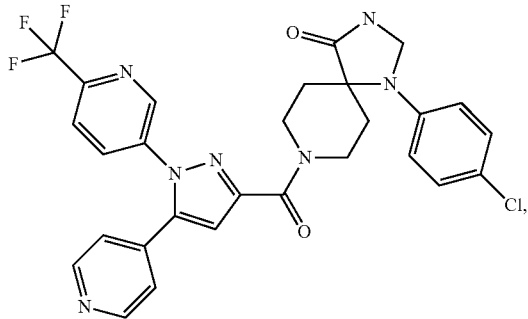
420
-continued
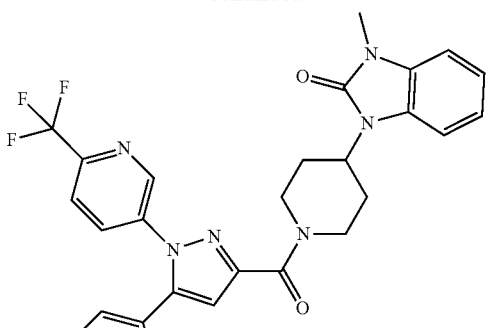
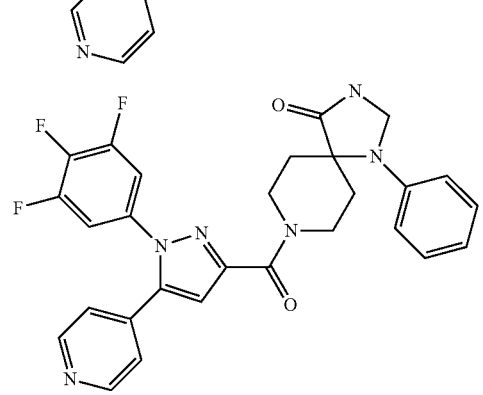
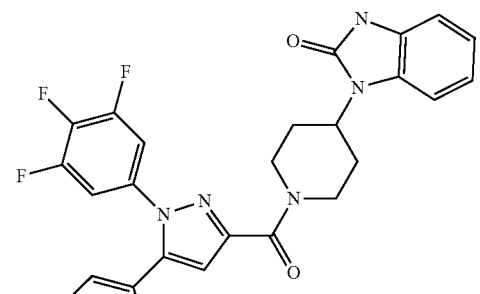
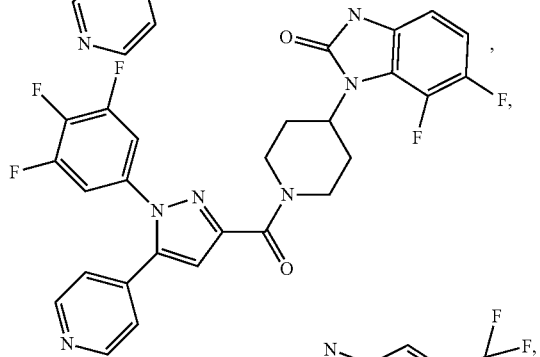
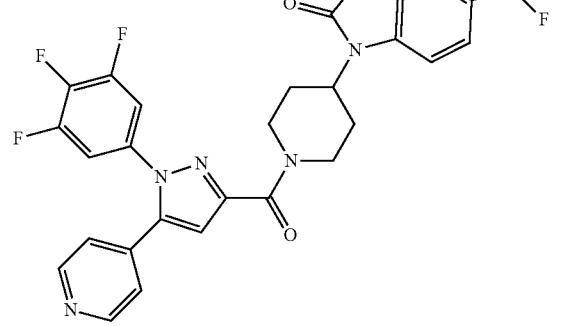

421
-continued
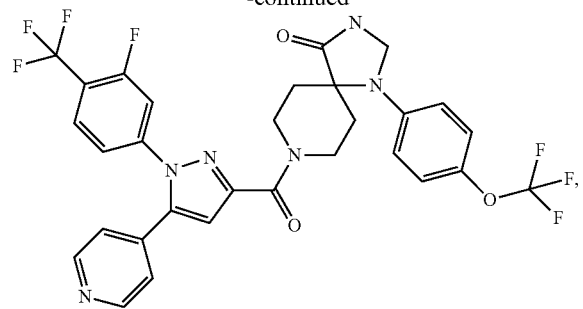
,
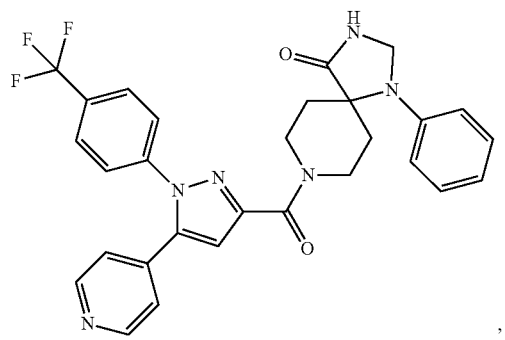
,
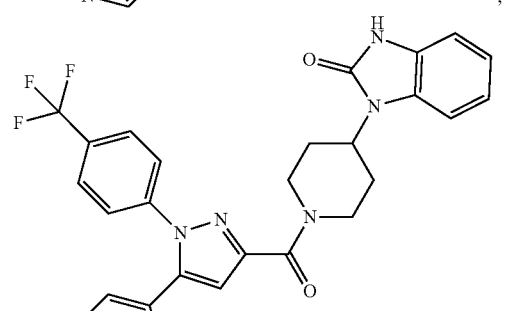
,
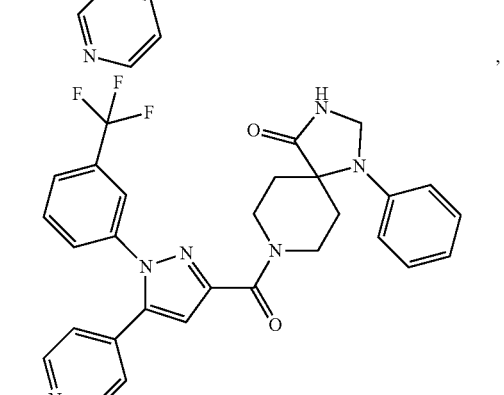
,
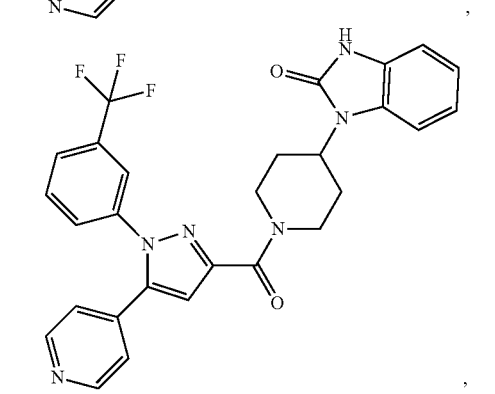
,
422
-continued
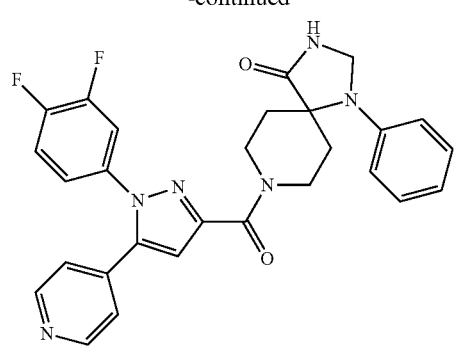
,
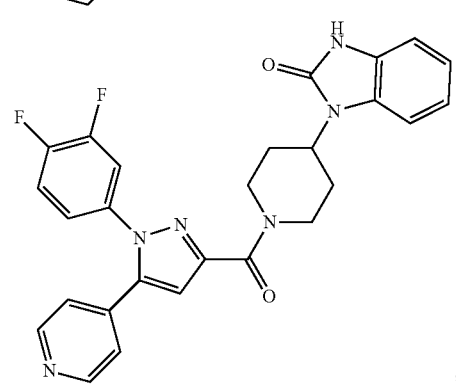
,
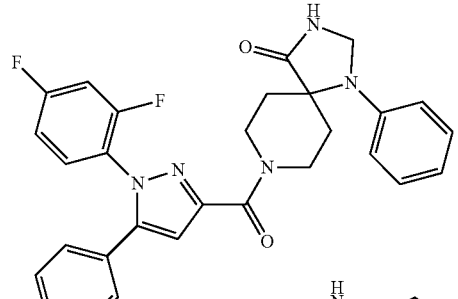
,
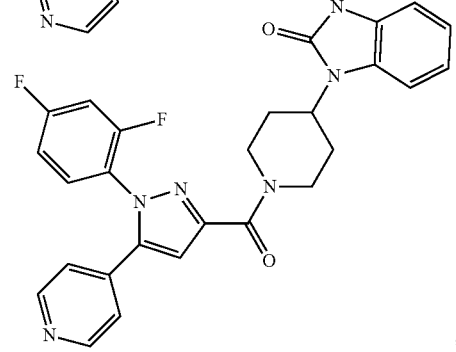
,
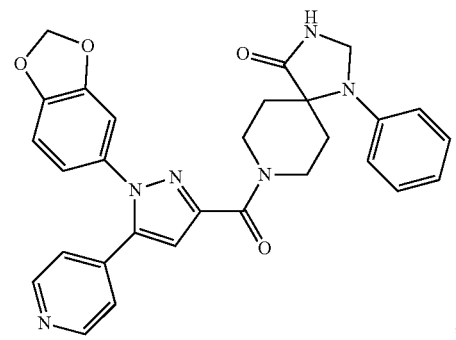
, 423
-continued
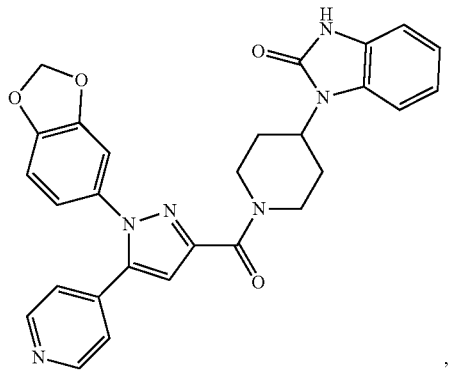
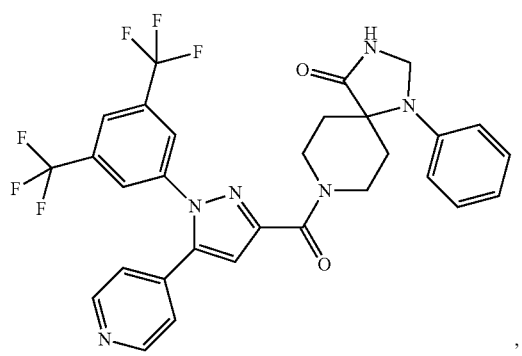
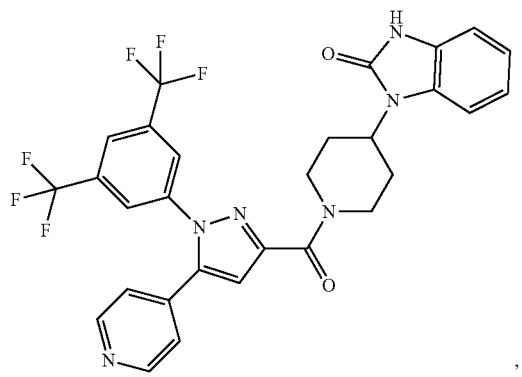
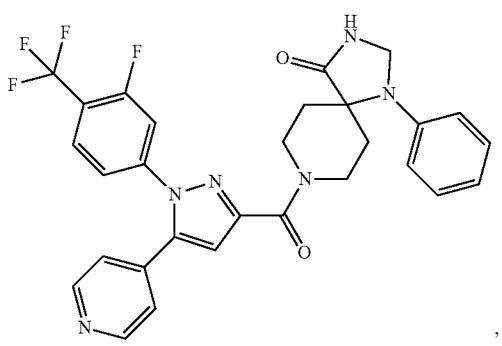
424
-continued
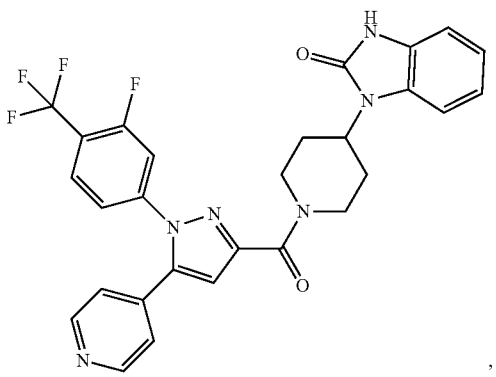
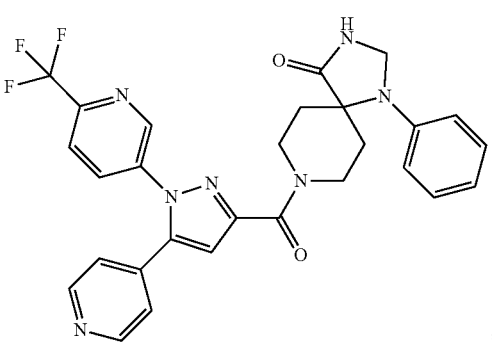
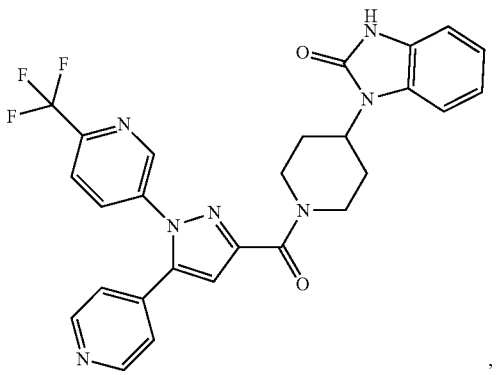
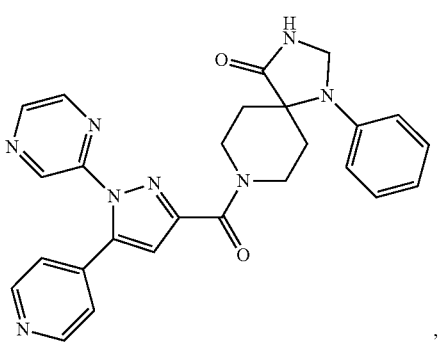

425
-continued
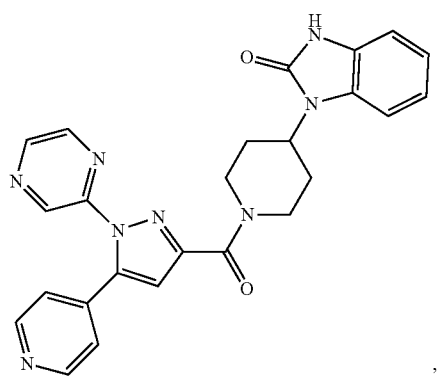
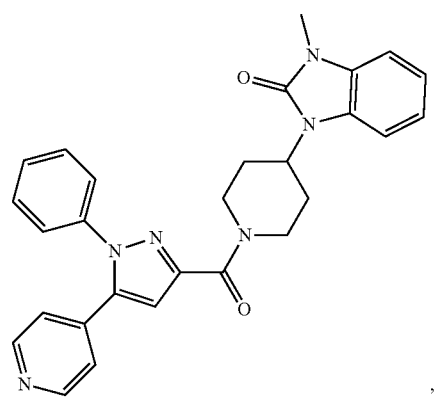
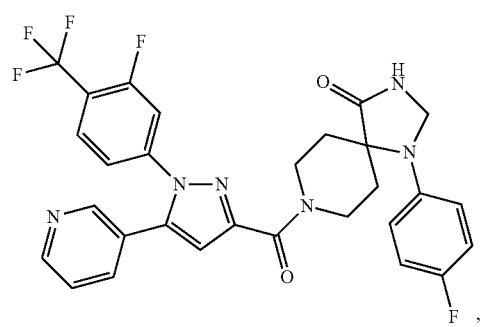
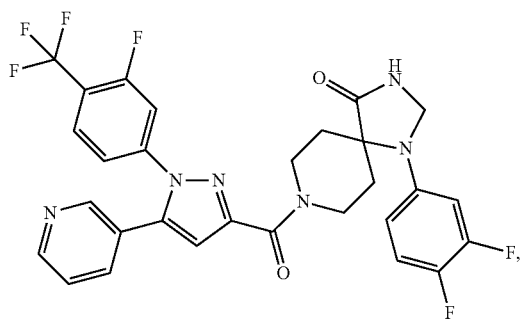
426
-continued
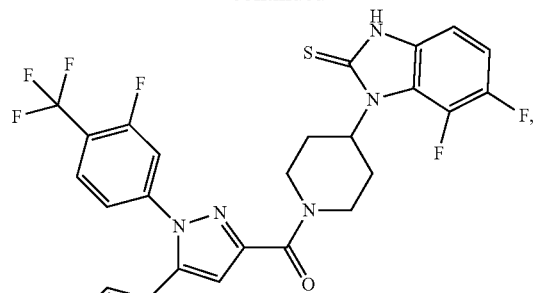
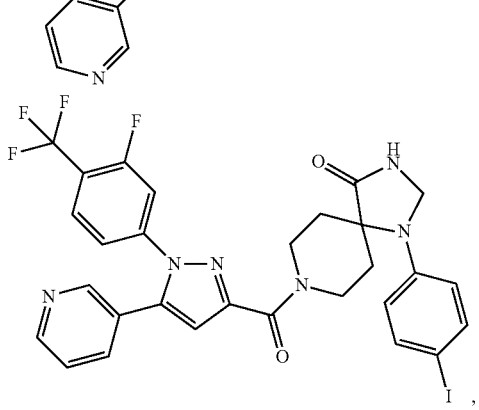
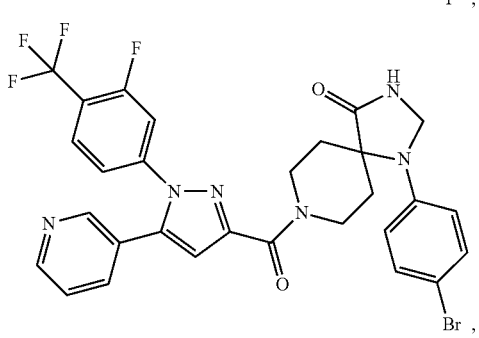
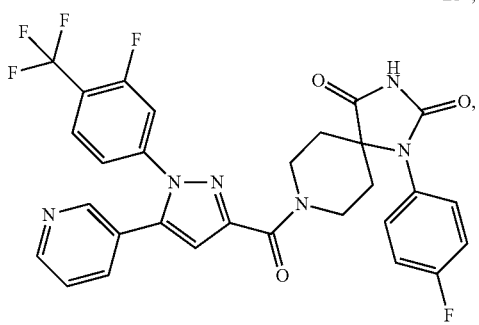

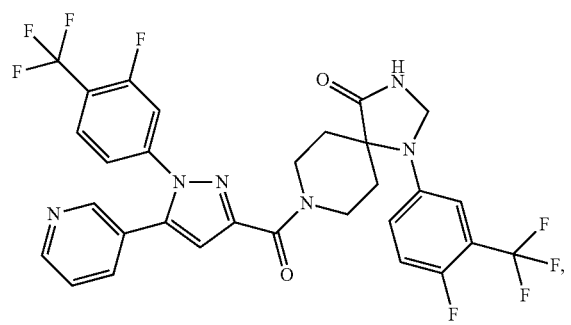

429
-continued
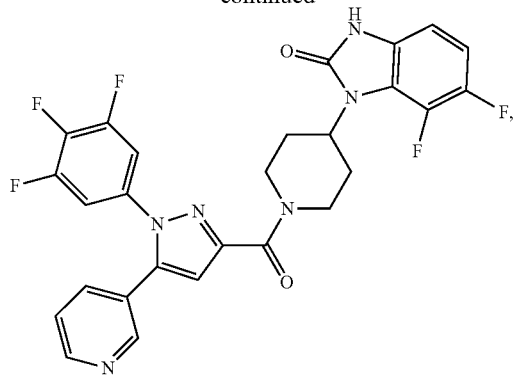
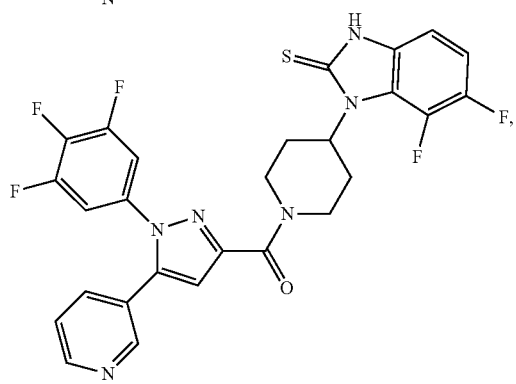
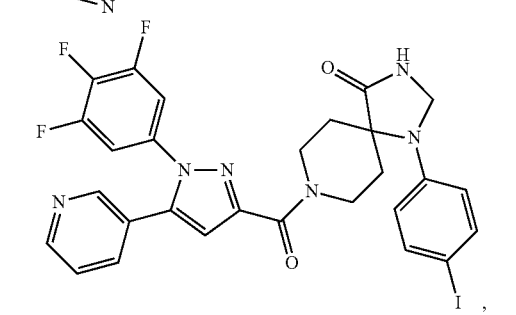
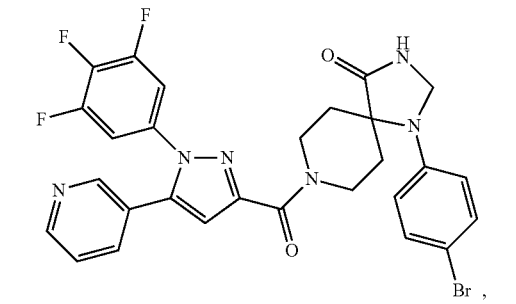
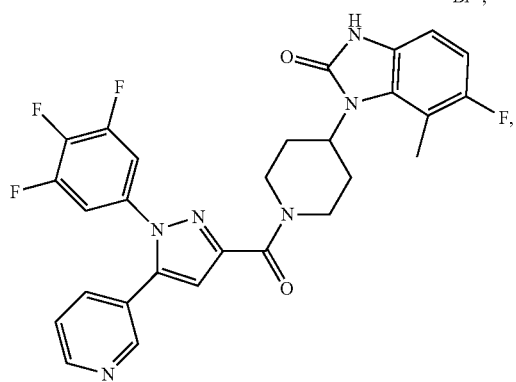
430
-continued
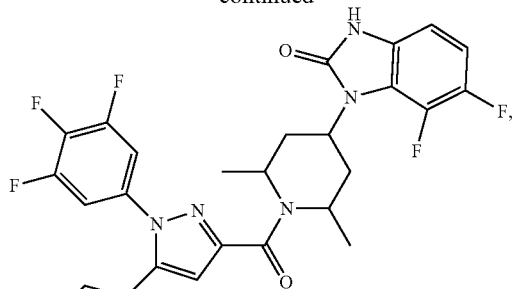
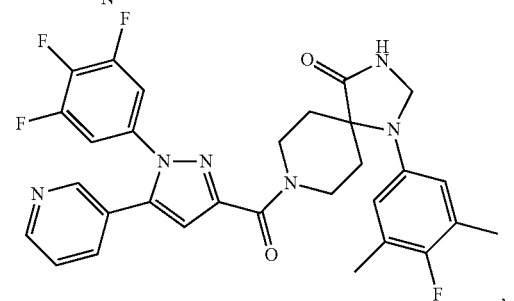
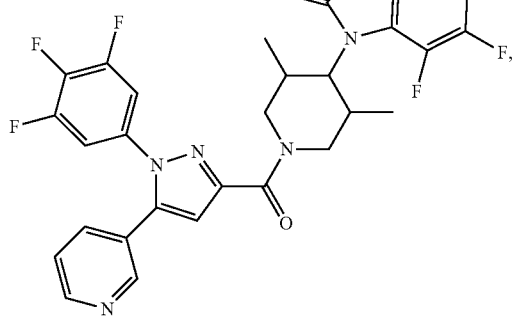
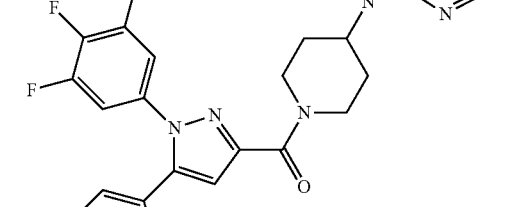
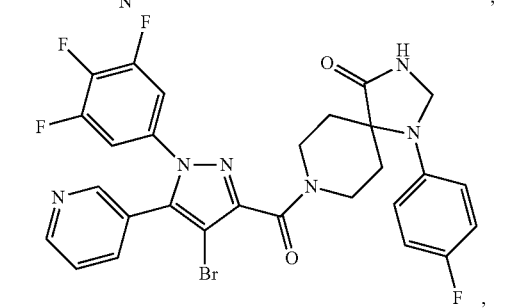

431
-continued
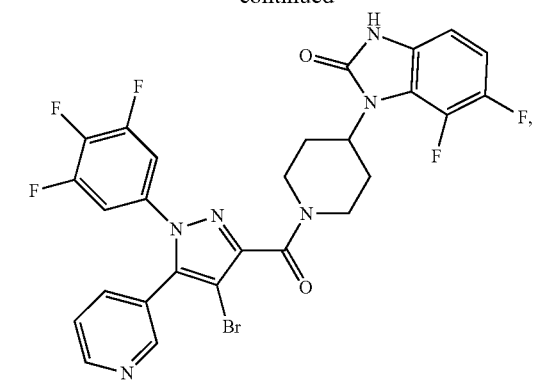
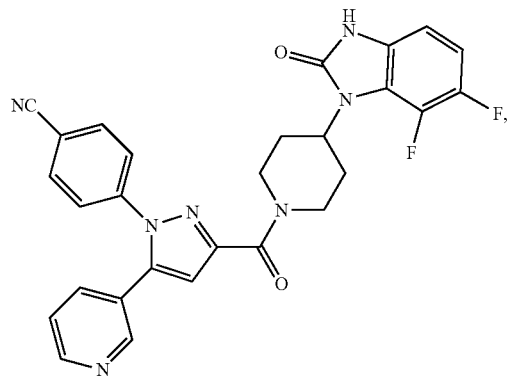
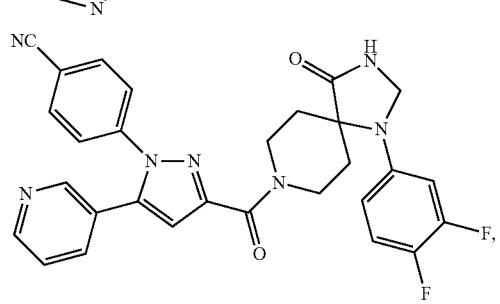
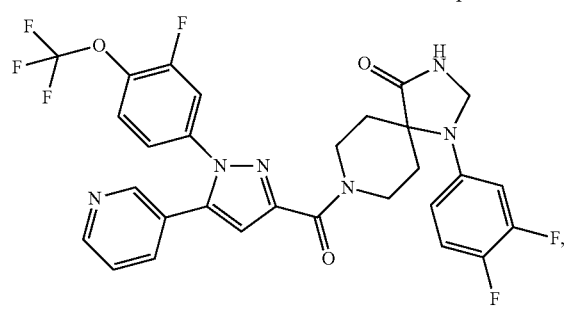
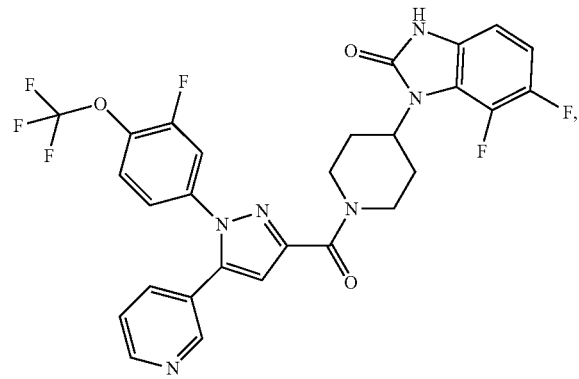
432
-continued
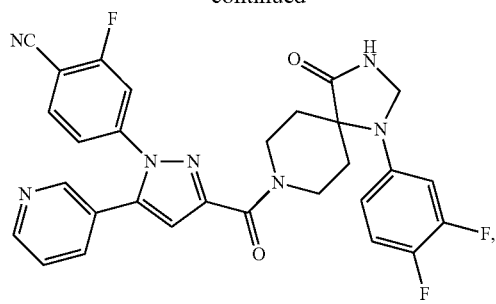
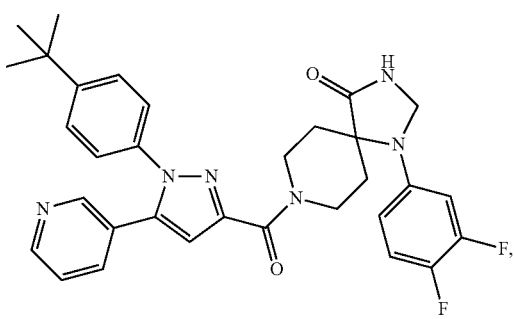
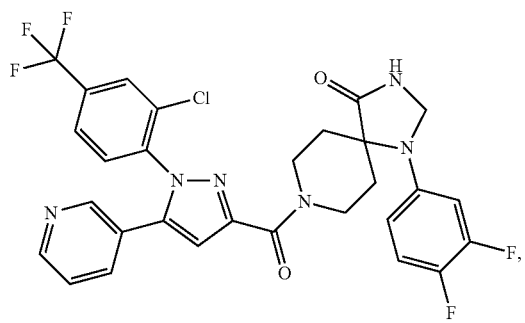
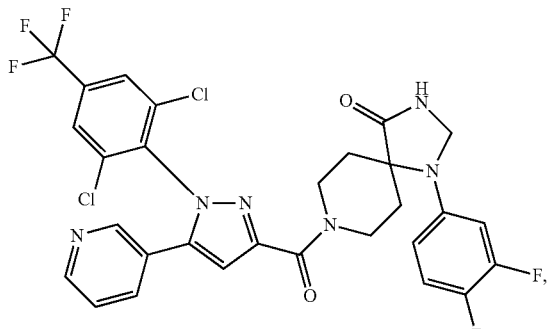
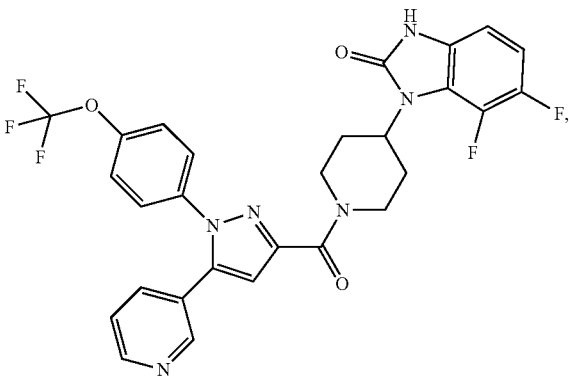

433
-continued
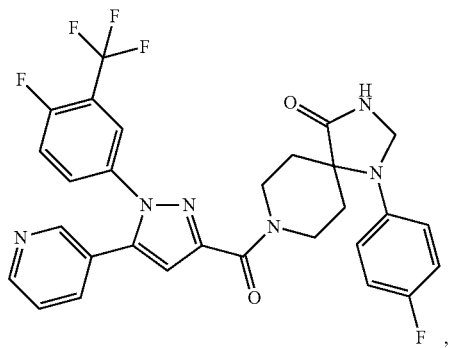
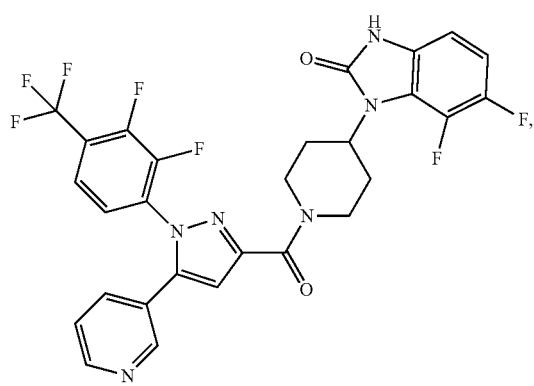
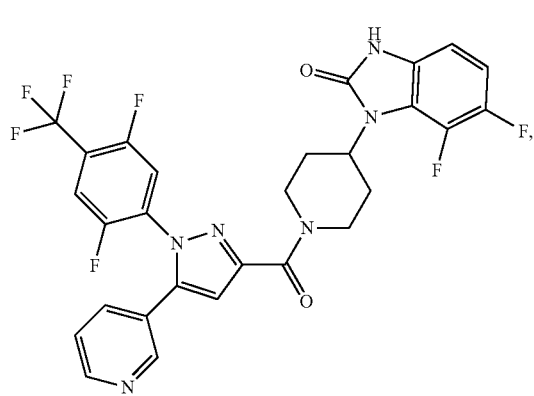
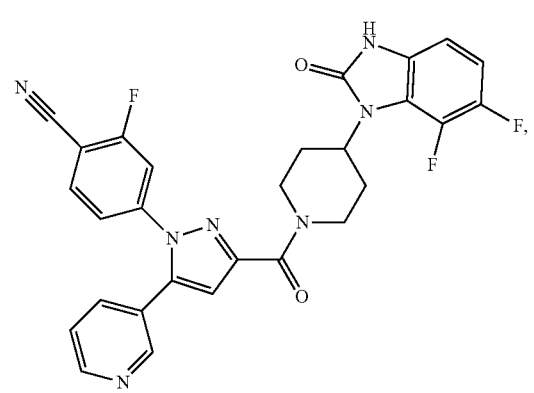
434
-continued
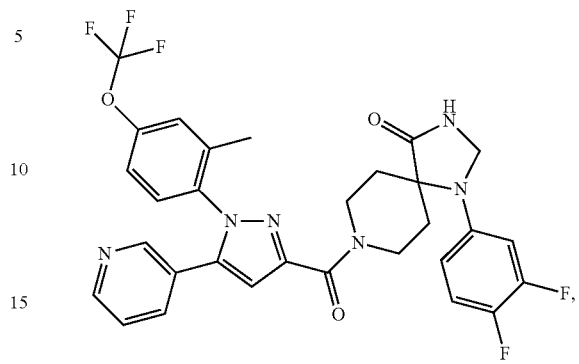
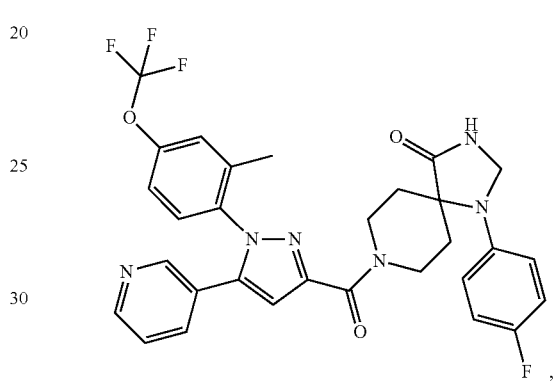
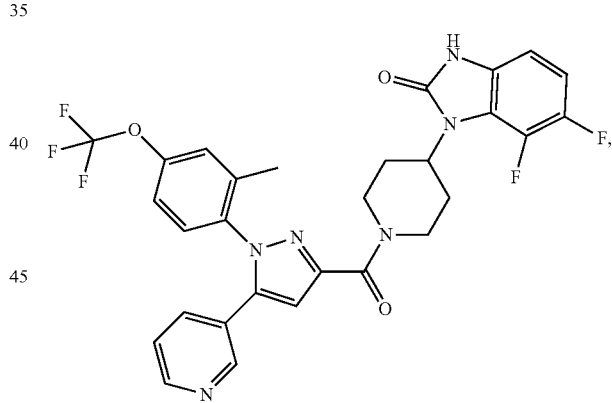
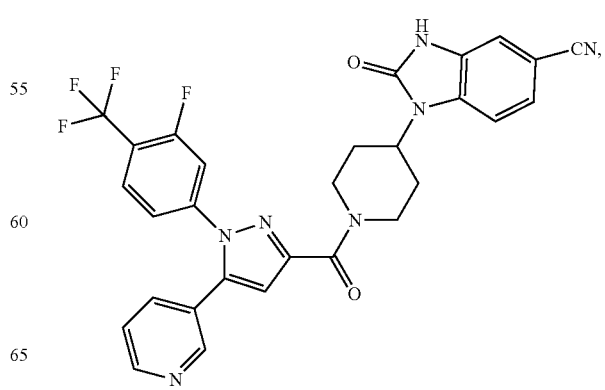

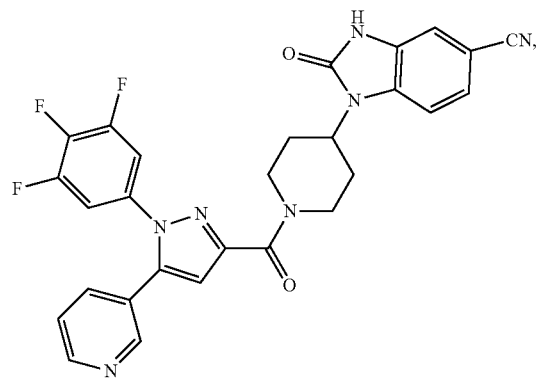
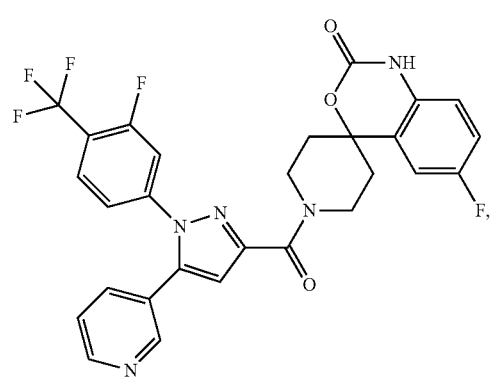
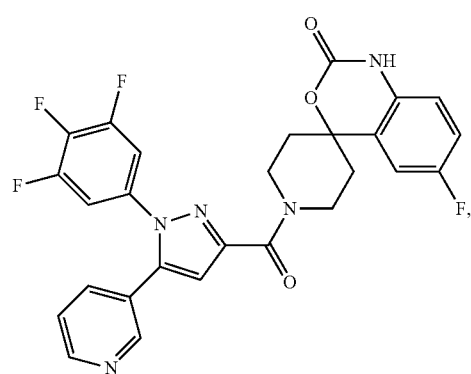
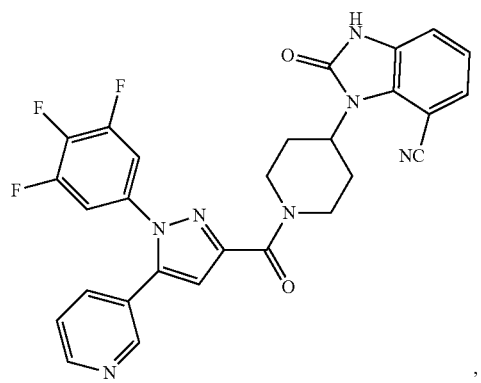
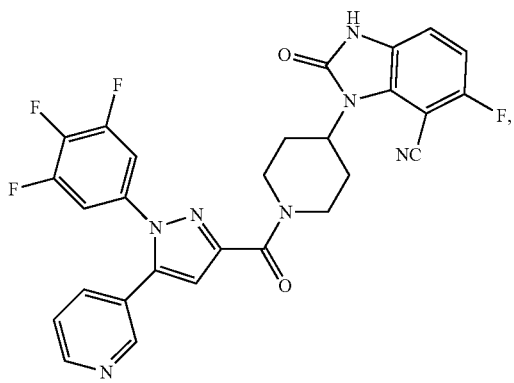
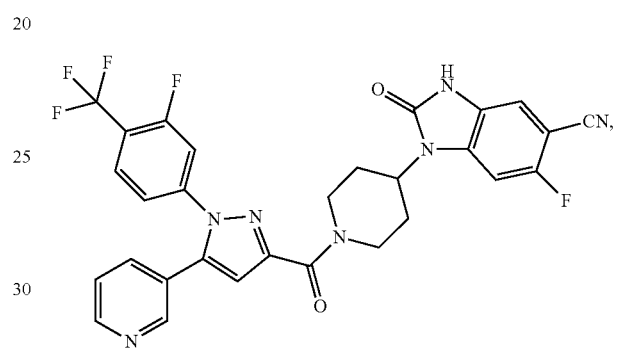
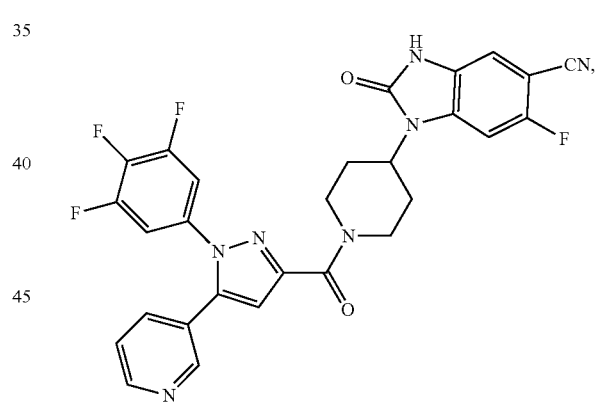
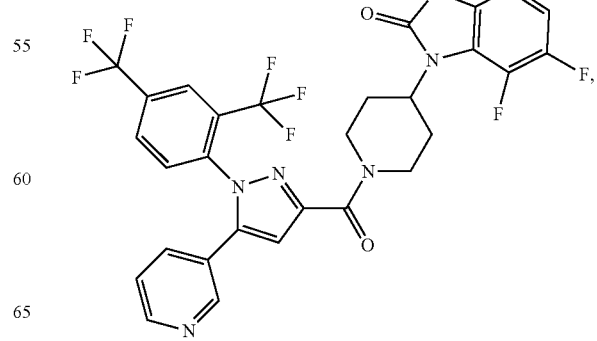

437
-continued
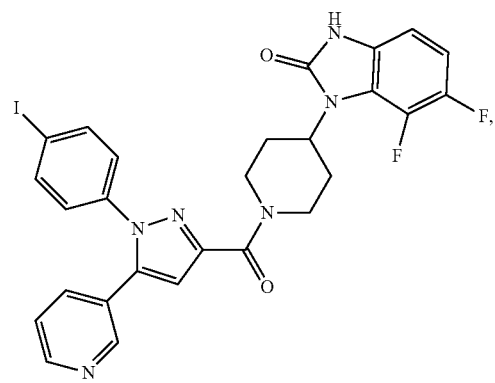
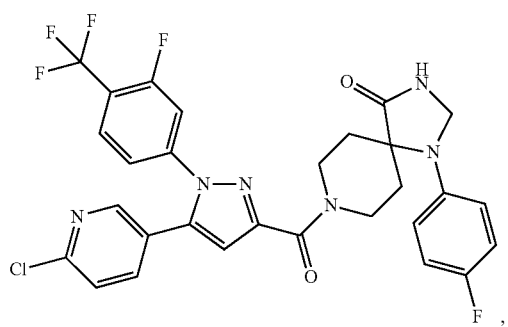
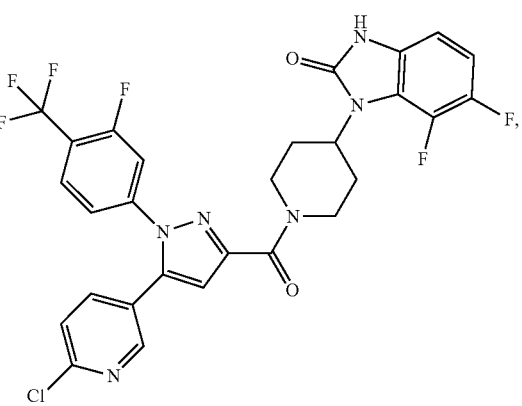
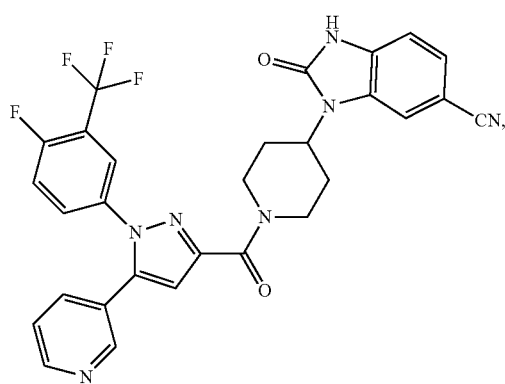
438
-continued
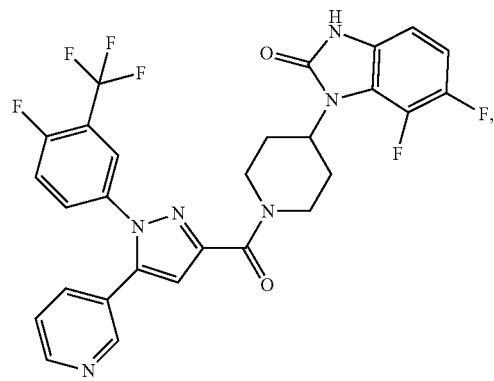
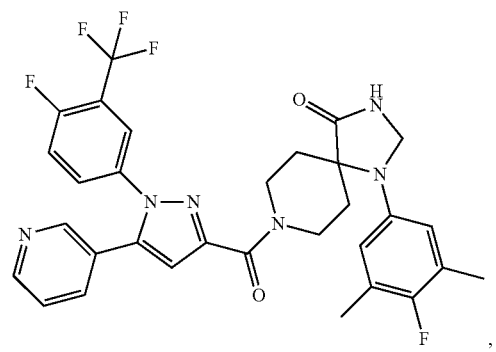
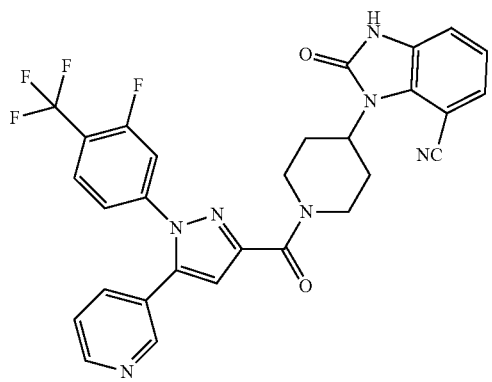
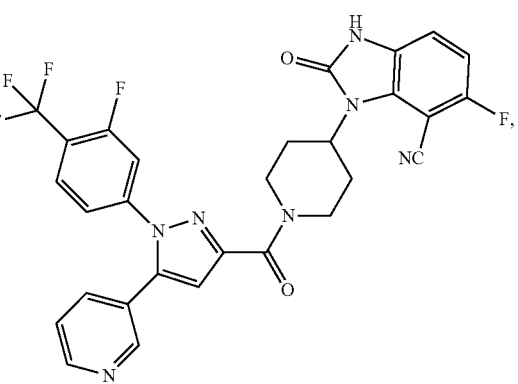

439
-continued
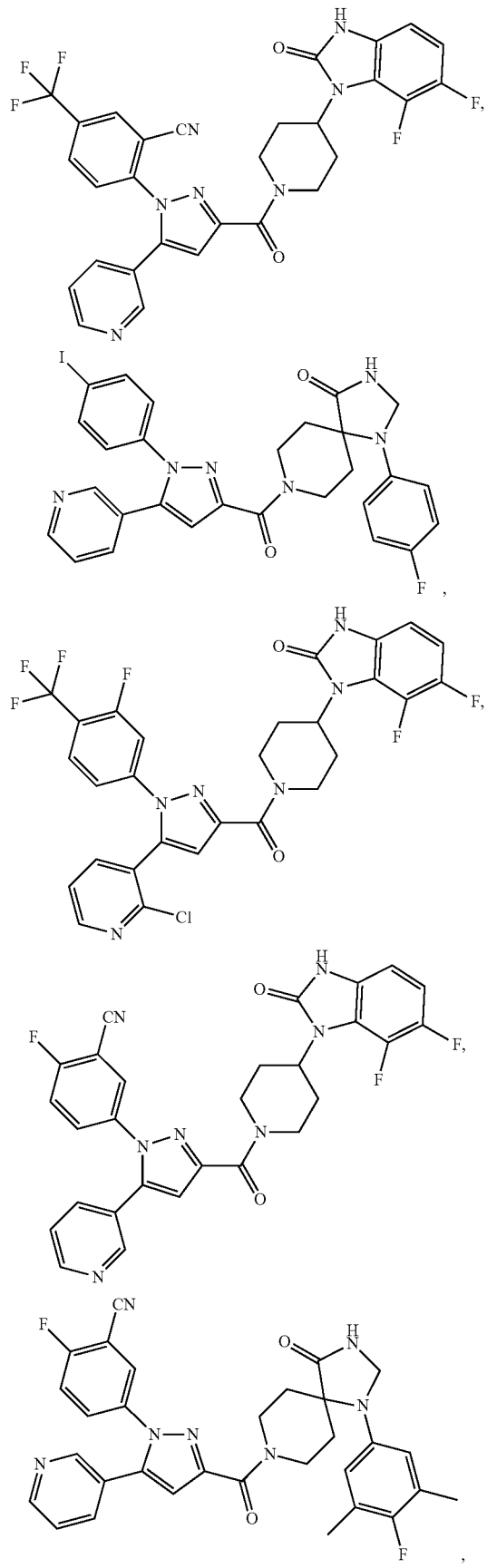
440
-continued
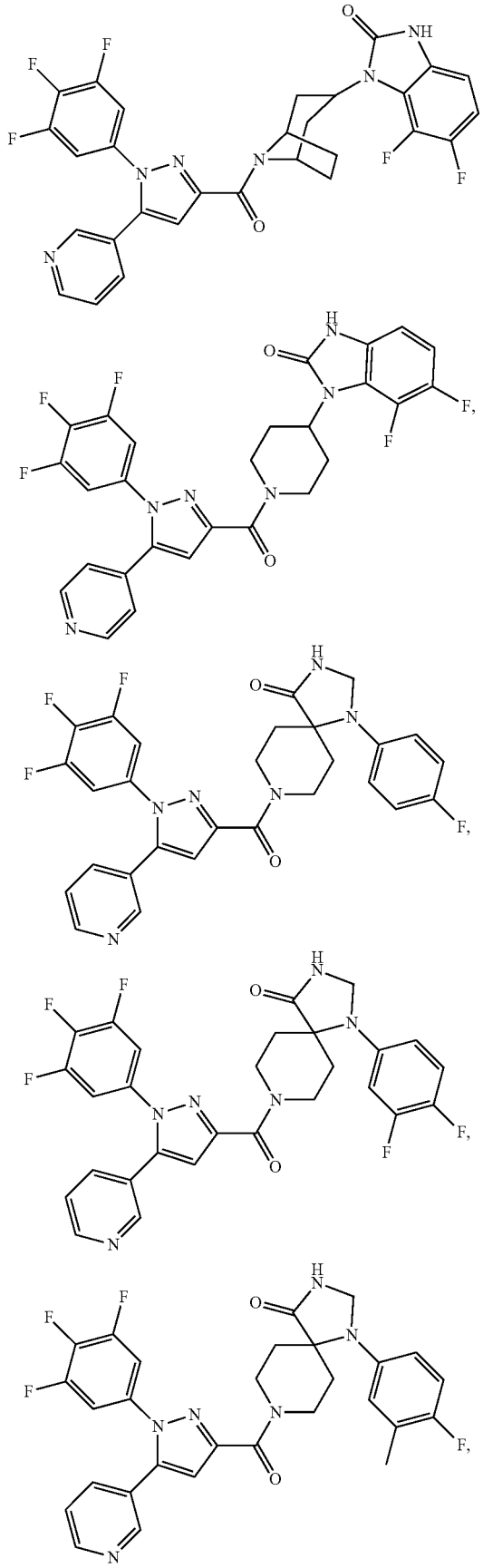

441
-continued
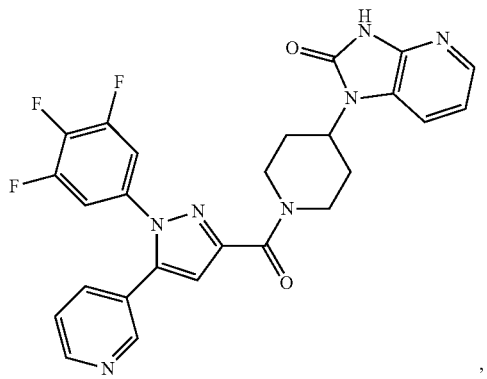
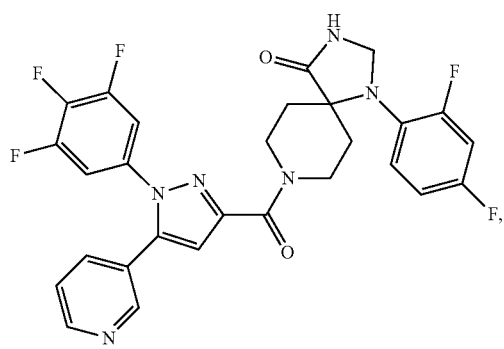
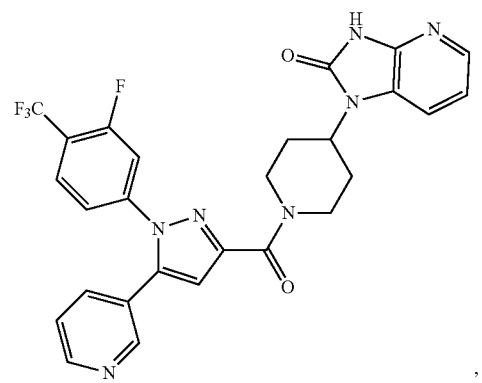
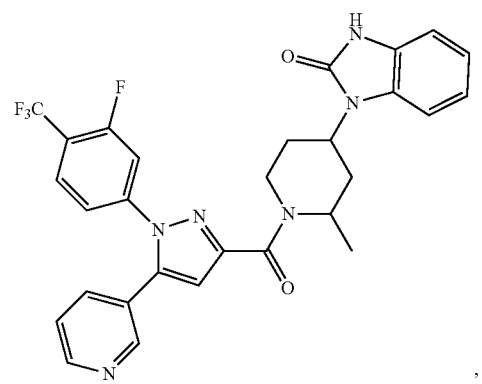
442
-continued
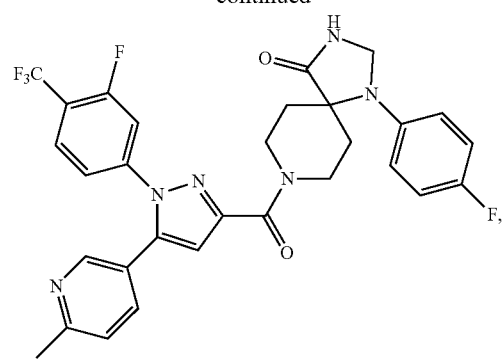
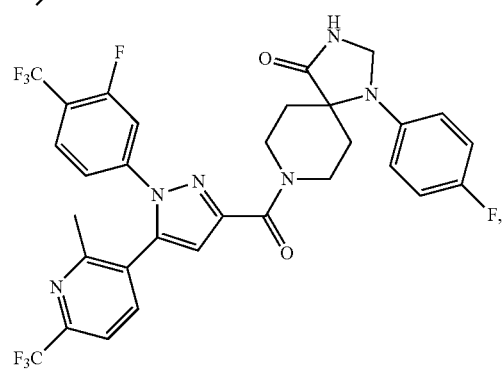
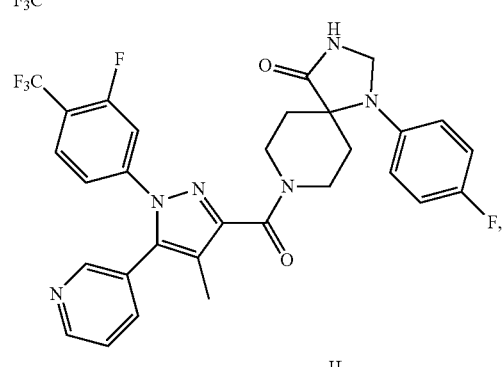
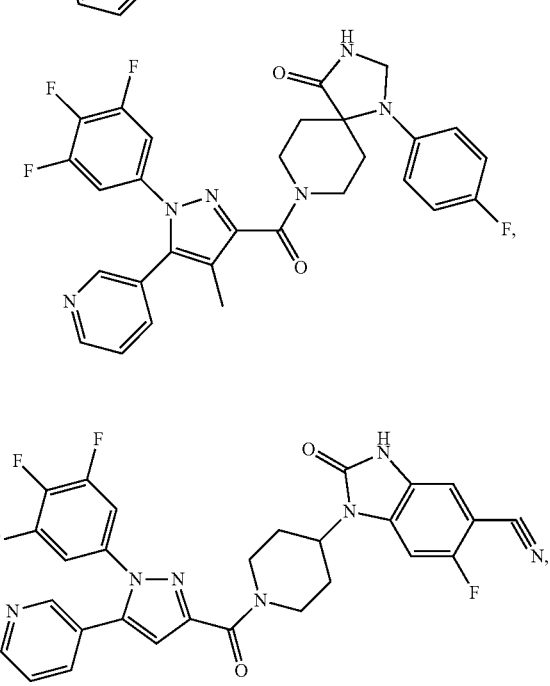

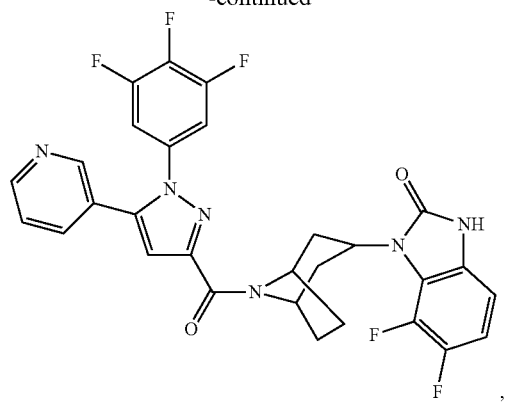
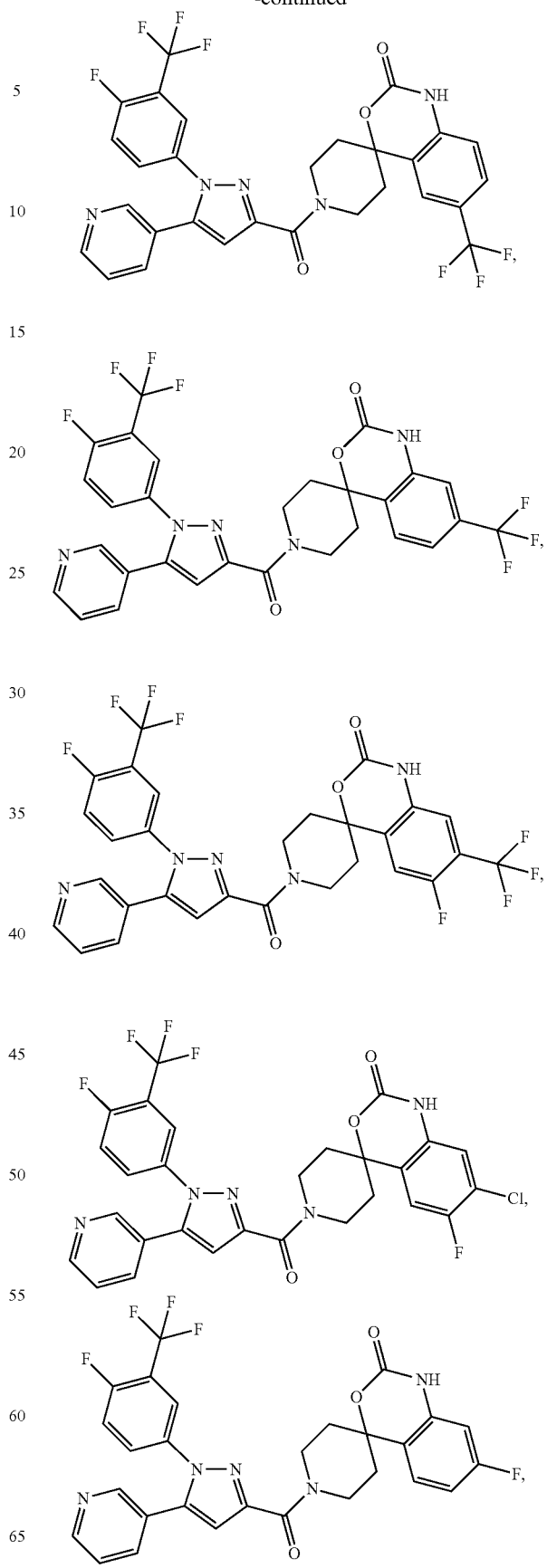

445
-continued
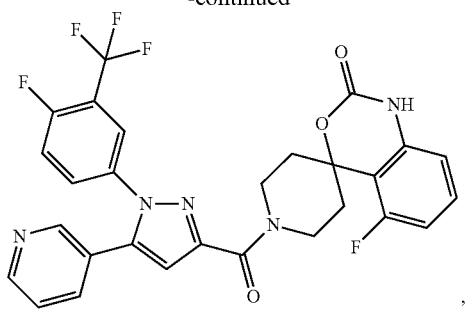,
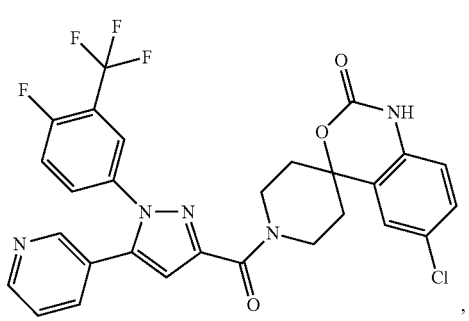,
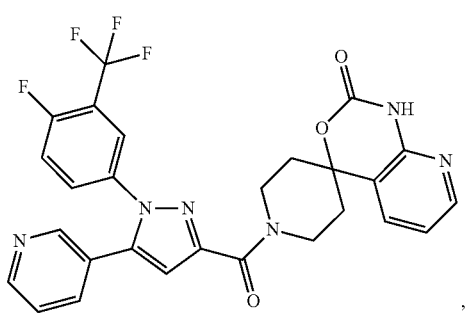,
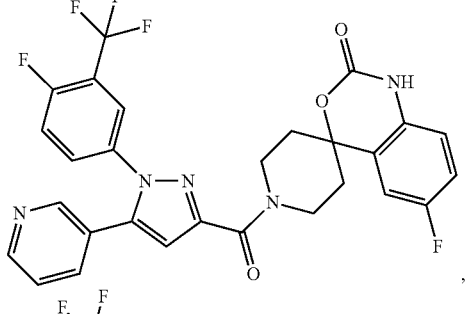,
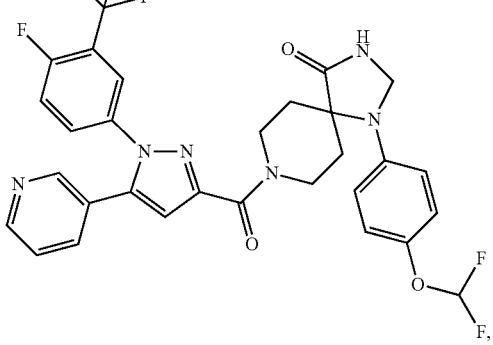
446
-continued
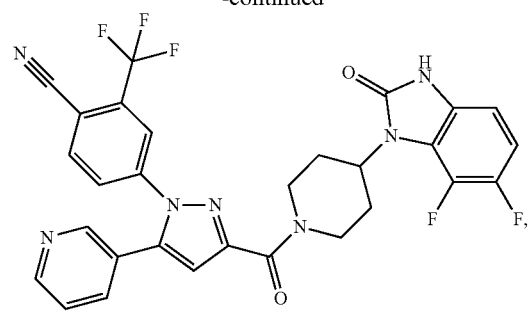,
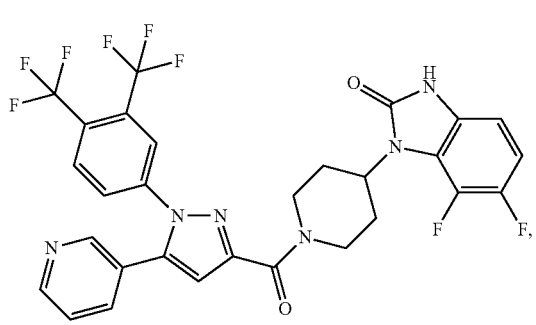,
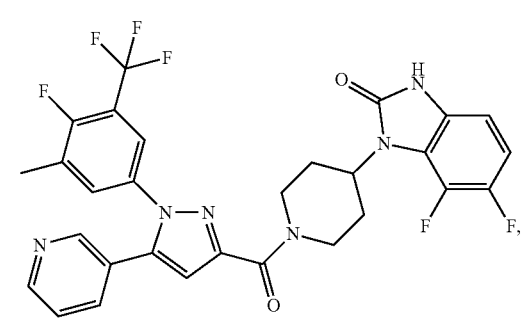,
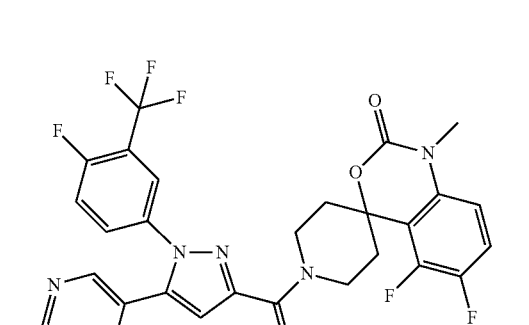,
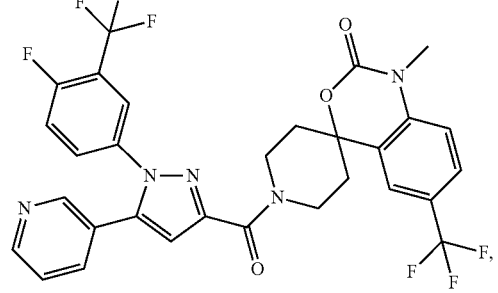

447
-continued
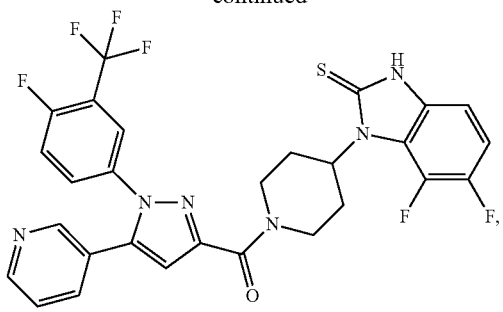
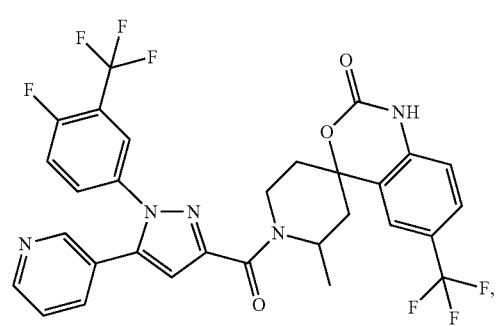
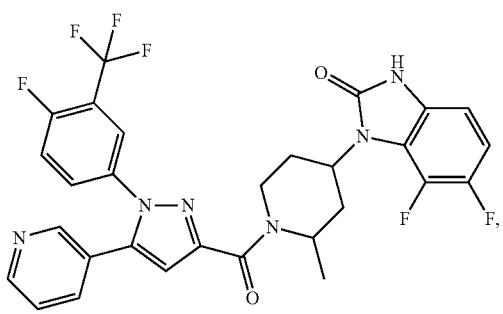
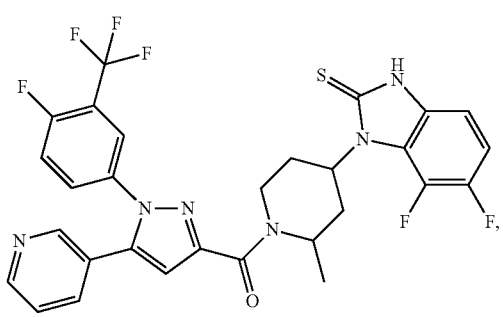
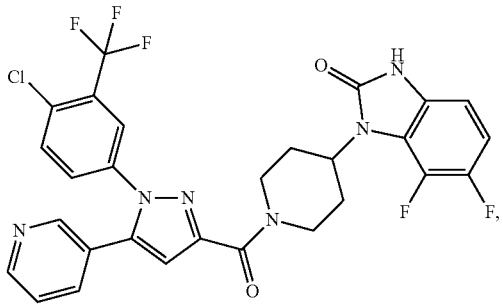
448
-continued
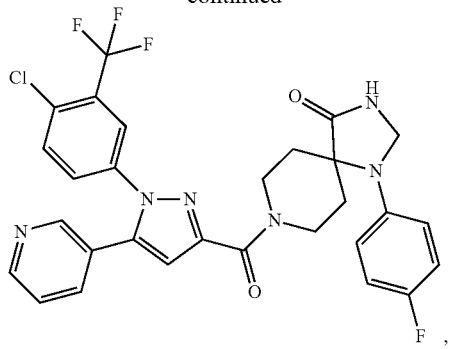
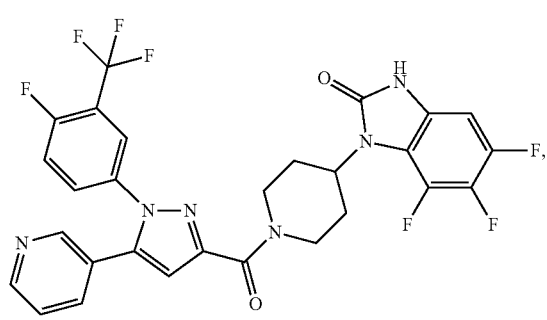
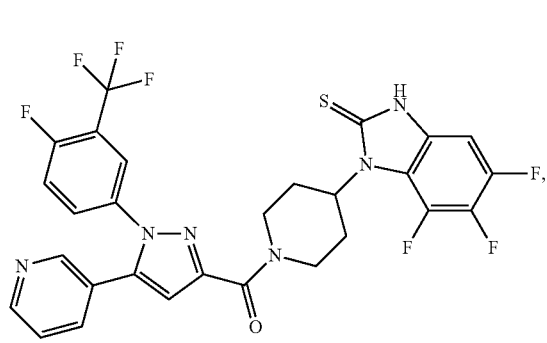
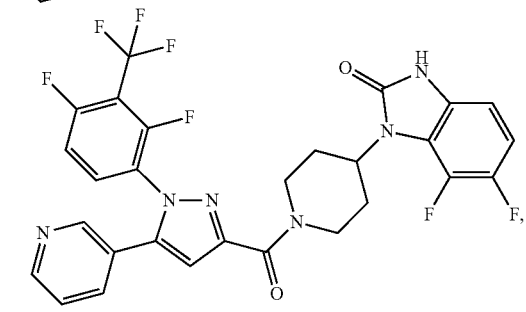
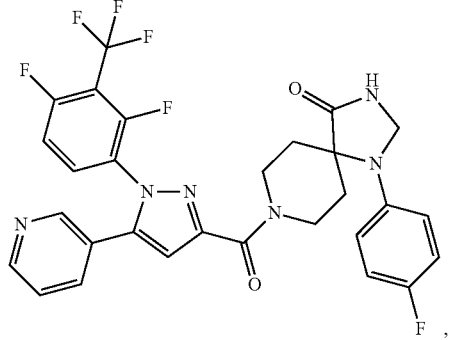

449 -continued

450 -continued

451
-continued
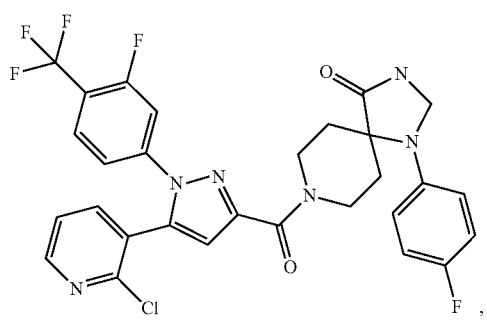
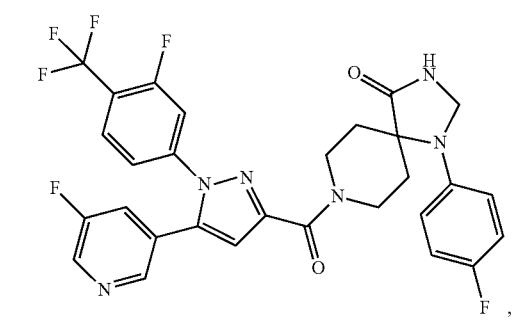
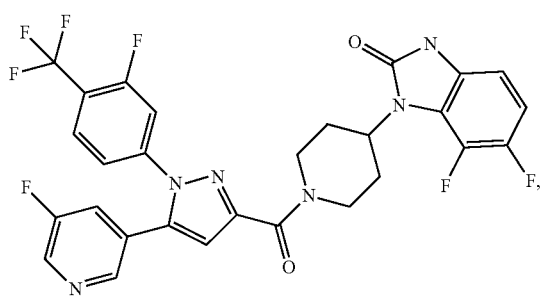
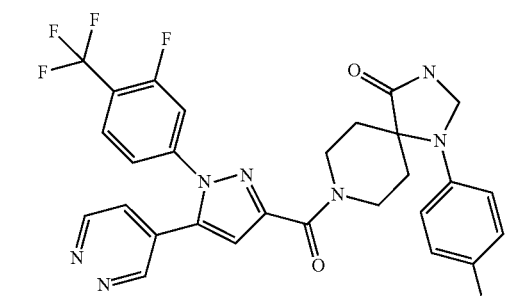
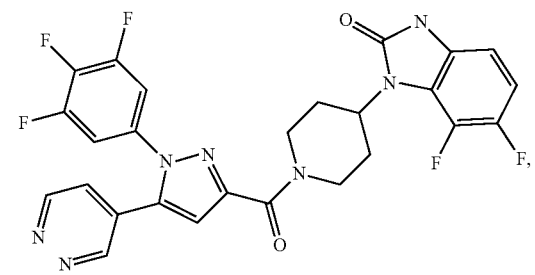
452
-continued
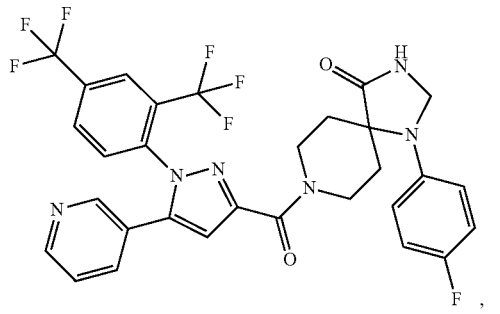
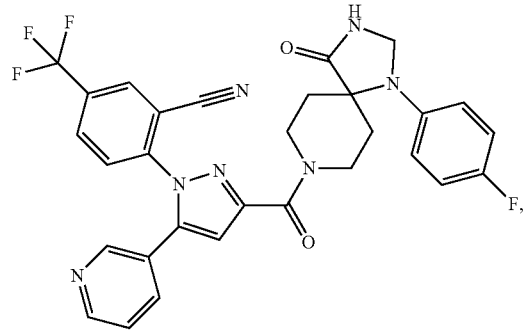
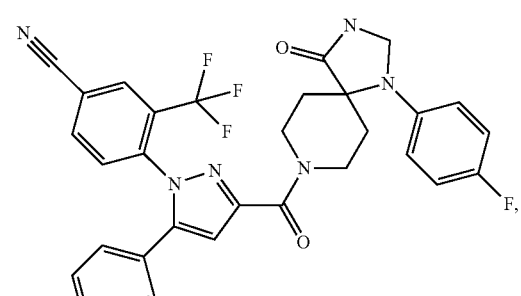
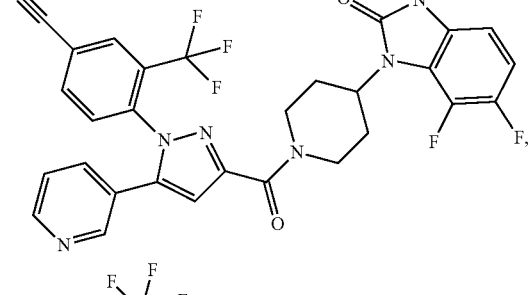
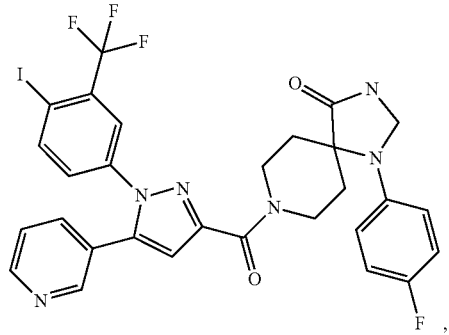

453
-continued

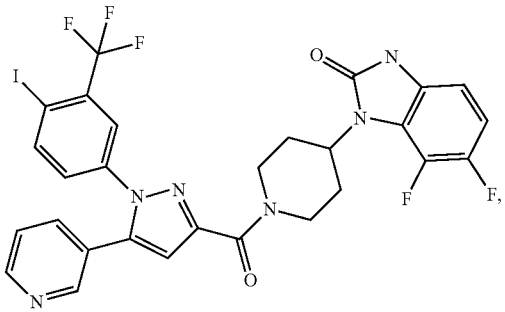

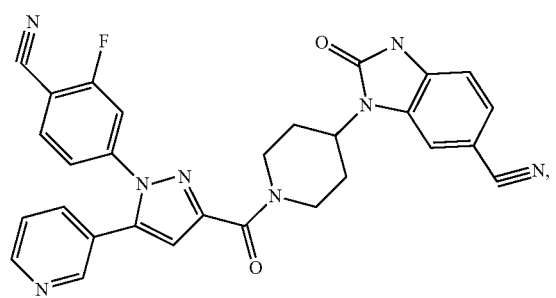

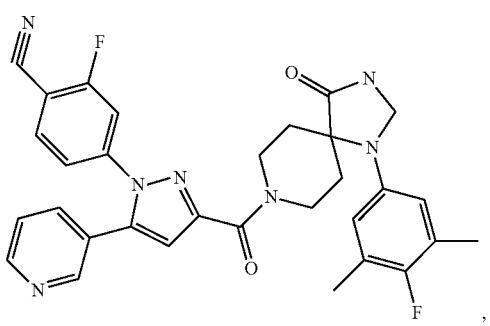

454
-continued

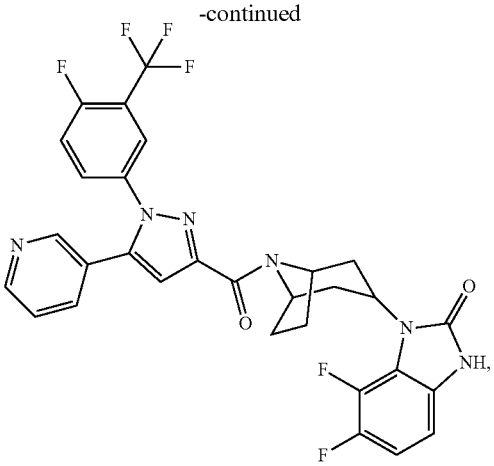

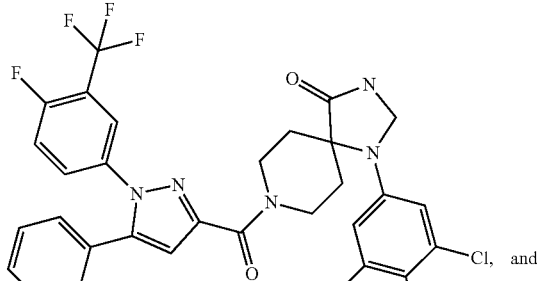

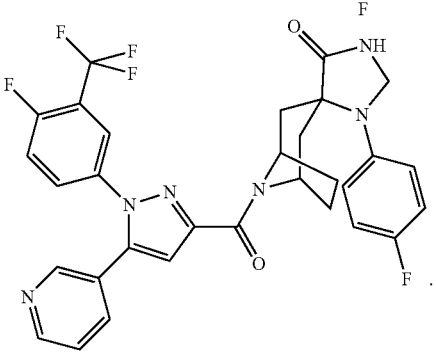

18. A pharmaceutical composition comprising a therapeutically effective amount of a compound of claim 1, or a pharmaceutically acceptable salt thereof, and at least one pharmaceutically acceptable carrier, excipient, or diluent.

19. A method of treating pain comprising administering to a patient in need thereof a therapeutically effective amount of a compound of claim 1, or a pharmaceutically acceptable salt thereof.

20. The method of claim 19, wherein said pain is selected from the group consisting of acute pain, chronic pain, inflammatory pain, neuropathic pain, diabetic peripheral neuropathic pain, chemotherapeutic-induced peripheral neuropathic pain, nociceptive pain, and periprocedural pain.

21. The method of claim 19, further comprising administering a second therapeutic agent for the treatment of pain or inflammation.

* * * * *

SEQUENCE LISTING

<160> NUMBER OF SEQ ID NOS: 7

<210> SEQ ID NO 1
<211> LENGTH: 1119
<212> TYPE: PRT
<213> ORGANISM: Homo sapiens
<220> FEATURE:
<221> NAME/KEY: VARIANT
<222> LOCATION: (1)...(1119)
<223> OTHER INFORMATION: wild-type transient receptor potential cation
channel subfamily A member 1 (TRPA1), ankyrin-like with
transmembrane domains protein 1 (ANKTM1), transformation sensitive
protein p120

<400> SEQUENCE: 1

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
                20                  25                  30

Lys Glu Ser Leu Lys Val Val Phe Glu Gly Ser Ala Tyr Gly Leu Gln
            35                  40                  45

Asn Phe Asn Lys Gln Lys Lys Leu Lys Arg Cys Asp Asp Met Asp Thr
50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Lys Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
        275                 280                 285

Lys Leu Met Ile Ser Ser Tyr Ser Gly Ser Val Asp Ile Val Asn Thr
290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

```
Lys Ile Asp Ser Glu Gly Arg Ser Pro Leu Ile Leu Ala Thr Ala Ser
            340                 345                 350

Ala Ser Trp Asn Ile Val Asn Leu Leu Ser Lys Gly Ala Gln Val
        355                 360                 365

Asp Ile Lys Asp Asn Phe Gly Arg Asn Phe Leu His Leu Thr Val Gln
        370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
                420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
            515                 520                 525

Thr Met Lys Val Ile Leu Asp Thr Asn Leu Lys Cys Thr Asp Arg Leu
            530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
            595                 600                 605

Leu Lys Ile Phe Ser His Asn Ser Pro Gly Asn Lys Cys Pro Ile Thr
            610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
                660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
            690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
                740                 745                 750
```

Asn Glu Thr Ser Asp His Ser Glu Ile Leu Asp Thr Asn Ser Tyr
            755                 760                 765

Leu Ile Lys Thr Cys Met Ile Leu Val Phe Leu Ser Ser Ile Phe Gly
770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Asn Leu Gln Asp
            885                 890                 895

Pro Phe Ser Ser Pro Leu Leu Ser Ile Ile Gln Thr Phe Ser Met Met
                900                 905                 910

Leu Gly Asp Ile Asn Tyr Arg Glu Ser Phe Leu Glu Pro Tyr Leu Arg
            915                 920                 925

Asn Glu Leu Ala His Pro Val Leu Ser Phe Ala Gln Leu Val Ser Phe
            930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
            995                 1000                1005

Lys Pro Arg Ser Gly Gly Met Leu Phe His Ile Phe Cys Phe Leu Phe
1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
            1060                1065                1070

Glu Ile Ile Ser Glu Thr Glu Asp Asp Ser His Cys Ser Phe Gln
            1075                1080                1085

Asp Arg Phe Lys Lys Glu Gln Met Glu Gln Arg Asn Ser Arg Trp Asn
            1090                1095                1100

Thr Val Leu Arg Ala Val Lys Ala Lys Thr His His Leu Glu Pro
1105                1110                1115

<210> SEQ ID NO 2
<211> LENGTH: 1119
<212> TYPE: PRT
<213> ORGANISM: Homo sapiens
<220> FEATURE:
<221> NAME/KEY: VARIANT
<222> LOCATION: (1)...(1119)
<223> OTHER INFORMATION: transient receptor potential cation channel
      subfamily A member 1 (TRPA1), variant rs13268757, VAR_020660, ankyrin-like with transmembrane domains protein 1 (ANKTM1),
transformation sensitive protein p120

<400> SEQUENCE: 2

| | | | | | | | | | | | | | | |
|---|---|---|---|---|---|---|---|---|---|---|---|---|---|---|
| Met | Lys | Cys | Ser | Leu | Arg | Lys | Met | Trp | Arg | Pro | Gly | Glu | Lys | Glu |
| 1 | | | | 5 | | | | | 10 | | | | | 15 |
| Pro | Gln | Gly | Val | Val | Tyr | Glu | Asp | Val | Pro | Asp | Asp | Thr | Glu | Asp | Phe |
| | | | 20 | | | | | 25 | | | | | 30 | | |
| Lys | Glu | Ser | Leu | Lys | Val | Val | Phe | Glu | Gly | Ser | Ala | Tyr | Gly | Leu | Gln |
| | | 35 | | | | | 40 | | | | | 45 | | | |
| Asn | Phe | Asn | Lys | Gln | Lys | Lys | Leu | Lys | Arg | Cys | Asp | Asp | Met | Asp | Thr |
| 50 | | | | | 55 | | | | | 60 | | | | | |
| Phe | Phe | Leu | His | Tyr | Ala | Ala | Glu | Gly | Gln | Ile | Glu | Leu | Met | Glu |
| 65 | | | | 70 | | | | | 75 | | | | | 80 |
| Lys | Ile | Thr | Arg | Asp | Ser | Ser | Leu | Glu | Val | Leu | His | Glu | Met | Asp | Asp |
| | | | | 85 | | | | | 90 | | | | | 95 | |
| Tyr | Gly | Asn | Thr | Pro | Leu | His | Cys | Ala | Val | Glu | Lys | Asn | Gln | Ile | Glu |
| | | | 100 | | | | | 105 | | | | | 110 | | |
| Ser | Val | Lys | Phe | Leu | Leu | Ser | Arg | Gly | Ala | Asn | Pro | Asn | Leu | Arg | Asn |
| | | 115 | | | | | 120 | | | | | 125 | | | |
| Phe | Asn | Met | Met | Ala | Pro | Leu | His | Ile | Ala | Val | Gln | Gly | Met | Asn | Asn |
| 130 | | | | | 135 | | | | | 140 | | | | | |
| Glu | Val | Met | Lys | Val | Leu | Leu | Glu | His | Arg | Thr | Ile | Asp | Val | Asn | Leu |
| 145 | | | | | 150 | | | | | 155 | | | | | 160 |
| Glu | Gly | Glu | Asn | Gly | Asn | Thr | Ala | Val | Ile | Ile | Ala | Cys | Thr | Thr | Asn |
| | | | | 165 | | | | | 170 | | | | | 175 | |
| Asn | Ser | Glu | Ala | Leu | Gln | Ile | Leu | Leu | Lys | Lys | Gly | Ala | Lys | Pro | Cys |
| | | | 180 | | | | | 185 | | | | | 190 | | |
| Lys | Ser | Asn | Lys | Trp | Gly | Cys | Phe | Pro | Ile | His | Gln | Ala | Ala | Phe | Ser |
| | | 195 | | | | | 200 | | | | | 205 | | | |
| Gly | Ser | Lys | Glu | Cys | Met | Glu | Ile | Ile | Leu | Arg | Phe | Gly | Glu | His |
| 210 | | | | | 215 | | | | | 220 | | | | | |
| Gly | Tyr | Ser | Arg | Gln | Leu | His | Ile | Asn | Phe | Met | Asn | Asn | Gly | Lys | Ala |
| 225 | | | | | 230 | | | | | 235 | | | | | 240 |
| Thr | Pro | Leu | His | Leu | Ala | Val | Gln | Asn | Gly | Asp | Leu | Glu | Met | Ile | Lys |
| | | | | 245 | | | | | 250 | | | | | 255 | |
| Met | Cys | Leu | Asp | Asn | Gly | Ala | Gln | Ile | Asp | Pro | Val | Glu | Lys | Gly | Arg |
| | | | 260 | | | | | 265 | | | | | 270 | | |
| Cys | Thr | Ala | Ile | His | Phe | Ala | Ala | Thr | Gln | Gly | Ala | Thr | Glu | Ile | Val |
| | | 275 | | | | | 280 | | | | | 285 | | | |
| Lys | Leu | Met | Ile | Ser | Ser | Tyr | Ser | Gly | Ser | Val | Asp | Ile | Val | Asn | Thr |
| | | 290 | | | | | 295 | | | | | 300 | | | |
| Thr | Asp | Gly | Cys | His | Glu | Thr | Met | Leu | His | Arg | Ala | Ser | Leu | Phe | Asp |
| 305 | | | | | 310 | | | | | 315 | | | | | 320 |
| His | His | Glu | Leu | Ala | Asp | Tyr | Leu | Ile | Ser | Val | Gly | Ala | Asp | Ile | Asn |
| | | | | 325 | | | | | 330 | | | | | 335 | |
| Lys | Ile | Asp | Ser | Glu | Gly | Arg | Ser | Pro | Leu | Ile | Leu | Ala | Thr | Ala | Ser |
| | | | 340 | | | | | 345 | | | | | 350 | | |
| Ala | Ser | Trp | Asn | Ile | Val | Asn | Leu | Leu | Leu | Ser | Lys | Gly | Ala | Gln | Val |
| | | 355 | | | | | 360 | | | | | 365 | | | |
| Asp | Ile | Lys | Asp | Asn | Phe | Gly | Arg | Asn | Phe | Leu | His | Leu | Thr | Val | Gln |
| | | 370 | | | | | 375 | | | | | 380 | | | |
| Gln | Pro | Tyr | Gly | Leu | Lys | Asn | Leu | Arg | Pro | Glu | Phe | Met | Gln | Met | Gln |
| 385 | | | | | 390 | | | | | 395 | | | | | 400 |

```
Gln Ile Lys Glu Leu Val Met Asp Glu Asp Asn Asp Gly Cys Thr Pro
                405                 410                 415
Leu His Tyr Ala Cys Arg Gln Gly Gly Pro Gly Ser Val Asn Asn Leu
                420                 425                 430
Leu Gly Phe Asn Val Ser Ile His Ser Lys Ser Lys Asp Lys Lys Ser
                435                 440                 445
Pro Leu His Phe Ala Ala Ser Tyr Gly Arg Ile Asn Thr Cys Gln Arg
                450                 455                 460
Leu Leu Gln Asp Ile Ser Asp Thr Arg Leu Leu Asn Glu Gly Asp Leu
465                 470                 475                 480
His Gly Met Thr Pro Leu His Leu Ala Ala Lys Asn Gly His Asp Lys
                485                 490                 495
Val Val Gln Leu Leu Lys Lys Gly Ala Leu Phe Leu Ser Asp His
                500                 505                 510
Asn Gly Trp Thr Ala Leu His His Ala Ser Met Gly Gly Tyr Thr Gln
                515                 520                 525
Thr Met Lys Val Ile Leu Asp Thr Asn Leu Lys Cys Thr Asp Arg Leu
                530                 535                 540
Asp Glu Asp Gly Asn Thr Ala Leu His Phe Ala Ala Arg Glu Gly His
545                 550                 555                 560
Ala Lys Ala Val Ala Leu Leu Leu Ser His Asn Ala Asp Ile Val Leu
                565                 570                 575
Asn Lys Gln Gln Ala Ser Phe Leu His Leu Ala Leu His Asn Lys Arg
                580                 585                 590
Lys Glu Val Val Leu Thr Ile Ile Arg Ser Lys Arg Trp Asp Glu Cys
                595                 600                 605
Leu Lys Ile Phe Ser His Asn Ser Pro Gly Asn Lys Cys Pro Ile Thr
                610                 615                 620
Glu Met Ile Glu Tyr Leu Pro Glu Cys Met Lys Val Leu Leu Asp Phe
625                 630                 635                 640
Cys Met Leu His Ser Thr Glu Asp Lys Ser Cys Arg Asp Tyr Tyr Ile
                645                 650                 655
Glu Tyr Asn Phe Lys Tyr Leu Gln Cys Pro Leu Glu Phe Thr Lys Lys
                660                 665                 670
Thr Pro Thr Gln Asp Val Ile Tyr Glu Pro Leu Thr Ala Leu Asn Ala
                675                 680                 685
Met Val Gln Asn Asn Arg Ile Glu Leu Leu Asn His Pro Val Cys Lys
                690                 695                 700
Glu Tyr Leu Leu Met Lys Trp Leu Ala Tyr Gly Phe Arg Ala His Met
705                 710                 715                 720
Met Asn Leu Gly Ser Tyr Cys Leu Gly Leu Ile Pro Met Thr Ile Leu
                725                 730                 735
Val Val Asn Ile Lys Pro Gly Met Ala Phe Asn Ser Thr Gly Ile Ile
                740                 745                 750
Asn Glu Thr Ser Asp His Ser Glu Ile Leu Asp Thr Thr Asn Ser Tyr
                755                 760                 765
Leu Ile Lys Thr Cys Met Ile Leu Val Phe Leu Ser Ser Ile Phe Gly
                770                 775                 780
Tyr Cys Lys Glu Ala Gly Gln Ile Phe Gln Gln Lys Arg Asn Tyr Phe
785                 790                 795                 800
Met Asp Ile Ser Asn Val Leu Glu Trp Ile Ile Tyr Thr Thr Gly Ile
                805                 810                 815
```

```
Ile Phe Val Leu Pro Leu Phe Val Glu Ile Pro Ala His Leu Gln Trp
                820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
    850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
    915                 920                 925

Asn Glu Leu Ala His Pro Val Leu Ser Phe Ala Gln Leu Val Ser Phe
930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
    995                 1000                1005

Lys Pro Arg Ser Gly Gly Met Leu Phe His Ile Phe Cys Phe Leu Phe
            1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
            1060                1065                1070

Glu Ile Ile Ser Glu Thr Glu Asp Asp Asp Ser His Cys Ser Phe Gln
    1075                1080                1085

Asp Arg Phe Lys Lys Glu Gln Met Glu Gln Arg Asn Ser Arg Trp Asn
1090                1095                1100

Thr Val Leu Arg Ala Val Lys Ala Lys Thr His His Leu Glu Pro
1105                1110                1115

<210> SEQ ID NO 3
<211> LENGTH: 1119
<212> TYPE: PRT
<213> ORGANISM: Homo sapiens
<220> FEATURE:
<221> NAME/KEY: VARIANT
<222> LOCATION: (1)...(1119)
<223> OTHER INFORMATION: transient receptor potential cation channel
      subfamily A member 1 (TRPA1), variant rs16937976, VAR_047471,
      ankyrin-like with transmembrane domains protein 1 (ANKTM1),
      transformation sensitive protein p120

<400> SEQUENCE: 3

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
```

-continued

```
                35                  40                  45
Asn Phe Asn Lys Gln Lys Lys Leu Lys Thr Cys Asp Asp Met Asp Thr
 50                  55                  60
Phe Phe Leu His Tyr Ala Ala Glu Gly Gln Ile Glu Leu Met Glu
 65                  70                  75                  80
Lys Ile Thr Arg Asp Ser Ser Leu Glu Val Leu His Glu Met Asp Asp
                 85                  90                  95
Tyr Gly Asn Thr Pro Leu His Cys Ala Val Glu Lys Asn Gln Ile Glu
                100                 105                 110
Ser Val Lys Phe Leu Leu Ser Arg Gly Ala Asn Pro Asn Leu Arg Asn
                115                 120                 125
Phe Asn Met Met Ala Pro Leu His Ile Ala Val Gln Gly Met Asn Asn
130                 135                 140
Glu Val Met Lys Val Leu Leu Glu His Arg Thr Ile Asp Val Asn Leu
145                 150                 155                 160
Glu Gly Glu Asn Gly Asn Thr Ala Val Ile Ile Ala Cys Thr Thr Asn
                165                 170                 175
Asn Ser Glu Ala Leu Gln Ile Leu Leu Lys Lys Gly Ala Lys Pro Cys
                180                 185                 190
Lys Ser Asn Lys Trp Gly Cys Phe Pro Ile His Gln Ala Ala Phe Ser
                195                 200                 205
Gly Ser Lys Glu Cys Met Glu Ile Ile Leu Arg Phe Gly Glu Glu His
210                 215                 220
Gly Tyr Ser Arg Gln Leu His Ile Asn Phe Met Asn Asn Gly Lys Ala
225                 230                 235                 240
Thr Pro Leu His Leu Ala Val Gln Asn Gly Asp Leu Glu Met Ile Lys
                245                 250                 255
Met Cys Leu Asp Asn Gly Ala Gln Ile Asp Pro Val Glu Lys Gly Arg
                260                 265                 270
Cys Thr Ala Ile His Phe Ala Ala Thr Gln Gly Ala Thr Glu Ile Val
                275                 280                 285
Lys Leu Met Ile Ser Ser Tyr Ser Gly Ser Val Asp Ile Val Asn Thr
290                 295                 300
Thr Asp Gly Cys His Glu Thr Met Leu His Arg Ala Ser Leu Phe Asp
305                 310                 315                 320
His His Glu Leu Ala Asp Tyr Leu Ile Ser Val Gly Ala Asp Ile Asn
                325                 330                 335
Lys Ile Asp Ser Glu Gly Arg Ser Pro Leu Ile Leu Ala Thr Ala Ser
                340                 345                 350
Ala Ser Trp Asn Ile Val Asn Leu Leu Leu Ser Lys Gly Ala Gln Val
                355                 360                 365
Asp Ile Lys Asp Asn Phe Gly Arg Asn Phe Leu His Leu Thr Val Gln
                370                 375                 380
Gln Pro Tyr Gly Leu Lys Asn Leu Arg Pro Glu Phe Met Gln Met Gln
385                 390                 395                 400
Gln Ile Lys Glu Leu Val Met Asp Glu Asp Asn Asp Gly Cys Thr Pro
                405                 410                 415
Leu His Tyr Ala Cys Arg Gln Gly Gly Pro Gly Ser Val Asn Asn Leu
                420                 425                 430
Leu Gly Phe Asn Val Ser Ile His Ser Lys Ser Lys Asp Lys Lys Ser
                435                 440                 445
Pro Leu His Phe Ala Ala Ser Tyr Gly Arg Ile Asn Thr Cys Gln Arg
450                 455                 460
```

-continued

```
Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Lys Lys Gly Ala Leu Phe Leu Ser Asp His
        500                 505                 510

Asn Gly Trp Thr Ala Leu His Ala Ser Met Gly Gly Tyr Thr Gln
            515                 520                 525

Thr Met Lys Val Ile Leu Asp Thr Asn Leu Lys Cys Thr Asp Arg Leu
530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
        595                 600                 605

Leu Lys Ile Phe Ser His Asn Ser Pro Gly Asn Lys Cys Pro Ile Thr
610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
        675                 680                 685

Met Val Gln Asn Asn Arg Ile Glu Leu Leu Asn His Pro Val Cys Lys
        690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
            725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Asn Ser Tyr
            755                 760                 765

Leu Ile Lys Thr Cys Met Ile Leu Val Phe Leu Ser Ser Ile Phe Gly
770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
        850                 855                 860

Val Ile Leu Lys Thr Leu Leu Arg Ser Thr Val Val Phe Ile Phe Leu
865                 870                 875                 880
```

-continued

```
Leu Leu Ala Phe Gly Leu Ser Phe Tyr Ile Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
            915                 920                 925

Asn Glu Leu Ala His Pro Val Leu Ser Phe Ala Gln Leu Val Ser Phe
        930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
                980                 985                 990

Trp Phe Leu Arg Lys Val Asp Gln Lys Ser Thr Ile Val Tyr Pro Asn
            995                1000                1005

Lys Pro Arg Ser Gly Gly Met Leu Phe His Ile Phe Cys Phe Leu Phe
        1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
                1060                1065                1070

Glu Ile Ile Ser Glu Thr Glu Asp Asp Asp Ser His Cys Ser Phe Gln
            1075                1080                1085

Asp Arg Phe Lys Lys Glu Gln Met Glu Gln Arg Asn Ser Arg Trp Asn
        1090                1095                1100

Thr Val Leu Arg Ala Val Lys Ala Lys Thr His His Leu Glu Pro
1105                1110                1115

<210> SEQ ID NO 4
<211> LENGTH: 1119
<212> TYPE: PRT
<213> ORGANISM: Homo sapiens
<220> FEATURE:
<221> NAME/KEY: VARIANT
<222> LOCATION: (1)...(1119)
<223> OTHER INFORMATION: transient receptor potential cation channel
      subfamily A member 1 (TRPA1), variant rs920829, VAR_020661,
      ankyrin-like with transmembrane domains protein 1 (ANKTM1),
      transformation sensitive protein p120

<400> SEQUENCE: 4

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
    50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
```

-continued

```
                100                 105                 110
Ser Val Lys Phe Leu Ser Arg Gly Ala Pro Asn Leu Arg Asn
            115                 120                 125
Phe Asn Met Met Ala Pro Leu His Ile Ala Val Gln Gly Met Asn Asn
130                 135                 140
Glu Val Met Lys Val Leu Leu Glu His Arg Thr Ile Asp Val Asn Leu
145                 150                 155                 160
Glu Gly Glu Asn Gly Asn Thr Ala Val Ile Ile Ala Cys Thr Thr Asn
                165                 170                 175
Asn Ser Lys Ala Leu Gln Ile Leu Leu Lys Lys Gly Ala Lys Pro Cys
            180                 185                 190
Lys Ser Asn Lys Trp Gly Cys Phe Pro Ile His Gln Ala Ala Phe Ser
        195                 200                 205
Gly Ser Lys Glu Cys Met Glu Ile Ile Leu Arg Phe Gly Glu Glu His
    210                 215                 220
Gly Tyr Ser Arg Gln Leu His Ile Asn Phe Met Asn Asn Gly Lys Ala
225                 230                 235                 240
Thr Pro Leu His Leu Ala Val Gln Asn Gly Asp Leu Glu Met Ile Lys
                245                 250                 255
Met Cys Leu Asp Asn Gly Ala Gln Ile Asp Pro Val Glu Lys Gly Arg
            260                 265                 270
Cys Thr Ala Ile His Phe Ala Ala Thr Gln Gly Ala Thr Glu Ile Val
        275                 280                 285
Lys Leu Met Ile Ser Ser Tyr Ser Gly Ser Val Asp Ile Val Asn Thr
    290                 295                 300
Thr Asp Gly Cys His Glu Thr Met Leu His Arg Ala Ser Leu Phe Asp
305                 310                 315                 320
His His Glu Leu Ala Asp Tyr Leu Ile Ser Val Gly Ala Asp Ile Asn
                325                 330                 335
Lys Ile Asp Ser Glu Gly Arg Ser Pro Leu Ile Leu Ala Thr Ala Ser
            340                 345                 350
Ala Ser Trp Asn Ile Val Asn Leu Leu Leu Ser Lys Gly Ala Gln Val
        355                 360                 365
Asp Ile Lys Asp Asn Phe Gly Arg Asn Phe Leu His Leu Thr Val Gln
    370                 375                 380
Gln Pro Tyr Gly Leu Lys Asn Leu Arg Pro Glu Phe Met Gln Met Gln
385                 390                 395                 400
Gln Ile Lys Glu Leu Val Met Asp Glu Asp Asn Asp Gly Cys Thr Pro
                405                 410                 415
Leu His Tyr Ala Cys Arg Gln Gly Gly Pro Gly Ser Val Asn Asn Leu
            420                 425                 430
Leu Gly Phe Asn Val Ser Ile His Ser Lys Ser Lys Asp Lys Lys Ser
        435                 440                 445
Pro Leu His Phe Ala Ala Ser Tyr Gly Arg Ile Asn Thr Cys Gln Arg
    450                 455                 460
Leu Leu Gln Asp Ile Ser Asp Thr Arg Leu Leu Asn Glu Gly Asp Leu
465                 470                 475                 480
His Gly Met Thr Pro Leu His Leu Ala Ala Lys Asn Gly His Asp Lys
                485                 490                 495
Val Val Gln Leu Leu Leu Lys Lys Gly Ala Leu Phe Leu Ser Asp His
            500                 505                 510
Asn Gly Trp Thr Ala Leu His His Ala Ser Met Gly Gly Tyr Thr Gln
        515                 520                 525
```

-continued

Thr Met Lys Val Ile Leu Asp Thr Asn Leu Lys Cys Thr Asp Arg Leu
530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
                580                 585                 590

Lys Glu Val Val Leu Thr Ile Ile Arg Ser Lys Arg Trp Asp Glu Cys
                595                 600                 605

Leu Lys Ile Phe Ser His Asn Ser Pro Gly Asn Lys Cys Pro Ile Thr
610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
                660                 665                 670

Thr Pro Thr Gln Asp Val Ile Tyr Glu Pro Leu Thr Ala Leu Asn Ala
                675                 680                 685

Met Val Gln Asn Asn Arg Ile Glu Leu Leu Asn His Pro Val Cys Lys
690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
                740                 745                 750

Asn Glu Thr Ser Asp His Ser Glu Ile Leu Asp Thr Thr Asn Ser Tyr
                755                 760                 765

Leu Ile Lys Thr Cys Met Ile Leu Val Phe Leu Ser Ser Ile Phe Gly
770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
                820                 825                 830

Gln Cys Gly Ala Ile Ala Val Tyr Phe Tyr Trp Met Asn Phe Leu Leu
                835                 840                 845

Tyr Leu Gln Arg Phe Glu Asn Cys Gly Ile Phe Ile Val Met Leu Glu
850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Asn Leu Gln Asp
                885                 890                 895

Pro Phe Ser Ser Pro Leu Leu Ser Ile Ile Gln Thr Phe Ser Met Met
                900                 905                 910

Leu Gly Asp Ile Asn Tyr Arg Glu Ser Phe Leu Glu Pro Tyr Leu Arg
                915                 920                 925

Asn Glu Leu Ala His Pro Val Leu Ser Phe Ala Gln Leu Val Ser Phe
930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
            965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
        995                 1000                1005

Lys Pro Arg Ser Gly Gly Met Leu Phe His Ile Phe Cys Phe Leu Phe
    1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
                1060                1065                1070

Glu Ile Ile Ser Glu Thr Glu Asp Asp Ser His Cys Ser Phe Gln
            1075                1080                1085

Asp Arg Phe Lys Lys Glu Gln Met Glu Gln Arg Asn Ser Arg Trp Asn
        1090                1095                1100

Thr Val Leu Arg Ala Val Lys Ala Lys Thr His His Leu Glu Pro
1105                1110                1115

<210> SEQ ID NO 5
<211> LENGTH: 1119
<212> TYPE: PRT
<213> ORGANISM: Homo sapiens
<220> FEATURE:
<221> NAME/KEY: VARIANT
<222> LOCATION: (1)...(1119)
<223> OTHER INFORMATION: transient receptor potential cation channel
      subfamily A member 1 (TRPA1), variant rs7819749, VAR_020662,
      ankyrin-like with transmembrane domains protein 1 (ANKTM1),
      transformation sensitive protein p120

<400> SEQUENCE: 5

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
    130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn

```
                165                 170                 175
Asn Ser Glu Ala Leu Gln Ile Leu Leu Asn Lys Gly Ala Lys Pro Cys
            180                 185                 190
Lys Ser Asn Lys Trp Gly Cys Phe Pro Ile His Gln Ala Ala Phe Ser
        195                 200                 205
Gly Ser Lys Glu Cys Met Glu Ile Ile Leu Arg Phe Gly Glu His
    210                 215                 220
Gly Tyr Ser Arg Gln Leu His Ile Asn Phe Met Asn Asn Gly Lys Ala
225                 230                 235                 240
Thr Pro Leu His Leu Ala Val Gln Asn Gly Asp Leu Glu Met Ile Lys
            245                 250                 255
Met Cys Leu Asp Asn Gly Ala Gln Ile Asp Pro Val Glu Lys Gly Arg
        260                 265                 270
Cys Thr Ala Ile His Phe Ala Ala Thr Gln Gly Ala Thr Glu Ile Val
    275                 280                 285
Lys Leu Met Ile Ser Ser Tyr Ser Gly Ser Val Asp Ile Val Asn Thr
    290                 295                 300
Thr Asp Gly Cys His Glu Thr Met Leu His Arg Ala Ser Leu Phe Asp
305                 310                 315                 320
His His Glu Leu Ala Asp Tyr Leu Ile Ser Val Gly Ala Asp Ile Asn
            325                 330                 335
Lys Ile Asp Ser Glu Gly Arg Ser Pro Leu Ile Leu Ala Thr Ala Ser
        340                 345                 350
Ala Ser Trp Asn Ile Val Asn Leu Leu Leu Ser Lys Gly Ala Gln Val
        355                 360                 365
Asp Ile Lys Asp Asn Phe Gly Arg Asn Phe Leu His Leu Thr Val Gln
    370                 375                 380
Gln Pro Tyr Gly Leu Lys Asn Leu Arg Pro Glu Phe Met Gln Met Gln
385                 390                 395                 400
Gln Ile Lys Glu Leu Val Met Asp Glu Asp Asn Asp Gly Cys Thr Pro
            405                 410                 415
Leu His Tyr Ala Cys Arg Gln Gly Gly Pro Gly Ser Val Asn Asn Leu
        420                 425                 430
Leu Gly Phe Asn Val Ser Ile His Ser Lys Ser Lys Asp Lys Lys Ser
        435                 440                 445
Pro Leu His Phe Ala Ala Ser Tyr Gly Arg Ile Asn Thr Cys Gln Arg
    450                 455                 460
Leu Leu Gln Asp Ile Ser Asp Thr Arg Leu Leu Asn Glu Gly Asp Leu
465                 470                 475                 480
His Gly Met Thr Pro Leu His Leu Ala Ala Lys Asn Gly His Asp Lys
            485                 490                 495
Val Val Gln Leu Leu Lys Lys Gly Ala Leu Phe Leu Ser Asp His
        500                 505                 510
Asn Gly Trp Thr Ala Leu His His Ala Ser Met Gly Gly Tyr Thr Gln
        515                 520                 525
Thr Met Lys Val Ile Leu Asp Thr Asn Leu Lys Cys Thr Asp Arg Leu
    530                 535                 540
Asp Glu Asp Gly Asn Thr Ala Leu His Phe Ala Arg Glu Gly His
545                 550                 555                 560
Ala Lys Ala Val Ala Leu Leu Leu Ser His Asn Ala Asp Ile Val Leu
            565                 570                 575
Asn Lys Gln Gln Ala Ser Phe Leu His Leu Ala Leu His Asn Lys Arg
        580                 585                 590
```

```
Lys Glu Val Val Leu Thr Ile Ile Arg Ser Lys Arg Trp Asp Glu Cys
            595                 600                 605

Leu Lys Ile Phe Ser His Asn Ser Pro Gly Asn Lys Cys Pro Ile Thr
            610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
            645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
            690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
            725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
            755                 760                 765

Leu Ile Lys Thr Cys Met Ile Leu Val Phe Leu Ser Ser Ile Phe Gly
            770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
            805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
            850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
            885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
            915                 920                 925

Asn Glu Leu Ala His Pro Val Leu Ser Phe Ala Gln Leu Val Ser Phe
            930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
            965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
            995                 1000                1005
```

-continued

```
Lys Pro Arg Ser Gly Gly Met Leu Phe His Ile Phe Cys Phe Leu Phe
    1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
                1060                1065                1070

Glu Ile Ile Ser Glu Thr Glu Asp Asp Ser His Cys Ser Phe Gln
            1075                1080                1085

Asp Arg Phe Lys Lys Glu Gln Met Glu Gln Arg Asn Ser Arg Trp Asn
    1090                1095                1100

Thr Val Leu Arg Ala Val Lys Ala Lys Thr His His Leu Glu Pro
1105                1110                1115
```

<210> SEQ ID NO 6
<211> LENGTH: 1119
<212> TYPE: PRT
<213> ORGANISM: Homo sapiens
<220> FEATURE:
<221> NAME/KEY: VARIANT
<222> LOCATION: (1)...(1119)
<223> OTHER INFORMATION: transient receptor potential cation channel
    subfamily A member 1 (TRPA1), familial episodic pain syndrome 1
    (FEPS1), VAR_069737, ankyrin-like with transmembrane domains
    protein 1 (ANKTM1), transformation sensitive protein p120

<400> SEQUENCE: 6

```
Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
                20                  25                  30

Lys Glu Ser Leu Lys Val Val Phe Glu Gly Ser Ala Tyr Gly Leu Gln
            35                  40                  45

Asn Phe Asn Lys Gln Lys Lys Leu Lys Arg Cys Asp Asp Met Asp Thr
50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
                100                 105                 110

Ser Val Lys Phe Leu Leu Ser Arg Gly Ala Asn Pro Asn Leu Arg Asn
            115                 120                 125

Phe Asn Met Met Ala Pro Leu His Ile Ala Val Gln Gly Met Asn Asn
130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Lys Lys Gly Ala Lys Pro Cys
            180                 185                 190

Lys Ser Asn Lys Trp Gly Cys Phe Pro Ile His Gln Ala Ala Phe Ser
            195                 200                 205

Gly Ser Lys Glu Cys Met Glu Ile Ile Leu Arg Phe Gly Glu Glu His
        210                 215                 220

Gly Tyr Ser Arg Gln Leu His Ile Asn Phe Met Asn Asn Gly Lys Ala
```

```
            225                 230                 235                 240
    Thr Pro Leu His Leu Ala Val Gln Asn Gly Asp Leu Glu Met Ile Lys
                        245                 250                 255
    Met Cys Leu Asp Asn Gly Ala Gln Ile Asp Pro Val Glu Lys Gly Arg
                        260                 265                 270
    Cys Thr Ala Ile His Phe Ala Ala Thr Gln Gly Ala Thr Glu Ile Val
                        275                 280                 285
    Lys Leu Met Ile Ser Ser Tyr Ser Gly Ser Val Asp Ile Val Asn Thr
                290                 295                 300
    Thr Asp Gly Cys His Glu Thr Met Leu His Arg Ala Ser Leu Phe Asp
    305                 310                 315                 320
    His His Glu Leu Ala Asp Tyr Leu Ile Ser Val Gly Ala Asp Ile Asn
                        325                 330                 335
    Lys Ile Asp Ser Glu Gly Arg Ser Pro Leu Ile Leu Ala Thr Ala Ser
                        340                 345                 350
    Ala Ser Trp Asn Ile Val Asn Leu Leu Leu Ser Lys Gly Ala Gln Val
                        355                 360                 365
    Asp Ile Lys Asp Asn Phe Gly Arg Asn Phe Leu His Leu Thr Val Gln
        370                 375                 380
    Gln Pro Tyr Gly Leu Lys Asn Leu Arg Pro Glu Phe Met Gln Met Gln
    385                 390                 395                 400
    Gln Ile Lys Glu Leu Val Met Asp Glu Asp Asn Asp Gly Cys Thr Pro
                        405                 410                 415
    Leu His Tyr Ala Cys Arg Gln Gly Gly Pro Gly Ser Val Asn Asn Leu
                        420                 425                 430
    Leu Gly Phe Asn Val Ser Ile His Ser Lys Ser Lys Asp Lys Lys Ser
                435                 440                 445
    Pro Leu His Phe Ala Ala Ser Tyr Gly Arg Ile Asn Thr Cys Gln Arg
        450                 455                 460
    Leu Leu Gln Asp Ile Ser Asp Thr Arg Leu Leu Asn Glu Gly Asp Leu
    465                 470                 475                 480
    His Gly Met Thr Pro Leu His Leu Ala Ala Lys Asn Gly His Asp Lys
                        485                 490                 495
    Val Val Gln Leu Leu Leu Lys Lys Gly Ala Leu Phe Leu Ser Asp His
                        500                 505                 510
    Asn Gly Trp Thr Ala Leu His His Ala Ser Met Gly Gly Tyr Thr Gln
                        515                 520                 525
    Thr Met Lys Val Ile Leu Asp Thr Asn Leu Lys Cys Thr Asp Arg Leu
        530                 535                 540
    Asp Glu Asp Gly Asn Thr Ala Leu His Phe Ala Ala Arg Glu Gly His
    545                 550                 555                 560
    Ala Lys Ala Val Ala Leu Leu Leu Ser His Asn Ala Asp Ile Val Leu
                        565                 570                 575
    Asn Lys Gln Gln Ala Ser Phe Leu His Leu Ala Leu His Asn Lys Arg
                        580                 585                 590
    Lys Glu Val Val Leu Thr Ile Ile Arg Ser Lys Arg Trp Asp Glu Cys
                595                 600                 605
    Leu Lys Ile Phe Ser His Asn Ser Pro Gly Asn Lys Cys Pro Ile Thr
        610                 615                 620
    Glu Met Ile Glu Tyr Leu Pro Glu Cys Met Lys Val Leu Leu Asp Phe
    625                 630                 635                 640
    Cys Met Leu His Ser Thr Glu Asp Lys Ser Cys Arg Asp Tyr Tyr Ile
                        645                 650                 655
```

-continued

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Asn His Pro Val Cys Lys
    690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
            755                 760                 765

Leu Ile Lys Thr Cys Met Ile Leu Val Phe Leu Ser Ser Ile Phe Gly
            770                 775                 780

Tyr Cys Lys Glu Ala Gly Gln Ile Phe Gln Gln Lys Arg Asn Tyr Phe
785                 790                 795                 800

Met Asp Ile Ser Ser Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
            850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
            915                 920                 925

Asn Glu Leu Ala His Pro Val Leu Ser Phe Ala Gln Leu Val Ser Phe
            930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
            995                 1000                1005

Lys Pro Arg Ser Gly Gly Met Leu Phe His Ile Phe Cys Phe Leu Phe
            1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
            1060                1065                1070

-continued

```
Glu Ile Ile Ser Glu Thr Glu Asp Asp Ser His Cys Ser Phe Gln
        1075                1080                1085

Asp Arg Phe Lys Lys Glu Gln Met Glu Gln Arg Asn Ser Arg Trp Asn
    1090                1095                1100

Thr Val Leu Arg Ala Val Lys Ala Lys Thr His His Leu Glu Pro
1105                1110                1115

<210> SEQ ID NO 7
<211> LENGTH: 1119
<212> TYPE: PRT
<213> ORGANISM: Homo sapiens
<220> FEATURE:
<221> NAME/KEY: VARIANT
<222> LOCATION: (1)...(1119)
<223> OTHER INFORMATION: transient receptor potential cation channel
      subfamily A member 1 (TRPA1), variant rs959976, VAR_020663,
      ankyrin-like with transmembrane domains protein 1 (ANKTM1),
      transformation sensitive protein p120

<400> SEQUENCE: 7

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Lys Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
        275                 280                 285

Lys Leu Met Ile Ser Ser Tyr Ser Gly Ser Val Asp Ile Val Asn Thr
```

```
                290                 295                 300
Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
                340                 345                 350

Ala Ser Trp Asn Ile Val Asn Leu Leu Ser Lys Gly Ala Gln Val
                355                 360                 365

Asp Ile Lys Asp Asn Phe Gly Arg Asn Phe Leu His Leu Thr Val Gln
                370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
                420                 425                 430

Leu Gly Phe Asn Val Ser Ile His Ser Lys Ser Lys Asp Lys Lys Ser
                435                 440                 445

Pro Leu His Phe Ala Ala Ser Tyr Gly Arg Ile Asn Thr Cys Gln Arg
450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
                500                 505                 510

Asn Gly Trp Thr Ala Leu His His Ala Ser Met Gly Gly Tyr Thr Gln
                515                 520                 525

Thr Met Lys Val Ile Leu Asp Thr Asn Leu Lys Cys Thr Asp Arg Leu
                530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
                580                 585                 590

Lys Glu Val Val Leu Thr Ile Ile Arg Ser Lys Arg Trp Asp Glu Cys
                595                 600                 605

Leu Lys Ile Phe Ser His Asn Ser Pro Gly Asn Lys Cys Pro Ile Thr
                610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
                660                 665                 670

Thr Pro Thr Gln Asp Val Ile Tyr Glu Pro Leu Thr Ala Leu Asn Ala
                675                 680                 685

Met Val Gln Asn Asn Arg Ile Glu Leu Leu Asn His Pro Val Cys Lys
                690                 695                 700

Glu Tyr Leu Leu Met Lys Trp Leu Ala Tyr Gly Phe Arg Ala His Met
705                 710                 715                 720
```

```
Met Asn Leu Gly Ser Tyr Cys Leu Gly Leu Ile Pro Met Thr Ile Leu
            725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
            755                 760                 765

Leu Ile Lys Thr Cys Met Ile Leu Val Phe Leu Ser Ser Ile Phe Gly
            770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
            805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
            850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
            885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
            915                 920                 925

Asn Glu Leu Ala His Pro Val Leu Ser Phe Ala Gln Leu Val Ser Phe
            930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
            965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
            995                 1000                1005

Lys Pro Arg Ser Gly Gly Met Leu Phe Arg Ile Phe Cys Phe Leu Phe
            1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
            1045                1050                1055

Leu Leu Glu Lys Gln His Glu Leu Ile Lys Leu Ile Ile Gln Lys Met
            1060                1065                1070

Glu Ile Ile Ser Glu Thr Glu Asp Asp Ser His Cys Ser Phe Gln
            1075                1080                1085

Asp Arg Phe Lys Lys Glu Gln Met Glu Gln Arg Asn Ser Arg Trp Asn
            1090                1095                1100

Thr Val Leu Arg Ala Val Lys Ala Lys Thr His His Leu Glu Pro
1105                1110                1115
```